US008975473B2

(12) United States Patent
McCourt et al.

(10) Patent No.: US 8,975,473 B2
(45) **Date of Patent: *Mar. 10, 2015**

(54) STRESS TOLERANCE AND DELAYED SENESCENCE IN PLANTS

(75) Inventors: Peter McCourt, Toronto (CA); Majid Ghassemian, Carlsbad, CA (US); Sean Cutler, Toronto (CA); Dario Bonetta, Palo Allto, CA (US)

(73) Assignee: Performance Plants, Inc., Kingston, Ontario (CA)

( * ) Notice: Subject to any disclaimer, the term of this patent is extended or adjusted under 35 U.S.C. 154(b) by 1030 days.

This patent is subject to a terminal disclaimer.

(21) Appl. No.: 12/331,143

(22) Filed: Dec. 9, 2008

(65) Prior Publication Data

US 2009/0293156 A1 Nov. 26, 2009

Related U.S. Application Data

(63) Continuation of application No. 11/229,371, filed on Sep. 16, 2005, now abandoned, which is a continuation of application No. 10/229,541, filed on Aug. 27, 2002, now Pat. No. 7,262,338, which is a continuation-in-part of application No. 10/160,764, filed on May 31, 2002, now Pat. No. 7,172,881, said application No. 12/331,143 is a continuation-in-part of application No. 10/210,760, filed on Aug. 1, 2002, now abandoned, and a continuation-in-part of application No. 09/191,687, filed on Nov. 13, 1998, now abandoned, which is a continuation-in-part of application No. PCT/US98/15664, filed on Jul. 29, 1998, and a continuation-in-part of application No. 09/124,867, filed on Jul. 30, 1998.

(60) Provisional application No. 60/294,766, filed on May 31, 2001, provisional application No. 60/348,909, filed on Oct. 22, 2001, provisional application No. 60/309,396, filed on Aug. 1, 2001, provisional application No. 60/337,084, filed on Dec. 4, 2001, provisional application No. 60/054,474, filed on Aug. 1, 1997.

(51) Int. Cl.

| | |
|---|---|
| ***A01H 5/00*** | (2006.01) |
| ***A01H 5/10*** | (2006.01) |
| ***A01H 1/08*** | (2006.01) |
| ***C12N 15/82*** | (2006.01) |
| ***C12N 9/50*** | (2006.01) |
| ***C12N 9/10*** | (2006.01) |

(52) U.S. Cl.

CPC .......... *C12N 9/1085* (2013.01); *C12N 15/8282* (2013.01); *C12N 15/8293* (2013.01); *C12N 15/8279* (2013.01); *C12N 15/8261* (2013.01); *C12N 9/50* (2013.01); *C12N 15/8273* (2013.01); *C12N 15/8266* (2013.01)

USPC ........................... 800/298; 800/276; 800/294

(58) Field of Classification Search

USPC ................................. 800/276, 278, 289, 298

See application file for complete search history.

(56) References Cited

U.S. PATENT DOCUMENTS

| | | | | |
|---|---|---|---|---|
| 5,097,025 | A | 3/1992 | Benfey et al. | |
| 5,107,065 | A | 4/1992 | Shewmaker et al. | |
| 5,759,829 | A | 6/1998 | Shewmaker et al. | |
| 7,172,881 | B2 | 2/2007 | Huang et al. | |
| 7,262,338 | B2 * | 8/2007 | McCourt et al. .............. | 800/289 |
| 2001/0044938 | A1 | 11/2001 | Mccourt et al. | |
| 2003/0061636 | A1 | 3/2003 | McCourt et al. | |
| 2003/0204865 | A1 | 10/2003 | Wan et al. | |
| 2005/0172361 | A1 | 8/2005 | Huang | |
| 2006/0021092 | A1 | 1/2006 | McCourt et al. | |
| 2006/0031966 | A1 | 2/2006 | McCourt et al. | |
| 2006/0037108 | A1 | 2/2006 | McCourt et al. | |

FOREIGN PATENT DOCUMENTS

| | | |
|---|---|---|
| EP | 1033405 | 9/2000 |
| WO | WO 98/05786 | 2/1998 |
| WO | WO 99/06580 | 2/1999 |
| WO | WO 00/14207 | 3/2000 |
| WO | WO 00/18880 | 4/2000 |
| WO | WO 02/16625 | 2/2002 |
| WO | WO 02/097097 | 12/2002 |

OTHER PUBLICATIONS

Dolferus et al. Sequence analysis of two null-mutant alleles of the single Arabidopsis Adh locus. Mol Gen Genet. Nov. 1990;224(2):297-302.*

Andres et al., "Mutational analysis of α-subunit of protein farnesyltransferase", *J. Bio. Chem*., 268(2):1383-1390 (1993).

Bird et al., " Manipulation of Plant Gene Expression by Antisense RNA", *Biology and Genetic Review*, 9:220-221 (1991).

Bartels et al., "Approaches to Improve Stress Tolerance Using Molecular Genetics", *Plant Cell and 4Env*., 17:659-667 (1994).

Bohnert et al., "Strategies for Engineering Water-Stress Tolerance in Plants", *Trends Biotech*., 14(3):89-97 (1996).

Bracha et al., '*Arabidopsis thaliana* CaaX processing zinc-metallic endoprotease (STE24)' retrieved from EBI, Accession No. AF353722 Database accession no. AF353722.

Broun et al., "Catalytic plasticity of fatty acid modification enzymes underlying chemical diversity of plant lipids" *Science*, 282(5392):1315-1317 (1998).

Chen et al., "cDNA cloning and expression of the peptide-binding beta subunit of rat p21 ras farnesyltransferas, the counterpart of yeast DPR1/RAM1", *Cell* 66(2):327-334 (1991).

Cutler et al., "A protein farnesyltranferase involved in abscisic acid signal transduction in *Arabidopsis", Science* 273:1239-1241 (1996).

(Continued)

*Primary Examiner* — Cynthia Collins

(74) *Attorney, Agent, or Firm* — Cooley LLP

(57) ABSTRACT

The novel constructs and methods of this invention improve tolerance in plants to environmental stresses and senescence. Nucleic acids encoding a plant farnesyl transferase are described, as are transgenic plants and seeds incorporating these nucleic acids and proteins. Also provided are non-naturally occurring mutations in the gene encoding farnesyl transferase which enhance drought tolerance in the plants, improve resistance to senescence and modify growth habit.

7 Claims, 42 Drawing Sheets

(56) References Cited

OTHER PUBLICATIONS

Delauney et al., "A stable bifunctional antisense transcript inhibiting Cutler et al., EMBL Sequence Data Library, XP002090869, Heidelberg, Germany, Accession No. U46574 (1996).

Cutler et al., EMBL Sequence Data Library, XP002090870, Heidelberg, Germany, Accession No. Q38920 (1996). gene expression in transgenic plants ", *PNAS*, 85:4300-4304 (1988).

Doerks et al., "Protein annotation: Detective work for function prediction", *Trends Genet.* 14(6):248-250 (1998).

Goodman et al., "Structure and expression of yeast DPR1, a gene essential for the processing and intracellular localization of ras proteins", *Yeast* 4:271 (1988).

Guo et al., "Protein tolerance to random amino acid change ", *PNAS*, 101:9205-9210 (2004).

Hill et al., Functional analysis of conserved histidines in ADP-glucose pyrophosphorylase from *Escherichia coli, Biochem. Biophys. Res. Comm.*, 244:573-577 (1998).

Kawabata et al., "Interaction of the transforming growth factor-β type I receptor with farnesyl-protein transferase-α", *J. Bio. Chem.* 270(50):29628-29631 (1995).

Koornneef et al., "The isolation and characterization of abscisic acid-insensitive mutants of *Arabidopsis thaliana", Plant Physiol.* 61:377-383 (1984).

Lazar et al., "Transforming growth factor alpha: mutation of aspartic acid 47 and leucine 48 results in different biological activities", *Mol. Cell. Biol.* 8:1247-1252 (1988).

Merlot et al., "Genetic analysis of abscisic acid signal transduction", *Plant Physiol.* 114:751-757 (1997).

Mizukami et al., "Separation of AG function in floral meristem determinacy from that in reproductive organ identity by expressing antisense AG mRNA", *Plant Molec. Biol.* 28(5):767-784 (1995).

Napoli et al., "Introduction of a Chimeric Chalcone Synthase Gene into Petunia Results in Reversible Co-Suppression of Homologous Genes in trans", *The Plant Cell* 2:279-289 (1990).

Pei et al., "Role of farnesyltransferase in ABA regulation of guard cell anion channels and plant water loss", *Science* 282:287-290 (1998).

Pei et al., "Type II CAAX prenyl endopeptidases belong to a novel superfamily of putative membrane-bound metalloproteases", *Trends Biochem. Sci.* (*TIBS*) 26(5):275-277 (2001).

Pusch et al., "Nucleotide sequence homology requirements of HIV-1-specific short hairpin RNA", *Nuc. Acids. Res.* 31(22):6444-6449 (2003).

Qian et al., "Protein farnesyltransferase in plants: Molecular characterization and involvement in cell cycle control", *The Plant Cell* 8:2381-2394 (1996).

Sandler et al., "Inhibition of gene expression in transformed plants by antisense RNA", *Plant Mol. Biol.* 11(3):301-310 (1988).

Schafer et al., "Protein prenylation: genes, enzymes, targets and functions", *Ann. Rev. Genet.* 30:209-237 (1992).

Smith et al., "Antisense RNA inhibition of polygalacturonase gene expression in transgenic tomatoes", *Nature* 334:724-726 (1988).

Stam et al., "The Silence of Genes in Transgenic Plants", *Annals of Botany* 79(1):3-12 (1997).

Tamura et al., "Osmotic stress tolerance of transgenic tobacco expressing a gene encoding a membrane-located receptor-like protein from tobacco plants", *Plant Physiol.* 131(2):454-462 (2003).

Temple et al., "Down-regulation of specific members of the glutamine synthetase gene family in alfalfa by antisense RNA technology", *Plant Mol. Biol.* 37(3):535-547 (1998).

van der Krol, "Inhibition of flower pigmentation by antisense CHS genes: promoter and minimal sequence requirements for the antisense effect", *Plant Mol. Biol.* 14(4):457-466 (1990).

Waterhouse et al., "Virus resistance and gene silencing: Killing the messenger", *Trends Plant Sci.* 4(11):452-457 (1999).

Wang et al., Molecular tailoring of farnesylation for plant drought tolerance and yield protection, *Plant J.* 43(3):413-424 (2005).

Xu et al., "Effects of Epibrassinolide and Abscisic Acid on Sorghum Plants Growing under Soil Water Deficit", *Jpn. J. Crop. Sci.*, 63(4):671-675 (1994).

Yang et al., "Protein farnesyltransferase in plants. Molecular cloning and expression of a homolog of the beta subunit from garden pea", *Plant Physiol.* 101:667-674 (1993).

Zhou et al., "Developmental and environmental regulation of tissue-and cell-specific expression for a pea protein farnesyltransferase gene in transgenic plants", *Plant J.*, 12(4):921-930 (1997).

Ziegelhoffer et al., "Cloning of the *Arabidopsis* WIGGUM gene identifies a role for farnesylation in meristem development ", *PNAS*, 97(13)7633-7638 (2000).

* cited by examiner

```
        10         20         30         40         50         60
ATGGAGATTC AGCGAGATAA GCAATTGGAT TATCTGATGA AAGGCTTAAG GCAGCTTGGT
        70         80         90        100        110        120
CCGCAGTTTT CTTCCTTAGA TGCTAAGTAA GTGACATGAT GCTTGGCTTC TTGTTTTCAT
       130        140        150        160        170        180
GAATTTCTTA GTACATTTTG TCCAGTGAGA GAGTAAAGCT TTGGAGCTTT GCCAATAGAC
       190        200        210        220        230        240
TTAGAAGTTT GATTTTGGCT TTTTGGATTT TGGAACAGTC GACCTTGGCT TTGTTACTGG
       250        260        270        280        290        300
ATTCTTCATT CAATAGCTTT GCTTGGGGAG ACTGTGGATG ATGAATTAGA AAGCAATGCC
       310        320        330        340        350        360
ATTGACTTCC TTGGACGCTG CCAGGTTAGT CTCAATTCCT TTTGCTTGTA CCCAATCATG
       370        380        390        400        410        420
AAAACTCTTC ATATTTGCTC TTGCATTCTT CTTGATTTTC TGCTCCTTTA GTTCACGTTT
       430        440        450        460        470        480
TCTTTTCCCG TTGCTATTAG TGTTATCTGT TATTGTTCTT TATGTACTTA GTTTGCTTTC
       490        500        510        520        530        540
TCATGTCGCT TGTCAGGGCT CTGAAGGTGG ATACGGTGGT GGTCCTGGCC AAGTAAGTAT
       550        560        570        580        590        600
ATGTCTGTTT CTTTAAAGTG TGTGGATCAC TTTCATTTCA TGCAATTGGA GAATAAACAT
       610        620        630        640        650        660
TGAGACCAGA TTATTTTATT CTGCCAGATC TCTTTTAGGT GTTTTTTTTA TGCATCATCT
       670        680        690        700        710        720
CATTGTTTGG TTGTGATGCC TTTAATTCAA GCAGCACACG TAGTTTAAGT TTAAGTTTTT
       730        740        750        760        770        780
TTCTGTGAAG ACGTAAAATG GTGTCTTTAG TTCAAGCAGC ATTTAGTTGT TTAAGTTTGT
       790        800        810        820        830        840
GGTTGTAAAT TTTCCAAACA TGGCAGAGAA AGTTAGGATA TATAACTTTT GGTCTGCCTT
       850        860        870        880        890        900
TTTCAGTTTC CTTTTTTTTT CTACTAGTAA TGGAGATATT TTTTCCCAGC TTCCACATCT
       910        920        930        940        950        960
TGCAACTACT TATGCTGCAG TGAATGCACT TGTTACTTTA GGAGGTGACA AAGCCCTTTC
       970        980        990       1000       1010       1020
TTCAATTAAT AGGTGGTGCA TTCTTTTTTC TTTGTGGTCA GTTTCTTTTA TTAAGAGTCT
      1030       1040       1050       1060       1070       1080
AGTGATGTTT CCTCTAGAAT ACTTACATGT GACTCATTCT TCTTTCAGAG AAAAAATGTC
      1090       1100       1110       1120       1130       1140
TTGTTTTTTA AGACGGATGA AGGATACAAG TGGAGGTTTC AGGTTTGATT CTCTTTCTGC
      1150       1160       1170       1180       1190       1200
TTGAACTTCT TAAAGGCATC ATTTTTACTG ACAGCGCACT CTTTATGCAT TCGTATCGCT
      1210       1220       1230       1240       1250       1260
GTTAATGCCA TACCTTCAGT CATGTTGTTT TTTTAATTCT TGCTTAATTC TACTTACTCA
      1270       1280       1290       1300       1310       1320
CTGATCGTTA GGATGCATGA TATGGGAGAA ATTGATGTTC GTGCATGCTA CACTGCAATT
```

FIGURE 1A

| 1330 | 1340 | 1350 | 1360 | 1370 | 1380 |
|---|---|---|---|---|---|
| TCGGTGAGTT | TTACCAACTT | CTATTTTCCT | TTTCTCTGTT | TTTGTGGACA | CCAAAACTTT |
| 1390 | 1400 | 1410 | 1420 | 1430 | 1440 |
| TTAGGATTAA | TGAGATCAAC | AAAGTCTGGA | CCCATTATGC | TATGTTTCTT | CCGTTTTCAT |
| 1450 | 1460 | 1470 | 1480 | 1490 | 1500 |
| GGCTTAAACA | TCACATTCAG | ATTACGATAT | GATCTTATTA | TTTGCACACT | TGCGCCCACC |
| 1510 | 1520 | 1530 | 1540 | 1550 | 1560 |
| AGGATACTTT | GAATAGAGAT | TACTCGTTTT | GAGACTTACA | CGTCTTGCAA | ATGCATCCTA |
| 1570 | 1580 | 1590 | 1600 | 1610 | 1620 |
| TGGCTGGTTT | TCTCCCTGAT | ATGTTTGACT | TCTCTCTTGT | GACACAGGTT | GCAAGCATCC |
| 1630 | 1640 | 1650 | 1660 | 1670 | 1680 |
| TAAATATTAT | GGATGATGAA | CTCACCCAGG | GCCTAGGAGA | TTACATCTTG | AGGTAGCTTT |
| 1690 | 1700 | 1710 | 1720 | 1730 | 1740 |
| TCTTATTACT | TTTATCTCGC | ATTATATATA | TATAGCTGAA | CTACTGTTAT | ACAGTTGTAA |
| 1750 | 1760 | 1770 | 1780 | 1790 | 1800 |
| ATTCAGGAAT | TCATTAATTT | CCCTGGGAAA | GCTCTTTTAA | CTCGATTTAT | ATTGAGCAGT |
| 1810 | 1820 | 1830 | 1840 | 1850 | 1860 |
| TGCCAAACTT | ATGAAGGTGG | CATTGGAGGG | GAACCTGGCT | CCGAAGCTCA | CGGTGGGTAT |
| 1870 | 1880 | 1890 | 1900 | 1910 | 1920 |
| GGTCTCCAAC | TAACTTCCAT | TATGTTGAGG | CTTAGATAAA | AATTGTGCTT | TGCTTCCCTC |
| 1930 | 1940 | 1950 | 1960 | 1970 | 1980 |
| TTCCTTGATG | ACATGGTTAT | TGATGGTTAA | GTATAATTAA | TTTTCTGAAA | TAGGATTTGT |
| 1990 | 2000 | 2010 | 2020 | 2030 | 2040 |
| CACCTGCAGC | TTGCATGCCT | GCCGCTTTGC | TTATTACCAA | GTTGTTTTTT | GTTTAGGTAT |
| 2050 | 2060 | 2070 | 2080 | 2090 | 2100 |
| ACCTACTGTG | GTTTGGCTGC | TATGATTTTA | ATCAATGAGG | TCGACCCGTT | TGAATTTGGA |
| 2110 | 2120 | 2130 | 2140 | 2150 | 2160 |
| TTCATTAATG | GTAACATACA | ATGCTGTTTG | GAGATGATTA | ATAATTTTCC | CTGAGAGATA |
| 2170 | 2180 | 2190 | 2200 | 2210 | 2220 |
| TTTTCCTTAC | CAAATAATTT | CCTTATGATT | CTAGAATTGG | GCTGTACATC | GACAAGGAGT |
| 2230 | 2240 | 2250 | 2260 | 2270 | 2280 |
| AGAAATGGGA | TTTCAAGGTA | GGACGAACAA | ATTGGTCGAT | GGTTGCTACA | CATTTTGGCA |
| 2290 | 2300 | 2310 | 2320 | 2330 | 2340 |
| GGTTAACTTT | CTATCTTTCA | GGATTATTAT | TGGCCCTACT | TCTAAATTCT | TCACCGTTGT |
| 2350 | 2360 | 2370 | 2380 | 2390 | 2400 |
| TGTCTTTTCT | TATTTCCTTT | GGGTATATGT | TAAACAGGCA | GCCCCTTGTG | TTCTACTACA |
| 2410 | 2420 | 2430 | 2440 | 2450 | 2460 |
| AAGATTATAT | TCAACCAATG | ATCATGACGT | TCATGGATCA | TCACATATAT | CAGAAGGGAC |
| 2470 | 2480 | 2490 | 2500 | 2510 | 2520 |
| AAATGAAGAA | CATCATGCTC | ATGATGAAGA | TGACCTTGAA | GACAGTGATG | ATGATGATGA |
| 2530 | 2540 | 2550 | 2560 | 2570 | 2580 |
| TTCTGATGAG | GACAACGATG | AAGGTATTCA | ATCAAATTTC | TCAACCATCA | AGTCCATCTG |
| 2590 | 2600 | 2610 | 2620 | 2630 | 2640 |
| ATAATTCAAA | ACACAACGAA | ATTTTAGTTA | GCTTATATTT | GCAGATTCAG | TGAATGGTCA |

FIGURE 1B

```
      2650       2660       2670       2680       2690       2700
CAGAATCCAT CATACATCCA CCTACATTAA CAGGAGAATG CAACTGGTTT TTGATAGCCT
      2710       2720       2730       2740       2750       2760
CGG?TTGCAG AGATATGTAC TCTTGTGCTC TAAGGTCAGT CCAGAACAAA ACATCCAGTC
      2770       2780       2790       2800       2810       2820
AAGTTAACAC TTAACATTTG TATAACACAA GCACACACAC TTGTATGCGC AGATCCCTGA
      2830       2840       2850       2860       2870       2880
CGGTGGATTC AGAGACAAGC CGAGGAAACC CCGTGACTTC TACCACACAT GTTACTGCCT
      2890       2900       2910       2920       2930       2940
GAGCGGCTTG TCTGTGGCTC AGCACGCTTG GTTAAAAGAC GAGGACACTC CTCCTTTGAC
      2950       2960       2970       2980       2990       3000
TCGCGACATT ATGGGTGGCT ACTCGAATCT CCTTGAACCT GTTCAACTTC TTCACAACAT
      3010       3020       3030       3040       3050       3060
TGTCATGGAT CAGTATAATG AAGCTATCGA GTTCTTCTTT AAAGCAGCAT GACCCGTTGT
      3070       3080       3090       3100       3110       3120
TGCTAATGTA TGGGAAACCC CAAACATAAG AGTTTCCGTA GTGTTGTAAC TTGTAAGATT
      3130       3140       3150       3160       3170       3180
TCAAAAGAAG TTTCACTAAT TTAACCTTAA AACCTGTTAC TTTTTATTAC GTATA.....
```

FIGURE 1C

MEIQRDKQLDYLMKGLRQLGPQFSSLDANRPWLCYWILHSIAL
LGETVDDELESNAIDFLGRCQGSEGGYGGGPGQLPHLA
TTYAAVNALVTLGGDKALSSINREKMSCFLRRMKDTSGGFR
MHDMGEIDVRACYTAISVASILNIMDDELTQGLGDYILS
CQTYEGGIGGEPGSEAHGGYTYCGLAAMILINEVDRLNLDSL
MNWAVHRQGVEMGFQGRTNKLVDGCYTFWQAAPCVLLQ
RLYSTNDHDVHGSSHISEGTNEEHHAHDEDDLEDSDDDDDSDE
DNDEDSVNGHRIHHTSTYINRRMQLVFDSLGLQRYVL
LCSEIPDGGFRDKPRKPRDFYHACYCLSGLSVAQHAWLKDED
TPPLTRDIMGGYSNLLEPVQLLHNIVMDQYNEAIEFFF
KAA

FIGURE 2

```
        10         20         30         40         50         60
CTCACTCATT AGCACCCCAG CTTTACACTT TATGCTTCCG CTCGTATGTT GTGTGGAATT
        70         80         90        100        110        120
GTGAGCGATA ACAATTTC?A CACAGGAAAC AGCTATGACA TGATTACGAA TTCAAAAAAA
       130        140        150        160        170        180
TAGAGATTGG CAATATTTTA GTGTGTGAAT AATATTCATC CCTAAAAAGA AGTCATCTTT
       190        200        210        220        230        240
CGACTTTGTG GCAACAGTTC TGTTATTAAA ATGTGTGAGC GTGACATATT TTGAAGAGGT
       250        260        270        280        290        300
ACCTCGACAA AATCGGAAGG TGTCTCATTT TCTTCTATCG GAAGGCTTTC TCGTTGAAGG
       310        320        330        340        350        360
TAGTCGTTGT AGCTGAAAAA TTAAGAAAAC CTAGTGAGCT CTTCATGTAT TCAAAAATTC
       370        380        390        400        410        420
AACCAGTGTA ATCAAACTCA AGAGGTAAAT AGTTAAAATC CCATACCAAA CCGTGTAATC
       430        440        450        460        470        480
TATGCAATAC CTAATTAACA AAGTTAAAAG CGTTAGTCTA GCAGTAATAT TGTATCAAAA
       490        500        510        520        530        540
GCTCTAACAG TAATTAATAA CCAGTGTCAC CAGAAACAAA TGTCAATAAC ATGGAAAATT
       550        560        570        580        590        600
GAATTTAGTT GAGTCCTGGA GGTCGTGGAC GTCGTGGAGG CTGTGGACGT CGTGAATACG
       610        620        630        640        650        660
CATAAAGAAA AATCTTATAA TCGTGCAAAT ATTCACCGTT CTTCTTATAC ATCACCTACG
       670        680        690        700        710        720
GTAATAAAAG AGTTTTATTT CAGCAATCGT ACATTCAAAT TGAAACTTAG ATACACTATA
       730        740        750        760        770        780
TATTTTTCAT CATAACTAAC TATAAACTAG TCTAAACCTT TTTTGCTTCG TTAGCAGAAG
       790        800        810        820        830        840
CAAAGTCAAC AGGCCATAGC ACCTATGGAT ACGCTTGGCG GTTACAAAAA GTCGAACACG
       850        860        870        880        890        900
AACAACTTCT CCAGCATCTT TGAAGAAATT GATGCTGTAA CAAACAGTGT AAGGTAAAAA
       910        920        930        940        950        960
TATCAGTCAT GCTCAGAGAA GGAAAGTGGA GATTGAAGAT GGTGCTACTT ACATATCTGA
       970        980        990       1000       1010       1020
TATTTTAGTT TGGGGAGGGA TATGGCCATT AAAGA?CGTC TTTTTTGTCA CCTGGATTTA
      1030       1040       1050       1060       1070       1080
ACAGCCAAGT GTGTTAGCAC AAGATTCTTA ATTGAACAGA AATTTGTACA AAATATCTAG
      1090       1100       1110       1120       1130       1140
CAAATCCGTT GGTTGTTTCC TCCTGTTACA TATGATACAA GATCAAAGAG TAGCCATTAG
      1150       1160       1170       1180       1190       1200
AAGAAGACAG TG?AAAGAAG ATTGTTTTGT CAAAGAAGAA GAGTAATACG AGGCCATCTT
      1210       1220       1230       1240       1250       1260
AGGGTTACCT TATTCTACTT ATGTCTCTTG AGAATGGAAT TGGTCACCAA ATCATCTTCT
      1270       1280       1290       1300       1310       1320
TCAGGGTTAC GCTTACCTAA AAGAAGAGCA ACAA??AAAA AACTCTTGAG ACAAGTTTAA
```

FIGURE 3A

```
      1330       1340       1350       1360       1370       1380
CACATTAGAT AAAAGAGAGA GAGAGAGAGG CAACCAAAAA CAAACCCAAT AAATTGCTAC
      1390       1400       1410       1420       1430       1440
TAGAAGTGGC CATGGAGAAG ATGAAACGAG GTTTATGTAT TTTTCCGTTA AGAGCAAGCA
      1450       1460       1470       1480       1490       1500
ATAATATAGC CCTAAAGAAA TATAGACCTA GCCTAGGAAG AAGTTTCTAA GACCATCCTT
      1510       1520       1530       1540       1550       1560
ATCAATGAAC TCTTACATAA AGTTCTAAAC AATTTTGATA TACAAAATAA TGTTTAAACA
      1570       1580       1590       1600       1610       1620
TTAGAATGGC TCTTACAAAA AAAGAGAATA AAGAAAAAAA AAACTTAGCT AAGAGCCATT
      1630       1640       1650       1660       1670       1680
TTTCATTTCT TAAGCACACT TTTTTATTTT TTTATTCTTA TTTTATTTAA TATAATATTT
      1690       1700       1710       1720       1730       1740
TGATAGTTCT TATGATATTG TTAACAACCT ATTGATAAGG ATGCTCTAAC TAATCTTATA
      1750       1760       1770       1780       1790       1800
AATAAAACAA TGAATCTGGT TTGGTCTGGG CGTAACAG?A ATTATACTCT TTTTTTTTTT
      1810       1820       1830       1840       1850       1860
TGTCAAGAGG AAATTATACT AAGAAGCAAC AGATTAAACA TTAAAGCGTA TAGTAAAATT
      1870       1880       1890       1900       1910       1920
AATTGTTTGA GAATCTTAAA CCAAACCGAA CCGGTATTAA ACCGGAACCA AATTGGCAAT
      1930       1940       1950       1960       1970       1980
GAAATTTAGA TGCCAGTAGT AACCCGCTTG ATTCGTTTGA AGTGTGTAGG GCTCAGACTT
      1990       2000       2010       2020       2030       2040
GACCGGAGTG GACTCAATCG GCGAATCTGT CACGGAGGAC ACGGGGAATC AACGCGGCGG
      2050       2060       2070       2080       2090       2100
AGAGTGATGG AAGAGTTTTC AAGCCTAACC GTGAGTCAGC GCGAGCAATT TCTGGTGGAG
      2110      21200       2130       2140       2150       2160
AACGATGTGT TCGGGATCTA TAATTACTTC GACGCCAGCG ACGTTTCTAC TCAAAAATAC
      2170       2180       2190       2200       2210       2220
ATGTAAGCTG ACGGATTGAT TTTCTAGTTT TCTTCATGAT CTGATGAATT TTAGTAGCGT
      2230       2240       2250       2260       2270       2280
CGTGAAAGAA TTATTTTCGT CGATAGATGA ATCTTACTGA TATGGAAGTT GTTCTATCCT
      2290       2300       2310       2320       2330       2340
AGGATG ... .......... .......... .......... .......... ..........
   └-First Codon
```

FIGURE 3B

```
                                                               29
Arab.   MEIQRDKQLD YLMKGLRQLG PQFSSLDAN- ---------- ----------
Pea     ..ASTAAETP TPTVSQ.DQW IVE.QVFHIY QLFANIPPNA QSII------
Yeast   .RQRVGRSIA RAKFINTA.L GRKRPVMERV VDIAHVDSSK AIQPLMKELE
Rat     .ASSSSFTYY CPPSSSPVWS EPLY..RPEH ARERLQDDSV ETVTSIEQAK

Arab.   ---------- ---------- ---------- ---------- ----------
Pea     ---------- ---------- ---------- ---------- ----------
Yeast   TDTTEARYKV LQSVLEIYDD EKNIEPALTK EFHKMYLDVA FEISLPPQMT
Rat     VEEKIQEVFS SYKFNHLVPR LVLQREKHFH YLKRGLRQ-- ----LTDAYE
                                                               73
Arab.   -----RPWLC YWILHSIALL G-ETVDDELE SNAIDFLGRC QGSEGGYGGG
Pea     -----..... ...I...... .-.SI..D.. D.TV...N.. .DPN...A..
Yeast   ALDASQ..ML ...AN.LKVM DRDWLS.DTK RKIV.K.FTI SP.G.PF...
Rat     CLDAS..... ......LE.. D-.PIPQIVA TDVCQ..EL. .SPD..F...
                                                              122
Arab.   PGQLPHLATT YAAVNALVTL GGDKALSS-I NREKMSCFLR RMKDTSGG.R
Pea     ...M...... .....T.I.. ..E.S.A.-. ..N.LYG.M. ...QPN....
Yeast   ....S...S. ...I...SLC DNIDGCWDR. D.KGIYQW.I SL.EPN...K
Rat     ...Y....P. .......CII .TEE.YNV-. ....LLQY.Y SL.QPD.S.L
                                                              171
Arab.   -MHDMGEIDV RACYTAISVA SILNIMDDEL TQGLGDYILS CQTYEGGIGG
Pea     -...E..... .......... .V...L.... IKNV..F... .......LA.
Yeast   TCLEV..V.T .GI.C.L.I. TL...LTE.. .E.VLN.LKN ..N....F.S
Rat     -..VG..V.. .SA.C.A... .LT..ITPD. FE.TAEW.AR ..NW......
                                                              218
Arab.   EP-GSEAHGG YTYCGL.AM- ILINEVDRLN LDSLMNWAVH RQGV-EMGFQ
Pea     ..-....... ..F......- ...G..N..D .PR.LD.V.F ...K-.C...
Yeast   C.HVD..... ..F.AT.SLA ..RSM-.QI. VEK.LE.SSA ..LQE.R..C
Rat     V.-.M..... ..F.....LV ..KK.-RS.. .K..LQ.VTS ..MRF.G...
                                                              267
Arab.   GRTNKLVDGC YTFWQAAPCV LLQR-LYSTN DHDVHGSSHI SEGTNEEHHA
Pea     .......... .S...GGAVA ....-.H.II .EQMAEA.QF VTVSDAPEEK
Yeast   ..S....... .S..VGGSAA I.EAFG.GQC ---------- ----------
Rat     ..C....... .S....GLLP ..H.A.HAQG .PALSM.--- ----------
                                                              316
Arab.   HDEDDLEDSD DDDDSDEDND EDSVNGHRIH HTSTYINRRM -QLVFDSLGL
Pea     ECL.GTSSHA TSHIRH.GMN .SCSSDVKNI GYNFISEW.Q SEPL.H.IA.
Yeast   ---------- ---------- ---------- ---------- ----.NKHA.
Rat     ---------- ---------- ---------- ---------- -HWM.HQQA.
                                                              364
Arab.   QRYVLLCSKI -PDGGFRDKP RKPRDFYHTC YCLSGLSVAQ HAWLKDE-DT
Pea     .Q.I....QE -Q...L.... G.R..H..S. .......LC. YS.S.RP-.S
Yeast   RD.I.Y.CQE KEQP.L.... GAHS.....N ...L..A..E SSYSCTPN.S
Rat     .E.I.M.CQC -.A..LL... G.S....... .......I.. -----HFGSG
                                                              404
Arab.   PPLTRDIMGG YSNLLEPVQL LHNIVMDQYN EAIEFFFKAA ----------
Pea     ...PKVV..P .......IHP .F.V.L.R.R ..H...SQL- ----------
Yeast   .HNIKCTPDR LIGSSKLTDV NPVYGLPIE. VRKIIHYFKS NLSSPS----
Rat     AM.HDVV..V PE.V.Q.THP VY..GP.KVI Q.TTH.LQKP VPGFEECEDA

Arab.   ----------
Pea     ----------
Yeast   ----------
Rat     VTSDPATD--
```

FIGURE 4

Wild-type Columbia eral-2 mutant

Day 0

Wild-type Columbia eral-2 mutant

Day 3

Wild-type Columbia eral-2 mutant

Day 6

Wild-type Columbia eral-2 mutant

Day 9

Wild-type Columbia eral-2 mutant

Day 12

Wild-type *eral-2*
Day After Bolting 0 4 8 0 4 8
FIG.9A CAB
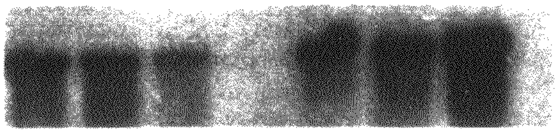
Wild-type *eral-2*
Day After Bolting 0 4 8 0 4 8
FIG.9B SAG12
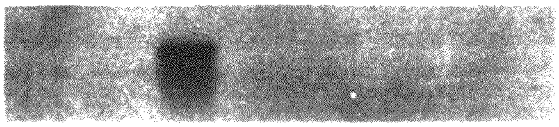
Wild-type *eral-2*
Day After Bolting 0 4 8 0 4 8
FIG.9C SAG13
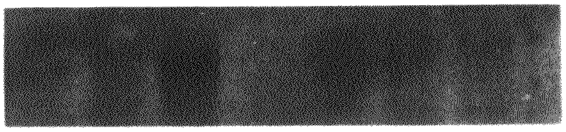

NO ABA

WT ERA1 9 21

1 μM ABA

WT ERA1 9 21

| DNA | Brassica napus | Arabidopsis thaliana | PPI Glycine max | Zea mays | Rice | Soy 1 | Soy 2 | Triticum | Tomato | Pea |
|---|---|---|---|---|---|---|---|---|---|---|
| Brassica napus | X | | | | | | | | | |
| Arabidopsis thaliana | 89 | X | | | | | | | | |
| PPI Glycine max | 61 | 55 | X | | | | | | | |
| Zea mays | 57 | 45 | 52 | X | | | | | | |
| Rice | 55 | 46 | 54 | 63 | X | | | | | |
| Soy 1 | 61 | 50 | 98 | 43 | 47 | X | | | | |
| Soy 2 | 61 | 50 | 99 | 41 | 46 | 99 | X | | | |
| Triticum | 58 | 45 | 52 | 56 | 66 | 43 | 41 | X | | |
| Tomato | 65 | 53 | 63 | 44 | 51 | 52 | 49 | 41 | X | |
| Pea | 66 | 55 | 78 | 46 | 50 | 70 | 69 | 44 | 49 | X |
| | | | | | | | | | | |
| | | | | | | | | | | |
| **PROTEIN** | Brassica napus | Arabidopsis thaliana | PPI Glycine max | Pea | Tomato | Rice | Zea mays | Soy 1 | Soy 2 | Triticum |
| Brassica napus | X | | | | | | | | | |
| Arabidopsis thaliana | 89 | X | | | | | | | | |
| PPI Glycine max | 65 | 63 | X | | | | | | | |
| Pea | 61 | 61 | 77 | X | | | | | | |
| Tomato | 60 | 59 | 57 | 58 | X | | | | | |
| Rice | 64 | 63 | 56 | 58 | 58 | X | | | | |
| Zea mays | 61 | 56 | 58 | 57 | 56 | 75 | X | | | |
| Soy 1 | 66 | 64 | 98 | 77 | 58 | 57 | 58 | X | | |
| Soy 2 | 66 | 64 | 98 | 78 | 58 | 57 | 58 | 99 | X | |
| Triticum | 61 | 60 | 57 | 59 | 60 | 80 | 73 | 58 | 58 | X |

Fig. 17

| DNA | Brassica napus | Arabidopsis thaliana | Wiggum | PPI Glycine max | Glycine max | PPI Zea maize | Zea maize | Pea | Tomato | Tobacco |
|---|---|---|---|---|---|---|---|---|---|---|
| Brassica napus | X | | | | | | | | | |
| Arabidopsis thaliana | 88 | X | | | | | | | | |
| Wiggum | 88 | 99 | X | | | | | | | |
| PPI Glycine max | 60 | 64 | 65 | X | | | | | | |
| Glycine max | 60 | 64 | 65 | 99 | X | | | | | |
| PPI Zea maize | 38 | 54 | 59 | 63 | 63 | X | | | | |
| Zea maize | 54 | 54 | 59 | 62 | 62 | 99 | X | | | |
| Pea | 65 | 57 | 45 | 78 | 77 | 56 | 56 | X | | |
| Tomato | 68 | 62 | 52 | 70 | 70 | 64 | 64 | 51 | X | |
| Tobacco | 68 | 64 | 60 | 71 | 71 | 65 | 65 | 55 | 83 | X |
| | | | | | | | | | | |
| | | | | | | | | | | |
| **PROTEIN** | Brassica napus | Arabidopsis thaliana | Wiggum | PPI Glycine max | Glycine max | PPI Zea maize | Zea maize | Pea | Tomato | Tobacco |
| Brassica napus | X | | | | | | | | | |
| Arabidopsis thaliana | 84 | X | | | | | | | | |
| Wiggum | 84 | 99 | X | | | | | | | |
| PPI Glycine max | 54 | 58 | 59 | X | | | | | | |
| Glycine max | 53 | 58 | 58 | 99 | X | | | | | |
| PPI Zea maize | 52 | 50 | 52 | 58 | 58 | X | | | | |
| Zea maize | 51 | 50 | 52 | 58 | 58 | 99 | X | | | |
| Pea | 58 | 56 | 57 | 78 | 78 | 56 | 56 | X | | |
| Tomato | 60 | 62 | 55 | 63 | 63 | 58 | 58 | 62 | X | |
| Tobacco | 62 | 63 | 59 | 64 | 63 | 58 | 58 | 64 | 83 | X |

Fig. 18

| Nucleic Acid | PPI-AtCPP | PPI-BnCPP | PPI-SoyCPP | BASF-AT1 | BASF-AT2 | BASF-Corn | BASF-Soy | AFC1 | AT4g01320 | AF007269 |
|---|---|---|---|---|---|---|---|---|---|---|
| PPI-AtCPP | X | | | | | | | | | |
| PPI-BnCPP | 92 | X | | | | | | | | |
| PPI-SoyCPP | 76 | 77 | X | | | | | | | |
| BASF-AT1 | 98 | 93 | 76 | X | | | | | | |
| BASF-AT2 | 99 | 93 | 76 | 99 | X | | | | | |
| BASF-Corn | 57 | 57 | 57 | 57 | 57 | X | | | | |
| BASF-Soy | 72 | 72 | 93 | 72 | 72 | 52 | X | | | |
| AFC1 | 99 | 93 | 77 | 99 | 99 | 57 | 72 | X | | |
| AT4g01320 | 99 | 92 | 70 | 99 | 99 | 50 | 64 | 99 | X | |
| AF007269 | 97 | 91 | 10 | 97 | 97 | 13 | 8 | 97 | 97 | X |

Fig. 26A

| Amino Acid | PPI-AtCPP | PPI-BnCPP | PPI-SoyCPP | BASF-AT1 | BASF-AT2 | BASF-Corn | BASF-Soy | AFC1 | AT4g01320 | AF007269 |
|---|---|---|---|---|---|---|---|---|---|---|
| PPI-AtCPP | X | | | | | | | | | |
| PPI-BnCPP | 94 | X | | | | | | | | |
| PPI-SoyCPP | 83 | 83 | X | | | | | | | |
| BASF-AT1 | 98 | 95 | 83 | X | | | | | | |
| BASF-AT2 | 99 | 95 | 83 | 99 | X | | | | | |
| BASF-Corn | 82 | 82 | 79 | 82 | 82 | X | | | | |
| BASF-Soy | 83 | 83 | 99 | 83 | 83 | 73 | X | | | |
| AFC1 | 98 | 95 | 83 | 99 | 99 | 82 | 83 | X | | |
| AT4g01320 | 95 | 93 | 82 | 96 | 96 | 72 | 76 | 96 | X | |
| AF007269 | 98 | 94 | 82 | 98 | 99 | 82 | 82 | 98 | 100 | X |

Fig. 26B

STRESS TOLERANCE AND DELAYED SENESCENCE IN PLANTS

RELATED APPLICATION

This application is a Continuation of U.S. Ser. No. 11/229,371, filed Sep. 16, 2005, which in turn is a Continuation of U.S. Ser. No. 10/229,541, filed Aug. 27, 2002, which in turn is a Continuation-in-Part of U.S. Ser. No. 10/160,764, filed May 31, 2002, which claims the benefit of U.S. Ser. No. 60/294,766, filed May 31, 2001 and U.S. Ser. No. 60/348,909, filed Oct. 22, 2001; this application is also a Continuation-in-Part of U.S. Ser. No. 10/210,760, filed Aug. 1, 2002, which claims the benefit of U.S. Ser. No. 60/309,396, filed Aug. 1, 2001 and U.S. Ser. No. 60/337,084, filed Dec. 4, 2001; this application is also a Continuation-in-Part of U.S. Ser. No. 09/191,687, filed Nov. 13, 1998, which in turn is a Continuation-in-Part of PCT Application No. PCT/US98/15664, filed Jul. 29, 1998, and a Continuation-in-Part of U.S. Ser. No. 09/124,867, filed Jul. 30, 1998, both of which claim the benefit of U.S. Provisional Application No. 60/054,474, filed Aug. 1, 1997. The contents of each of these applications are incorporated herein by reference in their entireties.

BACKGROUND OF THE INVENTION

Most higher plants encounter at least transient decreases in relative water content at some stage of their life cycle and, as a result, have evolved a number of desiccation protection mechanisms. If however, the change in water deficit is prolonged the effects on the plant's growth and development can be profound. Decreased water content due to drought, cold or salt stresses can irreparably damage plant cells which in turn limits plant growth and crop productivity in agriculture.

Plants respond to adverse conditions of drought, salinity and cold with a variety of morphological and physiological changes. Although our understanding of plant tolerance mechanisms to these stresses is fragmentary, the plant hormone abscisic acid (ABA) has been proposed to be an essential mediator between environmental stimulus and plant responses. ABA levels increase in response to water deficits and exogenously applied ABA mimics many of the responses normally induced by water stress. Once ABA is synthesized it causes the closure of the leaf stomata thereby decreasing water loss through transpiration.

The identification of genes that transduce ABA into a cellular response opens the possibility of exploiting these regulators to enhance desiccation tolerance in crop species. In principle, these ABA signaling genes can be coupled with the appropriate controlling elements to allow optimal plant growth and development. Thus, not only would these genes allow the genetic tailoring of crops to withstand transitory environmental insults, they should also broaden the environments where traditional crops can be grown.

In addition, little is known of the genetic mechanisms which control plant growth and development. Genes which further affect other metabolic processes such as senescence and growth habits of plants can be useful in a wide variety of crop and horticultural plants.

SUMMARY OF THE INVENTION

This invention relates to isolated nucleic acids which encode a farnesyl transferase comprising SEQ ID NO:1 or SEQ ID NO:172. Nucleic acids also encompassed by this invention are such hybridizing sequences which encode the functional equivalent or fragment thereof of SEQ ID NO:1 or SEQ ID NO:172. The present invention also relates to a method for enhancing the drought tolerance of plants using inhibitors of the products encoded by these nucleic acids. Further, this invention relates to the control of regulatory functions in photosynthetic organisms; for example, in the control of growth habit, flowering, seed production, seed germination, and senescence in such organisms.

This invention also relates to a method for enhancing the drought or stress tolerance of plants by means of alterations in isolated or recombinant nucleic acids encoding a farnesyl transferase (Ftase) protein or fragment thereof or its functional equivalent. Nucleic acids which hybridize to the Ftase-encoding gene (ERA1) are also encompassed by this invention when such hybridizing sequences encode the functional equivalent of the Ftase protein. The present invention also relates to a method for enhancing the drought tolerance of plants through the genetic manipulation of ERA1 gene and its functional equivalents to improve stress tolerance in crop plants. Loss of ERA1 gene function confers enhanced tolerance to drought at the level of the mature plant. The nature of an era1 mutant with loss of Ftase activity, for example, demonstrates that inhibition of farnesylation enhances ABA responses in a plant.

Further, this invention relates to inhibition of senescence in photosynthetic organisms through inhibition of farnesyl transferase activity. The resulting photosynthetic organisms stay green and tissue viability is maintained for a longer period of time. Thus, methods to provide greener plants and a reduction in senescence are part of this invention.

In yet another embodiment, methods are provided to modify the growth habit and flower induction of plants. Loss of ERA1 gene function under particular environmental conditions results in a reduction in the number of lateral branches produced on a plant and an increase in the number of flowers per inflorescence.

The invention also provides method of producing a transgenic plant, which has an altered phenotype such as increased tolerance to stress (e.g., water deficit, increased biomass, increased yield), delayed senescence or increased ABA sensitivity by introducing into a plant cell a compound that inhibits farnesylation of a polypeptide comprising a CaaX motif. By inhibit farnesylation is meant to include that the compound inhibits one or more steps in the three step process of farnesylation. In one aspect the compound inhibits farnesyltransferase, prenylprotease or prenylcysteine carboxyl methyltransferase expression or activity. Alternatively, the compound is an anti-sense farnesyl transferase nucleic acid or a farnesyl transferase double stranded RNA-inhibition hair pin nucleic acid. In some aspects the nucleic acid is operably linked to a promoter such as a constitutive promoter, an ABA inducible promoter, tissue specific promoters or a guard cell-specific promoter.

Exemplary anti-sense nucleic acids are 20 or more consecutive nucleic acids complementary to SEQ ID NO: 1, 14, 40, 43, 80-85 or 172. Alternatively the anti-sense nucleic acids include SEQ ID NO: 36, 41, 44 or 54-64.

In various aspects the compound is a nucleic acid encoding a farnesyltransferase, prenylprotease or prenylcysteine carboxyl methyltransferase polypeptide of fragment thereof. Alternatively, the compound is a nucleic acid encoding a mutated farnesyltransferase, prenylprotease or prenylcysteine carboxyl methyltransferase polypeptide of fragment thereof. By mutated is meant that the polypeptide lacks at least one activity of the wild type polypeptide such as for example, subunit interaction, substrate binding or enzyme catalysis. A mutated polypeptide forms a dimer, such as a heterodimer. For example, a mutated farnesyltransferase beta polypeptide forms a dimer with a farnesyltransferase alpha polypeptide. Preferably, the polypeptide is less than 400, 350, 314, 300 or 200 amino acids in length. For example, the compound includes SEQ ID NO: 1, 14, 40, 43, 80-85 or 172.

In a further aspect the compound is a nucleic acid encoding a CaaX motif or a nucleic acid encoding a CaaX motif operably linked to a promoter.

Also included in the invention are the plants produced by the methods of the invention and the seed produced by the plants which produce a plant that has an altered phenotype.

This invention also relates to a regulatory sequence useful for genetic engineering of plant cells to provide a method of controlling the tissue pattern of expression of DNA sequences linked to this novel regulatory sequence.

BRIEF DESCRIPTION OF THE DRAWINGS

FIGS. 1A-1C show the nucleic acid sequence of the ERA1 gene (SEQ ID NO: 1) in which the introns are underlined and the start codon (ATG) is at nucleotide positions 1-3.

FIG. 2 is the amino acid sequence of the ERA1 protein (SEQ ID NO:2).

FIGS. 3A-3B show the nucleic acid sequence of the ERA1 promoter (SEQ ID NO:3).

FIG. 4 is the amino acid sequence of the β subunit farnesylation domain from *Arabidopsis* (Arab.) (SEQ ID NO:2) aligned with the β subunit farnesylation domains from pea (SEQ ID NO:4), yeast (SEQ ID NO:5) and rat (SEQ ID NO:6). Residues that are identical to the *Arabidopsis* sequence are indicated with a dot. A dash indicates a blank. The amino acid positions of the *Arabidopsis* gene are indicated on the right-hand side.

FIGS. 9A-9C are comparisons of transcript levels in aging leaves from control (wild-type) and era-2 mutant plants.

FIG. 17 is an illustration of the homology among FTA nucleic acid (A) and amino acid (B) sequences from various plant species based on ClustalW analysis (percent identity shown).

FIG. 18 is an illustration of the homology among FTB nucleic acid and amino acid sequences from various plant species based on ClustalW analysis (percent identity shown).

FIG. 26 is an illustration of (A) nucleic acid and (B) amino acid sequence identities as determined by ClustalW analysis.

DETAILED DESCRIPTION OF THE INVENTION

Figure 5:
FIG. 5 is a photograph of an era1-transformed *Arabidopsis* plant (right) compared to the wild-type (control; i.e., naturally-occurring) plant (left) under extremely dry conditions.

This invention relates to transgenic plants that display an altered phenotype, e.g., increased tolerance to stress, delayed senescence, increased ABA sensitivity, increased yield, increased productivity and increased biomass and methods of producing the plants by introducing to a plant cell a compound that inhibits farnesylation of a polypeptide comprising a CaaX motif Protein farnesylation, the addition of a C-terminal, 15 carbon chain to protein and subsequent processing is a three step enzymatic reaction including farnesylation, proteolytic cleavage and methylation. First, a farnesyltransferase adds the C-terminal 15 carbon chain to a conserved cysteine residue of the CaaX terminal motif, where "C" is a cysteine, "a" is an aliphatic amino acid and "X" is any amino acid. Second, the last three amino acid residues (aaX) are cleaved by a prenyl protease. Lastly, the modified cysteine is methylated by a methylase to create the final active product of the protein farnesylation pathway. The Applicants have shown that over-expression and down-regulation of the alpha or the beta farnesyl transferase gene in plant cells (i.e., the first step in farnesylation) results in plants with an altered phenotype such as but not limited to drought tolerance and delayed senescence. Applicants have also shown that over-expression and down-regulation of the prenyl protease gene (i.e., the second step in farnesylation) in plant cells also results in a plant displaying an altered phenotype including for example but not limited to drought tolerance and increased resistance to biotic and abiotic stress. These results taken together support the hypothesis that modification of the expression of any of the enzymes in the farnesylation pathway (farnesyltransferase, prenylprotease or prenylcysteine carboxyl methyltransferase in a plant cell will result in a plant displaying an altered phenotype.

The present invention also provides novel farnesyltransferase (i.e., alpha and beta) (Ftase) and CaaX prenyl protease (CPP) nucleic acid sequences isolated from for example *Arabidopsis thaliana* (At), *Brassica napus* (Bn) and *Glycine Max* (Gm). The invention also provides farnesyltransferase and CaaX prenyl protease antisense nucleic acids and constructs comprising these nucleic acids. The sequences are collectively referred to as "PPI nucleic acids", "PPI polynucleotides" or "PPI antisense nucleic acids" and the corresponding encoded polypeptide is referred to as a "PPI polypeptide" or "PPI protein". Unless indicated otherwise, "PPI" is meant to refer to any of the novel sequences disclosed herein. Table A below summarizes the nucleic acids and polypeptides according to the invention.

TABLE A

| PPI Sequence Description | SEQ ID NO: |
|---|---|
| era1 (FTB) | 1 |
| era1 (FTB) | 2 |
| ERa1 promoter | 3 |
| FTB pea | 4 |
| FTB yeast | 5 |
| FTB rat | 6 |
| At FTA | 7 |
| At FTA | 8 |
| At FTA | 9 |
| pBI121-35S-anti-AtFTA | 10 |
| At FTA | 11 |
| Bn FTA | 12 |
| Bn FTA | 13 |
| Bn FTB | 14 |
| Bn FTB | 15 |
| primer | 16 |
| primer | 17 |
| primer | 18 |
| primer | 19 |
| primer | 20 |
| primer | 21 |
| primer | 22 |
| primer | 23 |
| primer | 24 |
| primer | 25 |
| primer | 26 |
| primer | 27 |
| primer | 28 |
| primer | 29 |
| primer | 30 |
| primer | 31 |
| primer | 32 |
| primer | 33 |
| primer | 34 |
| Bn FTA | 35 |
| Bn FTB | 36 |
| G max FTA | 37 |
| G max FTA | 38 |
| G max FTA | 39 |
| G max FTB | 40 |
| G max FTB | 41 |
| G max FTB | 42 |
| Zea maize FTB | 43 |
| Zea maize FTB | 44 |
| Zea maize FTB | 45 |
| pBI121-35S-AtFTA | 46 |
| pBI121-rd29A-anti-AtFTA | 47 |
| pBI121-35S-DA-AtFTA | 48 |
| pBI121-RD29A-DA-AtFTA | 49 |
| MuA-anti-GmFTA | 50 |
| RD29A-anti-GmFTA | 51 |
| MuA-HP-GmFTA-Nos-Term | 52 |
| RD29AP-HP-GmFTA-Nos-Term | 53 |
| pBI121-35S-Anti-AtFTB | 54 |
| pBI121-RD29AP-Anti-AtFTB | 55 |
| pBI121-35S-HP-AtFTB | 56 |
| pBI121-RD29AP-HP-AtFTB | 57 |
| pBI121-35S-AtFTB | 58 |
| MuA-anti-GmFTB-Nos-Term | 59 |
| RD29AP-anti-GmFTB-Nos-Term | 60 |
| MuA-HP-GmFTB-Nos-Term | 61 |
| RD29AP-HP-GmFTB-Nos-Term | 62 |
| MuA-anti-Zea maizeFTB-Nos-Term | 63 |
| MuA-HP-Zea maizeFTB-Nos-Term | 64 |

TABLE A-continued

| PPI Sequence Description | SEQ ID NO: |
|---|---|
| Pea-FT-A | 65 |
| Tomato-FTA | 66 |
| Rice-FT-A | 67 |
| Zea mays-FT-A | 68 |
| Soy1-Ft-A | 69 |
| Soy2-FT-A | 70 |
| Triticum-FT-A | 71 |
| Pea-FT-A | 72 |
| Tomato-FTA | 73 |
| Rice-FT-A | 74 |
| Zea mays-FT-A | 75 |
| Soy1-Ft-A | 76 |
| Soy2-FT-A | 77 |
| Triticum-FT-A | 78 |
| N90AtFTB truncated FTB vector | 79 |
| Wiggum (FTB) | 80 |
| Dup-Soy-FTB | 81 |
| Dup-Corn-FTB | 82 |
| Pea-FT-B | 83 |
| Tomato-FTB | 84 |
| Tobacco-FTB | 85 |
| Primer SacI forward | 86 |
| Wiggum (FTB) | 87 |
| Dup-Soy-FTB | 88 |
| Dup-Corn-FTB | 89 |
| Pea-FT-B | 90 |
| Tomato-FTB | 91 |
| Tobacco-FTB | 92 |
| Consensus FTA | 93 |
| Consensus FTB | 94 |
| Consensus FTA | 95 |
| Consensus FTB | 96 |
| AtCPP | 97 |
| AtCPP | 98 |
| At-AFC1 | |
| pBI121-AtCPP | 99 |
| pBI121-HP-AtCPP | 100 |
| AtCPP BamFW | 101 |
| AtCPP SmaRV | 102 |
| AtCPP-HP-SacFW | 103 |
| AtCPP-HP-SacRV | 104 |
| pBI121-AtCPP Forward | 105 |
| pBI121-antiAtCPP-SmaFW | 106 |
| pBI121-antiAtCPP-BamRV | 107 |
| p35S-HP-AtCPP Reverse | 108 |
| BnCPP | 109 |
| BnCPP | 110 |
| BnCPP antisense | 111 |
| GmCPP | 112 |
| GmCPP | 113 |
| GmCPP antisense | 114 |
| AtCPP antisense | 115 |
| BASF-AT1 | 116 |
| BASF-AT1 | 117 |
| BASF-AT2 | 118 |
| BASF-AT2 | 119 |
| BASF-Corn | 120 |
| BASF-Corn | 121 |
| BASF-Soy | 122 |
| BASF-Soy | 123 |
| AFC1 | 124 |
| AFC1 | 125 |
| AT4g01320 | 126 |
| AT4g01320 | 127 |
| AF007269 | 128 |
| AF007269 | 129 |
| pBI121-antisense-AtCPP | 130 |
| pRD29A-AtCPP | 131 |
| pRD29A-HP-AtCPP | 132 |
| pRD29A-antisense-AtCPP | 133 |
| MuA-AtCPP | 134 |
| MuA-GmCPP | 135 |
| pBI121-GmCPP | 136 |
| pBI121-HP-GmCPP | 137 |
| pBI121-antisense-GmCPP | 138 |
| pRD29A-GmCPP | 139 |
| pRD29A-HP-GmCPP | 140 |

TABLE A-continued

| PPI Sequence Description | SEQ ID NO: |
|---|---|
| pRD29A-antisense-GmCPP | 141 |
| pBI121-BnCPP | 142 |
| pBI121-HP-BnCPP | 143 |
| pBI121-antisense-BnCPP | 144 |
| pRD29A-BnCPP | 145 |
| pRD29A-HP-BnCPP | 146 |
| pRD29A-antisense-BnCPP | 147 |
| MuA-BnCPP | 148 |
| GmCPP SmaFW | 149 |
| GmCPP SacRV | 150 |
| BnCPP-anti-SmaFW | 151 |
| BnCPP-anti-BamRV | 152 |
| BnCPP-HP-Sac-FW | 153 |
| BnCPP-HP-Sac-RV | 154 |
| BnCPP-HP-BamFW | 155 |
| BnCPP-HP-XbaRV | 156 |
| GmCPP-HP-Sac-FW | 157 |
| GmCPP-HP-Sac-RV | 158 |
| GmCPP-HP-BamFW | 159 |
| GmCPP-HP-XbaRV | 160 |
| pRD29AP | 161 |
| Nosterm-RV | 162 |
| Consensus-BASF | 163 |
| Consensus-BASF | 164 |
| Consensus-Generic | 165 |
| Consensus-Generic | 166 |
| Consensus-PPI | 167 |
| Consensus-PPI | 168 |
| Consensus-PPI/Generic | 169 |
| Consensus-PPI/Generic | 170 |
| Primer BamHI REV | 171 |
| Full Length AtFTB | 172 |
| pBI121-AtFTB full length | 173 |
| primer | 174 |
| primer | 175 |
| isoprenylcysteine carboxyl methyltransferase | 176 |
| Full Length AtFTB | 177 |

This invention also relates to isolated nucleic acids and proteins encoded by these nucleic acids which modify the growth, reproduction and senescence of plants. In particular, the constructs of this invention include an isolated nucleic acid encoding a farnesyl transferase (Ftase) polypeptide comprising SEQ ID NO: 1 or 172 or its functional equivalent or fragment thereof, and the Ftase polypeptides or proteins of fragments thereof encoded by these nucleic acids. In particular, this invention relates to a protein wherein the sequence is SEQ ID NO:2 or SEQ ID NO:177.

Further included in this invention are nucleic acid constructs which comprise a promoter (ERA1 promoter) operably-linked to isolated nucleic acid comprising SEQ ID NO: 1 or 172 or its functional equivalent or a complement of either. When incorporated into a plant, the ERA1 promoter is regulated in the guard cells of the plant and can affect water loss through the stomates. This promoter consists of a nucleic acid comprising SEQ ID NO:3 (FIG. 3).

Transgenic plants, seeds, plant cell and tissues incorporating these constructs are also part of this invention. Accordingly, in one aspect of this invention, a method is provided for producing a gene product under the control of a promoter which operates primarily in guard cells through expression of a gene encoding the gene product in the cell of a plant comprising the steps of: transforming a plant cell with a DNA construct comprising a) a regulatory region comprising SEQ ID NO:3 or a functional portion thereof, DNA comprising a structural gene encoding a gene product, and a 3' untranslated region containing a polyadenylated region; regenerating a plant, photosynthetic organism or tissue culture from the cell;

and placing the plant, photosynthetic organisms or tissue culture under conditions so that the promoter induces transcription of the structural gene and the gene product is expressed.

In the context of this disclosure, the terms "regulatory region" or "promoter" refer to a sequence of DNA, usually upstream (5') to the coding sequence of a structural gene, which controls the expression of the coding region by providing recognition and binding sites for RNA polymerase and/or other factors required for transcription to start at the correct site. The term "functional portion" or "functional fragment" refers to a truncated sequence of a promoter of this invention which maintains the capability of inducing transcription of an ERA structural gene under the conditions described for activity of an Ftase protein.

The constructs and methods described herein can be applied to all types of plants and other photosynthetic organisms, including, but not limited to: angiosperms (monocots and dicots), gymnosperms, spore-bearing or vegetatively-reproducing plants and the algae, including the cyanophyta (blue-green algae). Particularly preferred plants are those plants which provide commercially-valuable crops, such as corn, wheat, cotton, rice, canola, sugar cane, sugar beet, sunflowers, potatoes, tomatoes, broccoli, carrots, lettuce, apple, plum, orange, lemon, rose, and the like.

Further, the constructs and methods of this invention can be adapted to any plant part, protoplast, or tissue culture wherein the tissue is derived from a photosynthetic organism. The term "plant part" is meant to include a portion of a plant capable of producing a regenerated plant. Preferable plant parts include roots and shoots and meristematic portions thereof. Other plant parts encompassed by this invention are: leaves, flowers, seeds, epicotyls, hypocotyls, cotyledons, cotyledonary nodes, explants, pollen, ovules, meristematic or embryonic tissue, protoplasts, and the like. Transgenic plants can be regenerated from any of these plant parts, including tissue culture or protoplasts, and also from explants. Methods will vary according to the species of plant.

This invention relates to compositions and constructs comprising isolated nucleic acids (both DNA and RNA) encoding an Ftase and portions thereof of photosynthetic organisms. This invention further relates to compositions and constructs comprising isolated nucleic acids encoding an Ftase promoter. In particular, the ERA1 gene encoding the β subunit of Ftase from *Arabidopsis* and a regulatory sequence which regulates the transcription of the ERA1 gene have been isolated and sequenced. Nucleic acids which encode Ftases from photosynthetic organisms, and homologues or analogs of these nucleic acids, are encompassed by this invention.

The invention further relates to methods using isolated and/or recombinant nucleic acids (DNA or RNA) that are characterized by their ability to hybridize to (a) a nucleic acid encoding an Ftase protein or polypeptide, such as a nucleic acid having the sequences of SEQ ID NO: 1 or 172 or (b) a portion of the foregoing (e.g., a portion comprising the minimum nucleotides required to encode a functional Ftase protein; or by the ability to encode a polypeptide having the amino acid sequence of an Ftase (e.g., SEQ ID NO:2 or SEQ ID NO: 177, or to encode functional equivalents thereof, e.g., a polypeptide having at least 80% sequence similarity to SEQ ID NO:2 or SEQ ID NO:177, which when incorporated into a plant cell, facilitates the growth habit, seed germination, and metabolism in a photosynthetic organism in the same manner as SEQ ID NO: 1 or 172). A functional equivalent of an Ftase therefore, would have at least an 80% similar amino acid sequence and similar characteristics to, or perform in substantially the same way as, the polypeptide encoded by SEQ ID NO:2 or SEQ ID NO:177. A nucleic acid which hybridizes to a nucleic acid encoding an Ftase polypeptide such as SEQ ID NO:2 or SEQ ID NO: 177 can be double- or single-stranded. Hybridization to DNA such as DNA having the sequence SEQ ID NO: 1 or 172, includes hybridization to the strand shown or its complementary strand.

In one embodiment, the percent amino acid sequence similarity between an Ftase polypeptide such as SEQ ID NO:2 or SEQ ID NO: 177, and functional equivalents thereof is at least about 60% (≥60%). In a preferred embodiment, the percent amino acid sequence similarity between an Ftase polypeptide and its functional equivalents is at least about 75% (≥75%). More preferably, the percent amino acid sequence similarity between an Ftase polypeptide and its functional equivalents is at least about 80%, and still more preferably, at least about 90%, when consecutive amino acids are compared.

Isolated and/or recombinant nucleic acids meeting these criteria comprise nucleic acids having sequences identical to sequences of naturally occurring ERA1 genes and portions thereof, or variants of the naturally occurring genes. Such variants include mutants differing by the addition, deletion or substitution of one or more nucleotides, modified nucleic acids in which one or more nucleotides are modified (e.g., DNA or RNA analogs), and mutants comprising one or more modified nucleotides.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1-2.10.16 (see particularly 2.10.8-11) and pages 6.3.1-6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures can (1) employ low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) employ during hybridization 50% (vol/vol) formamide with 5×Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5×SSC at 42° C.; or (3) employ hybridization with 50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. Moderate stringency conditions would be similar except that hybridization would employ 25% formamide in place of 50% formamide.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson (1991) *Methods in Enzymology,* 200:546-556. Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ≈17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding an Ftase polypeptide, such as the nucleic acids depicted as SEQ ID NO:1 or 172, (b) the complement of SEQ ID NO: 1 or 172, (c) or a portion of (a) or (b) (e.g. under high or moderate stringency conditions), may further encode a protein or polypeptide having at least one functional characteristic of an Ftase polypeptide, such as regulation of lateral branching under diurnal light cycles, or regulation of the response to ABA, or regulation of senescence.

Enzymatic assays, complementation tests, or other suitable methods can also be used in procedures for the identification and/or isolation of nucleic acids which encode a polypeptide such as a polypeptide of the amino acid sequence SEQ ID NO:2 or SEQ ID NO:177 or a functional equivalent or fragment thereof of this polypeptide. The antigenic properties of proteins or polypeptides encoded by hybridizing nucleic acids can be determined by immunological methods employing antibodies that bind to an Ftase polypeptide such as immunoblot, immunoprecipitation and radioimmunoassay. PCR methodology, including RAGE (Rapid Amplification of Genomic DNA Ends), can also be used to screen for and detect the presence of nucleic acids which encode Ftase-like proteins and polypeptides, and to assist in cloning such nucleic acids from genomic DNA. PCR methods for these purposes can be found in Innis, M. A., et al (1990) *PCR Protocols: A Guide to Methods and Applications*, Academic Press, Inc., San Diego, Calif., incorporated herein by reference.

The nucleic acids described herein are used in the methods of the present invention for production of proteins or polypeptides which are incorporated into cells, tissues, plant parts, plants and other photosynthetic organisms. In one embodiment, DNA containing all or part of the coding sequence for an Ftase polypeptide, or DNA which hybridizes to DNA having the sequence SEQ ID NO:2 or SEQ ID NO: 177 is incorporated into a vector for expression of the encoded polypeptide in suitable host cells. The encoded polypeptide consisting of an Ftase subunit or its functional equivalent is capable of farnesyl transferase activity. The term "vector" as used herein refers to a nucleic acid molecule capable of transporting another nucleic acid to which it has been linked.

Primers and probes consisting of 20 or more contiguous nucleotides of the above-described nucleic acids are also included as part of this invention. Thus, one nucleic acid of this invention comprises a specific sequence of about 20 to about 200 or more nucleotides which are identical or complementary to a specific sequence of nucleotides of the Ftase protein-encoding DNA or transcribed mRNA. These probes and primers can be used to identify and isolate Ftase-encoding nucleic acid from other photosynthetic organisms.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewmaker, et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO: 1 or 172. For example, an antisense nucleic acid or oligonucleotide can be complementary to a target nucleic acid having the sequence shown as the strand of the open reading frame of SEQ ID NO: 1 or 172, or nucleic acid encoding a functional equivalent or fragment thereof of Ftase, or to a portion of these nucleic acids sufficient to allow hybridization. A portion, for example, a sequence of 16 nucleotides could be sufficient to inhibit expression of the protein. Fragments comprising 25 or more consecutive nucleotides complementary to SEQ ID NO: 1 or 172 could also be used. Or, an antisense nucleic acid or oligonucleotide complementary to 5' or 3' untranslated regions, or overlapping the translation initiation codon (5' untranslated and translated regions), of the ERA1 gene, or a gene encoding a functional equivalent or fragment thereof can also be effective. In another embodiment, the antisense nucleic acid is wholly or partially complementary to and can hybridize with a target nucleic acid which encodes an Ftase polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding an Ftase polypeptide or its functional equivalent. Frank-Kamenetskii, M. D. and Mirkin, S. M. (1995) *Ann. Rev. Biochem.* 64:65-95. Such oligonucleotides of the invention are constructed using the base-pairing rules of triple helix formation and the nucleotide sequence of the gene or mRNA for Ftase. These oligonucleotides can block Ftase-type activity in a number of ways, including prevention of transcription of the ERA1 gene or by binding to mRNA as it is transcribed by the gene.

Another aspect of the invention pertains to the use of post transcriptional gene silencing (PTGS) to repress gene expression. Double stranded RNA can initiate the sequence specific repression of gene expression in plants and animals. Double stranded RNA is processed to short duplex oligomers of 21-23 nucleotides in length. These small interfering RNA's suppress the expression of endogenous and heterologous genes in a sequence specific manner (Fire et al. Nature 391: 806-811, Carthew, Curr. Opin. in Cell Biol., 13:244-248, Elbashir et al., Nature 411:494-498). A RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

Another aspect of the invention pertains to the use of post transcriptional gene silencing (PTGS) to repress gene expression. Double stranded RNA can initiate the sequence specific repression of gene expression in plants and animals. Double stranded RNA is processed to short duplex oligomers of 21-23 nucleotides in length. These small interfering RNA's suppress the expression of endogenous and heterologous genes in a sequence specific manner (Fire et al. Nature 391: 806-811, Carthew, Curr. Opin. in Cell Biol., 13:244-248, Elbashir et al., Nature 411:494-498). A RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

Another aspect of the invention pertains to the use of the dominant-negative genetic approach. Briefly the presence of a dominant trait, i.e. the expression of a transgene, results in a reduction of enzyme activity or reduced production of the enzymatic end-product. It has been demonstrated that FT is a heterodimer formed by α- and β-subunits. FT activity relies on the proper dimerization between these subunits to form functional enzyme. Expression of a non-functional subunit will interact with the second subunit to produce a non-functional enzyme and hence reduced enzymatic activity. The non-functional aspect may be in respect to, but not limited to, subunit interaction, substrate binding or enzyme catalysis, for example. Alternatively the expressed trait may produce a substrate analogue which competes with native substrate, the end result being decreased farnesylation of biologically active substrate.

The invention also relates to proteins or polypeptides encoded by the novel nucleic acids described herein. The proteins and polypeptides of this invention can be isolated and/or recombinant. Proteins or polypeptides referred to herein as "isolated" are proteins or polypeptides purified to a state beyond that in which they exist in cells. In a preferred embodiment, they are at least 10% pure; i.e., substantially purified. "Isolated" proteins or polypeptides include proteins or polypeptides obtained by methods described infra, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of an Ftase; for example, catalytic activity affecting, e.g., normal lateral branching, florets/inflorescence, seed germination, or stomatal opening, and binding function, and/or antigenic function (e.g., binding of antibodies that also bind to naturally occurring Ftase). As such, these proteins are referred to as Ftases of plant origin, and include, for example, naturally occurring Ftase, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

The invention also relates to isolated and/or recombinant portions of an Ftase as described above, especially the β subunit of an Ftase protein. Portions of the enzyme can be made which have full or partial function on their own, or which when mixed together (though fully, partially, or nonfunctional alone), spontaneously assemble with one or more other polypeptides to reconstitute a functional protein having at least one functional characteristic of an Ftase of this invention.

A number of genes have been identified that are induced by ABA. This suggests that ABA-induced tolerance to adverse environmental conditions is a complex multigenic event. Thus, identification and transfer of single genes into crop plants which improves the viability of the plant under different environmental conditions due to increased responsiveness to ABA is novel and extremely useful.

To identify genes that could be more global controllers of ABA-regulated plant processes, genetic screens were applied in a number of plant species to isolate mutations that alter the response of the plant to the hormone.

Mutations that confer enhanced response to ABA (era) in *Arabidopsis* seeds were identified by their ability to prevent seed germination with low concentrations of ABA that normally permit wild-type (controls, i.e., naturally-occurring) seed germination. Of these, the era1 mutant class, which includes one transferred DNA (T-DNA) line (era1-1, ecotype Wassilewskija) and two neutron-generated mutants (era1-2 and era1-3, ecotype Columbia), was of added interest because this class showed decreased germination efficiency under normal postimbibition. Mutations that enhance ABA responsiveness should, in principle, be more dormant. Dormancy in era1 alleles was alleviated by a 4-day chilling period; the efficiency of era1 germination increased with the length of time the seeds are chilled. In many plant species, breaking dormancy to allow germination requires vernalization and exposure to moist, low-temperature environments for an extended period (Baskin and Baskin, 1971). The germination profile of era mutants could reflect an increased state of ABA-induced dormancy; consequently, these seeds require longer vernalization to germinate. Support for this contention came from construction of double mutants of era1 with both ABA biosynthetic (aba1-1) and insensitive mutants (abi1-1 and abi3-6). In all cases, the double mutants had reduced dormancy as compared with era1, indicating that the increased dormancy observed in era1 seed was dependent on ABA synthesis or sensitivity.

Aside from broadening the spectrum of new ABA response mutants, supersensitivity screens were also used to identify negative regulators of ABA sensitivity. That is, inhibition of these gene functions enhances the ABA response. One of these genes (ERA1) has been cloned and demonstrated to encode the β-subunit of a heterodimeric protein farnesyl transferase (Ftase) (Cutler et al., 1996). The era1-1 mutation, which is due to a T-DNA insertion, allowed the isolation of plant genomic regions flanking the insertions. Using the flanking regions as probes, the wild-type cDNA and genomic clones were isolated. Sequence analysis of these described a gene encompassing 3.5 kb of genomic DNA. The gene contains 13 introns which are underlined in FIGS. 1A-1C and the T-DNA insertion site in era1-1 is in intron 8. Southern (DNA) analysis of wild-type DNA, era1-2, and era1-3 probed with Era1cDNA revealed that both fast-neutron alleles contain deletions spanning the ERA4 locus. Fast-neutron mutagenesis induced small deletions in *Arabidopsis* (Shirley et al., 1992), and subsequent genomic analysis with a 14-kb probe that spans the ERA1 locus determined the size of the era1-2 deletion to be about 7.5 kb and the era1-3 deletion to be slightly larger. Thus all three era1 alleles contained DNA disruptions at the same locus, confirming the identity of the ERA locus.

Conceptual translation of the longest open reading frame (404 amino acids) in the ERA1 gene produced a protein (FIGS. 2 and 4) with a high sequence similarity to yeast, pea, and mammalian protein farnesyl transferase β subunit genes (Goodman et al., 1988; Chen et al., 1991; Yang et al., 1993). Farnesyl transferases consist of α and β subunits that dimerize, forming an enzyme that catalyzes the attachment of farnesyl pyrophosphate (15 carbons) to proteins containing a COOH-terminal CaaX motif (Schafer and Rine, 1992), where C designates cysteine residue, aa is usually aliphatic amino acids, and X may designate a cysteine, serine, methionine, or glutamine residue. Both plant β subunit genes contain a region of about 50 amino acids near their COOH-terminus that is absent in yeast and animal β subunit genes.

In yeast and mammalian systems, Ftases modify several signal transduction proteins for membrane localization. This is achieved by the attachment of the lipophilic farnesyl sidechain to the protein target via the Ftase. The attachment of the farnesyl group causes a change in the overall hydrophobicity of the target allowing the protein to anchor itself into the membrane where it usually interacts with other signal transduction molecules. That the loss of farnesylation activity in the era1 mutant leads to an enhanced response of the seed to ABA suggests a target protein in *Arabidopsis* must be localized to the membrane to attenuate the ABA signal. Thus farnesylation in *Arabidopsis*, appears to be required for the normal function of a negative regulator of ABA sensitivity.

Figure 6:
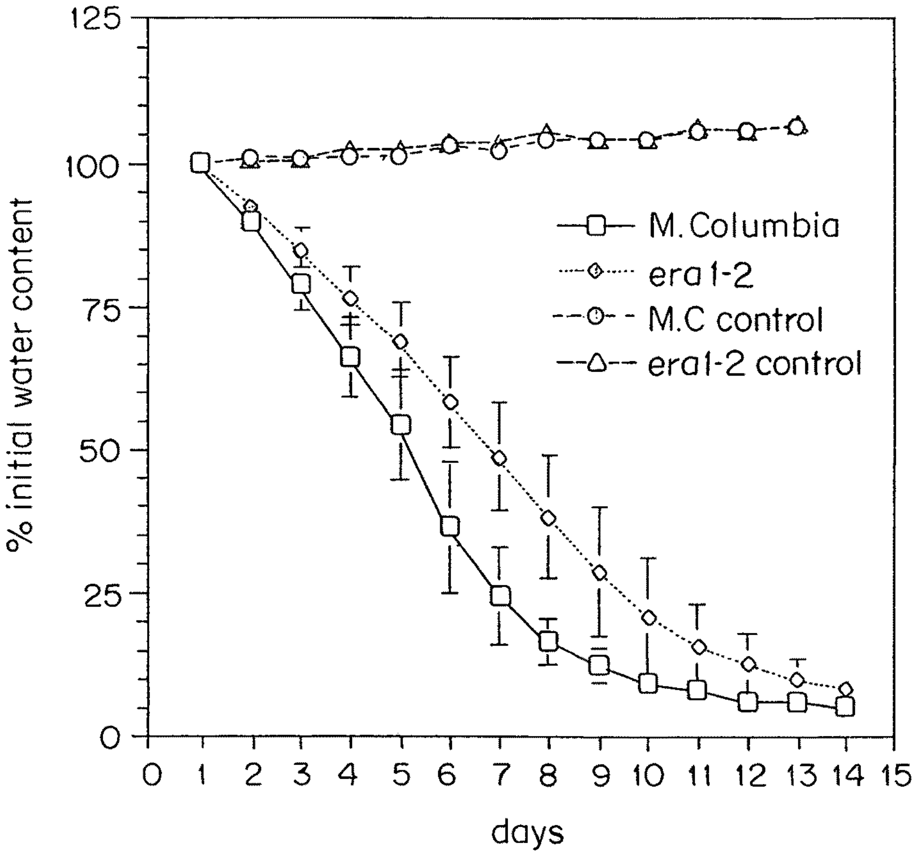
FIG. 6 is a graph comparing the water content of *Arabidopsis* plants with inactivated or mutant Ftase activity (M. Columbia, era1-2) and controls (M.C. control, era1-2 control).
Figure 7:
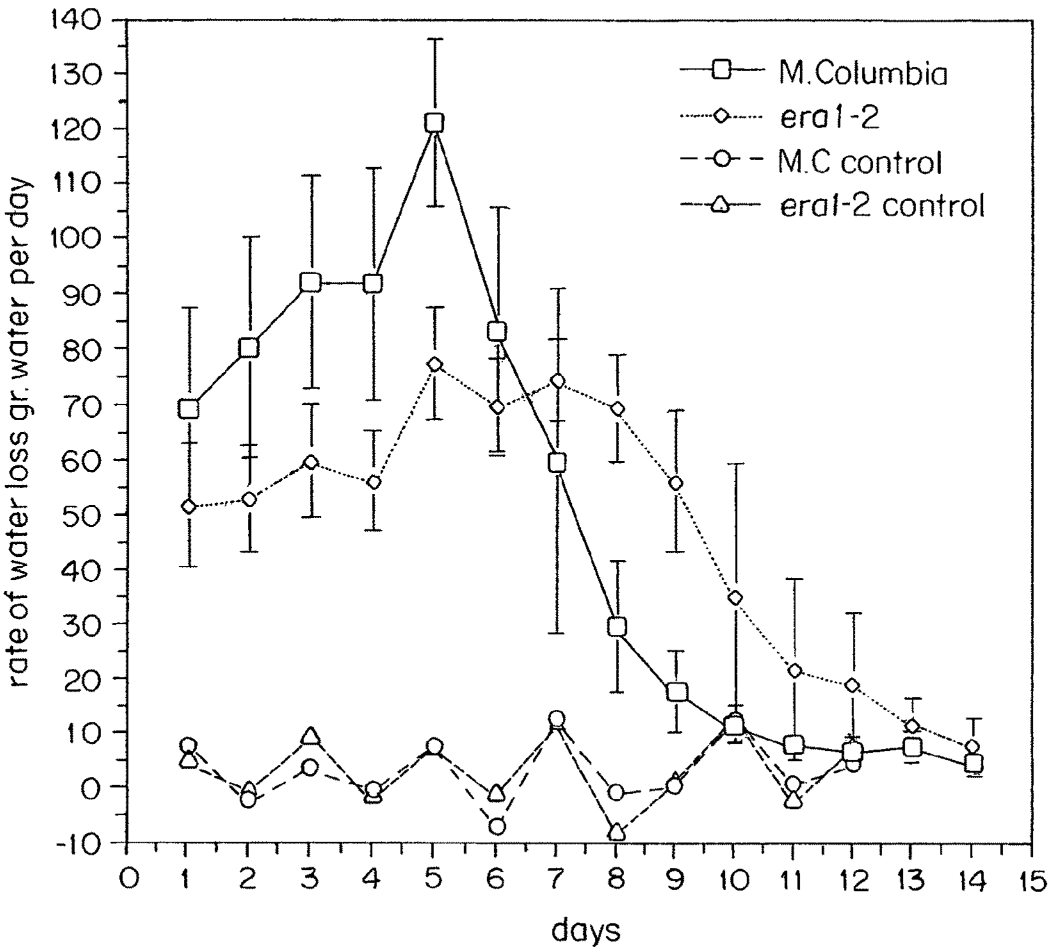
FIG. 7 is a graph comparing the rate of water loss for the *Arabidopsis* plants with inactivated or mutant Ftase activity (M. Columbia, era1-2) and controls (M.C. control, era1-2 control).
Figure 8A:
FIGS. 8A-8E are comparisons of aging leaves from control (wild-type) and era-2 mutant plants.
Figure 8B:
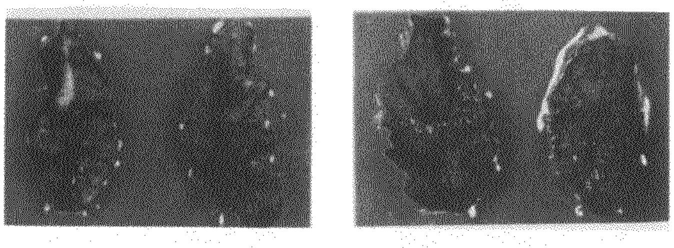
Figure 8C:
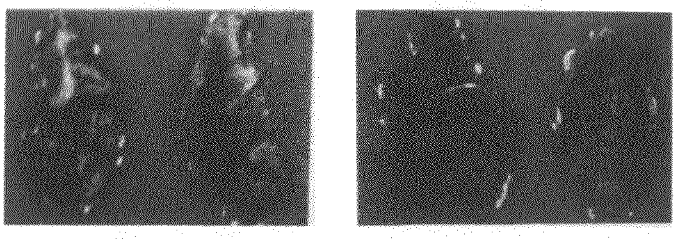
Figure 8D:
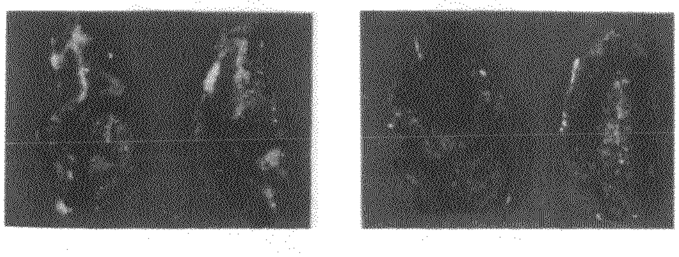
Figure 8E:
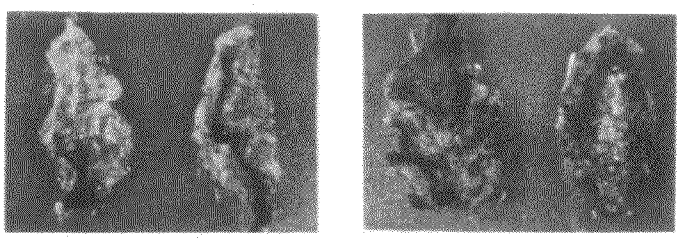

Subsequent work has shown that loss of ERA1 gene function in *Arabidopsis* confers an enhanced tolerance to environmental stresses at the level of the mature plant. For example, a comparison of wild-type plants and era1 mutant plants grown in soil under standard laboratory conditions (24 hr light, 150 μE $m^{-2}$ $sec^{-1}$, 30% humidity) showed that the mutants did not require water as frequently as the wild-type plants in order to maintain viability (FIG. 5). When mutant and wild-type plants were grown until flowering occurred, watering was stopped and the plants were observed each subsequent day for signs of stress. Water loss was significantly reduced in the mutant plants compared to the wild-type plants (FIGS. 6 and 7).

To determine if the observed increased drought tolerance of era mutants was related to ERA1 gene function, transgenic plants containing a ERA1 promoter fusion to a reporter GUS gene (made by inserting a 5 Kb fragment of the ERA1 promoter into a promoterless GUS T-DNA plasmid), were constructed. Analysis of the transgenic plants showed that ERA1 is transcriptionally expressed in the epidermal tissue of *Arabidopsis* and that this expression is guard-cell specific. Expression of ERA1 was also noted in the meristematic tissue of the plants and in root hairs. The guard cell expression of ERA1 is consistent with the drought tolerance of the mutant as these cells are the major regulators of water transpiration through the plant. It would be expected that ERA1-regulated stomatal conductance would require expression of the ERA1 gene in the guard cells. Hence loss of ERA1 gene function results in guard cells which are more responsive to ABA which, in turn, leads to more drought responsive guard cell regulation. Therefore, modification of Ftase expression or activity in higher plants, especially crop plants, will have profound effects on stomatal conductance and transpiration rates in the plants.

The nature of the era1 mutation in *Arabidopsis* demonstrates that inhibition of farnesylation will enhance ABA responses in a plant and alteration of this enzyme activity in crop species. Inhibition of Ftase activity in crop plants can be achieved via a number of methods. For example, antisense technology of cognate ERA1 genes in a variety of crop species can be used to reduce Ftase activity, thus increasing drought tolerance. By specifically producing ERA1 antisense RNA in guard cells, the amount of Ftase synthesized can be reduced to a level which would mimic era mutant phenotypes. The ERA1 promoter is regulated in a number of different tissues ranging from shoot meristems to root hairs. By determining the elements of the ERA1 promoter which allow expression in specific tissues, it is possible to tailor the expression of antisense ERA1 to only one tissue or cell type, such as guard cells.

Another method to inhibit Ftase activity in plants is the production of specific peptide inhibitors of farnesylation in transgenic plants. In mammalian and yeast systems, the carboxyl terminal target sequence (CaaX, where C=cysteine, x=aliphatic, X=any amino acid) which allows the attachment of the farnesyl group to specific proteins has been clearly defined. Peptides which mimic these target sequences have been made and shown to inhibit farnesylation of the endogenous target proteins in these systems. Moreover, CAIM is farnesylated in vivo in *Arabidopsis*. Thus, similar inhibitors can be applied to higher plants to competitively inhibit Ftase in vivo. Again, this can be done through expression of inhibitor peptides in transgenic plants by synthesizing the DNA sequence for a CaaX peptide and fusing it to a guard cell-specific promoter. In both methods, using the appropriate promoters, antisense Ftase or peptide inhibitors can be specifically targeted and controlled.

Also included in the invention are methods of producing a transgenic plant. The method includes introducing into one or more plant cells a compound that alters, e.g., inhibits farnesylation of a polypeptide having a carboxyl terminal CaaX motif in the plant to generate a transgenic plant cell and regenerating a transgenic plant from the transgenic cell. In some aspects the compound alters, e.g., increases or decreases CaaX prenyl protease expression or activity. Alternatively, the compound alters farnesyltransferase expression or activity. In other aspects the compound alters isoprenylcysteine carboxyl methyltransferase expression or activity. The compound can be, e.g., (i) a CaaX prenyl protease, farnesyltransferase or isoprenylcysteine carboxyl methyltransferase polypeptide; (ii) a nucleic acid encoding a CaaX prenyl protease, farnesyltransferase or isoprenylcysteine carboxyl methyltransferase polypeptide; (iii) a nucleic acid that increases expression of a nucleic acid that encodes a CaaX prenyl protease, farnesyltransferase or isoprenylcysteine carboxyl methyltransferase polypeptide; (iv) a nucleic acid that decreases the expression of a nucleic acid that encodes a CaaX prenyl protease, farnesyltransferase or isoprenylcysteine carboxyl methyltransferase polypeptide; (v) a CaaX prenyl protease, farnesyltransferase or isoprenylcysteine carboxyl methyltransferase antisense nucleic acid and derivatives, fragments, analogs and homologs thereof. A nucleic acid that increases expression of a nucleic acid that encodes a CaaX prenyl protease, farnesyltransferase or isoprenylcysteine carboxyl methyltransferase polypeptide includes, e.g., promoters, enhancers. The nucleic acid can be either endogenous or exogenous. Preferably, the compound is a CaaX prenyl protease, farnesyltransferase or isoprenylcysteine carboxyl methyltransferase polypeptide or a nucleic acid encoding a CaaX prenyl protease, farnesyltransferase or isoprenylcysteine carboxyl methyltransferase polypeptide.

Included in the invention are methods of producing a transgenic plant that has increased stress resistance, delayed senescence or increased sensitivity to ABA. The method includes introducing into one or more plant cells a compound that alters farnesyl transferase expression (i.e., farnesyl transferase alpha or beta) or activity in the plant. The compound can be, e.g., (i) a farnesyl transferase polypeptide inhibitor; (ii) a nucleic acid encoding a farnesyl transferase polypeptide inhibitor; (iii) a nucleic acid that decreases expression of a nucleic acid that encodes a farnesyl transferase polypeptide and, derivatives, fragments, analogs and homologs thereof; (iv) an antisense farnesyl transferase nucleic acid. A nucleic acid that decreases expression of a nucleic acid that encodes a farnesyl transferase polypeptide includes, e.g., antisense nucleic acids or RNA inhibitory nucleic acids. The nucleic acid can be either endogenous or exogenous. Preferably the compound is a farnesyl transferase polypeptide or a nucleic acid encoding a farnesyl transferase polypeptide. More preferably the compound is a nucleic acid complementary to a nucleic acid encoding a farnesyl transferase polypeptide. For example, an anti-sense nucleic acid molecule.

Alternatively the compound is a nucleic acid molecule comprising a nucleic acid sequence encoding a mutated farnesyl transferase, isoprenylcysteine carboxyl methyltransferase or CaaX prenyl protease polypeptide. By mutated is meant that the polypeptide lacks one or more function of a wild-type polypeptide. For example, a mutated farnesyltransferase beta polypeptide is a polypeptide has less amino acids than a full length wild type polypeptide by still retains the ability to dimerize with an alpha subunit. For example a mutated farnesyltransferase beta polypeptide is less than 314 amino acids in length. Preferably, the mutated farnesyltransferase beta polypeptide comprises the amino acid sequence of SEQ ID NO:1 or a fragment thereof.

In another aspect the compound is a nucleic acid encoding a CaaX motif. Alternatively, the CaaX motif is operably liked to a promoter.

Also included in the invention is a plant where a mutation has been introduced in the gene encoding farnesyl transferase (i.e., alpha or beta) which results in a plant that has decreased farnesyl transferase activity and increased tolerance to stress as compared to a wild type plant. The mutation may be introduced by chemical or mechanical means.

In various aspects the transgenic plant has an altered phenotype as compared to a wild type plant (i.e., untransformed). By altered phenotype is meant that the plant has a one or more characteristic that is different from the wild type plant. For example, the transgenic plant has an increased resistance to stress. Increased stress resistance is meant that the transgenic plant can grow under stress conditions (e.g., high salt, decreased water, low temperatures, high temperatures) or under conditions that normally inhibit the growth of an untransformed, Stresses include, for example, chilling stress, heat stress, heat shock, salt stress, water stress (i.e., drought), nutritional stress, disease, grazing pests, wound healing, pathogens such as for example fungi, bacteria, nematodes, viruses or parasitic weed and herbicides. Methodologies to determine plant growth or response to stress include for example, height measurements, weight or biomass measurements, leaf area or number, ability to flower, water use, transpiration rates and yield. Alternatively, the transformed plant has an increased (i.e., enhanced) ABA sensitivity. The enhanced ABA sensitivity is at the seedling growth stage. Alternatively, the enhanced ABA sensitivity is at the mature plant stage. Additional altered phenotypes include for example, enhanced vegetative growth (e.g., increased leaf number, thickness and overall biomass), delayed reproductive growth (e.g., flowering later); enhanced seedling vigor (e.g., increased root biomass and length), enhanced lateral root formation and therefore soil penetration more extensive vascular system resulting in an enhanced transport system.

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Gossypium, Picea, Caco*, and *Populus*.

This invention provides a method of producing drought-tolerant plants comprising: preparing a nucleic acid construct which comprises a promoter operably-linked to a nucleic acid comprising or encoding antisense to SEQ ID NO: 1, 14, 40, 43, 80-85 or 172, or nucleic acid comprising a functional equivalent or fragment thereof of the antisense; inserting the nucleic acid construct into a vector; transforming a plant, tissue culture, or plant cells with the vector; and growing the plant or regenerating a plant from the tissue culture or plant cells; wherein drought-tolerant plants are produced. This method can be used wherein the nucleic acid is selected from the group consisting of 25-200 or more consecutive nucleotides complementary to SEQ ID NO: 1, 14, 40, 43, 80-85 or 172, oligonucleotides consisting of 25 or more consecutive nucleotides of SEQ ID NO: 1, 14, 40, 43, 80-85 or 172 or its complement, or nucleic acid encoding a peptide inhibitor of farnesyl transferase In addition to stomatal regulation which is extremely sensitive to ABA, era plants also demonstrate delayed senescence under drought conditions, indicating that farnesylation negatively regulates a number of drought-induced responses in *Arabidopsis*. The era plants grown under normal laboratory conditions take longer to turn yellow. The mutant plants remained green and viable long after the wild-type had senesced and died. Detached leaves of an era mutant plant do not yellow as quickly as detached leaves of wild-type plants (FIG. 8). Similar-sized leaves which were developmentally identical were taken from wild-type and era plants and placed on agar-containing petri plates (See Example 7). Normally, a wild-type leaf begins to lose chlorophyll about five days later and eventually bleaches. The leaves of the mutant plants remained green for twice as long. Because the leaves were in constant contact with the agar they were not drought stressed, indicating the reduced senescence of the era1 mutant is not a drought-induced phenomenon.

Moreover, under a 10 hr day/16 hr night cycle, the plant life cycle can be doubled versus the wild-type plants (3 months). It appears therefore, that chlorophyll turnover and senescence signals are altered in the era1 mutant. For example, wild-type and mutant plants were grown in pots under well-watered conditions to stages of development where the wild-type plant leaves would begin to senesce (about the time of flower development). At this time, developmentally-similar leaves were assayed for senescence-induced marker genes by northern blot analysis (Example 8). Two genes, SAG12 and SAG13, in which transcription is normally induced during senescence in wild-type plants, were not induced in the era1 mutant (FIG. 9). Further, CAB transcription is maintained (FIG. 9). Taken together, these results indicate the senescence induction program in era1 mutants is delayed compared to wild-type plants, showing that loss of farnesylation activity causes a retardation of the induction of senescence in the plant even under conditions wherein water stress is not an environmental factor.

In addition to effects on senescence and water loss, the era1 mutants show a difference in branching and flowering habit when grown under diurnal light cycles. Under continuous (24 hours light/day) light, the branching pattern of mutants does not differ from that of wild-type plants. However, when given a dark period, the mutants do not produce as many lateral branches as wild-type plants. When measured, plants with loss of farnesylation activity produced only 2.4 branches per plant compared to 3.6 lateral branches per wild-type plant. This represents a 30% decrease in lateral branches per plant.

Flowering is affected by loss of Ftase activity as well. Plants lacking Ftase activity produce more flowers per plant (25-30 buds/inflorescence) than wild-type plants (10-15 buds/inflorescence). Thus, on average there are twice as many flower buds are present on the mutants than on the wild-type plants.

These pleiotrophic effects of the era1 loss of function mutants on whole plant development indicate that the ERA1 gene can be a coordinate regulator of a collection of plant developmental functions.

Until now, there was no known function for farnesylation in higher plants, including a role in ABA signal transduction. Ftases have been found in a number of higher plants such as tomato and pea, so it is clear that this enzyme has functions across species boundaries. Furthermore, overproduction of farnesyl transferase target peptides or the use of farnesylation inhibitors completely inactivates Ftase in mammalian and yeast systems. Thus, similar inhibitors can be applied to higher plants to inactivate Ftase in vivo. In both cases with the appropriate promoters, antisense Ftase or peptide inhibitors can be specifically targeted and controlled.

The farnesylation deficient mutants are also supersensitive to exogenous auxin. That these mutants show reduced branching and minor alterations in meristem organization, can be explained by altered auxin regulation. Thus other hormone functions are affected in this mutant, which indicates that, in addition to ABA pathways, other hormone regulated pathways are controlled by Ftase activity. These results demonstrate that the ERA1 gene provides a molecular mechanism to coordinate regulation of different hormone signaling molecules.

In accordance with the present invention, the plants included within the scope of this invention are higher and lower plants of the plant kingdom. Mature plants, seedlings and seeds are included in the scope of the invention. A mature plant includes a plant at any stage in development beyond the seedling. A seedling is a very young, immature plant in the early stages of development. Plant parts, protoplasts and tissue culture are also provided by this invention.

Transgenic plants are included within the scope of the present invention which have the phenotype characterized by the era1 mutation. Seed of transgenic plants are provided by this invention and can be used to propagate more plants containing the constructs of this invention.

ERA1 function in a number of crop plants can be inhibited to enhance the plant's response to adverse environmental conditions that require ABA-mediated signaling. Control of farnesylation in higher plants regulates both embryonic and vegetative tissue response to this hormone (Cutler, et al., 1996). The increased sensitivity translates into a faster response of the tissue to stress conditions which in turn confers increased protection of the plant to the environmental stress. Because this only requires the control of a single gene, ERA1, it should be possible to control farnesylation in a variety of plants by controlling the synthesis or activity of this enzyme. Furthermore, the work described herein clearly indicates that altering the ABA signal transduction pathway by manipulating the genes that control the ABA response makes it possible to improve the plant's response to adverse water stress conditions.

To produce transgenic plants of this invention, a construct comprising the gene encoding Ftase, or nucleic acid encoding its functional equivalent, and a promoter are incorporated into a vector through methods known and used by those of skill in the art. The promoter can comprise all or part of SEQ ID NO:3. The construct can also include any other necessary regulators such as terminators or the like, operably linked to the coding sequence. It can also be beneficial to include a 5' leader sequence, such as the untranslated leader from the coat protein mRNA of alfalfa mosaic virus (Jobling, S. A. and Gehrke, L. (1987) *Nature* 325:622-625) or the *maize* chlorotic mottle virus (MCMV) leader (Lommel, S. A., et al. (1991) *Virology* 81:382-385). Those of skill in the art will recognize the applicability of other leader sequences for various purposes. Exemplary constructs include SEQ ID NO: 54-64.

Targeting sequences are also useful and can be incorporated into the constructs of this invention. A targeting sequence is usually translated into a peptide which directs the polypeptide product of the coding nucleic acid sequence to a desired location within the cell, such as to the plastid, and becomes separated from the peptide after transit of the peptide is complete or concurrently with transit. Examples of targeting sequences useful in this invention include, but are not limited to, the yeast mitochondrial presequence (Schmitz, et al. (1989) *Plant Cell* 1:783-791), the targeting sequence from the pathogenesis-related gene (PR-1) of tobacco (Cornellisen, et al. (1986) *EMBO J.* 5:37-40), vacuole targeting signals (Chrispeels, M. J. and Raikhel, N. V. (1992) *Cell* 68:613-616), secretory pathway sequences such as those of the ER or Golgi (Chrispeels, M. J. (1991) *Ann. Rev. Plant Physiol. Plant Mol. Biol.* 42:21-53). Intraorganellar sequences may also be useful for internal sites, e.g., thylakoids in chloroplasts. Theg, S. M. and Scott, S. V. (1993) *Trends in Cell Biol.* 3:186-190.

In addition to 5' leader sequences, terminater sequences are usually incorporated into the construct. In plant constructs, a 3' untranslated region (3' UTR) is generally part of the expression plasmid and contains a polyA termination sequence. The termination region which is employed will generally be one of convenience, since termination regions appear to be relatively interchangeable. The octopine synthase and nopaline synthase termination regions, derived from the Ti-plasmid of *A. tumefaciens*, are suitable for such use in the constructs of this invention.

Any suitable technique can be used to introduce the nucleic acids and constructs of this invention to produce transgenic plants with an altered genome. For grasses such as *maize*, microprojectile bombardment (see for example, Sanford, J. C., et al., U.S. Pat. No. 5,100,792 (1992) can be used. In this embodiment, a nucleotide construct or a vector containing the construct is coated onto small particles which are then introduced into the targeted tissue (cells) via high velocity ballistic penetration. The vector can be any vector which permits the expression of the exogenous DNA in plant cells into which the vector is introduced. The transformed cells are then cultivated under conditions appropriate for the regeneration of plants, resulting in production of transgenic plants.

Transgenic plants carrying the construct are examined for the desired phenotype using a variety of methods including but not limited to an appropriate phenotypic marker, such as antibiotic resistance or herbicide resistance, or visual observation of the time of floral induction compared to naturally-occurring plants.

Other known methods of inserting nucleic acid constructs into plants include *Agrobacterium*-mediated transformation (see for example Smith, R. H., et al., U.S. Pat. No. 5,164,310 (1992)), electroporation (see for example, Calvin, N., U.S. Pat. No. 5,098,843 (1992)), introduction using laser beams (see for example, Kasuya, T., et al., U.S. Pat. No. 5,013,660 (1991)) or introduction using agents such as polyethylene glycol (see for example Golds, T. et al. (1993) *Biotechnology*, 11:95-97), and the like. In general, plant cells may be transformed with a variety of vectors, such as viral, episomal vectors, Ti plasmid vectors and the like, in accordance with well known procedures. The method of introduction of the nucleic acid into the plant cell is not critical to this invention.

The methods of this invention can be used with in planta or seed transformation techniques which do not require culture or regeneration. Examples of these techniques are described in Bechtold, N., et al. (1993) *CR Acad. Sci. Paris/Life Sciences* 316:118-93; Chang, S. S., et al. (1990) *Abstracts of the Fourth International Conference on Arabidopsis Research*, Vienna, p. 28; Feldmann, K. A. and Marks, D. M (1987) *Mol. Gen. Genet.* 208:1-9; Ledoux, L., et al. (1985) *Arabidopsis Inf. Serv.* 22:1-11; Feldmann, K. A. (1992) In: Methods in *Arabidopsis* Research (Eds. Koncz, C., Chua, N-H, Schell, J.) pp. 274-289; Chee, et al., U.S. Pat. No. 5,376,543.

The transcriptional initiation region may provide for constitutive expression or regulated expression. In addition to the ERA1 promoter, many promoters are available which are functional in plants.

Constitutive promoters for plant gene expression include, but are not limited to, the octopine synthase, nopaline synthase, or mannopine synthase promoters from *Agrobacterium*, the cauliflower mosaic virus (35S) promoter, the figwort mosaic virus (FMV) promoter, and the tobacco mosaic virus (TMV) promoter. Constitutive gene expression in plants can also be provided by the glutamine synthase promoter (Edwards, et al. (1990) *PNAS* 87:3459-3463), the *maize* sucrose synthetase 1 promoter (Yang, et al. (1990) *PNAS* 87:4144-4148), the promoter from the Rol-C gene of the TLDNA of Ri plasmid (Sagaya, et al. (1989) *Plant Cell Physiol.* 30:649-654), and the phloem-specific region of the pRVC-S-3A promoter (Aoyagi, et al. (1988) *Mol. Gen. Genet.* 213:179-185).

Heat-shock promoters, the ribulose-1,6-bisphosphate (RUBP) carboxylase small subunit (ssu) promoter, tissue specific promoters, and the like can be used for regulated expression of plant genes. Developmentally-regulated, stress-induced, wound-induced or pathogen-induced promoters are also useful.

The regulatory region may be responsive to a physical stimulus, such as light, as with the RUBP carboxylase ssu promoter, differentiation signals, or metabolites. The time and level of expression of the sense or antisense orientation can have a definite effect on the phenotype produced. Therefore, the promoters chosen, coupled with the orientation of the exogenous DNA, and site of integration of a vector in the genome, will determine the effect of the introduced gene.

Specific examples of regulated promoters also include, but are not limited to, the low temperature Kin1 and cor6.6 promoters (Wang, et al. (1995) *Plant Mol. Biol.* 28:605; Wang, et al. (1995) *Plant Mol. Biol.* 28:619-634), the ABA inducible promoter (Marcotte Jr., et al. (1989) *Plant Cell* 1:969-976), heat shock promoters, such as the inducible hsp70 heat shock promoter of *Drosphilia melanogaster* (Freeling, M., et al. (1985) *Ann. Rev. of Genetics* 19: 297-323), the cold inducible promoter from *B. napus* (White, T. C., et al. (1994) *Plant Physiol.* 106:917), the alcohol dehydrogenase promoter which is induced by ethanol (Nagao, R. T., et al., Miflin, B. J., Ed. *Oxford Surveys of Plant Molecular and Cell Biology*, Vol. 3, p 384-438, Oxford University Press, Oxford 1986), the phloem-specific sucrose synthase ASUS1 promoter from *Arabidopsis* (Martin, et al. (1993) *Plant J.* 4:367-377), the ACS1 promoter (Rodrigues-Pousada, et al. (1993) *Plant Cell* 5:897-911), the 22 kDa zein protein promoter from *maize* (Unger, et al. (1993) *Plant Cell* 5:831-841), the ps1 lectin promoter of pea (de Pater, et al. (1993) *Plant Cell* 5:877-886), the phas promoter from *Phaseolus vulgaris* (Frisch, et al. (1995) *Plant J.* 7:503-512), the lea promoter (Thomas, T. L. (1993) *Plant Cell* 5:1401-1410), the E8 gene promoter from tomato (Cordes, et al. (1989) *Plant Cell* 1: 1025-1034), the PCNA promoter (Kosugi, et al. (1995) *Plant J.* 7:877-886), the NTP303 promoter (Weterings, et al (1995) *Plant J.* 8:55-63), the OSEM promoter (Hattori, et al. (1995) *Plant J.* 7:913-925), the ADP GP promoter from potato (Muller-Rober, et al. (1994) *Plant Cell* 6:601-604), the Myb promoter from barley (Wissenbach, et al. (1993) *Plant J.* 4:411-422), and the plastocyanin promoter from *Arabidopsis* (Vorst, et al. (1993) *Plant J.* 4:933-945).

The vector can be introduced into cells by a method appropriate to the type of host cells (e.g., transformation, electroporation, transfection). For the purposes of this disclosure, the terms "transformed with", "transformant", "transformation", "transfect with", and "transfection" all refer to the introduction of a nucleic acid into a cell by one of the numerous methods known to persons skilled in the art. Transformation of prokaryotic cells, for example, is commonly achieved by treating the cells with calcium chloride so as to render them "competent" to take up exogenous DNA, and then mixing such DNA with the competent cells. Prokaryotic cells can also be infected with a recombinant bacteriophage vector.

Nucleic acids can be introduced into cells of higher organisms by viral infection, bacteria-mediated transfer (e.g., *Agrobacterium* T-DNA delivery system), electroporation, calcium phosphate co-precipitation, microinjection, lipofection, bombardment with nucleic-acid coated particles or other techniques, depending on the particular cell type. For grasses such as corn and sorghum, microprojectile bombardment as described, for example, in Sanford, J. C., et al., U.S. Pat. No. 5,100,792 (1992) can be used. Other useful protocols for the transformation of plant cells are provided in Gelvin et al., 1992. Suitable protocols for transforming and transfecting cells are also found in Sambrook et al., 1989. The nucleic acid constructs of this invention can also be incorporated into specific plant parts such as those described supra through the transformation and transfection techniques described herein.

To aid in identification of transformed plant cells, the constructs of this invention are further manipulated to include genes coding for plant selectable markers. Useful selectable markers include enzymes which provide for resistance to an antibiotic such as gentamycin, hygromycin, kanamycin, or the like. Similarly, enzymes providing for production of a compound identifiable by color change such as GUS (β-glucuronidase), or by luminescence, such as luciferase, are useful.

For example, antisense Ftase can be produced by integrating a complement of the ERA1 gene linked to DNA comprising SEQ ID NO:3 into the genome of a virus that enters the host cells. By infection of the host cells, the components of a system which permits the transcription of the antisense present in the host cells.

When cells or protoplasts containing the antisense gene driven by a promoter of the present invention are obtained, the cells or protoplasts are regenerated into whole plants. The transformed cells are then cultivated under conditions appropriate for the regeneration of plants, resulting in production of transgenic plants. Choice of methodology for the regeneration step is not critical, with suitable protocols being available for many varieties of plants, tissues and other photosynthetic organisms. See, e.g., Gelvin S. B. and Schilperoort R. A., eds. *Plant Molecular Biology Manual, Second Edition*, Suppl. 1 (1995) Kluwer Academic Publishers, Boston Mass., U.S.A.

Transgenic plants carrying the construct are examined for the desired phenotype using a variety of methods including but not limited to an appropriate phenotypic marker, such as antibiotic resistance or herbicide resistance as described supra, or visual observation of their growth compared to the growth of the naturally-occurring plants under the same conditions.

As used herein, the term transgenic plants includes plants that contain either DNA or RNA which does not naturally occur in the wild type (native) plant or known variants, or additional or inverted copies of the naturally-occurring DNA and which is introduced as described herein. Transgenic plants include those into which isolated nucleic acids have been introduced and their descendants, produced from seed, vegetative propagation, cell, tissue or protoplast culture, or the like wherein such alteration is maintained.

Such transgenic plants include, in one embodiment, transgenic plants which are angiosperms, both monocotyledons and dicotyledons. Transgenic plants include those into which DNA has been introduced and their progeny, produced from seed, vegetative propagation, cell, tissue or protoplast culture, or the like.

Seed can be obtained from the regenerated plant or from a cross between the regenerated plant and a suitable plant of the same species. Alternatively, the plant can be vegetatively propagated by culturing plant parts under conditions suitable for the regeneration of such plant parts.

In yet another aspect of this invention are provided plant tissue culture and protoplasts which contain DNA comprising antisense or an altered ERA1 nucleic acid operably linked to an ERA1 promoter, which alters the response of the tissue culture or protoplasts to varying environmental conditions.

The methods of this invention can also be used with in planta or seed transformation techniques which do not require culture or regeneration. Examples of these techniques are described in Bechtold, N., et al. (1993) *CR Acad. Sci. Paris/Life Sciences* 316:118-93; Chang, S. S., et al. (1990) *Abstracts of the Fourth International Conference on Arabidopsis Research*, Vienna, p. 28; Feldmann, K. A. and Marks, D. M (1987) *Mol. Gen. Genet.* 208:1-9; Ledoux, L., et al. (1985) *Arabidopsis Inf. Serv.* 22:1-11; Feldmann, K. A. (1992) In: Methods in *Arabidopsis* Research (Eds. Koncz, C., Chua, N-H, Schell, J.) pp. 274-289; Chee, et al., U.S. Pat. No. 5,376,543.

The isolated nucleic acid molecules of the invention can be used to express PPI protein (e.g., via a recombinant expression vector in a host cell), to detect PPI mRNA (e.g., in a biological sample) or a genetic lesion in a PPI gene, and to modulate PPI activity, as described further, below. In addition, the PPI proteins can be used to screen compounds that modulate the PPI protein activity or expression. In addition, the anti-PPI antibodies of the invention can be used to detect and isolate PPI proteins and modulate PPI activity.

The invention provides a method (also referred to herein as a "screening assay") for identifying modulators, i.e., candidate or test compounds or agents (e.g., peptides, peptidomimetics, small molecules or other drugs) that bind to PPI proteins or have a stimulatory or inhibitory effect on, e.g., PPI protein expression or PPI protein activity. The invention also includes compounds identified in the screening assays described herein.

In one embodiment, the invention provides assays for screening candidate or test compounds which bind to a PPI protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145. A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412-421), or on beads (Lam, 1991. *Nature* 354: 82-84), on chips (Fodor, 1993. *Nature* 364: 555-556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865-1869) or on phage (Scott and Smith, 1990. *Science* 249: 386-390; Devlin, 1990. *Science* 249: 404-406; Cwirla, et al., 1990. *Proc. Natl. Acad. Sci. U.S.A.* 87: 6378-6382; Felici, 1991. *J. Mol. Biol.* 222: 301-310; Ladner, U.S. Pat. No. 5,233,409).

In one embodiment, an assay is a cell-based assay in which a cell which expresses a PPI protein, or a biologically-active portion thereof, is contacted with a test compound and the ability of the test compound to bind to a PPI protein determined. The cell, for example, can be of mammalian origin, plant cell or a yeast cell. Determining the ability of the test compound to bind to the PPI protein can be accomplished, for example, by coupling the test compound with a radioisotope or enzymatic label such that binding of the test compound to the PPI protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a PPI protein, or a biologically-active portion thereof, with a known compound which binds PPI to form an assay mixture, contacting the assay mixture with a test compound, and determining the ability of the test compound to interact with a PPI protein, wherein determining the ability of the test compound to interact with a PPI protein comprises determining the ability of the test compound to preferentially bind to PPI protein or a biologically-active portion thereof as compared to the known compound.

In another embodiment, an assay is a cell-based assay comprising contacting a cell expressing a PPI protein, or a biologically-active portion thereof, with a test compound and determining the ability of the test compound to modulate (e.g., stimulate or inhibit) the activity of the PPI protein or biologically-active portion thereof. Determining the ability of the test compound to modulate the activity of PPI or a biologically-active portion thereof can be accomplished, for example, by determining the ability of the PPI protein to bind to or interact with a PPI target molecule. As used herein, a "target molecule" is a molecule with which a PPI protein binds or interacts in nature, for example, a molecule on the surface of a cell which expresses a PPI interacting protein, a molecule on the surface of a second cell, a molecule in the extracellular milieu, a molecule associated with the internal surface of a cell membrane or a cytoplasmic molecule. A PPI target molecule can be a non-PPI molecule or a PPI protein or polypeptide of the invention In one embodiment, a PPI target molecule is a component of a signal transduction pathway that facilitates transduction of an extracellular signal (e.g. a signal generated by binding of a compound to a membrane-bound molecule) through the cell membrane and into the cell. The target, for example, can be a second intercellular protein that has catalytic activity or a protein that facilitates the association of downstream signaling molecules with PPI.

Determining the ability of the PPI protein to bind to or interact with a PPI target molecule can be accomplished by one of the methods described above for determining direct binding. In one embodiment, determining the ability of the PPI protein to bind to or interact with a PPI target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a PPI-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a PPI protein or biologically-active portion thereof with a test compound and determining the ability of the test compound to bind to the PPI protein or biologically-active portion thereof. Binding of the test compound to the PPI protein can be determined either directly or indirectly as described above. In one such embodiment, the assay comprises contacting the PPI protein or biologically-active portion thereof with a known compound which binds PPI to form an assay mixture, contacting the assay mixture with a test compound, and determining the ability of the test compound to interact with a PPI protein, wherein determining the ability of the test compound to interact with a PPI protein comprises determining the ability of the test compound to preferentially bind to PPI or biologically-active portion thereof as compared to the known compound.

In still another embodiment, an assay is a cell-free assay comprising contacting PPI protein or biologically-active portion thereof with a test compound and determining the ability of the test compound to modulate (e.g. stimulate or inhibit) the activity of the PPI protein or biologically-active portion thereof. Determining the ability of the test compound to modulate the activity of PPI can be accomplished, for example, by determining the ability of the PPI protein to bind to a PPI target molecule by one of the methods described above for determining direct binding. In an alternative embodiment, determining the ability of the test compound to modulate the activity of PPI protein can be accomplished by determining the ability of the PPI protein further modulate a PPI target molecule. For example, the catalytic/enzymatic activity of the target molecule on an appropriate substrate can be determined as described above.

In yet another embodiment, the cell-free assay comprises contacting the PPI protein or biologically-active portion thereof with a known compound which binds PPI protein to form an assay mixture, contacting the assay mixture with a test compound, and determining the ability of the test compound to interact with a PPI protein, wherein determining the ability of the test compound to interact with a PPI protein comprises determining the ability of the PPI protein to preferentially bind to or modulate the activity of a PPI target molecule.

The cell-free assays of the invention are amenable to use of either the soluble form or the membrane-bound form of PPI protein. In the case of cell-free assays comprising the membrane-bound form of PPI protein, it may be desirable to utilize a solubilizing agent such that the membrane-bound form of PPI protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either PPI protein or its target molecule to facilitate separation of complexed from uncomplexed forms of one or both of the proteins, as well as to accommodate automation of the assay. Binding of a test compound to PPI protein, or interaction of PPI protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-PPI fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or PPI protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of PPI protein binding or activity determined using standard techniques.

Other techniques for immobilizing proteins on matrices can also be used in the screening assays of the invention. For example, either the PPI protein or its target molecule can be immobilized utilizing conjugation of biotin and streptavidin. Biotinylated PPI protein or target molecules can be prepared from biotin-NHS(N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with PPI protein or target molecules, but which do not interfere with binding of the PPI protein to its target molecule, can be derivatized to the wells of the plate, and unbound target or PPI protein trapped in the wells by antibody conjugation. Methods for detecting such complexes, in addition to those described above for the GST-immobilized complexes, include immunodetection of complexes using antibodies reactive with the PPI protein or target molecule, as well as enzyme-linked assays that rely on detecting an enzymatic activity associated with the PPI protein or target molecule.

In another embodiment, modulators of PPI protein expression are identified in a method wherein a cell is contacted with a candidate compound and the expression of PPI mRNA or protein in the cell is determined. The level of expression of PPI mRNA or protein in the presence of the candidate compound is compared to the level of expression of PPI mRNA or protein in the absence of the candidate compound. The candidate compound can then be identified as a modulator of PPI mRNA or protein expression based upon this comparison. For example, when expression of PPI mRNA or protein is greater (i.e., statistically significantly greater) in the presence of the candidate compound than in its absence, the candidate compound is identified as a stimulator of PPI mRNA or protein expression. Alternatively, when expression of PPI mRNA or protein is less (statistically significantly less) in the presence of the candidate compound than in its absence, the candidate compound is identified as an inhibitor of PPI mRNA or protein expression. The level of PPI mRNA or protein expression in the cells can be determined by methods described herein for detecting PPI mRNA or protein.

In yet another aspect of the invention, the PPI proteins can be used as "bait proteins" in a two-hybrid assay or three hybrid assay (see, e.g., U.S. Pat. No. 5,283,317; Zervos, et al., 1993. *Cell* 72: 223-232; Madura, et al., 1993. *J. Biol. Chem.* 268: 12046-12054; Bartel, et al., 1993. *Biotechniques* 14: 920-924; Iwabuchi, et al., 1993. *Oncogene* 8: 1693-1696; and Brent WO 94/10300), to identify other proteins that bind to or interact with PPI ("PPI-binding proteins" or "PPI-bp") and modulate PPI activity. Such PPI-binding proteins are also likely to be involved in the propagation of signals by the PPI proteins as, for example, upstream or downstream elements of the PPI pathway.

The two-hybrid system is based on the modular nature of most transcription factors, which consist of separable DNA-binding and activation domains. Briefly, the assay utilizes two different DNA constructs. In one construct, the gene that codes for PPI is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PPI-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with PPI.

In yet another aspect of the invention are methods which utilize the transgenic plants of the invention to identify PPI-interacting components via genetic screening protocols. These components can be for example, regulatory elements which modify PPI-gene expression, interacting proteins which directly modify PPI activity or interacting proteins which modify components of the same signal transduction pathway and thereby exert an effect on the expression or activity of PPI. Briefly, genetic screening protocols are applied to the transgenic plants of the invention and in so doing identify related genes which are not identified using a wild type background for the screen. For example an activation tagged library (Weigel, et al., 2000. *Plant Physiol.* 122: 1003-1013), can be produced using the transgenic plants of the invention as the genetic background. Plants are then screened for altered phenotypes from that displayed by the parent plants. Alternative methods of generating libraries from the transgenic plants of the invention can be used, for example, chemical or irradiation induced mutations, insertional inactivation or insertional activation methods.

The invention further pertains to novel agents identified by the aforementioned screening assays and uses thereof.

Recombinant Expression Vectors and Host Cells

Another aspect of the invention pertains to vectors, preferably expression vectors, containing a nucleic acid encoding a PPI protein, or derivatives, fragments, analogs or homologs thereof. As used herein, the term "vector" refers to a nucleic acid molecule capable of transporting another nucleic acid to which it has been linked. Exemplary expression vector constructs include for example the constructs of SEQ ID NO: 54-64. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication).

Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). Examples of suitable promoters include for example constitutive promoters, ABA inducible promoters, tissue specific promoters or guard cell specific promoters. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PPI proteins, mutant forms of PPI proteins, fusion proteins, etc.).

The recombinant expression vectors of the invention can be designed for expression of PPI proteins in prokaryotic or eukaryotic cells. For example, PPI proteins can be expressed in bacterial cells such as *Escherichia coli*, insect cells (using baculovirus expression vectors) yeast cells, plant cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., Gene Expression Technology: Methods in Enzymology 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

In another embodiment, the PPI expression vector is a yeast expression vector. Examples of vectors for expression in yeast *Saccharomyces cerivisae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, PPI can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In yet another embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CAMV) DNA and vectors such as pBI121.

For expression in plants, the recombinant expression cassette will contain in addition to the PPI nucleic acids, a plant promoter region, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector. Examples of suitable promoters include promoters from plant viruses such as the 35S promoter from cauliflower mosaic virus (CaMV). Odell, et al., Nature, 313: 810-812 (1985). and promoters from genes such as rice actin (McElroy, et al., Plant Cell, 163-171 (1990)); ubiquitin (Christensen, et al., Plant Mol. Biol., 12: 619-632 (1992); and Christensen, et al., Plant Mol. Biol., 18: 675-689 (1992)); pEMU (Last, et al., Theor. Appl. Genet., 81: 581-588 (1991)); MAS (Velten, et al., EMBO J., 3: 2723-2730 (1984)); *maize* H3 histone (Lepetit, et al., Mol. Gen. Genet., 231: 276-285 (1992); and Atanassvoa, et al., Plant Journal, 2(3): 291-300 (1992)), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as, Rsyn7, SCP and UCP promoters, ribulose-1,3-diphosphate carboxylase, fruit-specific promoters, heat shock promoters, seed-specific promoters and other transcription initiation regions from various plant genes, for example, include the various opine initiation regions, such as for example, octopine, mannopine, and nopaline.

Additional regulatory elements that may be connected to a PPI encoding nucleic acid sequence for expression in plant cells include terminaters, polyadenylation sequences, and nucleic acid sequences encoding signal peptides that permit localization within a plant cell or secretion of the protein from the cell. Such regulatory elements and methods for adding or exchanging these elements with the regulatory elements PPI gene are known, and include, but are not limited to, 3' termination and/or polyadenylation regions such as those of the *Agrobacterium tumefaciens* nopaline synthase (nos) gene (Bevan, et al., Nucl. Acids Res., 12: 369-385 (1983)); the potato proteinase inhibitor II (PINII) gene (Keil, et al., Nucl. Acids Res., 14: 5641-5650 (1986) and hereby incorporated by reference); and An, et al., Plant Cell, 1: 115-122 (1989)); and the CaMV 19S gene (Mogen, et al., Plant Cell, 2: 1261-1272 (1990)).

Plant signal sequences, including, but not limited to, signal-peptide encoding DNA/RNA sequences which target proteins to the extracellular matrix of the plant cell (Dratewka-Kos, et al., J. Biol. Chem., 264: 4896-4900 (1989)) and the *Nicotiana plumbaginifolia* extension gene (DeLoose, et al., Gene, 99: 95-100 (1991)), or signal peptides which target proteins to the vacuole like the sweet potato sporamin gene (Matsuka, et al., Proc. Nat'l Acad. Sci. (USA), 88: 834 (1991)) and the barley lectin gene (Wilkins, et al., Plant Cell, 2: 301-313 (1990)), or signals which cause proteins to be secreted such as that of PRIb (Lind, et al., Plant Mol. Biol., 18: 47-53 (1992)), or those which target proteins to the plastids such as that of rapeseed enoyl-ACP reductase (Verwaert, et al., Plant Mol. Biol., 26: 189-202 (1994)) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the patatin class I promoter is transcriptionally activated only in the potato tuber and can be used to target gene expression in the tuber (Bevan, M., 1986, *Nucleic Acids Research* 14:4625-4636). Another potato-specific promoter is the granule-bound starch synthase (GBSS) promoter (Visser, R. G. R, et al, 1991, *Plant Molecular Biology* 17:691-699).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, P., 1986, *Trans. R. Soc. London B*314:343).

For in situ production of the antisense mRNA of GST, those regions of the GST gene which are transcribed into GST mRNA, including the untranslated regions thereof, are inserted into the expression vector under control of the promoter system in a reverse orientation. The resulting transcribed mRNA is then complementary to that normally produced by the plant.

The resulting expression system or cassette is ligated into or otherwise constructed to be included in a recombinant vector which is appropriate for plant transformation. The vector may also contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in a an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of types of cells may act as suitable host cells for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana, Nicotiana tabacum, Brassica napus, Zea mays, Oryza sativa, Gossypium hirsutum* and *Glycine max.*

Alternatively, it may be possible to produce a polypeptide in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous proteins. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain a functional polypeptide, if the polypeptide is of sufficient length and conformation to have activity. Such covalent attachments may be accomplished using known chemical or enzymatic methods.

A polypeptide may be prepared by culturing transformed host cells under culture conditions suitable to express the recombinant protein. The resulting expressed polypeptide or protein may then be purified from such culture (e.g., from culture medium or cell extracts) using known purification processes, such as gel filtration and ion exchange chromatography. The purification of the polypeptide or protein may also include an affinity column containing agents which will bind to the protein; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, a polypeptide or protein may also be expressed in a form which will facilitate purification. For example, it may be expressed as a fusion protein containing a six-residue histidine tag. The histidine-tagged protein will then bind to a Ni-affinity column. After elution of all other proteins, the histidine-tagged protein can be eluted to achieve rapid and efficient purification. One or more reverse-phase high performance liquid chromatography (RP-HPLC) steps employing hydrophobic RP-HPLC media, e.g., silica gel having pendant methyl or other aliphatic groups, can be employed to further purify a polypeptide. Some or all of the foregoing purification steps, in various combinations, can also be employed to provide a substantially homogeneous isolated recombinant polypeptide. The protein or polypeptide thus purified is substantially free of other plant proteins or polypeptides and is defined in accordance with the present invention as "isolated."

Transformed Plants Cells and Transgenic Plants

The invention includes protoplast, plants cells, plant tissue and plants (e.g., monocots and dicots transformed with a PPI nucleic acid (i.e, sense or antisense), a vector containing a PPI nucleic acid (i.e, sense or antisense) or an expression vector containing a PPI nucleic acid (i.e, sense or antisense). As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Gossypium, Picea, Caco*, and *Populus.*

In some aspects of the invention, the transformed plant is resistant to biotic and abiotic stresses, e.g., chilling stress, salt stress, water stress (e.g., drought), disease, grazing pests and wound healing. Additionally, the invention also includes a transgenic plant that is resistant to pathogens such as for example fungi, bacteria, nematodes, viruses and parasitic weeds. Alternatively, the transgenic plant is resistant to herbicides or has delayed senescence. The transgenic plant has an increase in yield, productivity, biomass or ABA sensitivity. By resistant is meant the plant grows under stress conditions (e.g., high salt, decreased water, low temperatures) or under conditions that normally inhibit, to some degree, the growth of an untransformed plant. Methodologies to determine plant growth or response to stress include for example, height measurements, weight measurements, leaf area, ability to flower, water use, transpiration rates and yield.

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols. See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88 and Andrew Bent in, Clough S J and Bent A F, 1998. Floral dipping: a simplified method for *Agrobacterium*-mediated transformation of *Arabidopsis thaliana*. The methods chosen vary with the host plant, and include chemical transfection methods such as calcium phosphate, polyethylene glycol (PEG) transformation, microorganism-mediated gene transfer such as *Agrobacterium* (Horsch, et al., Science, 227: 1229-31 (1985)), electroporation, protoplast transformation, micro-injection, flower dipping and biolistic bombardment.

*Agrobacterium*-Mediated Transformation

The most widely utilized method for introducing an expression vector into plants is based on the natural transformation system of *Agrobacterium. A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, Crit. Rev. Plant Sci., 10:1-32 (1991).

Descriptions of the *Agrobacterium* vector systems and methods for *Agrobacterium*-mediated gene transfer are provided in Gruber et al., supra; and Moloney, et al, Plant Cell Reports, 8: 238-242 (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plant are inverted for 1 minute into a solution of *Agrobacterium* culture carrying the appropriate gene construct. Plants are then left horizontal in a tray and kept covered for two days to maintain humidity and then righted and bagged to continue growth and seed development. Mature seed is bulk harvested.

Direct Gene Transfer

A generally applicable method of plant transformation is microprojectile-mediated transformation, where DNA is carried on the surface of microprojectiles measuring about 1 to 4 mum. The expression vector is introduced into plant tissues with a biolistic device that accelerates the microprojectiles to speeds of 300 to 600 m/s which is sufficient to penetrate the plant cell walls and membranes. (Sanford, et al., Part. Sci. Technol., 5: 27-37 (1987); Sanford, Trends Biotech, 6: 299-302 (1988); Sanford, Physiol. Plant, 79: 206-209 (1990); Klein, et al., Biotechnology, 10: 286-291 (1992)).

Another method for physical delivery of DNA to plants is sonication of target cells as described in Zang, et al., BioTechnology, 9: 996-996 (1991). Alternatively, liposome or spheroplast fusions have been used to introduce expression vectors into plants. See, for example, Deshayes, et al., EMBO J., 4: 2731-2737 (1985); and Christou, et al., Proc. Nat'l. Acad. Sci. (USA), 84: 3962-3966 (1987). Direct uptake of DNA into protoplasts using CaCl.sub.2 precipitation, polyvinyl alcohol or poly-L-ornithine have also been reported. See, for example, Hain, et al., Mol. Gen. Genet., 199: 161 (1985); and Draper, et al., Plant Cell Physiol., 23: 451-458 (1982).

Electroporation of protoplasts and whole cells and tissues has also been described. See, for example, Donn, et al., (1990) In: Abstracts of the VIIth Intl. Congress on Plant Cell and Tissue Culture IAPTC, A2-38, page 53; D'Halluin et al., Plant Cell, 4: 1495-1505 (1992); and Spencer et al., Plant Mol. Biol., 24: 51-61 (1994).

Particle Wounding/*Agrobacterium* Delivery

Another useful basic transformation protocol involves a combination of wounding by particle bombardment, followed by use of *Agrobacterium* for DNA delivery, as described by Bidney, et al., Plant Mol. Biol., 18: 301-31 (1992). Useful plasmids for plant transformation include Bin 19. See Bevan, Nucleic Acids Research, 12: 8711-8721 (1984), and hereby incorporated by reference.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with cefotaxime plus kanamycin for the NPTII selection.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime plus kanamycin for selection.

Transfer by Plant Breeding

Alternatively, once a single transformed plant has been obtained by the foregoing recombinant DNA method, conventional plant breeding methods can be used to transfer the gene and associated regulatory sequences via crossing and backcrossing. Such intermediate methods will comprise the further steps of: (1) sexually crossing the transgenic plant with a plant from a second taxon; (2) recovering reproductive material from the progeny of the cross; and (3) growing transgenic plants from the reproductive material. Where desirable or necessary, the agronomic characteristics of the second taxon can be substantially preserved by expanding this method to include the further steps of repetitively: (1) backcrossing the transgenic progeny with non-transgenic plants from the second taxon; and (2) selecting for expression of an associated marker gene among the progeny of the backcross, until the desired percentage of the characteristics of the second taxon are present in the progeny along with the gene or genes imparting marker gene trait.

By the term "taxon" herein is meant a unit of botanical classification. It thus includes, genus, species, cultivars, varieties, variants and other minor taxonomic groups which lack a consistent nomenclature.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the gene and its activity to its progeny. A more preferred transgenic plant is homozygous for the gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the transgene.

EMBODIMENTS

The constructs and methods of this invention have numerous applications of commercial value, especially in the prevention of desiccation of plant tissues under periods of water stress. Genetic manipulation of crop plants incorporating inhibitors of Ftase or inactivation of the gene encoding endogenous plant Ftase would allow such plants to withstand transitory environmental stress and can broaden the environments where these plants can be grown. Thus, improving tolerance of crop plants to cold, salt and drought stress, can improve the yield of the plants under such adverse conditions.

The technology described herein can also be used to alter harvesting time and harvest quality of plants. For example, overexpression of Ftase could lead to faster drying times of crops, such as corn and other grasses. Drying corn involves the use of large amounts of propane gas. Drying times of crops such as hay, which dry naturally in the fields, could be shortened, making it less likely that rain would deteriorate the crop.

In addition, inhibition of farnesylation in plants can also be used to control the senescence program of the plants so that leaves can be maintained in a green state longer and fruits can be kept immature. For example, if an antisense construct of ERA1 or CaaX box inhibitor protein construct was placed under the control of a senescence-induced promoter, the plant would induce an inhibitor of farnesylation as the senescence program was initiated, which would in turn inhibit senescence. The result would be a plant which remains green or fruits which remain immature. Thus, the plant could be kept producing a product, such as a vegetative part, flower or fruit much longer. Thus, horticulturalists could produce plants which stayed green and continued to grow even though a wild-type plant of the same variety would senesce under the same conditions. Cut flowers could be maintained longer. Or a fruit could be kept immature, an important product for the vegetable industry where produce lifetime to market is extremely important.

Further, the inhibition of Ftase in fruits and vegetables can reduce wilting. Thus, wilting of produce during transport and shipping could be reduced. Fruits and vegetables on the grocery shelf would also require less misting to keep them fresh and flavorful, and there would be less need to wax produce such as cucumber, apples and oranges to keep them from drying out.

Less watering would also mean that fungal and bacterial attacks on the crops, or fruits and vegetables would be reduced. For example, plant diseases in the field which result from splashing of plant pathogens from the soil to the plant leaves and fruits could be inhibited.

In the field of horticulture, many drought-resistant varieties could be produced for landscaping and for use as ornamental house plants. Especially valuable would be varieties of plants which are used for potting, as ornamentals inside or outside homes and offices, and which can survive infrequent water. This would be a considerable boon for gardeners, especially during the droughty summer months where forgotten plants dry out quickly in the sun. Further, plants grown under trees and in other shady areas often experience drought conditions and limited light. The technology provided herein can provide plant varieties which can better survive under these conditions.

In a further embodiment, horticulturalists could find many uses for plants wherein lateral branching and/or flower numbers can be regulated with light/dark cycles. Examples of plants in which longer, unbranched stems would confer marketable advantage include roses, carnations, lilies, and the like. The ability to increase the number of flowers or florets on the plant is also a highly valuable asset. These traits could also be useful for many agricultural crops in that yields can be increased in a manner which also made harvesting of the crop easier.

Another benefit of the constructs and methods provided herein is that the ERA1 promoter is active in the guard cells of leaves. A portion of the ERA1 gene promoter can be fused to antisense nucleic acid to the ERA1 gene so Ftase activity is diminished only in the guard cells.

A further embodiment is the use of the drought-resistant trait as a selectable marker of transformation in plants, plant cells and plant tissues. One method of detecting transformation in plants consists of: (a) incorporating a nucleic acid construct comprising a promoter operably-linked to nucleic acid comprising antisense to SEQ ID NO: 1 or nucleic acid comprising a functional equivalent or fragment thereof of the antisense; (b) inserting the nucleic acid construct into a plant, plant cell or plant tissue; (c) growing the plant, or regenerating a plant from the plant cell or plant tissue until stomates are formed; and (d) placing the plant or regenerated plant under conditions wherein the plant is drought stressed, wherein survival of the plant under drought conditions compared to untransformed plants is indicative of transformation. Thus, this technology can be used as a selectable genetic marker, i.e., a visual marker especially when combined with plant selection and transformation schemes.

In addition, without resorting to stressing a transgenic plant, the branching and/or flowering habit of plants with loss of Ftase function differs substantially from that of wild-type plants and can be used as a marker for successful transformation. This method would be especially useful where in planta transformation techniques have been applied. Under diurnal light conditions, shoots of transgenic plants will demonstrate less lateral branching than that of untransformed shoots, thus indicating effective loss of Ftase activity without the use of selective antibiotic markers.

EXEMPLIFICATION

Example 1

Mutagenesis Conditions

*Arabidopsis* plants used in this study were grown under continuous light in soil- or agar-containing petri plates as described elsewhere (Haughn and Somerville 1986). Two distinct wild-types of *Arabidopsis* were used: Meyerowitz's Colombia (MCol) (Lelhe Seeds, Dripping Springs, Tex.) and Wassilewskija (Ws) (ABRC, Ohio State University). T-DNA mutagenized seeds were screened and mutants were isolated in the Wassilewskija background. These were obtained from the Ohio State *Arabidopsis* seed stock collection (ABRC stock numbers CS2606-2654). The T-DNA seed collection was comprised of 49 pools of 1200 fourth generation (T4) offspring derived from 100 mutagenized parents. A mutagenized parent was obtained by incubating wild-type (Ti) seeds overnight in a saturating *Agrobacterium* culture containing a T-DNA plasmid carrying a gene conferring kanamycin resistance. The seeds were then washed in water and planted into pots. T2 generation seed were obtained from each plant and tested for kanamycin resistance. Kanamycin-resistant plants were advanced to the T3 generation. T4 generation plants were given to the stock center. Each pool was screened separately.

Fast neutron-irradiated seeds were screened and mutants were isolated in Meyerowitz's Columbia background. Mutagenized wild-type seeds (N1) were irradiated with 60 Gy of fast neutrons and grown to the next generation. The N2 seeds were obtained as pools of approximately 11,000 seeds generated from 1387 N1 parents. Ten of these pools were screened separately for ABA supersensitive mutations. In the initial screen, all seeds had been stored at 4° C. and were plated without imbibing. For all subsequent screens, seeds were imbibed at 4° C. for one week on 0.3 μM ABA and scored for cotyledon emergence after 5-7 days at 22° C. in the light.

Example 2

Genetic Analysis

Mutant lines were backcrossed to wild type three times. T-DNA mutations were backcrossed to Ws and fast neutron mutants to MCol. Segregation of the era phenotype was followed by plating F2 seeds on both 0.3 μM ABA and imbibing four days at 4° C. Following imbibition, plates were transferred to room temperature in the light. Germination was measured as the presence or absence of expanded cotyledons in seedlings one week after imbibition. Double mutants were constructed by crossing lines homozygous for each mutation following segregation and identifying lines that carried one of the mutant phenotypes. The abi3 allele used in this study is abi3-6 (Nambara et al., 1994) and the abi1 allele is abi1-1 (Koomneef et al, 1982). The era1-2 allele was used as the era parent. Segregation analysis suggested era1 partially suppressed the insensitivity of abi1 to ABA, so F2 plants were first screened for insensitivity to 3 mM ABA, and F3 seed from these plants were scored for sensitivity to 0.3 μM ABA. Putative era1 abi1 double mutants were progeny-tested in the F4 generation and verified by DNA polymorphism analysis for both Era 1 and Abi1. For era1 abi3 double mutants, F2 seeds were screened for insensitivity to 3 μM ABA, and mature plants were scored for protruding carpels and immature green seeds (Nambara et al., 1994). Putative double mutant lines were also verified by DNA polymorphism analysis for both Era1 and Abi3.

Example 3

DNA and RNA Analysis

The methods employed for DNA (Dellaporta et al., 1983) and RNA (Verwoerd et al., 1989) extractions were as described elsewhere. High stringency Southern blots were carried out at 65° C. according to standard protocols described elsewhere (Sambrook et al., 1989). All genomic and cDNA library screening was done on Gelman BioTrace NT membranes according to the manufacturer's specifications (Gelman Sciences). To clone insertion junctions between T-DNA and genomic DNA in the era1-1 mutant (isolated from T12W DNA) a library of T12W DNA was made in γ-ZAPII (Stratagene). Genomic Southern blots of T12W DNA digested with restriction endonuclease EcoR I and probed with right border ($R^B$) T-DNA produced three bands (13.0 Kb, 7.0 Kb and 8.0 Kb). Subsequent analysis with additional restriction enzymes verified that the 7.0 and 8.0 Kb bands contained the insertion junctions between T-DNA and flanking plant DNA. These fragments were cloned by digesting genomic DNA with EcoR I, fractionating the digested DNA using a Prep Cell (Pharmacia), and identifying the fractions containing the 7.0 and 8.0 Kb by Southern blot analysis using the $R^B$ as a probe. Pooled fractions containing both the 7.0 and 8.0 Kb fragments were then ligated to the γ-ZAPII vector arms according to the manufacturer's instructions (Stratagene). A library containing approximately 40,000 individual recombinant bacteriophage was screened. Five positive plaques were identified and excised plasmid forms of the cloned inserts were isolated according to the manufacturer's instructions (Stratagene). Two plasmids which hybridized to the RB probe were designated pL4B and pL7 and selected for further characterization. A 2.3 kB EcoR I-BamH I restriction fragment from clone pL4B was subcloned into the plasmid pBluescript and designated pSC10. A 1.3 Kb Hind III-BamH I restriction fragment from clone pL7 was also subcloned into pBluescript and designated pSC11. Each of these plasmids contains approximately 1.2 Kb of T-DNA attached to the flanking plant genomic DNA. pSC10 was used as a probe to screen an *Arabidopsis* cDNA library called PRL2 λ-ZipLox (ABRC, Stock CD4-7). This screen identified five positive cDNAs, and the longest cDNA insert, clone pZL23, was used to screen an additional 200,000 recombinant PRL2 phage. Subsequently a longer cDNA insert, clone pZL51, which contained an insert of 1.35 Kb, was isolated. Both cDNA clones pZL23 and pZL51 were sequenced and used to screen 30,000 γ-ZAPII plaques made from wild-type Columbia genomic DNA partially digested with EcoR I. Construction of this library was as described above except the digested DNA was not size-fractionated. This screen identified four positive clones. The inserts were excised and excised plasmid forms of the cloned inserts were isolated according to the manufacturer's instructions. A 6 Kb region encompassing the entire pZL51 clone was completely sequenced. This genomic insert and a 14 Kb genomic insert isolated by screening a λ-FIX genomic library from *Lansberg erecta* via similar methods (ABRC Stock CD4-8) were used as probes to analyze deletion size in the fast neutron mutants era1-2 and era1-3.

Example 4

Protein Farnesyl Transferase Assay

Farnesyl transferase (Ftase) assays were performed using Ftase from cell-free extracts of wild-type and mutant plants and synthetic heptapeptides as substrate for the reaction. Peptides were purchased from Genemed Biotechnologies, Inc. The peptide sequences used were based on the data of Randall et al. (1993): GGCCAIM (-CAIM) and GGCCAIL (-CAIL). Solutions of peptides were prepared in 100% dimethyl sulfoxide (DMSO) containing 10 mM dithiotreitol (DTT) and diluted in 10 mM DTT without DMSO. The cell-free extracts contained soluble protein isolated from the buds of three week old plants, either wild-type or mutant strains. First 1 g of fresh buds was collected and homogenized in a buffer containing 50 mM Hepes (pH 7.5), 1 mM $MgCl_2$, 1 mM EGTA, 5 mM DTT, 2 μg/ml leupeptin, 2 μg/ml aprotinin, and 1 mM PMSF. Next, cellular debris and membranes were removed by centrifugation at 4° C. at 10,000×g for 10 minutes and 100,000×g for 30 minutes. Following the second centrifugation, the supernatant was decanted and total soluble protein was quantified by the method of Bradford (1976). Soluble protein extracts were incubated at 30° C. with a peptide substrate and radio-labeled $^3$H-farnesyl pyrophosphate (FPP) (Amersham) for 40 minutes. Each reaction mixture contained the following components in a final volume of 25 μl: 50 mM Hepes (pH 7.5), 5 mM $MgCl_2$, 5 mM DTT, 50 μM peptide, 0.5 μM [$^3$H]FPP, and 100 μg of soluble protein extract. One control reaction contained soluble protein extracts that had been boiled for 5 minutes to irreversibly denature all protein. Reactions were terminated by adding EDTA to a final concentration of 50 mM and then spotted onto Silica Gel 60 thin-layer chromatography (TLC) plates (Millipore). TLC plates were developed with n-propanol and water (7:3 v/v) for 4-5 hours. The plates were dried, sprayed with En$^3$Hance (New England Nuclear), and exposed to Kodak X-OMAT AR film at −70° C. for 4 days.

Example 5

ERA1-β-glucuronidase Gene Constructs and Transgenic Plants

ERA1-β-glucuronidase (ERA1-GUS) fusion constructs were made by inserting a 5 Kb EcoR I-Hind III genomic fragment of the ERA1 promoter into a promoterless GUS T-DNA plasmid pBT121 containing a gene conferring resistance to the antibiotic ampicillin. This construct was then transformed into *Agrobacterium* strain LB4404. The *Agrobacterium* was grown to a density of 0.8 O.D. units (measured at 595 nm). The cells were then washed extensively in water, resuspended in sterile 10% glycerol and purified plasmid DNA encoding the ERA1-GUS fusion construct was added. Finally, the mixture of cells and DNA was pulsed in an electroporator at 200 Ohms 25 RF, 2.5 kvolts. Cells were then plated on Luria Broth agar plates containing 100 μg/ml ampicillin and grown for 2 days at 28° C. Ampicillin-resistant transformants were cultured and plasmid DNA isolated from the cultures by standard techniques was used in subsequent plant transformation experiments.

Transgenic plants were made by vacuum infiltrating plants with a saturated *Agrobacterium* culture grown to a density of 0.8 O.D. units as measured at 595 nm. Wild-type plants were grown under standard laboratory conditions (at 25° C., 150 $μm^{-2}$ $sec^{-1}$, humidity, constant light) until they produced their first bolts at approximately 5 weeks. Next, plant stems were removed and the plants were submerged in a solution of *Agrobacterium* and placed under a 20 mBar vacuum for 5 minutes. After the vacuum was broken, the plants were transferred to soil and allowed to recover under standard laboratory conditions as described above. After two months, the plants produced new flowers and seed which was harvested and allowed to dry for 2 weeks. Seed from individual plants were planted onto Murashige and Skoog (MS) minimal medium plates containing 50 μg/ml kanamycin. Green kanamycin-resistant plantlets were identified and transferred to soil after 2 weeks and allowed to grow for seed. These seeds were germinated and the seedlings were tested for GUS activity using the fluorescent GUS substrate Imagene Green (Molecular Probes, Eugene, Oreg.). GUS activity was assayed by suspending seedlings in GUS buffer (50 mM Sodium phosphate, pH 7.0, 10 mM EDTA, 0.1% Triton X-100, 0.1% Sodium sarcosyl, 4 mM Imagene Green) for 2-4 hours in the dark at room temperature. Seedlings were viewed under a microscope at 25× magnification using blue light to generate a positive fluorescent signal. When this mixture is treated with blue light, GUS activity will produce yellow light in a background of red auto-fluorescence generated by red chlorophyll.

Example 6

Drought Experiments

Six wild-type and six era1-2 seedlings were grown for four weeks in constant light with constant watering (25° C., 150 $μm^{-2}$ $sec^{-1}$, 70% humidity, constant light). The plant and pot were weighed and the pots were then covered with aluminum foil to retard soil evaporation. At this time, plants were no longer watered and each pot was weighed daily. At the end of the experiment plants were removed from the pots, which were allowed to dry for another two weeks, when they were weighed to determine the weight of the dry soil and pot. This weight was subtracted from each sample.

Example 7

Age-Related Changes in Detached Leaves

The chlorophyll content in adult rosette leaves in wild-type Columbia and era1-2 mutants were compared after detachment from plants. The plants were grown under constant light and temperature (150 $μE/m^2$·sec, 22° C.) to a similar developmental age of 3 weeks after germination. At this time, the fifth leaves of several plants which had emerged after germination were removed and placed on petri plates containing 0.8% agar with minimal salts. The plates were sealed and placed at 22° C. under constant light (50 $μE/m^2$·sec) for 12 days. Photographs were taken and color comparisons made at 0, 3, 6, 9, and 12 days.

Example 8

Determination of Transcript Levels for Selected Genes in Aging Leaves

Mutant (era1-2) and wild-type plants were grown under constant light and temperature (150 $μE/m^2$·sec, 22° C.) to a similar developmental age of 4 weeks after germination. At that time, the fifth rosette leaf which had emerged following germination was removed from all plants. These leaves were assayed for expression levels of three genes: *Arabidopsis* chlorophyll binding protein (CAB) and senescence-activated genes 12 and 13 (SAG12 and SAG13). mRNA transcript levels were assayed by Northern blot analysis at 0, 4, 8 days after the plants bolted. The CAB gene encodes the *Arabidopsis* chlorophyll binding protein which is involved in capturing light for photosynthesis. It is required for the green color of the leaf and is a good marker of chlorophyll turnover in the plant. CAB in wild-type plants shows transcript level reduction upon induction of senescence. No transcript level reduction was observed in aging leaves of era1-2 mutants. SAG12 and SAG13 are *Arabidopsis* genes cloned by differential expression during senescence (SAG stands for senescence activated gene). Transcription of both genes is induced during the onset of senescence in wild-type *Arabidopsis* plants.

These genes were not induced under the same developmental conditions in the era1-2 mutants.

Example 9

Cloning of *Arabidopsis thaliana* FTA and Construction of Transformation Vector

The *Arabidopsis thaliana* FTA sequence was obtained by RT-PCR from total RNA isolated from leaf tissue using primers corresponding to SEQ ID NO: 17 and SEQ ID NO:18. The resulting fragment was digested with BamHI and SmaI and cloned into the plasmid pCR2.1 The Clonetech vector pBI121 was used as the backbone for the antisense construct. The GUS gene was removed by BamHI and Eco1 CR1 digestion and replaced with the FTA insert that was cut from pCR2.1-FTA using SmaI and BamHI and ligated into the vector SEQ ID NO: 10.

TABLE 1

| | |
|---|---|
| SEQ ID NO: 17: | 5'-AAAGGATCCTCAAATTGCTGCCACTGTAAT-3' |
| SEQ ID NO: 18: | 5'-AAACCCGGGATGAATTTCGACGAGAACGTG-3' |

Example 10

Cloning of Non-Full Length *Brassica napus* FTA and FTB Nucleic Acid Sequences

RNA was isolated from leaf and root tissue using the Qiagen RNeasy kit. RT-PCR was performed by known techniques using the primers shown in Table 2. The FTA sequence was obtained using the primer pair SEQ ID NO:25 and SEQ ID NO:26. The FTB sequence was obtained using the primer pair SEQ ID NO:27 and SEQ ID NO:28.

TABLE 2

| | |
|---|---|
| SEQ ID NO: 25: | 5'-GGATCCATGGATTACTTCCGTGCGATTTAC TTCTCC-3' |
| SEQ ID NO: 26: | 5'-AAAAAGCTTCCATGCCCAATAGTTAGCTCT TATTGGATC-3' |
| SEQ ID NO: 27: | 5'-AAAAAGCTTTGGCTTTGTTACTGGATTCTTCAT TCAAT-3' |
| SEQ ID NO: 28: | 5'-AAATCTAGAAGCTTCATAATACCGATCC AAGACAATGTT-3' |

PCR products were separated from the RT-PCR reaction mixture using the Qiagen PCR column spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 11

Cloning of Non-Full Length FTA and FTB Nucleic Acid Sequences from *Glycine max* and *Zea maize*

RNA was isolated from leaf and root tissue using the Qiagen RNeasy kit. RT-PCR was performed by known techniques using the primers shown in Table 3. The *Glycine max*

FTA sequence was obtained using the primer pair SEQ ID NO:29 and SEQ ID NO:30. The *Glycine max* FTB sequence was obtained using the primer pair SEQ ID NO:31 and SEQ ID NO:32. The *Zea maize* FTB sequence was obtained using the primer pair SEQ ID NO:33 and SEQ ID NO:34

TABLE 3

| | |
|---|---|
| SEQ ID NO: 29: | 5'-AAAGGATCCATGGAATCTGGGTCTAGCGA-3' |
| SEQ ID NO: 30: | 5'-AAATCTAGAAGGAAGTCTGCTCTTGCGC-3' |
| SEQ ID NO: 31: | 5'-AAATCTAGAGCCACCATTCCTCGCAACG-3' |
| SEQ ID NO: 32: | 5'-AAAGAGCTCGTGGTGGTGAATCTGGGTGC-3' |
| SEQ ID NO: 33: | 5'-GGCGGATCCCGACCTACCGAGG-3' |
| SEQ ID NO: 34: | 5'-AAAGAGCTCGTGGATGGATTGGCTCCAGC-3' |

PCR products were separated from the RT-PCR reaction mixture using the Qiagen PCR column spin kit and ligated into the cloning vector pBluescript KS +. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 12

Sequence Analysis

*Arabidopsis thaliana* FTA

A disclosed nucleic acid of 999 nucleotides (also referred to as FT1) is shown in Table 4A. The primers used in the PCR are depicted in bold.

TABLE 4A

| FT1 Nucleotide Sequence (SEQ ID NO: 7). |
|---|
| **Aaacccgggatgaatttcgacgagaccgtg**ccactgagccaacgattgga |
| gtggtcagacgtggtcccattgactcaggacgatggtccgaatccagtgg |
| tgccaattgcctacaaggaagagttccgcgagactatggattacttccgt |
| gcgatttacttttccgacgagcgatctcctcgcgcactacgactcacgga |
| agaaaccctcctcttaaactccggcaactacacagtgtggcatttcaggc |
| gcctagtactcgaggcccttaatcacgacttgtttgaagaactcgagttc |
| atcgaacgcattgctgaggataactctaagaactaccaactgtggcatca |
| tcggcgatgggttgcagagaaactgggtcctgatgttgcagggagagaac |
| ttgaatttacccgtagagtactttcacttgatgccaaacattatcatgct |
| tggtcacataggcagtggacactacgggcattaggaggatgggaagatga |
| gctcgattactgtcacgagctccttgaagctgacgtctttaacaattccg |
| cctggaatcagaggtattatgtcatcacccaatctcctttgttgggaggc |
| ctagaagccatgagagaatctgaagtaagctacacaatcaaagccatttt |
| aaccaatcctgcaaacgagagctcatggcgatacctaaaagcgctttaca |
| aagacgacaaagaatcctggattagtgatccaagtgtttcctcagtctgt |
| ttgaatgttctatcccgcacagattgcttccatggattcgctctgagcac |
| ccttttggatcttctatgtgatggactgagaccaaccaacgagcataaag |

TABLE 4A-continued

| FT1 Nucleotide Sequence (SEQ ID NO: 7). |
| --- |
| actcagtgagagctctagctaatgaagaaccagagactaacttggccaat |
| ttggtgtgtactattcttggtcgtgtagatcctataagagctaactattg |
| ggcatggaggaagagcaagatt**acagtggcagcaatttgaggatccttt** |

A disclosed FT1 polypeptide (SEQ ID NO: 11) encoded by SEQ ID NO:7 has 326 amino acid residues and is presented in Table 4B using the one-letter amino acid code.

TABLE 4B

| Encoded FT1 protein sequence (SEQ ID NO: 11). |
| --- |
| MNFDETVPLSQRLEWSDVVPLTQDDGPNPVVPIAYKEEFRETMDYFRAIY |
| FSDERSPRALRLTEETLLLNSGNYTVWHFRRLVLEALNHDLFEELEFIER |
| IAEDNSKNYQLWHHRRWVAEKLGPDVAGRELEFTRRVLSLDAKHYHAWSH |
| RQWTLRALGGWEDELDYCHELLEADVFNNSAWNQRYYVITQSPLLGGLEA |

TABLE 4B-continued

| Encoded FT1 protein sequence (SEQ ID NO: 11). |
| --- |
| MRESEVSYTIKAILTNPANESSWRYLKALYKDDKESWISDPSVSSVCLNV |
| LSRTDCFHGFALSTLLDLLCDGLRPTNEHKDSVRALANEEPETNLANLVC |
| TILGRVDPIRANYWAWRKSKITVAAI |

Due to the nature of the cloning strategy the sequence presented does not contain any 5' or 3' non-translated sequence. Using the sequences disclosed herein as hybridization probes, one is able to screen and isolate full length sequences from cDNA or genomic libraries or use the rapid amplification of cDNA ends (RACE) technology or other such PCR techniques. The percent identity of the *Arabidopsis thaliana* nucleotide sequence and its encoded amino acid sequence to that of published sequences is shown in FIG. 17.

The present invention also includes a nucleic acid sequence complementary to the *Arabidopsis thaliana* farnesyl transferase alpha subunit of SEQ ID NO:7. The disclosed complementary sequence is shown as SEQ ID NO:8. The nucleic acid sequence of SEQ ID NO:9 shows the nucleic acid sequence of SEQ ID NO:8 that has been prepared for ligation into an expression vector.

SEQ ID NO: 8 aaaggatcctcaaattgctgccactgtaatcttgctcttcctccatgcccaatagttagctctt ataggatctacacgaccaagaatagtacacaccaaattggccaagttagtctctggttcttcat tagctagagctctcactgagtctttatgctcgttggttggtctcagtccatcacatagaagatc caaaagggtgctcagagcgaatccatggaagcaatctgtgcgggatagaacattcaaacagact gaggaaacacttggatcactaatccaggattctttgtcgtctttgtaaagcgcttttaggtatc gccatgagctctcgtttgcaggattggttaaaatggctttgattgtgtagcttacttcagattc tctcatggcttctaggcctcccaacaaaggagattgggtgatgacataatacctctgattccag gcggaattgttaaagacgtcagcttcaaggagctcgtgacagtaatcgagctcatcttcccatc ctcctaatgcccgtagtgtccactgcctatgtgaccaagcatgataatgtttggcatcaagtga aagtactctacgggtaaattcaagttctctccctgcaacatcaggacccagtttctctgcaacc catcgccgatgatgccacagttggtagttcttagagttatcctcagcaatgcgttcgatgaact cgagttcttcaaacaagtcgtgattaagggcctcgagtactaggcgcctgaaatgccacactgt gtagttgccggagtttaagaggagggtttcttccgtgagtcgtagtgcgcgaggagatcgctcg tcggaaaagtaaatcgcacggaagtaatccatagtctcgcggaactcttccttgtaggcaattg gcaccactggattcggaccatcgtcctgagtcaatgggaccacgtctgaccactccaatcgttg gctcagtggcacggtctcgtcgaaattcatcccgggttt

SEQ ID NO: 9

*gat*tcaaattgctgccactgtaatcttgctcttcctccatgcccaatagttagctcttatag gatctacacgaccaagaatagtacacaccaaattggccaagttagtctctggttcttcattagc tagagctctcactgagtctttatgctcgttggttggtctcagtccatcacatagaagatccaaa agggtgctcagagcgaatccatggaagcaatctgtgcgggatagaacattcaaacagactgagg aaacacttggatcactaatccaggattctttgtcgtctttgtaaagcgcttttaggtatcgcca tgagctctcgtttgcaggattggttaaaatggctttgattgtgtagcttacttcagattctctc atggcttctaggcctcccaacaaaggagattgggtgatgacataatacctctgattccaggcgg aattgttaaagacgtcagcttcaaggagctcgtgacagtaatcgagctcatcttcccatcctcc -continued taatgcccgtagtgtccactgcctatgtgaccaagcatgataatgtttggcatcaagtgaaagt
actctacgggtaaattcaagttctctccctgcaacatcaggacccagtttctctgcaacccatc
gccgatgatgccacagttggtagttcttagagttatcctcagcaatgcgttcgatgaactcgag
ttcttcaaacaagtcgtgattaagggcctcgagtactaggcgcctgaaatgccacactgtgtag
ttgccggagtttaagaggagggtttcttccgtgagtcgtagtgcgcgaggagatcgctcgtcgg
aaaagtaaatcgcacggaagtaatccatagtctcgcggaactcttccttgtaggcaattggcac
cactggattcggaccatcgtcctgagtcaatgggaccacgtctgaccactccaatcgttggctc
agtgg**cacggtctcgtcgaaattcat*ccc***

*Brassica napus* FTA

A disclosed nucleic acid of 822 nucleotides (also referred to as FT2) is shown in Table 5A.

TABLE 5A

| FT2 Nucleotide Sequence (SEQ ID NO: 12). |
|---|
| ATGGATTACTTCCGTGCGATTTACTTCTCCGACGAGCGTTCTGCTCGCGC |
| GCTGCGACTCACGGAAGAAGCTCTCCGCTTAAACTCGGGCAACTACACCG |
| TGTGGCACTTCGGGCGCTTAGTACTCGAGGAGCTTAATAACGACTTGTAT |
| GAAGAGCTCAAGTTCATCGAAAGCATTGCTGAGGATAACTCTAAGAACTA |
| CCAGTTGTGGCATCATCGACGATGGGTCGCAGAGAAACTGGGTCCTGATG |
| TTGCAGGAAAGGAACTTGAGTTTACTCGGAGGGTACTATCACTTGATGCC |
| AAGCATTATCATGCTTGGTCACATAGGCAGTGGGCGCTACAAGCATTAGG |
| AGGATGGGAAAATGAGCTTAACTACTGCCACGAGCTCCTTGAAGCTGACG |
| TCTTTAACAACTCTGCATGGAATCAGAGGTATTACGTTATAACTAGATCA |
| CCTTCGTTGGGAGGCCTAGAAGCCATGAGAGAATCTGAAGTAAGCTACAC |
| AGTCAAAGCCATTTTAGCAAATCCCGGGAACGAGAGCTCTTGGAGGTACC |
| TGAAAGCCCTTTACAAAGACGACACAGAGTCTTGGATTAGTGATCCAAGT |
| GTTTCCTCAGTCTGTTTGAAAGTTCTCTCACGCGCGGACTGCTTCCATGG |
| ATTCGCTCTGAGCACCCTTTTGGATCTTCTGTGCGATGGGTTGAGACCAA |
| CCAACGAGCATAGAGACTCGGTGAAAGCTCTAGCTAATGAAGAACCAGAG |
| ACTAACTTGGCCAATTTGGTGTGTACCATTCTGTGTCGTGTTGATCCAAT |
| AAGAGCTAACTATTGGGCATGG |

A disclosed FT2 polypeptide (SEQ ID NO: 13) encoded by SEQ ID NO: 12 has 274 amino acid residues and is presented in Table 5B using the one-letter amino acid code.

TABLE 5B

| Encoded FT2 protein sequence (SEQ ID NO: 13). |
|---|
| MDYFRAIYFSDERSARALRLTEEALRLNSGNYTVWHFGRLVLEELNNDLY |
| EELKFIESIAEDNSKNYQLWHHRRWVAEKLGPDVAGLEKEFTRRVLSLDA |
| KHYHAWSHRQWALQALGGWENELNYCHELLEADVFNNSAWNQRYYVITRS |
| PSLGGLEAMRESEVSYTVKAILANPGNESSWRYLKALYKDDTESWISDPS |

TABLE 5B-continued

| Encoded FT2 protein sequence (SEQ ID NO: 13). |
|---|
| VSSVCLKVLSRADCFHGFALSTLLDLLCDGLRPTNEHRDSVKALANEEPE |
| TNLANLVCTILCRVDPIRANYWAWKL |

Due to the nature of the cloning strategy the sequence presented is not full length. Compared to the *Arabidopsis thaliana* sequence there are 42 amino acids missing from the amino terminus and 10 amino acids from the carboxy terminus. The percent identity of the *Brassica napus* nucleotide sequence and its encoded amino acid sequence to that of published sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complementary to the *Brassica napsus* farnesyl transferase alpha subunit of SEQ ID NO:12. The disclosed complementary sequence is shown as SEQ ID NO:35.

SEQ ID NO: 35

CCATGCCCAATAGTTAGCTCTTATTGGATCAACACGACACAGAATGGTAC
ACACCAAATTGGCCAAGTTAGTCTCTGGTTCTTCATTAGCTAGAGCTTT
CACCGAGTCTCTATGCTCGTTGGTTGGTCTCAACCCATCGCACAGAAG
ATCCAAAAGGGTGCTCAGAGCGAATCCATGGAAGCAGTCCGCGCGTGAG
AGAACTTTCAAACAGACTGAGGAAACACTTGGATCACTAATCCAAGACT
CTGTGTCGTCTTTGTAAAGGGCTTTCAGGTACCTCCAAGAGCTCTCGTT
CCCGGGATTTGCTAAAATGGCTTTGACTGTGTAGCTTACTTCAGATTCT
CTCATGGCTTCTAGGCCTCCCAACGAAGGTGATCTAGTTATAACGTAAT
ACCTCTGATTCCATGCAGAGTTGTTAAAGACGTCAGCTTCAAGGAGCTC
GTGGCAGTAGTTAAGCTCATTTTCCCATCCTCCTAATGCTTGTAGCGCC
CACTGCCTATGTGACCAAGCATGATAATGCTTGGCATCAAGTGATAGTA
CCCTCCGAGTAAACTCAAGTTCCTTTCCTGCAACATCAGGACCCAGTTT
CTCTGCGACCCATCGTCGATGATGCCACAACTGGTAGTTCTTAGAGTTA
TCCTCAGCAATGCTTTCGATGAACTTGAGCTCTTCATACAAGTCGTTATT
AAGCTCCTCGAGTACTAAGCGCCCGAAGTGCCACACGGTGTAGTTGCC

-continued

CGAGTTTAAGCGGAGAGCTTCTTCCGTGAGTCGCAGCGCGCGAGCAGA

ACGCTCGTCGGAGAAGTAAATCGCACGGAAGTAATCCAT

*Brassica napus* FTB

A disclosed nucleic acid of 1110 nucleotides (also referred to as FT3) is shown in Table 6A.

TABLE 6A

| FT3 Nucleotide Sequence (SEQ ID NO: 14). |
|---|
| TGGCTTTGTTACTGGATTCTTCATTCAATTGCTTTGCTTGGGGAGTCTGT |
| GGATGATGACTTAGAAAACAATGCAATCGATTTTCTTGGACGTTGCCAG |
| GGTTCTGATGGTGGATATGGTGGTGGTCCTGGCCAACTTCCACATCTTG |
| CAACAAGTTATGCTGCAGTGAATACACTTGTTACTTTAGGAGGTGAGAA |
| AGCCTTCTCTTCAATTAACAGAGAACAAATGGCTTGTTTCTTAAGACGAA |
| TGAAGGATACAAATGGAGGTTTCAGGATGCATAATATGGGAGAAATAGAT |
| GTGCGAGCGTGCTACACTGCGATTTTGATTGCAAGCATCCTGAACATTG |
| TGGATGATGAACTCACCCGCGGCTTAGGAGATTACATTTTGAGTTGCCA |
| ACTTATGAAGGTGGCATTGGAGGGGAACCTGGCTCCGAAGCTCATGGT |
| GGGTACACGTACTGTGGGTTGGCTACTATGATTTTAATCAATGAAGTCGA |
| CCGCTTGAATTTGGATTCGTTAATGAATTGGGTTGTACATCGACAAGGAG |
| TAGAAATGGGATTCCAAGGTAGGACGAACAAATTGGTCGACGGTTGCTA |
| CACGTTTTGGCAGGCAGCCCCCTGTGTTCTACTACAGCGATTTTTTTCAT |
| CCCAGGATATGGCACCTCATGGATCATCATCACATATGTCACAAGGGAC |
| AGATGAAGATCACGAGGAACATGGTCATGATGAAGATGATCCTGAAGAC |
| AGTGATGAAGATGATTCTGATGAGGATAGCGATGAAGATTCAGGGAATGG |
| TCACCAAGTTCATCATACGTCTACCTACATTGACAGGAGAATTCAACCTG |
| TTTTTGATAGCCTCGGCTTGCAAAGATATGTGCTCTTGTGCTCTCAGGT |
| TGCTGATGGTGGATTCAGAGACAAGCTGAGGAAACCCCGTGACTTCTA |
| CCACACATGTTACTGCCTAAGCGGTCTTTCCGTGGCTCAACACGCTTG |
| GTCAAAAGACGAGGACACTCCTCCTTTGACTCGTGACATTTTGGGTGG |
| CTACGCAAACCACCTTGAACCTGTTCACCTCCTCCACAACATTGTCTT |
| GGATCGGTATTATGAAGCTTCTAGATTT |

A disclosed FT3 polypeptide (SEQ ID NO: 15) encoded by SEQ ID NO: 13 has 370 amino acid residues and is presented in Table 6B using the one-letter amino acid code.

TABLE 6B

| Encoded FT3 protein sequence (SEQ ID NO: 15). |
|---|
| WLCYWILHSIALLGESVDDDLENNAIDFLGRCQGSDGGYGGGPGQLPHLA |
| TSYAAVNTLVTLGGEKAFSSINREQMACFLRRMKDTNGGFRMHNMGEIDV |
| RACYTAILIASILNIVDDELTRGLGDYILSCQTYEGGIGGEPGSEAHGGY |
| TYCGLATMILINEVDRLNLDSLMNWVVHRQGVEMGFQGRTNKLVDGCYTF |
| WQAAPCVLLQRFFSSQDMAPHGSSSHMSQGTDEDHEEHGHDEDDPEDSD |
| EDDSDEDSDEDSGNGHQVHHTSTYIDRRIQPVFDSLGLQRYVLLCSQVA |

TABLE 6B-continued

| Encoded FT3 protein sequence (SEQ ID NO: 15). |
|---|
| DGGFRDKLRKPRDFYHTCYCLSGLSVAQHAWSKDEDTPPLTRDILGGYA |
| NHLEPVHLLHNILVDRYYEASRF |

Due to the nature of the cloning strategy the sequence presented is not full length. Compared to the *Arabidopsis thaliana* sequence there are 31 amino acids missing from the amino terminus and 5 amino acids from the carboxy terminus. The percent identity of the *Brassica napus* nucleotide sequence and its encoded amino acid sequence to that of published sequences is shown in FIG. 18.

Using the sequences disclosed herein as hybridization probes, one is able to screen and isolate full length sequences from cDNA or genomic libraries or use the rapid amplification of cDNA ends (RACE) technology or other such PCR techniques. Sequence comparisons have been performed and percent identities are shown in FIG. 17 and FIG. 18.

The present invention also includes a nucleic acid sequence complementary to the *Brassica napsus* farnesyl transferase beta subunit of SEQ ID NO:14. The disclosed complementary sequence is shown as SEQ ID NO:36.

SEQ ID NO: 36

AAATCTAGAAGCTTCATAATACCGATCCAAGACAATGTTGTGGAGGAGGT

GAACAGGTTCAAGGTGGTTTGCGTAGCCACCCAAAATGTCACGAGTCAAA

GGAGGAGTGTCCTCGTCTTTTGACCAAGCGTGTTGAGCCACGGAAAGACC

GCTTAGGCAGTAACATGTGTGGTAGAAGTCACGGGGTTTCCTCAGCTTGT

CTCTGAATCCACCATCAGCAACCTGAGAGCACAAGAGCACATATCTTTG

CAAGCCGAGGCTATCAAAAACAGGTTGAATTCTCCTGTCAATGTAGGTAG

ACGTATGATGAACTTGGTGACCATTCCCTGAATCTTCATCGCTATCCTCA

TCAGAATCATCTTCATCACTGTCTTCAGGATCATCTTCATCATGACCATG

TTCCTCGTGATCTTCATCTGTCCCTTGTGACATATGTGATGATGATCCAT

GAGGTGCCATATCCTGGGATGAAAAAAATCGCTGTAGTAGAACACAGG

GGGCTGCCTGCCAAAACGTGTAGCAACCGTCGACCAATTTGTTCGTCC

TACCTTGGAATCCCATTTCTACTCCTTGTCGATGTACAACCCAATTCATT

AACGAATCCAAATTCAAGCGGTCGACTTCATTGATTAAAATCATAGTAG

CCAACCCACAGTACGTGTACCCACCATGAGCTTCGGAGCCAGGTTCC

CCTCCAATGCCACCTTCATAAGTTTGGCAACTCAAAATGTAATCTCCTA

AGCCGCGGGTGAGTTCATCATCCACAATGTTCAGGATGCTTGCAATCA

AAATCGCAGTGTAGCACGCTCGCACATCTATTTCTCCCATATTATGCAT

CCTGAAACCTCCATTTGTATCCTTCATTCGTCTTAAGAAACAAGCCATT

TGTTCTCTGTTAATTGAAGAGAAGGCTTTCTCACCTCCTAAAGTAACAA

GTGTATTCACTGCAGCATAACTTGTTGCAAGATGTGGAAGTTGGCCAG

GACCACCACCATATCCACCATCAGAACCCTGGCAACGTCCAAGAAAAT

CGATTGCATTGTTTTCTAAGTCATCATCCACAGACTCCCCAAGCAAAGCA

ATTGAATGAAGAATCCAGTAACAAAGCCA

*Glycine max* FTA

A disclosed nucleic acid of 1041 nucleotides (also referred to as FT4) is shown in Table 7A.

TABLE 7A

| FT4 Nucleotide Sequence (SEQ ID NO: 37). |
|---|
| ATGGAATCTGGGTCTAGCGAAGGAGAAGAGGTGCAGCAACGCGTGCCGTT |
| GAGGGAGAGAGTGGAGTGGTCAGATGTTACTCCGGTTCCTCAAAACGACG |
| GCCCTAACCCTGTCGTTCCGATCCAGTACACTGAAGAGTTTTCCGAAGTT |
| ATGGATTACTTTCGCGCCGTTTACCTCACCGATGAACGCTCCCCTCGCG |
| CCCTCGCTCTCACAGCCGAAGCCGTTCAATTCAACTCCGGCAACTACAC |
| TGTGTGGCATTTCCGACGGTTGTTACTTGAGTCGCTAAAAGTCGACTTG |
| AACGATGAACTGGAGTTTGTGGAGCGTATGGCCGCTGGAAATTCTAAAAA |
| TTATCAGATGTGnATGTTCTGTAGGCATCCTAGACGATGGGTTGCCGAGA |
| AGTTAGGTCCTGAAGCTAGAAACAATGAGCTCGAGTTCACCAAAAAGAT |
| ACTGTCCGTTGATGCCAAACATTATCATGCATGGTCTCATAGACAGTGG |
| GCTCTTCAAACACTAGGAGGATGGGAAGATGAACTTAATTATTGCACAG |
| AACTACTTAAAGAAGACATTTTTAACAATTCTGCTTGGAATCAGAGATAT |
| TTTGTCATAACAAGGTCTCCTTTCTTGGGGGGCCTAAAAGCTATGAGAG |
| AGTCTGAAGTGCTTTACACCATCGAAGCCATTATAGCCTACCCTGAAAA |
| TGAAAGCTCGTGGAGATATCTACGAGGACTTTATAAAGGTGAAACTACTT |
| CATGGGTAAATGATCCTCAAGTTTCTTCAGTATGCTTAAAGATTTTGAGA |
| ACTAAGAGCAACTACGTGTTTGCTCTTAGCACTATTTTAGATCTTATATG |
| CTTTGGTTATCAACCAAATGAAGACATTAGAGATGCCATTGACGCCTTAA |
| AGACCGCAGATATGGATAAACAAGATTTAGATGATGATGAGAAAGGGGAA |
| CAACAAAATTTAAATATAGCACGAAATATTTGTTCTATCCTAAAACAAG |
| TTGATCCAATTAGAACCAACTATTGGATTTGGCGCAAGAGCAGACTTCCT |

A disclosed FT4 polypeptide (SEQ ID NO:39) encoded by SEQ ID NO:37 has 347 amino acid residues and is presented in Table 7B using the one-letter amino acid code.

TABLE 7B

| Encoded FT4 protein sequence (SEQ ID NO: 39). |
|---|
| MESGSSEGEEVQQRVPLRERVEWSDVTPVPQNDGPNPVVPIQYTEEFSEV |
| MDYFRAVYLTDERSPRALALTAEAVQFNSGNYTVWHFRRLLLESLKVDLN |
| DELEFVERMAAGNSKNYQMXMFCRHPRRWVAEKLGPEARNNELEFTKKI |
| LSVDAKHYHAWSHRQWALQTLGGWEDELNYCTELLKEDIFNNSAWNQRYF |
| VITRSPFLGGLKAMRESEVLYTIEAIIAYPENESSWRYLRGLYKGETTSW |
| VNDPQVSSVCLKILRTKSNYVFALSTILDLICFGYQPNEDIRDAIDALKT |
| ADMDKQDLDDDEKGEQQNLNIARNICSILKQVDPIRTNYWIWRKSRLP |

Due to the nature of the cloning strategy the sequence presented is not full length. The percent identity of the *Glycine max* nucleotide sequence and its encoded amino acid sequence to that of other sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complementary to the *Glycine max* alpha subunit of SEQ ID NO:37. The disclosed complementary sequence is shown as SEQ ID NO:38.

SEQ ID NO: 38

AGGAAGTCTGCTCTTGCGCCAAATCCAATAGTTGGTTCTAATTGGATCAA
CTTGTTTTAGGATAGAACAAATATTTCGTGCTATATTTAAATTTTGTTGT
TCCCCTTTCTCATCATCATCTAAATCTTGTTTATCCATATCTGCGGTCTT
TAAGGCGTCAATGGCATCTCTAATGTCTTCATTTGGTTGATAACCAAA
GCATATAAGATCTAAAATAGTGCTAAGAGCAAACACGTAGTTGCTCTT
AGTTCTCAAAATCTTTAAGCATACTGAAGAAACTTGAGGATCATTTACC
CATGAAGTAGTTTCACCTTTATAAAGTCCTCGTAGATATCTCCACGAGC
TTTCATTTTCAGGGTAGGCTATAATGGCTTCGATGGTGTAAAGCACTTCA
GACTCTCTCATAGCTTTTAGGCCCCCCAAGAAAGGAGACCTTGTTATGA
CAAAATATCTCTGATTCCAAGCAGAATTGTTAAAAATGTCTTCTTTAAGT
AGTTCTGTGCAATAATTAAGTTCATCTTCCCATCCTCCTAGTGTTTGAAG
AGCCCACTGTCTATGAGACCATGCATGATAATGTTTGGCATCAACGGAC
AGTATCTTTTTGGTGAACTCGAGCTCATTGTTTCTAGCTTCAGGACCTA
ACTTCTCGGCAACCCATCGTCTAGGATGCCTACAGAACATNCACATC
TGATAATTTTTAGAATTTCCAGCGGCCATACGCTCCACAAACTCCAGT
TCATCGTTCAAGTCGACTTTTAGCGACTCAAGTAACAACCGTCGGAAA
TGCCACACAGTGTAGTTGCCGGAGTTGAATTGAACGGCTTCGGCTGTG
AGAGCGAGGGCGCGAGGGGAGCGTTCATCGGTGAGGTAAACGGCGCGA
AAGTAATCCATAACTTCGGAAAACTCTTCAGTGTACTGGATCGGAACG
ACAGGGTTAGGGCCGTCGTTTTGAGGAACCGGAGTAACATCTGACCAC
TCCACTCTCTCCCTCAACGGCACGCGTTGCTGCACCTCTTCTCCTTCG
CTAGACCCAGATTCCAT

*Glycine max* FTB

A disclosed nucleic acid of 1035 nucleotides (also referred to as FT5) is shown in Table 8A.

TABLE 8A

| FT5 Nucleotide Sequence (SEQ ID NO: 40). |
|---|
| GCCACCATTCCTCGCAACGCCCAAACCCTCATGTTGGAGCTTCAACGCGA |
| TAATCACATGCAGTATGTCTCCAAAGGCCTTCGCCATCTCAGTTCCGCAT |
| TTTCCGTTTTGGACGCTAATCGACCCTGGCTCTGCTACTGGATCTTCCA |
| CTCCATTGCTTTGTTGGGAGAATCCGTCGATGATGAACTCGAAGATAAC |
| GCTATCGATTTTCTTAACCGTTGCCAGGATCCGAATGGTGGATATGCC |
| GGGGGACCAGGCCAGATGCCTCATATTGCCACAACTTATGCTGCTGTT |
| AATTCACTTATTACTTTGGGTGGTGAGAAATCCCTGGCATCAATTAATA |
| GAGATAAACTGTATGGGTTTCTGCGGCGGATGAAGCAACCAAATGGT |
| GGATTCAGGATGCATGATGAAGGTGAAATTGATGTTCGAGCTTGCTAC |
| ACTGCCATTTCTGTTGCAAGTGTTTTGAACATTTTGGATGATGAGCTGA |
| TCCAGAATGTTGGAGACTACATTATAAGCTGTCAAACATATGAGGGTG |

TABLE 8A-continued

| FT5 Nucleotide Sequence (SEQ ID NO: 40). |
|---|
| GCATTGCTGGTGAGCCTGGTTCTGAGGCTCATGGTGGGTACACCTTT |
| TGTGGATTAGCTACAATGATTCTGATTGGTGAGGTTAATCACTTGGAT |
| CTGCCTCGATTAGTTGACTGGGTGGTATTCCGACAAGGTAAGGAATGT |
| GGATTCCAGGGGAGAACAAATAAACTGGTGGATGGATGCTATTCCTTT |
| TGGCAGGGAGGTGCTGTTGCTCTATTGCAAAGATTATCTTCTATTATCA |
| ACAAACAGATGGAAGAGACATCACAGATTTTTGCGGTATCTTATGTAT |
| CTGAAGCAAAAGAAAGTTTGGATGGAACCTCTAGTCATGCAACATGC |
| CGTGGTGAGCATGAAGGCACCAGTGAATCCAGTTCATCTGATTTTAA |
| AAATATTGCCTATAAATTTATTAATGAGTGGAGAGCACAAGAACCAC |
| TTTTTCACAGTATTGCTTTACAGCAATATATTCTCTTATGTGCACAGG |
| AGCAAGAGGGTGGACTGAGAGACAAACCGGGTAAACGTAGAGATC |
| ATTATCACACATGTTACTGTTTAAGTGGACTCTCATTGTGCCAGTATA |
| GTTGGTCAAAGCACCCAGATTCTCCACCAC |

A disclosed FT5 polypeptide (SEQ ID NO:42) encoded by SEQ ID NO:40 has 378 amino acid residues and is presented in Table 8B using the one-letter amino acid code.

TABLE 8B

| Encoded FT5 protein sequence (SEQ ID NO: 42). |
|---|
| ATIPRNAQTLMLELQRDNHMQYVSKGLRHLSSAFSVLDANRPWLCYWIF |
| HSIALLGESVDDELEDNAIDFLNRCQDPNGGYAGGPGQMPHIATTYAAV |
| NSLITLGGEKSLASINRDKLYGFLRRMKQPNGGFRMHDEGEIDVRACYT |
| AISVASVLNILDDELIQNVGDYIISCQTYEGGIAGEPGSEAHGGYTFCGL |
| ATMILIGEVNHLDLPRLVDWVVFRQGKECGFQGRTNKLVDGCYSFWQG |
| GAVALLQRLSSIINKQMEETSQIFAVSYVSEAKESLDGTSSHATCRGEH |
| EGTSESSSSDFKNIAYKFINEWRAQEPLFHSIALQQYILLCAQEQEGGLR |
| DKPGKRRDHYHTCYCLSGLSLCQYSWSKHPDSPP |

Due to the nature of the cloning strategy the sequence presented is not full length. The percent identity of the *Glycine max* nucleotide sequence and its encoded amino acid sequence to that of other sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complementary to the *Glycine max* beta subunit of SEQ ID NO:40. The disclosed complementary sequence is shown as SEQ ID NO:41.

SEQ ID NO: 41

GTGGTGGAGAATCTGGGTGCTTTGACCAACTATACTGGCACAATGAGAG

TCCACTTAAACAGTAACATGTGTGATAATGATCTCTACGTTTACCCGGTT

-continued

TGTCTCTCAGTCCACCCTCTTGCTCCTGTGCACATAAGAGAATATATTG

CTGTAAAGCAATACTGTGAAAAAGTGGTTCTTGTGCTCTCCACTCATTA

ATAAATTTATAGGCAATATTTTTAAAATCAGATGAACTGGATTCACTGGT

GCCTTCATGCTCACCACGGCATGTTGCATGACTAGAGGTTCCATCCAA

ACTTTCTTTTGCTTCAGATACATAAGATACCGCAAAAATCTGTGATGTCT

CTTCCATCTGTTTGTTGATAATAGAAGATAATCTTTGCAATAGAGCAAC

AGCACCTCCCTGCCAAAAGGAATAGCATCCATCCACCAGTTTATTTGTT

CTCCCCTGGAATCCACATTCCTTACCTTGTCGGAATACCACCCAGTCA

ACTAATCGAGGCAGATCCAAGTGATTAACCTCACCAATCAGAATCATT

GTAGCTAATCCACAAAAGGTGTACCCACCATGAGCCTCAGAACCAGGCT

CACCAGCAATGCCACCCTCATATGTTTGACAGCTTATAATGTAGTCTCCA

ACATTCTGGATCAGCTCATCATCCAAAATGTTCAAAACACTTGCAACAGA

AATGGCAGTGTAGCAAGCTCGAACATCAATTTCACCTTCATCATGCATCC

TGAATCCACCATTTGGTTGCTTCATCCGCCGCAGAAACCCATACAGTTTA

TCTCTATTAATTGATGCCAGGGATTTCTCACCACCCAAAGTAATAAGTGA

ATTAACAGCAGCATAAGTTGTGGCAATATGAGGCATCTGGCCTGGTCCC

CCGGCATATCCACCATTCGGATCCTGGCAACGGTTAAGAAAATCGATA

GCGTTATCTTCGAGTTCATCATCGACGGATTCTCCCAACAAAGCAATGG

AGTGGAAGATCCAGTAGCAGAGCCAGGGTCGATTAGCGTCCAAAACGGA

AAATGCGGAACTGAGATGGCGAAGGCCTTTGGAGACATACTGCATGTG

ATTATCGCGTTGAAGCTCCAACATGAGGGTTTGGGCGTTGCGAGGAATG

GTGGC

*Zea maize* FTB

A disclosed nucleic acid of 1235 nucleotides (also referred to as FT6) is shown in Table 9A.

TABLE 9A

| FT6 Nucleotide Sequence (SEQ ID NO: 43). |
|---|
| GGCGGATCCCGACCTACCGAGGCTCACGGTGACGCAGGTGGAGCAGAT |
| GAAGGTGGAGGCCAGGGTTGGCGACATCTACCGCTCCCTCTTCGGGGC |
| CGCGCCCAACACGAAATCCATCATGCTAGAGCTGTGGCGTGATCAGCA |
| TATCGAGTATCTGACGCCTGGGCTGAGGCATATGGGACCAGCCTTTCAT |
| GTTCTAGATGCCAATCGCCCTTGGCTATGCTACTGGATGGTTCATCCACT |
| TGCTTTGCTGGATGAAGCACTTGATGATGATCTTGAGAATGATATCATAG |
| ACTTCTTAGCTCGATGTCAGGATAAAGATGGTGGATATAGTGGTGGACC |
| TGGACAGTTGCCTCACCTAGCTACGACTTATGCTGCTGTAAATACACTT |
| GTGACAATAGGGAGCGAAAGAGCATTGTCATCAATCAATAGGGGCAAC |
| CTGTACAATTTTATGCTGCAGATGAAAGATGTATCAGGTGCTTTCAGAAT |
| GCATGATGGTGGCGAAATTGATGTCCGTGCTTCCTACACCGCTATATCG |
| GTTGCCAGCCTTGTGAATATTCTTGATTTTAAACTGGCAAAAGGTGTAGG |
| CGACTACATAGCAAGATGTCAAACTTATGAAGGTGGTATTGCTGGGGAG |
| CCTTATGCTGAAGCACATGGTGGGTATACATTCTGTGGATTGGCTGCTTT |

TABLE 9A-continued

| FT6 Nucleotide Sequence (SEQ ID NO: 43). |
|---|
| GATCCTGCTTAATGAGGCAGAGAAAGTTGACTTGCCTAGTTTGATTGGCT |
| GGGTGGCTTTTCGTCAAGGAGTGGAATGCGGATTTCAAGGACGAACTAA |
| TAAATTGGTTGATGGTTGCTACTCCTTTTGGCAGGGAGCTGCCATTGCTT |
| TCACACAAAAGTTAATTACGATTGTTGATAAGCAATTGAGGTCCTCGTAT |
| TCCTGCAAAAGGCCATCAGGAGAGGATGCCTGCAGCACCAGTTCATAT |
| GGGTGCACCGCGAATAAGTCTTCCTCTGCTGTGGACTATGCGAAGTTTG |
| GATTTGATTTTATACAACAGAGCAACCAAATTGGCCCACTCTTCCATAAC |
| ATTGCCCTGCAACAATACATCCTACTTTGTTCTCAGGTACTAGAGGGAG |
| GCTTGAGGGATAAGCCTGGAAAGAACAGAGATCACTATCATTCATGCTA |
| CTGCCTCAGTGGCCTCGCAGTTAGCCAGTACAGTGCCATGACTGATACT |
| GGTTCGTGCCCATTACCTCAGCATGTGCTTGGACCGTACTCTAATTTGCT |
| GGAGCCAATCCATCC |

A disclosed FT6 polypeptide (SEQ ID NO:45) encoded by SEQ ID NO:43 has 414 amino acid residues and is presented in Table 9B using the one-letter amino acid code.

TABLE 9B

| Encoded FT6 protein sequence (SEQ ID NO: 45). |
|---|
| ADPDLPRLTVTQVEQMKVEARVGDIYRSLFGAAPNTKSIMLELWRDQHIE |
| YLTPGLRHMGPAFHVLDANRPWLCYWMVHPLALLDEALDDDLENDIID |
| FLARCQDKDGGYSGGPGQLPHLATTYAAVNTLVTIGSERALSSINRGNL |
| YNFMLQMKDVSGAFRMHDGGEIDVRASYTAISVASLVNILDFKLAKGVG |
| DYIARCQTYEGGIAGEPYAEAHGGYTFCGLAALILLNEAEKVDLPSLIGW |
| VAFRQGVECGFQGRTNKLVDGCYSFWQGAAIAFTQKLITIVDKQLRSSY |
| SCKRPSGEDACSTSSYGCTANKSSSAVDYAKFGFDFIQQSNQIGPLFH |
| NIALQQYILLCSQVLEGGLRDKPGKNRDHYHSCYCLSGLAVSQYSAMTD |
| TGSCPLPQHVLGPYSNLLEPIH |

Due to the nature of the cloning strategy the sequence presented is not full length. The percent identity of the *Glycine max* nucleotide sequence and its encoded amino acid sequence to that of other sequences is shown in FIG. 17.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complementary to the *Zea maize* beta subunit of SEQ ID NO:43. The disclosed complementary sequence is shown as SEQ ID NO:44.

SEQ ID NO: 44

GGATGGATTGGCTCCAGCAAATTAGAGTACGGTCCAAGCACATGCTGAG
GTAATGGGCACGAACCAGTATCAGTCATGGCACTGTACTGGCTAACTGC
GAGGCCACTGAGGCAGTAGCATGAATGATAGTGATCTCTGTTCTTTCCAG
GCTTATCCCTCAAGCCTCCCTCTAGTACCTGAGAACAAAGTAGGATGTAT
TGTTGCAGGGCAATGTTATGGAAGAGTGGGCCAATTTGGTTGCTCTGTTG
TATAAAATCAAATCCAAACTTCGCATAGTCCACAGCAGAGGAAGACTTA
TTCGCGGTGCACCCATATGAACTGGTGCTGCAGGCATCCTCTCCTGATG
GCCTTTTGCAGGAATACGAGGACCTCAATTGCTTATCAACAATCGTAATT
AACTTTTGTGTGAAAGCAATGGCAGCTCCCTGCCAAAAGGAGTAGCAAC
CATCAACCAATTTATTAGTTCGTCCTTGAAATCCGCATTCCACTCCTTGA
CGAAAAGCCACCCAGCCAATCAAACTAGGCAAGTCAACTTTCTCTGCC
TCATTAAGCAGGATCAAAGCAGCCAATCCACAGAATGTATACCCACCA
TGTGCTTCAGCATAAGGCTCCCCAGCAATACCACCTTCATAAGTTTGAC
ATCTTGCTATGTAGTCGCCTACACCTTTTGCCAGTTTAAAATCAAGAATA
TTCACAAGGCTGGCAACCGATATAGCGGTGTAGGAAGCACGGACATCA
ATTTCGCCACCATCATGCATTCTGAAAGCACCTGATACATCTTTCATCTG
CAGCATAAAATTGTACAGGTTGCCCCTATTGATTGATGACAATGCTCTTT
CGCTCCCTATTGTCACAAGTGTATTTACAGCAGCATAAGTCGTAGCTAG
GTGAGGCAACTGTCCAGGTCCACCACTATATCCACCATCTTTATCCTGA
CATCGAGCTAAGAAGTCTATGATATCATTCTCAAGATCATCATCAAGTGC
TTCATCCAGCAAAGCAAGTGGATGAACCATCCAGTAGCATAGCCAAGG
GCGATTGGCATCTAGAACATGAAAGGCTGGTCCCATATGCCTCAGCCC
AGGCGTCAGATACTCGATATGCTGATCACGCCACAGCTCTAGCATGAT
GGATTTCGTGTTGGGCGCGGCCCCGAAGAGGGAGCGGTAGATGTCGC
CAACCCTGGCCTCCACCTTCATCTGCTCCACCTGCGTCACCGTGAGC
CTCGGTAGGTCGGGATCCGCC

The FTA and FTB nucleic acids and amino acids disclosed above have homology to other members of the FT protein family (GenBank ID NOs: U63298, U83707, and U73203; WO 00/14207; Cutler et al., Science 273(5279):1239-41, 1996; Ziegelhoffer et al., Proc Natl Acad Sci USA. 97(13): 7633-8, 2000). The homology between these and other sequences is shown graphically in the ClustalW analysis shown in Tables 10A-10D. In the ClustalW alignment, the black outlined amino acid residues indicate regions of conserved sequence (i.e., regions that may be required to preserve structural or functional properties), whereas non-highlighted amino acid residues are less conserved and can potentially be altered to a much broader extent without altering protein structure or function.

TABLE 10A

| ClustalW Nucleic Acid Analysis of FT Alpha Subunits |
|---|
| 1) BNA-12; FT2 (SEQ ID NO: 12)<br>2) At-FT-A; FT1 (SEQ ID NO: 7)<br>3) PPI-Soy-FTA; FT4 (SEQ ID NO: 37)<br>4) Pea-FT-A (SEQ ID NO: 65) |

TABLE 10A-continued

ClustalW Nucleic Acid Analysis of FT Alpha Subunits

5) Tomato-FTA (SEQ ID NO: 66)
6) Rice-FT-A (SEQ ID NO: 67)
7) Zea mays-FT-A (SEQ ID NO: 68)
8) Soy1-FT-A (SEQ ID NO: 69)
9) Soy2-FT-A (SEQ ID NO: 70)
10) Triticum-FT-A (SEQ ID NO: 71)

```
                            10        20        30        40        50        60        70
                    ....|....|....|....|....|....|....|....|....|....|....|....|....|....|
BnA-12              ----------------------------------------------------------------------
At-FT-A             ----------------------------------------------------------------------
PPI-Soy-FTA         ---------------------------------------------------------------AT--GGA
Pea-FT-A            CAACACCTACCTAGTGCTTCTAGTTCTGGTTCTAGGACTGAGAGTAAACAGAAGTGAAGAAGAATCCAGA
Tomato-FTA          ---TACCCCGAAGGCAATTCCAGTATTGAACTACCGCCGGCAGTTTTCCGATCGGATCCCGGAGCCGAGT
Rice-RT-A           -----------GCACGAGGTTCTAACGCCGCCGCCGCCGCCGCCGTCTCCGCA-GAATCTGATCGATGGC
Zea mays-FT-A       -----------------GCACGAGACAGCGCAATTACTTAAGCTATTTGTATTCGGATCTGATCCAACCC
Soy1-FT-A           --------------------------------------------GCACGAGGATTAACGAAGGAT--GGA
Soy2-FT-A           ------------------------GCACGAGCTTGCGTGTGGAGTGAAGAAGATTAACGAAGGAT--GGA
Triticum-FT-A       ----------------------------------------------------------------------

                            80        90       100       110       120       130       140
                    ....|....|....|....|....|....|....|....|....|....|....|....|....|....|
BnA-12              ----------------------------------------------------------------------
At-FT-A             ---GAGTCGGGGAACATGAATTTCGACGAG---A-CCGTG----CCACTGAGCCAACGATTGGAGTGGTC
PPI-Soy-FTA         AT----CTGGGTCTAGCGAAGGAGAAGAGGTGCAGCAACGCGTGCCGTTGAGGGAGAGAGTGGAGTGGTC
Pea-FT-A            ACATGGCCGGGAATATCGAAGTTGAAGAAG---ACGATCGTGTGCCGCTAAGATTACGACCTGAGTGGTC
Tomato-FTA          ATCAAATGGACAGTTGTGAGGT--GACGAA---A-ACGCGAATTCCTTTCAAGGAAAGGCCCGACTGGGC
Rice-RT-A           GCCGTCGTCGACGTCGTCGGAGGGTGCCTC-CGACGAGTGGTTGCCACCCAGCCGGCGGCCGGAGCTGGC
Zea mays-FT-A       TGGTGGTCAGCTGGACTCATCGCCCATGGA-GCACACTAACTCAGGCCCCAGCAGTTGGCCAGAACTGGC
Soy1-FT-A           AT----CTGGGTCTAGCGAAGGAGAAGAGGTGCAGCAACGCGTGCCGTTGAGGGAGAGAGTGGAGTGGTC
Soy2-FT-A           AT----CTGGGTCTAGCGAAGGAGAAGAGGTGCAGCAACGCGTGCCGTTGAGGGAGAGAGTGGAGTGGTC
Triticum-FT-A       ---------------------------------------------------------------------C

                           150       160       170       180       190       200       210
                    ....|....|....|....|....|....|....|....|....|....|....|....|....|....|
BnA-12              ----------------------------------------------------------------------
At-FT-A             AGACGTGGTCCCATTGACTCAGGACGATGGTCCGAATCCAGTGGTGCCAATTGCCTACAAGGAAGAGTTC
PPI-Soy-FTA         AGATGTTACTCCGGTTCCTCAAAACGACGGCCCTAACCCTGTCGTTCCGATCCAGTACACTGAAGAGTTT
Pea-FT-A            AGATGTTACTCCGATCCCACAAGACGATGGCCCTAGTCCCGTCGTGCCGATCAACTACTCCGAAGAGTTT
Tomato-FTA          CGATGTGAAGCCCGTTCCGCAAGACCACGGGCCCTGCCCGGTTGTTCCCATAGCCTACACAGAAGACTTC
Rice-RT-A           GGACGTGGTCCCCGTGACGCAGGACGACGGGCCCCACCCCGTGGTGGCCATCGCCTACCGGGACGAGTTC
Zea mays-FT-A       CGACGTGGTGCCGGTGCCGCAGGACGATGGGCCTAGCCCTGTGGTGTCCATCGCCTATCGAGATGACTTT
Soy1-FT-A           AGATGTTACTCCGGTTCCTCAAAACGACGGCCCTAACCCTGTCGTTCCGATCCAGTACACTGAAGAGTTT
Soy2-FT-A           AGATGTTACTCCGGTTCCTCAAAACGACGGCCCTAACCCTGTCGTTCCGATCCAGTACACTGAAGAGTTT
Triticum-FT-A       GGACGTGGCGCCGCTGCCGCAGGCCGACGGGCCCTGCCCCGTCGTCTCCATCGCTTACCGCGGCGACTTC

                           220       230       240       250       260       270       280
                    ....|....|....|....|....|....|....|....|....|....|....|....|....|....|
BnA-12              ---------ATGGATTACTTCCGTGCGATTTACTTCTCCGACGAGCGTTCTGCTCGCGCGCTGCGACTCA
At-FT-A             CGCGAGACTATGGATTACTTCCGTGCGATTTACTTTTCCGACGAGCGATCTCCTCGCGCACTACGACTCA
PPI-Soy-FTA         TCCGAAGTTATGGATTACTTTCGCGCCGTTTACCTCACCGATGAACGCTCCCCTCGCGCCCTCGCTCTCA
Pea-FT-A            TCAGAAGTTATGGATTACTTTCGTGCTGTTTACTTCGCCAAAGAACTTTCCTCTCGCGCTCTTGCTCTCA
Tomato-FTA          TCTGAAACCATGGACTACTTCCGGGCAATTTACGTAGCCGATGAGCGATCTACACGCGCCCTCCAGCTTA
Rice-RT-A           CGCGAGGTCATGGACTACTTCCGCGCCCTCTACTTCGCCGGCGAGCGCAGCGTCCGCGCCCTCCACCTCA
Zea mays-FT-A       CGTGAGGTCATGGATTACTTCCGCGCCCTCTACCTCACCGGTGAGCGAAGCCCTCGCGCTCTCCGCCTCA
Soy1-FT-A           TCCGAAGTTATGGATTACTTTCGCGCCGTTTACCTCACCGATGAACGCTCCCCTCGCGCCCTCGCTCTCA
Soy2-FT-A           TCCGAAGTTATGGATTACTTTCGCGCCGTTTACCTCACCGATGAACGCTCCCCTCGCGCCCTCGCTCTCA
Triticum-FT-A       CGCGAGGTCATGGACTACTTCCGCGCCCTCTACGCCGCCGGCGAGCGCAGCCCCCGCGCCCTCCGCCTCA

                           290       300       310       320       330       340       350
                    ....|....|....|....|....|....|....|....|....|....|....|....|....|....|
BnA-12              CGGAAGAAGCTCTCCGCTTAAACTCGGGCAACTACACCGTGTGGCACTTCGGGCGCTTAGTACTCGAGGA
At-FT-A             CGGAAGAAACCCTCCTCTTAAACTCCGGCAACTACACAGTGTGGCATTTCAGGCGCCTAGTACTCGAGGC
PPI-Soy-FTA         CAGCCGAAGCCGTTCAATTCAACTCCGGCAACTACACTGTGTGGCATTTCCGACGGTTGTTACTTGAGTC
Pea-FT-A            CCGCCGAAGCTATCGGTTTAAACGCCGGAAACTACACTGTGTGGCATTTCCGGCGGTTATTACTTGAGTC
Tomato-FTA          CTGGTGAAGCTATTCAGCTAAACCCTGGAAATTACACTGTATGGCAATTTAGGCGTGTTGTGCTGGAGGC
Rice-RT-A           CCGCCGAGGTCATCGACCTTAATCCCGGCAACTACACGGTGTGGCATTTTAGGCGTCTTGTTCTAGAGGC
Zea mays-FT-A       CCGCCGAGGCCATCGAGCTCAACCCCGGCAACTACACTGTCTGGCATTTCCGGCGCCTTATTCTGGAGTC
Soy1-FT-A           CAGCCGAAGCCGTTCAATTCAACTCCGGCAACTACACTGTGTGGCATTTCCGACGGTTGTTACTTGAGTC
Soy2-FT-A           CAGCCGAAGCCGTTCAATTCAACTCCGGCAACTACACTGTGTGGCATTTCCGACGGTTGTTACTTGAGTC
Triticum-FT-A       CCGCCGACGCCATCCACCTCAACCCCGGCAACTACACTGTATGGCATTTCAGGCGCGTTGTTCTAGAGGC

                           360       370       380       390       400       410       420
                    ....|....|....|....|....|....|....|....|....|....|....|....|....|....|
BnA-12              GCTTAATAACGACTTGTATGAAGAGCTCAAGTTCATCGAAAGCATTGCTGAGGATAACTCTAAGAACTAC
At-FT-A             CCTTAATCACGACTTGTTTGAAGAACTCGAGTTCATCGAACGCATTGCTGAGGATAACTCTAAGAACTAC
PPI-Soy-FTA         GCTAAAAGTCGACTTGAACGATGAACTGGAGTTTGTGGAGCGTATGGCCGCTGGAAATTCTAAAAATTAT
Pea-FT-A            ACTGAAAGTTGACCTACATGTTGAACGGGAATTCGTGGAGCGTGTTGCCAGTGGCAATTCAAAAAATTAT
Tomato-FTA          ATTGGGTGTTGATTTACTTGAAGAATTGAAGTTTGTTGATCGCATTGCTGGGGAGAATACCAAAAATTAT
Rice-RT-A           ACTGGATGCTGATCTGCGTGAGGAAATGGATTTTGTGGACCGAATTGTCGAATGTAACCCAAAAAATTAT
Zea mays-FT-A       ACTAGATTTTGATTTACTAGAGGAGATGAAATTTGTCGAAAAAATTGCTGAATGCAATCCAAAAAATTAC
Soy1-FT-A           GCTAAAAGTCGACTTGAACGATGAACTGGATTTTGTGGAGCGTATGGCCGCTGGAAATTCTAAAAATTAT
Soy2-FT-A           GCTAAAAGTCGACTTGAACGATGAACTGGAGTTTGTGGAGCGTATGGCCGCTGGAAATTCTAAAAATTAT
Triticum-FT-A       ACTGGATGCTGATTTATTGCTAGAAATGCATTTTGTGGACCAAATTGCTGAATCTAATCCAAAAAATTAC
```

TABLE 10A-continued

ClustalW Nucleic Acid Analysis of FT Alpha Subunits

```
                        430       440       450       460       470       480       490
                ....|....|....|....|....|....|....|....|....|....|....|....|....|....|
BnA-12          CAGTTGTGG------------------------------------CATCATCGACGATGGGTCGCAGAGA
At-FT-A         CAACTGTGG------------------------------------CATCATCGGCGATGGGTTGCAGAGA
PPI-Soy-FTA     CAGATGTGN----ATGTTCTG---------TAG-----------GCATCCTAGACGATGGGTTGCCGAGA
Pea-FT-A        CAGATTTGG------------------------------------CATCATAGACGATGGGTTGCTGAGA
Tomato-FTA      CAAATATGG------------------------------------CATCATAGACGGTGGCTTGCTGAGA
Rice-RT-A       CAAATCTGG------------------------------------CATCACAAGAGATGGCTTGCGGAGA
Zea mays-FT-A   CAAATCTGG------------------------------------CACCATAAGAGATGGCTTGCTGAGA
Soy1-FT-A       CAGATGTGG------------------------------------CATCATAGACGATGGGTTGCCGAGA
Soy2-FT-A       CAGATGTGGTGTGATGCTCTGCTCTGCTCTTTCTTCCATACTTTGCATCATAGACGATGGGTTGCCGAGA
Triticum-FT-A   CAAGTCTGG------------------------------------CATCACAAGAGATGGCTTGCTGAGA

                        500       510       520       530       540       550       560
                ....|....|....|....|....|....|....|....|....|....|....|....|....|....|
BnA-12          AACTGGGTCCTGATGTTGCAGGAAAGGAACTTGAGTTTACTCGGAGGGTACTATCACTTGATGCCAAGCA
At-FT-A         AACTGGGTCCTGATGTTGCAGGGAGAGAACTTGAATTTACCCGTAGAGTACTTTCACTTGATGCCAAACA
PPI-Soy-FTA     AGTTAGGTCCTGAAGCTAGAAACAATGAGCTCGAGTTCACCAAAAAGATACTGTCCGTTGATGCCAAACA
Pea-FT-A        AATTAGGACCTGAAGCTAGAAACAGTGAACTTGAGTTCACCAAAAAGATTCTGTCTGTTGACGCCAAACA
Tomato-FTA      AGCTGGGAGCTGATGCTGTGACAAATGAGCTAGAATTCACCAAGAAAATATTTTCTCAGGATGCAAAAAA
Rice-RT-A       AATTAGGACCAGATATTGCAAATAAAGAGCACGAATTTACAAGGAAGATACTTTCTATGGATGCTAAAAA
Zea mays-FT-A   AATTAGGACCTGGTATTGCAAACAAAGAGCATGAATTCACAATGAAGATACTTGCTATTGATCGAAAAAA
Soy1-FT-A       AGTTAGGTCCTGAAGCTAGAAACAATGAGCTCGAGTTCACCAAAAAGATACTGTCCGTTGATGCCAAACA
Soy2-FT-A       AGTTAGGTCCTGAAGCTAGAAACAATGAGCTCGAGTTCACCAAAAAGATACTGTCCGTTGATGCCAAACA
Triticum-FT-A   AAATAGGACCAGATGCTGCAAATAGTGAACATGACTTCACAAGGAAGATACTTGCTATGGATGCTAAAAA

                        570       580       590       600       610       620       630
                ....|....|....|....|....|....|....|....|....|....|....|....|....|....|
BnA-12          TTATCATGCTTGGTCACATAGGCAGTGGGCGCTACAAGCATTAGGAGGATGGAAAATGAGCTTAACTAC
At-FT-A         TTATCATGCTTGGTCACATAGGCAGTGGACACTACGGGCATTAGGAGGATGGAAGATGAGCTCGATTAC
PPI-Soy-FTA     TTATCATGCATGGTCTCATAGACAGTGGGCTCTTCAAACACTAGGAGGATGGAAGATGAACTTAATTAT
Pea-FT-A        CTATCATGCATGGTCTCATAGGCAGTGGGTTCTTCAAAATCTAGGAGGATGGAAGATGAACTCAGTTAT
Tomato-FTA      TTATCATGCTTGGTCCCATCGGCAGTGGGTCCTTCAAGCACTTGGAGGATGGAAGATGAGCTTGCTTAT
Rice-RT-A       TTACCATGCTTGGTCTCATAGGCAGTGGGTTCTTCAAGCACTGGGTGGATGGAGACTGAACTACAGTAT
Zea mays-FT-A   TTATCATGCTTGGTCTCATAGGCAGTGGGTTCTTCAAGCGTTGGGGGGATGGAGACTGAATTAGAATAC
Soy1-FT-A       TTATCATGCATGGTCTCATAGACAGTGGGCTCTTCAAACACTAGGAGGATGGAAGATGAACTTAATTAT
Soy2-FT-A       TTATCATGCATGGTCTCATAGACAGTGGGCTCTTCAAACACTAGGAGGATGGAAGATGAACTTAATTAT
Triticum-FT-A   CTACCATGCTTGGTCCCATAGGCAGTGGGTTCTTCAAGCATTGGGTGGATGGAGAGTGAACTGCAGTAC

                        640       650       660       670       680       690       700
                ....|....|....|....|....|....|....|....|....|....|....|....|....|....|
BnA-12          TGCCACGAGCTCCTTGAAGCTGACGTCTTTAACAACTCTGCATGGAATCAGAGGTATTACGTTATAACTA
At-FT-A         TGTCACGAGCTCCTTGAAGCTGACGTCTTTAACAATTCCGCCTGGAATCAGAGGTATTATGTCATCACCC
PPI-Soy-FTA     TGCACAGAACTACTTAAAGAAGACATTTTTAACAATTCTGCTTGGAATCAGAGATATTTTGTCATAACAA
Pea-FT-A        TGTAGTGAACTGCTTGCAGAAGACATATTTAACAATTCTGCTTGGAATCAGAGATACTTCGTCATAACAA
Tomato-FTA      TGTCAACAACTCCTTGAAGATGATATTTACAACAATTCTGCTTGGAATCAGAGATACTTTGTCGTAACAC
Rice-RT-A       TGCAACCAGCTGCTTGAGGAAGACGTCTTCAATAATTCAGCTTGGAATCAGAGATACCTTGTAATAACAA
Zea mays-FT-A   TGTGACCACTTACTTAAGGAAGACGTCTTCAATAATTCAGCTTGGAATCAGAGATACTTTGTTATAACAA
Soy1-FT-A       TGCACAGAACTACTTAAAGAAGACATTTTTAACAATTCTGCTTGGAATCAGAGATATTTTGTCATAACAA
Soy2-FT-A       TGCACAGAACTACTTAAAGAAGACATTTTTAACAATTCTGCTTGGAATCAGAGATATTTTGTCATAACAA
Triticum-FT-A   TGCAACCAGCTTCTTGAGGAAGATCTCTTCAATAACTCAGCTTGGAATCAGAGATACCTTGTGGTAACAC

                        710       720       730       740       750       760       770
                ....|....|....|....|....|....|....|....|....|....|....|....|....|....|
BnA-12          GATCACCTTCGTTGGGAGGCCTAGAAGCCATGAGAGAATCTGAAGTAAGCTACACAGTCAAAGCCATTTT
At-FT-A         AATCTCCTTTGTTGGGAGGCCTAGAAGCCATGAGAGAATCTGAAGTAAGCTACACAATCAAAGCCATTTT
PPI-Soy-FTA     GGTCTCCTTTCTTGGGGGGCCTAAAAGCTATGAGAGAGTCTGAAGTGCTTTACACCATCGAAGCCATTAT
Pea-FT-A        GGTCTCCCGTCTTGGGAGGGCTAAAAGCCATGAGAGAGTCTGAAGTGCTTTTCACCGTTGAAGCCATTAT
Tomato-FTA      GATCACCTCTACTAGGGGGCCTAGTGGCAATGAGGGAATTGGAAGTGAATTACACAGTTCAAGCCATCAG
Rice-RT-A       GTTCACCACTTCTTGGAGGCCTTGCAGCAATGCGTGACTCGGAAGTGGATTACACAGTTGGGGCTATTCT
Zea mays-FT-A   GATCACCATTTCTTGGTGGCCTTGCGGCAATGCGTGATTCAGAAGTAGACTACACAATTGAAGCTATTCT
Soy1-FT-A       GGTCTCCTTTCTTGGGGGGCCTAAAAGCTATGAGAGAGTCTGAAGTGCTTTACACCATTGAAGCCATTAT
Soy2-FT-A       GGTCTCCTTTCTTGGGGGGCCTAAAAGCTATGAGAGAGTCTGAAGTGCTTTACACCATTGAAGCCATTAT
Triticum-FT-A   GATCACCAATTCTTGGGGGCCTTGCGGCAATGCGCGACTCAGAAGTAGATTACACAGTTGAGGCCATTAT

                        780       790       800       810       820       830       840
                ....|....|....|....|....|....|....|....|....|....|....|....|....|....|
BnA-12          AGCAAATCCCGGGAACGAGAGCTCTTGGAGGTACCTGAAAGCCCTTTACAAAGACGACACAGAGTCTTGG
At-FT-A         AACCAATCCTGCAAACGAGAGCTCATGGCGATACCTAAAAGCGCTTTACAAAGACGACAAAGAATCCTGG
PPI-Soy-FTA     AGCCTACCCTGAAAATGAAAGCTCGTGGAGATATCTACGAGGACTTTATAAAGGTGAAACTACTTCATGG
Pea-FT-A        TTCTTACCCAGAAAATGAAAGCTCATGGAGATATCTTCGAGGACTTTTCAAAGATGAATCCACGTTATAT
Tomato-FTA      AGCTAGTCCAGAGAATGAAAGTCCTTGGAGGTATCTTCGTGGTCTTTACAAGAATGATACACAATCTCTA
Rice-RT-A       GGCTAACCCTCAGAATGAAAGCCCCTGGAGATACCTCAAAGGCCTGTACAAGGGTGAAAATAACTTGCTG
Zea mays-FT-A   AGCAAACGCTCAGAATGAAAGCCCCTGGAGGTACCTCAAGGGTCTATACAAGGGTGAGAATAACCTGCTA
Soy1-FT-A       AGCCTACCCTGAAAATGAAAGCTCGTGGAGATATCTACGAGGACTTTATAAAGGTGAAACTACTTCATGG
Soy2-FT-A       AGCCTACCCTGAAAATGAAAGCTCGTGGAGATATCTACGAGGACTTTATAAAGGTGAAACTACTTCATGG
Triticum-FT-A   GGTGAACCCTCAGAATGAAAGCCCCTGGAGATACCTCAGAGGTTTATATAAGGATGATAACAATTTGCTG
```

TABLE 10A-continued

ClustalW Nucleic Acid Analysis of FT Alpha Subunits

```
                       850       860       870       880       890       900       910
               ....|....|....|....|....|....|....|....|....|....|....|....|....|....|
BnA-12         ATTAGTGATCCAAGTGTTTCCTCAGTCTGTTTGAAAGTTCTCTCACGCGCGGACTGCTTCCATGGATTCG
At-FT-A        ATTAGTGATCCAAGTGTTTCCTCAGTCTGTTTGAATGTTCTATCCCGCACAGATTGCTTCCATGGATTCG
PPI-Soy-FTA    GTAAATGATCCTCAAGTTTCTTCAGTATGCTTAAAGATTTTGAGAACTAAGAGCAAC---TACGTGTTTG
Pea-FT-A       GTAAATGATGCCCAAGTATCTTCATTATGTTTAAAGATTTTGAAAACTAAGAGCAAC---TATTTGTTTG
Tomato-FTA     GTTCAGGATTCTCAAGTAGCATCAGTACTTTGGGACGTCTTAACCTCCCAAAATAGT---CATGTGCACG
Rice-RT-A      ATGGCTGATGAGCGCATCTCTGATGTTTGTCTCAAGGTCCTGAAACATGATTCGACG---TGCGTATTTG
Zea mays-FT-A  GTAGAGGACGAGCGCATCTCTGCTGTTTGTTTCAAGGTCCTGAAGAATGATTGGACT---TGTGTATTTG
Soy1-FT-A      GTAAATGATCCTCAAGTTTCTTCAGTATGCTTAAAGATTTTGAGAACTAAGAGCAAC---TACGTGTTTG
Soy2-FT-A      GTAAATGATCCTCAAGTTTCTTCAGTATGCTTAAAGATTTTGAGAACTAAGAGCAAC---TACGTGTTTG
Triticum-FT-A  GTGGCTGATAATCGCATTTCTGATGCTTGCCTCAAGGTCCTGAATAAGGATTGGACA---TGCGTATTTG

                       920       930       940       950       960       970       980
               ....|....|....|....|....|....|....|....|....|....|....|....|....|....|
BnA-12         CTCTGAGCACCCTTTTGGATCTTCTGTGCGATGGGT-TGAGACCAACCAACGAGCATAGAGACTCGGTGA
At-FT-A        CTCTGAGCACCCTTTTGGATCTTCTATGTGATGGAC-TGAGACCAACCAACGAGCATAAAGACTCAGTGA
PPI-Soy-FTA    CTCTTAGCACTATTTTAGATCTTATATGCTTTGGTTAT-CAACCAAATGAAGACATTAGAGATGCCATTG
Pea-FT-A       CTCTAAGTACTCTGCTGGATCT-ATCTGCCTCGGTTATTCAACCAAATGAAGATTTCAGAGATGCCATTG
Tomato-FTA     CTCTGAGGTTCTTGTTGGATCTTCTTTGTCATGATT-TGGAACCGAGCCAAGAATTGAAAAGTGCTGTAG
Rice-RT-A      CTTTGAGCTTGCTGCTCGATCTTCTTCAAATTGGTT-TACAACCTTCAGATGAACTCAAAGGAACTATCG
Zea mays-FT-A  CTTTGAGTTTGCTGCTCGATCTTCTCTGCACTGGTT-TGCAGCCTTCAGATGAACTTAGGTCCACTCTTG
Soy1-FT-A      CTCTTAGCACTATTTTAGATCTTATATGCTTTGGTTAT-CAACCAAATGAAGACATTAGAGATGCCATTG
Soy2-FT-A      CTCTTAGCACTATTTTAGATCTTATATGCTTTGGTTAT-CAACCAAATGAAGACATTAGAGATGCCATTG
Triticum-FT-A  CTTTGAGCTTCCTGCTTGATCTTCTTCGCATGGGTT-TGCAGCCTTCGAATGAACTTAAAGGAACCATCG

                       990      1000      1010      1020      1030      1040      1050
               ....|....|....|....|....|....|....|....|....|....|....|....|....|....|
BnA-12         AAGCTCTAG---CT------AATGAAGA--------------------------------A-CCAGAGAC
At-FT-A        GAGCTCTAG---CT------AATGAAGA--------------------------------A-CCAGAGAC
PPI-Soy-FTA    ACGCCTTAAAGACCGCAGATATGGATAAACAAGATTTAGATGATGATGAGAAAGGGGAACAACAAAATTT
Pea-FT-A       AGGCTTTAA-GACTTCAGATTTTGATAAA-------------------------------A-CAAGATTC
Tomato-FTA     ATGTTCTTA---CTCCC--C-GTCATGCTC------------------------------A-CCAGATTT
Rice-RT-A      AAGCAATAAAGAACTCTGATCCTGAAGCAGATGA--------------------AG---CA-GTAGATGC
Zea mays-FT-A  AAACAATAAGGAGCTCCCATCCTGAAACCGC---------------------------------GGATGA
Soy1-FT-A      ACGCCTTAAAGACCGCAGATATGGATAAACAAGATTTAGATGATGATGAGAAAGGGGAACAACAAAATTT
Soy2-FT-A      ACGCCTTAAAGACCGCAGATATGGATAAACAAGATTTAGATGATGATGAGAAAGGGGAACAACAAAATTT
Triticum-FT-A  AAGCAATGGAGAACTCTGATCCTGAAACGGG---------------------------------ACATGC

                      1060      1070      1080      1090      1100      1110      1120
               ....|....|....|....|....|....|....|....|....|....|....|....|....|....|
BnA-12         TAACTTGGCCAATTTGGTGTGTACCATTCTGTGTCGTGTTGATCCAATAAGAGCTAACTATTGGGCATGG
At-FT-A        TAACTTGGCCAATTTGGTGTGTACTATTCTTGGTCGTGTAGATCCTATAAGAGCTAACTATTGGGCATGG
PPI-Soy-FTA    AAATATAGCACGAAATATTTGTTCTATCCTAAAACAAGTTGATCCAATTAGAACCAACTATTGGATTTGG
Pea-FT-A       AGATATAGCAATAACTATTTGTTCTATTTTAGAACAAGTTGATCCAATTAGAGTCAACTATTGGGTCTGG
Tomato-FTA     AGCACTGACAAAGAAAATTTGTTCCATCTTGGAACATGCTGATCCAATGAGAGTAAAATATTGGAATTGG
Rice-RT-A      TGATCTTGCGACTGCAATCTGCTCAATATTGCAGAGATGTGATCCCCTGCGGATAAATTACTGGTCCTGG
Zea mays-FT-A  TGATCCTGCAGCCGCTGTTTGCTGTATCCTGCAGAAATGTGATCCCCTGCGGGTAAATTATTGGTCTTGG
Soy1-FT-A      AAATATAGCACGAAATATTTGTTCTATCCTAAAACAAGTTGATCCAATTAGAACCAACTATTGGATTTGG
Soy2-FT-A      AAATATAGCACGAAATATTTGTTCTATCCTAAAACAAGTTGATCCAATTAGAACCAACTATTGGATTTGG
Triticum-FT-A  TGATATTGCAGTAGCTGTCTGCTCAATCCTGCAGAAATGTGATCCCCTGCGGATAAACTACTGGTCATGG

                      1130      1140      1150      1160      1170      1180      1190
               ....|....|....|....|....|....|....|....|....|....|....|....|....|....|
BnA-12         ----------------------------------------------------------------------
At-FT-A        AGGAAGAGCAAGATTACA----GTGGC-AGCAATTTGAATATGTGACGCCCCAAAATCACACTTGAAAAA
PPI-Soy-FTA    CGCAAGAGCAGACTTC-------CT---------------------------------------------
Pea-FT-A       CGGAAGAGTAGACTTC-------CTCA-GGCAGCGTAAAGGACAAACTTATGTCATATGTGTAATTTTTA
Tomato-FTA     CGCAAGAGCATGGTTCGG----GTTCA-ATTACTTCAGAGTCAGAATGCAGAGAGGTTG-GCTAATTTGA
Rice-RT-A      TACAGGACCACTATTTCT----TCTCA-AAC--CTGAAG----CATGCAGTGGCCTCCATGA------GG
Zea mays-FT-A  TTCAAGGACACTCTTTCTCAGATCTCATGACTTCACATGGGTTCACCCCTTGTCCGCGCTGGTCCGGGCT
Soy1-FT-A      CGCAAGAGCAGACTTC-------CTCT-ATCAGCTTAGTAACCAAAGTAATTAAA---GGGCAACTCTGT
Soy2-FT-A      CGCAAGAGCAGACTTC-------CTCT-ATCAGCTTAGTAACCAAAGTAATTAAA---GGGCAACTCTGT
Triticum-FT-A  TACCAGACCACTCTTTCT----TCTTA-GACATCTGAAAA-TTCAGCTGAAGACAGTTTTAG------CA

                      1200      1210      1220      1230      1240      1250      1260
               ....|....|....|....|....|....|....|....|....|....|....|....|....|....|
BnA-12         ----------------------------------------------------------------------
At-FT-A        GACTTGATTAT--TAGT-TTTTACGT----------AATTAACTGCTTATTTATGAATCACATG-TTCAT
PPI-Soy-FTA    ----------------------------------------------------------------------
Pea-FT-A       GTCTATTGGAATTTGACGTCATGGAT----------AACAGGGTGGTTGTTTTTGTTATGATAT-GTTTT
Tomato-FTA     GTGTTCAAGAA--TGAC-TTGTGAGA----------ATATTGTACTGTGTTTACGAAATACATA-CTTGC
Rice-RT-A      TCATAATGGAGATATCTTCTAT------------------------CTTCGTGTGA---------TTCTG
Zea mays-FT-A  CTGTGAGATAGACATGTTTTAGATAGTTTCATTGGACACCCAAACAGAGCGGACAGAGTGTATGGCTGCT
Soy1-FT-A      GTTATGTGTAACCTAGT-TTATTGA-----------AACTGGATTTTTATTT--ATTATTATTT-TTTAT
Soy2-FT-A      GTTATGTGTAACCTAGT-TTATTGA-----------AACTGGATGTTTATTT--ATTATTATTT-TTTAT
Triticum-FT-A  GCATGATGTAAACTCAATCGAAGGGGTT--------------GACGCAGTGTATGAAAAACCT--TTCCT
```

TABLE 10A-continued

ClustalW Nucleic Acid Analysis of FT Alpha Subunits

| | |
|---|---|
| | 1270 1280 1290 1300 1310 1320 1330 |
| | ....\|....\|....\|....\|....\|....\|....\|....\|....\|....\|....\|....\|....\|....\| |
| BnA-12 | ---------------------------------------------------------------------- |
| At-FT-A | GT-TAACATGTATCAAAACAATCTTGATTTCTCAAAAAAAAAAAAAAAAAAAAAAAAAAAAAA------- |
| PPI-Soy-FTA | ---------------------------------------------------------------------- |
| Pea-FT-A | CC-AGATGTATTTCTATATTTAACAGCAAAGTTGATTTAACATTGGTCTTAACAAACCAATGATCTCCAA |
| Tomato-FTA | ATCTAAGGTGATCCTTCGGGCACATGTGCTGGGAAGTGACTGAATATCACGAAGAACTAAAAAAACTGTG |
| Rice-RT-A | GGCGTTGAGGTGCCT---AGCTACATTTGTTATGAACTTTCCTTGGGCATAACTGATCACTGATATTAC- |
| Zea mays-FT-A | ACCTTCTCCGTGACTGAAAGCAGTGCTTGTAACGA--TTTTGTTTAGTAAAATTTGTGAGTGTTACTGCT |
| Soy1-FT-A | GT-TGTCATGTATCTGTTTGT----GCAAATTT------ATCTTTTTGTCATGCCATTACTGGCATTTGA |
| Soy2-FT-A | GT-TGTCATGTATCTGTTTGT----GCAAATTT------ATCTTTTTGTCATGCCATTACTGGCATTTGA |
| Triticum-FT-A | GTGATCTTGGTGCGG---AGCAA--TTTGTACTGA--TTTTACTGGGAAAAATCAATCAATGACAGCATG |
| | 1340 1350 1360 1370 1380 1390 1400 |
| | ....\|....\|....\|....\|....\|....\|....\|....\|....\|....\|....\|....\|....\|....\| |
| BnA-12 | ---------------------------------------------------------------------- |
| At-FT-A | ---------------------------------------------------------------------- |
| PPI-Soy-FTA | ---------------------------------------------------------------------- |
| Pea-FT-A | AAAATCAATGTTTTATTTCTCTTCATTTGTCTGATTTTGTGGCATAACATTCTTGATGAT-TTTGTGGTA |
| Tomato-FTA | ATTGGCAACATTGTACTACTCCAAATAGGTCACTTTCGATGACTTTTTGTACTGCCTTGA-GTTTTGGCT |
| Rice-RT-A | TCCAATATTGTGTTCTAAA--------------------------------------------------- |
| Zea mays-FT-A | CCAAACAACACCTTATGCAACCATATTTGAATAT----TTCACATGTAAGCT---TGA--------A-TC |
| Soy1-FT-A | GTG--TAAGGATTGAAAGCCATGCA-------GAATAAGAAATTTAAGTTTTTT-------TTTCCGTTG |
| Soy2-FT-A | GTG--TAAGGATTGAAAGCCATGCA-------GAATAAGAAATTTAAGTTTTTT-------TTTCCGTTG |
| Triticum-FT-A | CCCAACAATGTCTTGTGTGAATATGTTACTGCCTGATATTCACATGTTAGCAGAATGAGAATAACCAATC |
| | 1410 1420 1430 1440 1450 1460 1470 |
| | ....\|....\|....\|....\|....\|....\|....\|....\|....\|....\|....\|....\|....\|....\| |
| BnA-12 | ---------------------------------------------------------------------- |
| At-FT-A | ---------------------------------------------------------------------- |
| PPI-Soy-FTA | ---------------------------------------------------------------------- |
| Pea-FT-A | AAAAAAAAAAAAAAAAAAAA-------------------------------------------------- |
| Tomato-FTA | CTGCTATGTTTTGTAAGTTTTGGATATGGATGCATAGCTTATTGATACTTTTGGTGACTTAAAATACTCT |
| Rice-RT-A | ---------------------------------------------------------------------- |
| Zea mays-FT-A | CAGGTGTGTTTGTTAATGTATTACACTT--G-CCATGGGAGCCTAAATGAGACCCATAATCACTTCCACT |
| Soy1-FT-A | AAAA------------------------------------------------------------------ |
| Soy2-FT-A | AAAAAAAAAAAAAAAAAAAA-------------------------------------------------- |
| Triticum-FT-A | AAACTCCAACGAGCAGATTGTTACAGTAACGGCCACTGGTGGTGTGAAAATCCTGAAATCTGCTTCAGTC |
| | 1480 1490 1500 1510 1520 1530 1540 |
| | ....\|....\|....\|....\|....\|....\|....\|....\|....\|....\|....\|....\|....\|....\| |
| BnA-12 | ---------------------------------------------------------------------- |
| At-FT-A | ---------------------------------------------------------------------- |
| PPI-Soy-FTA | ---------------------------------------------------------------------- |
| Pea-FT-A | ---------------------------------------------------------------------- |
| Tomato-FTA | GGAAGGCAGGTAGCATGTGTATAATTCACTGTTACTTCCCATGTCGAGTTAGATGCTTGAAAATTTTAGT |
| Rice-RT-A | ---------------------------------------------------------------------- |
| Zea mays-FT-A | AGAGTCGGAAGACCGT-GTCGAGCAGTTCACTCATATGGTCACTTAAAGCAAAAAAAAAAAAAAAAAAA- |
| Soy1-FT-A | ---------------------------------------------------------------------- |
| Soy2-FT-A | ---------------------------------------------------------------------- |
| Triticum-FT-A | ACTTTGCCTTGTTTACAGTTGAGTCTGTTGTTGTGATCTGTACCTAATGCATGTACACAATCATCAAATT |
| | 1550 1560 1570 1580 1590 1600 1610 |
| | ....\|....\|....\|....\|....\|....\|....\|....\|....\|....\|....\|....\|....\|....\| |
| BnA-12 | ---------------------------------------------------------------------- |
| At-FT-A | ---------------------------------------------------------------------- |
| PPI-Soy-FTA | ---------------------------------------------------------------------- |
| Pea-FT-A | ---------------------------------------------------------------------- |
| Tomato-FTA | AGGTGTTCTTTTATGAAGCACACATTAATGTGGAAAAAAAAAAAAAAAAAAAAAAAAAAAAAAAAAAAAA |
| Rice-RT-A | ---------------------------------------------------------------------- |
| Zea mays-FT-A | ---------------------------------------------------------------------- |
| Soy1-FT-A | ---------------------------------------------------------------------- |
| Soy2-FT-A | ---------------------------------------------------------------------- |
| Triticum-FT-A | ATTAGTTTTTGTACCAATGAGTATTCGATGAAAAAAAAAAAAAAAA------------------------ |
| | . |
| BnA-12 | - |
| At-FT-A | - |
| PPI-Soy-FTA | - |
| Pea-FT-A | - |
| Tomato-FTA | A |
| Rice-RT-A | - |
| Zea mays-FT-A | - |
| Soy1-FT-A | - |
| Soy2-FT-A | - |
| Triticum-FT-A | - |

TABLE 10B

ClustalW Amino Acid Analysis of FT Alpha Subunits

1) BNA-12; FT2 (SEQ ID NO: 13)
2) At-FT-A; FT1 (SEQ ID NO: 11)
3) PPI-Soy-FTA; FT4 (SEQ ID NO: 39)
4) Pea-FT-A (SEQ ID NO: 72)
5) Tomato-FTA (SEQ ID NO: 73)
6) Rice-FT-A (SEQ ID NO: 74)
7) Zea mays-FT-A (SEQ ID NO: 75)
8) Soy1-FT-A (SEQ ID NO: 76)
9) Soy2-FT-A (SEQ ID NO: 77)
10) Triticum-FT-A (SEQ ID NO: 78)

```
                           10        20        30        40        50        60        70
                   ....|....|....|....|....|....|....|....|....|....|....|....|....|....|
BnA-12             ---------------------------------------------------MDYFRAIYFSDERSARALR
At-FT-A            ---------MNFDETVPLSQRLEWSDVVPLTQDDGPNPVVPIAYKEEFRETMDYFRAIYFSDERSPRALR
PPI-Soy-FTA        -MESGSSEGEEVQQRVPLRERVEWSDVTPVPQNDGPNPVVPIQYTEEFSEVMDYFRAVYLTDERSPRALA
Pea-FT-A           --MAGNIEVEE-DDRVPLRLRPEWSDVTPIPQDDGPSPVVPINYSEEFSEVMDYFRAVYFAKELSSRALA
Tomato-FTA         -----MDSCEVTKTRIPFKERPDWADVKPVPQDDGPCPVVPIAYTEDFSETMDYFRAIYVADERSTRALQ
Rice-RT-A          MAPSSTSSEGASDEWLPPSRRPELADVVPVTQDDGPHPVVAIAYRDEFREVMDYFRALYFAGERSVRALH
Zea mays-FT-A      ----------MEHTLSGPSSWPELADVVPVPQDDGPSPVVSIAYRDDFRGVMDYFRALYLTGERSPRALR
Soy1-FT-A          -MESGSSEGEEVQQRVPLRERVEWSDVTPVPQNDGPNPVVPIQYTEEFSEVMDYFRAVYLTDERSPRALA
Soy2-FT-A          -MESGSSEGEEVQQRVPLRERVEWSDVTPVPQNDGPNPVVPIQYTEEFSEVMDYFRAVYLTDERSPRALA
Triticum-FT-A      -------------------------DVAPLPQADGPCPVVSIAYRGDFREVMDYFRALYAAGERSPRALR

                           80        90       100       110       120       130       140
                   ....|....|....|....|....|....|....|....|....|....|....|....|....|....|
BnA-12             LTEEALRLNSGNYTVWHFGRLVLEELNNDLYEELKFIESIAEDNSKNYQLW------------HHRRWVA
At-FT-A            LTEETLLLNSGNYTVWHFRRLVLEALNHDLFEELEFIERIAEDNSKNYQLW------------HHRRWVA
PPI-Soy-FTA        LTAEAVQFNSGNYTVWHFRRLLLESLKVDLNDELEFVERVAAGNSKNYQMX--------MFCRHPRRWVA
Pea-FT-A           LTAEAIGLNAGNYTVWHFRRLLLESLKVDLHVEREFVERVASGNSKNYQIW------------HHRRWVA
Tomato-FTA         LTGEAIQLNPGNYTVWQFRRVVLEALGVDLREELKFVDRIAGENIKNYQIW------------HHRRWLA
Rice-RT-A          LTAEVIDLNPGNYTVWHFRRLVLEALDADLREEMDFVDRIVEDNPKNYQIW------------HHKRWLA
Zea mays-FT-A      LTAEAIELNPGNYTVWHFRRLILESLDFDLLEEMKFVELIAECNPKNYQIW------------HHLRWLA
Soy1-FT-A          LTAEAVQFNSGNYTVWHFRRLLLESLKVDLNDELDFVERMAAGNSKNYQMW------------HHRRWVA
Soy2-FT-A          LTAEAVQFNSGNYTVWHFRRLLLESLKVDLNDELEFVERMAAGNSKNYQMWCDALLCSFFHTLHHRRWVA
Triticum-FT-A      LTADAIHLNPGNYTVWHFRRVVLGALDADLLLEMHFVDQIAESNPLNYQVW------------HHKRWLA

                          150       160       170       180       190       200       210
                   ....|....|....|....|....|....|....|....|....|....|....|....|....|....|
BnA-12             EKLGPDVAGLEKEFTRRVLSLDAKHYHAWSHRQWALQALGGWENELNYCHELLEADVFNNSAWNQRYYVI
At-FT-A            EKLGPDVAGRELEFTRRVLSLDAKHYHAWSHRQWTLRALGGWEDELDYCHELLEADVFNNSAWNQRYYVI
PPI-Soy-FTA        EKLGPEARNNELEFTKKILSVDAKHYHAWSHRQWALQTLGGWEDELNYCTELLKEDIFNNSAWNQRYFVI
Pea-FT-A           EKLGPEARNSELEFTKKILSVDAKHYHAWSHRQWVLQNLGGWEDELSYCSELLAEDIFNNSAWNQRYFVI
Tomato-FTA         EKLGADAVTNELEFTKKIFSQDAKNYHAWSHRQWVLQALGGWEDELAYCQQLLEDDIYNNSAWNQRYFVV
Rice-RT-A          EKLGPDIANKEHEFTRKILSMDAKNYHAWSHRQWVLQALGGWETELQYCNQLLEEDVFNNSAWNQRYLVI
Zea mays-FT-A      EKLGPGIANKEHEFTMKILAIDALNYHAWSHRQWVLQALGGWETELEYCDHLLKEDVFNNSAWNQRYFVI
Soy1-FT-A          EKLGPEARNNELEFTKKILSVDAKHYHAWSHRQWALQTLGGWEDELNYCTELLKEDIFNNSAWNQRYFVI
Soy2-FT-A          EKLGPEARNNELEFTKKILSVDAKHYHAWSHRQWALQTLGGWEDELNYCTELLKEDIFNNSAWNQRYFVI
Triticum-FT-A      EKTGPDAANSEHDFTKKILAMDAKNYHAWSHRQWVLQALGGWESELQYCNQLLEEDVFNNSAWNQRYLVV

                          220       230       240       250       260       270       280
                   ....|....|....|....|....|....|....|....|....|....|....|....|....|....|
BnA-12             TRSPSLGGLEAMRESEVSYTVKAILANPGNESSWRYLKALYKDDTESWISDPSVSSVCLKVLSRADCFHG
At-FT-A            TQSPLLGGLEAMRESEVSYTIKAILTNPANESSWRYLKALYKDDKESWISDPSVSSVCLNVLSRTDCFHG
PPI-Soy-FTA        TRSPFLGGLKAMRESEVLYTIEAIIAYPENESSWRYLRGLYKGETTSWVNDPQVSSVCLKIL-RTKSNYV
Pea-FT-A           TRSPVLGGLKAMRESEVLETVEAIISYPENESSWRYLRGLEKDESTLYVNDAQVSSLCLKIL-KTKSNYL
Tomato-FTA         TRSPLLGGLVAMRELEVNYTVQAIRASPENESPWRYLRGLYKNDTQSLVQDSQVASVLWDVL-TSQNSHV
Rice-RT-A          TSSPLLGGLAAMRDSEVDYTVGAILANPQNESPWRYLKGLYKGENNLLMADERISDVCLKVL-KHDSTCV
Zea mays-FT-A      TRSPFLGGLAAMRDSGVDYTIEAILANAQNGSPWRYLKGLYKGENNLLVEDGRISAVCFKVL-KNDWTCV
Soy1-FT-A          TRSPFLGGLKAMRESEVLYTIEAIIAYPENESSWRYLRGLYKGETTSWVNDPQVSSVCLKIL-RTKSNYV
Soy2-FT-A          TRSPFLGGLKAMRESEVLYTIEAIIAYPENESSWRYLRGLYKGETTSNVNDPQVSSVCLKIL-RTKSNYV
Triticum-FT-A      TRSPILGGLAAMRDSEVDYTVEAIMVNPQNESPWRYLRGLYKDDNNLLVADNRISDACLKVL-NKDWTCV

                          290       300       310       320       330       340       350
                   ....|....|....|....|....|....|....|....|....|....|....|....|....|....|
BnA-12             FALSTLLDLLCDGLRPTNEHRDSVKALANEEP---ETN--------------LANLVCTILCRVDPIRAN
At-FT-A            FALSTLLDLLCDGLRPTNEHKDSVRALANEEP---ETN--------------LANLVCTILGRVDPIRAN
PPI-Soy-FTA        FALSTILDLICFGYQPNEDIRDAIDALNTADM---DKQDLDDDEKGEQQNLNIARNICSILKQVDPIRTN
Pea-FT-A           FALSTLLDLSASVIQPNEDFRDAIEALRLQIL---IKQ--DSD---------IAITICSILEQVDPIRVN
Tomato-FTA         HALRFLLDLLCHDLEPSQELKSAVDVLTPQSC---SPD------------LALTKKICSILEHADPMRVK
Rice-RT-A          FALSLLLDLLQIGLQPSDELKGTIEAIKNSDPEADEAVDA--D---------LATAICSILQRCDPLRIN
Zea mays-FT-A      FALSLLLDLLCTGLQPSDGIRSTLGTIRSSHP---ETADD--D---------PAAAVCCILQKCDPLAVN
Soy1-FT-A          FALSTILDLICFGYQPNEDIRDAIDALKTADM---DKQDLDDDEKGEQQNLNIARNICSILKQVDPIRTN
Soy2-FT-A          FALSTILDLICFGYQPNEDIRDAIDALKTADM---DKQDLDDDEKGEQQNLNIARNICSILKQVDPIRTN
Triticum-FT-A      FALSFLLDLLRMGLQPSNELKGTIEAMENSDP---ETGHA--D---------IAVAVCSILQKCDPLRIN
```

TABLE 10B-continued

ClustalW Amino Acid Analysis of FT Alpha Subunits

```
                                 360       370
                   ....|....|....|....|....|....
BnA-12             YWAWKL-----------------------
At-FT-A            YWAWRKSKITVAAI---------------
PPI-Soy-FTA        YWIWRKSRLP-------------------
Pea-FT-A           YWVWRKSRLPQAA----------------
Tomato-FTA         YWNWRKSMVRVQLLQSQNAERLANLSVQE
Rice-RT-A          YWSWYRTTISSQT----------------
Zea mays-FT-A      YWSWFKDTLSQIS----------------
Soy1-FT-A          YWIWRKSRLPLSA----------------
Soy2-FT-A          YWIWRKSRLPLSA----------------
Triticum-FT-A      YWSWYQTTLSS------------------
```

TABLE 10C

ClustalW Nucleic Acid Analysis of FT Beta Subunits

1) PPI-BnFTb; FT3 (SEQ ID NO: 14)
2) eral (SEQ ID NO: 1)
3) Wiggum (SEQ ID NO: 80)
4) PPI-Soy-FTB; FT5 (SEQ ID NO: 40)
5) DuP-Soy-FTB (SEQ ID NO: 81)
6) PPI-Corn-FTB; FT6 (SEQ ID NO: 43)
7) DuP-Corn-FTB (SEQ ID NO: 82)
8) Pea-FT-B (SEQ ID NO: 83)
9) Tomato (SEQ ID NO: 84)
10) Tobacco (SEQ ID NO: 85)

```
                            10        20        30        40        50        60        70
               ....|....|....|....|....|....|....|....|....|....|....|....|....|....|
PPI-BnFTb      ----------------------------------------------------------------------
eral           ----------------------------------------------------------------------
Wiggum         ATGCCAGTAGTAACCCGCTTGATTCGTTTGAAGTGTGTAGGGCTCAGACTTGACCGGAGTGGACTCAATC
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       ----------------------------------------------------------------------
Tomato         ----------------------------------------------------GTAAACGAGCGTTGATTT
Tobacco        ----------------------------------------------------------------------

                            80        90       100       110       120       130       140
               ....|....|....|....|....|....|....|....|....|....|....|....|....|....|
PPI-BnFTb      ----------------------------------------------------------------------
eral           ----------------------------------------------------------------------
Wiggum         GGCGAATCTGTCACGGAGGACACGGGGAATCAACGCGGCGGAGAGTGATGGAAGAGCTTTCAAGCCTAAC
PPI-Soy-FTB    ----------------------------------------------------------------------
DuP-Soy-FTB    ----------------------------------------------------------------------
PPI-Corn-FTB   -------------------------------------------GGCGGATCCCGACCTACCGAGGCTCAC
DuP-Corn-FTB   -------------------------------------------GGCGGATCCCGACCTACCGAGGCTCAC
Pea FT-B       --------------------------------------------CGGACCCCCCCGTCCACAATCGTGAT
Tomato         GTCGCTGACGAAATTTACAGTCAAGAGTAGTAACCGGTTGTAGTGAAAAAATGGAGTCGAGGAAAGTGAC
Tobacco        -------------------------------------------------------GGCACGAGCGGC-AC

                           150       160       170       180       190       200       210
               ....|....|....|....|....|....|....|....|....|....|....|....|....|....|
PPI-BnFTb      ----------------------------------------------------------------------
eral           ----------------------------------------------------------------------
Wiggum         CGTGAGTCAGCGCGAGCAATTTCTGGTGGAGAACGATGTGTTCGGGATCTATAATTACTTCGACGCCAGC
PPI-Soy-FTB    ------------------------------------------------------------GCCACCATTC
DuP-Soy-FTB    ------------------------------------------------------------GCCACCATTC
PPI-Corn-FTB   GGTGACGCAGGTGGAGCAGATGAAGGTGGAGGCCAGGGTTGGCGACATCTACCGCTCCCTCTTCGGGGCC
DuP-Corn-FTB   GGTGACGCAGGTGGAGCAGATGAAGGTGGAGGCCAGGGTTGGCGACATCTACCGCTCCCTCTTCGGGGCC
Pea FT-B       GATGACGTCTCCGCGAGCATTTCAACAACCAGTTACTCAAACCACCGCGGAGTAACACATGGAAGCTTCA
Tomato         GAAGACGCTGGAAGATCAATGGGTGGTGGAGCGTCGAGTCCGAGAGATATACGATTATTTCTACAGCATT
Tobacco        GAGGACACTGGAAGATCAATGGATGGTGGAGCGTCAAGTTCGGGAGATATACAATTTTTTCTACAGCATT

                           220       230       240       250       260       270       280
               ....|....|....|....|....|....|....|....|....|....|....|....|....|....|
PPI-BnFTb      ----------------------------------------------------------------------
eral           ------------------------ATGGAGATTCAGCGAGATAAGCAATT-GGATTATC-----TGATGA
Wiggum         GACGTTTCTACTCAAAATACATGATGGAGATTCAGCGAGATAAGCAATT-GGATTATC-----TGATGA
PPI-Soy-FTB    CTCGCAACGCCCAAACCCTCAT-GTTGGAGCTTCAACGCGATAATCACAT-GCAGTAT-----GTCTCCA
DuP-Soy-FTB    CTCGCAACGCCCAAACCCTCAT-GTTGGAGCTTCAACGCGATAATCACAT-GCAGTAT-----GTCTCCA
PPI-Corn-FTB   GCGCCCAACACGAAATCCATCATGCTAGAGCTGTGGCGTGATCAGCATAT-CGAGTATC-----TGACGC
DuP-Corn-FTB   GCGCCCAACACGAAATCCATCATGCTAGAGCTGTGGCGTGATCAGCATAT-CGAGTATC-----TGACGC
Pea FT-B       ACCGCGGCGGAGACACCAACTCCGACGGTGAGTCAGAGAGATCAATGGATAGTAGAATCACAGGTCTTTC
Tomato         TCCCCCAACTCTCCGTCCGACCTCATAGAGATCGAACGTGACAAACACTT-CGGTTATC-----TAAGCC
Tobacco        CCNCCCAATTC---------CCACTTAGAGACTTCAACAGAAAAGCACTT-GCATTATC-----TCACTC
```

TABLE 10C-continued

ClustalW Nucleic Acid Analysis of FT Beta Subunits

```
                      290       300       310       320       330       340       350
              ....|....|....|....|....|....|....|....|....|....|....|....|....|....|
PPI-BnFTb     --------------------------------------------------------TGGCTTTGTTACTG
eral          AAGGCTTAAGGCAGCTT---GGTCCGCAGTTTTCTTCCTTAGATGCTAATCGACCTTGGCTTTGTTACTG
Wiggum        AAGGCTTAAGGCAGCTT---GGTCCGCAGTTTTCTTCCTTAGATGCTAATCGACCTTGGCTTTGTTACTG
PPI-Soy-FTB   AAGGCCTTCGCCATCTC---AGTTCCGCATTTTCCGTTTTGGACGCTAATCGACCCTGGCTCTGCTACTG
DuP-Soy-FTB   AAGGCCTTCGCCATCTC---AGTTCCGCATTTTCCGTTTTGGACGCTAATCGACCCTGGCTCTGCTACTG
PPI-Corn-FTB  CTGGGCTGAGGCATATG---GGACCAGCCTTTCATGTTCTAGATGCCAATCGCCCTTGGCTATGCTACTG
DuP-Corn-FTB  CTGGGCTGAGGCATATG---GGACCAGCCTTTCATGTTCTAGATGCCAATCGCCCTTGGCTATGCTACTG
Pea FT-B      ATATTTATCAACTCTTCGCCAATATTCCTCCTAACGCCCAATCTATCATTCGACCTTGGCTGTGTTACTG
Tomato        AAGGTCTCAGAAAACTT---GGTCCGTCGTTTTCCGTTTTGGATGCCAGTCGACCATGGCTTTGCTACTG
Tobacco       GAGGTCTCAGAAAACTT---GGTCCGTCGTTCTCCGTCTTGGATGCTAATCGACCATGGCTTTGCTACTG

                      360       370       380       390       400       410       420
              ....|....|....|....|....|....|....|....|....|....|....|....|....|....|
PPI-BnFTb     GATTCTTCATTCAATTGCTTTGCTTGGGGAGTCTGTGGATGATGACTTAGAAAACAATGCAATCGATTTT
eral          GATTCTTCATTCAATAGCTTTGCTTGGGGAGACTGTGGATGATGAATTAGAAAGCAATGCCATTGACTTC
Wiggum        GATTCTTCATTCAATAGCTTTGCTTGGGGAGACTGTGGATGATGAATTAGAAAGCAATGCCATTGACTTC
PPI-Soy-FTB   GATCTTCCACTCCATTGCTTTGTTGGGAGAATCCGTCGATGATGAACTCGAAGATAACGCTATCGATTTT
DuP-Soy-FTB   GATCTTCCACTCCATTGCTTTGTCGGGAGAATCCGTCGATGATGAACTCGAAGATAACGCTATCGATTTT
PPI-Corn-FTB  GATGGTTCATCCACTTGCTTTGCTGGATGAAGCACTTGATGATGATCTTGAGAATGATATCATAGACTTC
DuP-Corn-FTB  GATGGTTCATCCACTTGCTTTGCTGGATGAAGCACTTGATGATGATCTTGAGAATGATATCATAGACTTC
Pea FT-B      GATTATTCATTCAATTGCTTTGTTGGGAGAATCTATTGATGATGATCTCGAAGATAACACTGTCGATTTT
Tomato        GACACTTCATTCAATCGCTTTGTTGGGAGAATCTATTGGTGGCAAACTGGAAAATGATGCAATTGACTTT
Tobacco       GATACTTCATTCAATCGCTTTGTTGGGAGAATCTATTGATGCCCAACTGGAAAATGATGCAATTGACTTT

                      430       440       450       460       470       480       490
              ....|....|....|....|....|....|....|....|....|....|....|....|....|....|
PPI-BnFTb     CTTGGACGTTGCCAGGGTTCTGATGGTGGATATGGTGGTGGTCCTGGCCAACTTCCACATCTTGCAACAA
eral          CTTGGACGCTGCCAGGGCTCTGAAGGTGGATACGGTGGTGGTCCTGGCCAACTTCCACATCTTGCAACTA
Wiggum        CTTGGACGCTGCCAGGGCTCTGAAGGTGGATACGGTGGTGGTCCTGGCCAACTTCCACATCTTGCAACTA
PPI-Soy-FTB   CTTAACCGTTGCCAGGATCCGAATGGTGGATATGCCGGGGGACCAGGCCAGATGCCTCATATTGCCACAA
DuP-Soy-FTB   CTTAACCGTTGCCAGGATCCGAATGGTGGATATGCCGGGGGACCAGGCCAGATGCCTCATATTGCCACAA
PPI-Corn-FTB  TTAGCTCGATGTCAGGATAAAGATGGTGGATATAGTGGTGGACCTGGACAGTTGCCTCACCTAGCTACGA
DuP-Corn-FTB  TTAGCTCGATGTCAGGATAAAGATGGTGGATATAGTGGTGGACCTGGACAGTTGCCTCACCTAGCTACGA
Pea FT-B      CTTAACCGTTGCCAGGATCCAAATGGTGGATATGCTGGGGGACCTGGTCAGATGCCTCATCTTGCCACAA
Tomato        CTGACCCGTTGCCAGGATAAAGATGGTGGCTATGGAGGTGGACCTGGTCAGATGCCTCATCTTGCAACTA
Tobacco       CTGAGCCGTTGCCAGGATGAAGATGGTGGCTATGGTGGTGGACCTGGTCAGATGCCTCATCTTGCAACTA

                      500       510       520       530       540       550       560
              ....|....|....|....|....|....|....|....|....|....|....|....|....|....|
PPI-BnFTb     GTTATGCTGCAGTGAATACACTTGTTACTTTAGGAGGTGAGAAAGCCTTCTCTTCAATTAACAGAGAACA
eral          CTTATGCTGCAGTGAATGCACTTGTTACTTTAGGAGGTGACAAAGCCCTTTCTTCAATTAATAGAGAAAA
Wiggum        CTTATGCTGCAGTGAATGCACTTGTTACTTTAGGAGGTGACAAAGCCCTTTCTTCAATTAATAGAGAAAA
PPI-Soy-FTB   CTTATGCTGCTGTTAATTCACTTATTACTTTGGGTGGTGAGAAATCCCTGGCATCAATTAATAGAGATAA
DuP-Soy-FTB   CTTATGCTGCTGTTAATTCACTTATTACTTTGGGTGGTGAGAAATCCCTGGCATCAATTAATAGAGATAA
PPI-Corn-FTB  CTTATGCTGCTGTAAATACACTTGTGACAATAGGGAGCGAAAGAGCATTGTCATCAATCAATAGGGGCAA
DuP-Corn-FTB  CTTATGCTGCTGTAAATACACTTGTGACAATAGGGAGCCAAAGAGCATTGTCATCAATCAATAGGGGCAA
Pea FT-B      CTTATGCTGCAGTCAATACTCTTATTACTCTGGGTGGTGAGAAATCTTTGGCATCTATTAATAGAAATAA
Tomato        CTTATGCTGCAGTCAATTCACTAATAACTTTGGGCAAACCTGAAGCTCTGTCATCAATTAATAGAGAAAA
Tobacco       CTTATGCTGCAGTCAATTCACTCATAACTTTGGGCAGCCCTAAAGCTCTGTCATCAATCAATAGAGAAAA

                      570       580       590       600       610       620       630
              ....|....|....|....|....|....|....|....|....|....|....|....|....|....|
PPI-BnFTb     AATGGCTTGTTTCTTAAGACGAATGAAGGATACAAATGGAGGTTTCAGGATGCATAATATGGGAGAAATA
eral          AATGTCTTGTTTTTTAAGACGGATGAAGGATACAAGTGGAGGTTTCAGGATGCATGATATGGGAGAAATT
Wiggum        AATGTCTTGTTTTTTAAGACGGATGAAGGATACAAGTGGAGGTTTCAGGATGCATGATATGGGAGAAATG
PPI-Soy-FTB   ACTGTATGGGTTTCTGCGGCGGATGAAGCAACCAAATGGTGGATTCAGGATGCATGATGAAGGTGAAATT
DuP-Soy-FTB   ACTGTATGGGTTTCTGCGGCGGATGAAGCAACCAAATGGTGGATTCAGGATGCATGATGAAGGTGAAATT
PPI-Corn-FTB  CCTGTACAATTTTATGCTGCAGATGAAAGATGTATCAGGTGCTTTCAGAATGCATGATGGTGGCGAAATT
DuP-Corn-FTB  CCTGTACAATTTTATGCTGCAGATGAAAGATGTATCAGGTGCTTTCAGAATGCATGATGGTGGCGAAATT
Pea FT-B      GTTGTACGGGTTTATGCGGCGGATGAAACAGCCAAACGGCGGATTCAGGATGCATGACGAGGGAGAAATT
Tomato        GTTGTACACATTTTTGCTGCGAATGAAAGACGCAAGTGGTGGATTCAGGATGCACGATGGTGGAGAAGTA
Tobacco       ATTGTATACATTTTGGCTGCAAATGAAAGACACAAGTGGTGGCTTCAGGATGCATGATGGTGGAGAAGTA

                      640       650       660       670       680       690       700
              ....|....|....|....|....|....|....|....|....|....|....|....|....|....|
PPI-BnFTb     GATGTGCGAGCGTGCTACACTGCGATTTTGATTGCAAGCATCCTGAACATTGTGGATGATGAACTCACCC
eral          GATGTTCGTGCATGCTACACTGCAATTTCGGTTGCAAGCATCCTAAATATTATGGATGATGAACTCACCC
Wiggum        GATGTTCGTGCATGCTACACTGCAATTTCGGTTGCAAGCATCCTAAATATTATGGATGATGAACTCACCC
PPI-Soy-FTB   GATGTTCGAGCTTGCTACACTGCCATTTCTGTTGCAAGTGTTTTGAACATTTTGGATGATGAGCTGATCC
DuP-Soy-FTB   GATGTTCGAGCTTGCTACACTGCCATTTCTGTTGCAAGTGTTTTGAACATTTTGGATGATGAGCTGATCC
PPI-Corn-FTB  GATGTCCGTGCTTCCTACACCGCTATATCGGTTGCCAGCCTTGTGAATATTCTTGATTTTAAACTGGCAA
DuP-Corn-FTB  GATGTCCGTGCTTCCTACACCGCTATATCGGTTGCCAGCCTTGTGAATATTCTTGATTTTAAACTGGCAA
Pea FT-B      GACGTTCGAGCTTGCTACACTGCCATCTCTGTGGCAAGTGTTCTGAACATTTTGGATGATGAGCTGATCA
Tomato        GATGTTCGTGCCTGTTATACTGCCATTTCTGTTGCAAATATATTAAACATTGTGGATGACGAGCTGATTC
Tobacco       GATGTTCGTGCCTGTTATACTGCCATTTCTGTTGCAAGTATATTGCAAATTGTGGATGATGAACTGATTA
```

TABLE 10C-continued

ClustalW Nucleic Acid Analysis of FT Beta Subunits

```
                          710       720       730       740       750       760       770
                  ....|....|....|....|....|....|....|....|....|....|....|....|....|....|
PPI-BnFTb         GCGGCTTAGGAGATTACATTTTGAGTTGCCAAACTTATGAAGGTGGCATTGGAGGGGAACCTGGCTCCGA
eral              AGGGCCTAGGAGATTACATCTTGAGTTGCCAAACTTATGAAGGTGGCATTGGAGGGGAACCTGGCTCCGA
Wiggum            AGGGCCTAGGAGATTACATCTTGAGTTGCCAAACTTATGAAGGTGGCATTGGAGGGGAACCTGGCTCCGA
PPI-Soy-FTB       AGAATGTTGGAGACTACATTATAAGCTGTCAAACATATGAGGGTGGCATTGCTGGTGAGCCTGGTTCTGA
DuP-Soy-FTB       AGAATGTTGGAGACTACATTATAAGCTGTCAAACATATGAGGGTGGCATTGCTGGTGAGCCTGGTTCTGA
PPI-Corn-FTB      AAGGTGTAGGCGACTACATAGCAAGATGTCAAACTTATGAAGGTGGTATTGCTGGGGAGCCTTATGCTGA
DuP-Corn-FTB      AAGGTGTAGGCGACTACATAGCAAGATGTCAAACTTATGAAGGTGGTATTGCTGGGGAGCCTTATGCTGA
Pea FT-B          AGAATGTTGGAGACTTCATTTTAAGCTGTCAAACATATGAGGGAGGCCTTGCTGGTGAGCCTGGGTCTGA
Tomato            ATGGTGTTGGAAATTACATCCTAAGTTGTCAGACTTATGAAGGTGGAATTGCTGGCGAACCAGGTTCTGA
Tobacco           ATGATGTTGGGAATTACATCCTAAGTTGTCAGACTTATGAAGGTGGAATTGCTGGCGAACCAGGTTCTGA

                          780       790       800       810       820       830       840
                  ....|....|....|....|....|....|....|....|....|....|....|....|....|....|
PPI-BnFTb         AGCTCATGGTGGGTACACGTACTGTGGGTTGGCTACT TGATTTTAATCAATGAAGTCGACCGCTTGAAT
eral              AGCTCACGGTGGGTATACCTACTGTGGTTTGGCTGCT TGATTTTAATCAATGAGGTCGACCGTTTGAAT
Wiggum            AGCTCACGGTGGGTATACCTACTGTGGTTTGGCTGCT TGATTTTAATCAATGAGGTCGACCGTTTGAAT
PPI-Soy-FTB       CGCTCATGGTGGGTACACCTTTTGTGGATTAGCTACA TGATTCTGATTGGTGAGGTTAATCACTTGGAT
DuP-Soy-FTB       GGCTCATGGTGGGTACACCTTTTGTGGATTAGCTACA TGATTCTGATTGGTGAGGTTAATCACTTGGAT
PPI-Corn-FTB      AGCACATGGTGGGTATACATTCTGTGGATTGGCTGCTTTGATCCTGCTTAATGAGGCAGAGAAAGTTGAC
DuP-Corn-FTB      AGCACATGGTGGGTATACATTCTGTGGATTGGCTGCTTTGATCCTGCTTAATGAGGCAGAGAAAGTTGAC
Pea FT-B          CGCTCATGGCGGGTATACCTTTTGTGGGTTAGCTGCA TGATTCTGATTGGTGAGGTTAATCGCTTGGAT
Tomato            AGCTCATGGTGGGTATACTTTCTGTGGGTTGGCTGCA TGATTCTGATCAACGAAGTAGATCGATTGGAC
Tobacco           AGCTCATGGTGGGTATACCTTCTGTGGGTTGGCTGCA TGATTCTGATTAACGAAGCGAATCGATTGGAC

                          850       860       870       880       890       900       910
                  ....|....|....|....|....|....|....|....|....|....|....|....|....|....|
PPI-BnFTb         TTGGATTCGTTAATGAATTGGGTTGTACATCGACAAGGAGTAGAAATGGGATTCCAAGGTAGGACGAACA
eral              TTGGATTCATTAATGAATTGGGCTGTACATCGACAAGGAGTAGAAATGGGATTTCAAGGTAGGACGAACA
Wiggum            TTGGATTCATTAATGAATTGGGCTGTACATCGACAAGGAGTAGAAATGGGATTTCAAGGTAGGACGAACA
PPI-Soy-FTB       CTGCCTCGATTAGTTGACTGGGTGGTATTCCGACAAGGTAAGGAATGTGGATTCCAGGGGAGAACAAATA
DuP-Soy-FTB       CTGCCTCGATTAGTTGACTGGGTGGTATTCCGACAAGGTAAGGAATGTGGATTCCAGGGGAGAACAAATA
PPI-Corn-FTB      TTGCCTAGTTTGATTGGCTGGGTGGCTTTTCGTCAAGGACTGGAATGCGGATTTCAAGGACGAACTAATA
DuP-Corn-FTB      TTGCCTAGTTTGATTGGCTGGGTGGCTTTTCGTCAAGGAGTGGAATGCGGATTTCAAGGACGAACTAATA
Pea FT-B          CTGCCTCGTTTACTTGATTGGGTTGTGTTTCGGCAAGGTAAAGAGTGTGGATTTCAGGGGAGAACGAATA
Tomato            TTGCCAGGTTTAATTGATTGGGTGGTATTTAGACAAGGGGTCGAAGGTGGATTTCAAGGCAGGACAAATA
Tobacco           TTGCCAAGATTAATTGATTGGGTGGTATTTAGACAAGGAGTCGAAGGTGGATTTCAAGGCAGGACAAATA

                          920       930       940       950       960       970       980
                  ....|....|....|....|....|....|....|....|....|....|....|....|....|....|
PPI-BnFTb         AATTGGTCGACGGTTGCTACACGTTTTGGCAGGCAGCCCCCTGTGTTCTACTACAGCGATTTTTTTCATC
eral              AATTGGTCGATGGTTGCTACACATTTTGGCAGGCAGCCCCTTGTGTTCTACTACAAAGATTATATTCAAC
Wiggum            AATTGGTCGATGGTTGCTACACATTTTGGCAGGCAGCCCCTTGTGTTCTACTACAAAGATTATATTCAAC
PPI-Soy-FTB       AACTGGTGGATGGATGCTATTCCTTTTGGCAGGGAGGTGCTGTTGCTCTATTGCAAAGATTATCTTCTAT
DuP-Soy-FTB       AACTGGTGGATGGATGCTATTCCTTTTGGCAGGGAGGTGCTGTTGCTCTATTGCAAAGATTATCTTCTAT
PPI-Corn-FTB      AATTGGTTGATGGTTGCTACTCCTTTTGGCAGGGAGCTGCCATTGCTTTCACACAAAAGTTAATTACGAT
DuP-Corn-FTB      AATTGGTTGATGGTTGCTACTCCTTTTGGCAGGGAGCTGCCATTGCTTTCACACAAAAGTTAATTACGAT
Pea FT-B          AATTGGTAGATGGATGCTACTCGTTTTGGCAGGGAGGTGCTGTTGCCCTATTGCAAAGATTACATTCTAT
Tomato            AATTAGTCGATGGCTGCTATTCCTTTTGGCAGGGCGCGGTAGTGTTTCTTATACAAAGACTAAATTTGAT
Tobacco           AATTAGTCGATGGCTGCTATTCCTTTTGGCAGGCCGCGGTAGCTTTTCTTATACAAAGATTAAAATCGAC

                          990      1000      1010      1020      1030      1040      1050
                  ....|....|....|....|....|....|....|....|....|....|....|....|....|....|
PPI-BnFTb         CCAGGAT-ATGGCACC------TCATGGATCATCATCA-----------CATATGTCACAAGGGACAGAT
eral              CAATGATCATGACGT-------TCATGGATCATCA--------------CATATATCAGAAGGGACAAAT
Wiggum            CAATGATCATGACGT-------TCATGGATCATCA--------------CATATATCAGAAGGGACAAAT
PPI-Soy-FTB       TATCAACAAACAGATG------GAAGAGA-CATCA--------------CAGATTTTTGCGGTATCTTAT
DuP-Soy-FTB       TATCAACAAACAGATG------GAAGAGA-CATCA--------------CAGATTTTTGCGGTATCTTAT
PPI-Corn-FTB      TGTTGATAAGCAATTGAGGTCCTCGTA-----T--------------------TCCTGCAAAA----GG
DuP-Corn-FTB      TGTTGATAAGCAATTGAAGTCCTCGTA-----T--------------------TCCTGCAAAA----GG
Pea FT-B          TATCGACGAACAAATG------GCAGAGG-CATCA--------------CAGTTTGTTACAGTATCTGAT
Tomato            AGTCCATGAACAACTAGGGCTGTCAAATGACCTCAGTACAGAAAGTGCTGATGATTCTTCAGAGTCAGAG
Tobacco           AGTCCATGAACAACTAGGGCTGTCAAATGAACTCAGTACAGAAAGTGCTGATGATTCTTCGGAGTCAGAG

                         1060      1070      1080      1090      1100      1110      1120
                  ....|....|....|....|....|....|....|....|....|....|....|....|....|....|
PPI-BnFTb         GAAGATCACGAGGA-ACATGGTCATGATGAAGATGATCCTGAAGACAGTGATGAAGATGA---TTCTGAT
eral              GAAGAACAT-------CATGCTCATGATGAAGATGACCTTGAAGACAGTGATGATGATGATGATTCTGAT
Wiggum            GAAGAACAT-------CATGCTCATGATGAAGATGACCTTGAAGACAGTGATGATGATGATGATTCTGAT
PPI-Soy-FTB       GTATCTGAAG------CAAAAGAAAGTTTGGATGGAACCTCTAGTCA-TGCAACATGCCGTGGTGAGCAT
DuP-Soy-FTB       GTATCTGAAG------CAAAAGAAAGTTTGGATGGAACCTCTAGTCA-TGCAACATGCCGTGGTGAGCAT
PPI-Corn-FTB      CCATCAGGAGAG----GATGCCTGGAG----CACCAGTTCATAT----GGGTGCACC--------G-CGA
DuP-Corn-FTB      CCATCAGGAGAG----GATGCCTGCAG----CACCAGTTCATAT----GGGTGCACC--------G-CGA
Pea FT-B          GCACCTGAAG------AAAAGGAATGTTTGGACGGAACCTCAAGTCA-TGCAACTTCCCATATTAGGCAT
Tomato            TTATCTGATGAAGAAGAGCATTTGGAAGGGATATCCTCTCATGTTCA-GGATACTTTCCCTCTTGGACAA
Tobacco           TTATCTGATGAA---GAGCATTTGCAAGGGACATCATCTCATGTTCA-GAAGACTTGCCCTCTTGGACAA
```

TABLE 10C-continued

ClustalW Nucleic Acid Analysis of FT Beta Subunits

```
                      1130      1140      1150      1160      1170      1180      1190
                  ....|....|....|....|....|....|....|....|....|....|....|....|....|....|
PPI-BnFTb         GAGGAT---------AGCGATGAA---GATTCAGGGAATGGTCACCAAGTTCATCATACGTCTAC-CTAC
eral              GAGGAC---------AACGATGAA---GATTCAGTGAATGGTCACAGAATCCATCATACATCCAC-CTAC
Wiggum            GAGGAC---------AACGATGAA---GATTCAGTGAATGGTCACAGAATCCATCATACATCCAC-CTAC
PPI-Soy-FTB       GAAGGC---------ACCAGTGAATCCAGTTCATCTGATTTTAAAAATATTGCCTATAAATTTAT-TAAT
DuP-Soy-FTB       GAAGGC---------ACCAGTGAATCCAGTTCATCTGATTTTAAAAATATTGCCTATAAATTTAT-TAAT
PPI-Corn-FTB      ATAAGT----------------CTTCCTCTGCTGTGGACTATGCGAAGTTTGGATTTGATTTTATACAAC
DuP-Corn-FTB      AAAAGT----------------CTTCCTCTGCTGTGGACTATGCGAAGTTTGGATTTGATTTTATACAAC
Pea FT-B          GAAGGC---------ATGAATGAATCCTGCTCATCTGACGTTAAAAATATTGGTTATAACTTTAT-TAGT
Tomato            GCAGGTGCTTGTCAAGAAAATGCTTCTCATAGCCCAAAAATAGCAGATACTGGATATGAGTTTAT-CAAC
Tobacco           GAAGGA------CAGGAAAATGCTTCAGATCCCACAAAGATAGCAGATACTGGTTATGATTTTGT-CAAT

                      1200      1210      1220      1230      1240      1250      1260
                  ....|....|....|....|....|....|....|....|....|....|....|....|....|....|
PPI-BnFTb         ATTGACAGGAGAATTCAACCTGTTTTTGATAGCCTCGGCTTGCAAAGATATGTGCTCTTGTGCTCTCAGG
eral              ATTAACAGGAGAATGCAACTGGTTTTTGATAGCCTCGGCTTGCAGAGATATGTACTCTTGTGCTCTAAGA
Wiggum            ATTAACAGGAGAATGCAACTGGTTTTTGATAGCCTCGGCTTGCAGAGATATGTACTCTTGTGCTCTAAGA
PPI-Soy-FTB       GAGTGGAGAGCACAAGAACCACTTTTTCACAGTATTGCTTTACAGCAATATATTCTCTTATGTGCACAGG
DuP-Soy-FTB       GAGTGGAGAGCACAAGAACCACTTTTTCACAGTATTGCTTTACAGCAATATATTCTCTTATGTGCACAGG
PPI-Corn-FTB      AGAGCAACCAA-ATTGGCCCACTCTTCCATAACATTGCCCTGCAACAATACATCCTACTTTGTTCTCAGG
DuP-Corn-FTB      AGAGCAACCAA-ATTGGCCCACTCTTCCATAACATTGCCCTGCAACAATACATCCTACTTTGTTCTCAGG
Pea FT-B          GAGTGGAGACAAAGTGAACCACTTTTTCACAGCATTGCCTTACAGCAATATATTCTTTTATGTTCACAGG
Tomato            CGACCCATAGCTATGAGGCCTCTCTTTGACAGCATGTATCTGCAGCAATATGTTCTTCTTTGCTCTCAGA
Tobacco           CGNACGATAGCTATGCGACCTGTGTTTGACAGCTTTTATCTGCAGCAATACGTTCTTCTCTGCTCCCAGA

                      1270      1280      1290      1300      1310      1320      1330
                  ....|....|....|....|....|....|....|....|....|....|....|....|....|....|
PPI-BnFTb         TTGCTGATGGTGGATTCAGAGACAAGCTGAGGAAACCCCGTGACTTCTACCACACATGTTACTGCCTAAG
eral              TCCCTGACGGTGGATTCAGAGACAAGCCGAGGAAACCCCGTGACTTCTACCACACATGTTACTGCCTGAG
Wiggum            TCCCTGACGGTGGATTCAGAGACAAGCCGAGGAAACCCCGTGACTTCTACCACACATGTTACTGCCTGAG
PPI-Soy-FTB       AGCAAGAGGGTGGACTGAGAGACAAACCGGGTAAACGTAGAGATCATTATCACACATGTTACTGTTTAAG
DuP-Soy-FTB       AGCAAGAGGGTGGACTGAGAGACAAACCGGGTAAACGTAGAGATCATTATCACACATGTTACTGTTTAAG
PPI-Corn-FTB      TACTAGAGGGAGGCTTGAGGGATAAGCCTGGAAAGAACAGAGATCACTATCATTCATGCTACTGCCTCAG
DuP-Corn-FTB      TACTAGAGGGAGGCTTGAGGGATAAGCCTGGAAAGAACAGAGATCACTACCATTCATGCTACTGCCTCAG
Pea FT-B          AGCAAGATGGTGGGCTCAGGGACAAACCGGGTAAACGCAGGGATCATTATCATTCATGTTACTGTTTAAG
Tomato            TTGAAGTTGGTGGTTTCAGAGACAAACCTGGGAAGGGTAGAGACTACTACCATACCTGTTACTGTTTAAG
Tobacco           T---AGATGGAGGTTTCAGAGACAAACCTGGGAAGGGTAGAGACCACTACCATACTTGCTACTGTTTAAG

                      1340      1350      1360      1370      1380      1390      1400
                  ....|....|....|....|....|....|....|....|....|....|....|....|....|....|
PPI-BnFTb         CGGTCTTTCCGTGGCTCAACACGCTTGGTCAAAAGACGAGGACACTCCTCCTTTGACTCGTGACATTTTG
eral              CGGCTTGTCTGTGGCTCAGCACGCTTGGTTAAAAGACGAGGACACTCCTCCTTTGACTCGCGACATTATG
Wiggum            CGGCTTGTCTGTGGCTCAGCACGCTTGGTTAAAAGACGAGGACACTCCTCCTTTGACTCGCGACATTATG
PPI-Soy-FTB       TGGACTCTCATTGTGCCAGTATAGTTGGTCAAAGCACCCAGATTCTCCACCAC-----------------
DuP-Soy-FTB       TGGACTCTCATTGTGCCAGTATAGTTGGTCAAAGCACCCAGATTCTCCACCAC-----------------
PPI-Corn-FTB      TGGCCTCGCAGTTAGCCAGTACAGTGCCATGACTGATACTGGTTCGTGCCCATTACCTCAGCATGTGCTT
DuP-Corn-FTB      TGGCCTCGCAGTTAGCCAGTACAGTGCCATGACTGATACTGGTTCGTGCCCATTACCTCAGCATGTGCTT
Pea FT-B          TGGGTTGTCACTGTGCCAGTATAGTTGGTCGAAGCGCCCAGATTCTCCACCGCTGCCTAAGGTAGTAATG
Tomato            TGGTCTTTCAATTGCTCAGTATAGCTGGACCGACGAAGCTGATTCTACACCATTACCCAGGGATGTATTT
Tobacco           TGGTCTTTCAATTGCTCAATATAGCTGGACCAACGAAGCTGATGCGCCACCATTACCCAGGGATGTATTT

                      1410      1420      1430      1440      1450      1460      1470
                  ....|....|....|....|....|....|....|....|....|....|....|....|....|....|
PPI-BnFTb         GGTGGCTACGCA-AA--CCACCTTGAACCTGTTCACCTCCTCCACAACATTGTCTTGGATCGGTATTATG
eral              GGTGGCTACTCG-AA--TCTCCTTGAACCTGTTCAACTTCTTCACAACATTGTCATGGATCAGTATAATG
Wiggum            GGTGGCTACTCG-AA--TCTCCTTGAACCTGTTCAACTTCTTCACAACATTGTCATGGATCAGTATAATG
PPI-Soy-FTB       ----------------------------------------------------------------------
DuP-Soy-FTB       ----------------------------------------------------------------------
PPI-Corn-FTB      GGACCGTACTCT-AA--TTTGCTGGAGCCAATCCATCC--------------------------------
DuP-Corn-FTB      GGACCGTACTCT-AA--TTTGCTGGAGCCAATCCATCC--------------------------------
Pea FT-B          GGCCCATACTCC-AA--TCTCTTAGAACCCATCCATCCTCTCTTTAATGTTGTTTTGGATCGATATCGTG
Tomato            GGTCCTTATTCCAAATGTCTGTTGGAACAGGTTCACCCACTCTTCAACGTAGTGTTGGATCGGTATTATG
Tobacco           GGTCCTTATTCTCAAAATCTTTTGGAACAGATTCACCCACTTTACAACGTAGTGTTGGATCGGTATTATG

                      1480      1490      1500      1510      1520      1530      1540
                  ....|....|....|....|....|....|....|....|....|....|....|....|....|....|
PPI-BnFTb         AAGCTTCTAGATTT--------------------------------------------------------
eral              AAGCTATCGAGTTCTTCTTTAAAGCAGCATGACCCGTTGTTGCTAATGTATGGGAAACCCCAAACATAAG
Wiggum            AAGCTATCGAGTTCTTCTTTAAAGCAGCATGACCCGTTGTTGCTAATGTATGGGAAACTCCAAACATAAG
PPI-Soy-FTB       ----------------------------------------------------------------------
DuP-Soy-FTB       ----------------------------------------------------------------------
PPI-Corn-FTB      ----------------------------------------------------------------------
DuP-Corn-FTB      ----------------------------------------------------------------------
Pea FT-B          AAGCTCATGAATTCTTTTCTCAGTTGTGACGGATGACAAGGTTTTAGCTACCAATAGCTC-GATCATTAG
Tomato            AAGCTCGCGAATACT-CTCAGGCTTGTGAGACTGTTTCAC-CACTTTCATTAGCACCAAC--TTTTTCAG
Tobacco           AAGCTCGTAGCTTCTTCTCATGCTTGTGATAATATTTTACGCGATAGCTGTAGCTGGAAT--GTTACC--
```

TABLE 10C-continued

ClustalW Nucleic Acid Analysis of FT Beta Subunits

```
                      1550      1560      1570      1580      1590      1600      1610
              ....|....|....|....|....|....|....|....|....|....|....|....|....|....|
PPI-BnFTb     ----------------------------------------------------------------------
eral          AGTTTCCGTAGTCTTGTAACTTGTAAGATTTCAAAAG---------------------------------
Wiggum        AGTTTTCGTAGTGTTGTAACTTGTAAGATTTCAAAAGAAGTTTCACTAATTTAACCTTAAAACCTGTTAC
PPI-Soy-FTB   ----------------------------------------------------------------------
DuP-Soy-FTB   ----------------------------------------------------------------------
PPI-Corn-FTB  ----------------------------------------------------------------------
DuP-Corn-FTB  ----------------------------------------------------------------------
Pea FT-B      AATGTAAAATGTAAACTAAAATATGAAATATGAAATACCAAAAAGATATTATTGGATGAAATTCACGTGG
Tomato        AAACTTAGTTGCAATCCAGAAGTTAAAAGTGTCATTGGGTTCAAAAGAGTTGTGATCGTTTATGTACATA
Tobacco       ---TCTAGTTG---TTCAGAATCAGAGACTAATCTATTATTTTGAGGGATTGGATTCAAAAAAAAAAAAA

                      1620      1630      1640      1650      1660      1670      1680
              ....|....|....|....|....|....|....|....|....|....|....|....|....|....|
PPI-BnFTb     ----------------------------------------------------------------------
eral          ----------------------------------------------------------------------
Wiggum        TTTTTTATTACGTATATACCATTTATCATATCTTTGGTTTACGACTTAAAGAATTTGATGATTGTTGAAA
PPI-Soy-FTB   ----------------------------------------------------------------------
DuP-Soy-FTB   ----------------------------------------------------------------------
PPI-Corn-FTB  ----------------------------------------------------------------------
DuP-Corn-FTB  ----------------------------------------------------------------------
Pea FT-B      ATCTAATACAACTGCGTGGTTTTCATTCCTGATTTGATTTTGATTTACATGAGTTAAAACGTTAAACCCT
Tomato        TCCTTGCATTTGTATACGTGATACAAGTTGAGAGAATAACGGGTACTTTCTGAACTTGCTGAACTAGCAC
Tobacco       AAAAAAA---------------------------------------------------------------

                      1690      1700      1710      1720      1730      1740      1750
              ....|....|....|....|....|....|....|....|....|....|....|....|....|....|
PPI-BnFTb     ----------------------------------------------------------------------
eral          ----------------------------------------------------------------------
Wiggum        ----------------------------------------------------------------------
PPI-Soy-FTB   ----------------------------------------------------------------------
DuP-Soy-FTB   ----------------------------------------------------------------------
PPI-Corn-FTB  ----------------------------------------------------------------------
DuP-Corn-FTB  ----------------------------------------------------------------------
Pea FT-B      TCTTATTCATACATTTGTTAAGAGCTTAAGGCTTAATGGTTAAGCCAATGATATAAATATTTATGCAGAA
Tomato        GTAAATTCGTCTCTGGTTTACTGAGGTCTGTAAACATCAATGTGAAATTGCGAGATATGCATGTAATAGT
Tobacco       ----------------------------------------------------------------------

                      1760      1770      1780      1790      1800      1810      1820
              ....|....|....|....|....|....|....|....|....|....|....|....|....|....|
PPI-BnFTb     ----------------------------------------------------------------------
eral          ----------------------------------------------------------------------
Wiggum        ----------------------------------------------------------------------
PPI-Soy-FTB   ----------------------------------------------------------------------
DuP-Soy-FTB   ----------------------------------------------------------------------
PPI-Corn-FTB  ----------------------------------------------------------------------
DuP-Corn-FTB  ----------------------------------------------------------------------
Pea FT-B      AGCTGTTGCTTATCACCAACGGTAATATTAATAAGCAAACAAGTATTCTGTGAT----------------
Tomato        GGCTAAGATTTACAAATCTGGATACCGGTTATTAGTGATCAGAAATTTCATTCAATTTCCCAAACGGTCA
Tobacco       ----------------------------------------------------------------------

                      1830      1840      1850      1860      1870      1880      1890
              ....|....|....|....|....|....|....|....|....|....|....|....|....|....|
PPI-BnFTb     ----------------------------------------------------------------------
eral          ----------------------------------------------------------------------
Wiggum        ----------------------------------------------------------------------
PPI-Soy-FTB   ----------------------------------------------------------------------
DuP-Soy-FTB   ----------------------------------------------------------------------
PPI-Corn-FTB  ----------------------------------------------------------------------
DuP-Corn-FTB  ----------------------------------------------------------------------
Pea FT-B      ----------------------------------------------------------------------
Tomato        CCTAAGTTTAGGATATTGCTTTAAAATATTATTTATTTTTCATTTAAGAATCAAAAAAAAAAAAAAAAAA
Tobacco       ----------------------------------------------------------------------

              ....|....
PPI-BnFTb     ---------
eral          ---------
Wiggum        ---------
PPI-Soy-FTB   ---------
DuP-Soy-FTB   ---------
PPI-Corn-FTB  ---------
DuP-Corn-FTB  ---------
Pea FT-B      ---------
Tomato        AAAAAAAAA
Tobacco       ---------
```

TABLE 10D

ClustalW Amino Acid Analysis of FT Beta Subunits

1) PPI-BnFTB; FT3 (SEQ ID NO: 15)
2) eral (SEQ ID NO: 2)
3) Wiggum (SEQ ID NO: 87)
4) PPI-Soy-FTB; FT5 (SEQ ID NO: 42)
5) DuP-Soy-FTB (SEQ ID NO: 88)
6) PPI-Corn-FTB; FT6 (SEQ ID NO: 45)
7) DuP-Com-FTB (SEQ ID NO: 89)
8) Pea-FT-B (SEQ ID NO: 90)
9) Tomato (SEQ ID NO: 91)
10) Tobacco (SEQ ID NO: 92)

```
                       10        20        30        40        50        60        70
               ....|....|....|....|....|....|....|....|....|....|....|....|....|....|
PPI-BnFTB      ----------------------------------------------------------------------
eral           ----------------------------------------------------------------------
Wiggum         MPVVTRLIRLKCVGLRLDRSGLNRRICHGGHGESTRRRVMEELSSLTVSQREQFLVENDVFGIYNYFDAS
PPI-Soy-FTB    -------------------------------------------------------------------ATI
DuP-Soy-FTB    -------------------------------------------------------------------ATI
PPI-Corn-FTB   --------------------------------------ADPDLPRLTVTQVEQMKVEARVGDIYRSLFGA
DuP-Corn-FTB   --------------------------------------ADPDLPRLTVTQVEQMKVEARVGDIYRSLFGA
Pea FT-B       -------------------------------------------------------------------MEA
Tomato         ----------------------------------------MESRKVTKTLEDQWVVERRVREIYDYFYSI
Tobacco        ------------------------------------------GTSGTRTLEDQWMVERQVREIYNFFYSI

                       80        90       100       110       120       130       140
               ....|....|....|....|....|....|....|....|....|....|....|....|....|....|
PPI-BnFTB      -----------------------------------------WLCYWILHSIALLGESVDDVLENNAI
eral           --------MEIQRDKQLDYLMKGLRQLGPQFSSLDAN-----RPWLCYWILHSIALLGETVDDELESNAI
Wiggum         DVSTQKYMMEIQRDKQLDYLMKGLRQLGPQFSSLDAN-----RPWLCYWILHSIALLGETVDDELESNAI
PPI-Soy-FTB    PRNAQTLMLELQRDNHMQYVSKGLRHLSSAFSVLDAN-----RPWLCYWIFHSIALLGESVDDELEDNAI
DuP-Soy-FTB    PRNAQTLMLELQRDNHMQYVSKGLRHLSSAFSVLDAN-----RPWLCYWIFHSIALSGESVDDELEDNAI
PPI-Corn-FTB   APNTKSIMLELWRDQHIEYLTPGLRHMGPAFHVLDAN-----RPWLCYWMVHPLALLDEALDDDLENDII
DuP-Corn-FTB   APNTLSIMLELWRDQHIEYLTPGLRHMGPAFHVLDAN-----RPWLCYWMVHPLALLDEALDDDLENDII
Pea FT-B       STAAETPTPTVSQRDQWIVESQ-VFHIYQLFANIPPNAQSIIRPWLCYWIIHSIALLGESIDDDLEDNIV
Tomato         SPNSPSDLIEIERDKHFGYLSQGLRKLGPSFSVLDAS-----RPQLCYWTLHSIALLGESIGGKLENDAI
Tobacco        PPNS---HLETSTEKHFDYLTRGLRKLGPSFSVLDAN-----RPQLCYWILHSIALLGESIDAQLENDAI

                      150       160       170       180       190       200       210
               ....|....|....|....|....|....|....|....|....|....|....|....|....|....|
PPI-BnFTB      DFLGRCQGSDGGYGGGPGQLPHLATSYAAVNTLVTLGGEKAFSSINREQMACFLRRMKDTNGGFRMHNMG
eral           DFLGRCQGSEGGYGGGPGQLPHLATTYAAVNALVTLGGDKALSSINREKMSCFLRRMKDTSGGFRMHDMG
Wiggum         DFLGRCQGSEGGYGGGPGQLPHLATTYAAVNALVTLGGDKALSSINREKMSCFLRRMKDTSGGFRMHDMG
PPI-Soy-FTB    DFLMRCQDPNGGYAGGPGQMPHTATTYAAVNSLITLGGEKSLASINRDKLYGFLRRMKQPNGGFRMHDEG
DuP-Soy-FTB    DFLNRCQDPNGGYAGGPGQMPHTATTYAAVNSLITLGGEKSLASINRDKLYGFLRRMKQPNGGFRMHDEG
PPI-Corn-FTB   DFLARCQDKDGGYSGGPGQLPHLATTYAAVNTLVTIGSERALSSINRGNLYNFMLQMKDVSGAFRMHDGG
DuP-Corn-FTB   DFLARCQDKDGGYSGGPGQLPHLATTYAAVNTLVTIGSQRALSSINRGNLYNFMLQMKDVSGAFRMHDGG
Pea FT-B       DFLNRCQDPNGGYAGGPGQMPHLATTYAAVNTLITLGGEKSLASINRNKLYGFMRRMKQPNGGFRMHDEG
Tomato         DFLTRCQDKDGGYGGGPGQMPHLATTYAAVNSLITLGKPEALSSINREKLYTF LRMKDASGGFRMHDGG
Tobacco        DFLSRCQDEDGGYGGGPGQMPHLATTYAAVNSLITLGSPKALSSINREKLYTFWLQMKDTSGGFRMHDGG

                      220       230       240       250       260       270       280
               ....|....|....|....|....|....|....|....|....|....|....|....|....|....|
PPI-BnFTB      EIDVRACYTAILIASILNIVDDELTRGLGDYILSCQTYEGGIGGEPGSEAHGGYTYCGLATMILINEVDR
eral           EIDVRACYTAISVASILNIMDDELTQGLGDYILSCQTYEGGIGGEPGSEAHGGYTYCGLAAMILINEVDR
Wiggum         EMDVRACYTAISVASILNIMDDELTQGLGDYILSCQTYEGGIGGEPGSEAHGGYTYCGLAAMILINEVDR
PPI-Soy-FTB    EIDVRACYTAISVASVLNILDDELIQNVGDYIISCQTYEGGIAGEPGSEAHGGYTFCGLATMILIGEVNH
DuP-Soy-FTB    EIDVRACYTAISVASVLNILDDELIQNVGDYIISCQTYEGGIAGEPGSEAHGGYTFCGLATMILIGEVNH
PPI-Corn-FTB   EIDVRASYTAISVASLVNILDFKLAKGVGDYIARCQTYEGGIAGEPYAEAHGGYTFVGLAALILLNEAEK
DuP-Corn-FTB   EIDVRASYTAISVASLVNILDFKLAKGVGDYIARCQTYEGGIAGEPYAEAHGGYTFCGLAALILLNEAEK
Pea FT-B       EIDVRACYTAISVASVLNILDDELIKNVGDFILSCQTYEGGLAGEPGSEAHGGYTFCGLAAMILIGEVNR
Tomato         EVDVRACYTAISVANILNIVDDELIHGVGNYILSCQTYEGGIAGEPGSEAHGGYTFCGLAAMILINEVDR
Tobacco        EVDVRACYTAISVASILQIVDDELINDVGNYILSCQTYEGGIAGEPGSEAHGGYTFCGLAAMILINEANR

                      290       300       310       320       330       340       350
               ....|....|....|....|....|....|....|....|....|....|....|....|....|....|
PPI-BnFTB      LNLDSLMNWVVHRQGVEMGFQGRTNKLVDGCYTFWQAAPCVLLQRFFSSQDMAPHGSSSHMSQGTDEDHE
eral           LNLDSLMNWAVHRQGVEMGFQGRTNKLVDGCYTFWQAAPCVLLQRLYSTNDHDVHG-SSHISEGTNEEH-
Wiggum         LNLDSLMNWAVHRQGVEMGFQGRTNKLVDGCYTFWQAAPCVLLQRLYSTNDHDVHG-SSHISEGTNEEH-
PPI-Soy-FTB    LDLPRLVDWVVFRQGKECGFQGRTNKLVDGCYSFWQGGAVALLQRLSSIINKQMEETSQIFACSYVSEA-
DuP-Soy-FTB    LDLPRLVDWVVFRQGKECGFQGRTNKLVDGCYSFWQGGAVALLQRLSSIINKQMEETSQIFAVSYVSEA-
PPI-Corn-FTB   VDLPSLIGWVAFRQGVECGFQGRTNKLVDGCYSFWQGAAIAFTQKLI IVDKQLRSSYSCKRPSGEDACS
DuP-Corn-FTB   VDLPSLIGWVAFRQGVECGFQGRTNKLVDGCYSFWQGAAIAFTQKLI IVDKQLKSSYSCKRPSGEDACS
Pea FT-B       LDLPRLLDWVVFRQGKECGFQGRTNKLVDGCYSFWQGGAVALLQRLHSIIDEQMAEASQFVTVSDAPEE-
Tomato         LDLPGLIDWVVFRQGVEGGFQGRTNKLVDGCYSFWQGAVVFLIQRLNLIVHEQLGLSNDLSTESADDSSE
Tobacco        LDLPRLIDWVVFRQGVEGGFQGRTNKLVDGCYSFWQAAVAFLIQRLKSTVHEQLGLSNELSTESADDSSE
```

TABLE 10D-continued

ClustalW Amino Acid Analysis of FT Beta Subunits

```
                    430       440       450       460       470       480       490
               ....|....|....|....|....|....|....|....|....|....|....|....|....|....|
PPI-BnFTB      EHGHDED-DPE--DSDEDD-S--DEDS--DEDSGNGHQVHHT-STYIDR--RIQPVFDSLGLQRYVLLCS
eral           -HAHDED-DLE--DSDDDDDS--DEDN--DEDSVNGHRIHHT-STYINR--RMQLVFDSLGLQRYVLLCS
Wiggum         -HAHDED-DLE--DSDDDDDS--DEDN--DEDSVNGHRIHHT-STYINR--RMQLVFDSLGLQRYVLLCS
PPI-Soy-FTB    -----KE-SLDGTSSHATCRG--EHEG---TSESSSSDFKNIAYKFINEWRAQEPLFHSIALQQYILLCA
DuP-Soy-FTB    -----KE-SLDGTSSHATCRG--EHEG---TSESSSSDFKNIAYKFINEWRAQEPLFHSIALQQYILLCA
PPI-Corn-FTB   ------------TSSYGCTAN----------KSSSAVDYAKFGFDFIQQSNQIGPLFHNIALQQYILLCS
DuP-Corn-FTB   ------------TSSYGCTAK----------KSSSAVDYAKFGFDFIQQSNQIGPLFHNIALQQYILLCS
Pea FT-B       -----KE-CLDGTSSHATSHI--RHEG---MNESCSSDVKNIGYNFISEWRQSEPLFHSIALQQYILLCS
Tomato         SELSDEEEHLEGISSHVQDTFPLGQAGACQENASHSPKIADRGYEFINRPIAMRPLFDSMYLQQYVLLCS
Tobacco        SELSDEE-HLQGTSSHVQKTCPLGQEG--QENASDPTKIADTGYDFVNRTIAMRPVFDSFYLQQYVLLCS

                    430       440       450       460       470       480       490
               ....|....|....|....|....|....|....|....|....|....|....|....|....|....|
PPI-BnFTB      QVADGGFRDKLRKPRDFYHTCYCLSGLSVAQHAWSKDEDTPPLTRDILGGYAN-HLEPVHLLHNILVDRY
eral           KIPDGGFRDKPRKPRDFYHTCYCLSGLSVAQHAWLKDEDTPPLTRDIMGGYSN-LLEPVQLLHNIVMDQY
Wiggum         KIPDGGRRDKPRKPRDFYHTCYCLSGLSVAQHAWLKDEDTPPLTRDIMGGYSN-LLEPVQLLHNIVMDQY
PPI-Soy-FTB    QEQEGGLRDKPGKRRDHYHTCYCLSGLSLCQYSWSKHPDSPP----------------------------
DuP-Soy-FTB    QEQEGGLRDKPGKRRDHYHTCYCLSGLSLCQYSWSKHPDSPP----------------------------
PPI-Corn-FTB   QVLEGGLRDKPGKNRDHYHSCYCLSGLAVSQYSAMTDTGSCPLPQHVLGPYSN-LLEPIH----------
DuP-Corn-FTB   QVLEGGLRDKPGKNRDHYHSCYCLSGLAVSQYSAMTDTGSCPLPQHVLGPYSN-LLEPIH----------
Pea FT-B       QEQDGGLRDKPGKRRDHYHSCYCLSGLSLCQYSWSKRPDSPPLPKVVMGPYSSNLLEPIHPLFNVVLDRY
Tomato         QIEVGGFRDKPGKGRDYYHTCYCLSGLSIAQYSWTDEADSTPLPRDVFGPYSKCLLEQVHPLFNVVLDRY
Tobacco        QID-GGFRDKPGKGRDHYHTCYCLSGLSIAQYSWTNEADAPPLPRDVFGPYSQNLLEQIHPLYNVVLDRY

                    500       510
               ....|....|....|....|....|
PPI-BnFTB      YEASRF-------------------
eral           NEAIEFFFKAA--------------
Wiggum         NEAIEFFFKAA--------------
PPI-Soy-FTB    -------------------------
DuP-Soy-FTB    -------------------------
PPI-Corn-FTB   -------------------------
DuP-Corn-FTB   -------------------------
Pea FT-B       REAHEFFSQL---------------
Tomato         YEAREYSQACETVSPLSLAPTFSET
Tobacco        YEARSFFSCL---------------
```

Also included in the invention is the farnesyl transferase alpha consensus sequence of SEQ ID NO:93 and the farnesyl transferase beta consensus sequence of SEQ ID NO:94 To generate the consensus sequence, the farnesyl transferase alpha and farnesyl transferase beta sequences of the invention were aligned using the program BioEdit. The homology between the farnesyl transferase alpha (FTA) polypeptide sequences of the invention is shown graphically in the ClustalW analysis shown in Table 10E. The homology between the farnesyl transferase beta (FTB) polypeptide sequences of the invention is shown graphically in the ClustalW analysis shown in Table 10F.

TABLE 10E

ClustalW Amino Acid Analysis of FT Alpha

```
                       10        20        30        40        50        60        70
               ....|....|....|....|....|....|....|....|....|....|....|....|....|....|
BnA-12         --------------------------------------------------MDYFRAIYFSDERS RALRL
At-FT-A        --------MNFDETVPLSQRLEWSDVVPLTQDDGPNPVVPIAYKEEFRETMDYFRAIYFSDERSPRALRL
PPI-Soy-FTA    MESGSSEGEEVQQRVPLRERVEWSDVTPVPQNDGPNPVVPIQYTEEFSEVMDYFRAVYLTDERSPRALAL
Consensus      --------      VPL  R EWSDV P  Q DGPNPVVPI Y EEF E MDYFRAIYFSDERSORALRL

                       80        90       100       110       120       130       140
               ....|....|....|....|....|....|....|....|....|....|....|....|....|....|
BnA-12         TEEALRLNSGNYTVWHFGRLVLEELNNDLYEELKFIESIAEDNSKNYQL----WHHRRWVAEKLGPDVAG
At-FT-A        TEETLLLNSGNYTVWHFRRLVLEALNHDLFEELEFIERIAEDNSKNYQL----WHHRRWVAEKLGPDVAG
PPI-Soy-FTA    TAEAVQFNSGNYTVWHFRRLLLESLKVDLNDELEFVERMAAGNSKNYQMXMFCRHPRRWVAEKLGPEARN
Consensus      TEEAL LNSGNYTVWHFRRLVLE LN DL EELEFIERIAEDNSKNYQL----WHHRRWVAEKLGPDVAG

                      150       160       170       180       190       200       210
               ....|....|....|....|....|....|....|....|....|....|....|....|....|....|
BnA-12         LEKEFTRRVLSLDAKHYHAWSHRQWALQALGGWENELNYCHELLEADVFNNSAWNQRYYVITRSPSLGGL
At-FT-A        RELEFTRRVLSLDAKHYHAWSHRQWTLRALGGWEDELD CHELLEADVFNNSAWNQRTTVITQSPLLGGL
PPI-Soy-FTA    NELEFTKKILSVDAKHYHAWSHRQWALQTLGGWEDELNYCTELLKEDIFNNSAWNQRYFVITRSPFLGGL
Consensus       ELEFTRRVLSLDAKHYHAWSHRQWALQALGGWEDELNYCHELLEADVFNNSAWNQRYYVITRSP LGGL

                      220       230       240       250       260       270       280
               ....|....|....|....|....|....|....|....|....|....|....|....|....|....|
BnA-12         EAMRESEVSYTVKAILANPGNESSWRYLKALYKDDTESWISDPSVSSVCLKVLSRADCFHGFALSTLLDL
At-FT-A        EAMRESEVSYTIKAILTNPANESSWRYLKALYKDDKESWISDPSVSSVCLNVLSRTDCFHGFALSTLLDL
PPI-Soy-FTA    KAMRESEVLYTIEAITAYPENESSWRYLRGLYKGETTSWVNDPQ SSVCLKIL-RTKSNYVFALSTILDL
Consensus      EAMRESEVSYTIKAILANP NESSWRYLKALYKDDTESWISDPSVSSVCLKVLSRTDCFHGFALSTLLDL
```

TABLE 10E-continued

ClustalW Amino Acid Analysis of FT Alpha

| | 290 300 310 320 330 340 350 |
|---|---|
| BnA-12 | LCDGLRPTNEHRDSVKALAN--------------EEPETNLANLVCTILCRVDPIRANYWAWKL------ |
| At-FT-A | LCDGLRPRNEHKDSVRALAN--------------EEPETNLANLVCTILGRVDPIRANYWAWRKSKITVA |
| PPI-Soy-FTA | ICFGYQPNEDIRDAIDALKTADMDKQDLDDDEKGEQQNLNIARNICSILKQVDPIRTNYWIWRKSPLP-- |
| Consensus | LCDGLRPTNEHRDSV ALAN--------------EEPETNLANLVCTIL RVDPIRANYWAWRKS    -- |
| BnA-12 | -- (SEQ ID NO: 13) |
| At-FT-A | AI (SEQ ID NO: 8) |
| PPI-Soy-FTA | -- (SEQ ID NO: 39) |
| Consensus | -- (SEQ ID NO: 93) |

TABLE 10F

ClustalW Amino Acid Analysis of FT Beta

| | 10 20 30 40 50 60 70 |
|---|---|
| PPI-BnFTB | ---------------------------------------------------------------------- |
| PPI-Soy-FTB | -------ATIPR----------------------NAQTLMLELQRDNHMQYVSKGLRHLSSAFSVLDANR |
| PPI-Corn-FTB | ADPDLPRLTVTQVEQMKVEARVGDIYRSLFGAAPNTKSIMLELWRDQHIEYLTPGLRHMGPAFHVLDANR |
| Consensus | ------- T   ----------------------N    MLEL RD H  Y   GLRH   AF VLDANR |
| | 80 90 100 110 120 130 140 |
| PPI-BnFTB | -WLCYWILHSIALLGESVDDDLENNAIDFLGRCQGSDGGYGGGPGQLPHLATSYAAVNTLVTLGGEKAFS |
| PPI-Soy-FTB | PWLCYWIFHSIALLGESCDDELEDNAIDFLNRCQDPNGGYAGGPGQMPHIATTYAAVNSLITLGGEKSLA |
| PPI-Corn-FTB | PWLCYWMVHPLALLDEALDDDLENDIIDFLARCQDKDGGYSGGPGQLPHLATTYAAVNTLVTIGSERALS |
| Consensus | PWLCYWI HSIALLGESVDDDLENNAIDFL RCQD DGGY GGPGQLPHLATTYAAVNTLVTLGGEKALS |
| | 150 160 170 180 190 200 210 |
| PPI-BnFTB | SINREQMACFLRRMKDTNGGFRMHNMGEIDVRACYTAILIASILNIVDDELTRGLGDYILSCQTYEGGIG |
| PPI-Soy-FTB | SINRDKLYGFLRRMKQPNGGFRMHDEGEIDVRACYTAISVASVLNILDDELIQNVGDYIISCQTYEGGIA |
| PPI-Corn-FTB | SINRGNLYNFMLQMKDVSGAFRMHDGGEIDVRASYTAISVASLVNILDFKLAKGVGDYIARCQTYEGGIA |
| Consensus | SINR  LY FLRRMKD NGGFRMHD GEIDVRACYTAISVAS LNILDDEL  GVGDYI SCQTYEGGIA |
| | 220 230 240 250 260 270 280 |
| PPI-BnFTB | GEPGSEAHGGYTYCGLATMILINEVDRLNLDSLMNWVVHRQGVEMGFQGRTNKLVDGCYTFWQAAAPCVLL |
| PPI-Soy-FTB | GEPGSEAHGGYTFCGLATMILIGEVNHLDLPRLVDWVVFRQGKECGFQGRTNKLVDGCYSFWQGGAVALL |
| PPI-Corn-FTB | GEPYAEAHGGYTFCGLAALILLNEAEKVDLPSLIGWVAFRQGVECGFQGRTNKLVDGCYSFWQGAAIAFT |
| Consensus | GEPGSEAHGGYTFCGLATMILINEV  LDLPSL  WVVFRQGVECGFQGRTNKLVDGCYSFWQGAA ALL |
| | 290 300 310 320 330 340 350 |
| PPI-BnFTB | QRFFSSQDMAPHGSSS--HMSQGTDEDHEEHGHDEDDPEDSDEDDSDEDSDEDSGNGHQVHHTSTYIDRR |
| PPI-Soy-FTB | QRLSSIINKQMEETSQIFAVSYVSEAKESLDGTSSHATCRGEHEGTSESSSSDFKN---IAYKFINEWRA |
| PPI-Corn-FTB | QK ITIVDKQLRSS-----YSCKRPSGEDACSTSSYG-CTANKS----SSAVDYAK---FGFDFIQQSNQ |
| Consensus | QRL SI DKQ   SS --  S      E  GTSS   C        ESS  D   ---    FI   R |
| | 360 370 380 390 400 410 420 |
| PPI-BnFTB | IQPVFDSLGLQRYVLLCSQVADGGFRDKLRKPRDFYHTCYCLSGLSVAQHAWSKDEDTPP TRDILGGYA |
| PPI-Soy-FTB | QEPLFHSIALQQYILLCAQEQEGGLRDKPGKRRDHYHTCYCLSGLSLCQYSWSKHPDSPP---------- |
| PPI-Corn-FTB | IGPLFH IALQQYILLCSQVLEGGLRDKPGKNRDHYHSCYCLSGLAVSQYSAMTDTGSCPLPQHVLGPYS |
| Consensus | I PLFHSIALQQYILLCSQV EGGLRDKPGK RDHYHTCYCLSGLSV QYSWSKD DSPPL    LG Y |
| | 430 440 |
| PPI-BnFTB | NHLEPVHLLLHNILVDRYYEASRF (SEQ ID NO: 15) |
| PPI-Soy-FTB | ------------------------ (SEQ ID NO: 42) |
| PPI-Corn-FTB | NLLEPIH----------------- (SEQ ID NO: 45) |
| Consensus | N LEP H----------------- (SEQ ID NO: 94) |

Also included in the invention is the farnesyl transferase alpha consensus sequence of SEQ ID NO:95 and the farnesyl transferase beta consensus sequence of SEQ ID NO:96. To generate the consensus sequence, the farnesyl transferase alpha and farnesyl transferase beta sequences of the invention were aligned using the program BioEdit. The homology between the farnesyl transferase alpha (FTA) nucleic acid sequences of the invention is shown graphically in the ClustalW analysis shown in Table 10G. The homology between the farnesyl transferase beta (FTB) nucleic acid sequences of the invention is shown graphically in the ClustalW analysis shown in Table 10H.

TABLE 10G

ClustalW Nucleic Acid Analysis of FT Alpha

```
                          10        20        30        40        50        60
                 ....|....|....|....|....|....|....|....|....|....|....|....|
BnA-12           ------------------------------------------------------------     1
At-FT-A          -------------GAGTCGGGGAACATGAATTTCGACGAGACCGTGCCACTGAGCCAACG    47
PPI-Soy-FTA      ATGGAATCTGGGTCTAGCGAAGGAGAAGAGGTGCAGCAACGC-GTGCCGTTGAGGGAGAG    59
Consensus        -------------    CG  G A A GA  T C  C A  C GTGCC  TGAG  A  G    23

                          70        80        90       100       110       120
                 ....|....|....|....|....|....|....|....|....|....|....|....|
BnA-12           ------------------------------------------------------------     1
At-FT-A          ATTGGAGTGGTCAGACGTGGTCCCATTGACTCAGGACGATGGTCCGAATCCAGTGGTGCC   107
PPI-Soy-FTA      AGTGGAGTGGTCAGATGTTACTCCGGTTCCTCAAAACGACGGCCCTAACCCTGTCGTTCC   119
Consensus        A TGGAGTGGTCAGA GT    CC  T  CTCA  ACGA GG CC AA CC GT GT CC    64

                         130       140       150       160       170       180
                 ....|....|....|....|....|....|....|....|....|....|....|....|
BnA-12           -------------------------------ATGGATTACTTCCGTGCGATTTACTTCTC    29
At-FT-A          AATTGCCTACAAGGAAGAGTTCCGCGAGACTATGGATTACTTCCGTGCGATTTACTTTTC   167
PPI-Soy-FTA      GATCCAGTACACTGAAGAGTTTTCCGAAGTTATGGATTACTTTCGCGCCGTTTACCTCAC   179
Consensus         AT    TACA  GAAGAGTT   CGA   TATGGATTACTTCCGTGCGATTTACTTCTC   111

                         190       200       210       220       230       240
                 ....|....|....|....|....|....|....|....|....|....|....|....|
BnA-12           CGACGAGCGTTCTGCTCGCGCGCTGCGACTCACGGAAGAAGCTCTCCGCTTAAACTCGGG    89
At-FT-A          CGACGAGCGATCTCCTCGCGCACTACGACTCACGGAAGAAACCCTCCTCTTAAACTCCGG   227
PPI-Soy-FTA      CGATGAACGCTCC CTCGCGCCCTCGCTCTCACAGCCGAAGCCGTTCAATTCAACTCCGG   239
Consensus        CGACGAGCG TCTCCTCGCGC CT CGACTCACGGAAGAAGCCCTCC CTTAAACTCCGG   167

                         250       260       270       280       290       300
                 ....|....|....|....|....|....|....|....|....|....|....|....|
BnA-12           CAACTACACCGTGTGGCACTTCGGGCGCTTAGTACTCGAGGAGCTTAATAACGACTTGTA   149
At-FT-A          CAACTACACAGTGTGGCATTTCAGGCGCCTAGTACTCGAGGCCCTTAATCACGACTTGTT   287
PPI-Soy-FTA      CAACTACACTGTGTGGCATTTCCGACGGTTGTTACTTGAGTCGCTAAAAGTCGACTTGAA   299
Consensus        CAACTACAC GTGTGGCATTTC GGCGCTTAGTACTCGAGGCGCTTAAT ACGACTTGTA   224

                         310       320       330       340       350       360
                 ....|....|....|....|....|....|....|....|....|....|....|....|
BnA-12           TGAAGAGCTCAAGTTCATCGAAAGCATTGCTGAGGATAACTCTAAGAACTACCAGTTGTG   209
At-FT-A          TGAAGAACTCGAGTTCATCGAACGCATTGCTGAGGATAACTCTAAGAACTACCAACTGTG   347
PPI-Soy-FTA      CGATGAACTGGAGTTTGTGGAGCGTATGGCCGCTGGAAATTCTAAAAATTATCAGATGTG   359
Consensus        TGAAGAACTCGAGTTCATCGAACGCATTGCTGAGGATAACTCTAAGAACTACCAG TGTG   283

                         370       380       390       400       410       420
                 ....|....|....|....|....|....|....|....|....|....|....|....|
BnA-12           G------------CATCATCGACGATGGGTCGCAGAGAAACTGGGTCCTGATGTTGCAGG   257
At-FT-A          G------------CATCATCGGCGATGGGTTGCAGAGAAACTGGGTCCTGATGTTGCAGG   395
PPI-Soy-FTA      NATGTTCTGTAGGCATCCTAGACGATGGGTTGCCGAGAAGTTAGGTCCTGAAGCTAGAAA   419
Consensus        G------------CATCATCGACGATGGGTTGCAGAGAAACTGGGTCCTGATGTTGCAGG   331

                         430       440       450       460       470       480
                 ....|....|....|....|....|....|....|....|....|....|....|....|
BnA-12           AAAGGAACTTGAGTTTACTCGGAGGGTACTATCACTTGATGCCAAGCATTATCATGCTTG   317
At-FT-A          GAGAGAACTTGAATTTACCCGTAGAGTACTTTCACTTGATGCCAAACATTATCATGCTTG   455
PPI-Soy-FTA      CAATGAGCTCGAGTTCACCAAAAACATACTGTCCGTTGATGCCAAACATTATCATGCATG   479
Consensus         AA GAACTTGAGTTTACCCG AGGGTACT TCACTTGATGCCAAACATTATCATGCTTG   387

                         490       500       510       520       530       540
                 ....|....|....|....|....|....|....|....|....|....|....|....|
BnA-12           GTCACATAGGCAGTGGACACTACAAGCATTAGGAGGATGGGAAAATGAGCTTAACTACTG   377
At-FT-A          GTCACATAGGCAGTGGACACTACGGGCATTAGGAGGATGGGAAGATGAGCTCGATTACTG   515
PPI-Soy-FTA      GTCTCATAGACAGTGGGCTCTTCAAACACTAGGAGGATGGGAAGATGAACTTAATTATTG   539
Consensus        GTCACATAGGCAGTGGGC CTACAAGCATTAGGAGGATGGGAAGATGAGCTTAATTACTG   446

                         550       560       570       580       590       600
                 ....|....|....|....|....|....|....|....|....|....|....|....|
BnA-12           CCACGAGCTCCTTGAAGCTGACGTCTTTAACAACTCTGCATGGAATCAGAGGTATTACGT   437
At-FT-A          TCACGAGCTCCTTGAAGCTGACGTCTTTAACAATTCCGCCTGGAATCAGAGGTATTATGT   575
PPI-Soy-FTA      CACAGAACTACTTAAAGAAGACATTTTTAACAATTCTGCTTGGAATCAGAGATATTTTGT   599
Consensus        CCACGAGCTCCTTGAAGCTGACGTCTTTAACAATTCTGC TGGAATCAGAGGTATTATGT   505

                         610       620       630       640       650       660
                 ....|....|....|....|....|....|....|....|....|....|....|....|
BnA-12           TATAACTAGATCACCTTCGTTGGGAGGCCTAGAAGCCATGAGAGAATCTGAAGTAAGCTA   497
At-FT-A          CATCACCCAATCTCCTTTGTTGGGAGGCCTAGAAGCCATGAGAGAATCTGAAGTAAGCTA   635
PPI-Soy-FTA      CATAACAAGGTCTCCTTTCTTGGGGGGCCTAAAAGCTATGAGAGAGTCTGAAGTGCTTTA   659
Consensus        CATAAC AGATCTCCTTTGTTGGGAGGCCTAGAAGCCATGAGAGAATCTGAAGTAAGCTA   564
```

TABLE 10G-continued

ClustalW Nucleic Acid Analysis of FT Alpha

```
                   670       680       690       700       710       720
               ....|....|....|....|....|....|....|....|....|....|....|....|
BnA-12         CACAGTCAAAGCCATTTTAGCAAATCCCGGGAACGAGAGCTCTTGGAGGTACCTGAAAGC    557
At-FT-A        CACAATCAAAGCCATTTTAACCAATCCTGCAAACGAGAGCTCATGGCGATACCTAAAAGC    695
PPI-Soy-FTA    CACCATCGAAGCCATTATAGCCTACCCTGAAAATGAA GCTCGTGGAGATATCTACGAGG    719
Consensus      CACAATCAAAGCCATTTTAGCCAATCCTG AAACGAGAGCTC TGGAGATACCTAAAAGC    622

                   730       740       750       760       770       780
               ....|....|....|....|....|....|....|....|....|....|....|....|
BnA-12         CCTTTACAAAGACGACACAGAGTCTTGGATTAGTGATCCAAGTGTTTCCTCAGTCTGTTT    617
At-FT-A        GCTTTACAAAGACGACAAAGAATCCTGGATTAGTGATCCAAGTGTTTCCTCAGTCTGTTT    755
PPI-Soy-FTA    ACTTTATAAAGGTGAAACTACTTCATGGGTAAATGATCCTCAAGTTTCTTCAGTATGCTT    779
Consensus       CTTTACAAAGACGACACAGA TC TGGATTAGTGATCCAAGTGTTTCCTCAGTCTGTTT    679

                   790       800       810       820       830       840
               ....|....|....|....|....|....|....|....|....|....|....|....|
BnA-12         GAAAGTTCTCTCACGCGCGGACTGCTTCCATGGATTCGCTCTGAGCACCCTTTTGGATCT    677
At-FT-A        GAATGTTCTATCCCGCACAGATTGCTTCCATGGATTCGCTCTGAGCACCCTTTTGGATCT    815
PPI-Soy-FTA    AAAGATTTTGA---GAACTAAGAGCAACTACGTGTTTGCTCTTAGCACTATTTTAGATCT    836
Consensus      GAA GTTCT TC CGCAC GA TGCTTCCATGGATTCGCTCTGAGCACCCTTTTGGATCT    734

                   850       860       870       880       890       900
               ....|....|....|....|....|....|....|....|....|....|....|....|
BnA-12         TCTGTGCGATGGGTTGAGACCAACCAACGAGCATAGAGACTCGGTGAAAGCTCTAGCTAA    737
At-FT-A        TCTATGTGATGGACTGAGACCAACCAACGAGCATAAAGACTCAGTGAGAGCTCTAGCTAA    875
PPI-Soy-FTA    TATATGCTTTGGTTATCAACCAAATGAAGACATTAGAGATGCCATTGACGCCTTAAAGAC    896
Consensus      TCTATGCGATGG TTGAGACCAACCAACGAGCATAGAGACTC GTGAAAGCTCTAGCTAA    792

                   910       920       930       940       950       960
               ....|....|....|....|....|....|....|....|....|....|....|....|
BnA-12         TGAAGAACCAGAGACTAACTTGGCCAATTTGGTGTGTACCATTCTGTGTCGTGTTGATCC    797
At-FT-A        TGAAGAACCAGAGACTAACTTGGCCAATTTGGTGTGTACTATTCTTGGTCGTGTACATCC    935
PPI-Soy-FTA    CGCAGA--TATGGATAAACAAGATTTAGATGATGATGAGAAAGGGGAACAACAAAATTTA    954
Consensus      TGAAGAACCAGAGACTAACTTGGCCAATTTGGTGTGTAC ATTCTG GTCGTGTAGATCC    850

                   970       980       990      1000      1010      1020
               ....|....|....|....|....|....|....|....|....|....|....|....|
BnA-12         AATA-AGAGCTAACTATTGGGC--ATGG--------------------------------    822
At-FT-A        TATA-AGAGCTAACTATTGGGC--ATGGAGGAAG GCAAGATTACAGTGGCAGCAATTTG    992
PPI-Soy-FTA    AATATAGCACGAAATATTTGTTCTATCCTAAAAC AGTTGATCCAATTAGAACCAACTAT   1014
Consensus      AATA-AGAGCTAACTATTGGGC--ATGG   AA A    GAT   A T G A CAA T      889

                  1030      1040      1050      1060      1070      1080
               ....|....|....|....|....|....|....|....|....|....|....|....|
BnA-12         ------------------------------------------------------------    822
At-FT-A        AATATGTGACGCCCCAAAATCACACTTGAAAAAGACTTGATTATTAGTTTTTACGTAATT   1052
PPI-Soy-FTA    TGGATTTGGCGCAAGAGCAGACTTCCT---------------------------------   1041
Consensus         AT TG CGC   A  A     C T---------------------------------    900

                  1090      1100      1110      1120      1130      1140
               ....|....|....|....|....|....|....|....|....|....|....|....|
BnA-12         ------------------------------------------------------------    822
At-FT-A        AACTGCTTATTTATGAATCACATGTTCATGTTAACATGTATCAAAACAATCTTGATTTCT   1112
PPI-Soy-FTA    ------------------------------------------------------------   1041
Consensus      ------------------------------------------------------------    900

                  1150      1160      1170
               ....|....|....|....|....|....|.
BnA-12         -------------------------------    822 (SEQ ID NO: 12)
At-FT-A        CAAAAAAAAAAAAAAAAAAAAAAAAAAAAAA   1143 (SEQ ID NO: 7)
PPI-Soy-FTA    -------------------------------   1041 (SEQ ID NO: 37)
Consensus      -------------------------------    900 (SEQ ID NO: 95)
```

TABLE 10H

ClustalW Nucleic Acid Analysis of FT Beta

```
                   10        20        30        40        50        60
               ....|....|....|....|....|....|....|....|....|....|....|....|
PPI-BnFTb      ------------------------------------------------------------      1
eral           ------------------------------------------------------------      1
PPI-Soy-FTB    ------------------------------------------------------------      1
PPI-Corn-FTB   GGCGGATCCCGACCTACCGAGGCTCACGGTGACGCAGGTGGAGCAGATGAAGGTGGAGGC     60
Consensus      ------------------------------------------------------------      1
```

TABLE 10H-continued

ClustalW Nucleic Acid Analysis of FT Beta

```
                          70        80        90       100       110       120
                 ....|....|....|....|....|....|....|....|....|....|....|....|
PPI-BnFTb        ------------------------------------------------------------     1
eral             ------------------------------------------------------------     1
PPI-Soy-FTB      ----------------------------GCCACCATTCCTCGCAACGCCCAAACCCTCAT    32
PPI-Corn-FTB     CAGGGTTGGCGACATCTACCGCTCCCTCTTCGGGGCCGCGCCCAACACGAAATCCATCAT   120
Consensus        ----------------------------                                     1

                         130       140       150       160       170       180
                 ....|....|....|....|....|....|....|....|....|....|....|....|
PPI-BnFTb        ------------------------------------------------------------     1
eral             -ATGGAGATTCAGCGAGATAAGCAATTGGATTATCTGATGAAAGGCTTAAGGCAGCTTGG    59
PPI-Soy-FTB      GTTGGAGCTTCAACGCGATAATCACATGCAGTATGTCTCCAAAGGCCTTCGCCATCTCAG    92
PPI-Corn-FTB     GCTAGAGCTGTGGCGTGATCAGCATATCGAGTATCTGACGCCTGGCTGAGGCATATGGG   180
Consensus          T GAG T    CG GAT A CA  T  A TAT T       GG  T  G CA  T  G    27

                         190       200       210       220       230       240
                 ....|....|....|....|....|....|....|....|....|....|....|....|
PPI-BnFTb        ----------------------------------TGGCTTTGTTACTGGATTCTTCATTC    26
eral             TCCGCAGTTTTCTTCCTTAGATGCTAATCGACCTTGGCTTTGTTACTGGATTCTTCATTC   119
PPI-Soy-FTB      TTCCGCATTTTCCGTTTTGGACGCTAATCGACCCTGGCTCTGCTACTGGATCTTCCACTC   152
PPI-Corn-FTB     ACCAGCCTTTCATGTTCTAGATGCCAATCGCCCTTGGCTATGCTACTGGATGGTTCATCC   240
Consensus          C    TTT       T GA GC AATCG CC TGGCT TG TACTGGAT  TTCATTC    65

                         250       260       270       280       290       300
                 ....|....|....|....|....|....|....|....|....|....|....|....|
PPI-BnFTb        AATTGCTTTGCTTGGGGAGTCTGTGGATGATGACTTAGAAAACAATGCAATCGATTTTCT    86
eral             AATAGCTTTGCTTGGGGAGACTGTGGATGATGAATTAGAAAGCAATGCCATTGACTTCCT   179
PPI-Soy-FTB      CATTGCTTTGTTGGGAGAATCCGTCGATGATGAACTCGAAGATAACGCTATCGATTTTCT   212
PPI-Corn-FTB     ACTTGCTTTGCTGGATGAAGCACTTGATGATGATCTTGAGAATG  ATCATAGACTTCTT   300
Consensus        AATTGCTTTGCT GG GA  C GT GATGATGA  T GAAAA       AT GA TT CT   111

                         310       320       330       340       350       360
                 ....|....|....|....|....|....|....|....|....|....|....|....|
PPI-BnFTb        TGGACGTTGCCAGGGTTCTGATGGTGGATATGGTGGTGGTCCTGGCCAACTTCCACATCT   146
eral             TGGACGCTGCCAGGGCTCTGAAGGTGGATACGGTGGTGGTCCTGGCCAACTTCCACATCT   239
PPI-Soy-FTB      TAACCGTTGCCAGGATCCGAATGGTGGATATGCCGG GGACCAGGCCAGATGCCTCATAT   272
PPI-Corn-FTB     AGCTCGATGTCAGGATAAAGATGGTGGATATAGTGGTGGACCTGGACAGTTGCCTCACCT   360
Consensus        TG  CG TGCCAGG T C GATGGTGGATATGGTGGTGG CCTGGCCA  T CC CATCT   160

                         370       380       390       400       410       420
                 ....|....|....|....|....|....|....|....|....|....|....|....|
PPI-BnFTb        TGCAACAAGTTATGCTGCAGTGAATACACTTGTTACTTTAGGAGGTGAGAAAGCCTTCTC   206
eral             TGCAACTACTTATGCTGCAGTGAATGCACTTGTTACTTTAGGAGGTGACAAAGCCCTTTC   299
PPI-Soy-FTB      TGCCACAACTTATGCTGCTGTTAATTCACTTATTACTTTGGGTGGTGAGAAATCCCTGGC   332
PPI-Corn-FTB     AGCTACGACTTATGCTGCTGTAAATACACTTGTGACAATAGGGAGCGAAAGAGCATTGTC   420
Consensus        TGC AC ACTTATGCTGC GT AAT CACTTGTTACTTTAGG GGTGA AAAGCC T TC   211

                         430       440       450       460       470       480
                 ....|....|....|....|....|....|....|....|....|....|....|....|
PPI-BnFTb        TTCAATTAACAGAGAACAAATGGCTTGTTTCTTAAGACGAATGAAGGATACAAATGGAGG   266
eral             TTCAATTAATAGAGAAAAAATGTCTTGTTTTTTAAGACGGATGAAGGATACAAGTGGAGG   359
PPI-Soy-FTB      ATCAATTAATAGAGATAAACTGTATGGGTTTCTGCGGCGGATGAAGCAACCAAATGGTGG   392
PPI-Corn-FTB     ATCAATCAATAGG GCAACCTGTACAATTTTATGCTGCAGATGAAAGATGTATCAGGTGC   480
Consensus         TCAATTAATAGAGA AAA TGT T GTTTT T  G CGGATGAAGGAT CAA TGG GG   259

                         490       500       510       520       530       540
                 ....|....|....|....|....|....|....|....|....|....|....|....|
PPI-BnFTb        TTTCAGGATGCATAATATGGGAGAAATAGATGTGCGAGCGTGCTACACTGCGATTTTGAT   326
eral             TTTCAGGATGCATGATATGGGAGAAATTGATGTTCGTGCATGCTACACTGCAATTTCGGT   419
PPI-Soy-FTB      ATTCAGGATGCATGATGAAGGTGAAATTGATGTCCGTGCTTGCTACACTGCCATTTCTGT   452
PPI-Corn-FTB     TTTCAGAATGCATGATGGTGGCGAAATTGATGTCCGTGCTTCCTACACCGCTATATCGGT   540
Consensus        TTTCAGGATGCATGAT   GG GAAATTGATGT CG GC TGCTACACTGC ATTTCGGT   311

                         550       560       570       580       590       600
                 ....|....|....|....|....|....|....|....|....|....|....|....|
PPI-BnFTb        TGCAAGCATCCTGAACATTGTGGATGATGAACTCACCCGCGGCTTAGGAGATTACATTTT   386
eral             TGCAAGCATCCTAAATATTATGGATGATGAACTCACCCAGGGCCTAGGAGATTACATCTT   479
PPI-Soy-FTB      TGCAAGTGTTTTGAACATTTTGGATGATGAGCTGATCCAGAATGT GGAGACTACATTAT   512
PPI-Corn-FTB     TGCCAGCCTTGTGAATATTCTTGATTTTAAACTGGCAAAAGGTGTAGGCGACTACATAGC   600
Consensus        TGCAAGC T  TGAA ATT TGGATGATGAACT ACCCA GG  TAGGAGA TACAT  T   359

                         610       620       630       640       650       660
                 ....|....|....|....|....|....|....|....|....|....|....|....|
PPI-BnFTb        GAGTTGCCAAACTTATGAAGGTGGCATTGGAGGGGAACCTGGCTCCGAAGCTCATGGTGG   446
eral             GAGTTGCCAAACTTATGAAGGTGGCATTGGAGGGGAACCTGGCTCCGAAGCTCACGGTGG   539
PPI-Soy-FTB      AAGCTGTCAAACATATGAGGGTGGCATTGCTGGTGAGCCTGGTTCTGAGGCTCATGGTGG   572
PPI-Corn-FTB     AAGATGTCAAACTTATGAAGGTGGTATTGCTGGGGAGCCTTATGCTGAAGCACATGGTGG   660
Consensus         AG TG CAAACTTATGAAGGTGGCATTG  GGGGA CCTGG TC GAAGCTCATGGTGG   411
```

TABLE 10H-continued

ClustalW Nucleic Acid Analysis of FT Beta

```
                      670        680        690        700        710        720
              ....|....|....|....|....|....|....|....|....|....|....|....|
PPI-BnFTb     GTACACGTACTGTGGGTTGGCTACTATGATTTTAATCAATGAAGTCGACCGCTTGAATTT     506
eral          GTATACCTACTGTGGTTTGGCTGC ATGATTTTAATCAATGAGGTCGACCGTTTGAATTT     599
PPI-Soy-FTB   GTACACCTTTTGTGGATTAGCTACAATGATTCTGATTGGTGAGGTTAATCACTTGGATCT     632
PPI-Corn-FTB  GTATACATTCTGTGGATTGGCTGCTTTGATCCTGCTTAATGAGGCAGAGAAAGTTGACTT     720
Consensus     GTA AC T CTGTGG TTGGCT CTATGATT T AT AATGAGGT GA C  TTG ATTT     458

                      730        740        750        760        770        780
              ....|....|....|....|....|....|....|....|....|....|....|....|
PPI-BnFTb     GGATTCGTTAATGAATTGGGTTGTACATCGACAAGGAGTAGAAATGGGATTCCAAGGTAG     566
eral          GGATTCATTAATGAATTGGGCTGTACATCGACAAGGAGTAGAAATGGGATTTCAAGGTAG     659
PPI-Soy-FTB   GCCTCGATTAGTTGACTGGGTGGTATTCCGACAAGGTAAGGAATGTGGATTCCAGGGGAG     692
PPI-Corn-FTB  GCCTAGTTTGATTGGCTGGGTGCCTTTTCG CAAGGAGTGGAATGCGGATTTCAAGGCACG    780
Consensus     G T    TTAAT  A TGGGT GTA  TCGACAAGGAGT GAA   GGATT CAAGG AG     501

                      790        800        810        820        830        840
              ....|....|....|....|....|....|....|....|....|....|....|....|
PPI-BnFTb     GACGAACAAATTGGTCGACGGTTGCTACACGTTTTGGCAGGCAGCCCCCTGTGTTCTACT     626
eral          GACGAACAAATTGGTCGATGGTTGCTACACATTTTGGCAGGCAGCCCCTTGTGTTCTACT     719
PPI-Soy-FTB   AACAAATAAACTGGTGGATGGATGCTATTCCTTTTGGCAGGCAGGTGCTGTTGCTCTATT     752
PPI-Corn-FTB  AACTAATAAATTGGTTGATGGTTGCTACTGCTTTTGGCAGGGAGCTGCCATTGCTTTCAC     840
Consensus      AC AA AAATTGGT GATGGTTGCTAC C TTTTGGCAGG AGC  C   TG TCTA T     547

                      850        860        870        880        890        900
              ....|....|....|....|....|....|....|....|....|....|....|....|
PPI-BnFTb     ACAGCGATTTTTTTCATCCCAGGAT-ATGGCACCTCATGGATCATCATCACATATGTCAC     685
eral          ACAAAGATTATATTCAACCAATGATCATGACGT-TCATGGATCATCA---CATATATCAG     775
PPI-Soy-FTB   GCAAAGATTATCTTCTATTATCAAC-AAACAGATGGAAGAGACATCA-C-----AGATTT     805
PPI-Corn-FTB  ACAAAAGTTAATTACGATTGTTGAT-AAGCAA----------------------------     871
Consensus     ACAAAGATTAT TTC A     GAT-A G       A G  CATCA- -                574

                      910        920        930        940        950        960
              ....|....|....|....|....|....|....|....|....|....|....|....|
PPI-BnFTb     AAGGCACAGATGAAGATCACGAGGAACATGGTCATGATGAAGATGATCCTGAAGACAGTG     745
eral          AAGGACACAAATGAAGAACAT------CATGCTCATGATGAAGATGACCTTGAAGACAGTG    829
PPI-Soy-FTB   TTGCCGTATCTTATGTATCTGAAGCAAAAGAAAGTTTGGATGGAACCTCTAGTCATGCAA     865
PPI-Corn-FTB  TTGAGGT-CCTCGTATTGCTG---CAAAAGGCCATCAGGAGAGGATGCCTG--CA-GCAC     924
Consensus       G C  A  T A C  C TG   A A C  CAT A GA G     CCTG  A            598

                      970        980        990       1000       1010       1020
              ....|....|....|....|....|....|....|....|....|....|....|....|
PPI-BnFTb     ATGAAGATGAT---TCTGATGAGGATAGCGATGAAGATTCAGGGAATGGTCACCAAGTTC     802
eral          ATGATGATGATCATTCTGATGAGGACAACGATGAAGATTCAGTGAATGGTCACAGAATCC     889
PPI-Soy-FTB   CATGCCGTGGTCAGCATGAAGGCACCAGTGAATCCAGTTCATCTGATTTTAAAAATATTG     925
PPI-Corn-FTB  CAGTTCATA-TCGGTGCACCGCCAATAAGTCTTCCTCTGCTGTGGACTATGCGAAGTTTG     983
Consensus       G   ATG TG  T TGA G G A A GAT     TTCAG G AT  T A AA  TT      629

                     1030       1040       1050       1060       1070       1080
              ....|....|....|....|....|....|....|....|....|....|....|....|
PPI-BnFTb     ATCATACGTCTACCTACATTGACAGGAGAATTCAACCTGTTTTTGATAGCCTCGGCTTGC     862
eral          ATCATACATCCACCTACATTAACAGGAGAATGCAACTGGTTTTTGATAGCCTCGGCTTGC     949
PPI-Soy-FTB   CCTATAAATTTATTAATGAGTGGAGAGCACAAGAACCACTTTTTCACAGTATTGCTTTAC     985
PPI-Corn-FTB  GATTTGATTTTATACAACAGAGCAACCAAATTGGCCCACTCTTCCATAACATTGCCCTGC    1043
Consensus        ATA  T TA  A       CAG   AAT  AACC  TTTTT ATAGC T G CTTGC     663

                     1090       1100       1110       1120       1130       1140
              ....|....|....|....|....|....|....|....|....|....|....|....|
PPI-BnFTb     AAAGATATGTGCTCTTGTGCTCTCAGGT GCTGATGGTGGATTCAGAGACAAGCTGACGA     922
eral          AGAGATATGTACTCTTGTGCTCTAAGATCCCTGACGGTGGATTCAGAGACAAGCCGACGA    1009
PPI-Soy-FTB   AGCAATATATTCTCTTATGTG ACAGGAGCAAGAGGGTGGACTGAGAGACAAACCCGGTA    1045
PPI-Corn-FTB  AACAATACATCCTA TTTGTTCTCAGGTACTAGAGGGAGGCTTGAGGGATAAGCCTGGAA    1103
Consensus     A   ATAT T CTCTT TG TCTCAGGT C  GA GGTGGATT AGAGACAAGCC G A     709

                     1150       1160       1170       1180       1190       1200
              ....|....|....|....|....|....|....|....|....|....|....|....|
PPI-BnFTb     AACCCCGTGACTTCTACCACACATGTTACTGCCTAAGCGGTCTTTGCGTGGCTCAACAGG     982
eral          AACCCCGTGACTTCTACCACACATGTTACTGCCTGAGCGGCTTGTCTGTGGCTCAGCAGG    1069
PPI-Soy-FTB   AACGTAGAGATCATTATCACACATGTTACTGTTTAAGTGGACTCTCATTGTGCCAGTATA    1105
PPI-Corn-FTB  AGAACAGAGATCACTATCATTCATGCTACTGCCTCAGTGGCCTCGCAGTTAGCCAGTACA    1163
Consensus     AAC C G GA   CTA CACACATGTTACTGCCT AG GG CT TG GTG   CAG AC     752

                     1210       1220       1230       1240       1250       1260
              ....|....|....|....|....|....|....|....|....|....|....|....|
PPI-BnFTb     CTTGGTCAAAAGACGAGGACACTCCTCCTTTGACTCGTGACATTTTGGGTGGCTACGCAA    1042
eral          CTTGGTTAAAAGACGAGGACACTCCTCCTTTGACTCGCGACATTATGGGTGGCTACTCGA    1129
PPI-Soy-FTB   GTTGGTCAAAGCACCCAGATTCTCCACCAC------------------------------    1135
PPI-Corn-FTB  GTGCCATGACTGATACTCGTTCGTGCCCATTACCTCAGCATGTGCTTGGACCGTACTGTA    1223
Consensus      TTGGT AAA GAC   GA  CTCC CC TT  CTC AGC A  T  T GG    TAC C A    786
```

TABLE 10H-continued

ClustalW Nucleic Acid Analysis of FT Beta

| | | | |
|---|---|---|---|
| | 1270 1280 1290 1300 1310 1320 | | |
| | ....\|....\|....\|....\|....\|....\|....\|....\|....\|....\|....\|....\| | | |
| PPI-BnFTb | ACCACCTTGAACCTGTTCACCTCCTCCACAACATTGTCTTGGATCGGTATTATGAAGCTT | 1102 | |
| eral | ATCTCCTTGAACCTGTTCAACTTCTTCACAACATTGTCATGGATCAGTATAATGAAGCTA | 1189 | |
| PPI-Soy-FTB | ------------------------------------------------------------ | 1135 | |
| PPI-Corn-FTB | ATTTGCTGGAGCCAATCCATCC-------------------------------------- | 1245 | |
| Consensus | A    CT GA CC  T CA C | 797 | |
| | 1330 1340 1350 1360 1370 1380 | | |
| | ....\|....\|....\|....\|....\|....\|....\|....\|....\|....\|....\|....\| | | |
| PPI-BnFTb | CTAGATTT---------------------------------------------------- | 1110 | |
| eral | TCGAGTTCTTCTTTAAAGCAGCATGACCCGTTGTTGCTAATGTATGGGAAACCCCAAACA | 1249 | |
| PPI-Soy-FTB | ------------------------------------------------------------ | 1135 | |
| PPI-Corn-FTB | ------------------------------------------------------------ | 1245 | |
| Consensus | ---------------------------------------------------- | 797 | |
| | 1390 1400 1410 1420 | | |
| | ....\|....\|....\|....\|....\|....\|....\|....\|. | | |
| PPI-BnFTb | ----------------------------------------- | 1110 | (SEQ ID NO: 14) |
| eral | TAAGAGTTTCCGTAGTGTTGTAACTTGTAAGATTTCAAAAG | 1290 | (SEQ ID NO: 1) |
| PPI-Soy-FTB | ----------------------------------------- | 1135 | (SEQ ID NO: 40) |
| PPI-Corn-FTB | ----------------------------------------- | 1245 | (SEQ ID NO: 43) |
| Consensus | ----------------------------------------- | 797 | (SEQ ID NO: 97) |

Example 13

Vector constructs for Transformation

The FTA or FTB sequences have be used to produce constructs suitable for transformation into plants and under the control of appropriate regulatory sequences. The gene sequences were in either the sense orientation for over-expression or the antisense orientation for down-regulation. Portions of these sequences have been used to construct a double-stranded-RNA-inhibition (dsRNAi) construct. A sequence of preferably not less than 21 nt was cloned as an inverse repeat separated by a linker that when expressed results in down-regulation of the target gene. Double antisense (DA) vectors have been created in which a direct repeat of an antisense sequence is separated by a spacer sequence such as GUS. Promoters have been used for constitutive expression such as the 35S CaMV promoter, the MuA *Zea maize* promoter or inducible by specific environmental or cellular cues such as the ABA levels or drought conditions which induce expression of the RD29A promoter. Alternatively, tissue or organelle specific promoters such as the HIC or CUT1 promoter can be used. Such constructs have been transformed into *Arabidopsis thaliana, Brassica, Zea maize, Glycine max*. Other species can be transformed as desired. Each species to be transformed may make use of specific regulatory sequences as appropriate for those particular species. Transformed plants have be selected and their phenotypic properties analyzed. The transgenic plants were assessed for characteristics such as increased tolerance to drought, altered biomass accumulation, yield, nutritional requirements such as minerals or micro-nutrients, biotic stress such as fungal, bacterial, or other such pathogen infection or attack or any other such physical or biochemical characteristic.

Example 14

Plant Transformation

*Arabidopsis thaliana* transgenic plants were made by flower dipping method into an *Agrobacterium* culture. Wild type plants were grown under standard conditions until they began flowering. The plant was inverted for 2 min into a solution of *Agrobacterium* culture. Plants were then bagged for two days to maintain humidity and then uncovered to continue growth and seed development. Mature seed was bulk harvested.

Transformed T1 plants were selected by germination and growth on MS plates containing 50 μg/ml kanamycin. Green, kanamycin resistant seedlings were identified after 2 weeks growth and transplanted to soil. Plants were bagged to ensure self fertilization and the T2 seed of each plant harvested separately. During growth of T1 plants leaf samples were harvested, DNA extracted and Southern analysis performed.

T2 seeds were analyzed for $Kan^R$ segregation. From those lines that showed a 3:1 resistant phenotype surviving T2 plants were grown, bagged during seed set, and T3 seed harvested from each line. T3 seed was again used for $Kan^R$ segregation analysis and those lines showing 100% $Kan^R$ phenotype were selected as homozygous lines. Further analysis was done using T3 seed.

Transgenic *Brassica napus* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 μl Tween20) and left for approximately 15 minutes. Solution I was removed and replaced with 30 ml of solution II (0.25% mecuric chloride, 100 μl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained for 5 days at 24° C., with 16.8 hr light dark cycles. Explants were transferred to Medium II (Medium I, 300 mg/L timentin) for a further 7 days and then to Medium III (Medium II, 20 mg/L kanamycin). Any root or shoot tissue which had developed at this time was dissected away. Transfer explants to fresh plates of Medium III after 14-21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10×IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil.

Transgenic *Glycine max, Zea maize* and cotton can be produced using *Agrobacterium*-based methods which are known to one of skill in the art. Alternatively one can use a particle or non-particle biolistic bombardment transformation method. An example of non-particle biolistic transformation is given in U.S. Patent Application 20010026941. Viable plants are propogated and homozygous lines are generated. Plants are tested for the presence of drought tolerance, physiological and biochemical phenotypes as described elsewhere.

The following table identifies the constructs and the species which they have been transformed.

TABLE 11

| SEQ ID NO: | SEQ | Species Transformed | |
|---|---|---|---|
| SEQ ID NO: 10 | pBI121-35S-anti-AtFTA | *Arabidopsis thaliana* | |
| SEQ ID NO: 46 | pBI121-35S-AtFTA | *Arabidopsis thaliana* | *Brassica napus* |
| SEQ ID NO: 47 | pBI121-rd29A-anti-AtFTA | *Arabidopsis thaliana* | *Brassica napus* |
| SEQ ID NO: 48 | pBI121-35S-DA-AtFTA | *Arabidopsis thaliana* | *Brassica napus* |
| SEQ ID NO: 49 | pBI121-RD29A-DA-AtFTA | *Arabidopsis thaliana* | *Brassica napus* |
| SEQ ID NO: 50 | MuA-anti-GmFTA | *Glycine max* | |
| SEQ ID NO: 51 | RD29A-anti-GmFTA | *Glycine max* | |
| SEQ ID NO: 52 | MuA-HP-GmFTA-Nos-Term | *Glycine max* | |
| SEQ ID NO: 53 | RD29AP-HP-GmFTA-Nos-Term | *Glycine max* | |
| SEQ ID NO: 54 | pBI121-35S-Anti-AtFTB | *Arabidopsis thaliana* | *Brassica napus* |
| SEQ ID NO: 55 | pBI121-RD29AP-Anti-AtFTB | *Arabidopsis thaliana* | *Brassica napus* |
| SEQ ID NO: 56 | pBI121-35S-HP-AtFTB | *Arabidopsis thaliana* | *Brassica napus* |
| SEQ ID NO: 57 | pBI121-RD29AP-HP-AtFTB | *Arabidopsis thaliana* | *Brassica napus* |
| SEQ ID NO: 58 | pBI121-35S-AtFTB | *Arabidopsis thaliana* | |
| SEQ ID NO: 59 | MuA-anti-GmFTB-Nos-Term | *Glycine max* | |
| SEQ ID NO: 60 | RD29AP-anti-GmFTB-Nos-Term | *Glycine max* | |
| SEQ ID NO: 61 | MuA-HP-GmFTB-Nos-Term | *Glycine max* | |
| SEQ ID NO: 62 | RD29AP-HP-GmFTB-Nos-Term | *Glycine max* | |
| SEQ ID NO: 63 | MuA-anti-Zea maizeFTB-Nos-Term | *Zea maize* | |
| SEQ ID NO: 64 | MuA-HP-Zea maizeFTB-Nos-Term | *Zea maize* | |

Non-limiting examples of vector constructs suitable for plant transformation are given in SEQ ID NO: 10, 46-64.

SEQ ID NO: 10

*gtttacccgccaatatatcctgtc*aaacactgatagtttaaactgaaggcgggaaacgacaatctgatcatgagcgg agaattaagggagtcacgttatgacccccgccgatgacgcgggacaagccgttttacgtttggaactgacagaaccg caacgttgaaggagccactcagccgcgggtttctggagtttaatgagctaagcacatacgtcagaaaccattattgc gcgttcaaaagtcgcctaaggtcactatcagctagcaaatatttcttgtcaaaaatgctccactgacgttccataaa ttcccctcggtatccaattagagtctcatattcactctcaatccaaataatctgcaccggatctggatcgtttcgca tgattgaacaagatggattgcacgcaggttctccggccgcttgggtggagaggctattcggctatgactgggcacaa cagacaatcggctgctctgatgccgccgtgttccggctgtcagcgcaggggcgcccggttctttttgtcaagaccga cctgtccggtgccctgaatgaactgcaggacgaggcagcgcggctatcgtggctggccacgacgggcgttccttgcg cagctgtgctcgacgttgtcactgaagcgggaagggactggctgctattgggcgaagtgccggggcaggatctcctg tcatctcaccttgctcctgccgagaaagtatccatcatggctgatgcaatgcggcggctgcatacgcttgatccggc tacctgcccattcgaccaccaagcgaaacatcgcatcgagcgagcacgtactcggatggaagccggtcttgtcgatc aggatgatctggacgaagagcatcaggggctcgcgccagccgaactgttcgccaggctcaaggcgcgcatgcccgac ggcgatgatctcgtcgtgacccatggcgatgcctgcttgccgaatatcatggtggaaaatggccgcttttctggatt catcgactgtggccggctgggtgtggcggaccgctatcaggacatagcgttggctacccgtgatattgctgaagagc ttggcggcgaatgggctgaccgcttcctcgtgctttacggtatcgccgctcccgattcgcagcgcatcgccttctat cgccttcttgacgagttcttctgagcgggactctggggttcgaaatgaccgaccaagcgacgcccaacctgccatca cgagatttcgattccaccgccgccttctatgaaaggttgggcttcggaatcgttttccgggacgccggctggatgat cctccagcgcggggatctcatgctggagttcttcgcccacgggatctctgcggaacaggcggtcgaaggtgccgata -continued tcattacgacagcaacggccgacaagcacaacgccacgatcctgagcgacaatatgatcgggcccggcgtccacatc aacggcgtcggcggcgactgcccaggcaagaccgagatgcaccgcgatatcttgctgcgttcggatattttcgtgga gttcccgccacagacccggatgatccccgatcgttcaaacatttggcaataaagtttcttaagattgaatcctgttg ccggtcttgcgatgattatcatataatttctgttgaattacgttaagcatgtaataattaacatgtaatgcatgacg ttatttatgagatgggtttttatgattagagtcccgcaattatacatttaatacgcgatagaaaacaaaatatagcg cgcaaactaggataaattatcgcgcgcggtgtcatctatgttactagatcgggcctcctgtcaatgctggcggcggc tctggtggtggttctggtggcggctctgagggtggtggctctgagggtggcggttctgagggtggcggctctgaggg aggcggttccggtggtggctctggttccggtgattttgattatgaaaagatggcaaacgctaataagggggctatga ccgaaaatgccgatgaaaacgcgctacagtctgacgctaaaggcaaacttgattctgtcgctactgattacggtgct gctatcgatggtttcattggtgacgtttccggccttgctaatggtaatggtgctactggtgattttgctggctctaa ttcccaaatggctcaagtcggtgacggtgataattcacctttaatgaataatttccgtcaatatttaccttccctcc ctcaatcggttgaatgtcgcccttttgtctttggcccaatacgcaaaccgcctctccccgcgcgttggccgattcat taatgcagctggcacgacaggtttcccgactggaaagcgggcagtgagcgcaacgcaattaatgtgagttagctcac tcattaggcaccccaggctttacactttatgcttccggctcgtatgttgtgtggaattgtgagcggataacaatttc acacaggaaacagctatgaccatgattacgccaagcttgcatgcctgcagcccacagatggttagagaggcttacgc agcaggtctcatcaagacgatctacccgagcaataatctccaggaaatcaaataccttcccaagaaggttaaagatg cagtcaaaagattcaggactaactgcatcaagaacacagagaaagatatatttctcaagatcagaagtactattcca gtatggacgattcaaggcttgcttcacaaaccaaggcaagtaatagagattggagtctctaaaaaggtagttcccac tgaatcaaaggccatggagtcaaagattcaaatagaggacctaacagaactcgccgtaaagactggcgaacagttca tacagagtctcttacgactcaatgacaagaagaaaatcttcgtcaacatggtggagcacgacacacttgtctactcc aaaaatatcaaagatacagtctcagaagaccaaagggcaattgagacttttcaacaaagggtaatatccggaaacct cctcggattccattgcccagctatctgtcactttattgtgaagatagtggaaaaggaaggtggctcctacaaatgcc atcattgcgataaaggaaaggccatcgttgaagatgcctctgccgacagtggtcccaaagatggacccccacccacg aggagcatcgtggaaaaagaagacgttccaaccacgtcttcaaagcaagtggattgatgtgatatctccactgacgt aagggatgacgcacaatcccactatccttcgcaagacccttcctctatataaggaagttcatttcatttggagagaa cacggggactctagaggatcctcaaattgctgccactgtaatcttgctcttcctccatgcccaatagttagctctt ataggatctacacgaccaagaatagtacacaccaaattggccaagttagtctctggttcttcattagctagagctct cactgagtctttatgctcgttggttggtctcagtccatcacatagaagatccaaaagggtgctcagagcgaatccat ggaagcaatctgtgcgggatagaacattcaaacagactgaggaaacacttggatcactaatccaggattctttgtcg tctttgtaaagcgcttttaggtatcgccatgagctctcgtttgcaggattggttaaaatggctttgattgtgtagct tacttcagattctctcatggcttctaggcctcccaacaaaggagattgggtgatgacataatacctctgattccagg cggaattgttaaagacgtcagcttcaaggagctcgtgacagtaatcgagctcatcttcccatcctcctaatgcccgt agtgtccactgcctatgtgaccaagcatgataatgtttggcatcaagtgaaagtactctacgggtaaattcaagttc tctccctgcaacatcaggacccagtttctctgcaacccatcgccgatgatgccacagttggtagttcttagagttat cctcagcaatgcgttcgatgaactcgagttcttcaaacaagtcgtgattaagggcctcgagtactaggcgcctgaaa tgccacactgtgtagttgccggagtttaagaggagggtttcttccgtgagtcgtagtgcgcgaggagatcgctcgtc ggaaaagtaaatcgcacggaagtaatccatagtctcgcggaactcttccttgtaggcaattggcaccactggattcg gaccatcgtcctgagtcaatgggaccacgtctgaccactccaatcgttggctcagtggcacggtctcgtcgaaattc atccccctcgaatttccccgatcgttcaaacatttggcaataaagtttcttaagattgaatcctgttgccggtcttgc gatgattatcatataatttctgttgaattacgttaagcatgtaataattaacatgtaatgcatgacgttatttatga gatgggtttttatgattagagtcccgcaattatacatttaatacgcgatagaaaacaaaatatagcgcgcaaactag -continued gataaattatcgcgcgcggtgtcatctatgttactagatcgggaattcactggccgtcgttttacaacgtcgtgact gggaaaaccctggcgttacccaacttaatcgccttgcagcacatccccctttcgccagctggcgtaatagcgaagag gcccgcaccgatcgcccttcccaacagttgcgcagcctgaatggcgcccgctcctttcgctttcttcccttcctttc tcgccacgttcgccggctttccccgtcaagctctaaatcgggggctccctttagggttccgatttagtgctttacgg cacctcgaccccaaaaaacttgatttgggtgatggttcacgtagtgggccatcgccctgatagacggtttttcgccc tttgacgttggagtccacgttctttaatagtggactcttgttccaaactggaacaacactcaaccctatctcgggct attcttttgatttataagggattttgccgatttcggaaccaccatcaaacaggattttcgcctgctggggcaaacca gcgtggaccgcttgctgcaactctctcagggccaggcggtgaagggcaatcagctgttgcccgtctcactggtgaaa

**agaaaaaccaccccagtacattaaaaacgtccgcaatgtgttattaagttgtctaagcgtcaattt*gtttacaccac***

*aatatatcctgcca*

SEQ ID NO: 10 is the nucleic acid sequence of pBI121-antisense-FTA vector construct used to transform *Arabidopsis* plants. Italicized sequences are the right and left border repeats (1-24, 5226-5230). Underlined sequence is the 35S promoter (2515-3318). Bold sequence is the anti-sense Farnesyl transferase alpha sequence (3334-4317).

SEQ ID NO: 46

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag -continued catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggggactctagag gatccatgaatttcgacgagaccgtgccactgagccaacgattggagtggtcagacgtggtccc attgactcaggacgatggtccgaatccagtggtgccaattgcctacaaggaagagttccgcgag actatggattacttccgtgcgatttacttttccgacgagcgatctcctcgcgcactacgactca cggaagaaaccctcctcttaaactccggcaactacacagtgtggcatttcaggcgcctagtact cgaggcccttaatcacgacttgtttgaagaactcgagttcatcgaacgcattgctgaggataac tctaagaactaccaactgtggcatcatcggcgatgggttgcagagaaactgggtcctgatgttg cagggagagaacttgaatttacccgtagagtactttcacttgatgccaaacattatcatgcttg gtcacataggcagtggacactacgggcattaggaggatgggaagatgagctcgattactgtcac gagctccttgaagctgacgtctttaacaattccgcctggaatcagaggtattatgtcatcaccc aatctcctttgttgggaggcctagaagccatgagagaatctgaagtaagctacacaatcaaagc cattttaaccaatcctgcaaacgagagctcatggcgatacctaaaagctctttacaaagacgac aaagaatcctggattagtgatccaagtgtttcctcagtctgtttgaatgttctatcccgcacag attgcttccatggattcgctctgagcacccttttggatcttctatgtgatggactgagaccaac caacgagcataaagactcagtgagagctctagctaatgaagaaccagagactaacttggccaat ttggtgtgtactattcttggtcgtgtagatcctgtaagagctaactattgggcatggaggaaga

-continued gcaagattacagtggcagcaatttgactcgaatttccccgatcgttcaaacatttggcaataaa gtttcttaagattgaatcctgttgccggtcttgcgatgattatcatataatttctgttgaatta cgttaagcatgtaataattaacatgtaatgcatgacgttatttatgagatgggtttttatgatt agagtcccgcaattatacatttaatacgcgatagaaaacaaaatatagcgcgcaaactaggata aattatcgcgcgcggtgtcatctatgttactagatcgggaattcactggccgtcgttttacaac gtcgtgactgggaaaaccctggcgttacccaacttaatcgccttgcagcacatccccctttcgc cagctggcgtaatagcgaagaggcccgcaccgatcgcccttcccaacagttgcgcagcctgaat ggcgcccgctcctttcgctttcttcccttcctttctcgccacgttcgccggctttccccgtcaa gctctaaatcgggggctccctttagggttccgatttagtgctttacggcacctcgaccccaaaa aacttgatttgggtgatggttcacgtagtgggccatcgccctgatagacggtttttcgcccttt gacgttggagtccacgttctttaatagtggactcttgttccaaactggaacaacactcaaccct atctcgggctattcttttgatttataagggattttgccgatttcggaaccaccatcaaacagga ttttcgcctgctggggcaaaccagcgtggaccgcttgctgcaactctctcagggccaggcggtg aagggcaatcagctgttgcccgtctcactggtgaaaagaaaaaccaccccagtacattaaaaac gtccgcaatgtgttattaagttgtctaagcgtcaattt*gtttacaccacaatatatcctgcca*

(Underlined Seq: 35S promoter; Bold: AtFTA)

SEQ ID NO: 47

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg -continued tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttgtaacaaaatgtttttattattat tatagaattttactggttaaattaaaaatgaatagaaaaggtgaattaagaggagagaggaggt aaacattttcttctatttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaagactctagaggatcc tcaaattgctgccactgtaatcttgctcttcctccatgcccaatagttagctcttataggatct acacgaccaagaatagtacacaccaaattggccaagttagtctctggttcttcattagctagag ctctcactgagtctttatgctcgttggttggtctcagtccatcacatagaagatccaaaagggt gctcagagcgaatccatggaagcaatctgtgcgggatagaacattcaaacagactgaggaaaca cttggatcactaatccaggattctttgtcgtctttgtaaagcgcttttaggtatcgccatgagc tctcgtttgcaggattggttaaaatggctttgattgtgtagcttacttcagattctctcatggc ttctaggcctcccaacaaaggagattgggtgatgacataatacctctgattccaggcggaattg ttaaagacgtcagcttcaaggagctcgtgacagtaatcgagctcatcttcccatcctcctaatg cccgtagtgtccactgcctatgtgaccaagcatgataatgtttggcatcaagtgaaagtactct acgggtaaattcaagttctctccctgcaacatcaggacccagtttctctgcaacccatcgccga

-continued tgatgccacagttggtagttcttagagttatcctcagcaatgcgttcgatgaactcgagttctt caaacaagtcgtgattaagggcctcgagtactaggcgcctgaaatgccacactgtgtagttgcc ggagtttaagaggagggtttcttccgtgagtcgtagtgcgcgaggagatcgctcgtcggaaaag taaatcgcacggaagtaatccatagtctcgcggaactcttccttgtaggcaattggcaccactg gattcggaccatcgtcctgagtcaatgggaccacgtctgaccactccaatcgttggctcagtgg cacggtctcgtcgaaattcatcccctcgaatttccccgatcgttcaaacatttggcaataaagt ttcttaagattgaatcctgttgccggtcttgcgatgattatcatataatttctgttgaattacg ttaagcatgtaataattaacatgtaatgcatgacgttatttatgagatgggtttttatgattag agtcccgcaattatacatttaatacgcgatagaaaacaaaatatagcgcgcaaactaggataaa ttatcgcgcgcggtgtcatctatgttactagatcgggaattcactggccgtcgttttacaacgt cgtgactgggaaaaccctggcgttacccaacttaatcgccttgcagcacatccccctttcgcca gctggcgtaatagcgaagaggcccgcaccgatcgcccttcccaacagttgcgcagcctgaatgg cgcccgctcctttcgctttcttcccttcctttctcgccacgttcgccggctttccccgtcaagc tctaaatcgggggctccctttagggttccgatttagtgctttacggcacctcgaccccaaaaaa cttgatttgggtgatggttcacgtagtgggccatcgccctgatagacggtttttcgccctttga cgttggagtccacgttctttaatagtggactcttgttccaaactggaacaacactcaaccctat ctcgggctattcttttgatttataagggattttgccgatttcggaaccaccatcaaacaggatt ttcgcctgctggggcaaaccagcgtggaccgcttgctgcaactctctcagggccaggcggtgaa gggcaatcagctgttgcccgtctcactggtgaaaagaaaaaccaccccagtacattaaaaacgt ccgcaatgtgttattaagttgtctaagcgtcaattt*gtttacaccacaatatatcctgcca*

(Underlined Seq: RD29A promoter; Bold: Anti-sense-AtFTA)

SEQ ID NO: 48

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac -continued gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggggactctagag gatcctcGCTCTTCCTCCATGCCCAATAGTTAGCTCTTACAGGATCTACACGACCAAGAATAGT

ACACACCAAATTGGCCAAGTTAGTCTCTGGTTCTTCATTAGCTAGAGCTCTCACTGAGTCTTTA

TGCTCGTTGGTTGGTCTCAGTCCATCACATAGAAGATCCAAAAGGGTGCTCAGAGCGAATCCAT

GGAAGCAATCTGTGCGGGATAGAACATTCAAACAGACTGAGGAAACACTTGGATCACTAATCCA

GGATTCTTTGTCGTCTTTGTAAAGAGCTTTTAGGTATCGCCATGAGCTCTCGTTTGCAGGATTG

GTTAAAATGGCTTTGATTGTGTAGCTTACTTCAGATTCTCTCATGGCTTCTAGGCCTCCCAACA

AAGGAGATTGGGTGATGACATAATACCTCTGATTCCAGGCGGAATTGTTAAAGACGTCAGCTTC

AAGGAGCTCGTGACAGTAATCGAGCTCATCTTCCCATCCTCCTAATGCCCGgaggatccccATC

-continued

TACCCGCTTCGCGTCGGCATCCGGTCAGTGGCAGTGAAGGGCGAACAGTTCCTGATTAACCACA

AACCGTTCTACTTTACTGGCTTTGGTCGTCATGAAGATGCGGACTTGCGTGGCAAAGGATTCGA

TAACGTGCTGATGGTGCACGACCACGCATTAATGGACTGGATTGGGGCCAACTCCTACCGTACC

TCGCATTACCCTTACGCTGAAGAGATGCTCGACTGGGCAGATGAACATGGCATCGTGGTGATTG

ATGAAACTGCTGCTGTCGGCTTTTCGCTCTCTTTAGGCATTGGTTTCGAAGCGGGCAACAAGCC

GAAAGAACTGTACAGCGAAGAGGCAGTCAACGGGGAAACTCAGCAAGCGCACTTACAGGCGATT

AAAGAGCTGATAGCGCGTGACAAAAACCACCCAAGCGTGGTGATGTGGAGTATTGCCAACGAAC

CGGATACCCGTCCGCAAGGTGCACGGGAATATTTCGCGCCACTGGCGGAAGCAACGCGTAAACT

CGACCCGACGCGTCCGATCACCTGCGTCAATGTAATGTTCTGCGACGCTCACACCGATACCATC

AGCGATCTCTTTGATGTGCTGTGCCTGAACCGTTATTACGGATGGTATGTCCAAAGCGGCGATT

TGGAAACGGCAGAGAAGGTACTGGAAAAAGAACTTCTGGCCTGGCAGGAGAAACTGTACACCGA

CATGTGGAGTGAAGAGTATCAGTGTGCATGGCTGGATATGTATCACCGCGTCTTTGATCGCGTC

AGCGCCGTCGTCGGTGAACAGGTATGGAATTTCGCCGATTTTGCGACCTCGCAAGGCATATTGC

GCGTTGGCGGTAACAAGAAAGGGATCTTCACTCGCGACCGCAAACCGAAGTCGGCGGCTTTTCT

GCTGCAAAAACGCTGGACTGGCATGAACTTCGGTGAAAAACCGCAGCAGGGAGGCAAACAATGA

ATCAACAACTCTCCTGGCGCACCATCGTCGGCTACAGCCTCGGGAATTGCTACCGAGCTCGCTC

TTCCTCCATGCCCAATAGTTAGCTCTTACAGGATCTACACGACCAAGAATAGTACACACCAAAT

TGGCCAAGTTAGTCTCTGGTTCTTCATTAGCTAGAGCTCTCACTGAGTCTTTATGCTCGTTGGT

TGGTCTCAGTCCATCACATAGAAGATCCAAAAGGGTGCTCAGAGCGAATCCATGGAAGCAATCT

GTGCGGGATAGAACATTCAAACAGACTGAGGAAACACTTGGATCACTAATCCAGGATTCTTTGT

CGTCTTTGTAAAGAGCTTTTAGGTATCGCCATGAGCTCTCGTTTGCAGGATTGGTTAAAATGGC

TTTGATTGTGTAGCTTACTTCAGATTCTCTCATGGCTTCTAGGCCTCCCAACAAAGGAGATTGG

GTGATGACATAATACCTCTGATTCCAGGCGGAATTGTTAAAGACGTCAGCTTCAAGGAGCTCGT

GACAGTAATCGAGCTCATCTTCCCATCCTCCTAATGCCCGctcgaatttccccgatcgttcaaa catttggcaataaagtttcttaagattgaatcctgttgccggtcttgcgatgattatcatataa tttctgttgaattacgttaagcatgtaataattaacatgtaatgcatgacgttatttatgagat gggtttttatgattagagtcccgcaattatacatttaatacgcgatagaaaacaaaatatagcg cgcaaactaggataaattatcgcgcgcggtgtcatctatgttactagatcgggaattcactggc cgtcgttttacaacgtcgtgactgggaaaaccctggcgttacccaacttaatcgccttgcagca catccccctttcgccagctggcgtaatagcgaagaggcccgcaccgatcgcccttcccaacagt tgcgcagcctgaatggcgcccgctcctttcgctttcttcccttcctttctcgccacgttcgccg gctttccccgtcaagctctaaatcgggggctccctttagggttccgatttagtgctttacggca cctcgaccccaaaaaacttgatttgggtgatggttcacgtagtgggccatcgccctgatagacg gtttttcgccctttgacgttggagtccacgttctttaatagtggactcttgttccaaactggaa caacactcaaccctatctcgggctattcttttgatttataagggattttgccgatttcggaacc accatcaaacaggattttcgcctgctggggcaaaccagcgtggaccgcttgctgcaactctctc agggccaggcggtgaagggcaatcagctgttgcccgtctcactggtgaaaagaaaaaccacccc agtacattaaaaacgtccgcaatgtgttattaagttgtctaagcgtcaattt*gtttacaccaca*

*atatatcctgcca*

-continued (Underlined Seq: 35S promoter; Bold: AtFTA anti-sense sequence separated by GUS Seq.)

SEQ ID NO: 49

*gtttacccgccaatatatcctgtc*caaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat -continued gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc ctcGCTCTTCCTCCATGCCCAATAGTTAGCTCTTACAGGATCTACACGACCAAGAATAGTACAC

ACCAAATTGGCCAAGTTAGTCTCTGGTTCTTCATTAGCTAGAGCTCTCACTGAGTCTTTATGCT

CGTTGGTTGGTCTCAGTCCATCACATAGAAGATCCAAAAGGGTGCTCAGAGCGAATCCATGGAA

GCAATCTGTGCGGGATAGAACATTCAAACAGACTGAGGAAACACTTGGATCACTAATCCAGGAT

TCTTTGTCGTCTTTGTAAAGAGCTTTTAGGTATCGCCATGAGCTCTCGTTTGCAGGATTGGTTA

AAATGGCTTTGATTGTGTAGCTTACTTCAGATTCTCTCATGGCTTCTAGGCCTCCCAACAAAGG

AGATTGGGTGATGACATAATACCTCTGATTCCAGGCGGAATTGTTAAAGACGTCAGCTTCAAGG

AGCTCGTGACAGTAATCGAGCTCATCTTCCCATCCTCCTAATGCCCGgaggatccccATCTACC

CGCTTCGCGTCGGCATCCGGTCAGTGGCAGTGAAGGGCGAACAGTTCCTGATTAACCACAAACC

GTTCTACTTTACTGGCTTTGGTCGTCATGAAGATGCGGACTTGCGTGGCAAAGGATTCGATAAC

GTGCTGATGGTGCACGACCACGCATTAATGGACTGGATTGGGGCCAACTCCTACCGTACCTCGC

ATTACCCTTACGCTGAAGAGATGCTCGACTGGGCAGATGAACATGGCATCGTGGTGATTGATGA

AACTGCTGCTGTCGGCTTTTCGCTCTCTTTAGGCATTGGTTTCGAAGCGGGCAACAAGCCGAAA

GAACTGTACAGCGAAGAGGCAGTCAACGGGGAAACTCAGCAAGCGCACTTACAGGCGATTAAAG

AGCTGATAGCGCGTGACAAAAACCACCCAAGCGTGGTGATGTGGAGTATTGCCAACGAACCGGA

TACCCGTCCGCAAGGTGCACGGGAATATTTCGCGCCACTGGCGGAAGCAACGCGTAAACTCGAC

CCGACGCGTCCGATCACCTGCGTCAATGTAATGTTCTGCGACGCTCACACCGATACCATCAGCG

ATCTCTTTGATGTGCTGTGCCTGAACCGTTATTACGGATGGTATGTCCAAAGCGGCGATTTGGA

AACGGCAGAGAAGGTACTGGAAAAAGAACTTCTGGCCTGGCAGGAGAAACTGTACACCGACATG

TGGAGTGAAGAGTATCAGTGTGCATGGCTGGATATGTATCACCGCGTCTTTGATCGCGTCAGCG

CCGTCGTCGGTGAACAGGTATGGAATTTCGCCGATTTTGCGACCTCGCAAGGCATATTGCGCGT

TGGCGGTAACAAGAAAGGGATCTTCACTCGCGACCGCAAACCGAAGTCGGCGGCTTTTCTGCTG

CAAAAACGCTGGACTGGCATGAACTTCGGTGAAAAACCGCAGCAGGGAGGCAAACAATGAATCA

ACAACTCTCCTGGCGCACCATCGTCGGCTACAGCCTCGGGAATTGCTACCGAGCTCGCTCTTCC

TCCATGCCCAATAGTTAGCTCTTACAGGATCTACACGACCAAGAATAGTACACACCAAATTGGC

-continued

CAAGTTAGTCTCTGGTTCTTCATTAGCTAGAGCTCTCACTGAGTCTTTATGCTCGTTGGTTGGT

CTCAGTCCATCACATAGAAGATCCAAAAGGGTGCTCAGAGCGAATCCATGGAAGCAATCTGTGC

GGGATAGAACATTCAAACAGACTGAGGAAACACTTGGATCACTAATCCAGGATTCTTTGTCGTC

TTTGTAAAGAGCTTTTAGGTATCGCCATGAGCTCTCGTTTGCAGGATTGGTTAAAATGGCTTTG

ATTGTGTAGCTTACTTCAGATTCTCTCATGGCTTCTAGGCCTCCCAACAAAGGAGATTGGGTGA

TGACATAATACCTCTGATTCCAGGCGGAATTGTTAAAGACGTCAGCTTCAAGGAGCTCGTGACA

GTAATCGAGCTCATCTTCCCATCCTCCTAATGCCCGctcgaatttccccgatcgttcaaacatt tggcaataaagtttcttaagattgaatcctgttgccggtcttgcgatgattatcatataatttc tgttgaattacgttaagcatgtaataattaacatgtaatgcatgacgttatttatgagatgggt ttttatgattagagtcccgcaattatacatttaatacgcgatagaaaacaaaatatagcgcgca aactaggataaattatcgcgcgcggtgtcatctatgttactagatcgggaattcactggccgtc gttttacaacgtcgtgactgggaaaaccctggcgttacccaacttaatcgccttgcagcacatc ccccttttcgccagctggcgtaatagcgaagaggcccgcaccgatcgcccttcccaacagttgcg cagcctgaatggcgcccgctcctttcgctttcttcccttcctttctcgccacgttcgccggctt tccccgtcaagctctaaatcgggggctccctttagggttccgatttagtgctttacggcacctc gaccccaaaaaacttgatttgggtgatggttcacgtagtgggccatcgccctgatagacggttt ttcgccctttgacgttggagtccacgttctttaatagtggactcttgttccaaactggaacaac actcaaccctatctcgggctattcttttgatttataagggattttgccgatttcggaaccacca tcaaacaggattttcgcctgctggggcaaaccagcgtggaccgcttgctgcaactctctcaggg ccaggcggtgaagggcaatcagctgttgcccgtctcactggtgaaaagaaaaaccaccccagta cattaaaaacgtccgcaatgtgttattaagttgtctaagcgtcaattt*gtttacaccacaatat*

*atcctgcca*

(Underlined Seq: RD29A promoter; Bold: AtFTA anti-sense sequence, separated by GUS Seq.)

SEQ ID NO: 50

GAATTCAAATTTTTCGCCAGTTCTAAATATCCGGAAACCTCTTGGGATGCCATTGCCCATCTAT

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCAGGAAGTCTGCTCTTGCGCCAAAT

CCAATAGTTGGTTCTAATTGGATCAACTTGTTTTAGGATAGAACAAATATTTCGTGCTATATTT

AAATTTTGTTGTTCCCCTTTCTCATCATCATCTAAATCTTGTTTATCCATATCTGCGGTCTTTA

AGGCGTCAATGGCATCTCTAATGTCTTCATTTGGTTGATAACCAAAGCATATAAGATCTAAAAT

AGTGCTAAGAGCAAACACGTAGTTGCTCTTAGTTCTCAAAATCTTTAAGCATACTGAAGAAACT

TGAGGATCATTTACCCATGAAGTAGTTTCACCTTTATAAAGTCCTCGTAGATATCTCCACGAGC

TTTCATTTTCAGGGTAGGCTATAATGGCTTCGATGGTGTAAAGCACTTCAGACTCTCTCATAGC

TTTTAGGCCCCCCAAGAAAGGAGACCTTGTTATGACAAAATATCTCTGATTCCAAGCAGAATTG

TTAAAAATGTCTTCTTTAAGTAGTTCTGTGCAATAATTAAGTTCATCTTCCCATCCTCCTAGTG

TTTGAAGAGCCCACTGTCTATGAGACCATGCATGATAATGTTTGGCATCAACGGACAGTATCTT

TTTGGTGAACTCGAGCTgagctcgaatttccccgatcgttcaaacatttggcaataaagtttct

-continued taagattgaatcctgttgccggtcttgcgatgattatcatataatttctgttgaattacgttaa gcatgtaataattaacatgtaatgcatgacgttatttatgagatgggtttttatgattagagtc ccgcaattatacatttaatacgcgatagaaaacaaaatatagcgcgcaaactaggataaattat cgcgcgcggtgtcatctatgttactagatcgggaattc (Underlined MuA Promoter; Bold: *Glycine max* anti-FTA; lower case: NOS terminater Seq.)

SEQ ID NO: 51

GGAGCCATAGATGCAATTCAATCAAACTGAAATTTCTGCAAGAATCTCAAACACGGAGATCTCA

AAGTTTGAAAGAAAATTTATTTCTTCGACTCAAAACAAACTTACGAAATTTAGGTAGAACTTAT

ATACATTATATTGTAATTTTTTGTAACAAAATGTTTTTATTATTATTATAGAATTTTACTGGTT

AAATTAAAAATGAATAGAAAAGGTGAATTAAGAGGAGAGAGGAGGTAAACATTTTCTTCTATTT

TTTCATATTTTCAGGATAAATTATTGTAAAAGTTTACAAGATTTCCATTTGACTAGTGTAAATG

AGGAATATTCTCTAGTAAGATCATTATTTCATCTACTTCTTTTATCTTCTACCAGTAGAGGAAT

AAACAATATTTAGCTCCTTTGTAAATACAAATTAATTTTCCTTCTTGACATCATTCAATTTTAA

TTTTACGTATAAAATAAAAGATCATACCTATTAGAACGATTAAGGAGAAATACAATTCGAATGA

GAAGGATGTGCCGTTTGTTATAATAAACAGCCACACGACGTAAACGTAAAATGACCACATGATG

GGCCAATAGACATGGACCGACTACTAATAATAGTAAGTTACATTTTAGGATGGAATAAATATCA

TACCGACATCAGTTTTGAAAGAAAAGGGAAAAAAAGAAAAAATAAATAAAAGATATACTACCGA

CATGAGTTCCAAAAAGCAAAAAAAAAGATCAAGCCGACACAGACACGCGTAGAGAGCAAAATGA

CTTTGACGTCACACCACGAAAACAGACGCTTCATACGTGTCCCTTTATCTCTCTCAGTCTCTCT

ATAAACTTAGTGAGACCCTCCTCTGTTTTACTCACAAATATGCAAACTAGAAAACAATCATCAG

GAATAAAGGGTTTGATTACTTCTATTGGAAAGAGGAAGTCTGCTCTTGCGCCAAATCCAATAGT

TGGTTCTAATTGGATCAACTTGTTTTAGGATAGAACAAATATTTCGTGCTATATTTAAATTTTG

TTGTTCCCCTTTCTCATCATCATCTAAATCTTGTTTATCCATATCTGCGGTCTTTAAGGCGTCA

ATGGCATCTCTAATGTCTTCATTTGGTTGATAACCAAAGCATATAAGATCTAAAATAGTGCTAA

GAGCAAACACGTAGTTGCTCTTAGTTCTCAAAATCTTTAAGCATACTGAAGAAACTTGAGGATC

ATTTACCCATGAAGTAGTTTCACCTTTATAAAGTCCTCGTAGATATCTCCACGAGCTTTCATTT

TCAGGGTAGGCTATAATGGCTTCGATGGTGTAAAGCACTTCAGACTCTCTCATAGCTTTTAGGC

CCCCCAAGAAAGGAGACCTTGTTATGACAAAATATCTCTGATTCCAAGCAGAATTGTTAAAAAT

GTCTTCTTTAAGTAGTTCTGTGCAATAATTAAGTTCATCTTCCCATCCTCCTAGTGTTTGAAGA

GCCCACTGTCTATGAGACCATGCATGATAATGTTTGGCATCAACGGACAGTATCTTTTTGGTGA

ACTCGAGCTgagctcgaatttccccgatcgttcaaacatttggcaataaagtttcttaagattg aatcctgttgccggtcttgcgatgattatcatataatttctgttgaattacgttaagcatgtaa taattaacatgtaatgcatgacgttatttatgagatgggtttttatgattagagtcccgcaatt atacatttaatacgcgatagaaaacaaaatatagcgcgcaaactaggataaattatcgcgcgcg gtgtcatctatgttactagatcgggaattc (Underlined RD29A Promoter; Bold: *Glycine max* anti-*Glycine max* FTA; lower case: NOS terminater Seq.)

SEQ ID NO: 52

GAATTCAAATTTTTCGCCAGTTCTAAATATCCGGAAACCTCTTGGGATGCCATTGCCCATCTAT

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

-continued

TATCTCCATTGACGTAAGGGATGACGCACAATCCAACTATCCATCGCAAGACCATTGCTCTATA

TAAGAAAGTTAATATCATTTCGAGTGGCCACGCTGAGCTCAGGAAGTCTGCTCTTGCGCCAAAT

CCAATAGTTGGTTCTAATTGGATCAACTTGTTTTAGGATAGAACAAATATTTCGTGCTATATTT

AAATTTTGTTGTTCCCCTTTCTCATCATCATCTAAATCTTGTTTATCCATATCTGCGGTCTTTA

AGGCGTCAATGGCATCTCTAATGTCTTCATTTGGTTGATAACCAAAGCATATAAGATCTAAAAT

AGTGCTAAGAGCAAACACGTAGTTGCTCTTAGTTCTCAAAATCTTTAAGCATACTGAAGAAACT

TGAGGATCATTTACCCATGAAGTAGTTTCACCTTTATAAAGTCCTCGTAGATATCTCCACGAGC

TTTCATTTTCAGGGTAGGCTATAATGGCTTCGATGGTGTAAAGCACTTCAGACTCTCTCATAGC

TTTTAGGCCCCCCAAGAAAGGAGACCTTGTTATGACAAAATATCTCTGATTCCAAGCAGAATTG

TTAAAAATGTCTTCTTTAAGTAGTTCTGTGCAATAATTAAGTTCATCTTCCCATCCTCCTAGTG

TTTGAAGAGCCCACTGTCTATGAGACCATGCATGATAATGTTTGGCATCAACGGACAGTATCTT

TTTGGTGAACTCGAGCT*TAAAGGTGAAACTACTTCATGGGTAAATGATCCTCAAGTTTCTTCAG*

*TATGCTTAAAGATTTTGAGAACTAAGAGCAACTACGTGTTTGCTCTTAGCACTATTTTAGATCT*

*TATATGCTTTGGTTATCAACCAAATGAAGACATTAGAGATGCCATTGACGCCTTAAAGACCGCA*

*GATATGGATAAACAAGATTTAGATGATGATGAGAAAGGGGAACAACAAAATTTAAATATAGCAC*

*GAAATATTTGTTCTATCCTAAAACAAGTTGATCCAATTAGAACCAACTATTGGATTTGGCGCAA*

*GAGCAGACTTCCT*gagctcgaatttccccgatcgttcaaacatttggcaataaagtttcttaag attgaatcctgttgccggtcttgcgatgattatcatataatttctgttgaattacgttaagcat gtaataattaacatgtaatgcatgacgttatttatgagatgggtttttatgattagagtcccgc aattatacatttaatacgcgatagaaaacaaaatatagcgcgcaaactaggataaattatcgcg cgcggtgtcatctatgttactagatcgggaattc (Underlined: *Glycine max* FTA Anti-Sense section;
Bold: MuA Promoter; Italics: *Glycine max* FTA Sense section;
lower case: NOS terminater Seq.)

SEQ ID NO: 53 ggagccatagatgcaattcaatcaaactgaaatttctgcaagaatctcaaacacggagatctca aagtttgaaagaaaatttatttcttcgactcaaaacaaacttacgaaatttaggtagaacttat atacattatattgtaatttttgtaacaaaatgtttttattattattatagaattttactggtt aaattaaaaatgaatagaaaaggtgaattaagaggagagaggaggtaaacattttcttctattt tttcatattttcaggataaattattgtaaaagtttacaagatttccatttgactagtgtaaatg aggaatattctctagtaagatcattatttcatctacttcttttatcttctaccagtagaggaat aaacaatatttagctcctttgtaaatacaaattaattttccttcttgacatcattcaattttaa ttttacgtataaaataaaagatcatacctattagaacgattaaggagaaatacaattcgaatga gaaggatgtgccgtttgttataataaacagccacacgacgtaaacgtaaaatgaccacatgatg ggccaatagacatggaccgactactaataatagtaagttacattttaggatggaataaatatca taccgacatcagttttgaaagaaaagggaaaaaaagaaaaaataaataaaagatatactaccga catgagttccaaaaagcaaaaaaaaagatcaagccgacacagacacgcgtagagagcaaaatga ctttgacgtcacaccacgaaaacagacgcttcatacgtgtccctttatctctctcagtctctct ataaacttagtgagaccctcctctgttttactcacaaatatgcaaactagaaaacaatcatcag gaataaagggtttgattacttctattggaaagAGGAAGTCTGCTCTTGCGCCAAATCCAATAGT

TGGTTCTAATTGGATCAACTTGTTTTAGGATAGAACAAATATTTCGTGCTATATTTAAATTTTG

TTGTTCCCCTTTCTCATCATCATCTAAATCTTGTTTATCCATATCTGCGGTCTTTAAGGCGTCA

-continued

ATGGCATCTCTAATGTCTTCATTTGGTTGATAACCAAAGCATATAAGATCTAAAATAGTGCTAA

GAGCAAACACGTAGTTGCTCTTAGTTCTCAAAATCTTTAAGCATACTGAAGAAACTTGAGGATC

ATTTACCCATGAAGTAGTTTCACCTTTATAAAGTCCTCGTAGATATCTCCACGAGCTTTCATTT

TCAGGGTAGGCTATAATGGCTTCGATGGTGTAAAGCACTTCAGACTCTCTCATAGCTTTTAGGC

CCCCCAAGAAAGGAGACCTTGTTATGACAAAATATCTCTGATTCCAAGCAGAATTGTTAAAAAT

GTCTTCTTTAAGTAGTTCTGTGCAATAATTAAGTTCATCTTCCCATCCTCCTAGTGTTTGAAGA

GCCCACTGTCTATGAGACCATGCATGATAATGTTTGGCATCAACGGACAGTATCTTTTTGGTGA

ACTCGAGCTTAAAGGTGAAACTACTTCATGGGTAAATGATCCTCAAGTTTCTTCAGTATGCTTA

AAGATTTTGAGAACTAAGAGCAACTACGTGTTTGCTCTTAGCACTATTTTAGATCTTATATGCT

TTGGTTATCAACCAAATGAAGACATTAGAGATGCCATTGACGCCTTAAAGACCGCAGATATGGA

TAAACAAGATTTAGATGATGATGAGAAAGGGGAACAACAAAATTTAAATATAGCACGAAATATT

TGTTCTATCCTAAAACAAGTTGATCCAATTAGAACCAACTATTGGATTTGGCGCAAGAGCAGAC

TTCCTgagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattc (Bold lower case: RD29A Promoter; Underline, Upper case: Antisense GmFTA; Upper case: Sense GmFTA; lower case: NOS terminater)

SEQ ID NO: 54

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg -continued cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggggactctagag gatccgtccggaattcccgggtcgacccacgcgtccgggagattcagcgagataagcaattgga ttatctgatgaaaggcttaaggcagcttggtccgcagttttcttccttagatgctaatcgacct tggctttgttactggattcttcattcaatagctttgcttggggagactgtggatgatgaattag aaagcaatgccattgacttccttggacgctgccagggctctgaaggtggatacggtggtggtcc tggccaacttccacatcttgcaactacttatgctgcagtgaatgcacttgttactttaggaggt gacaaagccctttcttcaattaatagagaaaaaatgtcttgtttttaagacggatgaaggata caagtggaggtttcaggatgcatgatatgggagaaatggatgttcgtgcatgctacactgcaat ttcggttgcaagcatcctaaatattatggatgatgaactcacccagggcctaggagattacatc ttgagttgccaaacttatgaaggtggcattggaggggaacctggctccgaagctcacggtgggt -continued atacctactgtggtttggctgctatgattttaatcaatgaggtcgaccgtttgaatttggattc attaatgaattgggctgtacatcgacaaggagtagaaatgggatttcaaggtaggacgaacaaa ttggtcgatggttgctacacattttggcaggcagccccttgtgttctactacaaagattatatt caaccaatgatcatgacgttcatggatcatcacatatatcagaagggacaaatgaagaacatca tgctcatgatgaagatgaccttgaagacagtgatgatgatgatgattctgatgaggacaacgat gaagattcagtgaatggtcacagaatccatcatacatccacctacattaacaggagaatgcaac tggtttttgatagcctcggcttgcagagatatgtactcttgtgctctaagatccctgacggtgg attcagagacaagccgaggaaaccccgtgacttctaccacacatgttactgcctgagcggcttg tctgtggctcagcacgcttggttaaaagacgaggacactcctcctttgactcgcgacattatgg gtggctactcgaatctccttgaacctgttcaacttcttcacaacattgtcatggatcagtataa tgaagctatcgagttcttctttaaagcagcatgactcgaatttccccgatcgttcaaacatttg gcaataaagtttcttaagattgaatcctgttgccggtcttgcgatgattatcatataatttctg ttgaattacgttaagcatgtaataattaacatgtaatgcatgacgttatttatgagatgggttt ttatgattagagtcccgcaattatacatttaatacgcgatagaaaacaaaatatagcgcgcaaa ctaggataaattatcgcgcgcggtgtcatctatgttactagatcgggaattcactggccgtcgt tttacaacgtcgtgactgggaaaaccctggcgttacccaacttaatcgccttgcagcacatccc cctttcgccagctggcgtaatagcgaagaggcccgcaccgatcgcccttcccaacagttgcgca gcctgaatggcgcccgctcctttcgctttcttcccttcctttctcgccacgttcgccggctttc cccgtcaagctctaaatcgggggctccctttagggttccgatttagtgctttacggcacctcga ccccaaaaaacttgatttgggtgatggttcacgtagtgggccatcgccctgatagacggttttt cgccctttgacgttggagtccacgttctttaatagtggactcttgttccaaactggaacaacac tcaaccctatctcggctattcttttgatttataagggattttgccgatttcggaaccaccatc aaacaggattttcgcctgctggggcaaaccagcgtggaccgcttgctgcaactctctcagggcc aggcggtgaagggcaatcagctgttgcccgtctcactggtgaaaagaaaaaccaccccagtaca ttaaaaacgtccgcaatgtgttattaagttgtctaagcgtcaattt*gtttacaccacaatatat*

*cctgcca*

(Underline: 35S promoter; Bold: anti-AtFTB)

SEQ ID NO: 55

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag -continued ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttgtaacaaaatgtttttattattat
tatagaattttactggttaaattaaaaatgaatagaaaaggtgaattaagaggagagaggaggt
aaacattttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaggatc

-continued cgtccggaattcccgggtcgacccacgcgtccgggagattcagcgagataagcaattggattat ctgatgaaaggcttaaggcagcttggtccgcagttttcttccttagatgctaatcgaccttggc tttgttactggattcttcattcaatagctttgcttggggagactgtggatgatgaattagaaag caatgccattgacttccttggacgctgccagggctctgaaggtggatacggtggtggtcctggc caacttccacatcttgcaactacttatgctgcagtgaatgcacttgttactttaggaggtgaca aagccctttcttcaattaatagagaaaaaatgtcttgtttttaagacggatgaaggatacaag tggaggtttcaggatgcatgatatgggagaaatggatgttcgtgcatgctacactgcaatttcg gttgcaagcatcctaaatattatggatgatgaactcacccagggcctaggagattacatcttga gttgccaaacttatgaaggtggcattggaggggaacctggctccgaagctcacggtgggtatac ctactgtggtttggctgctatgattttaatcaatgaggtcgaccgtttgaatttggattcatta atgaattgggctgtacatcgacaaggagtagaaatgggatttcaaggtaggacgaacaaattgg tcgatggttgctacacattttggcaggcagccccttgtgttctactacaaagattatattcaac caatgatcatgacgttcatggatcatcacatatatcagaagggacaaatgaagaacatcatgct catgatgaagatgaccttgaagacagtgatgatgatgatgattctgatgaggacaacgatgaag attcagtgaatggtcacagaatccatcatacatccacctacattaacaggagaatgcaactggt ttttgatagcctcggcttgcagagatatgtactcttgtgctctaagatccctgacggtggattc agagacaagccgaggaaaccccgtgacttctaccacacatgttactgcctgagcggcttgtctg tggctcagcacgcttggttaaaagacgaggacactcctcctttgactcgcgacattatgggtgg ctactcgaatctccttgaacctgttcaacttcttcacaacattgtcatggatcagtataatgaa gctatcgagttcttctttaaagcagcatgactcgaatttccccgatcgttcaaacatttggcaa taaagtttcttaagattgaatcctgttgccggtcttgcgatgattatcatataatttctgttga attacgttaagcatgtaataattaacatgtaatgcatgacgttatttatgagatgggtttttat gattagagtcccgcaattatacatttaatacgcgatagaaaacaaaatatagcgcgcaaactag gataaattatcgcgcgcggtgtcatctatgttactagatcgggaattcactggccgtcgtttta caacgtcgtgactgggaaaaccctggcgttacccaacttaatcgccttgcagcacatccccctt tcgccagctggcgtaatagcgaagaggcccgcaccgatcgcccttcccaacagttgcgcagcct gaatggcgcccgctcctttcgctttcttcccttcctttctcgccacgttcgccggctttccccg tcaagctctaaatcgggggctccctttagggttccgatttagtgctttacggcacctcgacccc aaaaaacttgatttgggtgatggttcacgtagtgggccatcgccctgatagacggtttttcgcc ctttgacgttggagtccacgttctttaatagtggactcttgttccaaactggaacaacactcaa ccctatctcgggctattcttttgatttataagggattttgccgatttcggaaccaccatcaaac aggattttcgcctgctggggcaaaccagcgtggaccgcttgctgcaactctctcagggccaggc ggtgaagggcaatcagctgttgcccgtctcactggtgaaaagaaaaaccaccccagtacattaa aaacgtccgcaatgtgttattaagttgtctaagcgtcaattt*gtttacaccacaatatatcctg*

*cca*

(Underline: RD29A Promoter; Bold: anti-AtFTB)

SEQ ID NO: 56

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac -continued tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa -continued cagaactcgccgtaaagactggcgaacagttcatacagagtctcttacgactcaatgacaagaa
gaaaatcttcgtcaacatggtggagcacgacacacttgtctactccaaaaatatcaaagataca
gtctcagaagaccaaagggcaattgagacttttcaacaaagggtaatatccggaaacctcctcg
gattccattgcccagctatctgtcactttattgtgaagatagtggaaaaggaaggtggctccta
caaatgccatcattgcgataaaggaaaggccatcgttgaagatgcctctgccgacagtggtccc
aaagatggacccccacccacgaggagcatcgtggaaaaagaagacgttccaaccacgtcttcaa
agcaagtggattgatgtgatatctccactgacgtaagggatgacgcacaatcccactatccttc
gcaagacccttcctctatataaggaagttcatttcatttggagagaacacggggactctagag
gatcctcCTCCTAGGCCCTGGGTGAGTTCATCATCCATAATATTTAGGATGCTTGCAACCGAAA
TTGCAGTGTAGCATGCACGAACATCCATTTCTCCCATATCATGCATCCTGAAACCTCCACTTGT
ATCCTTCATCCGTCTTAAAAAACAAGACATTTTTTCTCTATTAATTGAAGAAAGGGCTTTGTCA
CCTCCTAAAGTAACAAGTGCATTCACTGCAGCATAAGTAGTTGCAAGATGTGGAAGTTGGCCAG
GACCACCACCGTATCCACCTTCAGAGCCCTGGCAGCGTCCAAGGAAGTCAATGGCATTGCTTTC
TAATTCATCATCCACAGTCTCCCCAAGCAAAGCTATTGAATGAAGAATCCAGTAACAAAGCCAA
GGTCGATTAGCATCTAAGGAAGAAAACTGCGGACCAAGCTGCCTTAAGCCTTTCATCAGATAAT
CCAATTGCTTATCTCGCTGAATCTCCCGGACGCGTGGGTCGACCCGGGAATTCCGGACgaggat
ccccATCTACCCGCTTCGCGTCGGCATCCGGTCAGTGGCAGTGAAGGGCGAACAGTTCCTGATT
AACCACAAACCGTTCTACTTTACTGGCTTTGGTCGTCATGAAGATGCGGACTTGCGTGGCAAAG
GATTCGATAACGTGCTGATGGTGCACGACCACGCATTAATGGACTGGATTGGGGCCAACTCCTA
CCGTACCTCGCATTACCCTTACGCTGAAGAGATGCTCGACTGGGCAGATGAACATGGCATCGTG
GTGATTGATGAAACTGCTGCTGTCGGCTTTTCGCTCTCTTTAGGCATTGGTTTCGAAGCGGGCA
ACAAGCCGAAAGAACTGTACAGCGAAGAGGCAGTCAACGGGGAAACTCAGCAAGCGCACTTACA
GGCGATTAAAGAGCTGATAGCGCGTGACAAAAACCACCCAAGCGTGGTGATGTGGAGTATTGCC
AACGAACCGGATACCCGTCCGCAAGGTGCACGGGAATATTTCGCGCCACTGGCGGAAGCAACGC
GTAAACTCGACCCGACGCGTCCGATCACCTGCGTCAATGTAATGTTCTGCGACGCTCACACCGA
TACCATCAGCGATCTCTTTGATGTGCTGTGCCTGAACCGTTATTACGGATGGTATGTCCAAAGC
GGCGATTTGGAAACGGCAGAGAAGGTACTGGAAAAAGAACTTCTGGCCTGGCAGGAGAAACTGT
ACACCGACATGTGGAGTGAAGAGTATCAGTGTGCATGGCTGGATATGTATCACCGCGTCTTTGA
TCGCGTCAGCGCCGTCGTCGGTGAACAGGTATGGAATTTCGCCGATTTTGCGACCTCGCAAGGC
ATATTGCGCGTTGGCGGTAACAAGAAAGGGATCTTCACTCGCGACCGCAAACCGAAGTCGGCGG
CTTTTCTGCTGCAAAAACGCTGGACTGGCATGAACTTCGGTGAAAAACCGCAGCAGGGAGGCAA
ACAATGAATCAACAACTCTCCTGGCGCACCATCGTCGGCTACAGCCTCGGGAATTGCTACCGAG
CTCgtccggaattcccgggtcgacccacgcgtccgggagattcagcgagataagcaattggatt
atctgatgaaaggcttaaggcagcttggtccgcagttttcttccttagatgctaatcgaccttg
gctttgttactggattcttcattcaatagctttgcttggggagactgtggatgatgaattagaa
agcaatgccattgacttccttggacgctgccagggctctgaaggtggatacggtggtggtcctg
gccaacttccacatcttgcaactacttatgctgcagtgaatgcacttgttactttaggaggtga
caaagccctttcttcaattaatagagaaaaaatgtcttgttttttaagacggatgaaggataca
agtggaggtttcaggatgcatgatatgggagaaatggatgttcgtgcatgctacactgcaattt
cggttgcaagcatcctaaatattatggatgatgaactcacccagggcctaggagctcgaatttc
cccgatcgttcaaacatttggcaataaagtttcttaagattgaatcctgttgccggtcttgcga -continued tgattatcatataatttctgttgaattacgttaagcatgtaataattaacatgtaatgcatgac gttatttatgagatgggtttttatgattagagtcccgcaattatacatttaatacgcgatagaa aacaaaatatagcgcgcaaactaggataaattatcgcgcgcggtgtcatctatgttactagatc gggaattcactggccgtcgttttacaacgtcgtgactgggaaaaccctggcgttacccaactta atcgccttgcagcacatccccctttcgccagctggcgtaatagcgaagaggcccgcaccgatcg cccttcccaacagttgcgcagcctgaatggcgcccgctcctttcgctttcttcccttcctttct cgccacgttcgccggctttccccgtcaagctctaaatcgggggctccctttagggttccgattt agtgctttacggcacctcgaccccaaaaaacttgatttgggtgatggttcacgtagtgggccat cgccctgatagacggtttttcgccctttgacgttggagtccacgttctttaatagtggactctt gttccaaactggaacaacactcaaccctatctcgggctattcttttgatttataagggattttg ccgatttcggaaccaccatcaaacaggattttcgcctgctggggcaaaccagcgtggaccgctt gctgcaactctctcagggccaggcggtgaagggcaatcagctgttgcccgtctcactggtgaaa agaaaaaccaccccagtacattaaaaacgtccgcaatgtgttattaagttgtctaagcgtcaat tt*gtttacaccacaatatatcctgcca*

(Underline: 35S promoter; Bold uppercase: antisense AtFTB; Lower case Bold: sense AtFTB)

SEQ ID NO: 57

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg -continued tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcaggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacatttttcttctattttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaatttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaggatc
ctcCTCCTAGGCCCTGGGTGAGTTCATCATCCATAATATTTAGGATGCTTGCAACCGAAATTGC
AGTGTAGCATGCACGAACATCCATTTCTCCCATATCATGCATCCTGAAACCTCCACTTGTATCC
TTCATCCGTCTTAAAAAACAAGACATTTTTTCTCTATTAATTGAAGAAAGGGCTTTGTCACCTC
CTAAAGTAACAAGTGCATTCACTGCAGCATAAGTAGTTGCAAGATGTGGAAGTTGGCCAGGACC
ACCACCGTATCCACCTTCAGAGCCCTGGCAGCGTCCAAGGAAGTCAATGGCATTGCTTTCTAAT
TCATCATCCACAGTCTCCCCAAGCAAAGCTATTGAATGAAGAATCCAGTAACAAAGCCAAGGTC
GATTAGCATCTAAGGAAGAAAACTGCGGACCAAGCTGCCTTAAGCCTTTCATCAGATAATCCAA
TTGCTTATCTCGCTGAATCTCCCGGACGCGTGGGTCGACCCGGGAATTCCGGACgaggatcccc
ATCTACCCGCTTCGCGTCGGCATCCGGTCAGTGGCAGTGAAGGGCGAACAGTTCCTGATTAACC
ACAAACCGTTCTACTTTACTGGCTTTGGTCGTCATGAAGATGCGGACTTGCGTGGCAAAGGATT
CGATAACGTGCTGATGGTGCACGACCACGCATTAATGGACTGGATTGGGGCCAACTCCTACCGT -continued

ACCTCGCATTACCCTTACGCTGAAGAGATGCTCGACTGGGCAGATGAACATGGCATCGTGGTGA

TTGATGAAACTGCTGCTGTCGGCTTTTCGCTCTCTTTAGGCATTGGTTTCGAAGCGGGCAACAA

GCCGAAAGAACTGTACAGCGAAGAGGCAGTCAACGGGGAAACTCAGCAAGCGCACTTACAGGCG

ATTAAAGAGCTGATAGCGCGTGACAAAAACCACCCAAGCGTGGTGATGTGGAGTATTGCCAACG

AACCGGATACCCGTCCGCAAGGTGCACGGGAATATTTCGCGCCACTGGCGGAAGCAACGCGTAA

ACTCGACCCGACGCGTCCGATCACCTGCGTCAATGTAATGTTCTGCGACGCTCACACCGATACC

ATCAGCGATCTCTTTGATGTGCTGTGCCTGAACCGTTATTACGGATGGTATGTCCAAAGCGGCG

ATTTGGAAACGGCAGAGAAGGTACTGGAAAAAGAACTTCTGGCCTGGCAGGAGAAACTGTACAC

CGACATGTGGAGTGAAGAGTATCAGTGTGCATGGCTGGATATGTATCACCGCGTCTTTGATCGC

GTCAGCGCCGTCGTCGGTGAACAGGTATGGAATTTCGCCGATTTTGCGACCTCGCAAGGCATAT

TGCGCGTTGGCGGTAACAAGAAAGGGATCTTCACTCGCGACCGCAAACCGAAGTCGGCGGCTTT

TCTGCTGCAAAAACGCTGGACTGGCATGAACTTCGGTGAAAAACCGCAGCAGGGAGGCAAACAA

TGAATCAACAACTCTCCTGGCGCACCATCGTCGGCTACAGCCTCGGGAATTGCTACCGAGCTCg tccggaattcccgggtcgacccacgcgtccgggagattcagcgagataagcaattggattatct gatgaaaggcttaaggcagcttggtccgcagttttcttccttagatgctaatcgaccttggctt tgttactggattcttcattcaatagctttgcttggggagactgtggatgatgaattagaaagca atgccattgacttccttggacgctgccagggctctgaaggtggatacggtggtggtcctggcca acttccacatcttgcaactacttatgctgcagtgaatgcacttgttactttaggaggtgacaaa gccctttcttcaattaatagagaaaaaatgtcttgtttttttaagacggatgaaggatacaagtg gaggtttcaggatgcatgatatgggagaaatggatgttcgtgcatgctacactgcaatttcggt tgcaagcatcctaaatattatggatgatgaactcacccagggcctaggagctcgaatttccccg atcgttcaaacatttggcaataaagtttcttaagattgaatcctgttgccggtcttgcgatgat tatcatataatttctgttgaattacgttaagcatgtaataattaacatgtaatgcatgacgtta tttatgagatgggtttttatgattagagtcccgcaattatacatttaatacgcgatagaaaaca aaatatagcgcgcaaactaggataaattatcgcgcgcggtgtcatctatgttactagatcggga attcactggccgtcgttttacaacgtcgtgactgggaaaaccctggcgttacccaacttaatcg ccttgcagcacatccccctttcgccagctggcgtaatagcgaagaggcccgcaccgatcgccct tcccaacagttgcgcagcctgaatggcgcccgctcctttcgctttcttcccttcctttctcgcc acgttcgccggctttccccgtcaagctctaaatcgggggctccctttagggttccgatttagtg ctttacggcacctcgaccccaaaaaacttgatttgggtgatggttcacgtagtgggccatcgcc ctgatagacggtttttcgccctttgacgttggagtccacgttctttaatagtggactcttgttc caaactggaacaacactcaaccctatctcgggctattcttttgatttataagggattttgccga tttcggaaccaccatcaaacaggattttcgcctgctggggcaaaccagcgtggaccgcttgctg caactctctcagggccaggcggtgaagggcaatcagctgttgcccgtctcactggtgaaaagaa aaaccaccccagtacattaaaaacgtccgcaatgtgttattaagttgtctaagcgtcaattt*gt*

*ttacaccacaatatatcctgcca*

(Underline: RD29A promoter; Bold uppercase: antisense AtFTB;
Lower case Bold: sense AtFTB)

SEQ ID NO: 58

*gtttacccgccaatatatcctgtc*caaacactgatagtttaaactgaaggcgggaaacgacaatc tgatcatgagcggagaattaagggagtcacgttatgacccccgccgatgacgcgggacaagccg -continued ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc -continued tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccatgccagtagtaacccgcttgattcgtttgaagtgtgtagggctcagacttgaccggag tggactcaatcggcgaatctgtcacggaggacacggggaatcaacgcggcggagagtgatggaa gagctttcaagcctaaccgtgagtcagcgcgagcaatttctggtggagaacgatgtgttcggga tctataattacttcgacgccagcgacgtttctactcaaaaatacatgatggagattcagcgaga taagcaattggattatctgatgaaaggcttaaggcagcttggtccgcagttttcttccttagat gctaatcgaccttggctttgttactggattcttcattcaatagctttgcttggggagactgtgg atgatgaattagaaagcaatgccattgacttccttggacgctgccagggctctgaaggtggata cggtggtggtcctggccaacttccacatcttgcaactacttatgctgcagtgaatgcacttgtt actttaggaggtgacaaagccctttcttcaattaatagagaaaaaatgtcttgtttttttaagac ggatgaaggatacaagtggaggtttcaggatgcatgatatgggagaaatggatgttcgtgcatg ctacactgcaatttcggttgcaagcatcctaaatattatggatgatgaactcacccagggccta ggagattacatcttgagttgccaaacttatgaaggtggcattggaggggaacctggctccgaag ctcacggtgggtatacctactgtggtttggctgctatgattttaatcaatgaggtcgaccgttt gaatttggattcattaatgaattgggctgtacatcgacaaggagtagaaatgggatttcaaggt aggacgaacaaattggtcgatggttgctacacattttggcaggcagccccttgtgttctactac aaagattatattcaaccaatgatcatgacgttcatggatcatcacatatatcagaagggacaaa tgaagaacatcatgctcatgatgaagatgaccttgaagacagtgatgatgatgatgattctgat gaggacaacgatgaagattcagtgaatggtcacagaatccatcatacatccacctacattaaca ggagaatgcaactggtttttgatagcctcggcttgcagagatatgtactcttgtgctctaagat ccctgacggtggattcagagacaagccgaggaaaccccgtgacttctaccacacatgttactgc ctgagcggcttgtctgtggctcagcacgcttggttaaaagacgaggacactcctcctttgactc gcgacattatgggtggctactcgaatctccttgaacctgttcaacttcttcacaacattgtcat ggatcagtataatgaagctatcgagttcttctttaaagcagcatgactcgaatttccccgatcg ttcaaacatttggcaataaagtttcttaagattgaatcctgttgccggtcttgcgatgattatc atataatttctgttgaattacgttaagcatgtaataattaacatgtaatgcatgacgttattta tgagatgggtttttatgattagagtcccgcaattatacatttaatacgcgatagaaaacaaaat atagcgcgcaaactaggataaattatcgcgcgcggtgtcatctatgttactagatcgggaattc actggccgtcgttttacaacgtcgtgactgggaaaaccctggcgttacccaacttaatcgcctt gcagcacatccccctttcgccagctggcgtaatagcgaagaggcccgcaccgatcgcccttccc aacagttgcgcagcctgaatggcgcccgctcctttcgctttcttcccttcctttctcgccacgt tcgccggctttccccgtcaagctctaaatcgggggctccctttagggttccgatttagtgcttt -continued acggcacctcgaccccaaaaaacttgatttgggtgatggttcacgtagtgggccatcgccctga tagacggtttttcgccctttgacgttggagtccacgttctttaatagtggactcttgttccaaa ctggaacaacactcaaccctatctcgggctattcttttgatttataagggattttgccgatttc ggaaccaccatcaaacaggattttcgcctgctggggcaaaccagcgtggaccgcttgctgcaac tctctcagggccaggcggtgaagggcaatcagctgttgcccgtctcactggtgaaaagaaaaac caccccagtacattaaaaacgtccgcaatgtgttattaagttgtctaagcgtcaattt*gtttac*

*accacaatatatcctgcca*

(Underlined: 35S promoter; Bold: Sense AtFTB)

SEQ ID NO: 59

GAATTCAAATTTTTCGCCAGTTCTAAATATCCGGAAACCTCTTGGGATGCCATTGCCCATCTAT

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTCGTGGTGGAGAATCTGGGTGCTTTG

ACCAACTATACTGGCACAATGAGAGTCCACTTAAACAGTAACATGTGTGATAATGATCTCTACG

TTTACCCGGTTTGTCTCTCAGTCCACCCTCTTGCTCCTGTGCACATAAGAGAATATATTGCTGT

AAAGCAATACTGTGAAAAAGTGGTTCTTGTGCTCTCCACTCATTAATAAATTTATAGGCAATAT

TTTTAAAATCAGATGAACTGGATTCACTGGTGCCTTCATGCTCACCACGGCATGTTGCATGACT

AGAGGTTCCATCCAAACTTTCTTTTGCTTCAGATACATAAGATACCGCAAAAATCTGTGATGTC

TCTTCCATCTGTTTGTTGATAATAGAAGATAATCTTTGCAATAGAGCAACAGCACCTCCCTGCC

AAAAGGAATAGCATCCATCCACCAGTTTATTTGTTCTCCCCTGGAATCCACATTCCTTACCTTG

TCGGAATACCACCCAGTCAACTAATCGAGGCAGATCCAAGTGATTAACCTCACCAATCAGAATC

ATTGTAGCTAATCCACAAAAGGTGTACCCACCATGAGCCTCAGAACCAGGCTCACCAGCAATGC

CACCCTCATATGTTTGACAGCTTATAATGTAGTCTCCAACATTCTGGATCAGCTCATCATCCAA

AATGTTCAAAACACTTGCAACAGAAATGGCAGTGTAGCAAGCTCGAACATCAATTTCACCTTCA

TCATGCATCCTGAATCCACCATTTGGTTGCTTCATCCGCCGCAGAAACCCATACAGTTTATCTC

TATTAATTGATGCCAGGGATTTCTCACCACCCAAAGTAATAAGTGAATTAACAGCAGCATAAGT

TGTGGCAATATGAGGCATCTGGCCTGGTCCCCCGGCATATCCACCATTCGGATCCTGGCAACGG

TTAAGAAAATCGATAGCGTTATCTTCGAGTTCATCATCGACGGATTCTCCCAACAAAGCAATGG

AGTGGAAGATCCAGTAGCAGAGCCAGGGTCGATTAGCGTCCAAAACGGAAAATGCGGAACTGAG

ATGGCGAAGGCCTTTGGAGACATACTGCATGTGATTATCGCGTTGAAGCTCCAACATGAGGGTT

TGGGCGTTGCGAGGAATGGTGGCgagctcgaatttccccgatcgttcaaacatttggcaataaa gtttcttaagattgaatcctgttgccggtcttgcgatgattatcatataatttctgttgaatta cgttaagcatgtaataattaacatgtaatgcatgacgttatttatgagatgggtttttatgatt agagtcccgcaattatacatttaatacgcgatagaaaacaaaatatagcgcgcaaactaggata aattatcgcgcgcggtgtcatctatgttactagatcgggaattc (Upper Case: MuA Promoter; Underlined: Antisense GmFTB; Lowercase: NOS terminater)

SEQ ID NO: 60

GGAGCCATAGATGCAATTCAATCAAACTGAAATTTCTGCAAGAATCTCAAACACGGAGATCTCA

AAGTTTGAAAGAAAATTTATTTCTTCGACTCAAAACAAACTTACGAAATTTAGGTAGAACTTAT

-continued

ATACATTATATTGTAATTTTTTGTAACAAAATGTTTTTATTATTATTATAGAATTTTACTGGTT

AAATTAAAAATGAATAGAAAAGGTGAATTAAGAGGAGAGAGGAGGTAAACATTTTCTTCTATTT

TTTCATATTTTCAGGATAAATTATTGTAAAAGTTTACAAGATTTCCATTTGACTAGTGTAAATG

AGGAATATTCTCTAGTAAGATCATTATTTCATCTACTTCTTTTATCTTCTACCAGTAGAGGAAT

AAACAATATTTAGCTCCTTTGTAAATACAAATTAATTTTCCTTCTTGACATCATTCAATTTTAA

TTTTACGTATAAAATAAAAGATCATACCTATTAGAACGATTAAGGAGAAATACAATTCGAATGA

GAAGGATGTGCCGTTTGTTATAATAAACAGCCACACGACGTAAACGTAAAATGACCACATGATG

GGCCAATAGACATGGACCGACTACTAATAATAGTAAGTTACATTTTAGGATGGAATAAATATCA

TACCGACATCAGTTTTGAAAGAAAAGGGAAAAAAAGAAAAAATAAATAAAAGATATACTACCGA

CATGAGTTCCAAAAAGCAAAAAAAAAGATCAAGCCGACACAGACACGCGTAGAGAGCAAAATGA

CTTTGACGTCACACCACGAAAACAGACGCTTCATACGTGTCCCTTTATCTCTCTCAGTCTCTCT

ATAAACTTAGTGAGACCCTCCTCTGTTTTACTCACAAATATGCAAACTAGAAAACAATCATCAG

GAATAAAGGGTTTGATTACTTCTATTGGAAAGGTGGTGGAGAATCTGGGTGCTTTGACCAACTA

TACTGGCACAATGAGAGTCCACTTAAACAGTAACATGTGTGATAATGATCTCTACGTTTACCCG

GTTTGTCTCTCAGTCCACCCTCTTGCTCCTGTGCACATAAGAGAATATATTGCTGTAAAGCAAT

ACTGTGAAAAAGTGGTTCTTGTGCTCTCCACTCATTAATAAATTTATAGGCAATATTTTTAAAA

TCAGATGAACTGGATTCACTGGTGCCTTCATGCTCACCACGGCATGTTGCATGACTAGAGGTTC

CATCCAAACTTTCTTTTGCTTCAGATACATAAGATACCGCAAAAATCTGTGATGTCTCTTCCAT

CTGTTTGTTGATAATAGAAGATAATCTTTGCAATAGAGCAACAGCACCTCCCTGCCAAAAGGAA

TAGCATCCATCCACCAGTTTATTTGTTCTCCCCTGGAATCCACATTCCTTACCTTGTCGGAATA

CCACCCAGTCAACTAATCGAGGCAGATCCAAGTGATTAACCTCACCAATCAGAATCATTGTAGC

TAATCCACAAAAGGTGTACCCACCATGAGCCTCAGAACCAGGCTCACCAGCAATGCCACCCTCA

TATGTTTGACAGCTTATAATGTAGTCTCCAACATTCTGGATCAGCTCATCATCCAAAATGTTCA

AAACACTTGCAACAGAAATGGCAGTGTAGCAAGCTCGAACATCAATTTCACCTTCATCATGCAT

CCTGAATCCACCATTTGGTTGCTTCATCCGCCGCAGAAACCCATACAGTTTATCTCTATTAATT

GATGCCAGGGATTTCTCACCACCCAAAGTAATAAGTGAATTAACAGCAGCATAAGTTGTGGCAA

TATGAGGCATCTGGCCTGGTCCCCCGGCATATCCACCATTCGGATCCTGGCAACGGTTAAGAAA

ATCGATAGCGTTATCTTCGAGTTCATCATCGACGGATTCTCCCAACAAAGCAATGGAGTGGAAG

ATCCAGTAGCAGAGCCAGGGTCGATTAGCGTCCAAAACGGAAAATGCGGAACTGAGATGGCGAA

GGCCTTTGGAGACATACTGCATGTGATTATCGCGTTGAAGCTCCAACATGAGGGTTTGGGCGTT

GCGAGGAATGGTGGCgagctcgaatttccccgatcgttcaaacatttggcaataaagtttctta agattgaatcctgttgccggtcttgcgatgattatcatataatttctgttgaattacgttaagc atgtaataattaacatgtaatgcatgacgttatttatgagatgggtttttatgattagagtccc gcaattatacatttaatacgcgatagaaaacaaaatatagcgcgcaaactaggataaattatcg cgcgcggtgtcatctatgttactagatcgggaattc (Upper Case: RD29A Promoter; Underlined: Antisense GmFTB; Lower case: NOS) terminater

SEQ ID NO: 61

GAATTCAAATTTTTCGCCAGTTCTAAATATCCGGAAACCTCTTGGGATGCCATTGCCCATCTAT

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

-continued

TATCTCCATTGACGTAAGGGATGACGCACAATCCAACTATCCATCGCAAGACCATTGCTCTATA

TAAGAAAGTTAATATCATTTCGAGTGGCCACGCTGAGCTCGTGGTGGAGAATCTGGGTGCTTTG

ACCAACTATACTGGCACAATGAGAGTCCACTTAAACAGTAACATGTGTGATAATGATCTCTACG

TTTACCCGGTTTGTCTCTCAGTCCACCCTCTTGCTCCTGTGCACATAAGAGAATATATTGCTGT

AAAGCAATACTGTGAAAAAGTGGTTCTTGTGCTCTCCACTCATTAATAAATTTATAGGCAATAT

TTTTAAAATCAGATGAACTGGATTCACTGGTGCCTTCATGCTCACCACGGCATGTTGCATGACT

AGAGGTTCCATCCAAACTTTCTTTTGCTTCAGATACATAAGATACCGCAAAAATCTGTGATGTC

TCTTCCATCTGTTTGTTGATAATAGAAGATAATCTTTGCAATAGAGCAACAGCACCTCCCTGCC

AAAAGGAATAGCATCCATCCACCAGTTTATTTGTTCTCCCCTGGAATCCACATTCCTTACCTTG

TCGGAATACCACCCAGTCAACTAATCGAGGCAGATCCAAGTGATTAACCTCACCAATCAGAATC

ATTGTAGCTAATCCACAAAAGGTGTACCCACCATGAGCCTCAGAACCAGGCTCACCAGCAATGC

CACCCTCATATGTTTGACAGCTTATAATGTAGTCTCCAACATTCTGGATCAGCTCATCATCCAA

AATGTTCAAAACACTTGCAACAGAAATGGCAGTGTAGCAAGCTCGAACATCAATTTCACCTTCA

TCATGCATCCTGAATCCACCATTTGGTTGCTTCATCCGCCGCAGAAACCCATACAGTTTATCTC

TATTAATTGATGCCAGGGATTTCTCACCACCCAAAGTAATAAGTGAATTAACAGCAGCATAAGT

TGTGGCAATATGAGGCATCTGGCCTGGTCCCCCGGCATATCCACCATTCGGATCCTGGCAACGG

TTAAGAAAATCGATAGCGTTATCTTCGAGTTCATCATCGACGGATTCTCCCAACAAAGCAATGG

AGTGGAAGATCCAGTAGCAGAGCCAGGGTCGATTAGCGTCCAAAACGGAAAATGCGGAACTGAG

ATGGCGAAGGCCTTTGGAGACATACTGCATGTGATTATCGCGTTGAAGCTCCAACATGAGGGTT

TGGGCGTTGCGAGGAATGGTGGCGGTGAGGTTAATCACTTGGATCTGCCTCGATTAGTTGACTG

GGTGGTATTCCGACAAGGTAAGGAATGTGGATTCCAGGGGAGAACAAATAAACTGGTGGATGGA

TGCTATTCCTTTTGGCAGGGAGGTGCTGTTGCTCTATTGCAAAGATTATCTTCTATTATCAACA

AACAGATGGAAGAGACATCACAGATTTTTGCGGTATCTTATGTATCTGAAGCAAAAGAAAGTTT

GGATGGAACCTCTAGTCATGCAACATGCCGTGGTGAGCATGAAGGCACCAGTGAATCCAGTTCA

TCTGATTTTAAAAATATTGCCTATAAATTTATTAATGAGTGGAGAGCACAAGAACCACTTTTTC

ACAGTATTGCTTTACAGCAATATATTCTCTTATGTGCACAGGAGCAAGAGGGTGGACTGAGAGA

CAAACCGGGTAAACGTAGAGATCATTATCACACATGTTACTGTTTAAGTGGACTCTCATTGTGC

CAGTATAGTTGGTCAAAGCACCCAGATTCTCCACCACgagctcgaatttccccgatcgttcaaa catttggcaataaagtttcttaagattgaatcctgttgccggtcttgcgatgattatcatataa tttctgttgaattacgttaagcatgtaataattaacatgtaatgcatgacgttatttatgagat gggtttttatgattagagtcccgcaattatacatttaatacgcgatagaaaacaaaatatagcg cgcaaactaggataaattatcgcgcgcggtgtcatctatgttactagatcgggaattc (Upper Case: MuA Promoter; Underlined: Antisense GmFTB; Bold: Sense GmFTB; Lower case: NOS terminater)

SEQ ID NO: 62

GGAGCCATAGATGCAATTCAATCAAACTGAAATTTCTGCAAGAATCTCAAACACGGAGATCTCA

AAGTTTGAAAGAAAATTTATTTCTTCGACTCAAAACAAACTTACGAAATTTAGGTAGAACTTAT

ATACATTATATTGTAATTTTTTGTAACAAAATGTTTTTATTATTATTATAGAATTTTACTGGTT

AAATTAAAAATGAATAGAAAAGGTGAATTAAGAGGAGAGAGGAGGTAAACATTTTCTTCTATTT

TTTCATATTTTCAGGATAAATTATTGTAAAAGTTTACAAGATTTCCATTTGACTAGTGTAAATG

AGGAATATTCTCTAGTAAGATCATTATTTCATCTACTTCTTTTATCTTCTACCAGTAGAGGAAT

-continued

AAACAATATTTAGCTCCTTTGTAAATACAAATTAATTTTCCTTCTTGACATCATTCAATTTTAA
TTTTACGTATAAAATAAAAGATCATACCTATTAGAACGATTAAGGAGAAATACAATTCGAATGA
GAAGGATGTGCCGTTTGTTATAATAAACAGCCACACGACGTAAACGTAAAATGACCACATGATG
GGCCAATAGACATGGACCGACTACTAATAATAGTAAGTTACATTTTAGGATGGAATAAATATCA
TACCGACATCAGTTTTGAAAGAAAAGGGAAAAAAAGAAAAAATAAATAAAAGATATACTACCGA
CATGAGTTCCAAAAAGCAAAAAAAAAGATCAAGCCGACACAGACACGCGTAGAGAGCAAAATGA
CTTTGACGTCACACCACGAAAACAGACGCTTCATACGTGTCCCTTTATCTCTCTCAGTCTCTCT
ATAAACTTAGTGAGACCCTCCTCTGTTTTACTCACAAATATGCAAACTAGAAAACAATCATCAG
GAATAAAGGGTTTGATTACTTCTATTGGAAAGGTGGTGGAGAATCTGGGTGCTTTGACCAACTA
TACTGGCACAATGAGAGTCCACTTAAACAGTAACATGTGTGATAATGATCTCTACGTTTACCCG
GTTTGTCTCTCAGTCCACCCTCTTGCTCCTGTGCACATAAGAGAATATATTGCTGTAAAGCAAT
ACTGTGAAAAAGTGGTTCTTGTGCTCTCCACTCATTAATAAATTTATAGGCAATATTTTTAAAA
TCAGATGAACTGGATTCACTGGTGCCTTCATGCTCACCACGGCATGTTGCATGACTAGAGGTTC
CATCCAAACTTTCTTTTGCTTCAGATACATAAGATACCGCAAAAATCTGTGATGTCTCTTCCAT
CTGTTTGTTGATAATAGAAGATAATCTTTGCAATAGAGCAACAGCACCTCCCTGCCAAAAGGAA
TAGCATCCATCCACCAGTTTATTTGTTCTCCCCTGGAATCCACATTCCTTACCTTGTCGGAATA
CCACCCAGTCAACTAATCGAGGCAGATCCAAGTGATTAACCTCACCAATCAGAATCATTGTAGC
TAATCCACAAAAGGTGTACCCACCATGAGCCTCAGAACCAGGCTCACCAGCAATGCCACCCTCA
TATGTTTGACAGCTTATAATGTAGTCTCCAACATTCTGGATCAGCTCATCATCCAAAATGTTCA
AAACACTTGCAACAGAAATGGCAGTGTAGCAAGCTCGAACATCAATTTCACCTTCATCATGCAT
CCTGAATCCACCATTTGGTTGCTTCATCCGCCGCAGAAACCCATACAGTTTATCTCTATTAATT
GATGCCAGGGATTTCTCACCACCCAAAGTAATAAGTGAATTAACAGCAGCATAAGTTGTGGCAA
TATGAGGCATCTGGCCTGGTCCCCCGGCATATCCACCATTCGGATCCTGGCAACGGTTAAGAAA
ATCGATAGCGTTATCTTCGAGTTCATCATCGACGGATTCTCCCAACAAAGCAATGGAGTGGAAG
ATCCAGTAGCAGAGCCAGGGTCGATTAGCGTCCAAAACGGAAAATGCGGAACTGAGATGGCGAA
GGCCTTTGGAGACATACTGCATGTGATTATCGCGTTGAAGCTCCAACATGAGGGTTTGGGCGTT
GCGAGGAATGGTGGCGGTGAGGTTAATCACTTGGATCTGCCTCGATTAGTTGACTGGGTGGTAT
TCCGACAAGGTAAGGAATGTGGATTCCAGGGGAGAACAAATAAACTGGTGGATGGATGCTATTC
CTTTTGGCAGGGAGGTGCTGTTGCTCTATTGCAAAGATTATCTTCTATTATCAACAAACAGATG
GAAGAGACATCACAGATTTTTGCGGTATCTTATGTATCTGAAGCAAAAGAAAGTTTGGATGGAA
CCTCTAGTCATGCAACATGCCGTGGTGAGCATGAAGGCACCAGTGAATCCAGTTCATCTGATTT
TAAAAATATTGCCTATAAATTTATTAATGAGTGGAGAGCACAAGAACCACTTTTTCACAGTATT
GCTTTACAGCAATATATTCTCTTATGTGCACAGGAGCAAGAGGGTGGACTGAGAGACAAACCGG
GTAAACGTAGAGATCATTATCACACATGTTACTGTTTAAGTGGACTCTCATTGTGCCAGTATAG
TTGGTCAAAGCACCCAGATTCTCCACCACgagctcgaatttccccgatcgttcaaacatttggc
aataaagtttcttaagattgaatcctgttgccggtcttgcgatgattatcatataatttctgtt
gaattacgttaagcatgtaataattaacatgtaatgcatgacgttatttatgagatgggttttt
atgattagagtcccgcaattatacatttaatacgcgatagaaaacaaaatatagcgcgcaaact
aggataaattatcgcgcgcggtgtcatctatgttactagatcgggaattc (Upper Case: RD29A Promoter; Underlined: Antisense GmFTB; Bold: Sense GmFTB; Lower case: NOS terminater)

SEQ ID NO: 63

GAATTCAAATTTTTCGCCAGTTCTAAATATCCGGAAACCTCTTGGGATGCCATTGCCCATCTAT

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTC<u>GGATGGATTGGCTCCAGCAAATTA</u>

<u>GAGTACGGTCCAAGCACATGCTGAGGTAATGGGCACGAACCAGTATCAGTCATGGCACTGTACT</u>

<u>GGCTAACTGCGAGGCCACTGAGGCAGTAGCATGAATGATAGTGATCTCTGTTCTTTCCAGGCTT</u>

<u>ATCCCTCAAGCCTCCCTCTAGTACCTGAGAACAAAGTAGGATGTATTGTTGCAGGGCAATGTTA</u>

<u>TGGAAGAGTGGGCCAATTTGGTTGCTCTGTTGTATAAAATCAAATCCAAACTTCGCATAGTCCA</u>

<u>CAGCAGAGGAAGACTTATTCGCGGTGCACCCATATGAACTGGTGCTGCAGGCATCCTCTCCTGA</u>

<u>TGGCCTTTTGCAGGAATACGAGGACCTCAATTGCTTATCAACAATCGTAATTAACTTTTGTGTG</u>

<u>AAAGCAATGGCAGCTCCCTGCCAAAAGGAGTAGCAACCATCAACCAATTTATTAGTTCGTCCTT</u>

<u>GAAATCCGCATTCCACTCCTTGACGAAAAGCCACCCAGCCAATCAAACTAGGCAAGTCAACTTT</u>

<u>CTCTGCCTCATTAAGCAGGATCAAAGCAGCCAATCCACAGAATGTATACCCACCATGTGCTTCA</u>

<u>GCATAAGGCTCCCCAGCAATACCACCTTCATAAGTTTGACATCTTGCTATGTAGTCGCCTACAC</u>

<u>CTTTTGCCAGTTTAAAATCAAGAATATTCACAAGGCTGGCAACCGATATAGCGGTGTAGGAAGC</u>

<u>ACGGACATCAATTTCGCCACCATCATGCATTCTGAAAGCACCTGATACATCTTTCATCTGCAGC</u>

<u>ATAAAATTGTACAGGTTGCCCCTATTGATTGATGACAATGCTCTTTCGCTCCCTATTGTCACAA</u>

<u>GTGTATTTACAGCAGCATAAGTCGTAGCTAGGTGAGGCAACTGTCCAGGTCCACCACTATATCC</u>

<u>ACCATCTTTATCCTGACATCGAGCTAAGAAGTCTATGATATCATTCTCAAGATCATCATCAAGT</u>

<u>GCTTCATCCAGCAAAGCAAGTGGATGAACCATCCAGTAGCATAGCCAAGGGCGATTGGCATCTA</u>

<u>GAACATGAAAGGCTGGTCCCATATGCCTCAGCCCAGGCGTCAGATACTCGATATGCTGATCACG</u>

<u>CCACAGCTCTAGCATGATGGATTTCGTGTTGGGCGCGGCCCCGAAGAGGGAGCGGTAGATGTCG</u>

<u>CCAACCCTGGCCTCCACCTTCATCTGCTCCACCTGCGTCACCGTGAGCCTCGGTAGGTCGGGAT</u>

<u>CCGCC</u>gagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattc (Upper Case: MuA Promoter; Underlined: Antisense Zea maize-FTB; Lowercase: NOS terminator)

SEQ ID NO: 64

GAATTCAAATTTTTCGCCAGTTCTAAATATCCGGAAACCTCTTGGGATGCCATTGCCCATCTAT

CTGTAATTTATTGACGAAATAGACGAAAAGGAAGGTGGCTCCTATAAAGCACATCATTGCGATA

ACAGAAAGGCCATTGTTGAAGATACCTCTGCTGACATTGGTCCCCAAGTGGAAGCACCACCCCA

TGAGGAGCACCGTGGAGTAAGAAGACGTTCGAGCCACGTCGAAAAAGCAAGTGTGTTGATGTAG

TATCTCCATTGACGTAAGGGATGACGCACAATCCAACTATCCATCGCAAGACCATTGCTCTATA

TAAGAAAGTTAATATCATTTCGAGTGGCCACGCTGAGCTC<u>GGATGGATTGGCTCCAGCAAATTA</u>

-continued

GAGTACGGTCCAAGCACATGCTGAGGTAATGGGCACGAACCAGTATCAGTCATGGCACTGTACT
GGCTAACTGCGAGGCCACTGAGGCAGTAGCATGAATGATAGTGATCTCTGTTCTTTCCAGGCTT
ATCCCTCAAGCCTCCCTCTAGTACCTGAGAACAAAGTAGGATGTATTGTTGCAGGGCAATGTTA
TGGAAGAGTGGGCCAATTTGGTTGCTCTGTTGTATAAAATCAAATCCAAACTTCGCATAGTCCA
CAGCAGAGGAAGACTTATTCGCGGTGCACCCATATGAACTGGTGCTGCAGGCATCCTCTCCTGA
TGGCCTTTTGCAGGAATACGAGGACCTCAATTGCTTATCAACAATCGTAATTAACTTTTGTGTG
AAAGCAATGGCAGCTCCCTGCCAAAAGGAGTAGCAACCATCAACCAATTTATTAGTTCGTCCTT
GAAATCCGCATTCCACTCCTTGACGAAAAGCCACCCAGCCAATCAAACTAGGCAAGTCAACTTT
CTCTGCCTCATTAAGCAGGATCAAAGCAGCCAATCCACAGAATGTATACCCACCATGTGCTTCA
GCATAAGGCTCCCCAGCAATACCACCTTCATAAGTTTGACATCTTGCTATGTAGTCGCCTACAC
CTTTTGCCAGTTTAAAATCAAGAATATTCACAAGGCTGGCAACCGATATAGCGGTGTAGGAAGC
ACGGACATCAATTTCGCCACCATCATGCATTCTGAAAGCACCTGATACATCTTTCATCTGCAGC
ATAAAATTGTACAGGTTGCCCCTATTGATTGATGACAATGCTCTTTCGCTCCCTATTGTCACAA
GTGTATTTACAGCAGCATAAGTCGTAGCTAGGTGAGGCAACTGTCCAGGTCCACCACTATATCC
ACCATCTTTATCCTGACATCGAGCTAAGAAGTCTATGATATCATTCTCAAGATCATCATCAAGT
GCTTCATCCAGCAAAGCAAGTGGATGAACCATCCAGTAGCATAGCCAAGGGCGATTGGCATCTA
GAACATGAAAGGCTGGTCCCATATGCCTCAGCCCAGGCGTCAGATACTCGATATGCTGATCACG
CCACAGCTCTAGCATGATGGATTTCGTGTTGGGCGCGGCCCCGAAGAGGGAGCGGTAGATGTCG
CCAACCCTGGCCTCCACCTTCATCTGCTCCACCTGCGTCACCGTGAGCCTCGGTAGGTCGGGAT
CCGCCggatccGCTGGGGAGCCTTATGCTGAAGCACATGGTGGGTATACATTCTGTGGATTGGC
TGCTTTGATCCTGCTTAATGAGGCAGAGAAAGTTGACTTGCCTAGTTTGATTGGCTGGGTGGCT
TTTCGTCAAGGAGTGGAATGCGGATTTCAAGGACGAACTAATAAATTGGTTGATGGTTGCTACT
CCTTTTGGCAGGGAGCTGCCATTGCTTTCACACAAAAGTTAATTACGATTGTTGATAAGCAATT
GAGGTCCTCGTATTCCTGCAAAAGGCCATCAGGAGAGGATGCCTGCAGCACCAGTTCATATGGG
TGCACCGCGAATAAGTCTTCCTCTGCTGTGGACTATGCGAAGTTTGGATTTGATTTTATACAAC
AGAGCAACCAAATTGGCCCACTCTTCCATAACATTGCCCTGCAACAATACATCCTACTTTGTTC
TCAGGTACTAGAGGGAGGCTTGAGGGATAAGCCTGGAAAGAACAGAGATCACTATCATTCATGC
TACTGCCTCAGTGGCCTCGCAGTTAGCCAGTACAGTGCCATGACTGATACTGGTTCGTGCCCAT
TACCTCAGCATGTGCTTGGACCGTACTCTAATTTGCTGGAGCCAATCCATCCaagcttgaattt
ccccgatcgttcaaacatttggcaataaagtttcttaagattgaatcctgttgccggtcttgcg
atgattatcatataatttctgttgaattacgttaagcatgtaataattaacatgtaatgcatga
cgttatttatgagatgggtttttatgattagagtcccgcaattatacatttaatacgcgataga
aaacaaaatatagcgcgcaaactaggataaattatcgcgcgcggtgtcatctatgttactagat
cggaagctt (Upper Case: MuA Promoter; Underlined: Antisense *Zea* maize-FTB; Bold: Sense *Zea* maize-FTB; Lower case: NOS terminater)

Example 15

PCR Analysis of Putative Transgenic Plants

To verify that the putative transgenic plants carried the gene of interest PCR analysis was performed. Genomic DNA was isolated and PCR run according to standard protocols and conditions which are known to one of skill in the art. A typical reaction was performed in a volume of 25 μl and primer pairs used were dependent on the gene and promoter combination of the particular construct (Table 12).

Figure 24:
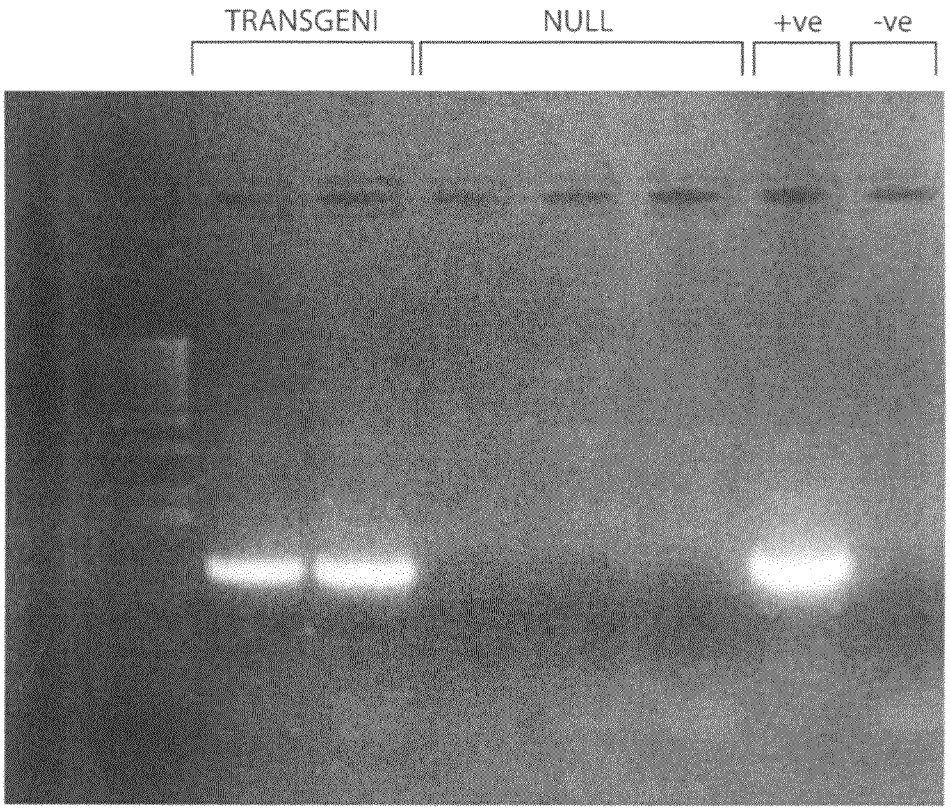
FIG. 24 is a representative illustration of gel electrophoresis analysis of PCR products in an assay to detect transgenic lines of *Brassica napus*.

Putative transgenic *Brassica napus* plants were screened using the primer combinations detailed in the table below. A representative gel showing PCR analysis results is shown in FIG. 24 which represents transgenic plants carrying the pRD29A-anti-FTA construct. Transformants were confirmed in an analogous manner for each species and construct transformation done.

TABLE 12

| Construct Name | Primer Name | Primer Sequence (5'-3') |
|---|---|---|
| 35S-antiFTA | SEQ ID NO: 16 | GCCGACAGTGGTCCCAAAGATGG |
| | SEQ ID NO: 17 | AAAGGATCCTCAAATTGCTGCCA CTGTAAT |
| rd29A-antiFTA | SEQ ID NO: 18 | AAACCCGGGATGAATTTCGACG AGAACGTG |
| | SEQ ID NO: 19 | GCAAGACCGGCAACAGGA |
| rd29B-antiFTA | SEQ ID NO: 20 | TTTAAGCTTGACAGAAACAGT CAGCGAGAC |
| | SEQ ID NO: 17 | AAACCCGGGATGAATTTCGACG AGAACGTG |
| 35S-DA-FTA | SEQ ID NO: 21 | GCTCTTCCTCCATGCCCA |
| | SEQ ID NO: 19 | GCAAGACCGGCAACAGGA |
| rd29A-DA-FTA | SEQ ID NO: 22 | TTTAAGCTTGGAGCCATAGA TGCAATTCAA |
| | SEQ ID NO: 23 | CGGGCATTAGGAGGATGGGAA |
| 35S-HP-FTB | SEQ ID NO: 16 | GCCGACAGTGGTCCCAAAGATGG |
| | SEQ ID NO: 24 | GTCCGGAATTCCCGGGTC |
| rd29A-HP-FTB | SEQ ID NO: 22 | TTTAAGCTTGGAGCCATAG ATGCAATTCAA |
| | SEQ ID NO: 24 | GTCCGGAATTCCCGGGTC |

Example 16

Southern Analysis

Figure 11:
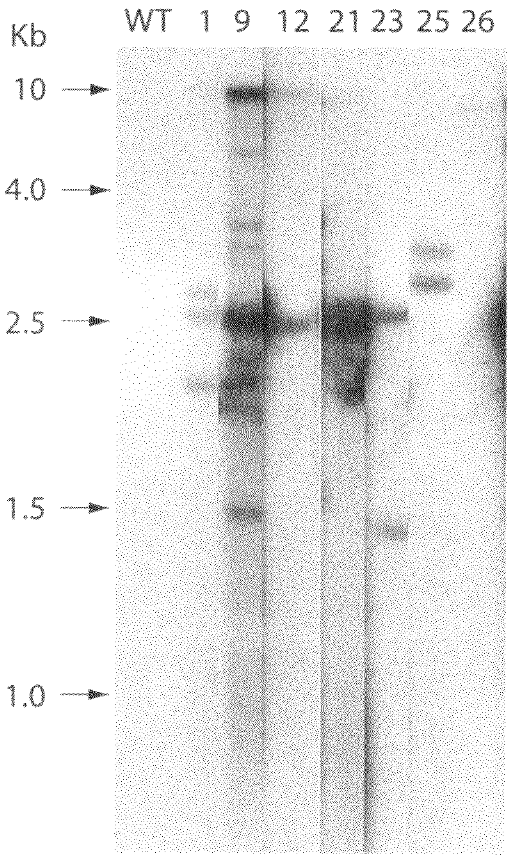
FIG. 11 is an illustration of genomic Southern hybridization analysis of anti-FTA transgenic *Arabidopsis thaliana*.

Genomic Southern analysis of anti-FTA transgenic *Arabidopsis thaliana*. The numbers indicate the line numbers. Five micrograms of genomic DNA of T1 plants was digested with HindIII (a unique site in the T-DNA plasmid) and separated in a 0.8% agarose gel. The NPTII coding region was used as the probe for radio-labeling. FIG. 11 shows a typical result from Southern analysis indicating the presence of the transgene.

Example 17

Northern Blots of Antisense FTA Lines

Figure 12:
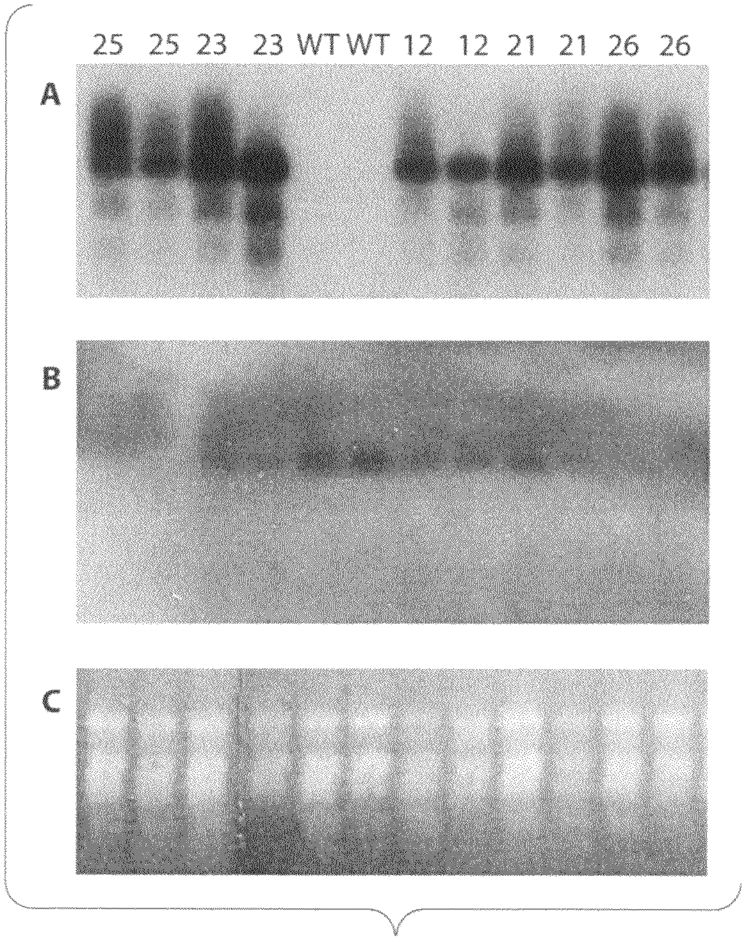
FIG. 12 is an illustration of Northern analysis of five 35S-anti-FTA *Arabidopsis thaliana* lines (T3 plants).

RNA was isolated from developing leaf tissue of five 35S-anti-FTA *Arabidopsis thaliana* lines (T3 plants). The blot was first probed with $P^{32}$ labeled, single-stranded sense transcript of FTA (FIG. 3 panel A) which detects antisense transcript, then stripped and re-probed with the single-stranded anti-sense transcript of FTA (FIG. 12 panel B) that detects the sense transcript. FIG. 3 panel C shows the ethidium bromide stained gel for the blot. Approximately 5 μg of total RNA was loaded into each lane. FIG. 3 indicates the accumulation of the transgene anti-sense transcript and a reduction in the sense transcript in transgenic plants.

Example 18

Western Blot Antisense FTA Lines with Anti-FT-1 Antibodies

Figure 13:
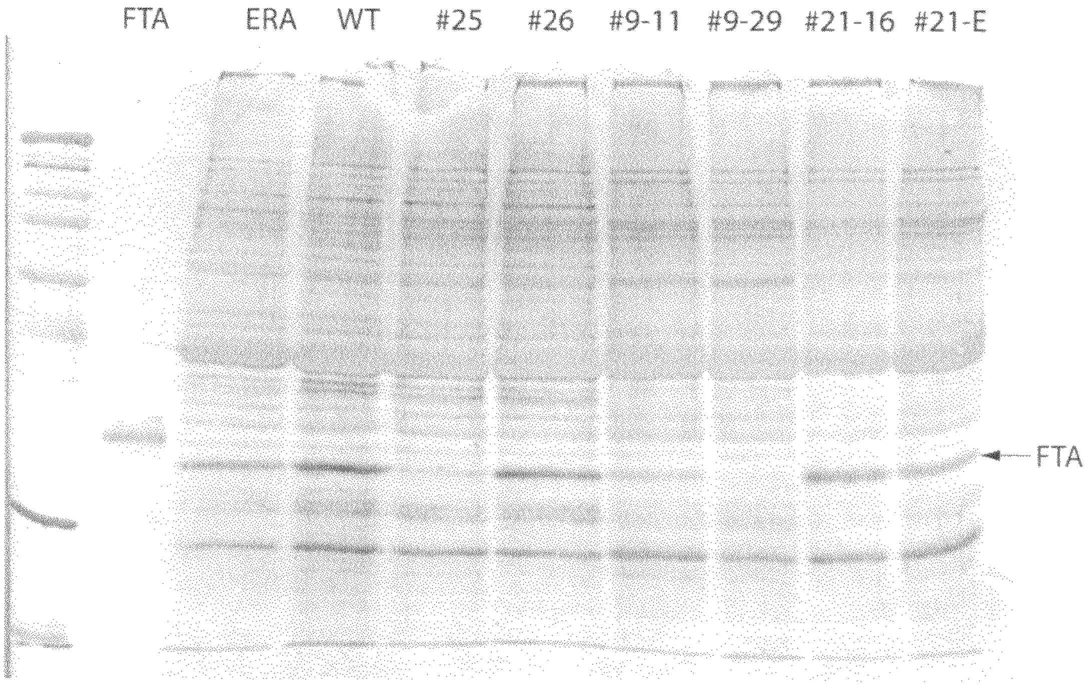
FIG. 13 shows a Western expression analysis using anti-FTA antibodies to detect the FTA polypeptides.

The antibodies produced according to the methods of Example 27 were used to analyze protein extracts from transgenic plants on western blots. Lane 1 of FIG. 13 is a molecular weight standard, lane 2 purified FTA protein, lanes 3-10 are protein extracts from the ERA1 mutant, wild type, and 4 lines of transgenic *Arabidopsis thaliana*. FIG. 13 illustrates the reduction of detectable FTA protein in transgenic lines.

Example 19

ABA Sensitivity of Transgenic Seedlings

Figure 14:
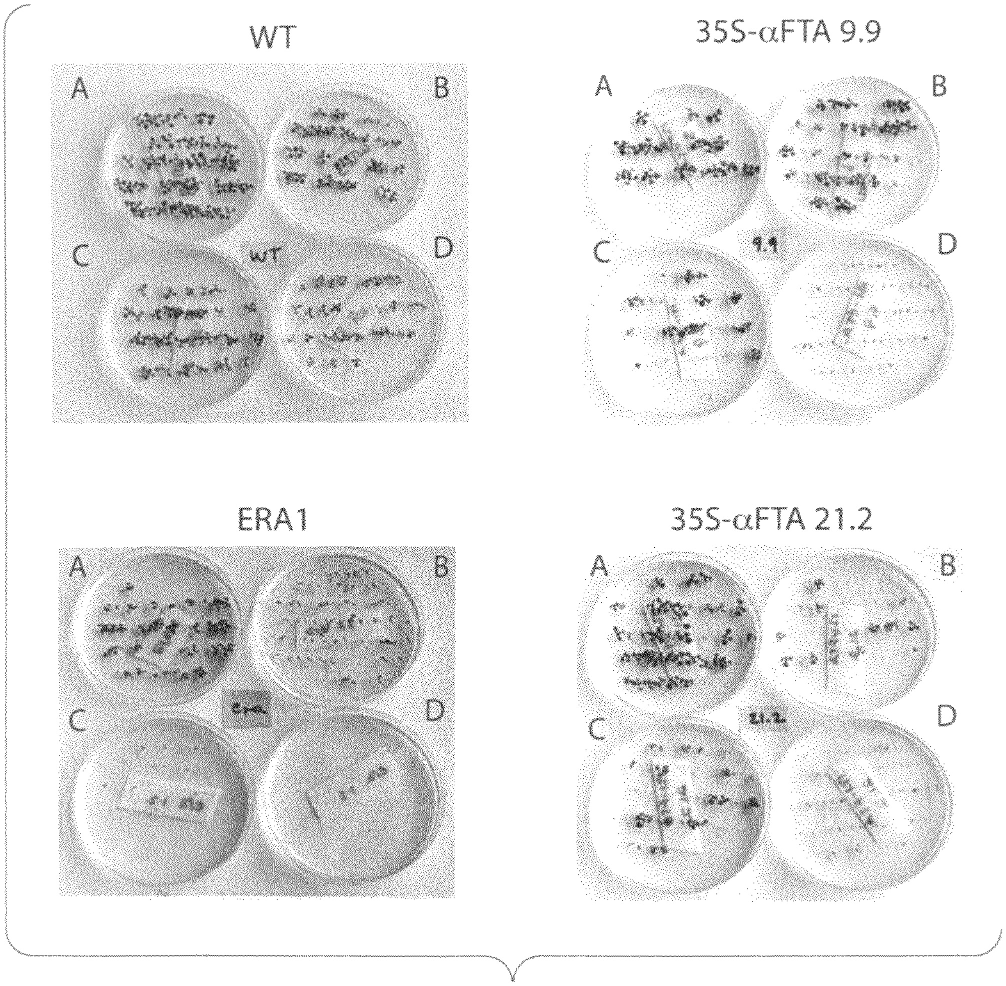
FIG. 14 is a set of photographs showing ABA effects on seedling growth and development. FTA antisense transgenic seedlings exhibit enhanced ABA sensitivity.

Seeds of wild type Columbia, era1-2 and T3 homozygous seeds of two antisense, drought tolerant lines of 35S-anti-sense-FTA were plated on minimum medium (½ MS) supplemented with no ABA (A), 0.3 μM (B), 0.5 μM (C) or 1.0 μM ABA (D). Plates were chilled for 3 days in 4° C. in the dark, and incubated for 11 days at 22° C. with 24 hour continuous light. era1 and transgenic lines were more inhibited in germination than wild type plants. Results are shown in FIG. 14.

Figure 15A:
FIG. 15 shows the effect of ABA on seedling growth and development.
Figure 15B:

Twelve day old seedling phenotypes of wild type Columbia, era1-2 and two drought tolerant 35S-antisense-FTA lines (9.9 & 21.2) in minimum medium without (A) or with (B) 1 μM ABA. FIG. 15 shows the reduced root growth and development of era1 and transgenic lines relative to wild type plants. The 35S-antisense-FTA lines show reduced root growth, similar to the era1 mutant, in response to ABA.

A transgenic *Brassica napus* line carrying the 35S-anti-sense-FTA construct was assessed for ABA sensitivity. At about 10 μm an effect was observed showing reduced seedling development and vigor at the cotyledon and first leaf stage, thereby indicating an increased sensitivity to ABA ABA sensitivity is assessed in all transgenic plants engineered to have reduced or increased FTA or FTB expression or activity by the methods above. The ABA concentration used varies depending upon the species under examination.

Example 20

Drought Experiment

To assess the response of plants under water stress or drought one can expose plants to various situations. For example, the plant can be removed from soil or media and placed on paper towel for a period of time, such as 4 hours, then returned to a plate to continue growth and development. Survival and vigour can be assessed.

Figure 16:
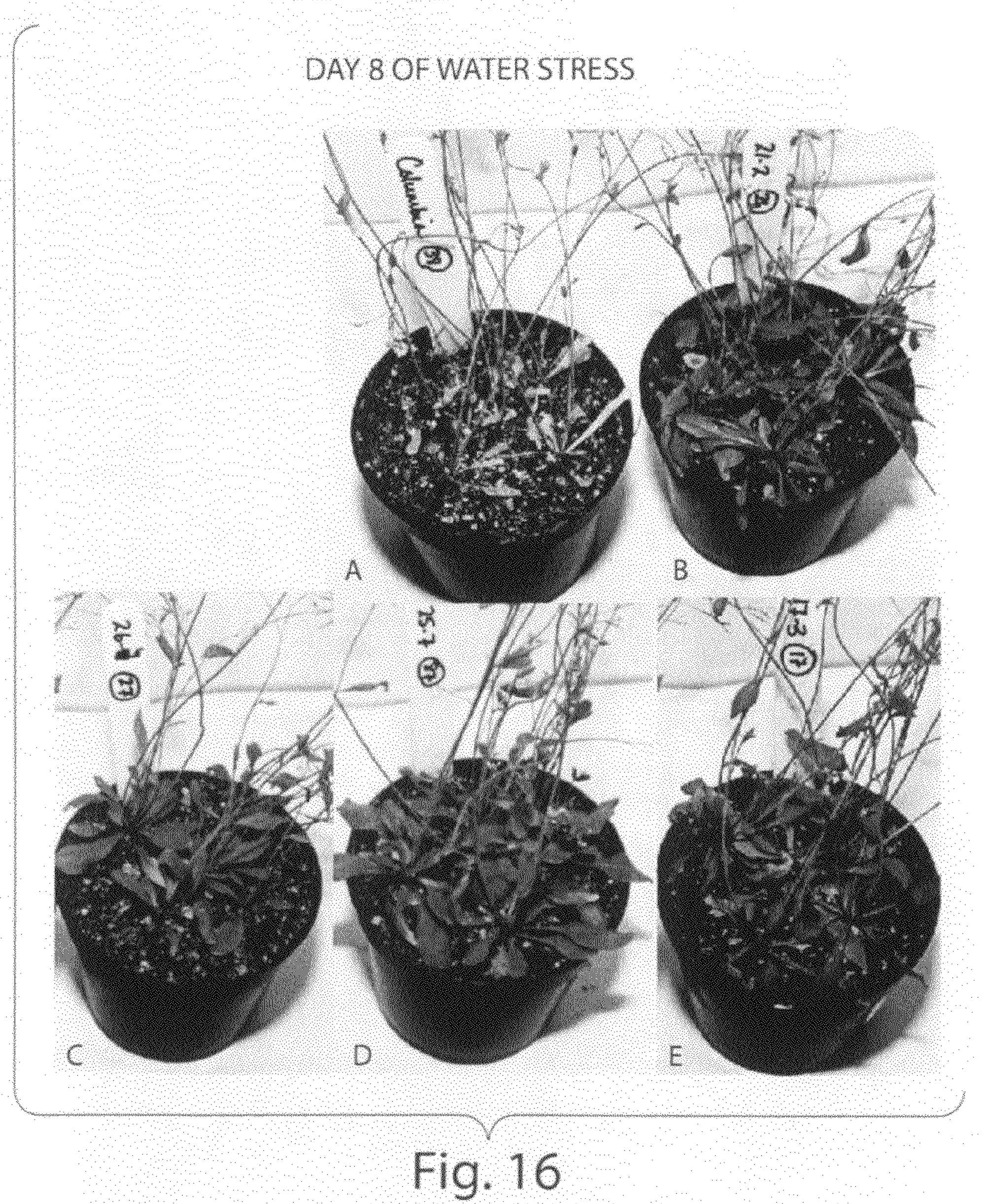
FIG. 16 shows photographs of wild type Columbia (A) and four antisense FTA transgenic lines (B, C, D, E) of *Arabidopsis thaliana* after 8 days without watering.
Figure 19:
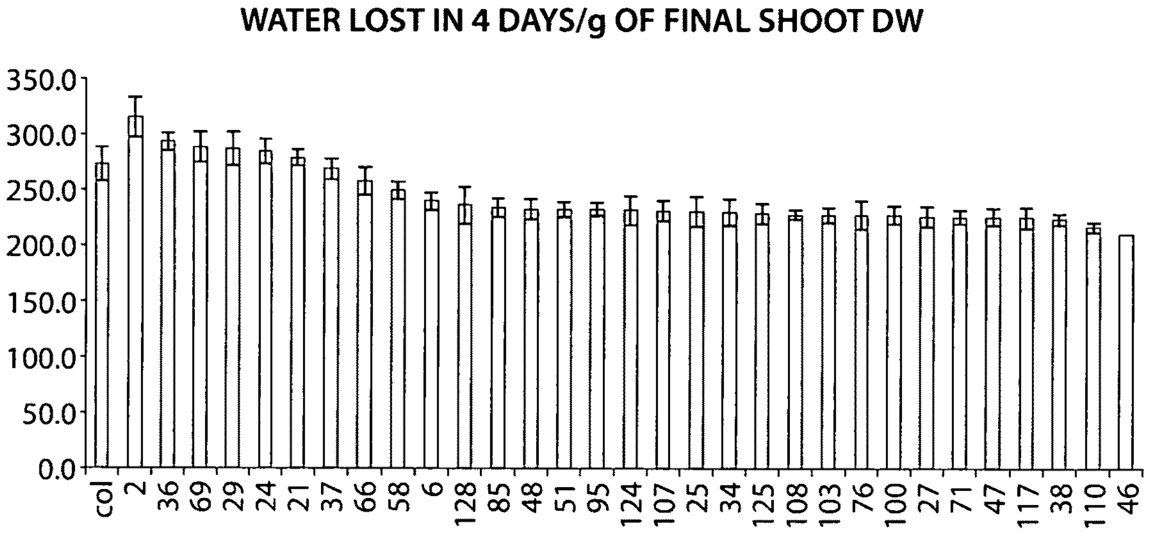
FIG. 19 is an illustration of transgenic performance during water stress.

Alternatively one can impose a water stress in such a way as to more closely resemble a field situation by withholding water for a period of time, such as up to 6 days. Plants were grown five plants per four inch pot, in a replicated water-stress experiment. All pots were filled with equal amounts of homogeneous premixed and wetted soil. Growth conditions were 16 hour daylight (150-200 μmol/$m^2$/s) at 22° C. and 70% relative humidity. On the day that the first flower opened drought treatment was initiated first by equalizing the soil water content in each pot on a weight basis and then cessation of watering. At the end of the water stress treatment plants were typically either harvested for biomass data or re-watered to complete the life cycle and determination of biomass and yield data. Physiological parameters have been assessed under stressed and optimal conditions, for example, shoot and root biomass accumulation, soil water content, water loss alone or as a function of parameters such as biomass, seed yield, and leaf number and leaf area. FIG. 16 shows photographs of wild type Columbia (A) and four 35S-antisense-FTA transgenic *Arabidopsis thaliana* lines (B, C, D, E) after 8 days of water stress treatment. The control plant is visibly stressed and less healthy. This experiment has been conducted on transgenic lines containing vectors described by SEQ ID NO: 10, 46-64.

Drought or water stress tolerance is assessed in all transgenic plants engineered to have reduced or increased FTA or FTB expression or activity by the described methods.

Example 21

Figure 10:
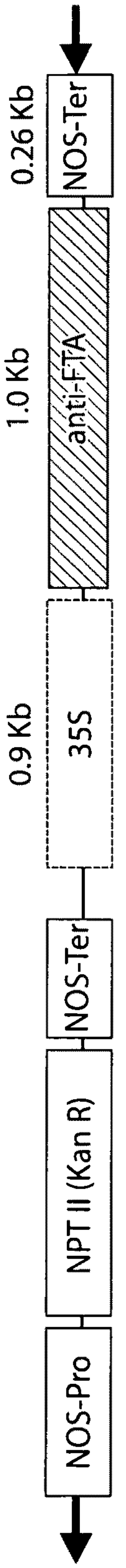
FIG. 10 is an illustration depicting the pBI121 antisense FTA vector construct.

Analysis of Water Loss in *Arabidopsis thaliana* pRD29A-DA-FTA Lines During Drought Stress Plants were grown 5 plants per 4 inch pot and 6 pots per line. When the plants had grown to the first flower stage drought treatment was initiated as described in Example 20. Pots were weighed daily and at the end of the 7 day drought treatment all plants were harvested for shoot fresh weight and dry weight determinations. FIG. 10 shows the water loss on a per shoot dry weight basis at 4 days of water stress treatment. Of the 31 lines examined in this experiment 25 showed lower water loss relative to the Columbia wild type, 22 of which were statistically significant. All lines had been assessed for ABA sensitivity as described in Example 14, increased ABA sensitivity ($ABA^S$) also correlated with a decreased water loss during drought treatment. Those lines determined to have wild type ABA sensitivity ($ABA^{WT}$) were the same 6 lines (lines 2, 36, 69, 29, 24, 21) that did not show a reduced water loss compared to wild type.

The above experiment was repeated using two $ABA^S$ lines, one $ABA^{WT}$ line and a Columbia control. Plants were harvested after 2, 4 and 6 days of water stress treatment for shoot dry weight determinations. $ABA^S$ transgenics had greater leaf and shoot biomass, greater soil water contents and lower water loss per shoot dry weight when compared to the $ABA^{WT}$ or Columbia controls. Results were consistent at all three harvest stages.

The data shown in this example was obtained using transgenic plants carrying the pRD29A-DA-FTA construct. The experiment has also been conducted on lines carrying variations of this construct such as 35S-DA-FTA, pRD29A-antisense-FTA or 35S-antisense-FTA, with similar water stress tolerant trends observed. Soil water loss is assessed in all transgenic plants engineered to have reduced or increased FTA or FTB expression or activity by the described methods.

Example 22

Figure 20:
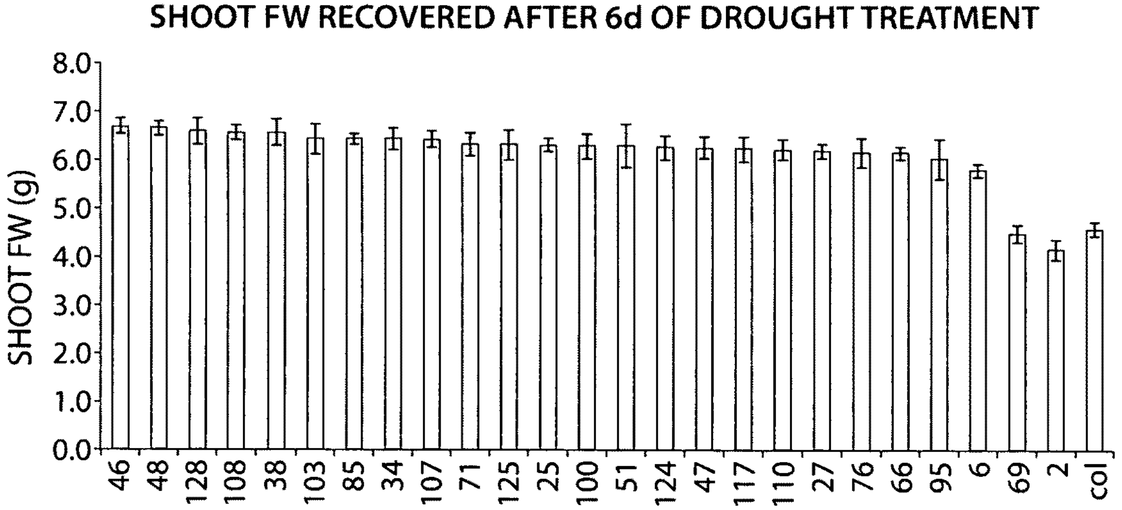
FIG. 20 is an illustration of shoot fresh weight, or biomass accumulation, after 6 days of water stress treatment and 6 days recovery time.

Analysis of Shoot Fresh Weight in *Arabidopsis thaliana* pRD29A-DA-FTA Lines During Drought Stress Plants were grown 5 plants per 4 inch pot and 8 pots per line. When the plants had grown to the first flower stage drought treatment was initiated as described in Example 20. Plants were re-watered after 6 days drought treatment and allowed to recover for an additional 6 days. Plants were harvested and shoot fresh weights determined. FIG. 20 shows the shoot fresh weights. This experiment consisted of 25 transgenic lines, 2 of which are $ABA^{WT}$ (line 2 and 69) and a Columbia wild type control. All 23 $ABA^S$ transgenic lines had statistically significant greater shoot fresh weights, on average 44% greater.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 23

Analysis of Seed Yield in *Arabidopsis thaliana* pRD29A-DA-FTA Lines During Drought Stress and Under Optimal Conditions Plants were grown 1 plant per 4 inch pot. When the plants had grown to the first flower stage drought treatment was initiated as described in Example 20. Plants were re-watered after 6 days drought treatment and allowed to grow to maturity. The optimal group was not exposed to the drought treatment.

Figure 21:
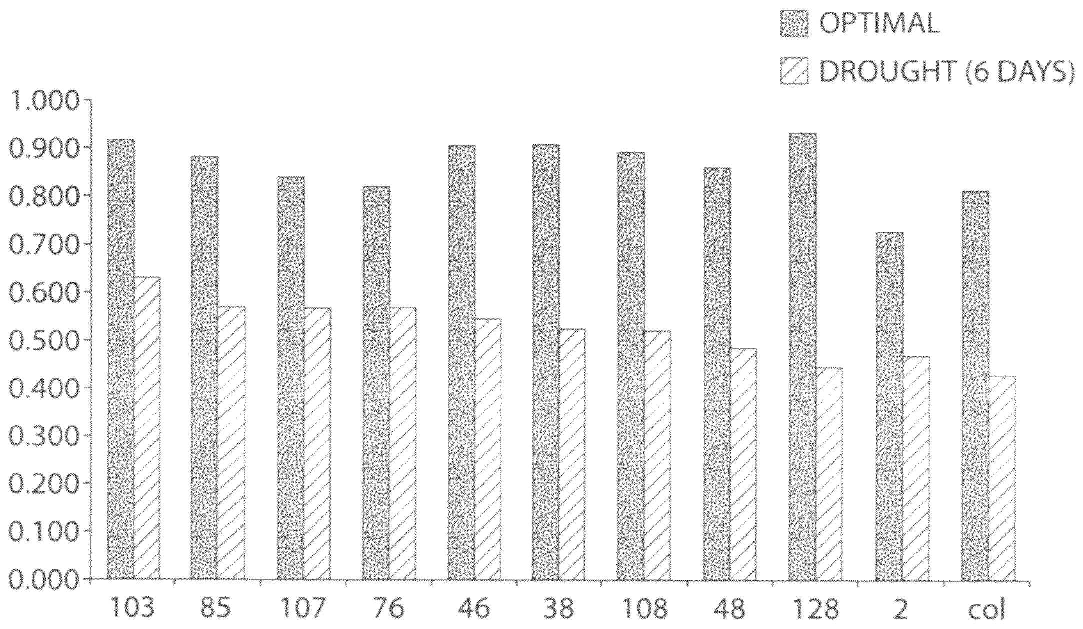
FIG. 21 is an illustration of seed yield (grams) obtained under optimal conditions or following a 6 day water stress treatment.

Yield analysis indicates that although drought treatment results in decreased yields, the transgenics do not suffer as severely as controls and maintain a productivity advantage (FIG. 21) as shown previously in Experiment 22. Comparison of the yields produced by the $ABA^S$ transgenics versus the control plants show that a 15% greater yield was obtained under optimal conditions and a 20% increase under drought conditions. In the drought treatment group 8 of 9 transgenic lines showed greater yield than controls. Expression of yield of each line obtained under drought treatment as a percentage of its performance under optimum conditions indicates that 8 of 9 $ABA^S$ lines outperformed the control line while 4 of 9 out performed the $ABA^{WT}$ controls.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 24

Figure 22:
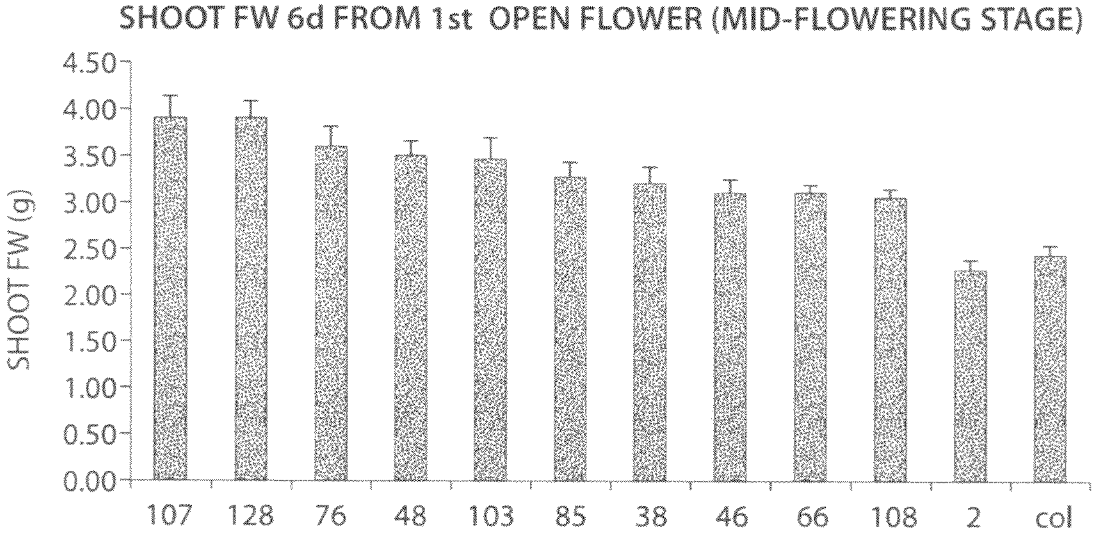
FIG. 22 is an illustration of vegetative growth under optimal conditions, shown is shoot fresh weight 6 days after the first flower opened.

Analysis of Vegetative Growth in *Arabidopsis thaliana* pRD29A-DA-FTA Lines Under Optimum Growth Conditions Plants were grown 1 plant per 3 inch pot and 8 pots per line. Plants were harvested at three stages and fresh weights determined. Vegetative stage was defined as 14 day old seedlings, bolting stage as the appearance of first flower (19-21 day seedlings) and mid-flowering as 6 days from first flower. At each of the above stages respectively 7, 8 and 10 of the 10 $ABA^S$ transgenic lines tested showed statistically greater shoot fresh weight biomass than the control plants (FIG. 22). One Columbia line and an $ABA^{WT}$ (line 2) line were used as the control group. Additionally, there was a statistically significant trend for the transgenic lines to have an increased number of rosette leaves.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 25

Figure 23:
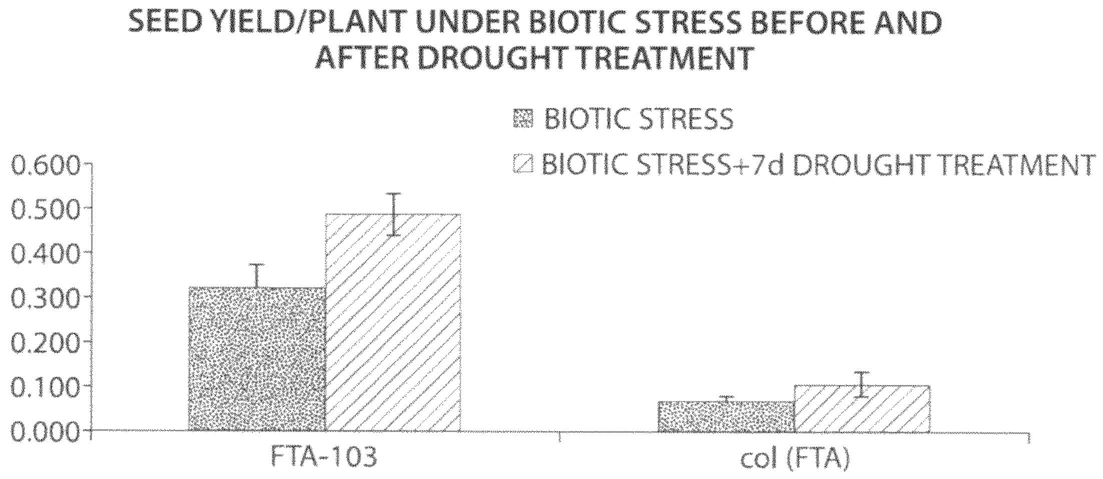
FIG. 23 is an illustration of the effect of a biotic stress coupled with drought stress treatment on seed yield.

Analysis of *Arabidopsis thaliana* pRD29A-DA-FTA Lines Under Drought Treatment and Biotic Stress Plants were grown 1 plant per 4 inch pot and 8 pots. When the plants had grown to the first flower stage drought treatment was initiated as described in Example 20. Plants were re-watered after 7 days drought treatment and allowed to grow to maturity. One Columbian control line (col) and one transgenic line were evaluated. Analysis of seed yield indicated less than normal yields, approximately 12% of expected optimal yield. It was determined that the soil used contained a fungal contaminant that was responsible for the reduced yields as the biotic stress could be negated by sterilization of the soil prior to use. This biotic stress was less severe in the transgenic line compared to the control which had a yield 22% of the transgenic line. In the drought treatment groups of plants the biotic stress was reduced however, transgenics outperformed controls by nearly 4.5 fold (FIG. 23).

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 26

Analysis of *Arabidopsis thaliana* pRD29A-DA-FTA Lines for Stomatal Number

The number of stomata on both the upper and lower surface of the leaf was assessed on two transgenic lines and a wild type Columbia control. Nail polish imprints were made of both upper and lower leaf surfaces of the fifth leaf, plants were at the early flowering stage. No differences in stoma density were observed.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 27

Production of Polyclonal Antibodies Against FT-A and FT-B

The isolated *Arabidopsis thaliana* FT sequences were cloned into the *E. coli* expression vector derived from pET11D. To generate the Histidine tagged FT-B construct the *Arabidopsis thaliana* FT-B clone and pET vector were digested with BamHI and ligated together. Restriction digests were performed to verify the orientation of the insert. To produce the FT-A construct the *Arabidopsis thaliana* FT-A clone and pET vector were digested with BamHI and EcoRI and subsequently ligated together. The resultant plasmids directed the expression of fusion proteins containing 6 consecutive histidine residues at the N-termini of AtFTA and AtFTB. The fusion proteins were expressed in the bacterial host BL21(DE3) and purified using Hi-Trap chelating chromatography as described by the manufacturer (Pharmacia). The soluble fraction of the crude bacterial extract containing the His-FT fusion proteins were loaded to a Hi-Trap column (1.5 cm×2.0 cm), and the proteins eluted with a 200 ml linear gradient of 0.0 to 0.3 M imidazole in column buffer (25 mM Tris-HCl, pH 7.5, 1 mM DTT). Fractions containing purified His-FT proteins were pooled, desalted and concentrated with a Centriprep-30 concentrator (Amicon). All purification steps were carried out at 4° C. To generate an antibody, the purified fusion protein was further separated by SDS/PAGE and the Coomassie stained band corresponding to the fusion protein was excised. Protein was eluted from the gel slice by electroelution and then emulsified in Ribi adjuvant (Ribi Immunochem) to a final volume of 1 ml. His-AtFTA or His-AtFTB (250 μg) were injected into a 3 kg New Zealand rabbit on day 1 and booster injections given on day 21 and day 35 with 200 μg of the protein. High-titer antisera were obtained one week after the final injection. These antibodies were used in the western analysis of example 18, FIG. 13.

Example 28

Screening for Related Genes

The transgenic plants of the invention can be used to identify genes which interact with the genes of the present invention. One can make use of the transgenic plants of the invention to screen for related genes, for example, suppressors, enhancers or modulators of gene expression or activity can be identified through genetic screening protocols. By way of example, a mutant library can be generated using the transgenic plants of the invention as the genetic background. Various methods are available and would be known to one of skill in the art. For example, chemical mutagens such as EMS can be used to induce point mutations in the genome, fast neutron irradiation of seeds can result in deletion mutations, T-DNA libraries can be produced that inactivate genes through insertional effects or activation tagging methods can be used to produce libraries with up-regulated genes. Analysis of these types of libraries can identify genes which rescue or modulate the phenotypes observed in the transgenic plants of the present invention.

Example 29

RT-PCR Amplification and Cloning of CaaX Prenyl Proteases

Total RNA was isolated from leaf tissue of *Arabidopsis thaliana, Brassica napus* and *Glycine max*, using the Qiagen RNeasy kit and used as template to amplify the CPP genes by RT-PCR. Reaction conditions were as follows; IX reaction buffer (10 mM Tris-HCl pH 8.8, 1.5 mM $MgCl_2$, 50 mM KCl), dNTP's at 200 μM, IpM AtCPP BamFW and AtCPP SmaRV primers, 2.5 U. Pfu DNA polymerase, and template plus water to a final volume of 100 μL. Reactions were run at 1 minute 94° C., 1 minute 60° C., 1 minute 72° C., for 30 cycles. Primers used to PCR amplify *Arabidopsis* and *Brassica* sequences were those identified by SEQ ID NO: 101 and SEQ ID NO: 102. Primers used to PCR amplify the *Glycine* sequence were those identified by SEQ ID NO: 149 and SEQ ID NO: 150. PCR products were separated from the RT-PCR reaction mixture using the Qiagen PCR column spin kit and ligated into the prepared cloning vector, pBluescript KS+. The vector had been prepared by digestion with EcoRV and treated with Taq polymerase in the presence of dTTP to produce a 3' overhand suitable for ligation with the PCR products. The ligation products were transformed into *E. coli* DH5α cells, positive colonies selected and the resulting inserts sequenced. The above methodology is applicable to obtain homologous sequences and may require alternative primers.

TABLE 13

| | | |
|---|---|---|
| AtCPP BamFW: | 5'-AAAGGATCCATGGCGAT TCCTTTCATGG-3' | (SEQ ID NO: 101 |
| AtCPP SmaRV: | 5'-AAACCCGGGTTAATCTGT CTTCTTGTCTTCTCCA-3' | (SEQ ID NO: 102) |
| GmCPP SmaFW: | 5'-AAACCCGGGATGGCGTT TCCCTACATGGAAGCC-3' | (SEQ ID NO: 149) |
| GmCPP SacRV: | 5'-AAAGAGCTCTTAGTCTTC CTTCTTATCCGGTTCG-3' | (SEQ ID NO: 150) |

Example 30

Vector Construction

Figure 25A:
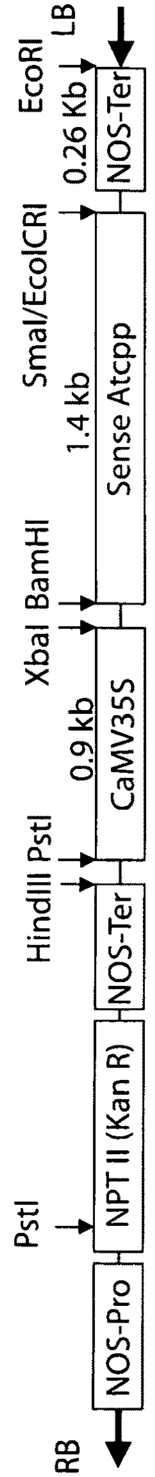
FIG. 25 is a schematic representation of the vector constructs; A) pBI121-AtCPP, B) pBI121-antisense-AtCPP, C) pBI121-HP-AtCPP.

Construction of the pBI121-AtCPP construct (SEQ ID NO: 99) was prepared as follows. The pBI121 vector was digested with BamHI and SmaI The AtCPP, 1.4 kb DNA fragment from RT-PCR (SEQ ID NO: 97) was digested with BamHI and SmaI and ligated into the pBI121 vector. The GUS sequence was then removed by digestion with SmaI and EcoICR1 and the vector ligated after purification of the vector from the GUS insert to produce the pBI121-AtCPP vector (FIG. 25A). This construct was used to further generate constructs expressing the CPP gene from *Brassica* and *Glycine*. To produce the pBI121-BnCPP construct (SEQ ID NO: 142) primer pairs identified by SEQ ID NO:101 and SEQ ID NO: 102 are used to PCR amplify the appropriate fragment which is ligated into the prepared parent vector. To produce the pBI121-GmCPP construct (SEQ ID NO: 136) primer pairs identified by SEQ ID NO: 149 and SEQ ID NO: 150 are used to PCR amplify the appropriate fragment which is ligated into the prepared parent vector.

Figure 25B:
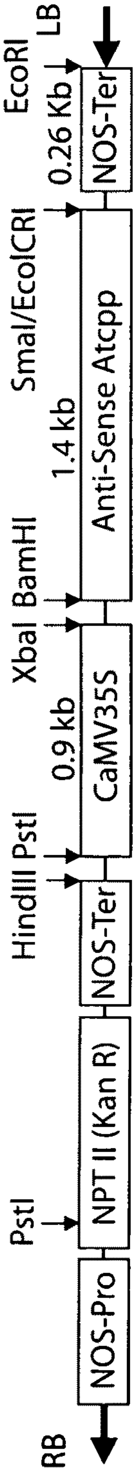

Construction of the pBI121-antisense-AtCPP construct (SEQ ID NO:130). The antisense fragment was produced using PCR amplification with SEQ ID NO:97 as template and primers identified as SEQ ID NO:106 and SEQ ID NO: 107, listed in Table 14. This fragment was digested with BamHI and SmaI and used to replace the sense fragment of the pBI121-AtCPP construct (SEQ ID NO:99), to yield SEQ ID NO:130 (FIG. 25B). This construct, SEQ ID NO: 130, was used to further generate constructs expressing the antisense CPP gene from *Brassica* and *Glycine*. To produce the pBI121-antisense-BnCPP construct (SEQ ID NO:144) primer pairs identified by SEQ ID NO:151 and SEQ ID NO:152 are used to PCR amplify the appropriate fragment which is ligated into the prepared parent vector. To produce the pBI121-antisense-GmCPP construct (SEQ ID NO:138) primer pairs identified by SEQ ID NO:153 and SEQ ID NO:154 are used to PCR amplify the appropriate fragment which is ligated into the prepared parent vector.

Figure 25C:
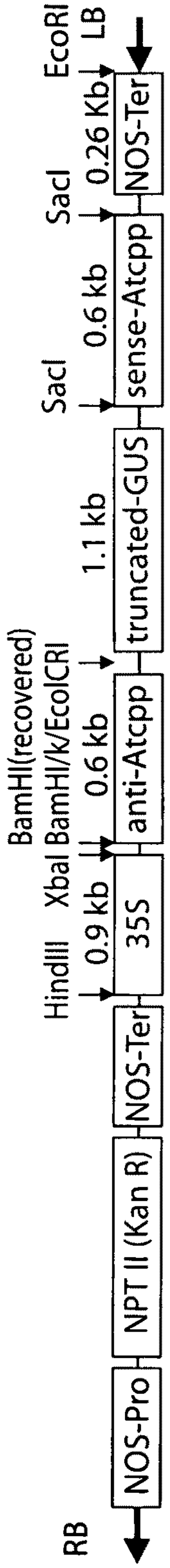

Construction of the pBI121-HP-AtCPP construct (SEQ ID NO:100). The cloning strategy involved truncating the GUS gene of pBI121 and flanking the GUS sequence with a AtCPP fragment in the antisense orientation upstream of the GUS and in the sense orientation on the downstream side of GUS. The pBI121 vector was digested with SmaI and Sad, the GUS sequence and the vector fragments were purified from one another. The isolated GUS fragment was digested using EcoRV and the 1079 bp. blunt ended EcoRVISacI fragment isolated. This was ligated back into the digested parent vector at the Small SacI sites. This intermediate vector was used in the subsequent production of the hair-pin vectors. The AtCPP fragment to be used as the gene specific hair-pin sequence was isolated by PCR. Primers identified as SEQ ID NO:103 and SEQ ID NO:104, listed in Table 14, were used to generate a 596 bp fragment. Cloning of the sense orientation fragment was achieved by digesting the PCR AtCPP fragment with Sad and ligation into the Sad site at the 3' end of GUS. To insert the same fragment upstream of GUS, the BamHI site was opened and the ends blunted with Klenow. The PCR amplified AtCPP fragment was digested with Eco1CRI, which is an isoschizomer of Sad but leaves blunt ends, and ligated into the blunted BamHI site of the vector to yield the final construct (FIG. 25C). The intermediate construct used to produce SEQ ID NO:100 above contained only the truncated GUS gene and no CPP sequences this intermediate vector was used to further generate constructs expressing hair-pin CPP gene constructs from *Brassica* and *Glycine*. To produce the pBI121-HP-BnCPP construct (SEQ ID NO:143) primer pairs identified by SEQ ID NO:153 and SEQ ID NO:154 are used to PCR amplify the sense fragment and primer pairs identified by SEQ ID NO:155 and SEQ ID NO:156 are used to PCR amplify the antisense fragment. These fragments are cloned into the prepared intermediate vector described above. To produce the pBI121-HP-GmCPP construct (SEQ ID NO:137) primer pairs identified by SEQ ID NO:157 and SEQ ID NO:158 are used to PCR amplify the sense fragment and primer pairs identified by SEQ ID NO:159 and SEQ ID NO:160 are used to PCR amplify the antisense fragment. These fragments are cloned into the prepared intermediate vector described above.

The above vector constructs were modified to place the genes under the control of alternative promoters, such as, but not limited to, the RD29A or MuA. This was accomplished by excising the 35S promoter sequence and replacing it with an appropriate promoter sequence. In this way SEQ ID NO's: 134 and 135 were generated and SEQ ID NO's: 133, 136-148 can be constructed.

TABLE 14

| | | |
|---|---|---|
| AtCPP-HP-SacFW | 5'-CTGGAGCTCT TTTACCGAGGTT GGGCCTTGATCC-3' | (SEQ ID NO: 103) |
| AtCPP-HP-SacRV | 5'-ATTGAGCTCCC AATGTCCAAGCT CGTGTGCAATA-3' | (SEQ ID NO: 104) |
| AtCPP-anti-SmaFW | 5'-AAACCCGGGATGG CGATTCCTTTCATGG-3' | (SEQ ID NO: 106) |
| AtCPP-anti-BamRV | 5'-AAAGGATCCTTAA TCTGTCTTCTT GTCTTCTCCA-3' | (SEQ ID NO: 107) |
| BnCPP-anti-SmaFW | 5'-AAACCCGGGAT GGCGATTCCT TTCATGG-3' | (SEQ ID NO: 151) |
| BnCPP-anti-BamRV | 5'-AAAGGATCCTTA ATCTGTCTTCTT GTCTTCTCC-3' | (SEQ ID NO: 152) |
| BnCPP-HP-Sac-FW | 5'-AAAGAGCTCTTCTAC CAATGGTGGGACTCG-3' | (SEQ ID NO: 153) |
| BnCPP-HP-Sac-RV | 5'-AAAGAGCTCCCAGTG TCCCAGCTCGTGTG-3' | (SEQ ID NO: 154) |
| BnCPP-HP-BamFW | 5'-AAAGGATCCTTCTAC CAATGGTGGGACTCG-3' | (SEQ ID NO: 155) |
| BnCPP-HP-XbaRV | 5'-AAATCTAGACCAGTG TCCCAGCTCGTGTG-3' | (SEQ ID NO: 156) |

TABLE 14-continued

| | | |
|---|---|---|
| GmCPP-HP-Sac-FW | 5'-GATGAGCTCACAA GATCAAGTCAC AGCAATGCCT-3' | (SEQ ID NO: 157) |
| GmCPP-HP-Sac-RV | 5'-AAAGAGCTCCCGGTT CGTCCAGCGCGGCC-3' | (SEQ ID NO: 158) |
| GmCPP-HP-BamFW | 5'-GATGGATCCACAA GATCAAGTCACA GCAATGCCT-3' | (SEQ ID NO: 159) |
| GmCPP-HP-XbaRV | 5'-CCTTCTAGACCGGTT CGTCCAGCGCGGCC-3' | (SEQ ID NO: 160) |

Example 31

Sequence Analysis

*Arabidopsis thaliana* CPP (AtCPP)

A disclosed nucleic acid of 1275 nucleotides (SEQ ID NO:97) and also referred to as AtCPP, is shown in Table 15.

TABLE 15A

| AtCPP Nucleotide Sequence (SEQ ID NO: 97). |
|---|
| ATGGCGATTCCTTTCATGGAAACCGTCGTGGGTTTTATGATA |
| GTGATGTACATTTTTGAGACGTATTTGGATCTGAGGCAACTC |
| ACTGCTCTCAAGCTTCCAACTCTCCCGAAAACCTTGGTTGG |
| TGTAATTAGCCAAGAGAAGTTTGAGAAATCACGAGCATAC |
| AGTCTTGACAAAAGCTATTTTCACTTTGTTCATGAGTTTGTA |
| ACTATACTTATGGACTCTGCAATTTTGTTCTTTGGGATCTTG |
| CCTTGGTTTTGGAAGATGTCTGGAGCTGTTTTACCGAGGTT |
| GGGCCTTGATCCGGAGAATGAAATACTGCATACTCTTTCATT |
| CTTGGCTGGTGTTATGACATGGTCACAGATCACTGATTTGCCA |
| TTTTCTTTGTACTCAACTTTCGTGATCGAGTCTCGGCATGGGTTC |
| AACAAACAAACAATATGGATGTTCATTAGGGACATGATCAAAGGAACA |
| TTCCTCTCTGTCATACTAGGCCCACCCATTGTTGCTGCGATAAT |
| TTTCATAGTCCAGAAAGGAGGTCCTTATCTTGCCATCTATCTGTG |
| GGCATTCATGTTTATCCTGTCTCTAGTGATGATGACTATATACCCG |
| GTCTTGATAGCACCGCTCTTCAACAAATTCACTCCTCTTCCAGATG |
| GAGACCTCCGGGAGAAGATTGAGAAACTTGCTTCTTCCCTAAAGTT |
| TCCTTTGAAGAAGCTGTTTGTTGTCGATGGATCTACAAGGTCAAGCC |
| ATAGCAATGCTTACATGTATGGTTTCTTTAAGAACAAAAGGATTGTTC |
| TTTATGATACGTTGATTCAGCAGTGCAAGAATGAGGATGAAATTGTGGCG |
| GTTATTGCACACGAGCTTGGACATTGGAAACTGAATCACACTACATACTC |
| GTTCATTGCAGTTCAAATCCTTGCCTTCTTACAATTTGGAGGATACACT |
| CTTCTCAGAAACTCCACTGATCTCTTCAGGAGTTTCGGATTTGATACAC |
| AGCCTGTTCTCATTGGTTTGATCATATTTCAGCACACTGTAATACCACTG |
| CAACATCTAGTAAGCTTTGGCCTGAACCTCGTTAGTCGAGCGTTTGAGT |
| TTCAGGCTGATGCTTTTGCTGTGAAGCTTGACTATGCAAAAGATCTT |

TABLE 15A-continued

| AtCPP Nucleotide Sequence (SEQ ID NO: 97). |
|---|
| CGTCCTGCTCTAGTGAAACTACAGGAAGAGAACTTATCAACAATGAAC |
| ACTGATCCATTGTACTCAGCTTATCACTACTCACATCCTCCTCTTGTTG |
| AAAGGCTTCGAGCCACTGATGGAGAAGAC**AAGAAGACAGATTAA** |

A disclosed CPP polypeptide (SEQ ID NO:98) encoded by SEQ ID NO:97 has 424 amino acid residues and is presented in Table 15B using the one-letter amino acid code.

TABLE 15B

| Encoded CPP protein sequence (SEQ ID NO: 98). |
|---|
| MAIPFMETVVGFMIVMYIFETYLDLRQLTALKLPTLPKTLVGVISQE |
| KFEKSRAYSLDKSYFHFVHEFVTILMDSAILFFGILPWFWKMSGAV |
| LPRLGLDPENEILHTLSFLAGVMTWSQITDLPFSLYSTFVIESRHGF |
| NKQTIWMFIRDMIKGTFLSVILGPPIVAAIIFIVQKGGPYLAIYLWAFM |
| FILSLVMMTIYPVLIAPLFNKFTPLPDGDLREKIEKLASSLKFPLKKL |
| FVVDGSTRSSHSNAYMYGFFKNKRIVLYDTLIQQCKNEDEIVAVIAH |
| ELGHWKLNHTTYSFIAVQILAFLQFGGYTLLRNSTDLFRSFGFDTQP |
| VLIGLIIFQHTVIPLQHLVSFGLNLVSRAFEFQADAFAVKLDYAKDLRP |
| ALVKLQEENLSTMNTDPLYSAYHYSHPPLVERLRATDGEDKKTD |

The present invention also includes a nucleic acid sequence complimentary to the *Arabidopsis thaliana* CaaX prenyl protease of SEQ ID NO:97. The disclosed complimentary sequence is shown as SEQ ID NO:115.

SEQ ID NO: 115

TTAATCTGTCTTCTTGTCTTCTCCATCAGTGGCTCGAAGCCTTTC

AACAAGAGGAGGATGTGAGTAGTGATAAGCTGAGTACAATGGAT

CAGTGTTCATTGTTGATAAGTTCTCTTCCTGTAGTTTCACTAGAGC

AGGACGAAGATCTTTTGCATAGTCAAGCTTCACAGCAAAAGCATC

AGCCTGAAACTCAAACGCTCGACTAACGAGGTTCAGGCCAAAGC

TTACTAGATGTTGCAGTGGTATTACAGTGTGCTGAAATATGATCAAA

CCAATGAGAACAGGCTGTGTATCAAATCCGAAACTCCTGAAGAGAT

CAGTGGAGTTTCTGAGAAGAGTGTATCCTCCAAATTGTAAGAAGGC

AAGGATTTGAACTGCAATGAACGAGTATGTAGTGTGATTCAGTTTCCA

ATGTCCAAGCTCGTGTGCAATAACCGCCACAATTTCATCCTCATTCTT

GCACTGCTGAATCAACGTATCATAAAGAACAATCCTTTTGTTCTTAAAG

AAACCATACATGTAAGCATTGCTATGGCTTGACCTTGTAGATCCATCG

ACAACAAACAGCTTCTTCAAAGGAAACTTTAGGGAAGAAGCAAGTTTC

TCAATCTTCTCCCGGAGGTCTCCATCTGGAAGAGGAGTGAATTTGTTGA

AGAGCGGTGCTATCAAGACCGGGTATATAGTCATCATCACTAGAGACA

GGATAAACATGAATGCCCACAGATAGATGGCAAGATAAGGACCTCCTT

TCTGGACTATGAAAATTATCGCAGCAACAATGGGTGGGCCTAGTATGAC

-continued

AGAGAGGAATGTTCCTTTGATCATGTCCCTAATGAACATCCATATTGTTT

GTTTGTTGAACCCATGCCGAGACTCGATCACGAAAGTTGAGTACAAAG

AAAATGGCAAATCAGTGATCTGTGACCATGTCATAACACCAGCCAAGAAT

GAAAGAGTATGCAGTATTTCATTCTCCGGATCAAGGCCCAACCTCGGTAA

AACAGCTCCAGACATCTTCCAAAACCAAGGCAAGATCCCAAAGAACAAA

ATTGCAGAGTCCATAAGTATAGTTACAAACTCATGAACAAAGTGAAAATA

GCTTTTGTCAAGACTGTATGCTCGTGATTTCTCAAACTTCTCTTGGCTAA

TTACACCAACCAAGGTTTTCGGGAGAGTTGGAAGCTTGAGAGCAGTGAG

TTGCCTCAGATCCAAATACGTCTCAAAAATGTACATCACTATCATAAAAC

CCACGACGGTTTCCATGAAAGGAATCGCCAT

Due to the nature of the cloning strategy the sequence presented is not full length but is missing the 5' and 3' non-translated regions. The percent identities of the *Arabidopsis thaliana* nucleotide sequence and its encoded amino acid sequence to that of other CPP sequences as determined by ClustalW analysis are shown in FIG. 26.

Using the sequences disclosed herein as hybridization probes, one is able to screen and isolate full length sequences from cDNA or genomic libraries or use the rapid amplification of cDNA ends (RACE) technology or other such PCR techniques.

*Brassica napus* CPP (BnCPP)

A disclosed nucleic acid of 1275 nucleotides (SEQ ID NO:109) and also referred to as BnCPP, is shown in Table 16.

TABLE 16A

| BnCPP Nucleotide Sequence (SEQ ID NO: 109). |
|---|
| ATGGCGATTCCTTTCATGGAAACCGTCGTTGGTTTTATGATAGTGATGTA |
| CGTTTTTGAGACGTATTTGGATCTGAGGCAACATACTGCTCTCAAGCTTC |
| CCACTCTCCCAAAGACTTTGGTTGGAGTCATTAGCCAAGAGAAGTTTGAG |
| AAATCTCGAGCTTACAGTCTTGACAAAAGCCATTTTCACTTTGTTCATGA |
| GTTTGTTACTATACTTATGGACTCTGCGATTCTGTTCTTTGGGATCTTG |
| CCTTGGTTTTGGAAGATATCTGGCGGCTTTCTACCAATGGTGGGACTCG |
| ATCCAGAGAATGAAATCCTGCACACTCTTTCATTCTTGGCTGGTCTTATG |
| ACATGGTCACAGATCACTGATTTGCCATTTTCTTTGTACTCAACTTTCGT |
| GATCGAGTCTCGGCATGGGTTCAACAAACAAACAATATGGATGTTCATTA |
| GGGACATGATCAAAGGAATACTCCTCTCTGTCATACCTGCCCCTCCTATC |
| GTTGCCGCAATTATTGTTATAGTTCAGAAAGGAGGTCCTTACCTCGCCAT |
| CTATCTGTGGGCATTCATGTTTATCCTGTCTCTAGTGATGATGACTATAT |
| ACCCTGTTTTGATTGCACCTCTTTTCAACAAGTTCACTCCTCTTCCTGAT |
| GGAGACCTCCGGGAGAAGATTGAGAAACTTGCTTCTTCTCTAAAGTTTCC |
| TCTGAAGAAGCTGTTTGTTGTCGATGGATCTACAAGGTCAAGCCATAGTA |
| ATGCTTACATGTATGGTTTCTTCAAGAACAAAAGGATTGTTCTTTATGAC |
| ACATTGATTCAGCAGTGCCAGAATGAGAATGAAATTGTGGCGGTTATTGC |
| ACACGAGCTGGGACACTGGAAGCTGAATCACACTACATACTCGTTCATTG |
| CTGTTCAAATCCTTGCCTTCTTGCAATTTGGAGGATACACTCTTGTCAGA |

TABLE 16A-continued

| BnCPP Nucleotide Sequence (SEQ ID NO: 109). |
|---|
| AACTCCACTGATCTCTTCAGGAGTTTTGGTTTTGATACACAACCAGTTCT |
| CATTGGTTTGATCATATTTCAGCACACTGTAATACCACTTCAACACCTAG |
| TAAGCTTTGACCTCAACCTTGTTAGTCGAGCGTTTGAGTTTCAGGCTGA |
| TGCTTTTGCAGTGAATCTTGGTTATGCAAAGGATCTACGTCCTGCCCTA |
| GTGAAGCTACAGGAAGAGAACTTATCAGCGATGAACACAGACCCATTG |
| TACTCAGCTTATCACTACTCACACCCTCCTCTTGTAGAGAGGCTTCGA |
| GCCATTGATGGAGAAGACAAGAAGACAGATTAA |

A disclosed CPP polypeptide (SEQ ID NO:110) encoded by SEQ ID NO:109 has 424 amino acid residues and is presented in Table 16B using the one-letter amino acid code.

TABLE 16B

| Encoded CPP protein sequence (SEQ ID NO: 110). |
|---|
| MAIPFMETVVGFMIVMYVFETYLDLRQHTALKLPTLPKTLVGVISQEKFE |
| KSRAYSLDKSHFHFVHEFVTILMDSAILFFGILPWFWKISGGFLPMVGLD |
| PENEILHTLSFLAGLMTWSQITDLPFSLYSTFVIESRHGFNKQTIWMFIR |
| DMIKGILLSVIPAPPIVAAIIVIVQKGGPYLAIYLWAFMFILSLVMMTIY |
| PVLIAPLFNKFTPLPDGDLREKIEKLASSLKFPLKKLFVVDGSTRSSHSN |
| AYMYGFFKNKRIVLYDTLIQQCQNENEIVAVIAHELGHWKLNHTTYSFIA |
| VQILAFLQFGGYTLVRNSTDLFRSFGFDTQPVLIGLIIFQHTVIPLQHLV |
| SFDLNLVSRAFEFQADAFAVNLGYAKDLRPALVKLQEENLSAMNTDPLYS |
| AYHYSHPPLVERLRAIDGEDKKTD |

The present invention also includes a nucleic acid sequence complimentary to the *Brassica napus* CaaX prenyl protease of SEQ ID NO:109. The disclosed complimentary sequence is shown as SEQ ID NO:111.

SEQ ID NO: 111

TTAATCTGTCTTCTTGTCTTCTCCATCAATGGCTCGAAGCCTCTCTAC

AAGAGGAGGGTGTGAGTAGTGATAAGCTGAGTACAATGGGTCTGTGT

TCATCGCTGATAAGTTCTCTTCCTGTAGCTTCACTAGGGCAGGACGTA

GATCCTTTGCATAACCAAGATTCACTGCAAAAGCATCAGCCTGAAACTC

AAACGCTCGACTAACAAGGTTGAGGTCAAAGCTTACTAGGTGTTGAAG

TGGTATTACAGTGTGCTGAAATATGATCAAACCAATGAGAACTGGTTGT

GTATCAAAACCAAAACTCCTGAAGAGATCAGTGGAGTTTCTGACAAGAG

TGTATCCTCCAAATTGCAAGAAGGCAAGGATTTGAACAGCAATGAACG

AGTATGTAGTGTGATTCAGCTTCCAGTGTCCCAGCTCGTGTGCAATAA

CCGCCACAATTTCATTCTCATTCTGGCACTGCTGAATCAATGTGTCAT

AAAGAACAATCCTTTTGTTCTTGAAGAAACCATACATGTAAGCATTACT

ATGGCTTGACCTTGTAGATCCATCGACAACAAACAGCTTCTTCAGAGG

AAACTTTAGAGAAGAAGCAAGTTTCTCAATCTTCTCCCGGAGGTCTCC

-continued

ATCAGGAAGAGGAGTGAACTTGTTGAAAAGAGGTGCAATCAAAACAG

GGTATATAGTCATCATCACTAGAGACAGGATAAACATGAATGCCCACA

GATAGATGGCGAGGTAAGGACCTCCTTTCTGAACTATAACAATAATTGC

GGCAACGATAGGAGGGGCAGGTATGACAGAGAGGAGTATTCCTTTGAT

CATGTCCCTAATGAACATCCATATTGTTTGTTTGTTGAACCCATGCCGAG

ACTCGATCACGAAAGTTGAGTACAAAGAAAATGGCAAATCAGTGATCTGT

GACCATGTCATAAGACCAGCCAAGAATGAAAGAGTGTGCAGGATTTCATT

CTCTGGATCGAGTCCCACCATTGGTAGAAAGCCGCCAGATATCTTCCAAA

ACCAAGGCAAGATCCCAAAGAACAGAATCGCAGAGTCCATAAGTATAGTA

ACAAACTCATGAACAAAGTGAAAATGGCTTTTGTCAAGACTGTAAGCTCG

AGATTTCTCAAACTTCTCTTGGCTAATGACTCCAACCAAAGTCTTTGGGA

GAGTGGGAAGCTTGAGAGCAGTATGTTGCCTCAGATCCAAATACGTCTC

AAAAACGTACATCACTATCATAAAACCAACGACGGTTTCCATGAAAGGA

ATCGCCAT

Due to the nature of the cloning strategy the sequence presented is not full length but is missing the 5' and 3' non-translated regions. The percent identities of the *Brassica napus* nucleotide sequence and its encoded amino acid sequence to that of other CPP sequences as determined by ClustalW analysis are shown in FIG. 26.

Using the sequences disclosed herein as hybridization probes, one is able to screen and isolate full length sequences from cDNA or genomic libraries or use the rapid amplification of cDNA ends (RACE) technology or other such PCR techniques.

*Glycine max* CPP (GmCPP)

A disclosed nucleic acid of 1275 nucleotides (SEQ ID NO:112) and also referred to as GmCPP, is shown in Table 17.

TABLE 17A

| GmCPP Nucleotide Sequence (SEQ ID NO: 112). |
|---|
| ATGGCGTTTCCCTACATGGAAGCCGTTGTCGGATTTATGATATTAATGTA |
| CATTTTTGAAACTTACTTGGATGTGCGACAACATAGGGCCCTCAAAC |
| TTCCTACTCTTCCAAAGACTTTAGAGGGTGTTATCAGCCAAGAGAAA |
| TTTGAGAAATCTAGAGCCTATAGTCTTGATAAAAGCCACTTCCATTTT |
| GTTCACGAGTTTGTGACAATAGTGACAGACTCTACAATTTTGTACTTT |
| GGGGTATTGCCCTGGTTTTGGAAGAAATCAGGAGATTTTATGACAATA |
| GCTGGTTTCAATGCTGAGAATGAAATACTGCATACCCTTGCCTTCTTA |
| GCAGGGCTGATGATTTGGTCACAGATAACAGATTTGCCCTTTTCTCTG |
| TACTCAACTTTTGTGATTGAGGCCCGTCATGGTTTTAATAAGCAAACA |
| CCATGGTTATTCTTTAGGGACATGCTTAAAGGAATTTTCCTTTCTGTAA |
| TAATTGGTCCACCTATTGTGGCTGCAATCATTGTAATAGTACAGAAAG |
| GAGGTCCATACTTGGCCATCTATCTTTGGGTTTTTACGTTTGGTCTTT |
| CTATTGTGATGATGACCCTTTATCCAGTACTAATAGCTCCACTCTTCA |
| ATAAGTTCACTCCACTTCCAGATGGTCAACTCAGGGAGAAAATCGAG |
| AAACTTGCTTCCTCCCTCAACTATCCGTTAAAGAAACTATTTGTTGTCG |

TABLE 17A-continued

| GmCPP Nucleotide Sequence (SEQ ID NO: 112). |
|---|
| ATGGATCCACAAGATCAAGTCACAGCAATGCCTATATGTATGGATTCT |
| TCAAGAACAAGAGGATTGTCCCTTATGACACATTAATTCAACAGTGCA |
| AAGACGATGAGGAAATTGTTGCTGTTATTGCCCATGAGTTGGGACACTG |
| GAAGCTCAACCATACTGTGTACACATTTGTTGCTATGCAGATTCTTACAC |
| TTCTACAATTTGGAGGATATACACTAGTGCGAAATTCAGCTGATCTGTA |
| TCGAAGCTTTGGGTTTGATACGCAGCCAGTCCTCATTGGGCTCATCATA |
| TTTCAGCATACTGTAATCCCACTTCAGCAATTGGTCAGCTTTGGTCTGAA |
| CCTAGTCAGCCGATCATTTGAATTTCAGGCTGATGGCTTTGCCAAGAAG |
| CTTGGATATGCATCTGGATTACGCGGTGGTCTTGTGAAACTACAGGAGG |
| AGAATCTGTCAGCTATGAATACAGATCCTTGGTACTCTGCTTATCACTAT |
| TCTCATCCTCCCCTTGTTGAAAGATTGGCCGCGCTGGACGAACCGGAT |
| AAGAAGGAAGACTAA |

A disclosed CPP polypeptide (SEQ ID NO:113) encoded by SEQ ID NO:112 has 424 amino acid residues and is presented in Table 17B using the one-letter amino acid code.

TABLE 17B

| Encoded CPP protein sequence (SEQ ID NO: 113). |
|---|
| MAFPYMEAVVGFMILMYIFETYLDVRQHRALKLPTLPKTLEGVISQEKFE |
| KSRAYSLDKSHFHFVHEFVTIVTDSTILYFGVLPWFWKKSGDFMTIAGF |
| NAENEILHTLAFLAGLMIWSQITDLPFSLYSTFVIEARHGFNKQTPWLFF |
| RDMLKGIFLSVIIGPPIVAAIIVIVQKGGPYLAIYLWVFTFGLSIVMMT |
| LYPVLIAPLFNKFTPLPDGQLREKIEKLASSLNYPLKKLFVVDGSTRS |
| SHSNAYMYGFFKNKRIVPYDTLIQQCKDDEEIVAVIAHELGHWKLN |
| HTVYTFVAMQILTLLQFGGYTLVRNSADLYRSFGFDTQPVLIGLIIFQ |
| HTVIPLQQLVSFGLNLVSRSFEFQADGFAKKLGYASGLRGGLVKL |
| QEENLSAMNTDPWYSAYHYSHPPLVERLAALDEPDKKED |

The present invention also includes a nucleic acid sequence complimentary to the *Glycine max* CaaX prenyl protease of SEQ ID NO:112. The disclosed complimentary sequence is shown as SEQ ID NO:114.

SEQ ID NO: 114

TTAGTCTTCCTTCTTATCCGGTTCGTCCAGCGCGGCCAATCTTTCAACA

AGGGGAGGATGAGAATAGTGATAAGCAGAGTACCAAGGATCTGTATT

CATAGCTGACAGATTCTCCTCCTGTAGTTTCACAAGACCACCGCGTA

ATCCAGATGCATATCCAAGCTTCTTGGCAAAGCCATCAGCCTGAAA

TTCAAATGATCGGCTGACTAGGTTCAGACCAAAGCTGACCAATTGC

TGAAGTGGGATTACAGTATGCTGAAATATGATGAGCCCAATGAGGA

CTGGCTGCGTATCAAACCCAAAGCTTCGATACAGATCAGCTGAAT

TTCGCACTAGTGTATATCCTCCAAATTGTAGAAGTGTAAGAATCTGC

-continued

```
ATAGCAACAAATGTGTACACAGTATGGTTGAGCTTCCAGTGTCCCA

ACTCATGGGCAATAACAGCAACAATTTCCTCATCGTCTTTGCACTGT

TGAATTAATGTGTCATAAGGGACAATCCTCTTGTTCTTGAAGAATCCA

TACATATAGGCATTGCTGTGACTTGATCTTGTGGATCCATCGACAAC

AAATAGTTTCTTTAACGGATAGTTGAGGGAGGAAGCAAGTTTCTCGA

TTTTCTCCCTGAGTTGACCATCTGGAAGTGGAGTGAACTTATTGAAG

AGTGGAGCTATTAGTACTGGATAAAGGGTCATCATCACAATAGAAA

GACCAAACGTAAAAACCCAAAGATAGATGGCCAAGTATGGACCTCC

TTTCTGTACTATTACAATGATTGCAGCCACAATAGGTGGACCAATT

ATTACAGAAAGGAAAATTCCTTTAAGCATGTCCCTAAAGAATAACCA

TGGTGTTTGCTTATTAAAACCATGACGGGCCTCAATCACAAAAGTTG

AGTACAGAGAAAAGGGCAAATCTGTTATCTGTGACCAAATCATCAG

CCCTGCTAAGAAGGCAAGGGTATGCAGTATTTCATTCTCAGCATTG

AAACCAGCTATTGTCATAAAATCTCCTGATTTCTTCCAAAACCAGG

GCAATACCCCAAAGTACAAAATTGTAGAGTCTGTCACTATTGTCAC
```

-continued

```
AAACTCGTGAACAAAATGGAAGTGGCTTTTATCAAGACTATAGGCT

CTAGATTTCTCAAATTTCTCTTGGCTGATAACACCCTCTAAAGTCTT

TGGAAGAGTAGGAAGTTTGAGGGCCCTATGTTGTCGCACATCCAA

GTAAGTTTCAAAAATGTACATTAATATCATAAATCCGACAACGGCT

TCCATGTAGGGAAACGCCAT
```

Due to the nature of the cloning strategy the sequence presented is not full length but is missing the 5' and 3' non-translated regions. The percent identities of the *Glycine max* nucleotide sequence and its encoded amino acid sequence to that of other CPP sequences as determined by ClustalW analysis are shown in FIG. 26.

Using the sequences disclosed herein as hybridization probes, one is able to screen and isolate full length sequences from cDNA or genomic libraries or use the rapid amplification of cDNA ends (RACE) technology or other such PCR techniques.

The CPP nucleic acids and amino acids disclosed above have homology to other disclosed CPP sequences (GenBank ID NOs: AL161491 (AT4g01320), AF007269 and AF353722; WO 02/16625 A2). The homology between these and other sequences is shown in the ClustalW alignment analysis shown in Tables 18A-18B.

TABLE 18A

ClustalW Nucleic Acid Analysis of CaaX Prenyl Protease

```
1: PPI-AtCPP  SEQ ID NO: 97

2: PPI-BnCPP  SEQ ID NO: 109

3: PPI-GmCPP  SEQ ID NO: 112

4: BASF_AT1   SEQ ID NO: 116

5: BASF_AT2   SEQ ID NO: 118

6: BASF-Corn  SEQ ID NO: 120

7: BASF-Gm    SEQ ID NO: 122

8: AFC1       SEQ ID NO: 124

9: AT4g01320  SEQ ID NO: 126

10: AF007269  SEQ ID NO: 128

CLUSTAL W (1.81) multiple sequence alignment

PPI-GmCPP     ------------------------------------------------------------
BASF-Gm       ------------------------------------------------------------
AT4g01320     ------------------------------------------------------------
AF007269      ATGGCGATTCCTTTCATGGAAACCGTCGTGGGTAAGCTTCAAAACCTTTTTCTGAGACAT
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------

PPI-GmCPP     ------------------------------------------------------------
BASF-Gm       ------------------------------------------------------------
AT4g01320     ------------------------------------------------------------
AF007269      TTTACTATCCTGTTTCACTCATCGTATTTCGTTTTTGTTTGGGTTTTGCTTTCTGTGTTG
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------
```

TABLE 18A-continued

ClustalW Nucleic Acid Analysis of CaaX Prenyl Protease

```
PPI-GmCPP    ------------------------------------------------------------
BASF-Gm      ------------------------------------------------------------
AT4g01320    ------------------------------------------------------------
AF007269     TGTGTGTTGAGATTCCATGACTCGTTTGTTTCATATACCATCGTCTCTGCTTCTCGTTTC
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------------------------------------------------------
BASF-Gm      ------------------------------------------------------------
AT4g01320    ------------------------------------------------------------
AF007269     TAAATTTTGTTCTTTTCTAATAGTGCGTACCTTGATCTGAGGTTTTATTACTCCTACTAG
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------------------------------------------------------
BASF-Gm      ------------------------------------------------------------
AT4g01320    ------------------------------------------------------------
AF007269     TTTCTTGTCTTACTCGTGCGTTTGATTTGATTTGAGCTTATGTGATTTCATCATCTCTTC
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------------------------------------------------------
BASF-Gm      ------------------------------------------------------------
AT4g01320    ------------------------------------------------------------
AF007269     CTCGGTTTTAGAATGTACGGAGCTTCTCTGTTAACCAAAATCTAGGATTTGGGAAGAAAA
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------------------------------------------------------
BASF-Gm      ------------------------------------------------------------
AT4g01320    ------------------------------------------------------------
AF007269     GTCGGAGTCTTTTTTTTCCTCATTCCCGATTGGAAATTGAGAATCTTGAAATTTTTCTTT
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------------------------------------------------------
BASF-Gm      --------------------------------------CTAATACGACTCACTATAGGGC
AT4g01320    ------------------------------------------------------------
AF007269     GTTCAAGTCATACAGCTTGAGGTTTTGGGTTTTCTTGTCAGGGTATTATTATGTTCGTGA
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------------------------------------------------------
BASF-Gm      AAGCAGTGGTAACAACGCAGAGTACGCGGGGGGAGACGCATGGTTCTGAACTAATTGTTA
AT4g01320    ------------------------------------------------------------
AF007269     CTGCAACTAGAGTTTTCTGGAGTTTTTTGAAATGGGTTTTGTGTTGTGGAACCGTATGTG
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------
```

TABLE 18A-continued

ClustalW Nucleic Acid Analysis of CaaX Prenyl Protease

```
PPI-GmCPP     ------------------------------------------------------------
BASF-Gm       TAAATAATACCTAAAATTTTGAGTTGTCCTAAACATTGGGGTTTAAACAAATCCAATCTC
AT4g01320     ------------------------------------------------------------
AF007269      AATGTTGCATCAAAACTCTTTCAGTGCTCCAATGTTTCCATCAGTAGTCAGCACAAGAGA
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------

PPI-GmCPP     ------------------------------------------------------------
BASF-Gm       TCAATATAAAACCCAATGATCTCACC--CTCACTCCGTTTCTGATTTCTCACTCTTCGTT
AT4g01320     ------------------------------------------------------------
AF007269      TCTTTTTATATCTGGTTGATCAAAAAAGTAGATGATGTTATTGAATTTTCAGTGATGGAG
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------

PPI-GmCPP     ---------------------------------ATGGCGTTTCCC--TACATGGAAGCCG
BASF-Gm       TCTCGTTCGGTTCATCAGCGTGTGTCTCAGC-CATGGCGTTTCCC--TACATGGAAGCCG
AT4g01320     ---------------------------------ATGGCGATTCCT--TTCATGGAAACCG
AF007269      TATCTGTTGTTGTGGCATTTAGAGTAGATTCGTATTTCATCTTCTGTTTTATTCTTTTTC
PPI-AtCPP     ---------------------------------ATGGCGATTCCT--TTCATGGAAACCG
BASF_AT2      ---------------------------------ATGGCGATTCCT--TTCATGGAAACCG
afc1          ---------------------------------ATGGCGATTCCT--TTCATGGAAACCG
BASF_AT1      ---------------------------------ATGGCGATTCCT--TTCATGGAAACCG
PPI-BnCPP     ---------------------------------ATGGCGATTCCT--TTCATGGAAACCG
BASF-Corn     ------------------------------------------------------------

PPI-GmCPP     TTGTCGGATTTATGATATTAATGTACATTTTTGAAACTTACTTGGATGTGCGACAACATA
BASF-Gm       TTGTCGGATTTATGATATTAATGTACATTTTTGAAACTTACTTGGATGTGCGACAACATA
AT4g01320     TCGTGGGTTTTATGATAGTGATGTACATTTTTGAGACGTATTTGGATCTGAGGCAACTCA
AF007269      TTACAGGTTTTATGATAGTGATGTACATTTTTGAGACGTATTTGGATCTGAGGCAACTCA
PPI-AtCPP     TCGTGGGTTTTATGATAGTGATGTACATTTTTGAGACGTATTTGGATCTGAGGCAACTCA
BASF_AT2      TCGTGGGTTTTATGATAGTGATGTACATTTTTGAGACGTATTTGGATCTGAGGCAACTCA
afc1          TCGTGGGTTTTATGATAGTGATGTACATTTTTGAGACGTATTTGGATCTGAGGCAACTCA
BASF_AT1      TCGTGGGTTTTATGATAGTGATGTACATTTTTGAGACGTATTTGGATCTGAGGCAACTCA
PPI-BnCPP     TCGTTGGTTTTATGATAGTGATGTACGTTTTTGAGACGTATTTGGATCTGAGGCAACATA
BASF-Corn     ------------------------------------------------------------

PPI-GmCPP     GGGCCCTCAAACTTCCTACTCTTCCAAAGACTTTAGAGGGTGTTATCAGCCAAGAGAAAT
BASF-Gm       GGGCCCTCAAACTTCCTACTCTTCCAAAGACTTTAGAAGGTGTTATCAGCCAAGAGAAAT
AT4g01320     CTGCTCTCAAGCTTCCAACTCTCCCGAAAACCTTGGTTGGTGTAATTAGCCAAGAGAAGT
AF007269      CTGCTCTCAAGCTTCCAACTCTCCCGAAAACCTTGGTTGGTGTAATTAGCCAAGAGAAGT
PPI-AtCPP     CTGCTCTCAAGCTTCCAACTCTCCCGAAAACCTTGGTTGGTGTAATTAGCCAAGAGAAGT
BASF_AT2      CTGCTCTCAAGCTTCCAACTCTCCCGAAAACCTTGGTTGGTGTAATTAGCCAAGAGAAGT
afc1          CTGCTCTCAAGCTTCCAACTCTCCCGAAAACCTTGGTTGGTGTAATTAGCCAAGAGAAGT
BASF_AT1      CTGCTCTCAAGCTTCCAACTCTCCCGAAAACCTTGGTTGGTGTAATTAGCCAAGAGAAGT
PPI-BnCPP     CTGCTCTCAAGCTTCCCACTCTCCCAAAGACTTTGGTTGGAGTCATTAGCCAAGAGAAGT
BASF-Corn     ------------------------------------------------------------

PPI-GmCPP     TTGAGAAATCTAGAGCCTATAG--------------------------------------
BASF-Gm       TTGAGAAATCTAGAGCCTATAG--------------------------------------
AT4g01320     TTGAGAAATCACGAGCATACAG--------------------------------------
AF007269      TTGAGAAATCACGAGCATACAGTCTTGACAAAAGGTTTCGTCTTGATCATATTTATATCA
PPI-AtCPP     TTGAGAAATCACGAGCATACAG--------------------------------------
BASF_AT2      TTGAGAAATCACGAGCATACAG--------------------------------------
afc1          TTGAGAAATCACGAGCATACAG--------------------------------------
BASF_AT1      TTGAGAAATCACGAGCATACAG--------------------------------------
PPI-BnCPP     TTGAGAAATCTCGAGCTTACAG--------------------------------------
BASF-Corn     ------------------------------------------------------------

PPI-GmCPP     ------------------------------------------TCTTGATAAA---AGCCA
BASF-Gm       ------------------------------------------TCTTGATAAA---AGCCA
AT4g01320     ------------------------GGATATCATCACTGAGAACTTTAATATATGCAGCTA
AF007269      TTTTAGTTTTTTATAATTGCCAGGGGATATCATCACTGAGAACTTTAATATATGCAGCTA
PPI-AtCPP     ------------------------------------------TCTTGACAAA---AGCTA
BASF_AT2      ------------------------------------------TCTTGACAAA---AGCTA
afc1          ------------------------------------------TCTTGACAAA---AGCTA
BASF_AT1      ------------------------------------------TCTTGACAAA---AGCTA
PPI-BnCPP     ------------------------------------------TCTTGACAAA---AGCCA
BASF-Corn     ------------------------------------------------------------
```

TABLE 18A-continued

ClustalW Nucleic Acid Analysis of CaaX Prenyl Protease

```
PPI-GmCPP     CTTCCATTTTGTTCACGAGTTTGTGACAATAGTGACAGACTCTACAATTTTGTACTTTGG
BASF-Gm       CTTCCATTTTGTTCACGAGTTTGTGACAATAGTGACAGACTCTACAATTTTGTACTTTGG
AT4g01320     TTTTCACTTTGTTCATGAGTTTGTAACTATACTTATGGACTCTGCAATTTTGTTCTTTGG
AF007269      TTTTCACTTTGTTCATGAGTTTGTAACTATACTTATGGACTCTGCAATTTTGTTCTTTGG
PPI-AtCPP     TTTTCACTTTGTTCATGAGTTTGTAACTATACTTATGGACTCTGCAATTTTGTTCTTTGG
BASF_AT2      TTTTCACTTTGTTCATGAGTTTGTAACTATACTTATGGACTCTGCAATTTTGTTCTTTGG
afc1          TTTTCACTTTGTTCATGAGTTTGTAACTATACTTATGGACTCTGCAATTTTGTTCTTTGG
BASF_AT1      TTTTCACTTTGTTCATGAGTTTGTAACTATACTTATGGACTCTGCAATTTTGTTCTTTGG
PPI-BnCPP     TTTTCACTTTGTTCATGAGTTTGTTACTATACTTATGGACTCTGCGATTCTGTTCTTTGG
BASF-Corn     ------------------------------------------------------------

PPI-GmCPP     GGTATTGCCCTGGTTTTGGAAG--------------------------------------
BASF-Gm       GGTATTGCCCTGGTTTTGGAAG--------------------------------------
AT4g01320     GATCTTGCCTTGGTTTTGGAAG--------------------------------------
AF007269      GATCTTGCCTTGGTTTTGGAAGGTACATATCTGGTTTCGGTATACAGTATCTCATTTTGA
PPI-AtCPP     GATCTTGCCTTGGTTTTGGAAG--------------------------------------
BASF_AT2      GATCTTGCCTTGGTTTTGGAAG--------------------------------------
afc1          GATCTTGCCTTGGTTTTGGAAG--------------------------------------
BASF_AT1      GATCTTGCCTTGGTTTTGGAAG--------------------------------------
PPI-BnCPP     GATCTTGCCTTGGTTTTGGAAG--------------------------------------
BASF-Corn     ------------------------------------------------------------

PPI-GmCPP     ------------------------------------------------AAATCAGGAGAT
BASF-Gm       ------------------------------------------------AAATCAGGAGAT
AT4g01320     ------------------------------------------------ATGTCTGGAGCT
AF007269      ATATAGAGTTGTTACATTACAATTGTAAAGTTTTCATTTTTACCTTAGATGTCTGGAGCT
PPI-AtCPP     ------------------------------------------------ATGTCTGGAGCT
BASF_AT2      ------------------------------------------------ATGTCTGGAGCA
afc1          ------------------------------------------------ATGTCTGGAGCT
BASF_AT1      ------------------------------------------------ATGTCTGGAGCT
PPI-BnCPP     ------------------------------------------------ATATCTGGCGGC
BASF-Corn     ------------------------------------------------------------

PPI-GmCPP     TTTATGACAATAGCTGGTTTCAATGCTGAGAATGAAATACTGCATACCCTTGCCTTCTTA
BASF-Gm       TTTATGACAATAGCTGGTTTCAATGCTGAGAATGAAATACTGCATACCCTTGCCTTCTTA
AT4g01320     GTTTTACCGAGGTTGGGCCTTGATCCAGAGAATGAAATACTGCATACTCTTTCATTCTTG
AF007269      GTTTTACCGAGGTTGGGCCTTGATCCAGAGAATGAAATACTGCATACTCTTTCATTCTTG
PPI-AtCPP     GTTTTACCGAGGTTGGGCCTTGATCCGGAGAATGAAATACTGCATACTCTTTCATTCTTG
BASF_AT2      GTTTTACCGAGGTTGGGCCTTGATCCAGAGAATGAAATACTGCATACTCTTTCATTCTTG
afc1          GTTTTACCGAGGTTGGGCCTTGATCCAGAGAATGAAATACTGCATACTCTTTCATTCTTG
BASF_AT1      GTTTTACCGAGGTTGGGCCTTGATCCAGAGAATGAAATACTGCATACTCTTTCATTCTTG
PPI-BnCPP     TTTCTACCAATGGTGGGACTCGATCCAGAGAATGAAATCCTGCACACTCTTTCATTCTTG
BASF-Corn     ------------ACGAGGCTGAGTGCTGAGAATGAGATAATACACACCCTTGCTTTCTTA
                              *  *   * * ******** **  * ** ** *** * *****

PPI-GmCPP     GCAGGGCTGATGATTTGGTCACAG------------------------------------
BASF-Gm       GCAGGGCTGATGATTTGGTCACAG------------------------------------
AT4g01320     GCTGGTGTTATGACATGGTCACAG------------------------------------
AF007269      GCTGGTGTTATGACATGGTCACAGGTGTTCCAAATAAACCCCTTCATATAGTCCTATACG
PPI-AtCPP     GCTGGTGTTATGACATGGTCACAG------------------------------------
BASF_AT2      GCTGGTGTTATGACATGGTCACAG------------------------------------
afc1          GCTGGTGTTATGACATGGTCACAG------------------------------------
BASF_AT1      GCTGGTGTTATGACATGGTCACAC------------------------------------
PPI-BnCPP     GCTGGTCTTATGACATGGTCACAG------------------------------------
BASF-Corn     GCTGGTTCCATGGTTTGGTCGCAG------------------------------------
              ** **    ***   ***** **

PPI-GmCPP     ------------------------------------------------------------
BASF-Gm       ------------------------------------------------------------
AT4g01320     ------------------------------------------------------------
AF007269      TTTAGCATCAPAATATCTATTTTCTTAAGATAATAATATTTCTTTTATATTCTGATGCAG
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------

PPI-GmCPP     ATAACAGATTTGCCCTTTTCTCTGTACTCAACTTTTGTGATTGAGGCCCGTCATGGTTTT
BASF-Gm       ATAACAGATTTGCCCTTTTCTCTGTACTCAACTTTTGTGATTGAGGCCCGTCATGGTTTT
AT4g01320     ATCACTGATTTGCCATTTTCTTTGTACTCAACTTTCGTGATCGAGTCTCGGCATGGGTTC
AF007269      ATCACTGATTTGCCATTTTCTTTGTACTCAACTTTCGTGATCGAGTCTCGGCATGGGTTC
PPI-AtCPP     ATCACTGATTTGCCATTTTCTTTGTACTCAACTTTCGTGATCGAGTCTCGGCATGGGTTC
BASF_AT2      ATCACTGATTTGCCATTTTCTTTGTACTCAACTTTCGTGATCGAGTCTCGGCATGGGTTC
afc1          ATCACTGATTTGCCATTTTCTTTGTACTCAACTTTCGTGATCGAGTCTCGGCATGGGTTC
BASF_AT1      ATCACTGATTTGCCATTTTCTTTGTACTCAACTTTCGTGATCGAGTCTCGGCATGGGTTC
```

TABLE 18A-continued

ClustalW Nucleic Acid Analysis of CaaX Prenyl Protease

```
PPI-BnCPP     ATCACTGATTTGCCATTTTCTTTGTACTCAACTTTCGTGATCGAGTCTCGGCATGGGTTC
BASF-Corn     ATTACAGACTTGCCGTTCTCTCTATTCAACTTTTGTTATAGAGGCTCGACATGGTTTT
              ** ** ** ***** ** *** * ** ******** ** **  *** * ** ***** **

PPI-GmCPP     AATAAG------------------------------------------------------
BASF-Gm       AATAAG------------------------------------------------------
AT4g01320     AACAAA------------------------------------------------------
AF007269      AACAAAGTATGTCGTATTTCCAACACTACCTTGTGACTTACGTTTTTTTATCAGAGATGT
PPI-AtCPP     AACAAA------------------------------------------------------
BASF_AT2      AACAAA------------------------------------------------------
afc1          AACAAA------------------------------------------------------
BASF_AT1      AACAAA------------------------------------------------------
PPI-BnCPP     AACAAA------------------------------------------------------
BASF-Corn     AACAAG------------------------------------------------------
              ** **

PPI-GmCPP     --------------------------------CAAACACCATGGTTATTCTTTAGGGACA
BASF-Gm       --------------------------------CAAACACCATGGTTATTCTTTAGGGACA
AT4g01320     --------------------------------CAAACAATATGGATGTTCATTAGGGACA
AF007269      GGATTAATTTGCTTCTAAATTCTGTTGACAGCAAACAATATGGATGTTCATTAGGGACA
PPI-AtCPP     --------------------------------CAAACAATATGGATGTTCATTAGGGACA
BASF_AT2      --------------------------------CAAACAATATGGATGTTCATTAGGGACA
afc1          --------------------------------CAAACAATATGGATGTTCATTAGGGACA
BASF_AT1      --------------------------------CAAACAATATGGATGTTCATTAGGGACA
PPI-BnCPP     --------------------------------CAAACAATATGGATGTTCATTAGGGACA
BASF-Corn     --------------------------------CAAACTATATGGCTCTTCATTAGGGATA
                                              *****   **** * *** ******* *

PPI-GmCPP     TGCTTAAAGGAATTTTCCTTTCTGTAATAATTGGTCCACCTATTGTGGCTGCAATCATTG
BASF-Gm       TGCTTAAAGGAATTTTCCTTTCCGTAATAATTGGTCCACCTATTGTGGCTGCAATCATTG
AT4g01320     TGATCAAAGGAACATTCCTCTCTGTCATACTAGGCCCACCCATTGTTGCTGCGATAATTT
AF007269      TGATCAAAGGAACATTCCTCTCTGTCATACTAGGCCCACCCATTGTTGCTGCGATAATTT
PPI-AtCPP     TGATCAAAGGAACATTCCTCTCTGTCATACTAGGCCCACCCATTGTTGCTGCGATAATTT
BASF_AT2      TGATCAAAGGAACATTCCTCTCTGTCATACTAGGCCCACCCATTGTTGCTGCGATAATTT
afc1          TGATCAAAGGAACATTCCTCTCTGTCATACTAGGCCCACCCATTGTTGCTGCGATAATTT
BASF_AT1      TGATCAAAGGAACATTCCTCTCTGTCATACTAGGCCCACCCATTGTTGCCGCGATAATTT
PPI-BnCPP     TGATCAAAGGAATACTCCTCTCTGTCATACCTGCCCCTCCTATCGTTGCCGCAATTATTG
BASF-Corn     TGATCAAAGGAATTTTACTATCCATGATATTGGGGCCACCAATCGTGGCTGCTATCATCT
              ** * *******   * ** **  * ***   *  ** ** ** ** ** ** ** **

PPI-GmCPP     TAATAGTACAG-------------------------------------------------
BASF-Gm       TAATAGTACAG-------------------------------------------------
AT4g01320     TCATAGTCCAG-------------------------------------------------
AF007269      TCATAGTCCAGGTTTGATGATTCTGGATTCATCTTATTTCTGAGTTTTTCACATGGATGA
PPI-AtCPP     TCATAGTCCAG-------------------------------------------------
BASF_AT2      TCATAGTCCAG-------------------------------------------------
afc1          TCATAGTCCAG-------------------------------------------------
BASF_AT1      TCATAGTCCAG-------------------------------------------------
PPI-BnCPP     TTATAGTTCAG-------------------------------------------------
BASF-Corn     ACATAGTACAG-------------------------------------------------
                ***** ***

PPI-GmCPP     ------------------------------------------------------------
BASF-Gm       ------------------------------------------------------------
AT4g01320     ------------------------------------------------------------
AF007269      CTATTCTCCATTGAGTGTGAGCTTCAAAGTTTTTAGTTTTCGTGTTAAAAATTTAAAATT
PPI-AtCPP     ------------------------------------------------------------
BASF_AT2      ------------------------------------------------------------
afc1          ------------------------------------------------------------
BASF_AT1      ------------------------------------------------------------
PPI-BnCPP     ------------------------------------------------------------
BASF-Corn     ------------------------------------------------------------

PPI-GmCPP     ------------------------------------AAAGGAGGTCCATACTTGGCCATC
BASF-Gm       ------------------------------------AAAGGAGGTCCATACTTGGCCATC
AT4g01320     ------------------------------------AAAGGAGGTCCTTATCTTGCCATC
AF007269      TGCTTCTCTGAGCATGAAGTTTCTATCTTTTTCCAGAAAGGAGGTCCTTATCTTGCCATC
PPI-AtCPP     ------------------------------------AAAGGAGGTCCTTATCTTGCCATC
BASF_AT2      ------------------------------------AAAGGAGGTCCTTATCTTGCCATC
afc1          ------------------------------------AAAGGAGGTCCTTATCTTGCCATC
BASF_AT1      ------------------------------------AAAGGAGGTCCTTATCTTGCCATC
PPI-BnCPP     ------------------------------------AAAGGAGGTCCTTACCTCGCCATC
BASF-Corn     ------------------------------------ATTGGAGGACCTTACCTGGCTATA
                                                  *  ***** ** **  * ** **

PPI-GmCPP     TATCTTTGGGTTTTTACGTTTGGTCTTTCTATTGTGATGATGACCCTTTATCCAGTACTA
BASF-Gm       TATCTTTGGGTTTTTACGTTTGGTCTTTCTATTGTGATGATGACCCTTTATCCAGTACTA
AT4g01320     TATCTGTGGGCATTCATGTTTATCCTGTCTCTAGTGATGATGACTATATACCCGGTCTTG
```

TABLE 18A-continued

| ClustalW Nucleic Acid Analysis of CaaX Prenyl Protease | |
|---|---|
| AF007269 | TATCTGTGGGCATTCATGTTTATCCTGTCTCTAGTGATGATGACTATATACCCGGTCTTG |
| PPI-AtCPP | TATCTGTGGGCATTCATGTTTATCCTGTCTCTAGTGATGATGACTATATACCCGGTCTTG |
| BASF_AT2 | TATCTGTGGGCATTCATGTTTATCCTGTCTCTAGTGATGATGACTATATACCCGGTCTTG |
| afc1 | TATCTGTGGGCATTCATGTTTATCCTGTCTCTAGTGATGATGACTATATACCCGGTCTTG |
| BASF_AT1 | TATCTGTGGGCATTCATGTTTATCCTGTCTCTAGTGATGATGACTATATACCCGGTCTTG |
| PPI-BnCPP | TATCTGTGGGCATTCATGTTTATCCTGTCTCTAGTGATGATGACTATATACCCTGTTTTG |
| BASF-Corn | TATCTCTGGGGTTTTATGTTTGTATTAGCTCTACTGATGATGACAATATACCCCATTGTG |
| | ***** ****  ** * ****    *  ** *   **********  * ** **  *  * |
| | |
| PPI-GmCPP | ATAGCTCCACTCTTCAATAAGTTCACTCCA------------------------------ |
| BASF-Gm | ATAGCTCCACTCTTCAATAAGTTCACTCCA------------------------------ |
| AT4g01320 | ATAGCACCGCTCTTCAACAAGTTCACTCCT------------------------------ |
| AF007269 | ATAGCACCGCTCTTCAACAAGTTCACTCCTGTGTGTATTTCTGTCATGGCCATTTTACAA |
| PPI-AtCPP | ATAGCACCGCTCTTCAACAAATTCACTCCT------------------------------ |
| BASF_AT2 | ATAGCACCGCTCTTCAACAAGTTCACTCCT------------------------------ |
| afc1 | ATAGCACCGCTCTTCAACAAGTTCACTCCT------------------------------ |
| BASF_AT1 | ATAGCACCGCTCTTCAACAAGTTCACTCCT------------------------------ |
| PPI-BnCPP | ATTGCACCTCTTTTCAACAAGTTCACTCCT------------------------------ |
| BASF-Corn | ATAGCTCCTCTGTTCAACAAGTTCACTCCT------------------------------ |
| | ** ** ** ** ***** ** ******** |
| | |
| PPI-GmCPP | ------------------------------------------------------------ |
| BASF-Gm | ------------------------------------------------------------ |
| AT4g01320 | ------------------------------------------------------------ |
| AF007269 | TTCACTGCTTGTTTGCATATGTTGTTACCAGACAATATAATCTCCCGCTTTTTTATGGCT |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | ------------------------------------------------------------ |
| | |
| PPI-GmCPP | ----CTTCCAGATGGTCAACTCAGGGAGAAAATCGAGAAACTTGCTTCCTCCCTCAACTA |
| BASF-Gm | ----CTTCCAGATGGTCAACTCAGGGAGAAAATCGAGAAACTTGCTTCCTCCCTCAACTA |
| AT4g01320 | ----CTTCCAGATGGAGACCTCCGGGAGAAGATTGAGAAACTTGCTTCTTCTCTAAAGTT |
| AF007269 | ATAGCTTCCAGATGGAGACCTCCGGGAGAAGATTGAGAAACTTGCTTCTTCTCTAAAGTT |
| PPI-AtCPP | ----CTTCCAGATGGAGACCTCCGGGAGAAGATTGAGAAACTTGCTTCTTCCCTAAAGTT |
| BASF_AT2 | ----CTTCCAGATGGAGACCTCCGGGAGAAGATTGAGAAACTTGCTTCTTCTCTAAAGTT |
| afc1 | ----CTTCCAGATGGAGACCTCCGGGAGAAGATTGAGAAACTTGCTTCTTCTCTAAAGTT |
| BASF_AT1 | ----CTTCCAGATGGAGACCTCCGGGAGAAGATTGAGAAACTTGCTTCTTCTCTAAAGTT |
| PPI-BnCPP | ----CTTCCTGATGGAGACCTCCGGGAGAAGATTGAGAAACTTGCTTCTTCTCTAAAGTT |
| BASF-Corn | ----CTTCCTGAAGGAGTCCTCAGGGAAAAAATAGAGAAGCTGGCAGCTTCCCTCAAGTT |
| | ***** ** **     *** ****  ** **  ***** ** **  * ** ** ** * |
| | |
| PPI-GmCPP | TCCGTTAAAGAAACTATTTGTTGTCGATGGATCCACAAGATCAAGTCACAGCAATG---- |
| BASF-Gm | TCCGTTAAAGAAACTATTTGTTGTCGATGGATCCACAAGATCAAGTCACAGCAATG---- |
| AT4g01320 | TCCTTTGAAGAAGCTGTTTGTTGTCGATGGATCTACAAGGTCAAGCCATAGCAATG---- |
| AF007269 | TCCTTTGAAGAAGCTGTTTGTTGTCGATGGATCTACAAGGTCAAGCCATAGCAATGTGAG |
| PPI-AtCPP | TCCTTTGAAGAAGCTGTTTGTTGTCGATGGATCTACAAGGTCAAGCCATAGCAATG---- |
| BASF_AT2 | TCCTTTGAAGAAGCTGTTTGTTGTCGATGGATCTACAAGGTCAAGCCATAGCAATG--- |
| afc1 | TCCTTTGAAGAAGCTGTTTGTTGTCGATGGATCTACAAGGTCAAGCCATAGCAATG---- |
| BASF_AT1 | TCCTTTGAAGAAGCTGTTTGTTGTCGATGGATCTACAAGGTCAAGCCATAGCAATG--- |
| PPI-BnCPP | TCCTCTGAAGAAGCTGTTTGTTGTCGATGGATCTACAAGGTCAAGCCATAGTAATG---- |
| BASF-Corn | TCCTTTGAAAAAGCTTTTCGTGGTAGATGGGTCTACCAGATCAAGCCACAGTAATG--- |
| | ***  * ** ** ** ** ** ** ***** ** ** ** ***** ** ** **** |
| | |
| PPI-GmCPP | ------------------------------------------------------------ |
| BASF-Gm | ------------------------------------------------------------ |
| AT4g01320 | ------------------------------------------------------------ |
| AF007269 | AAGCTTGAGATCTCTTCCTACCTACTTTACTCTAGTTTACCATTAGAAGCTTACGTATCT |
| PPI-AtCPP | ------------------------------------------------------------ |
| BASF_AT2 | ------------------------------------------------------------ |
| afc1 | ------------------------------------------------------------ |
| BASF_AT1 | ------------------------------------------------------------ |
| PPI-BnCPP | ------------------------------------------------------------ |
| BASF-Corn | ------------------------------------------------------------ |
| | |
| PPI-GmCPP | ----------------CCTATATGTATGGATTCTTCAAGAACAAGAGGATTGTCCCTTA |
| BASF-Gm | ----------------CCTATATGTATGGATTCTTCAAGAACAAGAGGATTGTCCTTTA |
| AT4g01320 | ----------------CTTACATGTATGGTTTCTTTAAGAACAAAAGGATTGTTCTTTAT |
| AF007269 | TGTTACATCATACAGGCTTACATGTATGGTTTCTTTAAGAACAAAAGGATTGTTCTTTAP |
| PPI-AtCPP | ----------------CTTACATGTATGGTTTCTTTAAGAACAAAAGGATTGTTCTTTAT |
| BASF_AT2 | ----------------CTTACATGTATGGTTTCTTTAAGAACAAAAGGATTGTTCTTTAT |
| afc1 | ----------------CTTACATGTATGGTTTCTTTAAGAACAAAAGGATTGTTCTTTAT |
| BASF_AT1 | ----------------CTTACATGTATGGTTTCTTTAAGAACAAAAGGATTGTTCTTTA |
| PPI-BnCPP | ----------------CTTACATGTATGGTTTCTTCAAGAACAAAAGGATTGTTCTTTAT |
| BASF-Corn | ----------------CCTACATGTATGGTTTTTTCAAGAACAAGCGCATAGTACTCTAT |
| | * ** ******** ** ** ********  * ** ** *  *** |

TABLE 18A-continued

ClustalW Nucleic Acid Analysis of CaaX Prenyl Protease

```
PPI-GmCPP    GACACATTAATTCAACAG------------------------------------------
BASF-Gm      GACACATTAATTCAACAG------------------------------------------
AT4g01320    GATACGTTGATTCAGCAG------------------------------------------
AF007269     GATACGTTGATTCAGCAGGTACTGTGACTCTTGATGCTTCAAACGAGCTATACTCACATT
PPI-AtCPP    GATACGTTGATTCAGCAG------------------------------------------
BASF_AT2     GATACGTTGATTCAGCAG------------------------------------------
afc1         GATACGTTGATTCAGCAG------------------------------------------
BASF_AT1     GATACGTTGATTCAGCAG------------------------------------------
PPI-BnCPP    GACACATTGATTCAGCAG------------------------------------------
BASF-Corn    GACACATTGATTCAGCAG------------------------------------------
             ** ** ** ***** ***

PPI-GmCPP    --------------------------------------------TGCAAAGACGATGAGG
BASF-Gm      --------------------------------------------TGCAAAGACGATGAGG
AT4g01320    --------------------------------------------TGCAAGAATGAGGATG
AF007269     TCTGTTTCTGGTTCTGAAACATAACATAATCTTCTATTGTGCAGTGCAAGAATGAGGATG
PPI-AtCPP    --------------------------------------------TGCAAGAATGAGGATG
BASF_AT2     --------------------------------------------TGCAAGAATGAGGATG
afc1         --------------------------------------------TGCAAGAATGAGGATG
BASF_AT1     --------------------------------------------TGCAAGAATGAGGATG
PPI-BnCPP    --------------------------------------------TGCCAGAATGAGAATG
BASF-Corn    --------------------------------------------TGTAGCAATGAGGATG
                                                         **     * **  * *

PPI-GmCPP    AAATTGTTGCTGTTATTGCCCATGAGTTGGGACACTGGAAGCTCAACCATACTGTGTACA
BASF-Gm      AAATTGTTGCTGTTATTGCCCATGAGTTGGGACACTGGAAGCTCAACCATACTGTGTACA
AT4g01320    AAATTGTGGCGGTTATTGCACACGAGCTTGGACATTGGAAACTGAATCACACTACATACT
AF007269     AAATTGTGGCGGTTATTGCACACGAGCTTGGACATTGGAAACTGAATCACACTACATACT
PPI-AtCPP    AAATTGTGGCGGTTATTGCACACGAGCTTGGACATTGGAAACTGAATCACACTACATACT
BASF_AT2     AAATTGTGGCGGTTATTGCACACGAGCTTGGACATTGGAAACTGAATCACACTACATACT
afc1         AAATTGTGGCGGTTATTGCACACGAGCTTGGACATTGGAAACTGAATCACACTACATACT
BASF_AT1     AAATTGTGGCGGTTATTGCACACGAGCTTGGACATTGGAAACTGAATCACACTACATACT
PPI-BnCPP    AAATTGTGGCGGTTATTGCACACGAGCTGGGACACTGGAAGCTGAATCACACTACATACT
BASF-Corn    AGATAGTTTCTGTTATAGCACATGAACTTGGACACTGGAAACTCAATCATACTGTCTATT
             * ** **  * ***** ** ** **  * ***** ***** ** ** ** ***    **

PPI-GmCPP    CATTTGTTGCTATGCAG-------------------------------------------
BASF-Gm      CATTTGTTGCTATGCAG-------------------------------------------
AT4g01320    CGTTCATTGCAGTTCAA-------------------------------------------
AF007269     CGTTCATTGCAGTTCAAGTGAGGCTCAACCGACAGTTCAAAAACTTACTCACATCTACAT
PPI-AtCPP    CGTTCATTGCAGTTCAA-------------------------------------------
BASF_AT2     CGTTCATTGCAGTTCAA-------------------------------------------
afc1         CGTTCATTGCAGTTCAA-------------------------------------------
BASF_AT1     CGTTCATTGCAGTTCAA-------------------------------------------
PPI-BnCPP    CGTTCATTGCTGTTCAA-------------------------------------------
BASF-Corn    CCTTTGTAGCTGTCCAG-------------------------------------------
             * **  * **  * **

PPI-GmCPP    ---------------------------------------------------ATTCTTACA
BASF-Gm      ---------------------------------------------------ATTCTTACA
AT4g01320    ---------------------------------------------------ATCCTTGCC
AF007269     TTCACTTAAGAAATCATGTCTTATGACCCTCTCTCAATGTTTTGCTTGCAGATCCTTGCC
PPI-AtCPP    ---------------------------------------------------ATCCTTGCC
BASF_AT2     ---------------------------------------------------ATCCTTGCC
afc1         ---------------------------------------------------ATCCTTGCC
BASF_AT1     ---------------------------------------------------ATCCTTGCC
PPI-BnCPP    ---------------------------------------------------ATCCTTGCC
BASF-Corn    ---------------------------------------------------CTGCTTATG
                                                                 * ***

PPI-GmCPP    CTTCTACAATTTGGAGGATATACACTAGTGCGAAATTCAGCTGATCTGTATCGAAGCTTT
BASF-Gm      CTTCTACAATTTGGAGGATATACACTAGTGCGAAATTCAGCTGATCTGTATCGAAGCTTT
AT4g01320    TTCTTACAATTTGGAGGATACACTCTTGTCAGAAACTCCACTGATCTCTTCAGGAGTTTC
AF007269     TTCTTACAATTTGGAGGATACACTCTTGTCAGAAACTCCACTGATCTCTTCAGGAGTTTC
PPI-AtCPP    TTCTTACAATTTGGAGGATACACTCTTCTCAGAAACTCCACTGATCTCTTCAGGAGTTTC
BASF_AT2     TTCTTACAATTTGGAGGATACACTCTTGTCAGAAACTCCACTGATCTCTTCAGGAGTTTC
afc1         TTCTTACAATTTGGAGGATACACTCTTGTCAGAAACTCCACTGATCTCTTCAGGAGTTTC
BASF_AT1     TTCTTACAATTTGGAGGATACACTCTTGTCAGAAACTCCACTGATCTCTTCAGGAGTTTC
PPI-BnCPP    TTCTTGCAATTTGGAGGATACACTCTTGTCAGAAACTCCACTGATCTCTTCAGGAGTTTT
BASF-Corn    TTTCTTCAATTTGGAGGATATACTCTAGTAAGGAGCTCCAAAGATCTATTTGGAAGTTTT
              *  * ************** ** **  *  * *  **    ***** *   *  ** **

PPI-GmCPP    GGGTTTGATACGCAGCCAGTCCTCATTGGGCTCATCATATTTCAG---------------
BASF-Gm      GGGTTTGATACGCAGCCAGTCCTCATTGGGCTCATCATATTTCAG---------------
AT4g01320    GGATTTGATACACAGCCTGTTCTCATTGGTTTGATCATATTTCAG---------------
AF007269     GGATTTGATACACAGCCTGTTCTCATTGGTTTGATCATATTTCAGGTTTGTTATTTTTGC
PPI-AtCPP    GGATTTGATACACAGCCTGTTCTCATTGGTTTGATCATATTTCAG---------------
```

TABLE 18A-continued

ClustalW Nucleic Acid Analysis of CaaX Prenyl Protease

```
BASF_AT2     GGATTTGATACACAGCCTGTTCTCATTGGTTTGATCATATTTCAG---------------
afc1         GGATTTGATACACAGCCTGTTCTCATTGGTTTGATCATATTTCAG---------------
BASF_AT1     GGATTTGATACACAGCCTGTTCTCATTGGTTTGATCATATTTCAG---------------
PPI-BnCPP    GGTTTTGATACACAACCAGTTCTCATTGGTTTGATCATATTTCAG---------------
BASF-Corn    GGCTTCAAGGACCAGCCAGTAATAATTGGATTGATCATTTTCCCG---------------
             ** **  *    ** ** **  * *****  * ***** ** * *

PPI-GmCPP    ------------------------------------------------------------
BASF-Gm      ------------------------------------------------------------
AT4g01320    ------------------------------------------------------------
AF007269     CTTTTGACACTAATCTAATGAATCAAGGATGGATTAAGAAAAAAAAACTCTAAACCTTTG
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ---------------------------CATACTGTAATCCCACTTCAGCAATTGGTCAGC
BASF-Gm      ---------------------------CATACTGTAATCCCACTTCAGCAATTGGTCAGC
AT4g01320    ---------------------------CACACTGTAATACCACTGCAACATCTAGTAAGC
AF007269     GTTATATCTCCTGTCTGATTATCACAGCACACTGTAATACCACTGCAACATCTAGTAAGC
PPI-AtCPP    ---------------------------CACACTGTAATACCACTGCAACATCTAGTAAGC
BASF_AT2     ---------------------------CACACTGTAATACCACTGCAACATCTAGTAAGC
afc1         ---------------------------CACACTGTAATACCACTGCAACATCTAGTAAGC
BASF_AT1     ---------------------------CACACTGTAATACCACTGCAACATCTAGTAAGC
PPI-BnCPP    ---------------------------CACACTGTAATACCACTTCAACACCTAGTAAGC
BASF-Corn    ---------------------------CACACCATAATACCCATCCAACACCTTCTGAGC
                                        ** **  **** **  * ** **     * ***

PPI-GmCPP    TTTGGTCTGAACCTAGTCAGCCGATCATTTGAATTTCAGG--------------------
BASF-Gm      TTTGGTCTGAACCTAGTCAGCCGATCATTTGAATTTCAGG--------------------
AT4g01320    TTTGGCCTGAACCTCGTTAGTCGAGCGTTTGAGTTTCAGG--------------------
AF007269     TTTGGCCTGAACCTCGTTAGTCGAGCGTTTGAGTTTCAGGTACCATCTTACAATCCCTCA
PPI-AtCPP    TTTGGCCTGAACCTCGTTAGTCGAGCGTTTGAGTTTCAGG--------------------
BASF_AT2     TTTGGCCTGAACCTCGTTAGTCGAGCGTTTGAGTTTCAGG--------------------
afc1         TTTGGCCTGAACCTCGTTAGTCGAGCGTTTGAGTTTCAGG--------------------
BASF_AT1     TTTGGCCTCAACCTTGTTAGTCGAGCGTTTGAGTTTCAGG--------------------
PPI-BnCPP    TTTGACCTCAACCTTGTTAGTCGAGCGTTTGAGTTTCAGG--------------------
BASF-Corn    TTTCGCCTGAACCTTGTCAGCAGAGCATTTGAATTTCAGG--------------------
             ***   ** ***** ** **  ** * ***** *******

PPI-GmCPP    ------------------------------------------------------------
BASF-Gm      ------------------------------------------------------------
AT4g01320    ------------------------------------------------------------
AF007269     AGATCCAACCATAGTTTCTTTATTGCAATGGCAGCCTCATCTACTAATCTGAGTTAACGT
PPI-AtCPP    ------------------------------------------------------------
BASF_AT2     ------------------------------------------------------------
afc1         ------------------------------------------------------------
BASF_AT1     ------------------------------------------------------------
PPI-BnCPP    ------------------------------------------------------------
BASF-Corn    ------------------------------------------------------------

PPI-GmCPP    ------------CTGATGGCTTTGCCAAGAAGCTTGGATATGCATCTGGATTACGCGGTG
BASF-Gm      ------------CTGATGGCTTTGCCAAGAAGCTTGGATATGCATCTGGATTACGCGGTG
AT4g01320    ------------CTGATGCTTTTGCTGTGAAGCTTGGCTATGCAAAAGATCTTCGTCCTG
AF007269     TCCTTTTGCAGGCTGATGCTTTTGCTGTGAAGCTTGGCTATGCAAAAGATCTTCGTCCTG
PPI-AtCPP    ------------CTGATGCTTTTGCTGTGAAGCTTGACTATGCAAAAGATCTTCGTCCTG
BASF_AT2     ------------CTGATGCTTTTGCTGTGAAGCTTGGCTATGCAAAAGATCTTCGTCCTG
afc1         ------------CTGATGCTTTTGCCGTGAAGCTTGGCTATGCAAAAGATCTTCGTCCTG
BASF_AT1     ------------CTGATGCTTTTGCTGTGAAGCTTGGCTATGCAAAAGATCTTCGTCCTA
PPI-BnCPP    ------------CTGATGCTTTTGCAGTGAATCTTGGTTATGCAAAGGATCTACGTCCTG
BASF-Corn    ------------CTGATGCCTTTGCCAAGAACCTTGGATATGCCCCTCAGCTCCGAGCAG
                         ******  *****   *** ****  *****        * **

PPI-GmCPP    GTCTTGTGAAACTACAGG------------------------------------------
BASF-Gm      GTCTTGTGAAACTACAGG------------------------------------------
AT4g01320    CTCTAGTGAAACTACAGGTCAGAGAAGATAACAACAGAACACAAACTGTTACCTCAATTT
AF007269     CTCTAGTGAAACTACAGGTCAGAGAAGATAACAACAGAACACAAACTGTTACCTCAATTT
PPI-AtCPP    CTCTAGTGAAACTACAGG------------------------------------------
BASF_AT2     CTCTAGTGAAACTACAGG------------------------------------------
afc1         CTCTAGTGAAACTACAGG------------------------------------------
BASF_AT1     CTCTAGTGAAACTACAGG------------------------------------------
PPI-BnCPP    CCCTAGTGAAGCTACAGG------------------------------------------
BASF-Corn    CCCTTGTTAAACTACAGG------------------------------------------
               ** ** **  *******
```

TABLE 18A-continued

ClustalW Nucleic Acid Analysis of CaaX Prenyl Protease

```
PPI-GmCPP      ------------------------------------------AGGAGAATCTGTCAGCTA
BASF-Gm        ------------------------------------------AGGAGAATCTGTCAGCTA
AT4g01320      GTGTCACACACTTAAATGGATTTTTTGTTGGGATTTTGCAGGAAGAGAACTTATCAGCAA
AF007269       GTGTCACACACTTAAATGGATTTTTTGTTGGGATTTTGCAGGAAGAGAACTTATCAGCAA
PPI-AtCPP      ------------------------------------------AAGAGAACTTATCAACAA
BASF_AT2       ------------------------------------------AAGAGAACTTATCAGCAA
afc1           ------------------------------------------AAGAGAACTTATCAGCAA
BASF_AT1       ------------------------------------------AAGAGAACTTATCAGCAA
PPI-BnCPP      ------------------------------------------AAGAGAACTTATCAGCGA
BASF-Corn      ------------------------------------------AGGAGAACTTGTCTGCGA
                                                         * *****  * **  * *

PPI-GmCPP      TGAATACAGATCCTTGGTACTCTGCTTATCACTATTCTCATCCTCCCCTTGTTGAAAGAT
BASF-Gm        TGAATACAGATCCTTGCT--CGTGCCG---------------------------------
AT4g01320      TGAACACTGATCCATTGTACTCAGCTTATCACTACTCACATCCTCCTCTTGTTGAAAGGC
AF007269       TGAACACTGATCCATTGTACTCAGCTTATCACTACTCACATCCTCCTCTTGTTGAAAGGC
PPI-AtCPP      TGAACACTGATCCATTGTACTCAGCTTATCACTACTCACATCCTCCTCTTGTTGAAAGGC
BASF_AT2       TGAAAACTGATCTATTGTACTCAGCTTATCACTACTCACATCCTCCTCTTGTTGAAAGGC
afc1           TGAACACTGATCCATTGCACTCAGCTTATCACTACTCACATCCTCCTCTTGTTGAAAGGC
BASF_AT1       TGAATACTGATCCATTGTACTCAGCTTATCACTACTCACATCCTCCTCTTGTTGAAAGGC
PPI-BnCPP      TGAACACAGACCCATTGTACTCAGCTTATCACTACTCACACCCTCCTCTTGTAGAGAGGC
BASF-Corn      TGAACACCGATCCTTGGTATTCGGCATATCACTACTCCCACCCACCACTCGTCGAGAGGC
               **** ** ** *  *        **

PPI-GmCPP      TGGCCGCGCTGGACGA---ACCGGATAAGAAGGAAGACTAA-------------------
BASF-Gm        ------------------------------------------------------------
AT4g01320      TTCGAGCCATTGATGG---AGAAGACAAGAAGACAGATTAA-------------------
AF007269       TTCGAGCCATTGATGG---AGAAGACAAGAAGACAGATTAA-------------------
PPI-AtCPP      TTCGAGCCACTGATGG---AGAAGACAAGAAGACAGATTAA-------------------
BASF_AT2       TTCGAGCCATTGATGG---AGAAGACAAGAAGACAGATTAA-------------------
afc1           TTCGAGCCATTGATGG---AGAAGACAAGAAGACAGATTAA-------------------
BASF_AT1       TTCGAGCCATTGATGG---AGAAGACAAGAAGACAGATTAA-------------------
PPI-BnCPP      TTCGAGCCATTGATGG---AGAAGACAAGAAGACAGATTAA-------------------
BASF-Corn      TGCAAGCTTTGGAAGATTCAGACGACAAAAAAGAAGATTAGTCGATCCTTGTATGAGGTT

PPI-GmCPP      ------------------------------------------------------------
BASF-Gm        ------------------------------------------------------------
AT4g01320      ------------------------------------------------------------
AF007269       ------------------------------------------------------------
PPI-AtCPP      ------------------------------------------------------------
BASF_AT2       ------------------------------------------------------------
afc1           ------------------------------------------------------------
BASF_AT1       ------------------------------------------------------------
PPI-BnCPP      ------------------------------------------------------------
BASF-Corn      TACATATGGATTTTTCCCTGCCACATGCACACCGATTCAGTGCTTGGATGGTGAGGGTTT

PPI-GmCPP      ------------------------------------------------------------
BASF-Gm        ------------------------------------------------------------
AT4g01320      ------------------------------------------------------------
AF007269       ------------------------------------------------------------
PPI-AtCPP      ------------------------------------------------------------
BASF_AT2       ------------------------------------------------------------
afc1           ------------------------------------------------------------
BASF_AT1       ------------------------------------------------------------
PPI-BnCPP      ------------------------------------------------------------
BASF-Corn      TGACATAGGAGTGTTGTCAAAGCTTTAGAGTGCATCTTTCGGTCAGGTGCAACAGCCTTT

PPI-GmCPP      ------------------------------------------------------------
BASF-Gm        ------------------------------------------------------------
AT4g01320      ------------------------------------------------------------
AF007269       ------------------------------------------------------------
PPI-AtCPP      ------------------------------------------------------------
BASF_AT2       ------------------------------------------------------------
afc1           ------------------------------------------------------------
BASF_AT1       ------------------------------------------------------------
PPI-BnCPP      ------------------------------------------------------------
BASF-Corn      CGGTCATTGAGACATATAAGCGAATTAGCTATTAAAAAAAACAGAACTGTTGCATCAAAA

PPI-GmCPP      ------------------------------------------------------------
BASF-Gm        ------------------------------------------------------------
AT4g01320      ------------------------------------------------------------
AF007269       ------------------------------------------------------------
PPI-AtCPP      ------------------------------------------------------------
BASF_AT2       ------------------------------------------------------------
afc1           ------------------------------------------------------------
BASF_AT1       ------------------------------------------------------------
```

TABLE 18A-continued

ClustalW Nucleic Acid Analysis of CaaX Prenyl Protease

```
PPI-BnCPP    ------------------------------------------------------------
BASF-Corn    AAAAAAAAAAAAAAGAAACAAAAAAAAAAAAAAAAAAAAAAAAAGAAAAAAAAAAAAAAAA

PPI-GmCPP    ----------------------------------------------------
BASF-Gm      ----------------------------------------------------
AT4g01320    ----------------------------------------------------
AF007269     ----------------------------------------------------
PPI-AtCPP    ----------------------------------------------------
BASF_AT2     ----------------------------------------------------
afc1         ----------------------------------------------------
BASF_AT1     ----------------------------------------------------
PPI-BnCPP    ----------------------------------------------------
BASF-Corn    AAAAAGTGCTCTGCGTTGTTACCACTGCTTGCCCTATAGTGATCGTATCAGA
```

TABLE 18B

ClustalW Amino Acid Analysis of CaaX Prenyl Protease

1: PPI-AtCPP SEQ ID NO: 98

2: PPI-BnCPP SEQ ID NO: 110

3: PPI-GmCPP SEQ ID NO: 113

4: BASF_AT1 SEQ ID NO: 117

5: BASF_AT2 SEQ ID NO: 119

6: BASF-Corn SEQ ID NO: 121

7: BASF-Gm SEQ ID NO: 123

8: AFC1 SEQ ID NO: 125

9: AT4g01320 SEQ ID NO: 127

10: AF007269 SEQ ID NO: 129

```
PPI-GmCPP    MAFPYMEAVVGFMILMYIFETYLDVRQHRALKLPTLPKTLEG-------VISQEKFEKSR
BASF-Gm      MAFPYMEAVVGFMILMYIFETYLDVRQHRALKLPTLPKTLEG-------VISQEKFEKSR
AF007269     MAIPFMETVVGFMIVMYIFETYLDLRQLTALKLPTLPKTLI-------------------
AT4g-AtCPP   MAIPFMETVVGFMIVMYIFETYLDLRQLTALKLPTLPKTLVGVISQEKFEKSRAYRDIIT
BASF_AT2     MAIPFMETVVGFMIVMYIFETYLDLRQLTALKLPTLPKTLVG-------VISQEKFEKSR
AFC1         MAIPFMETVVGFMIVMYIFETYLDLRQLTALKLPTLPKTLVG-------VISQEKFEKSR
BASF_AT1     MAIPFMETVVGFMIVMYIFETYLDLRQLTALKLPTLPKTLVG-------VISQEKFEKSR
PPI-AtCPP    MAIPFMETVVGFMIVMYIFETYLDLRQLTALKLPTLPKTLVG-------VISQEKFEKSR
PPI-BnCPP    MAIPFMETVVGFMIVMYIFETYLDLRQLTALKLPTLPKTLVG-------VISQEKFEKSR
BASF-Corn    ------------------------------------------------------------

PPI-GmCPP    AYSLDKSHFHFVHEFVTIVTDSTILYFGVLPWFWKKSGDFMTIAGFNAENEILHTLAFLA
BASF-Gm      AYSLDKSHFHFVHEFVTIVTDSTILYFGVLPWFWKKSGDFMTIAGFNAENEILHTLAFLA
AF007269     ------------------------------------------------------------
AT4g-AtCPP   ENFNICSYFHFVHEFVTILMDSAILFFGILPWFWKMSGAVLPRLGLDPENEILHTLSFLA
BASF_AT2     AYSLDKSYFHFVHEFVTILMDSAILFFGILPWFWKMSGAVLPRLGLDPENEILHTLSFLA
AFC1         AYSLDKSYFHFVHEFVTILMDSAILFFGILPWFWKMSGAVLPRLGLDPENEILHTLSFLA
BASF_AT1     AYSLDKSYFHFVHEFVTILMDSAILFFGILPWFWKMSGAVLPRLGLDPENEILHTLSFLA
PPI-AtCPP    AYSLDKSYFHFVHEFVTILMDSAILFFGILPWFWKMSGAVLPRLGLDPENEILHTLSFLA
PPI-BnCPP    AYSLDKSYFHFVHEFVTILMDSAILFFGILPWFWKISGGFLPMVGLDPENEILHTLSFLA
BASF-Corn    -------------------------------------------TRLSAENEIIHTLAFLA

PPI-GmCPP    GLMIWSQITDLPFSLYSTFVIEARHGFNKQTPWLFFRDMLKGIFLSVIIGPPIVAAIIVI
BASF-Gm      GLMIWSQITDLPFSLYSTFVIEARHGFNKQTPWLFFRDMLKGIFLSVIIGPPIVAAIIVI
AF007269     --------TDLPFSLYSTFVIESRHGFNKQTIWMFIRDMIKGTFLSVILGPPIVAAIIFI
AT4g-AtCPP   GVMTWSQITDLPFSLYSTFVIESRHGFNKQTIWMFIRDMIKGTFLSVILGPPIVAAIIFI
BASF_AT2     GVMTWSQITDLPFSLYSTFVIESRHGFNKQTIWMFIRDMIKGTFLSVILGPPIVAAIIFI
AFC1         GVMTWSQITDLPFSLYSTFVIESRHGFNKQTIWMFIRDMIKGTFLSVILGPPIVAAIIFI
BASF_AT1     GVMTWSQITDLPFSLYSTFVIESRHGFNKQTIWMFIRDMIKGTFLSVILGPPIVAAIIFI
PPI-AtCPP    GVMTWSQITDLPFSLYSTFVIESRHGFNKQTIWMFIRDMIKGTFLSVILGPPIVAAIIFI
PPI-BnCPP    GVMTWSQITDLPFSLYSTFVIESRHGFNKQTIWMFIRDMIKGILLSVIPAPPIVAAIIVI
BASF-Corn    GSMVWSQITDLPFSLYSTFVIEARHGFNKQTIWLFIRDMIKGILLSMILGPPIVAAIIYI
                     **************:******** *:*:***:** :**:* .******** *

PPI-GmCPP    VQKGGPYLAIYLWVFTFGLSIVMMTLYPVLIAPLFNKFTPLPDGQLREKIEKLASSLNYP
BASF-Gm      VQKGGPYLAIYLWVFTFGLSIVMMTLYPVLIAPLFNKFTPLPDGQLREKIEKLASSLNYP
AF007269     VQKGGPYLAIYLWAFMFILSLVMMTIYPVLIAPLFNKFTPLPDGDLREKIEKLASSLKFP
```

TABLE 18B-continued

ClustalW Amino Acid Analysis of CaaX Prenyl Protease

```
AT4g-AtCPP     VQKGGPYLAIYLWAFMFILSLVMMTIYPVLIAPLFNKFTPLPDGDLREKIEKLASSLKFP
BASF_AT2       VQKGGPYLAIYLWAFMFILSLVMMTIYPVLIAPLFNKFTPLPDGDLREKIEKLASSLKFP
AFC1           VQKGGPYLAIYLWAFMFILSLVMMTIYPVLIAPLFNKFTPLPDGDLREKIEKLASSLKFP
BASF_AT1       VQKGGPYLAIYLWAFMFILSLVMMTIYPVLIAPLFNKFTPLPDGDLREKIEKLASSLKFP
PPI-AtCPP      VQKGGPYLAIYLWAFMFILSLVMMTIYPVLIAPLFNKFTPLPDGDLREKIEKLASSLKFP
PPI-BnCPP      VQKGGPYLAIYLWAFMFILSLVMMTIYPVLIAPLFNKFTPLPDGDLREKIEKLASSLKFP
BASF-Corn      VQIGGPYLAIYLWGFMFVLALLMMTIYPIVIAPLFNKFTPLPEGVLREKIEKLAASLKFP
               ** ********** * * *:::***:**::************:* *********:**::*

PPI-GmCPP      LKKLFVVDGSTRSSHSNAYMYGFFKNKRIVPYDTLIQQCKDDEEIVAVIAHELGHWKLNH
BASF-Gm        LKKLFVVDGSTRSSHSNAYMYGFFKNKRIVLYDTLIQQCKDDEEIVAVIAHELGHWKLNH
AF007269       LKKLFVVDGSTRSSHSNAYMYGFFKNKRIVLYDTLIQQCKNEDEIVAVIAHELGHWKLNH
AT4g-AtCPP     LKKLFVVDGSTRSSHSNAYMYGFFKNKRIVLYDTLIQQCKNEDEIVAVIAHELGHWKLNH
BASF_AT2       LKKLFVVDGSTRSSHSNAYMYGFFKNKRIVLYDTLIQQCKNEDEIVAVIAHELGHWKLNH
AFC1           LKKLFVVDGSTRSSHSNAYMYGFFKNKRIVLYDTLIQQCKNEDEIVAVIAHELGHWKLNH
BASF_AT1       LKKLFVVDGSTRSSHSNAYMYGFFKNKRIVLYDTLIQQCKNEDEIVAVIAHELGHWKLNH
PPI-AtCPP      LKKLFVVDGSTRSSHSNAYMYGFFKNKRIVLYDTLIQQCKNEDEIVAVIAHELGHWKLNH
PPI-BnCPP      LKKLFVVDGSTRSSHSNAYMYGFFKNKRIVLYDTLIQQCQNENEIVAVIAHELGHWKLNH
BASF-Corn      LKKLFVVDGSTRSSHSNAYMYGFFKNKRIVLYDTLIQQCSNEDEIVSVIAHELGHWKLNH
               ****************************** ********.:::***:*************

PPI-GmCPP      TVYTFVAMQILTLLQFGGYTLVRNSADLYRSFGFDTQPVLIGLIIFQHTVIPLQQLVSFG
BASF-Gm        TVYTFVAMQILTLLQFGGYTLVRNSADLYRSFGFDTQPVLIGLIIFQHTVIPLQQLVSFG
AF007269       TTYSFIAV--------------------------------------QHTVIPLQHLVSFG
AT4g-AtCPP     TTYSFIAVQILAFLQFGGYTLVRNSTDLFRSFGFDTQPVLIGLIIFQHTVIPLQHLVSFG
BASF_AT2       TTYSFIAVQILAFLQFGGYTLVRNSTDLFRSFGFDTQPVLIGLIIFQHTVIPLQHLVSFG
AFC1           TTYSFIAVQILAFLQFGGYTLVRNSTDLFRSFGFDTQPVLIGLIIFQHTVIPLQHLVSFG
BASF_AT1       TTYSFIAVQILAFLQFGGYTLVRNSTDLFRSFGFDTQPVLIGLIIFQHTVIPLQHPVSFG
PPI-AtCPP      TTYSFIAVQILAFLQFGGYTLLRNSTDLFRSFGFDTQPVLIGLIIFQHTVIPLQHLVSFG
PPI-BnCPP      TTYSFIAVQILAFLQFGGYTLVRNSTDLFRSFGFDTQPVLIGLIIFQHTVIPLQHLVSFD
BASF-Corn      TVYSFVAVQLLMFLQFGGYTLVRSSKDLFGSFGFKDQPVIIGLIIFPHTIIPIQHLLSFR
               *.*:*:*:                                       **:**:*: :**

PPI-GmCPP      LNLVSRSFEFQADGFAKKLGYASGLRG---------------------------------
BASF-Gm        LNLVSRSFEFQADGFAKKLGYASGLRG---------------------------------
AF007269       LNLVSRAFEFQADAFAVKLGYAKDLR-------PALV----KLQVREDNNRTQ-------
AT4g-AtCPP     LNLVSRAFEFQADAFAVKLGYAKDLR-------PALV----KLQVREDNNRTQTVTSICV
BASF_AT2       LNLVSRAFEFQADAFAVKLGYAKDLR-------PALV----KLQE---------------
AFC1           LNLVSRAFEFQADAFAVKLGYAKDLR-------PALVKLQE-------------------
BASF_AT1       LNLVSRAFEFQADAFAVKLGYAKDLRPTLVKLQ---------------------------
PPI-AtCPP      LNLVSRAFEFQADAFAVKLDYAKDLRPALVKLQ---------------------------
PPI-BnCPP      LNLVSRAFEFQADAFAVNLGYAKDLRP---------------------------------
BASF-Corn      LNLVSRAFEFQADAFAKNLGYAPQLR----------------------------------
               ******:******.** :*.**  **

PPI-GmCPP      ------GLVKLQEENLSAMNTDPWYSAYHYSHPPLVERLAALDEPDKKED-
BASF-Gm        ------GLVKLQEENLSAMNTDPCSC-------------------------
AF007269       -----------TEENLSAMNTDPLYSAYHYSHPPLVERLRAIDGEDKKTD-
AT4g-AtCPP     THLNGFFVGILQEENLSAMNTDPLYSAYHYSHPPLVERLRAIDGEDKKTD-
BASF_AT2       -------------ENLSAMNTDPLYSAYHYSHPPLVERLRAIDGEDKKTD-
AFC1           -------------ENLSAMNTDPLHSAYHYSHPPLVERLRAIDGEDKKTD-
BASF_AT1       ------------EENLSAMNTDPLYSAYHYSHPPLVERLRAIDGEDKKTD-
PPI-AtCPP      ------------EENLSTMNTDPLYSAYHYSHPPLVERLRATDGEDKKTD-
PPI-BnCPP      ------ALVKLQEENLSAMNTDPLYSAYHYSHPPLVERLRAIDGEDKKTD-
BASF-Corn      -----AALVKLQEENLSAMNTDPWYSAYHYSHPPLVERLQALEDSDDKKED
                            ****:*****  .
```

Example 32

Plant Transformation

*Arabidopsis* transgenic plants were made by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants were grown under standard conditions until the plant has both developing flowers and open flowers. The plant was inverted for 2 minutes into a solution of *Agrobacterium* culture carrying the appropriate gene construct. Plants were then left horizontal in a tray and kept covered for two days to maintain humidity and then righted and bagged to continue growth and seed development. Mature seed was bulk harvested.

Transformed T1 plants were selected by germination and growth on MS plates containing 50 μg/ml kanamycin. Green, kanamycin resistant ($Kan^R$) seedlings were identified after 2 weeks growth and transplanted to soil. Plants were bagged to ensure self fertilization and the T2 seed of each plant harvested separately. During growth of T1 plants leaf samples were harvested, DNA extracted and Southern blot and PCR analysis performed.

T2 seeds were analysed for $Kan^R$ segregation. From those lines that showed a 3:1 resistant phenotype, surviving T2 plants were grown, bagged during seed set, and T3 seed harvested from each line. T3 seed was again used for $Kan^R$ segregation analysis and those lines showing 100% $Kan^R$ phenotype were selected as homozygous lines. Further molecular and physiological analysis was done using T3 seedlings.

Transgenic *Brassica napus, Glycine max* and *Zea maize* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 μl Tween20) and left for approximately 15 minutes. Solution I was removed and replaced with 30 ml of solution II (0.25% mecuric chloride, 100 μl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained for 5 days at 24° C., with 16.8 hr light dark cycles.

Explants were transferred to Medium II (Medium I, 300 mg/L timentin) for a further 7 days and then to Medium III (Medium II, 20 mg/L kanamycin). Any root or shoot tissue which had developed at this time was dissected away. Transfer explants to fresh plates of Medium III after 14-21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10×IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil. The above method, with or without modifications, is suitable for the transformation of numerous plant species including *Glycine max, Zea maize* and cotton.

Transgenic *Glycine max, Zea maize* and cotton can be produced using *Agrobacterium*-based methods which are known to one of skill in the art. Alternatively one can use a particle or non-particle biolistic bombardment transformation method. An example of non-particle biolistic transformation is given in U.S. Patent Application 20010026941. This method has been used to produce transgenic *Glycine max* and *Zea maize* plants. Viable plants are propagated and homozygous lines are generated. Plants are tested for the presence of drought tolerance, physiological and biochemical phenotypes as described elsewhere.

The following table identifies the constructs and the species which they have been transformed.

TABLE 19

Transformation List

| SEQ ID NO: | Construct | Species Transformed |
|---|---|---|
| 99 | pBI121-AtCPP | *A. thaliana, B. napus* |
| 100 | pBI121-HP-AtCPP | *A. thaliana* |
| 131 | pRD29A-AtCPP | *A. thaliana, B. napus* |
| 132 | pRD29A-HP-AtCPP | *A. thaliana* |
| 134 | MuA-AtCPP | *Glycine max, Zea mays* |

Non-limiting examples of vector constructs suitable for plant transformation are given in SEQ ID NO: 99, 5, 35-53.

SEQ ID NO: 99

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac -continued gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccatggcgattcctttcatggaaaccgtcgtgggttttatgatagtgatgtacatttttga gacgtatttggatctgaggcaactcactgctctcaagcttccaactctcccgaaaaccttggtt ggtgtaattagccaagagaagtttgagaaatcacgagcatacagtcttgacaaaagctattttc actttgttcatgagtttgtaactatacttatggactctgcaattttgttctttgggatcttgcc ttggttttggaagatgtctggagctgttttaccgaggttgggccttgatccggagaatgaaata ctgcatactctttcattcttggctggtgttatgacatggtcacagatcactgatttgccatttt ctttgtactcaactttcgtgatcgagtctcggcatgggttcaacaaacaaacaatatggatgtt cattagggacatgatcaaaggaacattcctctctgtcatactaggcccacccattgttgctgcg

-continued ataattttcatagtccagaaaggaggtccttatcttgccatctatctgtgggcattcatgttta tcctgtctctagtgatgatgactatatacccggtcttgatagcaccgctcttcaacaaattcac tcctcttccagatggagacctccgggagaagattgagaaacttgcttcttccctaaagtttcct ttgaagaagctgtttgttgtcgatggatctacaaggtcaagccatagcaatgcttacatgtatg gtttctttaagaacaaaaggattgttctttatgatacgttgattcagcagtgcaagaatgagga tgaaattgtggcggttattgcacacgagcttggacattggaaactgaatcacactacatactcg ttcattgcagttcaaatccttgccttcttacaatttggaggatacactcttctcagaaactcca ctgatctcttcaggagtttcggatttgatacacagcctgttctcattggtttgatcatatttca gcacactgtaataccactgcaacatctagtaagctttggcctgaacctcgttagtcgagcgttt gagtttcaggctgatgcttttgctgtgaagcttgactatgcaaaagatcttcgtcctgctctag tgaaactacaggaagagaacttatcaacaatgaacactgatccattgtactcagcttatcacta ctcacatcctcctcttgttgaaaggcttcgagccactgatggagaagacaagaagacagattaa cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaatttgtttacaccacaatatatcctgcca SEQ ID NO:99 is the nucleic acid sequence of pBI121-AtCPP. Italicized sequences are the right and left border repeats. Underlined sequence is the 35S promoter and bolded sequence is the AtCPP sense sequence.

SEQ ID NO: 100

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg -continued aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa -continued agcaagtggattgatgtgatatctccactgacgtaagggatgacgcacaatcccactatccttc gcaagacccttcctctatataaggaagttcatttcatttggagagaacacggggactctagag gatcctcccaatgtccaagctcgtgtgcaataaccgccacaatttcatcctcattcttgcactg ctgaatcaacgtatcataaagaacaatccttttgttcttaaagaaaccatacatgtaagcattg ctatggcttgaccttgtagatccatcgacaacaaacagcttcttcaaaggaaactttagggaag aagcaagtttctcaatcttctcccggaggtctccatctggaagaggagtgaatttgttgaagag cggtgctatcaagaccgggtatatagtcatcatcactagagacaggataaacatgaatgcccac agatagatggcaagataaggacctcctttctggactatgaaaattatcgcagcaacaatgggtg ggcctagtatgacagagaggaatgttcctttgatcatgtccctaatgaacatccatattgtttg tttgttgaacccatgccgagactcgatcacgaaagttgagtacaaagaaaatggcaaatcagtg atctgtgaccatgtcataacaccagccaagaatgaaagagtatgcagtatttcattctccggat caaggcccaacctcggtaaaagaggatccccATCTACCCGCTTCGCGTCGGCATCCGGTCAGTG

GCAGTGAAGGGCGAACAGTTCCTGATTAACCACAAACCGTTCTACTTTACTGGCTTTGGTCGTC

ATGAAGATGCGGACTTGCGTGGCAAAGGATTCGATAACGTGCTGATGGTGCACGACCACGCATT

AATGGACTGGATTGGGGCCAACTCCTACCGTACCTCGCATTACCCTTACGCTGAAGAGATGCTC

GACTGGGCAGATGAACATGGCATCGTGGTGATTGATGAAACTGCTGCTGTCGGCTTTTCGCTCT

CTTTAGGCATTGGTTTCGAAGCGGGCAACAAGCCGAAAGAACTGTACAGCGAAGAGGCAGTCAA

CGGGGAAACTCAGCAAGCGCACTTACAGGCGATTAAAGAGCTGATAGCGCGTGACAAAAACCAC

CCAAGCGTGGTGATGTGGAGTATTGCCAACGAACCGGATACCCGTCCGCAAGGTGCACGGGAAT

ATTTCGCGCCACTGGCGGAAGCAACGCGTAAACTCGACCCGACGCGTCCGATCACCTGCGTCAA

TGTAATGTTCTGCGACGCTCACACCGATACCATCAGCGATCTCTTTGATGTGCTGTGCCTGAAC

CGTTATTACGGATGGTATGTCCAAAGCGGCGATTTGGAAACGGCAGAGAAGGTACTGGAAAAAG

AACTTCTGGCCTGGCAGGAGAAACTGTACACCGACATGTGGAGTGAAGAGTATCAGTGTGCATG

GCTGGATATGTATCACCGCGTCTTTGATCGCGTCAGCGCCGTCGTCGGTGAACAGGTATGGAAT

TTCGCCGATTTTGCGACCTCGCAAGGCATATTGCGCGTTGGCGGTAACAAGAAAGGGATCTTCA

CTCGCGACCGCAAACCGAAGTCGGCGGCTTTTCTGCTGCAAAAACGCTGGACTGGCATGAACTT

CGGTGAAAAACCGCAGCAGGGAGGCAAACAATGAATCAACAACTCTCCTGGCGCACCATCGTCG

GCTACAGCCTCGGGAATTGCTACCGAGCTCttttaccgaggttgggccttgatccggagaatga aatactgcatactctttcattcttggctggtgttatgacatggtcacagatcactgatttgcca ttttctttgtactcaactttcgtgatcgagtctcggcatgggttcaacaaacaaacaatatgga tgttcattagggacatgatcaaaggaacattcctctctgtcatactaggcccacccattgttgc tgcgataattttcatagtccagaaaggaggtccttatcttgccatctatctgtgggcattcatg tttatcctgtctctagtgatgatgactatatacccggtcttgatagcaccgctcttcaacaaat tcactcctcttccagatggagacctccgggagaagattgagaaacttgcttcttccctaaagtt tcctttgaagaagctgtttgttgtcgatggatctacaaggtcaagccatagcaatgcttacatg tatggtttctttaagaacaaaaggattgttctttatgatacgttgattcagcagtgcaagaatg aggatgaaattgtggcggttattgcacacgagcttggacattgggagctcgaatttccccgatc gttcaaacatttggcaataaagtttcttaagattgaatcctgttgccggtcttgcgatgattat catataatttctgttgaattacgttaagcatgtaataattaacatgtaatgcatgacgttattt atgagatgggtttttatgattagagtcccgcaattatacatttaatacgcgatagaaaacaaaa tatagcgcgcaaactaggataaattatcgcgcgcggtgtcatctatgttactagatcgggaatt -continued cactggccgtcgttttacaacgtcgtgactgggaaaaccctggcgttacccaacttaatcgcct
tgcagcacatccccctttcgccagctggcgtaatagcgaagaggcccgcaccgatcgcccttcc
caacagttgcgcagcctgaatggcgcccgctcctttcgctttcttcccttcctttctcgccacg
ttcgccggctttccccgtcaagctctaaatcgggggctccctttagggttccgatttagtgctt
tacggcacctcgaccccaaaaaacttgatttgggtgatggttcacgtagtgggccatcgccctg
atagacggtttttcgccctttgacgttggagtccacgttctttaatagtggactcttgttccaa
actggaacaacactcaaccctatctcgggctattcttttgatttataagggattttgccgattt
cggaaccaccatcaaacaggattttcgcctgctggggcaaaccagcgtggaccgcttgctgcaa
ctctctcagggccaggcggtgaagggcaatcagctgttgcccgtctcactggtgaaaagaaaaa
ccaccccagtacattaaaaacgtccgcaatgtgttattaagttgtctaagcgtcaatttgttta
caccacaatatatcctgcca SEQ ID NO:100 is the nucleic acid sequence of pBI121-HP-AtCPP. Italicized sequences are the right and left border repeats. Underlined sequence is the 35S promoter and bolded sequence is the AtCPP anti-sense sequence. Sequence in upper case is the truncated GUS fragment. Sequence in bold and underlined is the AtCPP sense sequence.

SEQ ID NO: 130

*gtttacccgccaatatatcctgtc*aaacactgatagtttaaactgaaggcgggaaacgacaatc
tgatcatgagcggagaattaagggagtcacgttatgacccccgccgatgacgcgggacaagccg
ttttacgtttggaactgacagaaccgcaacgttgaaggagccactcagccgcgggtttctggag
tttaatgagctaagcacatacgtcagaaaccattattgcgcgttcaaaagtcgcctaaggtcac
tatcagctagcaaatatttcttgtcaaaaatgctccactgacgttccataaattcccctcggta
tccaattagagtctcatattcactctcaatccaaataatctgcaccggatctggatcgtttcgc
atgattgaacaagatggattgcacgcaggttctccggccgcttgggtggagaggctattcggct
atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt -continued aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccTTAATCTGTCTTCTTGTCTTCTCCATCAGTGGCTCGAAGCCTTTCAACAAGAGGAGGAT

GTGAGTAGTGATAAGCTGAGTACAATGGATCAGTGTTCATTGTTGATAAGTTCTCTTCCTGTAG

TTTCACTAGAGCAGGACGAAGATCTTTTGCATAGTCAAGCTTCACAGCAAAAGCATCAGCCTGA

AACTCAAACGCTCGACTAACGAGGTTCAGGCCAAAGCTTACTAGATGTTGCAGTGGTATTACAG

TGTGCTGAAATATGATCAAACCAATGAGAACAGGCTGTGTATCAAATCCGAAACTCCTGAAGAG

ATCAGTGGAGTTTCTGAGAAGAGTGTATCCTCCAAATTGTAAGAAGGCAAGGATTTGAACTGCA

ATGAACGAGTATGTAGTGTGATTCAGTTTCCAATGTCCAAGCTCGTGTGCAATAACCGCCACAA

TTTCATCCTCATTCTTGCACTGCTGAATCAACGTATCATAAAGAACAATCCTTTTGTTCTTAAA

GAAACCATACATGTAAGCATTGCTATGGCTTGACCTTGTAGATCCATCGACAACAAACAGCTTC

TTCAAAGGAAACTTTAGGGAAGAAGCAAGTTTCTCAATCTTCTCCCGGAGGTCTCCATCTGGAA

GAGGAGTGAATTTGTTGAAGAGCGGTGCTATCAAGACCGGGTATATAGTCATCATCACTAGAGA

CAGGATAAACATGAATGCCCACAGATAGATGGCAAGATAAGGACCTCCTTTCTGGACTATGAAA

ATTATCGCAGCAACAATGGGTGGGCCTAGTATGACAGAGAGGAATGTTCCTTTGATCATGTCCC

TAATGAACATCCATATTGTTTGTTTGTTGAACCCATGCCGAGACTCGATCACGAAAGTTGAGTA

-continued

CAAAGAAAATGGCAAATCAGTGATCTGTGACCATGTCATAACACCAGCCAAGAATGAAAGAGTA

TGCAGTATTTCATTCTCCGGATCAAGGCCCAACCTCGGTAAAACAGCTCCAGACATCTTCCAAA

ACCAAGGCAAGATCCCAAAGAACAAAATTGCAGAGTCCATAAGTATAGTTACAAACTCATGAAC

AAAGTGAAAATAGCTTTTGTCAAGACTGTATGCTCGTGATTTCTCAAACTTCTCTTGGCTAATT

ACACCAACCAAGGTTTTCGGGAGAGTTGGAAGCTTGAGAGCAGTGAGTTGCCTCAGATCCAAAT

ACGTCTCAAAAATGTACATCACTATCATAAAACCCACGACGGTTTCCATGAAAGGAATCGCCAT cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:130 is the nucleic acid sequence of pBI121-antisense-AtCPP. Italicized sequences are the right and left border repeats. Underlined sequence is the 35S promoter. Sequence in upper case is the AtCPP anti-sense sequence.

SEQ ID NO: 131

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc -continued ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttgtaacaaaatgtttttattattat tatagaattttactggttaaattaaaaatgaatagaaaaggtgaattaagaggagagaggaggt aaacattttcttctatttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc catggcgattcctttcatggaaaccgtcgtgggttttatgatagtgatgtacatttttgagacg tatttggatctgaggcaactcactgctctcaagcttccaactctcccgaaaaccttggttggtg

-continued taattagccaagagaagtttgagaaatcacgagcatacagtcttgacaaaagctattttcactt tgttcatgagtttgtaactatacttatggactctgcaattttgttctttgggatcttgccttgg ttttggaagatgtctggagctgttttaccgaggttgggccttgatccggagaatgaaatactgc atactctttcattcttggctggtgttatgacatggtcacagatcactgatttgccattttcttt gtactcaactttcgtgatcgagtctcggcatgggttcaacaaacaaacaatatggatgttcatt agggacatgatcaaaggaacattcctctctgtcatactaggcccacccattgttgctgcgataa ttttcatagtccagaaaggaggtccttatcttgccatctatctgtgggcattcatgtttatcct gtctctagtgatgatgactatatacccggtcttgatagcaccgctcttcaacaaattcactcct cttccagatggagacctccgggagaagattgagaaacttgcttcttccctaaagtttcctttga agaagctgtttgttgtcgatggatctacaaggtcaagccatagcaatgcttacatgtatggttt ctttaagaacaaaaggattgttctttatgatacgttgattcagcagtgcaagaatgaggatgaa attgtggcggttattgcacacgagcttggacattggaaactgaatcacactacatactcgttca ttgcagttcaaatccttgccttcttacaatttggaggatacactcttctcagaaactccactga tctcttcaggagtttcggatttgatacacagcctgttctcattggtttgatcatatttcagcac actgtaataccactgcaacatctagtaagctttggcctgaacctcgttagtcgagcgtttgagt ttcaggctgatgcttttgctgtgaagcttgactatgcaaaagatcttcgtcctgctctagtgaa actacaggaagagaacttatcaacaatgaacactgatccattgtactcagcttatcactactca catcctcctcttgttgaaaggcttcgagccactgatggagaagacaagaagacagattaacccc tcgaatttccccgatcgttcaaacatttggcaataaagtttcttaagattgaatcctgttgccg gtcttgcgatgattatcatataatttctgttgaattacgttaagcatgtaataattaacatgta atgcatgacgttatttatgagatgggtttttatgattagagtcccgcaattatacatttaatac gcgatagaaaacaaaatatagcgcgcaaactaggataaattatcgcgcgcggtgtcatctatgt tactagatcgggaattcactggccgtcgttttacaacgtcgtgactgggaaaaccctggcgtta cccaacttaatcgccttgcagcacatccccctttcgccagctggcgtaatagcgaagaggcccg caccgatcgcccttcccaacagttgcgcagcctgaatggcgcccgctcctttcgctttcttccc ttcctttctcgccacgttcgccggctttccccgtcaagctctaaatcgggggctccctttaggg ttccgatttagtgctttacggcacctcgaccccaaaaaacttgatttgggtgatggttcacgta gtgggccatcgccctgatagacggtttttcgccctttgacgttggagtccacgttctttaatag tggactcttgttccaaactggaacaacactcaaccctatctcgggctattcttttgatttataa gggattttgccgatttcggaaccaccatcaaacaggattttcgcctgctggggcaaaccagcgt ggaccgcttgctgcaactctctcagggccaggcggtgaagggcaatcagctgttgcccgtctca ctggtgaaaagaaaaaccaccccagtacattaaaaacgtccgcaatgtgttattaagttgtcta agcgtcaattt*gtttacaccacaatatatcctgcca*

SEQ ID NO:131 is the nucleic acid sequence of RD29A-AtCPP. Italicized sequences are the right and left border repeats. Underlined sequence is the RD29A promoter. Sequence in bold is the AtCPP sense sequence.

SEQ ID NO: 132

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac -continued tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc -continued atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaggatc
ctcccaatgtccaagctcgtgtgcaataaccgccacaatttcatcctcattcttgcactgctga
atcaacgtatcataaagaacaatccttttgttcttaaagaaccatacatgtaagcattgctat
ggcttgaccttgtagatccatcgacaacaaacagcttcttcaaaggaaactttagggaagaagc
aagtttctcaatcttctcccggaggtctccatctggaagaggagtgaatttgttgaagagcggt
gctatcaagaccgggtatatagtcatcatcactagagacaggataaacatgaatgcccacagat
agatggcaagataaggacctcctttctggactatgaaaattatcgcagcaacaatgggtgggcc
tagtatgacagagaggaatgttcctttgatcatgtccctaatgaacatccatattgtttgtttg
ttgaacccatgccgagactcgatcacgaaagttgagtacaaagaaaatggcaaatcagtgatct
gtgaccatgtcataacaccagccaagaatgaaagagtatgcagtatttcattctccggatcaag
gcccaacctcggtaaaagaggatccccATCTACCCGCTTCGCGTCGGCATCCGGTCAGTGGCAG
TGAAGGGCGAACAGTTCCTGATTAACCACAAACCGTTCTACTTTACTGGCTTTGGTCGTCATGA
AGATGCGGACTTGCGTGGCAAAGGATTCGATAACGTGCTGATGGTGCACGACCACGCATTAATG
GACTGGATTGGGGCCAACTCCTACCGTACCTCGCATTACCCTTACGCTGAAGAGATGCTCGACT
GGGCAGATGAACATGGCATCGTGGTGATTGATGAAACTGCTGCTGTCGGCTTTTCGCTCTCTTT
AGGCATTGGTTTCGAAGCGGGCAACAAGCCGAAAGAACTGTACAGCGAAGAGGCAGTCAACGGG
GAAACTCAGCAAGCGCACTTACAGGCGATTAAAGAGCTGATAGCGCGTGACAAAAACCACCCAA
GCGTGGTGATGTGGAGTATTGCCAACGAACCGGATACCCGTCCGCAAGGTGCACGGGAATATTT
CGCGCCACTGGCGGAAGCAACGCGTAAACTCGACCCGACGCGTCCGATCACCTGCGTCAATGTA
ATGTTCTGCGACGCTCACACCGATACCATCAGCGATCTCTTTGATGTGCTGTGCCTGAACCGTT
ATTACGGATGGTATGTCCAAAGCGGCGATTTGGAAACGGCAGAGAAGGTACTGGAAAAAGAACT
TCTGGCCTGGCAGGAGAAACTGTACACCGACATGTGGAGTGAAGAGTATCAGTGTGCATGGCTG
GATATGTATCACCGCGTCTTTGATCGCGTCAGCGCCGTCGTCGGTGAACAGGTATGGAATTTCG
CCGATTTTGCGACCTCGCAAGGCATATTGCGCGTTGGCGGTAACAAGAAAGGGATCTTCACTCG
CGACCGCAAACCGAAGTCGGCGGCTTTTCTGCTGCAAAAACGCTGGACTGGCATGAACTTCGGT
GAAAAACCGCAGCAGGGAGGCAAACAATGAATCAACAACTCTCCTGGCGCACCATCGTCGGCTA
CAGCCTCGGGAATTGCTACCGAGCTCttttaccgaggttgggccttgatccggagaatgaaata
ctgcatactctttcattcttggctggtgttatgacatggtcacagatcactgatttgccatttt
ctttgtactcaactttcgtgatcgagtctcggcatgggttcaacaaacaaacaatatggatgtt
cattagggacatgatcaaaggaacattcctctctgtcatactaggcccacccattgttgctgcg
ataattttcatagtccagaaaggaggtccttatcttgccatctatctgtgggcattcatgttta
tcctgtctctagtgatgatgactatatacccggtcttgatagcaccgctcttcaacaaattcac

-continued tcctcttccagatggagacctccgggagaagattgagaaacttgcttcttccctaaagtttcct ttgaagaagctgtttgttgtcgatggatctacaaggtcaagccatagcaatgcttacatgtatg gtttctttaagaacaaaaggattgttctttatgatacgttgattcagcagtgcaagaatgagga tgaaattgtggcggttattgcacacgagcttggacattgggagctcgaatttccccgatcgttc aaacatttggcaataaagtttcttaagattgaatcctgttgccggtcttgcgatgattatcata taatttctgttgaattacgttaagcatgtaataattaacatgtaatgcatgacgttatttatga gatgggtttttatgattagagtcccgcaattatacatttaatacgcgatagaaaacaaaatata gcgcgcaaactaggataaattatcgcgcgcggtgtcatctatgttactagatcgggaattcact ggccgtcgttttacaacgtcgtgactgggaaaaccctggcgttacccaacttaatcgccttgca gcacatccccctttcgccagctggcgtaatagcgaagaggcccgcaccgatcgcccttcccaac agttgcgcagcctgaatggcgcccgctcctttcgctttcttcccttcctttctcgccacgttcg ccggctttccccgtcaagctctaaatcgggggctccctttagggttccgatttagtgctttacg gcacctcgaccccaaaaaacttgatttgggtgatggttcacgtagtgggccatcgccctgatag acggtttttcgccctttgacgttggagtccacgttctttaatagtggactcttgttccaaactg gaacaacactcaaccctatctcgggctattcttttgatttataagggattttgccgatttcgga accaccatcaaacaggattttcgcctgctggggcaaaccagcgtggaccgcttgctgcaactct ctcagggccaggcggtgaagggcaatcagctgttgcccgtctcactggtgaaaagaaaaaccac cccagtacattaaaaacgtccgcaatgtgttattaagttgtctaagcgtcaatttgtttacacc

*acaatatatcctgcca*

SEQ ID NO:132 is the nucleic acid sequence of RD29A-HP-AtCPP. Italicized sequences are the right and left border repeats. Underlined sequence is the RD29A promoter. Sequence in bold is the AtCPP anti-sense sequence. Upper case sequence represents the truncated GUS fragment. Bold and underlined sequence represents the *A. thaliana* CaaX prenyl protease sense fragment.

SEQ ID NO: 133

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga -continued atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc cTTAATCTGTCTTCTTGTCTTCTCCATCAGTGGCTCGAAGCCTTTCAACAAGAGGAGGATGTGA

GTAGTGATAAGCTGAGTACAATGGATCAGTGTTCATTGTTGATAAGTTCTCTTCCTGTAGTTTC

ACTAGAGCAGGACGAAGATCTTTTGCATAGTCAAGCTTCACAGCAAAAGCATCAGCCTGAAACT

-continued

CAAACGCTCGACTAACGAGGTTCAGGCCAAAGCTTACTAGATGTTGCAGTGGTATTACAGTGTG

CTGAAATATGATCAAACCAATGAGAACAGGCTGTGTATCAAATCCGAAACTCCTGAAGAGATCA

GTGGAGTTTCTGAGAAGAGTGTATCCTCCAAATTGTAAGAAGGCAAGGATTTGAACTGCAATGA

ACGAGTATGTAGTGTGATTCAGTTTCCAATGTCCAAGCTCGTGTGCAATAACCGCCACAATTTC

ATCCTCATTCTTGCACTGCTGAATCAACGTATCATAAAGAACAATCCTTTTGTTCTTAAAGAAA

CCATACATGTAAGCATTGCTATGGCTTGACCTTGTAGATCCATCGACAACAAACAGCTTCTTCA

AAGGAAACTTTAGGGAAGAAGCAAGTTTCTCAATCTTCTCCCGGAGGTCTCCATCTGGAAGAGG

AGTGAATTTGTTGAAGAGCGGTGCTATCAAGACCGGGTATATAGTCATCATCACTAGAGACAGG

ATAAACATGAATGCCCACAGATAGATGGCAAGATAAGGACCTCCTTTCTGGACTATGAAAATTA

TCGCAGCAACAATGGGTGGGCCTAGTATGACAGAGAGGAATGTTCCTTTGATCATGTCCCTAAT

GAACATCCATATTGTTTGTTTGTTGAACCCATGCCGAGACTCGATCACGAAAGTTGAGTACAAA

GAAAATGGCAAATCAGTGATCTGTGACCATGTCATAACACCAGCCAAGAATGAAAGAGTATGCA

GTATTTCATTCTCCGGATCAAGGCCCAACCTCGGTAAAACAGCTCCAGACATCTTCCAAAACCA

AGGCAAGATCCCAAAGAACAAAATTGCAGAGTCCATAAGTATAGTTACAAACTCATGAACAAAG

TGAAAATAGCTTTTGTCAAGACTGTATGCTCGTGATTTCTCAAACTTCTCTTGGCTAATTACAC

CAACCAAGGTTTTCGGGAGAGTTGGAAGCTTGAGAGCAGTGAGTTGCCTCAGATCCAAATACGT

CTCAAAAATGTACATCACTATCATAAAACCCACGACGGTTTCCATGAAAGGAATCGCCATcccc tcgaatttccccgatcgttcaaacatttggcaataaagtttcttaagattgaatcctgttgccg gtcttgcgatgattatcatataatttctgttgaattacgttaagcatgtaataattaacatgta atgcatgacgttatttatgagatgggtttttatgattagagtcccgcaattatacatttaatac gcgatagaaaacaaaatatagcgcgcaaactaggataaattatcgcgcgcggtgtcatctatgt tactagatcgggaattcactggccgtcgttttacaacgtcgtgactgggaaaaccctggcgtta cccaacttaatcgccttgcagcacatccccctttcgccagctggcgtaatagcgaagaggcccg caccgatcgcccttcccaacagttgcgcagcctgaatggcgcccgctcctttcgctttcttccc ttcctttctcgccacgttcgccggctttccccgtcaagctctaaatcgggggctccctttaggg ttccgatttagtgctttacggcacctcgaccccaaaaaacttgatttgggtgatggttcacgta gtgggccatcgccctgatagacggtttttcgccctttgacgttggagtccacgttctttaatag tggactcttgttccaaactggaacaacactcaaccctatctcgggctattcttttgatttataa gggattttgccgatttcggaaccaccatcaaacaggattttcgcctgctggggcaaaccagcgt ggaccgcttgctgcaactctctcagggccaggcggtgaagggcaatcagctgttgcccgtctca ctggtgaaaagaaaaaccaccccagtacattaaaaacgtccgcaatgtgttattaagttgtcta agcgtcaatttg*tttacaccacaatatatcctgcca*

SEQ ID NO:133 is the nucleic acid sequence of RD29A-antisense-AtCPP. Italicized sequences are the right and left border repeats. Underlined sequence is the RD29A promoter. Sequence in upper case sequence is the AtCPP anti-sense sequence.

SEQ ID NO: 134

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac -continued tatcagctagcaaatatttcttgtcaaaaatgctccactgacgttccataaattcccctcggta
tccaattagagtctcatattcactctcaatccaaataatctgcaccggatctggatcgtttcgc
atgattgaacaagatggattgcacgcaggttctccggccgcttgggtggagaggctattcggct
atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagctGGGAAATTTTTCGCCAGTTCTAAATATCCGGAAACCTCTTGGGATGCCATTGCCCATCT
ATCTGTAATTTATTGACGAAATAGACGAAAAGGAAGGTGGCTCCTATAAAGCACATCATTGCGA
TAACAGAAAGGCCATTGTTGAAGATACCTCTGCTGACATTGGTCCCCAAGTGGAAGCACCACCC
CATGAGGAGCACCGTGGAGTAAGAAGACGTTCGAGCCACGTCGAAAAAGCAAGTGTGTTGATGT
AGTATCTCCATTGACGTAAGGGATGACGCACAATCCAACTATCCATCGCAAGACCATTGCTCTA -continued TATAAGAAAGTTAATATCATTTCGAGTGGCCACGCTGAGGGGGATCCatggcgattcctttcat ggaaaccgtcgtgggttttatgatagtgatgtacatttttgagacgtatttggatctgaggcaa ctcactgctctcaagcttccaactctcccgaaaaccttggttggtgtaattagccaagagaagt ttgagaaatcacgagcatacagtcttgacaaaagctattttcactttgttcatgagtttgtaac tatacttatggactctgcaattttgttctttgggatcttgccttggttttggaagatgtctgga gctgttttaccgaggttgggccttgatccggagaatgaaatactgcatactctttcattcttgg ctggtgttatgacatggtcacagatcactgatttgccattttctttgtactcaactttcgtgat cgagtctcggcatgggttcaacaaacaaacaatatggatgttcattagggacatgatcaaagga acattcctctctgtcatactaggcccacccattgttgctgcgataattttcatagtccagaaag gaggtccttatcttgccatctatctgtgggcattcatgtttatcctgtctctagtgatgatgac tatatacccggtcttgatagcaccgctcttcaacaaattcactcctcttccagatggagacctc cgggagaagattgagaaacttgcttcttccctaaagtttcctttgaagaagctgtttgttgtcg atggatctacaaggtcaagccatagcaatgcttacatgtatggtttctttaagaacaaaaggat tgttctttatgatacgttgattcagcagtgcaagaatgaggatgaaattgtggcggttattgca cacgagcttggacattggaaactgaatcacactacatactcgttcattgcagttcaaatccttg ccttcttacaatttggaggatacactcttctcagaaactccactgatctcttcaggagtttcgg atttgatacacagcctgttctcattggtttgatcatatttcagcacactgtaataccactgcaa catctagtaagctttggcctgaacctcgttagtcgagcgtttgagtttcaggctgatgcttttg ctgtgaagcttgactatgcaaaagatcttcgtcctgctctagtgaaactacaggaagagaactt atcaacaatgaacactgatccattgtactcagcttatcactactcacatcctcctcttgttgaa aggcttcgagccactgatggagaagacaagaagacagattaacccctcgaatttccccgatcgt tcaaacatttggcaataaagtttcttaagattgaatcctgttgccggtcttgcgatgattatca tataatttctgttgaattacgttaagcatgtaataattaacatgtaatgcatgacgttatttat gagatgggtttttatgattagagtcccgcaattatacatttaatacgcgatagaaaacaaaata tagcgcgcaaactaggataaattatcgcgcgcggtgtcatctatgttactagatcgggaattca ctggccgtcgttttacaacgtcgtgactgggaaaaccctggcgttacccaacttaatcgccttg cagcacatccccctttcgccagctggcgtaatagcgaagaggcccgcaccgatcgcccttccca acagttgcgcagcctgaatggcgcccgctcctttcgctttcttcccttcctttctcgccacgtt cgccggctttccccgtcaagctctaaatcgggggctccctttagggttccgatttagtgcttta cggcacctcgaccccaaaaaacttgatttgggtgatggttcacgtagtgggccatcgccctgat agacggtttttcgccctttgacgttggagtccacgttctttaatagtggactcttgttccaaac tggaacaacactcaaccctatctcgggctattcttttgatttataagggattttgccgatttcg gaaccaccatcaaacaggattttcgcctgctggggcaaaccagcgtggaccgcttgctgcaact ctctcagggccaggcggtgaagggcaatcagctgttgcccgtctcactggtgaaaagaaaaacc accccagtacattaaaaacgtccgcaatgtgttattaagttgtctaagcgtcaatttt*gtttaca*

*ccacaatatatcctgcca*

SEQ ID NO:134 is the nucleic acid sequence of MuA-AtCPP. Italicized sequences are the right and left border repeats. Sequence in upper case is the MuA promoter. The *A. thaliana* CaaX prenyl protease sense sequence is in bold.

SEQ ID NO: 135

*gtttacccgccaatatatcctgtc*aaacactgatagtttaaactgaaggcgggaaacgacaatc tgatcatgagcggagaattaagggagtcacgttatgacccccgccgatgacgcgggacaagccg -continued tttacgtttggaactgacagaaccgcaacgttgaaggagccactcagccgcgggtttctggag
tttaatgagctaagcacatacgtcagaaaccattattgcgcgttcaaaagtcgcctaaggtcac
tatcagctagcaaatatttcttgtcaaaaatgctccactgacgttccataaattcccctcggta
tccaattagagtctcatattcactctcaatccaaataatctgcaccggatctggatcgtttcgc
atgattgaacaagatggattgcacgcaggttctccggccgcttgggtggagaggctattcggct
atgactgggcacaacagacaatcggctgctctgatgccgccgtgttccggctgtcagcgcaggg
gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagctGGGAAATTTTTCGCCAGTTCTAAATATCCGGAAACCTCTTGGATGCCATTGCCCATCT
ATCTGTAATTTATTGACGAAATAGACGAAAAGGAAGGTGGCTCCTATAAAGCACATCATTGCGA
TAACAGAAAGGCCATTGTTGAAGATACCTCTGCTGACATTGGTCCCCAAGTGGAAGCACCACCC -continued

CATGAGGAGCACCGTGGAGTAAGAAGACGTTCGAGCCACGTCGAAAAAGCAAGTGTGTTGATGT

AGTATCTCCATTGACGTAAGGGATGACGCACAATCCAACTATCCATCGCAAGACCATTGCTCTA

TATAAGAAAGTTAATATCATTTCGAGTGGCCACGCTGAGGGGGATCGGGATGGCGTTTCCCTAC

ATGGAAGCCGTTGTCGGATTTATGATATTAATGTACATTTTTGAAACTTACTTGGATGTGCGAC

AACATAGGGCCCTCAAACTTCCTACTCTTCCAAAGACTTTAGAGGGTGTTATCAGCCAAGAGAA

ATTTGAGAAATCTAGAGCCTATAGTCTTGATAAAAGCCACTTCCATTTTGTTCACGAGTTTGTG

ACAATAGTGACAGACTCTACAATTTTGTACTTTGGGGTATTGCCCTGGTTTTGGAAGAAATCAG

GAGATTTTATGACAATAGCTGGTTTCAATGCTGAGAATGAAATACTGCATACCCTTGCCTTCTT

AGCAGGGCTGATGATTTGGTCACAGATAACAGATTTGCCCTTTTCTCTGTACTCAACTTTTGTG

ATTGAGGCCCGTCATGGTTTTAATAAGCAAACACCATGGTTATTCTTTAGGGACATGCTTAAAG

GATTTTCCTTTCTGTAATAATTGGTCCACCTATTGTGGCTGCAATCATTGTAATAGTACAGAA

AGGAGGTCCATACTTGGCCATCTATCTTTGGGTTTTTACGTTTGGTCTTTCTATTGTGATGATG

ACCCTTTATCCAGTACTAATAGCTCCACTCTTCAATAAGTTCACTCCACTTCCAGATGGTCAAC

TCAGGGAGAAAATCGAGAAACTTGCTTCCTCCCTCAACTATCCGTTAAAGAAACTATTTGTTGT

CGATGGATCCACAAGATCAAGTCACAGCAATGCCTATATGTATGGATTCTTCAAGAACAAGAGG

ATTGTCCCTTATGACACATTAATTCAACAGTGCAAAGACGATGAGGAAATTGTTGCTGTTATTG

CCCATGAGTTGGGACACTGGAAGCTCAACCATACTGTGTACACATTTGTTGCTATGCAGATTCT

TACACTTCTACAATTTGGAGGATATACACTAGTGCGAAATTCAGCTGATCTGTATCGAAGCTTT

GGGTTTGATACGCAGCCAGTCCTCATTGGGCTCATCATATTTCAGCATACTGTAATCCCACTTC

AGCAATTGGTCAGCTTTGGTCTGAACCTAGTCAGCCGATCATTTGAATTTCAGGCTGATGGCTT

TGCCAAGAAGCTTGGATATGCATCTGGATTACGCGGTGGTCTTGTGAAACTACAGGAGGAGAAT

CTGTCAGCTATGAATACAGATCCTTGGTACTCTGCTTATCACTATTCTCATCCTCCCCTTGTTG

AAAGATTGGCCGCGCTGGACGAACCGGATAAGAAGGAAGACTAAgagctcgaatttccccgatc gttcaaacatttggcaataaagtttcttaagattgaatcctgttgccggtcttgcgatgattat catataatttctgttgaattacgttaagcatgtaataattaacatgtaatgcatgacgttattt atgagatgggtttttatgattagagtcccgcaattatacatttaatacgcgatagaaaacaaaa tatagcgcgcaaactaggataaattatcgcgcgcggtgtcatctatgttactagatcgggaatt cactggccgtcgttttacaacgtcgtgactgggaaaaccctggcgttacccaacttaatcgcct tgcagcacatccccctttcgccagctggcgtaatagcgaagaggcccgcaccgatcgcccttcc caacagttgcgcagcctgaatggcgcccgctcctttcgctttcttcccttcctttctcgccacg ttcgccggctttccccgtcaagctctaaatcgggggctccctttagggttccgatttagtgctt tacggcacctcgaccccaaaaaacttgatttgggtgatggttcacgtagtgggccatcgccctg atagacggtttttcgccctttgacgttggagtccacgttctttaatagtggactcttgttccaa actggaacaacactcaaccctatctcgggctattcttttgatttataagggattttgccgattt cggaaccaccatcaaacaggattttcgcctgctggggcaaaccagcgtggaccgcttgctgcaa ctctctcagggccaggcggtgaagggcaatcagctgttgcccgtctcactggtgaaaagaaaaa ccaccccagtacattaaaaacgtccgcaatgtgttattaagttgtctaagcgtcaattt*gttta*

*caccacaatatatcctgcca*

SEQ ID NO:135 is the nucleic acid sequence of MuA-GmCPP. Italicized sequences are the right and left border repeats. Sequence in upper case is the MuA promoter. The *G. max* CaaX prenyl protease sense sequence is in upper case and bold.

SEQ ID NO: 136

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa -continued ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagag gatccccgggatggcgtttccctacatggaagccgttgtcggatttatgatattaatgtacatt tttgaaacttacttggatgtgcgacaacatagggccctcaaacttcctactcttccaaagactt tagagggtgttatcagccaagagaaatttgagaaatctagagcctatagtcttgataaaagcca cttccattttgttcacgagtttgtgacaatagtgacagactctacaattttgtactttggggta ttgccctggttttggaagaaatcaggagattttatgacaatagctggtttcaatgctgagaatg aaatactgcatacccttgccttcttagcagggctgatgatttggtcacagataacagatttgcc cttttctctgtactcaacttttgtgattgaggcccgtcatggttttaataagcaaacaccatgg ttattctttagggacatgcttaaaggaattttcctttctgtaataattggtccacctattgtgg ctgcaatcattgtaatagtacagaaaggaggtccatacttggccatctatctttgggtttttac gtttggtctttctattgtgatgatgaccctttatccagtactaatagctccactcttcaataag ttcactccacttccagatggtcaactcagggagaaaatcgagaaacttgcttcctccctcaact atccgttaaagaaactatttgttgtcgatggatccacaagatcaagtcacagcaatgcctatat gtatggattcttcaagaacaagaggattgtcccttatgacacattaattcaacagtgcaaagac gatgaggaaattgttgctgttattgcccatgagttgggacactggaagctcaaccatactgtgt acacatttgttgctatgcagattcttacacttctacaatttggaggatatacactagtgcgaaa ttcagctgatctgtatcgaagctttgggtttgatacgcagccagtcctcattgggctcatcata tttcagcatactgtaatcccacttcagcaattggtcagctttggtctgaacctagtcagccgat catttgaatttcaggctgatggctttgccaagaagcttggatatgcatctggattacgcggtgg tcttgtgaaactacaggaggagaatctgtcagctatgaatacagatccttggtactctgcttat cactattctcatcctccccttgttgaaagattggccgcgctggacgaaccggataagaaggaag actaagagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattcactggccgtcgttttacaacgtcgtgactgggaaaacc -continued ctggcgttacccaacttaatcgccttgcagcacatcccccttcgccagctggcgtaatagcga agaggcccgcaccgatcgcccttcccaacagttgcgcagcctgaatggcgcccgctcctttcgc tttcttcccttcctttctcgccacgttcgccggctttccccgtcaagctctaaatcgggggctc cctttagggttccgatttagtgctttacggcacctcgaccccaaaaaacttgatttgggtgatg gttcacgtagtgggccatcgccctgatagacggtttttcgccctttgacgttggagtccacgtt ctttaatagtggactcttgttccaaactggaacaacactcaaccctatctcgggctattctttt gatttataagggattttgccgatttcggaaccaccatcaaacaggattttcgcctgctggggca aaccagcgtggaccgcttgctgcaactctctcagggccaggcggtgaagggcaatcagctgttg cccgtctcactggtgaaaagaaaaaccaccccagtacattaaaaacgtccgcaatgtgttatta agttgtctaagcgtcaattt*gtttacaccacaatatatcctgcca*

SEQ ID NO:135 is the nucleic acid sequence of pBI121-GmCPP. Italicized sequences are the right and left border repeats. Underlined sequence is the 35S promoter. The *G. max* CaaX prenyl protease sense sequence is in bold.

SEQ ID NO: 137

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc -continued cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagcccacagatggttagagaggcttacgcagcaggtctcatcaagacg
atctacccgagcaataatctccaggaaatcaaataccttcccaagaaggttaaagatgcagtca
aaagattcaggactaactgcatcaagaacacagagaaagatatatttctcaagatcagaagtac
tattccagtatggacgattcaaggcttgcttcacaaaccaaggcaagtaatagagattggagtc
tctaaaaaggtagttcccactgaatcaaaggccatggagtcaaagattcaaatagaggacctaa
cagaactcgccgtaaagactggcgaacagttcatacagagtctcttacgactcaatgacaagaa
gaaaatcttcgtcaacatggtggagcacgacacacttgtctactccaaaaatatcaaagataca
gtctcagaagaccaaagggcaattgagacttttcaacaaagggtaatatccggaaacctcctcg
gattccattgcccagctatctgtcactttattgtgaagatagtggaaaaggaaggtggctccta
caaatgccatcattgcgataaaggaaaggccatcgttgaagatgcctctgccgacagtggtccc
aaagatggacccccacccacgaggagcatcgtggaaaaagaagacgttccaaccacgtcttcaa
agcaagtggattgatgtgatatctccactgacgtaagggatgacgcacaatcccactatccttc
gcaagacccttcctctatataaggaagttcatttcatttggagagaacacgggggactctagac
cggttcgtccagcgcggccaatctttcaacaaggggaggatgagaatagtgataagcagagtac
caaggatctgtattcatagctgacagattctcctcctgtagtttcacaagaccaccgcgtaatc
cagatgcatatccaagcttcttggcaaagccatcagcctgaaattcaaatgatcggctgactag
gttcagaccaaagctgaccaattgctgaagtgggattacagtatgctgaaatatgatgagccca
atgaggactggctgcgtatcaaacccaaagcttcgatacagatcagctgaatttcgcactagtg
tatatcctccaaattgtagaagtgtaagaatctgcatagcaacaaatgtgtacacagtatggtt
gagcttccagtgtcccaactcatgggcaataacagcaacaatttcctcatcgtctttgcactgt
tgaattaatgtgtcataagggacaatcctcttgttcttgaagaatccatacatataggcattgc
tgtgacttgatcttgtggatccccATCTACCCGCTTCGCGTCGGCATCCGGTCAGTGGCAGTGA
AGGGCGAACAGTTCCTGATTAACCACAAACCGTTCTACTTTACTGGCTTTGGTCGTCATGAAGA
TGCGGACTTGCGTGGCAAAGGATTCGATAACGTGCTGATGGTGCACGACCACGCATTAATGGAC
TGGATTGGGGCCAACTCCTACCGTACCTCGCATTACCCTTACGCTGAAGAGATGCTCGACTGGG
CAGATGAACATGGCATCGTGGTGATTGATGAAACTGCTGCTGTCGGCTTTTCGCTCTCTTTAGG
CATTGGTTTCGAAGCGGGCAACAAGCCGAAAGAACTGTACAGCGAAGAGGCAGTCAACGGGGAA
ACTCAGCAAGCGCACTTACAGGCGATTAAAGAGCTGATAGCGCGTGACAAAAACCACCCAAGCG
TGGTGATGTGGAGTATTGCCAACGAACCGGATACCCGTCCGCAAGGTGCACGGGAATATTTCGC -continued

GCCACTGGCGGAAGCAACGCGTAAACTCGACCCGACGCGTCCGATCACCTGCGTCAATGTAATG

TTCTGCGACGCTCACACCGATACCATCAGCGATCTCTTTGATGTGCTGTGCCTGAACCGTTATT

ACGGATGGTATGTCCAAAGCGGCGATTTGGAAACGGCAGAGAAGGTACTGGAAAAAGAACTTCT

GGCCTGGCAGGAGAAACTGTACACCGACATGTGGAGTGAAGAGTATCAGTGTGCATGGCTGGAT

ATGTATCACCGCGTCTTTGATCGCGTCAGCGCCGTCGTCGGTGAACAGGTATGGAATTTCGCCG

ATTTTGCGACCTCGCAAGGCATATTGCGCGTTGGCGGTAACAAGAAAGGGATCTTCACTCGCGA

CCGCAAACCGAAGTCGGCGGCTTTTCTGCTGCAAAAACGCTGGACTGGCATGAACTTCGGTGAA

AAACCGCAGCAGGGAGGCAAACAATGAatcaacaactctcctggcgcaccatcgtcggctacag cctcgggaattgctaccgagctcacaagatcaagtcacagcaatgcctatatgtatggattctt caagaacaagaggattgtcccttatgacacattaattcaacagtgcaaagacgatgaggaaatt gttgctgttattgcccatgagttgggacactggaagctcaaccatactgtgtacacatttgttg ctatgcagattcttacacttctacaatttggaggatatacactagtgcgaaattcagctgatct gtatcgaagctttgggtttgatacgcagccagtcctcattgggctcatcatatttcagcatact gtaatcccacttcagcaattggtcagctttggtctgaacctagtcagccgatcatttgaatttc aggctgatggctttgccaagaagcttggatatgcatctggattacgcggtggtcttgtgaaact acaggaggagaatctgtcagctatgaatacagatccttggtactctgcttatcactattctcat cctccccttgttgaaagattggccgcgctggacgaaccgggagctcgaatttccccgatcgttc aaacatttggcaataaagtttcttaagattgaatcctgttgccggtcttgcgatgattatcata taatttctgttgaattacgttaagcatgtaataattaacatgtaatgcatgacgttatttatga gatgggtttttatgattagagtcccgcaattatacatttaatacgcgatagaaaacaaaatata gcgcgcaaactaggataaattatcgcgcgcggtgtcatctatgttactagatcgggaattcact ggccgtcgttttacaacgtcgtgactgggaaaaccctggcgttacccaacttaatcgccttgca gcacatccccctttcgccagctggcgtaatagcgaagaggcccgcaccgatcgcccttcccaac agttgcgcagcctgaatggcgcccgctcctttcgctttcttcccttcctttctcgccacgttcg ccggctttccccgtcaagctctaaatcgggggctccctttagggttccgatttagtgctttacg gcacctcgaccccaaaaaacttgatttgggtgatggttcacgtagtgggccatcgccctgatag acggtttttcgccctttgacgttggagtccacgttctttaatagtggactcttgttccaaactg gaacaacactcaaccctatctcgggctattcttttgatttataagggattttgccgatttcgga accaccatcaaacaggattttcgcctgctggggcaaaccagcgtggaccgcttgctgcaactct ctcagggccaggcggtgaagggcaatcagctgttgcccgtctcactggtgaaaagaaaaaccac cccagtacattaaaaacgtccgcaatgtgttattaagttgtctaagcgtcaattt*gtttacacc*

*acaatatatcctgcca*

SEQ ID NO:137 is the nucleic acid sequence of pBI121-HP-GmCPP. Italicized sequences are the right and left border repeats. Underlined sequence is the 35S promoter. Bold sequence is the antisense prenyl protease fragment of *G. max*. Bold and underlined sequence is the *G. max* sense prenyl protease fragment and sequence in upper case is the truncated GUS fragment.

SEQ ID NO: 138
*gtttacccgccaatatatcctgtc*aaacactgatagtttaaactgaaggcgggaaacgacaatc tgatcatgagcggagaattaagggagtcacgttatgacccccgccgatgacgcgggacaagccg -continued tttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac -continued tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggactctagag gatccccgggttagtcttccttcttatccggttcgtccagcgcggccaatctttcaacaagggg aggatgagaatagtgataagcagagtaccaaggatctgtattcatagctgacagattctcctcc tgtagtttcacaagaccaccgcgtaatccagatgcatatccaagcttcttggcaaagccatcag cctgaaattcaaatgatcggctgactaggttcagaccaaagctgaccaattgctgaagtgggat tacagtatgctgaaatatgatgagcccaatgaggactggctgcgtatcaaacccaaagcttcga tacagatcagctgaatttcgcactagtgtatatcctccaaattgtagaagtgtaagaatctgca tagcaacaaatgtgtacacagtatggttgagcttccagtgtcccaactcatgggcaataacagc aacaatttcctcatcgtctttgcactgttgaattaatgtgtcataagggacaatcctcttgttc ttgaagaatccatacatataggcattgctgtgacttgatcttgtggatccatcgacaacaaata gtttctttaacggatagttgagggaggaagcaagtttctcgattttctccctgagttgaccatc tggaagtggagtgaacttattgaagagtggagctattagtactggataaagggtcatcatcaca atagaaagaccaaacgtaaaaacccaaagatagatggccaagtatggacctcctttctgtacta ttacaatgattgcagccacaataggtggaccaattattacagaaaggaaaattcctttaagcat gtccctaaagaataaccatggtgtttgcttattaaaaccatgacgggcctcaatcacaaaagtt gagtacagagaaaagggcaaatctgttatctgtgaccaaatcatcagccctgctaagaaggcaa gggtatgcagtatttcattctcagcattgaaaccagctattgtcataaaatctcctgatttctt ccaaaaccagggcaataccccaaagtacaaaattgtagagtctgtcactattgtcacaaactcg tgaacaaaatggaagtggcttttatcaagactataggctctagatttctcaaatttctcttggc tgataacaccctctaaagtctttggaagagtaggaagtttgagggccctatgttgtcgcacatc caagtaagtttcaaaaatgtacattaatatcataaatccgacaacggcttccatgtagggaaac gccatgagctcgaatttccccgatcgttcaaacatttggcaataaagtttcttaagattgaatc ctgttgccggtcttgcgatgattatcatataatttctgttgaattacgttaagcatgtaataat taacatgtaatgcatgacgttatttatgagatgggtttttatgattagagtcccgcaattatac atttaatacgcgatagaaaacaaaatatagcgcgcaaactaggataaattatcgcgcgcggtgt catctatgttactagatcgggaattcactggccgtcgttttacaacgtcgtgactgggaaaacc ctggcgttacccaacttaatcgccttgcagcacatccccctttcgccagctggcgtaatagcga agaggcccgcaccgatcgcccttcccaacagttgcgcagcctgaatggcgcccgctcctttcgc tttcttcccttcctttctcgccacgttcgccggctttccccgtcaagctctaaatcgggggctc cctttagggttccgatttagtgctttacggcacctcgaccccaaaaaacttgatttgggtgatg gttcacgtagtgggccatcgccctgatagacggtttttcgccctttgacgttggagtccacgtt ctttaatagtggactcttgttccaaactggaacaacactcaaccctatctcgggctattctttt -continued gatttataagggattttgccgatttcggaaccaccatcaaacaggattttcgcctgctggggca aaccagcgtggaccgcttgctgcaactctctcagggccaggcggtgaagggcaatcagctgttg cccgtctcactggtgaaaagaaaaaccaccccagtacattaaaaacgtccgcaatgtgttatta agttgtctaagcgtcaattt*gtttacaccacaatatatcctgcca*

SEQ ID NO:138 is the nucleic acid sequence of pBI121-antisense-GmCPP. Italicized sequences are the right and left border repeats. Underlined sequence is the 35S promoter. Sequence in bold is the GmCPP anti-sense sequence.

SEQ ID NO: 139
*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc -continued cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacattttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaggatc
cccgggatggcgtttccctacatggaagccgttgtcggatttatgatattaatgtacattttg
aaacttacttggatgtgcgacaacatagggccctcaaacttcctactcttccaaagactttaga
gggtgttatcagccaagagaaatttgagaaatctagagcctatagtcttgataaaagccacttc
cattttgttcacgagtttgtgacaatagtgacagactctacaattttgtactttggggtattgc
cctggttttggaagaaatcaggagattttatgacaatagctggtttcaatgctgagaatgaaat
actgcatacccttgccttcttagcagggctgatgatttggtcacagataacagatttgcccttt
tctctgtactcaacttttgtgattgaggcccgtcatggttttaataagcaaacaccatggttat
tctttagggacatgcttaaaggaattttcctttctgtaataattggtccacctattgtggctgc
aatcattgtaatagtacagaaaggaggtccatacttggccatctatctttgggtttttacgttt
ggtctttctattgtgatgatgaccctttatccagtactaatagctccactcttcaataagttca
ctccacttccagatggtcaactcagggagaaaatcgagaaacttgcttcctccctcaactatcc
gttaaagaaactatttgttgtcgatggatccacaagatcaagtcacagcaatgcctatatgtat
ggattcttcaagaacaagaggattgtcccttatgacacattaattcaacagtgcaaagacgatg
aggaaattgttgctgttattgcccatgagttgggacactggaagctcaaccatactgtgtacac
atttgttgctatgcagattcttacacttctacaatttggaggatatacactagtgcgaaattca
gctgatctgtatcgaagctttgggtttgatacgcagccagtcctcattgggctcatcatatttc
agcatactgtaatcccacttcagcaattggtcagctttggtctgaacctagtcagccgatcatt
tgaatttcaggctgatggctttgccaagaagcttggatatgcatctggattacgcggtggtctt
gtgaaactacaggaggagaatctgtcagctatgaatacagatccttggtactctgcttatcact -continued attctcatcctccccttgttgaaagattggccgcgctggacgaaccggataagaaggaagacta agagctcgaatttccccgatcgttcaaacatttggcaataaagtttcttaagattgaatcctgt tgccggtcttgcgatgattatcatataatttctgttgaattacgttaagcatgtaataattaac atgtaatgcatgacgttatttatgagatgggtttttatgattagagtcccgcaattatacattt aatacgcgatagaaaacaaaatatagcgcgcaaactaggataaattatcgcgcgcggtgtcatc tatgttactagatcgggaattcactggccgtcgttttacaacgtcgtgactgggaaaaccctgg cgttacccaacttaatcgccttgcagcacatcccccttcgccagctggcgtaatagcgaagag gcccgcaccgatcgcccttcccaacagttgcgcagcctgaatggcgcccgctcctttcgctttc ttcccttcctttctcgccacgttcgccggctttccccgtcaagctctaaatcgggggctccctt tagggttccgatttagtgctttacggcacctcgaccccaaaaaacttgatttgggtgatggttc acgtagtgggccatcgccctgatagacggtttttcgccctttgacgttggagtccacgttcttt aatagtggactcttgttccaaactggaacaacactcaaccctatctcgggctattcttttgatt tataagggattttgccgatttcggaaccaccatcaaacaggattttcgcctgctggggcaaacc agcgtggaccgcttgctgcaactctctcagggccaggcggtgaagggcaatcagctgttgcccg tctcactggtgaaaagaaaaaccaccccagtacattaaaaacgtccgcaatgtgttattaagtt gtctaagcgtcaattt*gtttacaccacaatatatcctgcca*

SEQ ID NO:139 is the nucleic acid sequence of pRD29A-GmCPP. Italicized sequences are the right and left border repeats. Underlined sequence is the RD29A promoter. Sequence in bold is the GmCPP sense sequence.

SEQ ID NO: 140

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg -continued cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacattttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaccggt tcgtccagcgcggccaatctttcaacaaggggaggatgagaatagtgataagcagagtaccaag gatctgtattcatagctgacagattctcctcctgtagtttcacaagaccaccgcgtaatccaga tgcatatccaagcttcttggcaaagccatcagcctgaaattcaaatgatcggctgactaggttc agaccaaagctgaccaattgctgaagtgggattacagtatgctgaaatatgatgagcccaatga ggactggctgcgtatcaaacccaaagcttcgatacagatcagctgaatttcgcactagtgtata tcctccaaattgtagaagtgtaagaatctgcatagcaacaaatgtgtacacagtatggttgagc ttccagtgtcccaactcatgggcaataacagcaacaatttcctcatcgtctttgcactgttgaa ttaatgtgtcataagggacaatcctcttgttcttgaagaatccatacatataggcattgctgtg

-continued acttgatcttgtggatccccATCTACCCGCTTCGCGTCGGCATCCGGTCAGTGGCAGTGAAGGG

CGAACAGTTCCTGATTAACCACAAACCGTTCTACTTTACTGGCTTTGGTCGTCATGAAGATGCG

GACTTGCGTGGCAAAGGATTCGATAACGTGCTGATGGTGCACGACCACGCATTAATGGACTGGA

TTGGGGCCAACTCCTACCGTACCTCGCATTACCCTTACGCTGAAGAGATGCTCGACTGGGCAGA

TGAACATGGCATCGTGGTGATTGATGAAACTGCTGCTGTCGGCTTTTCGCTCTCTTTAGGCATT

GGTTTCGAAGCGGGCAACAAGCCGAAAGAACTGTACAGCGAAGAGGCAGTCAACGGGGAAACTC

AGCAAGCGCACTTACAGGCGATTAAAGAGCTGATAGCGCGTGACAAAAACCACCCAAGCGTGGT

GATGTGGAGTATTGCCAACGAACCGGATACCCGTCCGCAAGGTGCACGGGAATATTTCGCGCCA

CTGGCGGAAGCAACGCGTAAACTCGACCCGACGCGTCCGATCACCTGCGTCAATGTAATGTTCT

GCGACGCTCACACCGATACCATCAGCGATCTCTTTGATGTGCTGTGCCTGAACCGTTATTACGG

ATGGTATGTCCAAAGCGGCGATTTGGAAACGGCAGAGAAGGTACTGGAAAAAGAACTTCTGGCC

TGGCAGGAGAAACTGTACACCGACATGTGGAGTGAAGAGTATCAGTGTGCATGGCTGGATATGT

ATCACCGCGTCTTTGATCGCGTCAGCGCCGTCGTCGGTGAACAGGTATGGAATTTCGCCGATTT

TGCGACCTCGCAAGGCATATTGCGCGTTGGCGGTAACAAGAAAGGGATCTTCACTCGCGACCGC

AAACCGAAGTCGGCGGCTTTTCTGCTGCAAAAACGCTGGACTGGCATGAACTTCGGTGAAAAAC

CGCAGCAGGGAGGCAAACAATGAatcaacaactctcctggcgcaccatcgtcggctacagcctc gggaattgctaccgagctcacaagatcaagtcacagcaatgcctatatgtatggattcttcaag aacaagaggattgtcccttatgacacattaattcaacagtgcaaagacgatgaggaaattgttg ctgttattgcccatgagttgggacactggaagctcaaccatactgtgtacacatttgttgctat gcagattcttacacttctacaatttggaggatatacactagtgcgaaattcagctgatctgtat cgaagctttgggtttgatacgcagccagtcctcattgggctcatcatatttcagcatactgtaa tcccacttcagcaattggtcagctttggtctgaacctagtcagccgatcatttgaatttcaggc tgatggctttgccaagaagcttggatatgcatctggattacgcggtggtcttgtgaaactacag gaggagaatctgtcagctatgaatacagatccttggtactctgcttatcactattctcatcctc cccttgttgaaagattggccgcgctggacgaaccgggagctcgaatttccccgatcgttcaaac atttggcaataaagtttcttaagattgaatcctgttgccggtcttgcgatgattatcatataat ttctgttgaattacgttaagcatgtaataattaacatgtaatgcatgacgttatttatgagatg ggtttttatgattagagtcccgcaattatacatttaatacgcgatagaaaacaaaatatagcgc gcaaactaggataaattatcgcgcgcggtgtcatctatgttactagatcgggaattcactggcc gtcgttttacaacgtcgtgactgggaaaaccctggcgttacccaacttaatcgccttgcagcac atccccctttcgccagctggcgtaatagcgaagaggcccgcaccgatcgcccttcccaacagtt gcgcagcctgaatggcgcccgctcctttcgctttcttcccttcctttctcgccacgttcgccgg ctttccccgtcaagctctaaatcgggggctccctttagggttccgatttagtgctttacggcac ctcgaccccaaaaaacttgatttgggtgatggttcacgtagtgggccatcgccctgatagacgg tttttcgccctttgacgttggagtccacgttctttaatagtggactcttgttccaaactggaac aacactcaaccctatctcgggctattcttttgatttataagggattttgccgatttcggaacca ccatcaaacaggattttcgcctgctggggcaaaccagcgtggaccgcttgctgcaactctctca gggccaggcggtgaagggcaatcagctgttgcccgtctcactggtgaaaagaaaaaccacccca gtacattaaaaacgtccgcaatgtgttattaagttgtctaagcgtcaattt*gtttacaccacaa*

*tatatcctgcca*

SEQ ID NO:140 is the nucleic acid sequence of pRD29A-HP-GmCPP. Italicized sequences are the right and left border repeats. Underlined sequence is the RD29A promoter. Sequence in bold is the GmCPP antisense sequence, bold and underlined sequence is the GmCPP sense sequence.

SEQ ID NO: 141

*gtttacccgccaatatatcctgtc*aaacactgatagtttaaactgaaggcgggaaacgacaatctgatcatgagcggagaattaagg gagtcacgttatgacccccgccgatgacgcgggacaagccgttttacgtttggaactgacagaaccgcaacgttgaaggagccac tcagccgcgggtttctggagtttaatgagctaagcacatacgtcagaaaccattattgcgcgttcaaaagtcgcctaaggtcactat cagctagcaaatatttcttgtcaaaaatgctccactgacgttccataaattcccctcggtatccaattagagtctcatattcactctcaa tccaaataatctgcaccggatctggatcgtttcgcatgattgaacaagatggattgcacgcaggttctccggccgcttgggtggaga ggctattcggctatgactgggcacaacagacaatcggctgctctgatgccgccgtgttccggctgtcagcgcaggggcgcccggtt ctttttgtcaagaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcaggatctcctgtc atctcaccttgctcctgccgagaaagtatccatcatggctgatgcaatgcggcggctgcatacgcttgatccggctacctgcccattc gaccaccaagcgaaacatcgcatcgagcgagcacgtactcggatggaagccggtcttgtcgatcaggatgatctggacgaagag catcaggggctcgcgccagccgaactgttcgccaggctcaaggcgcgcatgcccgacggcgatgatctcgtcgtgacccatggcg atgcctgcttgccgaatatcatggtggaaaatggccgcttttctggattcatcgactgtggccggctgggtgtggcggaccgctatca ggacatagcgttggctacccgtgatattgctgaagagcttggcggcgaatgggctgaccgcttcctcgtgctttacggtatcgccgct cccgattcgcagcgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgggacgccggctgg atgatcctccagcgcggggatctcatgctggagttcttcgcccacgggatctctgcggaacaggcggtcgaaggtgccgatatcatt acgacagcaacggccgacaagcacaacgccacgatcctgagcgacaatatgatcgggcccggcgtccacatcaacggcgtcgg cggcgactgcccaggcaagaccgagatgcaccgcgatatcttgctgcgttcggatattttcgtggagttcccgccacagacccgga tgatccccgatcgttcaaacatttggcaataaagtttcttaagattgaatcctgttgccggtcttgcgatgattatcatataatttctgtt gaattacgttaagcatgtaataattaacatgtaatgcatgacgttatttatgagatgggtttttatgattagagtcccgcaattatacat ttaatacgcgatagaaaacaaaatatagcgcgcaaactaggataaattatcgcgcgcggtgtcatctatgttactagatcgggcct cctgtcaatgctggcggcggctctggtggtggttctggtggcggctctgagggtggtggctctgagggtggcggttctgagggtggc ggctctgagggaggcggttccggtggtggctctggttccggtgattttgattatgaaaagatggcaaacgctaataagggggctatg accgaaaatgccgatgaaaacgcgctacagtctgacgctaaaggcaaacttgattctgtcgctactgattacggtgctgctatcgat ggtttcattggtgacgtttccggccttgctaatggtaatggtgctactggtgattttgctggctctaattcccaaatggctcaagtcggt gacggtgataattcacctttaatgaataatttccgtcaatatttaccttccctccctcaatcggttgaatgtcgcccttttgtctttggccc aatacgcaaaccgcctctccccgcgcgttggccgattcattaatgcagctggcacgacaggtttcccgactggaaagcgggcagtg agcgcaacgcaattaatgtgagttagctcactcattaggcaccccaggctttacactttatgcttccggctcgtatgttgtgtggaatt gtgagcggataacaatttcacacaggaaacagctatgaccatgattacgccaagcttgcatgcctgcaggagccatagatgcaa ttcaatcaaactgaaatttctgcaagaatctcaaacacggagatctcaaagtttgaaagaaaatttatttcttcgactcaaaacaaa cttacgaaatttaggtagaacttatatacattatattgtaatttttgtaacaaaatgttttattattattatagaattttactggttaaat taaaaatgaatagaaaaggtgaattaagaggagagaggaggtaaacattttcttctatttttcatattttcaggataaattattgta aaagtttacaagatttccatttgactagtgtaaatgaggaatattctctagtaagatcattatttcatctacttcttttatcttctaccagt agaggaataaacaatatttagctcctttgtaaatacaaattaattttccttcttgacatcattcaattttaattttacgtataaaataaa agatcatacctattagaacgattaaggagaaatacaattcgaatgagaaggatgtgccgtttgttataataaacagccacacgacg taaacgtaaaatgaccacatgatgggccaatagacatggaccgactactaataatagtaagttacattttaggatggaataaatat cataccgacatcagttttgaaagaaaagggaaaaaaagaaaaaataaataaaagatatactaccgacatgagttccaaaagc -continued aaaaaaaaagatcaagccgacacagacacgcgtagagagcaaaatgactttgacgtcacaccacgaaaacagacgcttcatac gtgtccctttatctctctcagtctctctataaacttagtgagaccctcctctgttttactcacaaatatgcaaactagaaaacaatcatc aggaataaagggtttgattacttctattggaaaggactctagaggatccccgggttagtcttccttcttatccggttcgtccagcgcggcc aatctttcaacaaggggaggatgagaatagtgataagcagagtaccaaggatctgtattcatagctgacagattctcctcctgtagtttcacaa gaccaccgcgtaatccagatgcatatccaagcftcftggcaaagccatcagcctgaaattcaaatgatcggctgactaggttcagaccaaag ctgaccaattgctgaagtgggattacagtatgctgaaatatgatgagcccaatgaggactggctgcgtatcaaacccaaagcttcgatacag atcagctgaatttcgcactagtgtatatcctccaaattgtagaagtgtaagaatctgcatagcaacaaatgtgtacacagtatggttgagcttcc agtgtcccaactcatgggcaataacagcaacaatttcctcatcgtctttgcactgttgaattaatgtgtcataagggacaatcctcttgttcttgaa gaatccatacatataggcattgctgtgacttgatcttgtggatccatcgacaacaaatagtttctttaacggatagttgagggaggaagcaagtt tctcgattttctccctgagttgaccatctggaagtggagtgaacttattgaagagtggagctattagtactggataaagggtcatcatcacaata gaaagaccaaacgtaaaaacccaaagatagatggccaagtatggacctcctttctgtactattacaatgattgcagccacaataggtggacc aattattacagaaaggaaaattcctttaagcatgtccctaaagaataaccatggtgtttgcttattaaaaccatgacgggcctcaatcacaaaag ttgagtacagagaaaagggcaaatctgttatctgtgaccaaatcatcagccctgctaagaaggcaagggtatgcagtatttcattctcagcatt gaaaccagctattgtcataaaatctcctgatttcttccaaaaccagggcaataccccaaagtacaaaattgtagagtctgtcactattgtcacaa actcgtgaacaaaatggaagtggcttttatcaagactataggctctagatttctcaaatttctcttggctgataacaccctctaaagtctttggaag agtaggaagtttgagggccctatgttgtcgcacatccaagtaagtttcaaaaatgtacattaatatcataaatccgacaacggcttccatgtag ggaaacgccatgagctcgaatttccccgatcgttcaaacatttggcaataaagtttcttaagattgaatcctgttgccggtcttgcgat gattatcatataatttctgttgaattacgttaagcatgtaataattaacatgtaatgcatgacgttatttatgagatgggtttttatgatt agagtcccgcaattatacatttaatacgcgatagaaaacaaaatatagcgcgcaaactaggataaattatcgcgcgcggtgtcatc tatgttactagatcgggaattcactggccgtcgttttacaacgtcgtgactgggaaaaccctggcgttacccaacttaatcgccttgc agcacatccccctttcgccagctggcgtaatagcgaagaggcccgcaccgatcgcccttcccaacagttgcgcagcctgaatggcg cccgctcctttcgctttcttcccttcctttctcgccacgttcgccggctttccccgtcaagctctaaatcgggggctccctttagggttccg atttagtgctttacggcacctcgaccccaaaaaacttgatttgggtgatggttcacgtagtgggccatcgccctgatagacggtttttc gccctttgacgttggagtccacgttctttaatagtggactcttgttccaaactggaacaacactcaaccctatctcgggctattcttttg atttataagggattttgccgatttcggaaccaccatcaaacaggattttcgcctgctggggcaaaccagcgtggaccgcttgctgca actctctcagggccaggcggtgaagggcaatcagctgttgcccgtctcactggtgaaaagaaaaaccaccccagtacattaaaaa

**cgtccgcaatgtgttattaagttgtctaagcgtcaattt*gtttacaccacaatatatcctgcca***

SEQ ID NO:141 is the nucleic acid sequence of pRD29A-antisense-GmCPP. Italicized sequences are the right and left border repeats. Underlined sequence is the RD29A promoter. Sequence in bold is the GmCPP antisense sequence.

SEQ ID NO: 142

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg -continued aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa -continued agcaagtggattgatgtgatatctccactgacgtaagggatgacgcacaatcccactatccttc gcaagacccttcctctatataaggaagttcatttcatttggagagaacacggggactctagag gatccatggcgattcctttcatggaaaccgtcgttggttttatgatagtgatgtacgtttttga gacgtatttggatctgaggcaacatactgctctcaagcttcccactctcccaaagactttggtt ggagtcattagccaagagaagtttgagaaatctcgagcttacagtcttgacaaaagccattttc actttgttcatgagtttgttactatacttatggactctgcgattctgttctttgggatcttgcc ttggttttggaagatatctggcggctttctaccaatggtgggactcgatccagagaatgaaatc ctgcacactctttcattcttggctggtcttatgacatggtcacagatcactgatttgccatttt ctttgtactcaactttcgtgatcgagtctcggcatgggttcaacaaacaaacaatatggatgtt cattagggacatgatcaaaggaatactcctctctgtcatacctgcccctcctatcgttgccgca attattgttatagttcagaaaggaggtccttacctcgccatctatctgtgggcattcatgttta tcctgtctctagtgatgatgactatataccctgttttgattgcacctcttttcaacaagttcac tcctcttcctgatggagacctccgggagaagattgagaaacttgcttcttctctaaagtttcct ctgaagaagctgtttgttgtcgatggatctacaaggtcaagccatagtaatgcttacatgtatg gtttcttcaagaacaaaaggattgttctttatgacacattgattcagcagtgccagaatgagaa tgaaattgtggcggttattgcacacgagctgggacactggaagctgaatcacactacatactcg ttcattgctgttcaaatccttgccttcttgcaatttggaggatacactcttgtcagaaactcca ctgatctcttcaggagttttggttttgatacacaaccagttctcattggtttgatcatatttca gcacactgtaataccacttcaacacctagtaagctttgacctcaaccttgttagtcgagcgttt gagtttcaggctgatgcttttgcagtgaatcttggttatgcaaaggatctacgtcctgccctag tgaagctacaggaagagaacttatcagcgatgaacacagacccattgtactcagcttatcacta ctcacaccctcctcttgtagagaggcttcgagccattgatggagaagacaagaagacagattaa cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:142 is the nucleic acid sequence of pBI121-BnCPP. Italicized sequences are the right and left border repeats. Underlined sequence is the 35S promoter. Sequence in bold is the BnCPP antisense sequence.

SEQ ID NO: 143

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg -continued atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacgggggactctagac cagtgtcccagctcgtgtgcaataaccgccacaatttcattctcattctggcactgctgaatca atgtgtcataaagaacaatccttttgttcttgaagaaaccatacatgtaagcattactatggct tgaccttgtagatccatcgacaacaaacagcttcttcagaggaaactttagagaagaagcaagt ttctcaatcttctcccggaggtctccatcaggaagaggagtgaacttgttgaaaagaggtgcaa tcaaaacagggtatatagtcatcatcactagagacaggataaacatgaatgcccacagatagat ggcgaggtaaggacctcctttctgaactataacaataattgcggcaacgataggaggggcaggt atgacagagaggagtattcctttgatcatgtccctaatgaacatccatattgtttgtttgttga acccatgccgagactcgatcacgaaagttgagtacaaagaaaatggcaaatcagtgatctgtga ccatgtcataagaccagccaagaatgaaagagtgtgcaggatttcattctctggatcgagtccc accattggtagaaggatccccATCTACCCGCTTCGCGTCGGCATCCGGTCAGTGGCAGTGAAGG

GCGAACAGTTCCTGATTAACCACAAACCGTTCTACTTTACTGGCTTTGGTCGTCATGAAGATGC

GGACTTGCGTGGCAAAGGATTCGATAACGTGCTGATGGTGCACGACCACGCATTAATGGACTGG

ATTGGGGCCAACTCCTACCGTACCTCGCATTACCCTTACGCTGAAGAGATGCTCGACTGGGCAG

ATGAACATGGCATCGTGGTGATTGATGAAACTGCTGCTGTCGGCTTTTCGCTCTCTTTAGGCAT

TGGTTTCGAAGCGGGCAACAAGCCGAAAGAACTGTACAGCGAAGAGGCAGTCAACGGGGAAACT

CAGCAAGCGCACTTACAGGCGATTAAAGAGCTGATAGCGCGTGACAAAAACCACCCAAGCGTGG

TGATGTGGAGTATTGCCAACGAACCGGATACCCGTCCGCAAGGTGCACGGGAATATTTCGCGCC

ACTGGCGGAAGCAACGCGTAAACTCGACCCGACGCGTCCGATCACCTGCGTCAATGTAATGTTC

TGCGACGCTCACACCGATACCATCAGCGATCTCTTTGATGTGCTGTGCCTGAACCGTTATTACG

GATGGTATGTCCAAAGCGGCGATTTGGAAACGGCAGAGAAGGTACTGGAAAAAGAACTTCTGGC

CTGGCAGGAGAAACTGTACACCGACATGTGGAGTGAAGAGTATCAGTGTGCATGGCTGGATATG

TATCACCGCGTCTTTGATCGCGTCAGCGCCGTCGTCGGTGAACAGGTATGGAATTTCGCCGATT

TTGCGACCTCGCAAGGCATATTGCGCGTTGGCGGTAACAAGAAAGGGATCTTCACTCGCGACCG

CAAACCGAAGTCGGCGGCTTTTCTGCTGCAAAAACGCTGGACTGGCATGAACTTCGGTGAAAAA

CCGCAGCAGGGAGGCAAACAATGAatcaacaactctcctggcgcaccatcgtcggctacagcct cgggaattgctaccgagctcttctaccaatggtgggactcgatccagagaatgaaatcctgcac actctttcattcttggctggtcttatgacatggtcacagatcactgatttgccattttctttgt actcaactttcgtgatcgagtctcggcatgggttcaacaaacaaacaatatggatgttcattag ggacatgatcaaaggaatactcctctctgtcatacctgcccctcctatcgttgccgcaattatt

-continued gttatagttcagaaaggaggtccttacctcgccatctatctgtgggcattcatgtttatcctgt ctctagtgatgatgactatataccctgttttgattgcacctcttttcaacaagttcactcctct tcctgatggagacctccgggagaagattgagaaacttgcttcttctctaaagtttcctctgaag aagctgtttgttgtcgatggatctacaaggtcaagccatagtaatgcttacatgtatggtttct tcaagaacaaaaggattgttctttatgacacattgattcagcagtgccagaatgagaatgaaat tgtggcggttattgcacacgagctgggacactgggagctcgaatttccccgatcgttcaaacat ttggcaataaagtttcttaagattgaatcctgttgccggtcttgcgatgattatcatataattt ctgttgaattacgttaagcatgtaataattaacatgtaatgcatgacgttatttatgagatggg tttttatgattagagtcccgcaattatacatttaatacgcgatagaaaacaaaatatagcgcgc aaactaggataaattatcgcgcgcggtgtcatctatgttactagatcgggaattcactggccgt cgttttacaacgtcgtgactgggaaaaccctggcgttacccaacttaatcgccttgcagcacat ccccctttcgccagctggcgtaatagcgaagaggcccgcaccgatcgcccttcccaacagttgc gcagcctgaatggcgcccgctcctttcgctttcttcccttcctttctcgccacgttcgccggct ttccccgtcaagctctaaatcgggggctccctttagggttccgatttagtgctttacggcacct cgaccccaaaaaacttgatttgggtgatggttcacgtagtgggccatcgccctgatagacggtt tttcgccctttgacgttggagtccacgttctttaatagtggactcttgttccaaactggaacaa cactcaaccctatctcgggctattcttttgatttataagggattttgccgatttcggaaccacc atcaaacaggattttcgcctgctggggcaaaccagcgtggaccgcttgctgcaactctctcagg gccaggcggtgaagggcaatcagctgttgcccgtctcactggtgaaaagaaaaaccaccccagt acattaaaaacgtccgcaatgtgttattaagttgtctaagcgtcaattt*gtttacaccacaata*

*tatcctgcca*

SEQ ID NO:143 is the nucleic acid sequence of pBI121-HP-BnCPP. Italicized sequences are the right and left border repeats. Underlined sequence is the 35S promoter. Sequence in bold is the BnCPP antisense sequence, bold and underlined sequence is the BnCPP sense fragment and upper case indicates the truncated GUS fragment.

SEQ ID NO: 144
*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc -continued ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagcccacagatggttagagaggcttacgcagcaggtctcatcaagacg atctacccgagcaataatctccaggaaatcaaataccttcccaagaaggttaaagatgcagtca aaagattcaggactaactgcatcaagaacacagagaaagatatatttctcaagatcagaagtac tattccagtatggacgattcaaggcttgcttcacaaaccaaggcaagtaatagagattggagtc tctaaaaaggtagttcccactgaatcaaaggccatggagtcaaagattcaaatagaggacctaa cagaactcgccgtaaagactggcgaacagttcatacagagtctcttacgactcaatgacaagaa gaaaatcttcgtcaacatggtggagcacgacacacttgtctactccaaaaatatcaaagataca gtctcagaagaccaaagggcaattgagacttttcaacaaagggtaatatccggaaacctcctcg gattccattgcccagctatctgtcactttattgtgaagatagtggaaaaggaaggtggctccta caaatgccatcattgcgataaaggaaaggccatcgttgaagatgcctctgccgacagtggtccc aaagatggacccccacccacgaggagcatcgtggaaaaagaagacgttccaaccacgtcttcaa agcaagtggattgatgtgatatctccactgacgtaagggatgacgcacaatcccactatccttc gcaagacccttcctctatataaggaagttcatttcatttggagagaacacggggactctagag gatccttaatctgtcttcttgtcttctccatcaatggctcgaagcctctctacaagaggagggt gtgagtagtgataagctgagtacaatgggtctgtgttcatcgctgataagttctcttcctgtag cttcactagggcaggacgtagatcctttgcataaccaagattcactgcaaaagcatcagcctga aactcaaacgctcgactaacaaggttgaggtcaaagcttactaggtgttgaagtggtattacag

-continued tgtgctgaaatatgatcaaaccaatgagaactggttgtgtatcaaaaccaaaactcctgaagag atcagtggagtttctgacaagagtgtatcctccaaattgcaagaaggcaaggatttgaacagca atgaacgagtatgtagtgtgattcagcttccagtgtcccagctcgtgtgcaataaccgccacaa tttcattctcattctggcactgctgaatcaatgtgtcataaagaacaatccttttgttcttgaa gaaaccatacatgtaagcattactatggcttgaccttgtagatccatcgacaacaaacagcttc ttcagaggaaactttagagaagaagcaagtttctcaatcttctcccggaggtctccatcaggaa gaggagtgaacttgttgaaaagaggtgcaatcaaaacagggtatatagtcatcatcactagaga caggataaacatgaatgcccacagatagatggcgaggtaaggacctcctttctgaactataaca ataattgcggcaacgataggaggggcaggtatgacagagaggagtattcctttgatcatgtccc taatgaacatccatattgtttgtttgttgaacccatgccgagactcgatcacgaaagttgagta caaagaaaatggcaaatcagtgatctgtgaccatgtcataagaccagccaagaatgaaagagtg tgcaggatttcattctctggatcgagtcccaccattggtagaaagccgccagatatcttccaaa accaaggcaagatcccaaagaacagaatcgcagagtccataagtatagtaacaaactcatgaac aaagtgaaaatggcttttgtcaagactgtaagctcgagatttctcaaacttctcttggctaatg actccaaccaaagtctttgggagagtgggaagcttgagagcagtatgttgcctcagatccaaat acgtctcaaaaacgtacatcactatcataaaaccaacgacggtttccatgaaaggaatcgccat cccctcgaatttccccgatcgttcaaacatttggcaataaagtttcttaagattgaatcctgtt gccggtcttgcgatgattatcatataatttctgttgaattacgttaagcatgtaataattaaca tgtaatgcatgacgttatttatgagatgggtttttatgattagagtcccgcaattatacattta atacgcgatagaaaacaaaatatagcgcgcaaactaggataaattatcgcgcgcggtgtcatct atgttactagatcgggaattcactggccgtcgttttacaacgtcgtgactgggaaaaccctggc gttacccaacttaatcgccttgcagcacatccccctttcgccagctggcgtaatagcgaagagg cccgcaccgatcgcccttcccaacagttgcgcagcctgaatggcgcccgctcctttcgctttct tcccttcctttctcgccacgttcgccggctttccccgtcaagctctaaatcgggggctcccttt agggttccgatttagtgctttacggcacctcgaccccaaaaaacttgatttgggtgatggttca cgtagtgggccatcgccctgatagacggtttttcgccctttgacgttggagtccacgttcttta atagtggactcttgttccaaactggaacaacactcaaccctatctcgggctattcttttgattt ataagggattttgccgatttcggaaccaccatcaaacaggattttcgcctgctggggcaaacca gcgtggaccgcttgctgcaactctctcagggccaggcggtgaagggcaatcagctgttgcccgt ctcactggtgaaaagaaaaaccaccccagtacattaaaaacgtccgcaatgtgttattaagttg tctaagcgtcaattt*gtttacaccacaatatatcctgcca*

SEQ ID NO:144 is the nucleic acid sequence of pBI121-antisense-BnCPP. Italicized sequences are the right and left border repeats. Underlined sequence is the 35S promoter. Sequence in bold is the BnCPP antisense sequence.

SEQ ID NO: 145

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc -continued atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttttgtaacaaaatgtttttattattat tatagaattttactggttaaattaaaaatgaatagaaaaggtgaattaagaggagagaggaggt aaacatttcttctatttttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt -continued gacatcattcaattttaattttacgtataaaataaaagatcatacctattagaacgattaagga
gaaatacaattcgaatgagaaggatgtgccgtttgttataataaacagccacacgacgtaaacg
taaaatgaccacatgatgggccaatagacatggaccgactactaataatagtaagttacatttt
aggatggaataaatatcataccgacatcagttttgaaagaaaagggaaaaaaagaaaaaataaa
taaaagatatactaccgacatgagttccaaaaagcaaaaaaaaagatcaagccgacacagacac
gcgtagagagcaaaatgactttgacgtcacaccacgaaaacagacgcttcatacgtgtcccttt
atctctctcagtctctctataaacttagtgagaccctcctctgttttactcacaaatatgcaaa
ctagaaaacaatcatcaggaataaagggtttgattacttctattggaaaggactctagaggatc
catggcgattcctttcatggaaaccgtcgttggttttatgatagtgatgtacgtttttgagacg
tatttggatctgaggcaacatactgctctcaagcttcccactctcccaaagactttggttggag
tcattagccaagagaagtttgagaaatctcgagcttacagtcttgacaaaagccattttcactt
tgttcatgagtttgttactatacttatggactctgcgattctgttctttgggatcttgccttgg
ttttggaagatatctggcggctttctaccaatggtgggactcgatccagagaatgaaatcctgc
acactctttcattcttggctggtcttatgacatggtcacagatcactgatttgccattttcttt
gtactcaactttcgtgatcgagtctcggcatgggttcaacaaacaaacaatatggatgttcatt
agggacatgatcaaaggaatactcctctctgtcatacctgcccctcctatcgttgccgcaatta
ttgttatagttcagaaaggaggtccttacctcgccatctatctgtgggcattcatgtttatcct
gtctctagtgatgatgactatataccctgttttgattgcacctcttttcaacaagttcactcct
cttcctgatggagacctccgggagaagattgagaaacttgcttcttctctaaagtttcctctga
agaagctgtttgttgtcgatggatctacaaggtcaagccatagtaatgcttacatgtatggttt
cttcaagaacaaaaggattgttctttatgacacattgattcagcagtgccagaatgagaatgaa
attgtggcggttattgcacacgagctgggacactggaagctgaatcacactacatactcgttca
ttgctgttcaaatccttgccttcttgcaatttggaggatacactcttgtcagaaactccactga
tctcttcaggagttttggttttgatacacaaccagttctcattggtttgatcatatttcagcac
actgtaataccacttcaacacctagtaagctttgacctcaaccttgttagtcgagcgtttgagt
ttcaggctgatgcttttgcagtgaatcttggttatgcaaaggatctacgtcctgccctagtgaa
gctacaggaagagaacttatcagcgatgaacacagacccattgtactcagcttatcactactca
caccctcctcttgtagagaggcttcgagccattgatggagaagacaagaagacagattaacccc
tcgaatttccccgatcgttcaaacatttggcaataaagtttcttaagattgaatcctgttgccg
gtcttgcgatgattatcatataatttctgttgaattacgttaagcatgtaataattaacatgta
atgcatgacgttatttatgagatgggtttttatgattagagtcccgcaattatacatttaatac
gcgatagaaaacaaaatatagcgcgcaaactaggataaattatcgcgcgcggtgtcatctatgt
tactagatcgggaattcactggccgtcgttttacaacgtcgtgactgggaaaaccctggcgtta
cccaacttaatcgccttgcagcacatccccctttcgccagctggcgtaatagcgaagaggcccg
caccgatcgcccttcccaacagttgcgcagcctgaatggcgcccgctcctttcgctttcttccc
ttcctttctcgccacgttcgccggctttccccgtcaagctctaaatcgggggctccctttaggg
ttccgatttagtgctttacggcacctcgaccccaaaaaacttgatttgggtgatggttcacgta
gtgggccatcgccctgatagacggtttttcgccctttgacgttggagtccacgttctttaatag
tggactcttgttccaaactggaacaacactcaaccctatctcgggctattcttttgatttataa
gggattttgccgatttcggaaccaccatcaaacaggattttcgcctgctggggcaaaccagcgt
ggaccgcttgctgcaactctctcagggccaggcggtgaagggcaatcagctgttgcccgtctca -continued ctggtgaaaagaaaaaccaccccagtacattaaaaacgtccgcaatgtgttattaagttgtcta agcgtcaatttgtttacaccacaatatatcctgcca SEQ ID NO:145 is the nucleic acid sequence of pRD29A-BnCPP. Italicized sequences are the right and left border repeats. Underlined sequence is the RD29A promoter. Sequence in bold is the BnCPP sense sequence.

SEQ ID NO: 146

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc -continued ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc aagcttgcatgcctgcagggagccatagatgcaattcaatcaaactgaaatttctgcaagaatc tcaaacacggagatctcaaagtttgaaagaaaatttatttcttcgactcaaaacaaacttacga aatttaggtagaacttatatacattatattgtaatttttgtaacaaaatgtttttattattat tatagaattttactggttaaattaaaaatgaatagaaaaggtgaattaagaggagagaggaggt aaacattttcttctatttttcatattttcaggataaattattgtaaaagtttacaagatttcc atttgactagtgtaaatgaggaatattctctagtaagatcattatttcatctacttcttttatc ttctaccagtagaggaataaacaatatttagctcctttgtaaatacaaattaattttccttctt gacatcattcaattttaattttacgtataaaataaaagatcatacctattagaacgattaagga gaaatacaattcgaatgagaaggatgtgccgtttgttataataaacagccacacgacgtaaacg taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaccagt gtcccagctcgtgtgcaataaccgccacaatttcattctcattctggcactgctgaatcaatgt gtcataaagaacaatccttttgttcttgaagaaaccatacatgtaagcattactatggcttgac cttgtagatccatcgacaacaaacagcttcttcagaggaaactttagagaagaagcaagtttct caatcttctcccggaggtctccatcaggaagaggagtgaacttgttgaaaagaggtgcaatcaa aacagggtatatagtcatcatcactagagacaggataaacatgaatgcccacagatagatggcg aggtaaggacctcctttctgaactataacaataattgcggcaacgataggaggggcaggtatga cagagaggagtattcctttgatcatgtccctaatgaacatccatattgtttgtttgttgaaccc atgccgagactcgatcacgaaagttgagtacaaagaaaatggcaaatcagtgatctgtgaccat gtcataagaccagccaagaatgaaagagtgtgcaggatttcattctctggatcgagtcccacca ttggtagaaggatccccATCTACCCGCTTCGCGTCGGCATCCGGTCAGTGGCAGTGAAGGGCGA

ACAGTTCCTGATTAACCACAAACCGTTCTACTTTACTGGCTTTGGTCGTCATGAAGATGCGGAC

TTGCGTGGCAAAGGATTCGATAACGTGCTGATGGTGCACGACCACGCATTAATGGACTGGATTG

GGGCCAACTCCTACCGTACCTCGCATTACCCTTACGCTGAAGAGATGCTCGACTGGGCAGATGA

ACATGGCATCGTGGTGATTGATGAAACTGCTGCTGTCGGCTTTTCGCTCTCTTTAGGCATTGGT

TTCGAAGCGGGCAACAAGCCGAAAGAACTGTACAGCGAAGAGGCAGTCAACGGGGAAACTCAGC

AAGCGCACTTACAGGCGATTAAAGAGCTGATAGCGCGTGACAAAAACCACCCAAGCGTGGTGAT

GTGGAGTATTGCCAACGAACCGGATACCCGTCCGCAAGGTGCACGGGAATATTTCGCGCCACTG

GCGGAAGCAACGCGTAAACTCGACCCGACGCGTCCGATCACCTGCGTCAATGTAATGTTCTGCG

ACGCTCACACCGATACCATCAGCGATCTCTTTGATGTGCTGTGCCTGAACCGTTATTACGGATG

GTATGTCCAAAGCGGCGATTTGGAAACGGCAGAGAAGGTACTGGAAAAAGAACTTCTGGCCTGG

CAGGAGAAACTGTACACCGACATGTGGAGTGAAGAGTATCAGTGTGCATGGCTGGATATGTATC

-continued

ACCGCGTCTTTGATCGCGTCAGCGCCGTCGTCGGTGAACAGGTATGGAATTTCGCCGATTTTGC

GACCTCGCAAGGCATATTGCGCGTTGGCGGTAACAAGAAAGGGATCTTCACTCGCGACCGCAAA

CCGAAGTCGGCGGCTTTTCTGCTGCAAAAACGCTGGACTGGCATGAACTTCGGTGAAAAACCGC

AGCAGGGAGGCAAACAATGAATCAACAACTCTCCTGGCGCACCATCGTCGGCTACAGCCTCGGG

AATTGCTACCGAGCTCttctaccaatggtgggactcgatccagagaatgaaatcctgcacactc tttcattcttggctggtcttatgacatggtcacagatcactgatttgccattttctttgtactc aactttcgtgatcgagtctcggcatgggttcaacaaacaaacaatatggatgttcattagggac atgatcaaaggaatactcctctctgtcatacctgcccctcctatcgttgccgcaattattgtta tagttcagaaaggaggtccttacctcgccatctatctgtgggcattcatgtttatcctgtctct agtgatgatgactatataccctgttttgattgcacctcttttcaacaagttcactcctcttcct gatggagacctccgggagaagattgagaaacttgcttcttctctaaagtttcctctgaagaagc tgtttgttgtcgatggatctacaaggtcaagccatagtaatgcttacatgtatggtttcttcaa gaacaaaaggattgttctttatgacacattgattcagcagtgccagaatgagaatgaaattgtg gcggttattgcacacgagctgggacactgggagctcgaatttccccgatcgttcaaacatttgg caataaagtttcttaagattgaatcctgttgccggtcttgcgatgattatcatataatttctgt tgaattacgttaagcatgtaataattaacatgtaatgcatgacgttatttatgagatgggtttt tatgattagagtcccgcaattatacatttaatacgcgatagaaaacaaaatatagcgcgcaaac taggataaattatcgcgcgcggtgtcatctatgttactagatcgggaattcactggccgtcgtt ttacaacgtcgtgactgggaaaaccctggcgttacccaacttaatcgccttgcagcacatcccc ctttcgccagctggcgtaatagcgaagaggcccgcaccgatcgcccttcccaacagttgcgcag cctgaatggcgcccgctcctttcgctttcttcccttcctttctcgccacgttcgccggctttcc ccgtcaagctctaaatcgggggctccctttagggttccgatttagtgctttacggcacctcgac cccaaaaaacttgatttgggtgatggttcacgtagtgggccatcgccctgatagacggtttttc gccctttgacgttggagtccacgttctttaatagtggactcttgttccaaactggaacaacact caaccctatctcgggctattcttttgatttataagggattttgccgatttcggaaccaccatca aacaggattttcgcctgctggggcaaaccagcgtggaccgcttgctgcaactctctcagggcca ggcggtgaagggcaatcagctgttgcccgtctcactggtgaaaagaaaaaccaccccagtacat taaaaacgtccgcaatgtgttattaagttgtctaagcgtcaattt*gtttacaccacaatatatc*

*ctgcca*

SEQ ID NO:146 is the nucleic acid sequence of pRD29A-HP-BnCPP. Italicized sequences are the right and left border repeats. Underlined sequence is the RD29A promoter. Sequence in bold is the BnCPP antisense sequence, bold and underlined sequence is BnCPP sense fragment and the upper case sequence represents the truncated GUS fragment.

SEQ ID NO: 147

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg -continued gcgcccggttctttttgtcaagaccgacctgtccggtgccctgaatgaactgcaggacgaggca
gcgcggctatcgtggctggccacgacgggcgttccttgcgcagctgtgctcgacgttgtcactg
aagcgggaagggactggctgctattgggcgaagtgccggggcaggatctcctgtcatctcacct
tgctcctgccgagaaagtatccatcatggctgatgcaatgcggcggctgcatacgcttgatccg
gctacctgcccattcgaccaccaagcgaaacatcgcatcgagcgagcacgtactcggatggaag
ccggtcttgtcgatcaggatgatctggacgaagagcatcaggggctcgcgccagccgaactgtt
cgccaggctcaaggcgcgcatgcccgacggcgatgatctcgtcgtgacccatggcgatgcctgc
ttgccgaatatcatggtggaaaatggccgcttttctggattcatcgactgtggccggctgggtg
tggcggaccgctatcaggacatagcgttggctacccgtgatattgctgaagagcttggcggcga
atgggctgaccgcttcctcgtgctttacggtatcgccgctcccgattcgcagcgcatcgccttc
tatcgccttcttgacgagttcttctgagcgggactctggggttcgaaatgaccgaccaagcgac
gcccaacctgccatcacgagatttcgattccaccgccgccttctatgaaaggttgggcttcgga
atcgttttccgggacgccggctggatgatcctccagcgcggggatctcatgctggagttcttcg
cccacgggatctctgcggaacaggcggtcgaaggtgccgatatcattacgacagcaacggccga
caagcacaacgccacgatcctgagcgacaatatgatcgggcccggcgtccacatcaacggcgtc
ggcggcgactgcccaggcaagaccgagatgcaccgcgatatcttgctgcgttcggatattttcg
tggagttcccgccacagacccggatgatccccgatcgttcaaacatttggcaataaagtttctt
aagattgaatcctgttgccggtcttgcgatgattatcatataatttctgttgaattacgttaag
catgtaataattaacatgtaatgcatgacgttatttatgagatgggtttttatgattagagtcc
cgcaattatacatttaatacgcgatagaaaacaaaatatagcgcgcaaactaggataaattatc
gcgcgcggtgtcatctatgttactagatcgggcctcctgtcaatgctggcggcggctctggtgg
tggttctggtggcggctctgagggtggtggctctgagggtggcggttctgagggtggcggctct
gagggaggcggttccggtggtggctctggttccggtgattttgattatgaaaagatggcaaacg
ctaataagggggctatgaccgaaaatgccgatgaaaacgcgctacagtctgacgctaaaggcaa
acttgattctgtcgctactgattacggtgctgctatcgatggtttcattggtgacgtttccggc
cttgctaatggtaatggtgctactggtgattttgctggctctaattcccaaatggctcaagtcg
gtgacggtgataattcacctttaatgaataatttccgtcaatatttaccttccctccctcaatc
ggttgaatgtcgcccttttgtctttggcccaatacgcaaaccgcctctccccgcgcgttggccg
attcattaatgcagctggcacgacaggtttcccgactggaaagcgggcagtgagcgcaacgcaa
ttaatgtgagttagctcactcattaggcaccccaggctttacactttatgcttccggctcgtat
gttgtgtggaattgtgagcggataacaatttcacacaggaaacagctatgaccatgattacgcc
aagcttgcatgcctgcagggagccatagatgcaattcaatcaaactgaaatttctgcaagaatc
tcaaacacggagatctcaaagtttgaaagaaaatttatttcttcgactcaaaacaaacttacga
aatttaggtagaacttatatacattatattgtaatttttttgtaacaaaatgtttttattattat
tatagaattttactggttaaattaaaaatgaatagaaaaggtgaattaagaggagagaggaggt
aaacattttcttctatttttttcatattttcaggataaattattgtaaaagtttacaagatttcc
atttgactagtgtaaatgaggaatattctctagtaagatcattatttcatctacttcttttatc
ttctaccagtagaggaataaacaatatttagctcctttgtaaatacaaattaattttccttctt
gacatcattcaattttaattttacgtataaaataaaagatcatacctattagaacgattaagga
gaaatacaattcgaatgagaaggatgtgccgtttgttataataaacagccacacgacgtaaacg -continued taaaatgaccacatgatgggccaatagacatggaccgactactaataatagtaagttacatttt aggatggaataaatatcataccgacatcagttttgaaagaaaagggaaaaaaagaaaaaataaa taaaagatatactaccgacatgagttccaaaaagcaaaaaaaaagatcaagccgacacagacac gcgtagagagcaaaatgactttgacgtcacaccacgaaaacagacgcttcatacgtgtcccttt atctctctcagtctctctataaacttagtgagaccctcctctgttttactcacaaatatgcaaa ctagaaaacaatcatcaggaataaagggtttgattacttctattggaaaggactctagaggatc cttaatctgtcttcttgtcttctccatcaatggctcgaagcctctctacaagaggagggtgtga gtagtgataagctgagtacaatgggtctgtgttcatcgctgataagttctcttcctgtagcttc actagggcaggacgtagatcctttgcataaccaagattcactgcaaaagcatcagcctgaaact caaacgctcgactaacaaggttgaggtcaaagcttactaggtgttgaagtggtattacagtgtg ctgaaatatgatcaaaccaatgagaactggttgtgtatcaaaaccaaaactcctgaagagatca gtggagtttctgacaagagtgtatcctccaaattgcaagaaggcaaggatttgaacagcaatga acgagtatgtagtgtgattcagcttccagtgtcccagctcgtgtgcaataaccgccacaatttc attctcattctggcactgctgaatcaatgtgtcataaagaacaatccttttgttcttgaagaaa ccatacatgtaagcattactatggcttgaccttgtagatccatcgacaacaaacagcttcttca gaggaaactttagagaagaagcaagtttctcaatcttctcccggaggtctccatcaggaagagg agtgaacttgttgaaaagaggtgcaatcaaaacagggtatatagtcatcatcactagagacagg ataaacatgaatgcccacagatagatggcgaggtaaggacctcctttctgaactataacaataa ttgcggcaacgataggagggcaggtatgacagagaggagtattcctttgatcatgtccctaat gaacatccatattgtttgtttgttgaacccatgccgagactcgatcacgaaagttgagtacaaa gaaaatggcaaatcagtgatctgtgaccatgtcataagaccagccaagaatgaaagagtgtgca ggatttcattctctggatcgagtcccaccattggtagaaagccgccagatatcttccaaaacca aggcaagatcccaaagaacagaatcgcagagtccataagtatagtaacaaactcatgaacaaag tgaaaatggcttttgtcaagactgtaagctcgagatttctcaaacttctcttggctaatgactc caaccaaagtctttgggagagtgggaagcttgagagcagtatgttgcctcagatccaaatacgt ctcaaaaacgtacatcactatcataaaaccaacgacggtttccatgaaaggaatcgccatcccc tcgaatttccccgatcgttcaaacatttggcaataaagtttcttaagattgaatcctgttgccg gtcttgcgatgattatcatataatttctgttgaattacgttaagcatgtaataattaacatgta atgcatgacgttatttatgagatgggtttttatgattagagtcccgcaattatacatttaatac gcgatagaaaacaaaatatagcgcgcaaactaggataaattatcgcgcgcggtgtcatctatgt tactagatcgggaattcactggccgtcgttttacaacgtcgtgactgggaaaaccctggcgtta cccaacttaatcgccttgcagcacatccccctttcgccagctggcgtaatagcgaagaggcccg caccgatcgcccttcccaacagttgcgcagcctgaatggcgcccgctcctttcgctttcttccc ttcctttctcgccacgttcgccggctttccccgtcaagctctaaatcgggggctccctttaggg ttccgatttagtgctttacggcacctcgaccccaaaaaacttgatttgggtgatggttcacgta gtgggccatcgccctgatagacggtttttcgccctttgacgttggagtccacgttctttaatag tggactcttgttccaaactggaacaacactcaaccctatctcgggctattcttttgatttataa gggattttgccgatttcggaaccaccatcaaacaggattttcgcctgctggggcaaaccagcgt ggaccgcttgctgcaactctctcagggccaggcggtgaagggcaatcagctgttgcccgtctca ctggtgaaaagaaaaaccaccccagtacattaaaaacgtccgcaatgtgttattaagttgtcta agcgtcaattt*gtttacaccacaatatatcctgcca*

SEQ ID NO:147 is the nucleic acid sequence of pRD29A-antisense-BnCPP. Italicized sequences are the right and left border repeats. Underlined sequence is the RD29A promoter. Sequence in bold is the BnCPP antisense sequence.

SEQ ID NO: 148

*gtttacccgccaatatatcctgtc*aaacactgatagtttaaactgaaggcgggaaacgacaatc tgatcatgagcggagaattaagggagtcacgttatgacccccgccgatgacgcgggacaagccg ttttacgtttggaactgacagaaccgcaacgttgaaggagccactcagccgcgggtttctggag tttaatgagctaagcacatacgtcagaaaccattattgcgcgttcaaaagtcgcctaaggtcac tatcagctagcaaatatttcttgtcaaaaatgctccactgacgttccataaattcccctcggta tccaattagagtctcatattcactctcaatccaaataatctgcaccggatctggatcgtttcgc atgattgaacaagatggattgcacgcaggttctccggccgcttgggtggagaggctattcggct atgactgggcacaacagacaatcggctgctctgatgccgccgtgttccggctgtcagcgcaggg gcgcccggttctttttgtcaagaccgacctgtccggtgccctgaatgaactgcaggacgaggca gcgcggctatcgtggctggccacgacgggcgttccttgcgcagctgtgctcgacgttgtcactg aagcgggaagggactggctgctattgggcgaagtgccggggcaggatctcctgtcatctcacct tgctcctgccgagaaagtatccatcatggctgatgcaatgcggcggctgcatacgcttgatccg gctacctgcccattcgaccaccaagcgaaacatcgcatcgagcgagcacgtactcggatggaag ccggtcttgtcgatcaggatgatctggacgaagagcatcaggggctcgcgccagccgaactgtt cgccaggctcaaggcgcgcatgcccgacggcgatgatctcgtcgtgacccatggcgatgcctgc ttgccgaatatcatggtggaaaatggccgcttttctggattcatcgactgtggccggctgggtg tggcggaccgctatcaggacatagcgttggctacccgtgatattgctgaagagcttggcggcga atgggctgaccgcttcctcgtgctttacggtatcgccgctcccgattcgcagcgcatcgccttc tatcgccttcttgacgagttcttctgagcgggactctggggttcgaaatgaccgaccaagcgac gcccaacctgccatcacgagatttcgattccaccgccgccttctatgaaaggttgggcttcgga atcgttttccgggacgccggctggatgatcctccagcgcggggatctcatgctggagttcttcg cccacgggatctctgcggaacaggcggtcgaaggtgccgatatcattacgacagcaacggccga caagcacaacgccacgatcctgagcgacaatatgatcgggcccggcgtccacatcaacggcgtc ggcggcgactgcccaggcaagaccgagatgcaccgcgatatcttgctgcgttcggatattttcg tggagttcccgccacagacccggatgatccccgatcgttcaaacatttggcaataaagtttctt aagattgaatcctgttgccggtcttgcgatgattatcatataatttctgttgaattacgttaag catgtaataattaacatgtaatgcatgacgttatttatgagatgggtttttatgattagagtcc cgcaattatacatttaatacgcgatagaaaacaaaatatagcgcgcaaactaggataaattatc gcgcgcggtgtcatctatgttactagatcgggcctcctgtcaatgctggcggcggctctggtgg tggttctggtggcggctctgagggtggtggctctgagggtggcggttctgagggtggcggctct gagggaggcggttccggtggtggctctggttccggtgattttgattatgaaaagatggcaaacg ctaataagggggctatgaccgaaaatgccgatgaaaacgcgctacagtctgacgctaaaggcaa acttgattctgtcgctactgattacggtgctgctatcgatggtttcattggtgacgtttccggc cttgctaatggtaatggtgctactggtgattttgctggctctaattcccaaatggctcaagtcg gtgacggtgataattcacctttaatgaataatttccgtcaatatttaccttccctccctcaatc ggttgaatgtcgcccttttgtctttggcccaatacgcaaaccgcctctccccgcgcgttggccg attcattaatgcagctggcacgacaggtttcccgactggaaagcgggcagtgagcgcaacgcaa ttaatgtgagttagctcactcattaggcaccccaggctttacactttatgcttccggctcgtat gttgtgtggaattgtgagcggataacaatttcacacaggaaacagctatgaccatgattacgcc -continued aagctgggaaattttcgccagttctaaatatccggaaacctcttgggatgccattgcccatct atctgtaatttattgacgaaatagacgaaaaggaaggtggctcctataaagcacatcattgcga taacagaaaggccattgttgaagatacctctgctgacattggtccccaagtggaagcaccaccc catgaggagcaccgtggagtaagaagacgttcgagccacgtcgaaaaagcaagtgtgttgatgt agtatctccattgacgtaagggatgacgcacaatccaactatccatcgcaagaccattgctcta tataagaaagttaatatcatttcgagtggccacgctgaggggatccatggcgattcctttcat ggaaaccgtcgttggttttatgatagtgatgtacgtttttgagacgtatttggatctgaggcaa catactgctctcaagcttcccactctcccaaagactttggttggagtcattagccaagagaagt ttgagaaatctcgagcttacagtcttgacaaaagccattttcactttgttcatgagtttgttac tatacttatggactctgcgattctgttctttgggatcttgccttggttttggaagatatctggc ggctttctaccaatggtgggactcgatccagagaatgaaatcctgcacactctttcattcttgg ctggtcttatgacatggtcacagatcactgatttgccattttctttgtactcaactttcgtgat cgagtctcggcatgggttcaacaaacaaacaatatggatgttcattagggacatgatcaaagga atactcctctctgtcatacctgcccctcctatcgttgccgcaattattgttatagttcagaaag gaggtccttacctcgccatctatctgtgggcattcatgtttatcctgtctctagtgatgatgac tatataccctgttttgattgcacctcttttcaacaagttcactcctcttcctgatggagacctc cgggagaagattgagaaacttgcttcttctctaaagtttcctctgaagaagctgtttgttgtcg atggatctacaaggtcaagccatagtaatgcttacatgtatggtttcttcaagaacaaaaggat tgttctttatgacacattgattcagcagtgccagaatgagaatgaaattgtggcggttattgca cacgagctgggacactggaagctgaatcacactacatactcgttcattgctgttcaaatccttg ccttcttgcaatttggaggatacactcttgtcagaaactccactgatctcttcaggagttttgg ttttgatacacaaccagttctcattggtttgatcatatttcagcacactgtaataccacttcaa cacctagtaagctttgacctcaaccttgttagtcgagcgtttgagtttcaggctgatgcttttg cagtgaatcttggttatgcaaaggatctacgtcctgccctagtgaagctacaggaagagaactt atcagcgatgaacacagacccattgtactcagcttatcactactcacaccctcctcttgtagag aggcttcgagccattgatggagaagacaagaagacagattaacccctcgaatttccccgatcgt tcaaacatttggcaataaagtttcttaagattgaatcctgttgccggtcttgcgatgattatca tataatttctgttgaattacgttaagcatgtaataattaacatgtaatgcatgacgttatttat gagatgggtttttatgattagagtcccgcaattatacatttaatacgcgatagaaaacaaaata tagcgcgcaaactaggataaattatcgcgcgcggtgtcatctatgttactagatcgggaattca ctggccgtcgttttacaacgtcgtgactgggaaaaccctggcgttacccaacttaatcgccttg cagcacatccccctttcgccagctggcgtaatagcgaagaggcccgcaccgatcgcccttccca acagttgcgcagcctgaatggcgcccgctcctttcgctttcttcccttcctttctcgccacgtt cgccggctttccccgtcaagctctaaatcgggggctccctttagggttccgatttagtgcttta cggcacctcgaccccaaaaaacttgatttgggtgatggttcacgtagtgggccatcgccctgat agacggtttttcgccctttgacgttggagtccacgttctttaatagtggactcttgttccaaac tggaacaacactcaaccctatctcgggctattcttttgatttataagggattttgccgatttcg gaaccaccatcaaacaggattttcgcctgctggggcaaaccagcgtggaccgcttgctgcaact ctctcagggccaggcggtgaagggcaatcagctgttgcccgtctcactggtgaaaagaaaaacc -continued accccagtacattaaaaacgtccgcaatgtgttattaagttgtctaagcgtcaattt*gtttaca*

*ccacaatatatcctgcca*

SEQ ID NO:148 is the nucleic acid sequence of MuA-BnCPP. Italicized sequences are the right and left border repeats. Underlined sequence is the MuA promoter. Sequence in bold is the BnCPP sense sequence.

Example 33

Southern Analysis

Genomic Southern blot analysis of transgenic *Arabidopsis* was performed using standard techniques known to one skilled in the art. Typically, 10 g of DNA was electrophoresed in a 0.8% agarose gel and transferred to an appropriate membrane such as Hybond N+ (Amersham Pharmacia Biotech). Pre-hybridization and hybridization conditions were as suggested by the membrane manufacturer, typically at 65° C. The final stringency wash was typically at 1×SSC and 0.1% SDS at 65° C. The NPTII coding region was typically used as the radiolabeled probe in Southern blot analysis.

Example 34

PCR Analysis of Transgenic Plants

PCR was used as a method to confirm the presence of the transgene in all transgenic lines and every construct. Typical PCR mixtures contained: 1× reaction buffer (10 mM Tris-HCl pH 8.8, 1.5 mM $MgCl_2$, 50 mM KCl), dNTP's at 200 μM, 1 pM forward and reverse primer, 2.5 U. Taq DNA polymerase, and template plus water to a final volume of 50 μL. Reactions were run at 1 minute 94° C., 1 minute 60° C., 1 minute 72° C., for 30 cycles. Primers used in the analysis of pBI121-AtCPP and pBI121-HP-AtCPP transgenic plants were as shown in Table 20. Primers used in the analysis of pRD29A-AtCPP were RD29AP1 (SEQ ID NO:161) and SEQ ID NO:102. Primers used in the analysis of pRD29A-HP-AtCPP transgenic plants were those identified as RD29AP1 (SEQ ID NO:161), SEQ ID NO:103 and SEQ ID NO:103, Nosterm-RV (SEQ ID NO:162).

TABLE 20

| | | |
|---|---|---|
| pBI121-AtCPP BamFW: | 5'-GCCGACAGTGGTCCCAAAGATGG-3' | (SEQ ID NO: 105) |
| p35S-AtCPP SmaRV: | 5'-AAACCCGGGTTAATCTGTCTTCTTGTCTTCTCCA-3' | (SEQ ID NO: 102) |
| p35S-HP-AtCPP BamFW: | 5'-CTGGAGCTCTTTTACCGAGGTTGGGCCTTGATCC-3' | (SEQ ID NO: 103) |
| p35S-HP-AtCPP SmaRV: | 5'-GCAAGACCGGCAACAGGA-3' | (SEQ ID NO: 108) |
| pRD29AP1: | 5'-TTTAAGCTTGGAGCCATAGATGCAATTCAA-3' | (SEQ ID NO: 161) |
| pRD29AP1: | 5'-TTTAAGCTTGGAGCCATAGATGCAATTCAA-3' | (SEQ ID NO: 161) |
| Nosterm-RV: | 5'-GCAAGACCGGCAACAGGA-3' | (SEQ ID NO: 162) |

Figure 27:
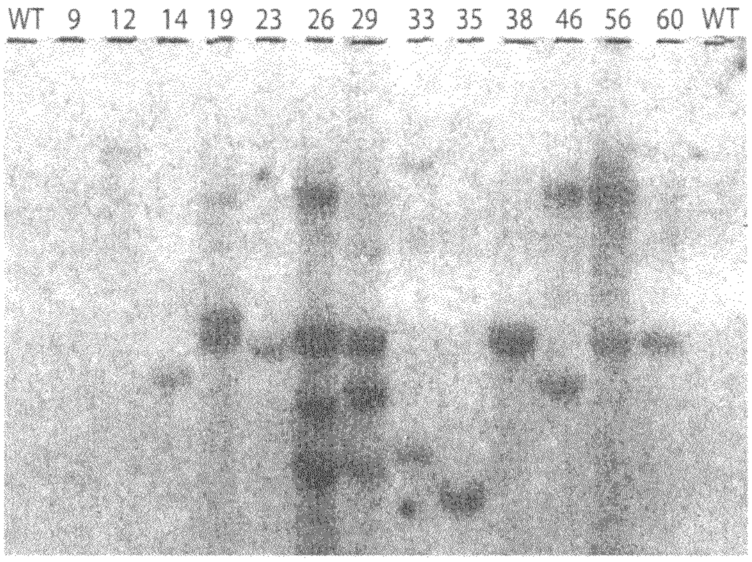
FIG. 27 is a scan of a typical Southern blot of transgenic *Arabidopsis* T1 lines carrying the pBI121-AtCPP construct.

Thirty-seven *Arabidopsis* lines were selected as homozygous pBI121-AtCPP over-expression lines for further examination. FIG. 27 shows a representative blot confirming the presence of the pBI121-AtCPP transgene. Lines were confirmed to be transgenic by PCR analysis using transgene specific primers in the PCR assays.

Figure 28:
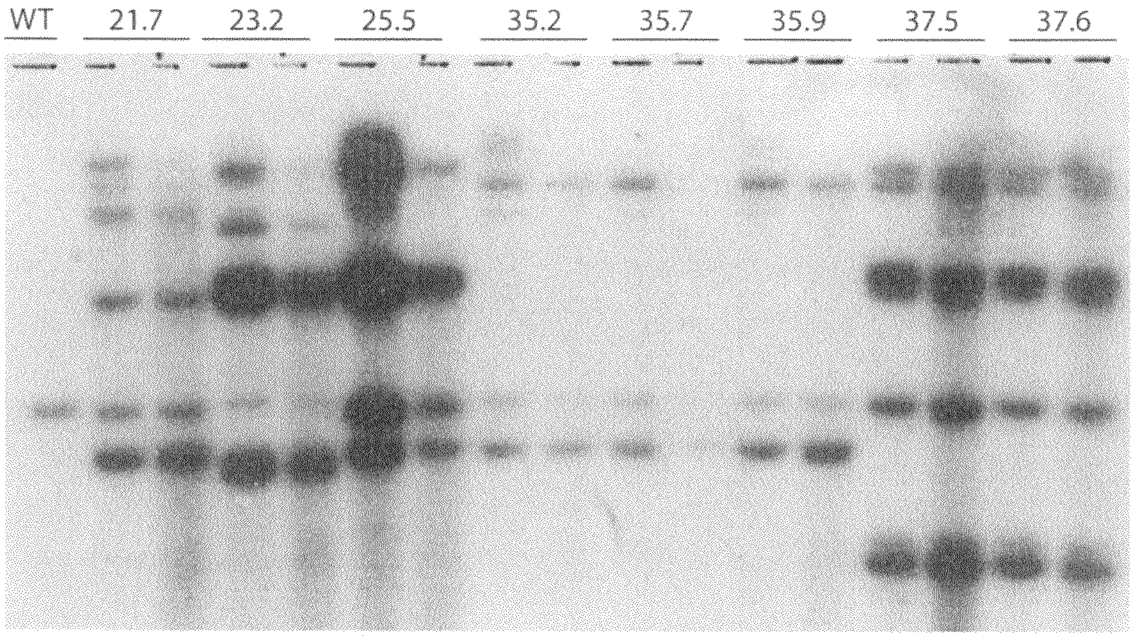
FIG. 28 is a scan of a typical Southern blot of transgenic *Arabidopsis* T3 lines carrying the pBI121-HP-AtCPP construct.

Thirty-three *Arabidopsis* lines were selected as homozygous pBI121-HP-AtCPP hair-pin down-regulation lines for further examination. FIG. 28 shows a representative blot confirming the presence of the pBI121-HP-AtCPP hair-pin construct. All lines were confirmed to be transgenic by PCR analysis using transgene specific primers in the PCR assays.

Figure 29:
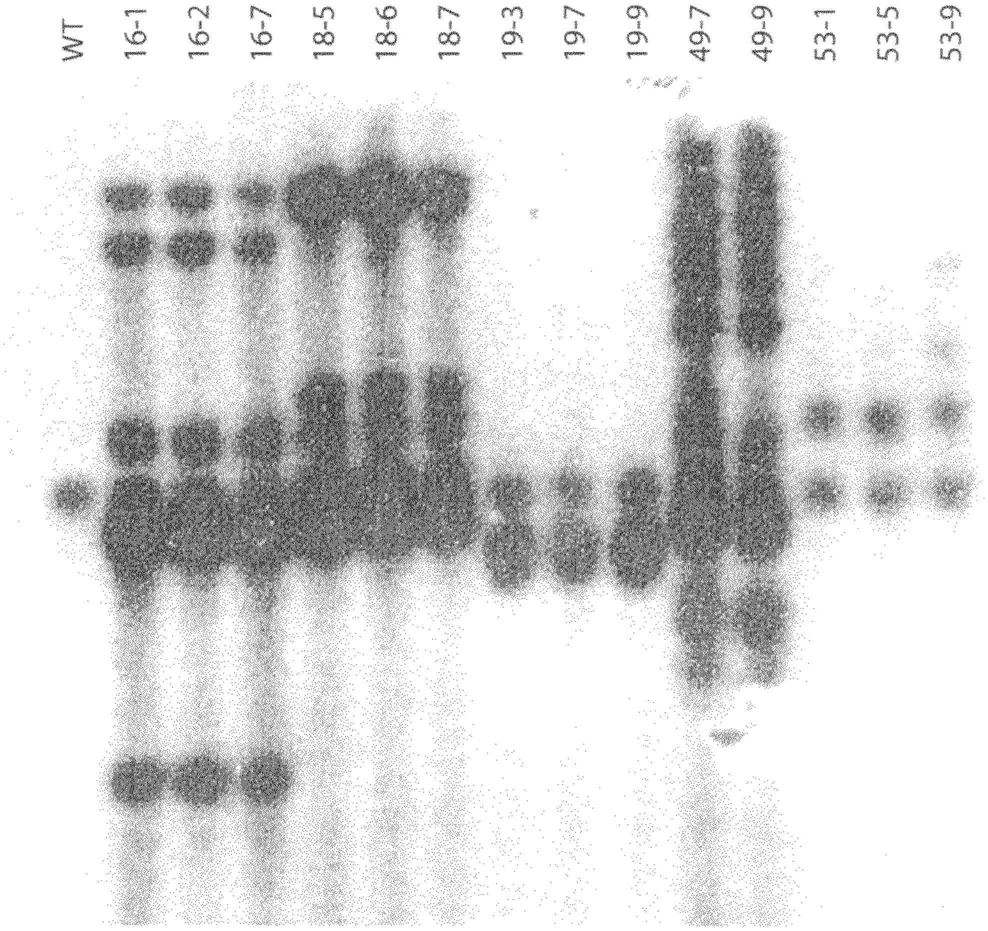
FIG. 29 is a scan of a typical Southern blot of transgenic *Arabidopsis* lines carrying the pRD29A-AtCPP construct.

*Arabidopsis* lines were selected as homozygous pRD29A-AtCPP over-expression lines for further examination. FIG. 29 shows a representative blot confirming the presence of the pRD29A-AtCPP transgene. Lines were confirmed to be transgenic by PCR analysis using transgene specific primers in the PCR assays.

Figure 30:
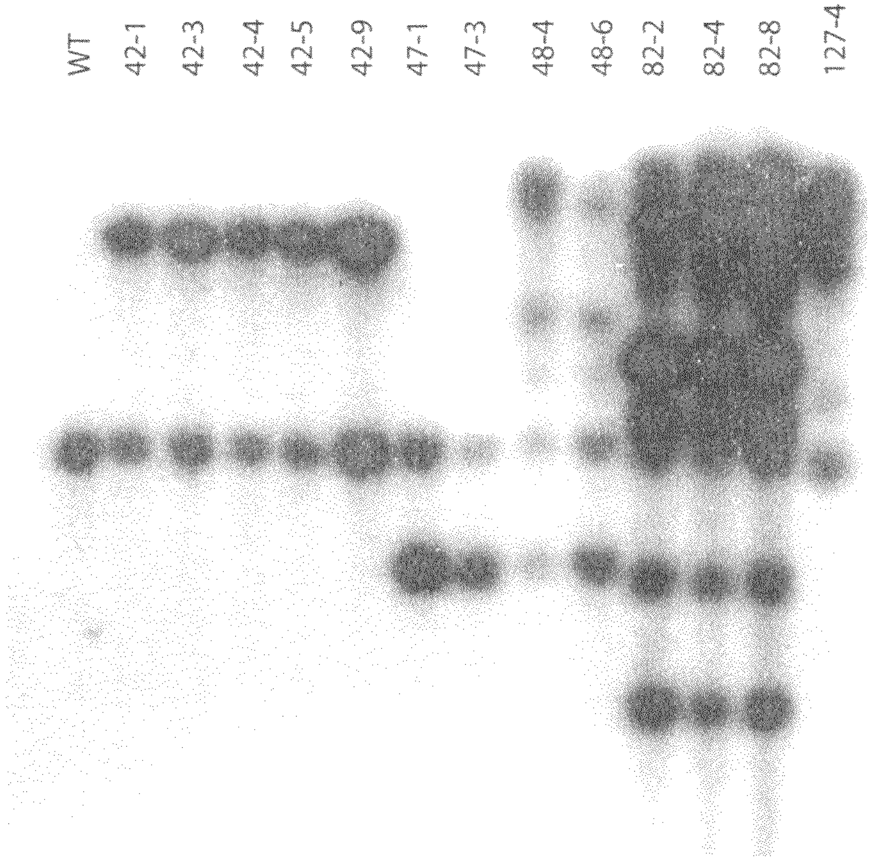
FIG. 30 is a scan of a typical Southern blot of transgenic *Arabidopsis* lines carrying the pRD29A-HP-AtCPP construct.

*Arabidopsis* lines were selected as homozygous pRD29A-HP-AtCPP lines for further examination. FIG. 30 shows a representative blot confirming the presence of the pRD29A-HP-AtCPP transgene. Lines were confirmed to be transgenic by PCR analysis using transgene specific primers in the PCR assays.

Example 35

Northern Analysis of Transgenic Plants

Figure 31:
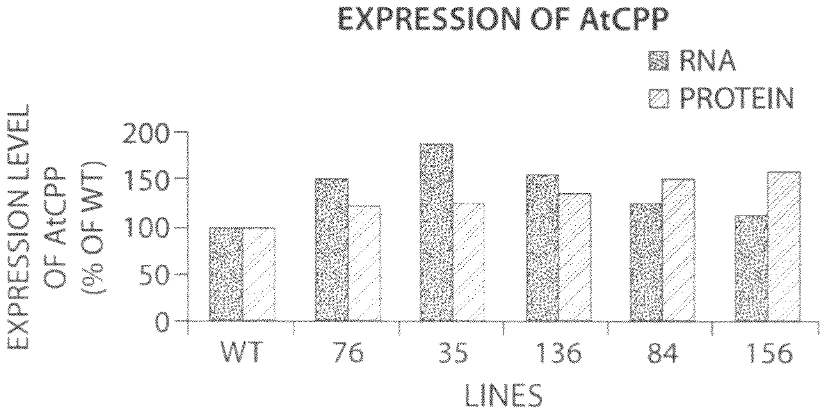
FIG. 31 is an illustration showing the relative expression of AtCPP mRNA transcript (solid bars) and AtCPP protein levels (stippled bars) in several pBI121-AtCPP transgenic lines.

Total RNA was isolated from developing leaf tissue of 27 35S-AtCPP *Arabidopsis* lines (T3 plants). Approximately 10 μg of total RNA was loaded into each lane. The Northern blot was first probed with $P^{32}$ labeled, single-stranded antisense transcript of AtCPP which detects sense transcript, then stripped and re-probed with cDNA of β-tubulin that was used as a reference. The hybridizing bands of AtCPP and β-tubulin were scanned and quantified using the UN-Scan-It programme (Silk Scientific, Utah, USA), and the ratio of the two hybridizing bands for each sample was obtained. The ratio of the wild type plants was set to 100%, and was compared with those of the transgenic lines. Twenty-one out of twenty-seven lines showed higher expression of AtCPP transcript as compared to the wild type. Values ranged from 104% to 282% of wild type. The results of five lines (35, 84, 76, 136, and 156) of the 21 over-expressing lines is shown in FIG. 31.

Example 36

Production of Polyclonal Antibodies Against AtCPP

Anti-AtCPP antibodies were generated using AtCPP fusion protein over-expressed in *E. coli*. The over-expression vector, pMAL-p2, contains 1175 bp male gene that is located upstream of AtCPP and encodes a 43 KDa maltose-binding protein (MBP). The 1275 bp BamHI/SmaI DNA fragment of AtCPP was inserted into pMAL-p2 at BamHI and SalI sites. The SalI site was converted into blunt end using Klenow fragment. The resulting fusion protein MBP-AtCPP was then over-expressed in DH5α, and purified by one-step affinity for MBP as described by the manufacturer (New England Biolab). The soluble fraction of the crude bacterial extract containing the MBP-AtCPP fusion protein was loaded to a amylose column (1.5 cm×10.0 cm), and the proteins were eluted with 10 mM maltose in column buffer (50 mM Tris-HCl, pH 7.5, 1 mM EDTA, and 200 mM NaCl). Fractions containing purified MBP-AtCPP fusion protein were pooled, and concentrated with a Centriprep-30 concentrator (Amicon). All purification steps were carried out at 4° C. To generate an antibody, the purified fusion protein was further separated by SDS-PAGE and the Coomassie stained band corresponding to the fusion protein was excised. The identity of the fusion protein was confirmed by Western analysis using anti-MBP antibodies (purchased from New England Biolab). The protein was eluted from the gel slice by electroelution and then emulsified in Ribi adjuvant (Ribi Immunochem) to a final volume of 1 ml. MBP-AtCPP protein was injected into a 3 kg New Zealand rabbit on day 1 and booster injections were given on day 21 and day 35 with 175 μg of the protein each time. High-titer antisera were obtained one week after the final injection.

Example 37

Western Blot Analysis of 35S-AtCPP Transgenic Lines Using Anti-AtCPP Antibodies Western analysis was performed to examine expression level of AtCPP in the transgenic lines compared with that of wild type plants. Anti-Bip antibody, an ER lumenal protein (Stressgen, Victoria, BC, Canada) was used as a reference. Total proteins were extracted from developing leaf tissue of five $ABA^S$ lines and a wild type control. The antigenic protein bands of AtCPP and Bip were scanned and quantified using the UN-Scan-It programme (Silk Scientific, Utah, USA) and the ratio of the two protein bands for each sample was obtained. The ratio of the wild type plants was set to 100%, and was compared with those of the transgenic lines. Data is presented in FIG. 31 indicating that the AtCPP protein level was increased in the transgenic lines compared to the wild type plants.

Example 38

ABA Sensitivity of Transgenic Seedlings

Approximately 100 seeds were assessed per line per 9 cm plate. Seeds were plated on minimal medium (½ MS) supplemented with no ABA or 1.0 μM ABA. Plates were chilled for 3 days at 4° C. in the dark, and incubated for up to 21 days at 22° C. with 24 hour continuous light. Plates were assessed for germination, cotyledon expansion, true leaf development and seedling vigor. Seedlings were assessed for ABA sensitivity over 21 days of growth at which time sensitive seedlings were arrested at the cotyledon stage, lacked true leaves, and showed inhibition of root growth. Wild type control Columbia plants had two to three pairs of true leaves and a well developed root system. Lines were categorized as ABA sensitive ($ABA^S$) if less than 1% of plants looked like control, moderately ABA sensitive (ABAMS) if more than 1% but less than 50% of looked like control, or ABA insensitive ($ABA^{Wt}$) if greater than 50% looked like control.

For example, if a plate had 20 healthy seedlings and the control plate had 60 healthy seedlings, the line would be 33% of control and categorized as moderately ABA sensitive.

Figure 32:
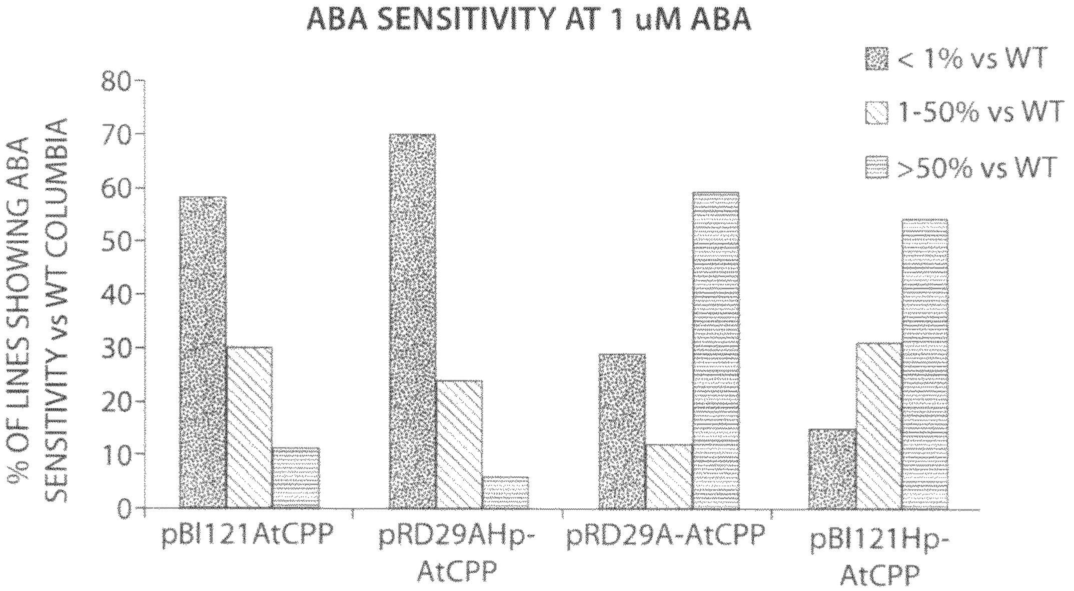
FIG. 32 is a histogram showing the percentage of lines which were categorized as ABA sensitive, moderately ABA sensitive or ABA insensitive. Seedlings were assessed on agar plates containing 1 μM ABA and scored at 21 days growth. Thirty-six lines of the pBI121-AtCPP over-expression construct were assessed at 21 days by leaf and seedling development. Thirty-two lines of the 35S-HP-AtCPP down-regulation construct were assessed at 21 days for leaf and seedling development. Each line was assessed by plating approximately 100 seeds per plate and the seedlings scored and recorded as the percent insensitive seedlings per plate. Each line was then expressed as a percent of wild type (Wt). Lines were categorized as sensitive (less than 1% of Wt) solid bars, intermediate (1-50% of Wt) diagonally lined or insensitive (greater than 50% of Wt) stippled, based on their relationship to Wt and the percentage of each category plotted as a histogram.
Figure 33:
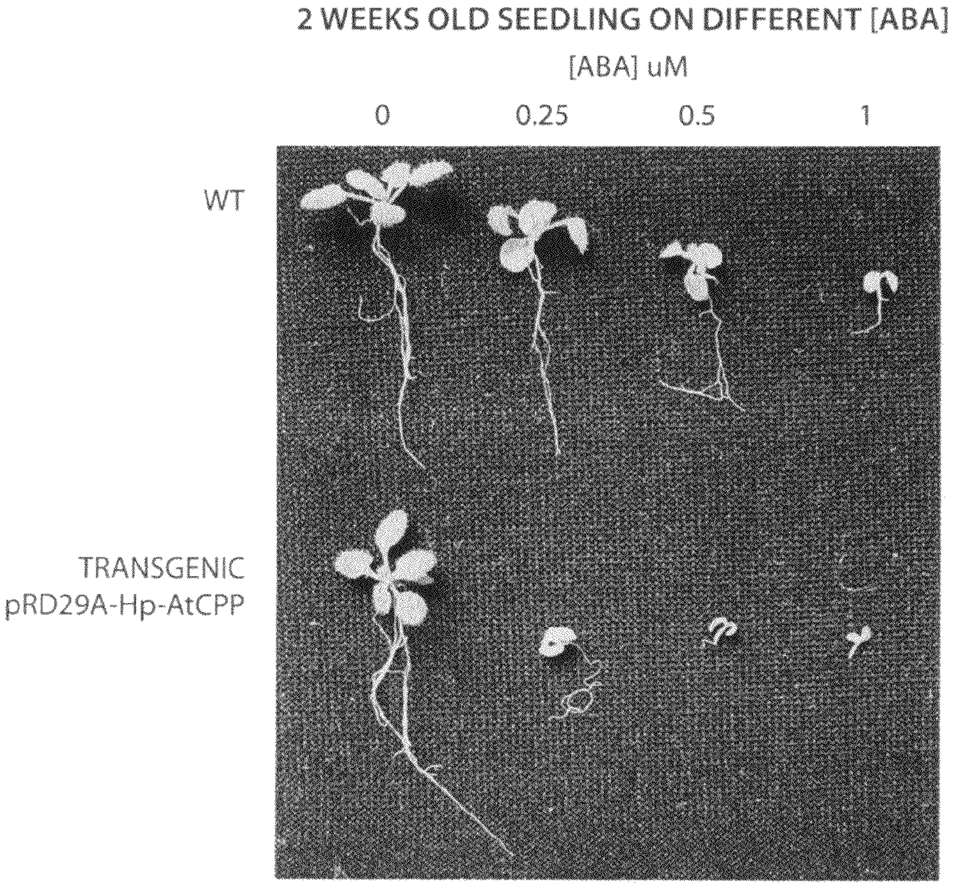
FIG. 33 is an illustration showing the response of wild type and a pRD29A-HP-AtCPP transgenic line to various concentrations of ABA in two week old seedlings.

All four vector constructs (pBI121-AtCPP, pBI121Hp-AtCPP, pRD29AHp-AtCPP, pRD29A-ATCPP) have resulted in transgenic lines of *Arabidopsis* which have increased sensitivity to ABA which is indicative of stress tolerance. The data for all 4 constructs is shown in FIG. 32. Of the lines transformed with the pBI121-AtCPP construct to over-express the AtCPP gene, 58% (21 out of 36) were classified as sensitive and an added 30% (11 out of 36) were classified as moderately sensitive. These lines were tested again in T4 and T5 generations and their ABA sensitivity was still present indicating that ABA sensitivity is an inheritable trait. Of the lines transformed with the pBI121-HP-AtCPP construct to down-regulate the AtCPP gene by double stranded RNA-inhibition, 15% (7 out of 45) were classified as sensitive and 31% (14 out of 45) were classified as moderately sensitive. To illustrate the increased sensitivity of transgenic lines to ABA, FIG. 33 shows the results of germination and seedling development over a range of ABA concentrations. Wild type and pRD29A-HP-AtCPP are compared. Of the lines transformed with pRD29AHp-AtCPP 70% (12 out of 17) showed high sensitivity and 24% (4 out of 17) showed moderate sensitivity to ABA. Of the lines transformed with pRD29A-AtCPP 29% (5 out of 17) showed high sensitivity and 12% (2 out of 17) moderate sensitivity to ABA. Clearly all 4 transgene constructs are altering ABA sensitivity and ABA signal transduction.

Example 39

Drought Experiments

*Arabidopsis* plants were grown five plants per 4" or 3" pot, in a replicated water-stress experiment. All pots were filled with equal amounts of homogeneous premixed and wetted soil. Plants were grown under 16 hour daylight (150-200 μmol/$m^2$/s) at 22° C. and 70% relative humidity. On the day that the first flower opened drought treatment was initiated. First soil water content in each pot was equalized on a weight basis and any further watering of plants was stopped. Daily measurements of soil water content were taken by recording total pot weight. At the end of the drought treatment (6 to 9 days for experiments in 4" pots and 4-5 days for experiments in 3" pots) plants were harvested and shoot dry weights determined. Differences in plant growth were factored into the analysis by expressing water loss on a per gram shoot dry weight basis.

Figure 34:
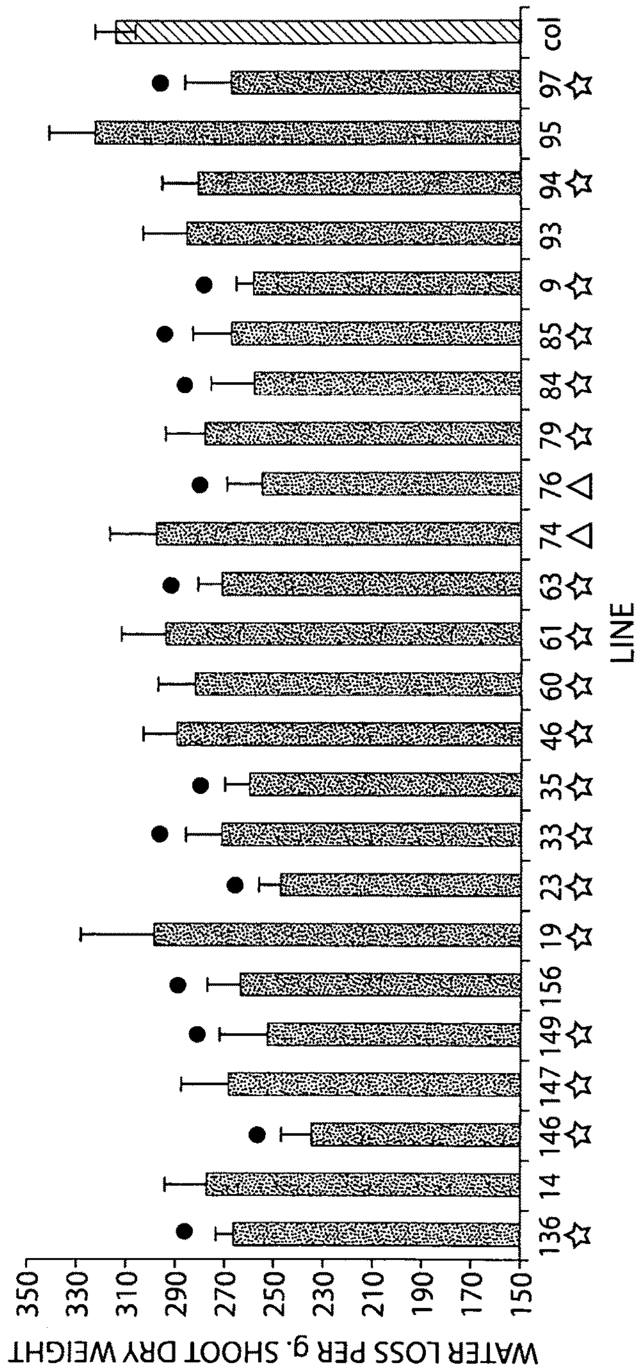
FIG. 34 is a histogram showing the analysis of transgenic plants containing the pBI121-AtCPP over-expression construct (SEQ ID NO:4). Water loss per gram shoot dry weight after four days of water stress treatment. Lines that are marked with a star are those which were strongly ABA sensitive. Lines marked with a triangle are moderately ABA sensitive. Bars represent means of eight replicates. Lines marked with a filled dot above the bar represents lines which were significantly different from control at a p=0.05 value.

39a) pBI121-AtCPP, Drought Stress Screen:

Analysis of pBI121-AtCPP transgenic lines during water-stress treatment experiments of up to an eight day period, shows a strong trend towards increased soil water content and reduced water loss per gram of shoot biomass. After three days of water-stress treatment most lines had increased soil water content relative to the wild type control with four out of twenty-four lines, 146, 149, 156 and 97, showing a statistically significant difference. The amount of water lost per gram of shoot biomass was lower for all lines except one (95), and thirteen of these lines were significantly different from the wild type Columbia control (FIG. 34). All of the lines showing a statistically significant lower water loss per gram shoot biomass also showed an increased ABA sensitivity. There is also a strong trend, for all but one line (95), which is $ABA^{Wt}$, towards greater shoot biomass at the end of the drought stress treatment. Seven of those lines 136, 146, 23, 46, 76, 84 and 9, were statistically significant from control at a p=0.05 value.

39b) pBI121-AtCPP, Water Loss Per Gram Shoot Biomass During Water Stress Treatment:

Lines 35, 76, 95 and a wild type control were grown and placed under a water-stress treatment as above. Plants were harvested at 2 days, 4 days and 6 days of drought treatment. The $ABA^S$ lines, 35 and 76, showed a statistically significant reduction in water-loss relative to shoot dry weight at all three time points (Table 21). Additionally, the two $ABA^S$ transgenic lines had increased shoot biomass, due to increased leaf biomass, and maintained higher soil water contents during drought treatment.

TABLE 21

Water loss (g) per Shoot dry weight (g) after 2, 4 and 6 days of drought-stress treatment. Values in bold indicate statistcally significant differences from Columbia.

| | 2 days | | 4 days | | 6 days | |
|---|---|---|---|---|---|---|
| Line | Mean | Std. Error | Mean | Std. Error | Mean | Std. Error |
| 35 | **212.5** | 3.5 | **308.0** | 9.9 | **297.7** | 11.2 |
| 76 | **227.2** | 5.8 | **321.2** | 8.5 | **293.8** | 5.0 |
| 95 | 287.0 | 5.1 | **377.3** | 14.8 | 348.5 | 25.5 |
| Columbia Wild type | 265.3 | 11.8 | 408.2 | 7.7 | 345.9 | 6.7 |

39c) pBI121-AtCPP, Drought Stress and Shoot Recovery:

Water-stress tolerance and determination of post drought-treatment recovery ability was assessed using 20 of the 24 pBI121-AtCPP transgenic lines. Drought treatment was imposed for 6 days after which the plants were watered and allowed to grow for 6 days. Recovered shoot fresh biomass was then determined. Soil water content of these plants was measured daily during the drought treatment and the results confirm previously seen trends. All ABA sensitive ($ABA^S$) lines that showed a statistically significantly reduction of water loss on a per gram dry weight basis in experiment 39a, continued to show a significant greater soil water content than control plants in this experiment (Table 22). Additionally, Table 22 shows that the recovered shoot fresh biomass after 6 days of drought treatment was significantly greater in all the ABAs lines than Columbia.

TABLE 22

Soil water content on day 3 of drought treatment and recovered shoot fresh weight after 6 days of drought treatment (values in bold were significantly different from Columbia at p = 0.05)

| | ABA status | soil water content day 3 Mean | | recovered shoot biomass | |
|---|---|---|---|---|---|
| Line | ABA | (% initial) | Std Error | Mean (g) | Std Error |
| 136 | $ABA^S$ | **46.6** | 1.9 | **4.5** | 0.16 |
| 14 | $ABA^S$ | **50.25** | 0.7 | **4.1** | 0.12 |
| 146 | $ABA^S$ | **45.9** | 2.5 | **4.0** | 0.11 |
| 147 | $ABA^S$ | 45.1 | 1.7 | **4.0** | 0.15 |
| 149 | $ABA^S$ | 45.3 | 1.8 | **3.8** | 0.17 |
| 156 | $ABA^S$ | **47.1** | 1.9 | **4.0** | 0.134 |
| 23 | $ABA^S$ | **49** | 1.4 | **4.0** | 0.17 |
| 33 | $ABA^S$ | **46.9** | 1.6 | **4.3** | 0.14 |
| 35 | $ABA^S$ | 41.7 | 1.7 | **4.0** | 0.11 |
| 46 | $ABA^S$ | 44.8 | 1.7 | **3.8** | 0.09 |
| 63 | $ABA^S$ | **46.3** | 1.4 | **4.0** | 0.19 |
| 76 | $ABA^S$ | **47.8** | 1.0 | **3.9** | 0.17 |

TABLE 22-continued

Soil water content on day 3 of drought treatment and recovered shoot fresh weight after 6 days of drought treatment (values in bold were significantly different from Columbia at p = 0.05)

| | ABA status | soil water content day 3 Mean | | recovered shoot biomass | |
|---|---|---|---|---|---|
| Line | ABA | (% initial) | Std Error | Mean (g) | Std Error |
| 79 | $ABA^S$ | 45.4 | 1.1 | **4.1** | 0.09 |
| 84 | $ABA^S$ | **46.8** | 1.9 | **4.1** | 0.16 |
| 85 | $ABA^S$ | 45.3 | 1.9 | **4.0** | 0.12 |
| 9 | $ABA^S$ | 45.2 | 2.1 | **3.9** | 0.12 |
| 93 | $ABA^{wt}$ | 43.5 | 1.2 | 2.8 | 0.07 |
| 94 | $ABA^S$ | **46.9** | 1.5 | **3.9** | 0.13 |
| 97 | $ABA^S$ | **53** | 1.2 | **3.8** | 0.16 |
| 95 | $ABA^{Wt}$ | 41.9 | 1.2 | 2.7 | 0.06 |
| Columbia | $ABA^{Wt}$ | 41.3 | 1.0 | 2.7 | 0.04 |

39d) pBI121-AtCPP, Seed Yield after Drought Stress Treatment:

Seed yield after drought stress during flowering was examined using ten pBI121-AtCPP transgenic lines, eight of which were $ABA^S$. Plants were grown one per 4" pot and were exposed to 9 days of drought treatment as described above. A second group of plants was grown and maintained under well watered conditions as the optimal group. After 9 days of drought treatment plants were re-watered and allowed to continue growth and seed set to maturity. After drought-treatment conditions all eight $ABA^S$ lines had increased yields relative to controls, which ranged from 109% to 126% of the Columbia (Table 23). Drought-treatment resulted in a reduction of yield in all lines, including controls, relative to plants grown under optimal conditions. Expression of the seed yields obtained from drought-treated group relative to the same line under optimal conditions shows that the transgenics preserve a larger percentage of optimal seed yield than do wild type lines.

TABLE 23

Seed Yield following 9 days drought-treatment

| | ABA status | Seed Yield (g per plant) | | | |
|---|---|---|---|---|---|
| Line | ABA | Mean (g) | Std Error | % Columbia | % Optimal |
| 156 | $ABA^S$ | 0.735 | 0.044 | 126.2 | 83.7 |
| 63 | $ABA^S$ | 0.675 | 0.061 | 116.0 | 71.0 |
| 146 | $ABA^S$ | 0.666 | 0.053 | 114.4 | 72.9 |
| 94 | $ABA^S$ | 0.644 | 0.052 | 110.6 | 68.8 |
| 84 | $ABA^S$ | 0.642 | 0.049 | 110.4 | 61.8 |
| 76 | $ABA^S$ | 0.631 | 0.055 | 108.5 | 66.6 |
| 136 | $ABA^S$ | 0.630 | 0.051 | 108.3 | 74.1 |
| 35 | $ABA^S$ | 0.614 | 0.054 | 105.6 | 74.2 |
| 93 | $ABA^{Wt}$ | 0.567 | 0.041 | 97.5 | 60.0 |
| 95 | $ABA^{Wt}$ | 0.388 | 0.088 | 66.7 | 43.4 |
| Columbia | $ABA^{Wt}$ | 0.582 | 0.060 | 100 | 53.8 |

Figure 35:
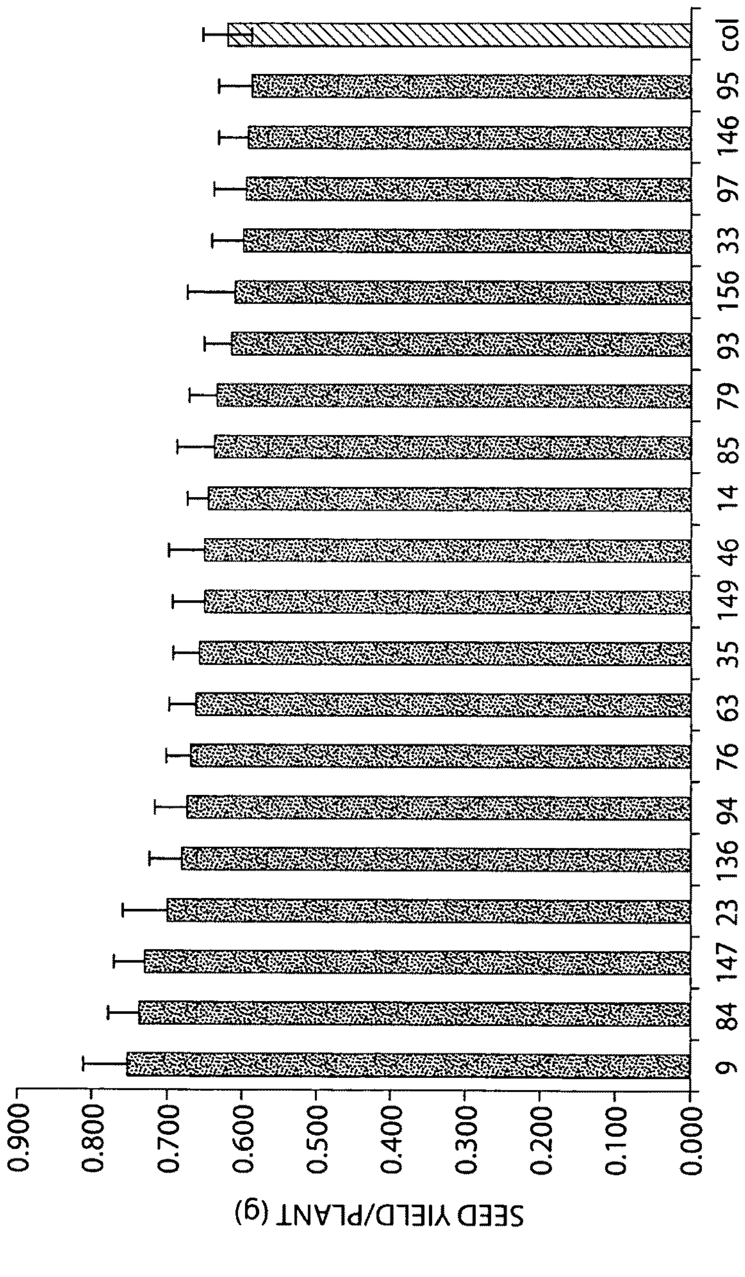
FIG. 35 is a histogram showing seed yield in grams of transgenic *Arabidopsis* lines of pBI121-AtCPP grown under optimal water conditions.

39e) pBI121-AtCPP, Seed Yield and Growth Under Optimal Water Conditions:

The lines evaluated above and a number of additional lines were examined in a growth and yield experiment under optimal, well-watered conditions. Results indicated that the $ABA^S$ lines were shorter at the stage of first open flower, had more rosette leaves, however, by maturity there were no differences in plant height of transgenics and Columbia. Moreover, the $ABA^S$ transgenics showed similar or higher seed yields ranging from 95% to 121% of the wild type control (FIG. 35).

39g) pRD29A-HP-AtCPP Screen for Drought Tolerant Phenotype:

Analysis of 17 transgenic lines identified 7 candidate drought tolerant lines (12, 22, 23, 47, 82, 83, 90) on the basis of higher soil water content and lower water loss per g of shoot dry weight (Table 24). All 7 drought tolerant candidate lines showed strong ABA sensitivity and lines that did not show drought tolerance did not show ABA sensitivity.

TABLE 24

Soil water content after 3 days of drought treatment and water lost per g shoot dry weight. Values in bold are statistically different from those of Columbia wild type (p = 0.05)

| Line | ABA status ABA | soil water content day 2 Mean (% initial) | Std Error | water lost in 2days/g shootDW Mean (g/g) | Std Error |
|---|---|---|---|---|---|
| 10 | $ABA^S$ | 33.4 | 1.6 | 199.1 | 4.5 |
| 11 | $ABA^S$ | 34.6 | 3.3 | **173.1** | 1.6 |
| 12 | $ABA^S$ | 36.2 | 2.0 | 179.5 | 5.0 |
| 126 | $ABA^{MS}$ | 32.5 | 2.6 | 199.1 | 4.1 |
| 127 | $ABA^{MS}$ | 33.5 | 2.0 | 195.6 | 10.6 |
| 14 | $ABA^S$ | 32.7 | 1.2 | 203 | 4.9 |
| 17 | $ABA^S$ | 29.9 | 1.8 | 200.7 | 7.3 |
| 22 | $ABA^S$ | **39.3** | 2.1 | **170.0** | 3.0 |
| 23 | $ABA^S$ | 35.7 | 1.4 | **174.9** | 2.6 |
| 42 | $ABA^{MS}$ | 28 | 0.7 | 185.4 | 5.8 |
| 47 | $ABA^S$ | 35.9 | 2.2 | 181.2 | 7.7 |
| 7 | $ABA^{Wt}$ | 35 | 1.3 | 201.8 | 5.1 |
| 82 | $ABA^S$ | 36.7 | 2.2 | 178.3 | 4.0 |
| 83 | $ABA^S$ | **40** | 1.4 | 180.7 | 6.9 |
| 9 | $ABA^S$ | 31.4 | 1.4 | 173.8 | 8.7 |
| 90 | $ABA^S$ | **38.2** | 1.3 | **177.6** | 6.2 |
| 93 | $ABA^{Wt}$ | 30.7 | 1.8 | 175.3 | 4.6 |
| Columbia | $ABA^{Wt}$ | 32.1 | 1.2 | 196.9 | 6.2 |

Example 40

Growth Analysis

The growth analysis of most promising constructs has been set up at 3 stages. Eight plants per line were grown in 3" pots with one plant per pot at 22 C, 16 hr light (150-200 μmol/$m^2$/s) and 70% RH. Plants were harvested at vegetative growth stage (2 week old seedlings), bolting growth stage (at first open flower) and mid-flowering growth stage (5 to 7 days from first open flower). Also, in some growth experiments additional group of plants was grown in 4" pots (one per pot and 10 plants per line) to maturity for seed yield determinations.

40a) pBI121-AtCPP Growth Under Optimal and Biotic Stress Conditions

The growth and productivity of pBI121-AtCPP transgenic *Arabidopsis* lines was examined at several stages of development under optimal growth conditions. Although optimal growth conditions were maintained, plants were assessed to be under a degree of stress that was later determined to be a result of the soil properties. Soil analysis found a fungal contaminant that was believed to be responsible for the biotic stress. This stress could be negated by sterilization of the soil prior to use. Eight $ABA^S$ lines, two with normal ABA sensitivity ($ABA^{Wt}$) and a wild type Columbia control were analyzed.

Figure 36:
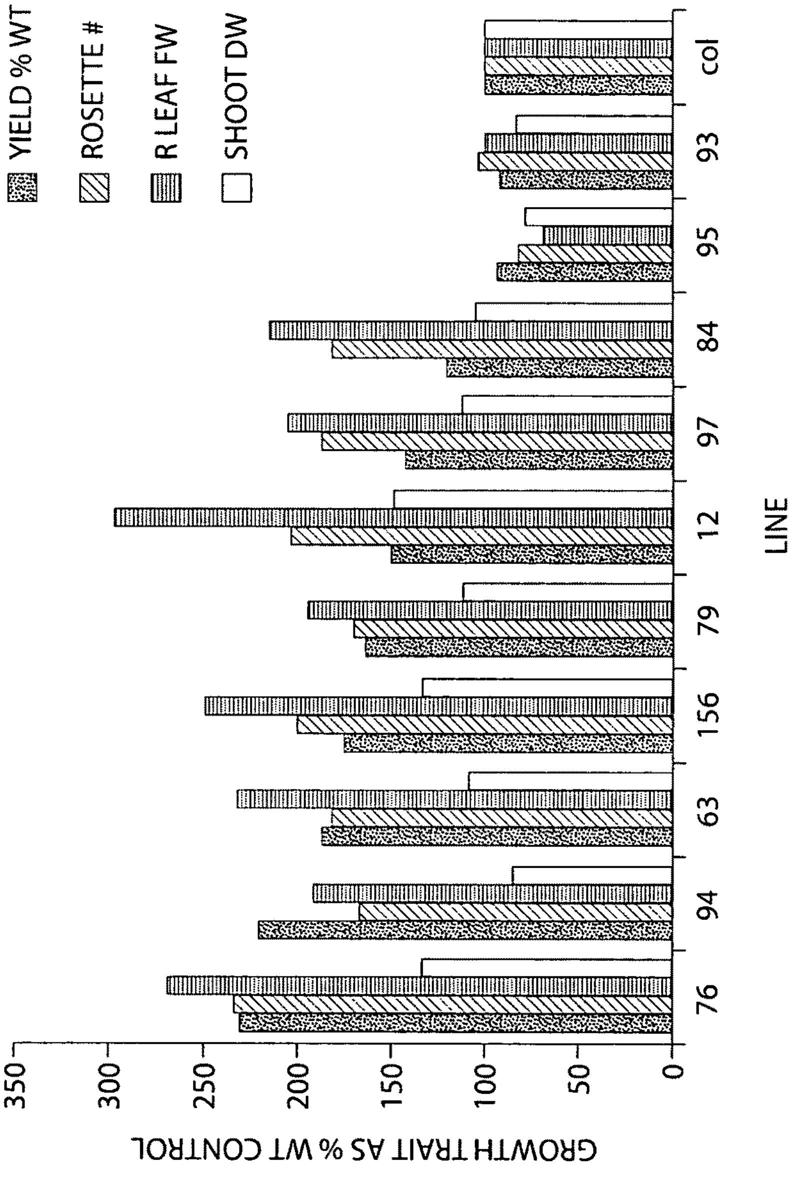
FIG. 36 is a bar chart showing growth and yield of transgenic *Arabidopsis* lines of pBI121-AtCPP grown under optimal watering conditions plus a biotic stress condition. Yields as % of wild type, rosette leaf number, rosette leaf fresh weight and shoot dry weight are plotted.
Figure 37:
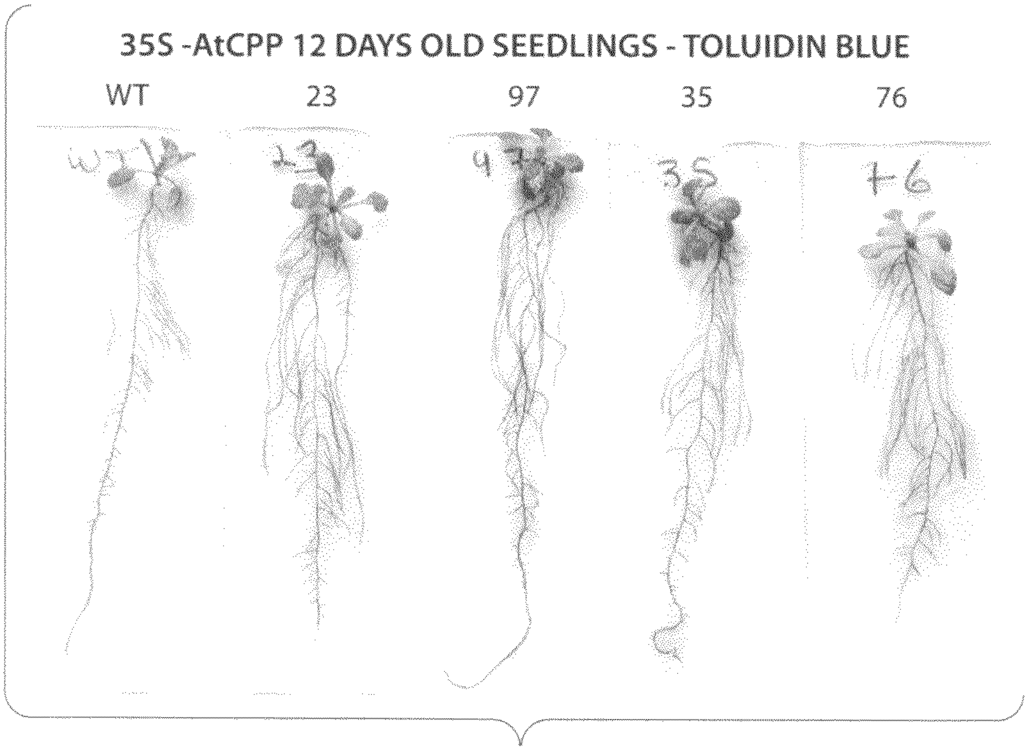
FIG. 37 are photographs showing growth of transgenic *Arabidopsis* lines of pBI121-AtCPP grown on agar plates. Changes to root growth are visible.

FIG. 36 presents the results of various growth (from mid-flowering stage) and yield parameters and each trait is expressed as a percentage of the Columbia control. The results strongly support an enhanced growth phenotype. This enhanced growth phenotype is present at all growth stages. At the vegetative stage, all $ABA^S$ transgenic plants showed an increase in leaf number relative to that of the wild type with four of the eight lines showing a statistically significant difference. The two $ABA^{Wt}$ lines showed the same or fewer leaves relative to wild type.

At the bolting stage $ABA^S$ transgenics showed an increase in leaf number but plants were shorter at this stage (first open flower) than controls. The shoot fresh weight of transgenics was significantly increased relative to that of controls, ranging from 80% to 342% of the wild type. The $ABA^S$ transgenics displayed a delay in flowering from one to three days. The $ABA^{Wt}$ transgenics did not show delayed flowering, increased shoot fresh weight or increased height.

At the flowering stage of development the enhanced growth phenotype is maintained (greater leaf number and fresh weight), however, there were no observable differences in plant height indicating that transgenics bolt shorter but reach same final plant height.

Of particular significance is the observation, that under these conditions (biotic stress due to presence of fungi in the soil) yields of the $ABA^S$ transgenics were significantly higher, ranging from 120% to 229% of the wild type control. The $ABA^{Wt}$ lines showed similar or slightly reduced yields relative to the Columbia control. This finding indicates that $ABA^S$ transgenic lines are affected less by the biotic stress. This observation has been confirmed, where 5 of the drought tolerant lines were grown in contaminated soil to maturity. The seed yields of transgenic lines, even though greatly reduced relative to optimal conditions, were 2.5 to 4.5 fold higher than those of Columbia wild type (Table 25).

TABLE 25

Seed yield of pBI121-AtCPP lines grown in contaminated soil. Values in bold indicate statistical differences at p = 0.05

| Line | ABA sensitivity | Seed Yield per plant (g) | % of Columbia |
|---|---|---|---|
| **156** | $ABA^S$ | **0.33 ± 0.04** | 316% |
| **23** | $ABA^S$ | **0.35 ± 0.05** | 336% |
| **76** | $ABA^S$ | **0.31 ± 0.04** | 296% |
| **84** | $ABA^S$ | **0.25 ± 0.33** | 237% |
| **9** | $ABA^S$ | **0.48 ± 0.05** | 455% |
| **Columbia** | $ABA^{Wt}$ | 0.11 ± 0.03 | |

40b) pBI121-AtCPP Early Seedling Growth:

Four $ABA^S$ and one $ABA^{Wt}$ line plus Columbia were examined for early seedling growth on agar plates. Twenty seeds were plated in a line on agar plates containing 50% MS with 1% sucrose and vitamins and 6 plates per line were used. Plates were placed on slants, which allowed roots to grow downwards. Root length was measured on 7-day old seedlings and shoot and root biomass determined on 11-day old seedlings. Two of the $ABA^S$ transgenic lines had significantly longer roots and all 4 $ABA^S$ lines had shoot dry weights 114% to 123% of controls and root dry weights of 116% to 151% of controls. As a result, the shoot biomass to rootbiomass ratios were slightly reduced in transgenics. These results indicate that enhanced growth of these transgenics is evident in the early growth stage, shortly after germination, and the root growth is more enhanced relative to shoot growth. In a different experiment seedlings were pulled out of agar and roots were stained with toluidine blue to show their structure. FIG. 13 shows that transgenic lines had more extensive lateral root system, which would account for greater root biomass.

40c) pRD29A-HP-AtCPP Optimal Growth Characteristics

Figure 38:
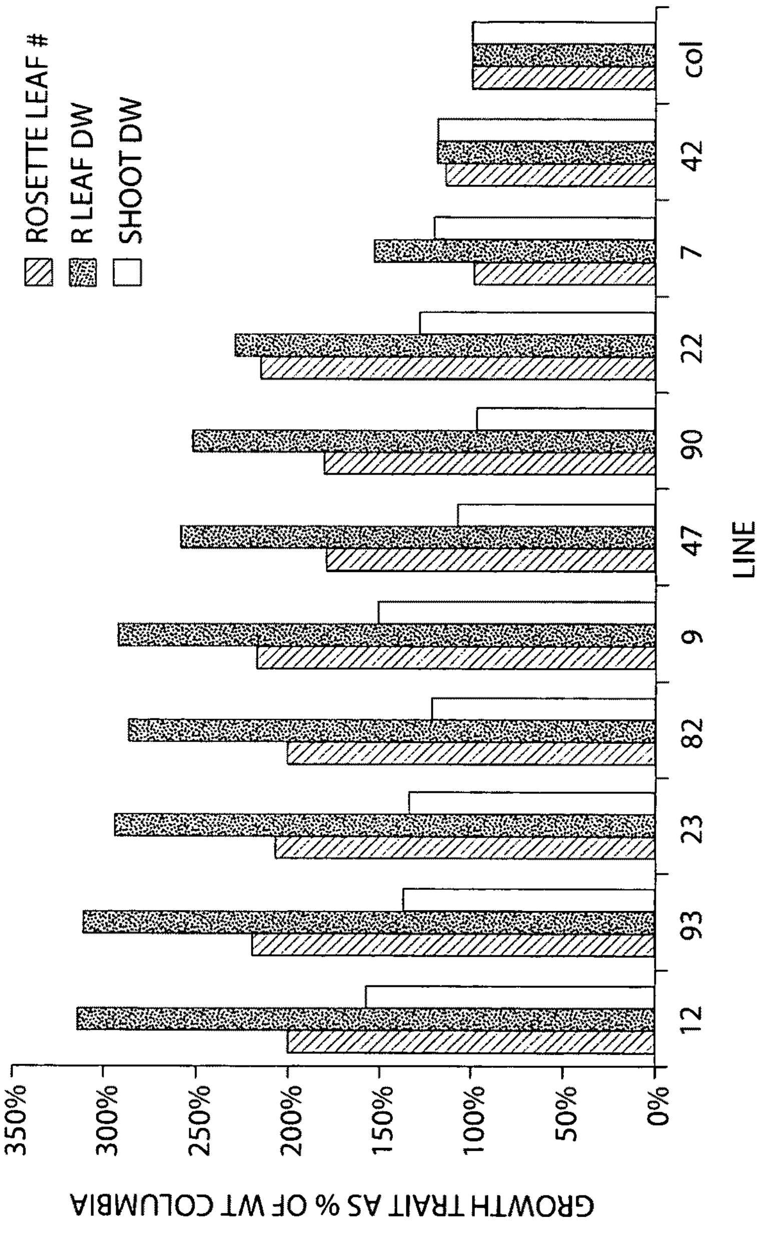
FIG. 38 is a bar chart showing growth of transgenic *Arabidopsis* lines of pRD29A-HP-AtCPP grown under optimal watering conditions. Rosette leaf number, rosette leaf dry weight and shoot dry weight are plotted.
Figure 39A:
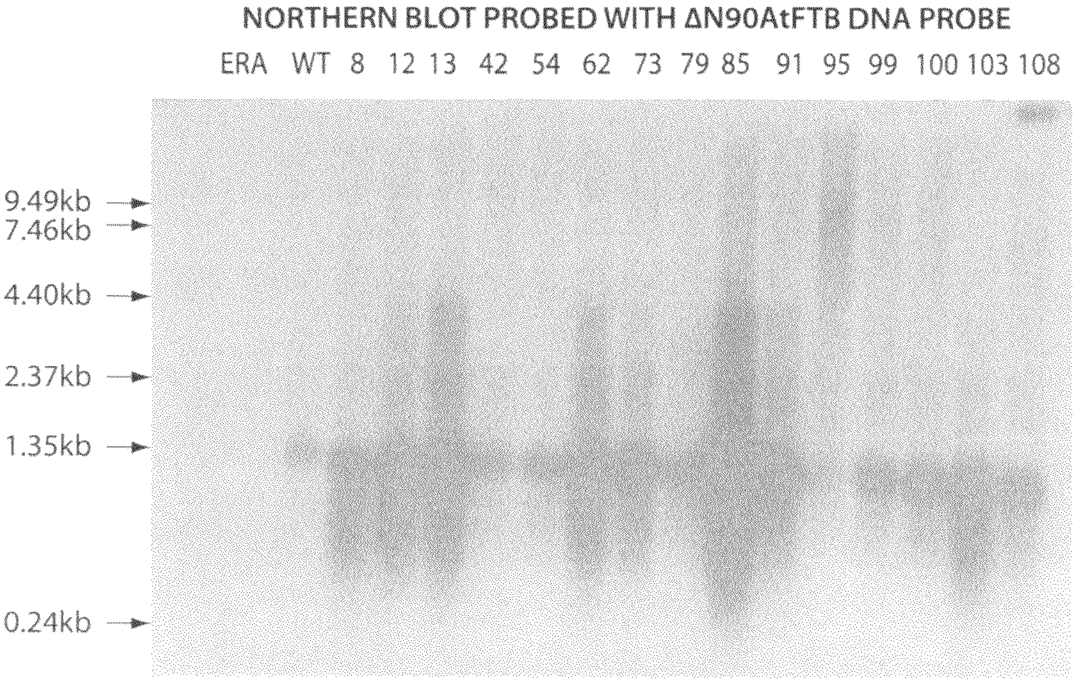
FIG. 39 is a photograph showing Northern blot of ΔN90AtFTB *Arabidopsis* plants, The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.
Figure 39B:
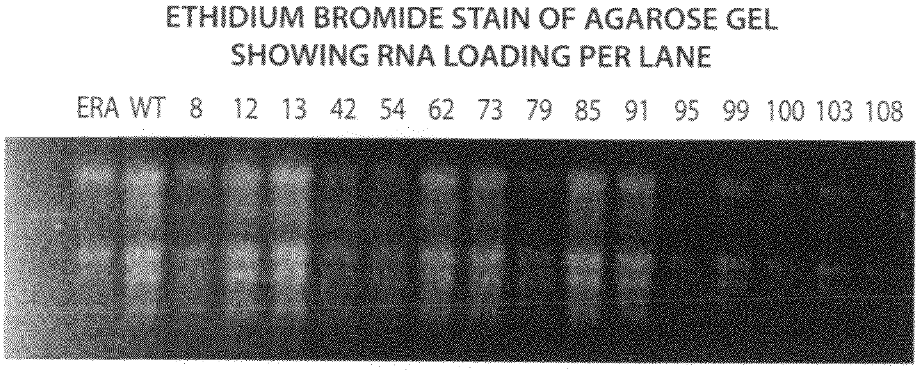

An optimal growth study has been conducted with 10 lines as described before. Vegetative growth data showed that two of the lines (12 and 9) had significantly more leaves and seven of the lines (12, 22, 23, 47, 82, 9) had significantly greater shoot biomass. Bolting data showed that eight of the lines (12, 22, 23, 47, 82, 9, 90, 93) were significantly delayed in flowering by one to two days, and seven of the lines were significantly shorter than Columbia at first open flower. All of the lines except 42 and 7 had significantly greater number of rosette leaves and shoot FW and this trend is maintained into the mid-flowering harvest (FIG. 38). The plant height, however, by mid-flowering harvest was not significantly different between the transgenic lines and control. All the lines that showed this enhanced growth also showed drought tolerance and ABA sensitivity.

Example 41

Ultrastructure pBI121-AtCPP

Two of the drought tolerant and $ABA^S$ lines (35 and 76) plus Wt Columbia were used to examine stem and root cross-sections for any differences in ultrastructure. Free hand sections of mature stems (plants flowering for 10 days) were obtained from above the first node, stained with toluidine blue and preserved with glycerol. The stems of transgenic plants appeared to have more dense cellular structure and contain one or two more vascular bundles than those of Columbia Wt indicating more enhanced water and nutrient transport system.

Leaf disks were taken and fresh weights determined. Transgenic leaf disks were significantly heavier, 20-24% greater than corresponding wild type controls. This increase is believed to be as a result of a thicker leaf.

Example 42

Cold Stress Experiment pBI121-AtCPP

Four drought tolerant, $ABA^S$ lines (156, 23, 35, 76) and one $ABA^{Wt}$(95) line plus wild type Columbia were included in a cold stress study. Plants were grown in 3" pots one per pot) with 10 replicate pots per line at 22 C for 10 days (7 days on agar plates and 4 in soil). The cold stress group was moved into 7° C. for 5 days while the optimal group was left at 22 C. After 5 days in the cold both cold stress group and the optimal group were harvested for shoot biomass determination. $ABA^S$ and drought tolerant lines had significantly greater shoot biomass than Columbia in both optimal (25 to 39% greater shoot fresh weight) and cold stress groups (18 to 44% greater shoot DW) (Table 26). Results of an eight-day cold stress showed that differences between the transgenic lines and Columbia were even more pronounced (53 to 61% greater shoot fresh weight). This result indicates greater plant vigor and better ability of transgenics to cope with cold stress.

TABLE 26

Shoot fresh weight of optimal and cold stressed (5C for 5d) pBI121-AtCPP.
Values in bold indicate statistical difference at p = 0.05

| Line | ABA sensitivity | Optimal shoot FW mg | Optimal shoot FW % of Columbia | Cold stress shoot FW mg | Cold stress shoot FW % of Columbia |
|---|---|---|---|---|---|
| 156 | $ABA^S$ | **95.4 ± 3.7** | 137% | **23.1 0.7** | 118% |
| 23 | $ABA^S$ | **96.3 ± 3.9** | 139% | **28.3 1.5** | 144% |
| 35 | $ABA^S$ | **87.0 ± 1.7** | 125% | **25.3 1.4** | 130% |
| 76 | $ABA^S$ | **94.7 ± 2.2** | 136% | **27.3 1.5** | 140% |
| 95 | ABAWt | 67 ± 2.4 | 96% | 21.4 1.0 | 109% |
| Columbia | ABAWt | 69 ± 1.9 | | 19.6 1.1 | |

Example 43

Drought Stress Under High Temperature pBI121-AtCPP

A drought stress experiment was conducted as described above except that day temperature of 32° C. (16 hr) and night temperature of 22° C. (8 hr) was maintained. These temperatures were achieved daily over a 2 hr ramping period. Four $ABA^S$ and one $ABA^{Wt}$ line plus Columbia were included. Plants were monitored daily for water loss and soil water content and after 5 days of drought treatment half of the plants were harvested and the other half was re-watered and allowed to recover for four days. Shoots were harvested and shoot fresh weight determined. The results (Table 27) of this experiment showed that previously identified drought tolerant lines maintained their drought tolerant phenotype at high temperature and were able to recover well from the drought stress at high temperature

TABLE 27

Soil water content on day 2 and water lost in 2 days/final shoot dry weight plus recovery shoot FW after 5days of drought stress at 32 C. day and 22 C. night temperatures.
Values in bold indicate significant differences from the Columbia control.

| line | ABA sensitivity | soil water content day 2 | water lost in 2 d/shoot DW | recovered shoot FW (g) |
|---|---|---|---|---|
| 136 | $ABA^S$ | 50.4 ± 1.1 | **485.7** ± 18.5 | **1.30** ± 0.04 |
| 146 | $ABA^S$ | **52.1** ± 1.0 | **504.5** ± 7.9 | **1.15** ± 0.04 |
| 35 | $ABA^S$ | **52.2** ± 0.8 | **502.8** ± 15.8 | **1.19** ± 0.02 |
| 76 | $ABA^S$ | **52.1** ± 0.6 | **435.6** ± 10.5 | **1.11** ± 0.03 |
| 95 | ABAWt | 50.0 ± 0.9 | 518.2 ± 13.0 | 0.86 ± 0.03 |
| Columbia | ABAWt | 48.6 ± 0.6 | 559.7 ± 19.0 | 0.84 ± 0.03 |

Example 44

Heat Stress and Seed Yield pBI121-AtCPP

Two $ABA^S$ lines and one $ABA^{Wt}$ line plus Columbia were examined for the effect of heat stress during flowering on the final seed yield. Plants were grown in 4 inch pots (one/pot) as described above and 9 days from first open flower the temperature was ramped from 22 C to 43 C over 2 hours and plants were kept at 43 C for 2 hr. Temperature was then ramped back to 22 C over 2 hours and plants were grown under optimal conditions until maturity. The seed yields from this experiment are shown in Table 28. One of the drought tolerant lines (35) had significantly greater yield than Columbia.

TABLE 28

| Seed yield of pBI121-AtCPP lines after two hour 43 C. heat stress 9 days from first open flower. Values in bold are statistically significant from Columbia. | | | |
|---|---|---|---|
| Line | ABA sensitivity | seed yield (g/plant) | seed yield (% of col.) |
| 35 | $ABA^S$ | **0.55** ± 0.05 | 347% |
| 76 | $ABA^S$ | 0.24 ± 0.03 | 148% |
| 95 | ABAWt | 0.11 ± 0.02 | 69% |
| Columbia | ABAWt | 0.16 ± 0.03 | |

The effect of heat shock on lines of pBI121-AtCPP at the early flowering stage was assessed. Three $ABA^S$ lines (76, 136, 97) a $ABA^{Wt}$ line (95) and a Columbia wild type control were seeded in 128 cell flats, one flat per line. At the early flowering stage flats were exposed to a temperature of 46.8° C. for 50 minutes and then returned to normal growth conditions. Lack of continued growth from main meristems was defined as main meristem death and scored for each line. Data is shown in Table 29.

TABLE 29

| Meristem death due to heat shock | | | | | |
|---|---|---|---|---|---|
| | Line | | | | |
| | Wt | 95 | 76 | 136 | 97 |
| % Death | 91 | 97 | 79 | 59 | 18 |

Example 45

Stomata Density Determinations pBI121AtCPP

Two $ABA^S$ lines (76 and 35) plus Columbia were examined for stomata density on the upper and lower leaf surface. Nail polish imprints of the upper and lower epidermis were obtained from a fully expanded leaf #5. These imprints were analyzed under the microscope and the number of stomata per $8.7\times10^{-8}$ $m^2$ were counted. There were no significant differences found between transgenics and Columbia in the stomata of the upper or lower epidermis (Table 30). The increases seen in drought tolerance and reduced water loss is not attributable to a reduced number of leaf stomata.

TABLE 30

| Stomata numbers per $8.7 \times 10^{-8}$ $m^2$ of abaxial and adaxial epidermis of fully expanded leaf #5 in pBI121AtCPP. | | | |
|---|---|---|---|
| Line | ABA sensitivity | stomata on upper epidermis | stomata on lower epidermis |
| 35 | $ABA^S$ | 68 ± 5 | 103 ± 7 |
| 76 | $ABA^S$ | 58 ± 6 | 120 ± 16 |
| Columbia | ABAWt | 57 ± 6 | 116 ± 11 |

Example 46

CPP Consensus Sequences

Also included in the invention is the CPP consensus sequences. The consensus sequences were generated by alignment of the CPP polypeptide and nucleic acid sequences as well as sequences homologous using the program BioEdit.

The "x" in the consensus sequence represents any amino acid or nucleotide. Preferably "x" a conservative amino acid or nucleotide substitution. More preferably, "x" is the most amino acid or nucleotide most prevalent at a given position. For example, the amino acid at position 145 of SEQ ID NO: 168 is a proline as it occurs 66% of the time.

TABLE 31

ClustalW Analysis of BASF Nucleic Acids

```
1) BASF_AT1 (SEQ ID NO: 116)
2) BASF_AT2 (SEQ ID NO: 118)
3) BASF-Corn (SEQ ID NO: 120)
4) BASF-Soy (SEQ ID NO: 122)
5) Consensus (SEQ ID NO: 163)

                   10        20        30        40        50        60
           ....|....|....|....|....|....|....|....|....|....|....|....|
BASF_AT1   ------------------------------------------------------------      1
BASF_AT2   ------------------------------------------------------------      1
BASF-Corn  ------------------------------------------------------------      1
BASF-Soy   CTAATACGACTCACTATAGGGCAAGCAGTGGTAACAACGCAGAGTACGCGGGGGGAGACG     60
Consensus  XXXXXXXXXXXXXXXXXXXXXXXXXXXXXXXXXXXXXXXXXXXXXXXXXXXXXXXXXXXX     60

                   70        80        90       100       110       120
           ....|....|....|....|....|....|....|....|....|....|....|....|
BASF_AT1   ------------------------------------------------------------      1
BASF_AT2   ------------------------------------------------------------      1
BASF-Corn  ------------------------------------------------------------      1
BASF-Soy   CATGGTTCTGAACTAATTGTTATAAATAATACCTAAAATTTTGAGTTGTCCTAAACATTG    120
Consensus  XXXXXXXXXXXXXXXXXXXXXXXXXXXXXXXXXXXXXXXXXXXXXXXXXXXXXXXXXXXX    120

                  130       140       150       160       170       180
           ....|....|....|....|....|....|....|....|....|....|....|....|
BASF_AT1   ------------------------------------------------------------      1
BASF_AT2   ------------------------------------------------------------      1
BASF-Corn  ------------------------------------------------------------      1
BASF-Soy   GGGTTTAAACAAATCCAATCTCTCAATATAAAACCCAATGATCTCACCCTCACTCCGTTT    180
Consensus  XXXXXXXXXXXXXXXXXXXXXXXXXXXXXXXXXXXXXXXXXXXXXXXXXXXXXXXXXXXX    180
```

TABLE 31-continued

ClustalW Analysis of BASF Nucleic Acids

```
                       190       200       210       220       230       240
                ....|....|....|....|....|....|....|....|....|....|....|....|
BASF_AT1        ----------------------------------------------------ATGGCGAT      8
BASF_AT2        ----------------------------------------------------ATGGCGAT      8
BASF-Corn       ------------------------------------------------------------      1
BASF-Soy        CTGATTTCTCACTCTTCGTTTCTCGTTCGGTTCATCAGCGTGTGTCTCAGCCATGGCGTT    240
Consensus       XXXXXXXXXXXXXXXXXXXXXXXXXXXXXXXXXXXXXXXXXXXXXXXXXXXXXXXXXXXX    240

                       250       260       270       280       290       300
                ....|....|....|....|....|....|....|....|....|....|....|....|
BASF_AT1        TCCTTTCATGGAAACCGTCGTGGGTTTTATGATAGTGATGTACATTTTTGAGACGTATTT     68
BASF_AT2        TCCTTTCATGGAAACCGTCGTGGGTTTTATGATAGTGATGTACATTTTTGAGACGTATTT     68
BASF-Corn       ------------------------------------------------------------      1
BASF-Soy        TCCCTACATGGAAGCCGTTGTCGGATTTATGATATTAATGTACATTTTTGAAACTTACTT    300
Consensus       XXXXXXXXXXXXXXXXXXXXXXXXXXXXXXXXXXXXXXXXXXXXXXXXXXXXXXXXXXXX    300

                       310       320       330       340       350       360
                ....|....|....|....|....|....|....|....|....|....|....|....|
BASF_AT1        GGATCTGAGGCAACTCACTGCTCTCAAGCTTCCAACTCTCCCGAAAACCTTGGTTGGTGT    128
BASF_AT2        GGATCTGAGGCAACTCACTGCTCTCAAGCTTCCAACTCTCCCGAAAACCTTGGTTGGTGT    128
BASF-Corn       ------------------------------------------------------------      1
BASF-Soy        GGATGTGCGACAACATAGGGCCCTCAAACTTCCTACTCTTCCAAAGACTTTAGAAGGTGT    360
Consensus       XXXXXXXXXXXXXXXXXXXXXXXXXXXXXXXXXXXXXXXXXXXXXXXXXXXXXXXXXXXX    360

                       370       380       390       400       410       420
                ....|....|....|....|....|....|....|....|....|....|....|....|
BASF_AT1        AATTAGCCAAGAGAAGTTTGAGAAATCACGAGCATACAGTCTTGACAAAAGCTATTTTCA    188
BASF_AT2        AATTAGCCAAGAGAAGTTTGAGAAATCACGAGCATACAGTCTTGACAAAAGCTATTTTCA    188
BASF-Corn       ------------------------------------------------------------      1
BASF-Soy        TATCAGCCAAGAGAAATTTGAGAAATCTAGAGCCTATAGTCTTGATAAAAGCCACTTCCA    420
Consensus       XXXXXXXXXXXXXXXXXXXXXXXXXXXXXXXXXXXXXXXXXXXXXXXXXXXXXXXXXXXX    420

                       430       440       450       460       470       480
                ....|....|....|....|....|....|....|....|....|....|....|....|
BASF_AT1        CTTTGTTCATGAGTTTGTAACTATACTTATGGACTCTGCAATTTTGTTCTTTGGGATCTT    248
BASF_AT2        CTTTGTTCATGAGTTTGTAACTATACTTATGGACTCTGCAATTTTGTTCTTTGGGATCTT    248
BASF-Corn       ------------------------------------------------------------      1
BASF-Soy        TTTTGTTCACGAGTTTGTGACAATAGTGACAGACTCTACAATTTTGTACTTTGGGGTATT    480
Consensus       XXXXXXXXXXXXXXXXXXXXXXXXXXXXXXXXXXXXXXXXXXXXXXXXXXXXXXXXXXXX    480

                       490       500       510       520       530       540
                ....|....|....|....|....|....|....|....|....|....|....|....|
BASF_AT1        GCCTTGGTTTTGGAAGATGTCTGGAGCTGTTTTACCGAGGTTGGGCCTTGATCCAGAGAA    308
BASF_AT2        GCCTTGGTTTTGGAAGATGTCTGGAGCAGTTTTACCGAGGTTGGGCCTTGATCCAGAGAA    308
BASF-Corn       ----------------------------------------ACGAGGCTGAGTGCTGAGAA     20
BASF-Soy        GCCCTGGTTTTGGAAGAAATCAGGAGATTTTATGACAATAGCTGGTTTCAATGCTGAGAA    540
Consensus       XXXXXXXXXXXXXXXXXXXXXXXXXXXXXXXXXXXXXXXXXXXXGXXTXXXTXCXGAGAA    540

                       550       560       570       580       590       600
                ....|....|....|....|....|....|....|....|....|....|....|....|
BASF_AT1        TGAAATACTGCATACTCTTTCATTCTTGGCTGGTGTTATGACATGGTCACACATCACTGA    368
BASF_AT2        TGAAATACTGCATACTCTTTCATTCTTGGCTGGTGTTATGACATGGTCACAGATCACTGA    368
BASF-Corn       TGAGATAATACACACCCTTGCTTTCTTAGCTGGTTCCATGGTTTGGTCGCAGATTACAGA     80
BASF-Soy        TGAAATACTGCATACCCTTGCCTTCTTAGCAGGGCTGATGATTTGGTCACAGATAACAGA    600
Consensus       TGAXATAXTXCAXACXCTTXCXTTCTTXGCXGGXXXXATGXXXTGGTCXCAXATXACXGA    600

                       610       620       630       640       650       660
                ....|....|....|....|....|....|....|....|....|....|....|....|
BASF_AT1        TTTGCCATTTTCTTTGTACTCAACTTTCGTGATCGAGTCTCGGCATGGGTTCAA AAACA    428
BASF_AT2        TTTGCCATTTTCTTTGTACTCAACTTTCGTGATCGAGTCTCGGCATGGGTTCAA AAACA    428
BASF-Corn       CTTGCCGTTCTCTCTCTATTCAACTTTTGTTATAGAGGCTCGACATGGTTTTAA AAGCA    140
BASF-Soy        TTTGCCCTTTTCTCTGTACTCAACTTTTGTGATTGAGGCCCGTCATGGTTTTAATAAGCA    660
Consensus       XTTGCCXTTXTCTXTXTAXTCAACTTTXGTXATXGAGXCXCGXCATGGXTTXAAXAAXCA    660

                       670       680       690       700       710       720
                ....|....|....|....|....|....|....|....|....|....|....|....|
BASF_AT1        AACAATATGGATGTTCATTAGGGACATGATCAAAGGAACATTCCTCTCTGTCATACTAGG    488
BASF_AT2        AACAATATGGATGTTCATTAGGGACATGATCAAAGGAACATTCCTCTCTGTCATACTAGG    488
BASF-Corn       AACTATATGGCTCTTCATTAGGGATATGATCAAAGGAATTTTACTATCCATGATATTGGG    200
BASF-Soy        AACACCATGGTTATTCTTTAGGGACATGCTTAAAGGAATTTTCCTTTCCGTAATAATTGG    720
Consensus       AACXXXATGGXTXTTCXTTAGGGAXATGXTXAAAGGAAXXTTXCTXTCXXTXATAXTXGG    720

                       730       740       750       760       770       780
                ....|....|....|....|....|....|....|....|....|....|....|....|
BASF_AT1        CCCACCCATTGTTGCCGCCATAATTTTCATAGTCCAGAAAGGAGGTCCTTATCTTGCCAT    548
BASF_AT2        CCCACCCATTGTTGCTGCGATAATTTTCATAGTCCAGAAAGGAGGTCCTTATCTTGCCAT    548
BASF-Corn       GCCACCAATCGTGGCTGCTATCATCTACATAGTACAGATTGGAGGACCTTACCTGGCTAT    260
BASF-Soy        TCCACCTATTGTGGCTGCAATCATTGTAATAGTACAGAAAGGAGGTCCATACTTGGCCAT    780
Consensus       XCCACCXATXGTXGCXGCXATXATXXXXATAGTXCAGAXXGGAGGXCCXTAXXTXGCXAT    780
```

TABLE 31-continued

ClustalW Analysis of BASF Nucleic Acids

```
                    790       800       810       820       830       840
            ....|....|....|....|....|....|....|....|....|....|....|....|
BASF_AT1    CTATCTGTGGGCATTCATGTTTATCCTGTCTCTAGTGATGATGACTATATACCCGGTCTT     608
BASF_AT2    CTATCTGTGGGCATTCATGTTTATCCTGTCTCTAGTGATGATGACTATATACCCGGTCTT     608
BASF-Corn   ATATCTCTGGGGTTTTATGTTTGTATTAGCTCTACTGATGATGACAATATACCCCATTGT     320
BASF-Soy    CTATCTTTGGGTTTTTACGTTTGGTCTTTCTATTGTGATGATGACCCTTTATCCAGTACT     840
Consensus   XTATCTXTGGGXXTTXAXGTTTXXXXTXX TXTXXTGATGATGACXXTXTAXCCXXTXXT     840

                    850       860       870       880       890       900
            ....|....|....|....|....|....|....|....|....|....|....|....|
BASF_AT1    GATAGCACCGCTCTTCAACAAGTTCACTCCTCTTCCAGATGGAGACCTCCGGGAGAAGAT     668
BASF_AT2    GATAGCACCGCTCTTCAACAAGTTCACTCCTCTTCCAGATGGAGACCTCCGGGAGAAGAT     668
BASF-Corn   GATAGCTCCTCTGTTCAACAAGTTCACTCCTCTTCCTGAAGGAGTCCTCAGGGAAAAAAT     380
BASF-Soy    AATAGCTCCACTCTTCAATAAGTTCACTCCACTTCCAGATGGTCAACTCAGGGAGAAAAT     900
Consensus   XATAGCXCCXCTXTTCAAXAAGTTCACTCCXCTTCCXGAXGGXXXXCTCXGGGAXAAXAT     900

                    910       920       930       940       950       960
            ....|....|....|....|....|....|....|....|....|....|....|....|
BASF_AT1    TGAGAAACTTGCTTCTTCTCTAAAGTTTCCTTTGAAGAAGCTGTTTGTTGTCGATGGATC     728
BASF_AT2    TGAGAAACTTGCTTCTTCTCTAAAGTTTCCTTTGAAGAAGCTGTTTGTTGTCGATGGATC     728
BASF-Corn   AGAGAAGCTGGCAGCTTCCCTCAAGTTTCCTTTGAAAAAGCTTTTCGTGGTAGATGGGTC     440
BASF-Soy    CGAGAAACTTGCTTCCTCCCTCAACTATCCGTTAAAGAAACTATTTGTTGTCGATGGATC     960
Consensus   XGAGAAXCTXGCXXCXTCXCTXAAXTXTCCXTTXAAXAAXCTXTTXGTXGTXGATGGXTC     960

                    970       980       990      1000      1010      1020
            ....|....|....|....|....|....|....|....|....|....|....|....|
BASF_AT1    TACAAGGTCAAGCCATAGCAATGCTTACATGTATGGTTTCTTTAAGAACAAAAGGATTGT     788
BASF_AT2    TACAAGGTCAAGCCATAGCAATGCTTACATGTATGGTTTCTTTAAGAACAAAAGGATTGT     788
BASF-Corn   TACCAGATCAAGCCACAGTAATGCCTACATGTATGGTTTTTTCAAGAACAAGCGCATAGT     500
BASF-Soy    CACAAGATCAAGTCACAGCAATGCCTATATGTATGGATTCTTCAAGAACAAGAGGATTGT    1020
Consensus   XACXAGXTCAAGXCAXAGXAATGCXTAXATGTATGGXTTXTTXAAGAACAAXXGXATXGT    1020

                   1030      1040      1050      1060      1070      1080
            ....|....|....|....|....|....|....|....|....|....|....|....|
BASF_AT1    TCTTTATGATACGTTGATTCAGCAGTGCAAGAATGAGGATGAAATTGTGGCGGTTATTGC     848
BASF_AT2    TCTTTATGATACGTTGATTCAGCAGTGCAAGAATGAGGATGAAATTGTGGCGGTTATTGC     848
BASF-Corn   ACTCTATGACACATTGATTCAGCAGTGTAGCAATGAGGATGAGATAGTTTCTGTTATAGC     560
BASF-Soy    CCTTTATGACACATTAATTCAACAGTGCAAAGACGATGAGGAAATTGTTGCTGTTATTGC    1080
Consensus   XCTXTATGAXACXTTXATTCAXCAGTGXAXXXAXGAXGAXGAXATXGTXXCXGTTATXGC    1080

                   1090      1100      1110      1120      1130      1140
            ....|....|....|....|....|....|....|....|....|....|....|....|
BASF_AT1    ACACGAGCTTGGACATTGGAAACTGAATCACACTACATACTCGTTCATTGCAGTTCAAAT     908
BASF_AT2    ACACGAGCTTGGACATTGGAAACTGAATCACACTACATACTCGTTCATTGCAGTTCAAAT     908
BASF-Corn   ACATGAACTTGGACACTGGAAACTCAATCATACTGTCTATTCCTTTGTAGCTGTCCAGCT     620
BASF-Soy    CCATGAGTTGGGACACTGGAAGCTCAACCATACTGTGTACACATTTGTTGCTATGCAGAT    1140
Consensus   XCAXGAXXTXGGACAXTGGAAXCTXAAXCAXACTXXXTAXXCXTTXXTXGCXXTXCAXXT    1140

                   1150      1160      1170      1180      1190      1200
            ....|....|....|....|....|....|....|....|....|....|....|....|
BASF_AT1    CCTTGCCTTCTTACAATTTGGAGGATACACTCTTGTCAGAAACTCCACTGATCTCTTCAG     968
BASF_AT2    CCTTGCCTTCTTACAATTTGGAGGATACACTCTTGTCAGAAACTCCACTGATCTCTTCAG     968
BASF-Corn   GCTTATGTTTCTTCAATTTGGAGGATATACTCTAGTAAGGAGCTCCAAAGATCTATTTGG     680
BASF-Soy    TCTTACACTTCTACAATTTGGAGGATATACACTAGTGCGAAATTCAGCTGATCTGTATCG    1200
Consensus   XCTTXXXXTXXTXCAATTTGGAGGATAXACXCTXGTXXGXAXXTCXXXXGATCTXTXXXG    1200

                   1210      1220      1230      1240      1250      1260
            ....|....|....|....|....|....|....|....|....|....|....|....|
BASF_AT1    GAGTTTCGGATTTGATACACAGCCTGTTCTCATTGGTTTGATCATATTTCAGCACACTGT    1028
BASF_AT2    GAGTTTCGGATTTGATACACAGCCTGTTCTCATTGGTTTGATCATATTTCAGCACACTGT    1028
BASF-Corn   AAGTTTTGGCTTCAAGGACCAGCCAGTAATAATTGGATTGATCATTTTCCCGCACACCAT     740
BASF-Soy    AAGCTTTGGGTTTGATACGCAGCCAGTCCTCATTGGGCTCATCATATTTCAGCATACTGT    1260
Consensus   XAGXTTXGGXTTXXAXXXXCAGCCXGTXXTXATTGGXXTGATCATXTTXCXGCAXACXXT    1260

                   1270      1280      1290      1300      1310      1320
            ....|....|....|....|....|....|....|....|....|....|....|....|
BASF_AT1    AATACCACTGCAACATCCAGTAAGCTTTGGCCTCAACCTTGTTAGTCGAGCGTTTGAGTT    1088
BASF_AT2    AATACCACTGCAACATCTAGTAAGCTTTGGCCTGAACCTCGTTAGTCGAGCGTTTGAGTT    1088
BASF-Corn   AATACCCATCCAACACCTTCTGAGCTTTCG CTGAACCTTGTCAGCAGAGCATTTGAATT     800
BASF-Soy    AATCCCACTTCAGCAATTGGTCAGCTTTGGTCTGAACCTAGTCAGCCGATCATTTGAATT    1320
Consensus   AATXCCXXTXCAXCAXXXXXTXAGCTTTXGXCTXAACCTXGTXAGXXGAXCXTTTGAXTT    1320

                   1330      1340      1350      1360      1370      1380
            ....|....|....|....|....|....|....|....|....|....|....|....|
BASF_AT1    TCAGGCTGATGCTTTTGCTGTGAAGCTTGGCTATGCAAAAGATCTTCGTCCTACTCTAGT    1148
BASF_AT2    TCAGGCTGATGCTTTTGCTGTGAAGCTTGGCTATGCAAAAGATCTTCGTCCTGCTCTAGT    1148
BASF-Corn   TCAGGCTGATGCCTTTGCCAAGAACCTTGGATATGCCCCTCAGCTCCGAGCAGCCCTTGT     860
BASF-Soy    TCAGGCTGATGGCTTTGCCAAGAAGCTTGGATATGCATCTGGATTACGCGGTGGTCTTGT    1380
Consensus   TCAGGCTGATGXXTTTGCXXXGAAXCTTGGXTATGCXXXXXXXXTXCGXXXXXXXCTXGT    1380
```

TABLE 31-continued

ClustalW Analysis of BASF Nucleic Acids

```
                    1390      1400      1410      1420      1430      1440
           ....|....|....|....|....|....|....|....|....|....|....|....|
BASF_AT1   GAAACTACAGGAAGAGAACTTATCAGCAATGAATACTGATCCATTGTACTCAGCTTATCA   1208
BASF_AT2   GAAACTACAGGAAGAGAACTTATCAGCAATGAAAACTGATCTATTGTACTCAGCTTATCA   1208
BASF-Corn  TAAACTACAGGAGGAGAACTTGTCTGCGATGAACACCGATCCTTGGTATTCGGCATATCA    920
BASF-Soy   GAAACTACAGGAGGAGAATCTGTCAGCTATGAATACAGATCC-TTGCTCGTGCCG-----   1434
Consensus  XAAACTACAGGAXGAGAAXXTXTCXGCXATGAAXACXGATCXXTXGXXXXXXXCXXXXXX   1440

                    1450      1460      1470      1480      1490      1500
           ....|....|....|....|....|....|....|....|....|....|....|....|
BASF_AT1   CTACTCACATCCTCCTCTTGTTGAAAGGCTTCGAGCCATTGATGGAGAAGACAAGAAGAC   1268
BASF_AT2   CTACTCACATCCTCCTCTTGTTGAAAGGCTTCGAGCCATTGATGGAGAAGACAAGAAGAC   1268
BASF-Corn  CTACTCCCACCCACCACTCGTCGAGAGGCTGCAAGCTTTGGAAGATTCAGACGACAAAAA    980
BASF-Soy   ------------------------------------------------------------   1434
Consensus  XXXXXXXXXXXXXXXXXXXXXXXXXXXXXXXXXXXXXXXXXXXXXXXXXXXXXXXXXXXX   1500

                    1510      1520      1530      1540      1550      1560
           ....|....|....|....|....|....|....|....|....|....|....|....|
BASF_AT1   AGATTAA-----------------------------------------------------   1275
BASF_AT2   AGATTAA-----------------------------------------------------   1275
BASF-Corn  AGAAGATTAGTCGATCCTTGTATGAGGTTTACATATGGATTTTTCCCTGCCACATGCACA   1040
BASF-Soy   ------------------------------------------------------------   1434
Consensus  XXXXXXXXXXXXXXXXXXXXXXXXXXXXXXXXXXXXXXXXXXXXXXXXXXXXXXXXXXXX   1560

                    1570      1580      1590      1600      1610      1620
           ....|....|....|....|....|....|....|....|....|....|....|....|
BASF_AT1   ------------------------------------------------------------   1275
BASF_AT2   ------------------------------------------------------------   1275
BASF-Corn  CCGATTCAGTGCTTGGATGGTGAGGGTTTTGACATAGGAGTGTTGTCAAAGCTTTAGAGT   1100
BASF-Soy   ------------------------------------------------------------   1434
Consensus  XXXXXXXXXXXXXXXXXXXXXXXXXXXXXXXXXXXXXXXXXXXXXXXXXXXXXXXXXXXX   1620

                    1630      1640      1650      1660      1670      1680
           ....|....|....|....|....|....|....|....|....|....|....|....|
BASF_AT1   ------------------------------------------------------------   1275
BASF_AT2   ------------------------------------------------------------   1275
BASF-Corn  GCATCTTTCGGTCAGGTGCAACAGCCTTTCGGTCATTGAGACATATAAGCGAATTAGCTA   1160
BASF-Soy   ------------------------------------------------------------   1434
Consensus  XXXXXXXXXXXXXXXXXXXXXXXXXXXXXXXXXXXXXXXXXXXXXXXXXXXXXXXXXXXX   1680

                    1690      1700      1710      1720      1730      1740
           ....|....|....|....|....|....|....|....|....|....|....|....|
BASF_AT1   ------------------------------------------------------------   1275
BASF_AT2   ------------------------------------------------------------   1275
BASF-Corn  TTAAAAAAAACAGAACTGTTGCATCAAAAAAAAAAAAAAAAAGAAACAAAAAAAAAAAA   1220
BASF-Soy   ------------------------------------------------------------   1434
Consensus  XXXXXXXXXXXXXXXXXXXXXXXXXXXXXXXXXXXXXXXXXXXXXXXXXXXXXXXXXXXX   1740

                    1750      1760      1770      1780      1790      1800
           ....|....|....|....|....|....|....|....|....|....|....|....|
BASF_AT1   ------------------------------------------------------------   1275
BASF_AT2   ------------------------------------------------------------   1275
BASF-Corn  AAAAAAAAAAAAGAAAAAAAAAAAAAAAAAAAAAAAGTGCTCTGCGTTGTTACCACTGCTTG   1280
BASF-Soy   ------------------------------------------------------------   1434
Consensus  XXXXXXXXXXXXXXXXXXXXXXXXXXXXXXXXXXXXXXXXXXXXXXXXXXXXXXXXXXXX   1800

                    1810      1820
           ....|....|....|....|.
BASF_AT1   ---------------------   1275
BASF_AT2   ---------------------   1275
BASF-Corn  CCCTATAGTGATCGTATCAGA   1301
BASF-Soy   ---------------------   1434
Consensus  XXXXXXXXXXXXXXXXXXXXX   1821
```

TABLE 32

ClustalW Analysis of BASF Amino Acids

1) BASF_AT1 (SEQ ID NO: 117)
2) BASF_AT2 (SEQ ID NO: 119)
3) BASF-Corn (SEQ ID NO: 121)
4) BASF-Soy (SEQ ID NO: 123)
5) Consensus (SEQ ID NO: 164)

TABLE 32-continued

ClustalW Analysis of BASF Amino Acids

```
                          10        20        30        40        50        60
                  ....|....|....|....|....|....|....|....|....|....|....|....|
BASF_AT1          MAIPFMETVVGFMIVMYIFETYLDLRQLTALKLPTLPKTLVGVISQEKFEKSRAYSLDKS      60
BASF_AT2          MAIPFMETVVGFMIVMYIFETYLDLRQLTALKLPTLPKTLVGVISQEKFEKSRAYSLDKS      60
BASF-Corn         ------------------------------------------------------------       1
BASF-Soy          MAFPYMEAVVGFMILMYIFETYLDVRQHRALKLPTLPKTLEGVISQEKFEKSRAYSLDKS      60
Consensus BASF    XXXXXXXXXXXXXXXXXXXXXXXXXXXXXXXXXXXXXXXXXXXXXXXXXXXXXXXXXXXX      60

                          70        80        90       100       110       120
                  ....|....|....|....|....|....|....|....|....|....|....|....|
BASF_AT1          YFHFVHEFVTILMDSAILFFGILPWFWKMSGAVLPRLGLDPENEILHTLSFLAGVMIWSH     120
BASF_AT2          YFHFVHEFVTILMDSAILFFGILPWFWKMSGAVLPRLGLDPENEILGTLSFLAGVMIWSQ     120
BASF-Corn         ------------------------------------TFLSAENEIIHTLAFLAGSMVWSQ      24
BASF-Soy          HFHFVHEFVTIVTDSTILYFGVLPWFWKKSGDFMTIAGFNAENEILHTLAFLAGLMIWSQ     120
Consensus BASF    XXXXXXXXXXXXXXXXXXXXXXXXXXXXXXXXXXXXXXXXENEIXHTLXFLAGXMXWSX     120

                         130       140       150       160       170       180
                  ....|....|....|....|....|....|....|....|....|....|....|....|
BASF_AT1          ITDLPFSLYSTFVIESRHGFNKQTIWMFIRDMIKGTFLSVILGPPIVAAIIFIVQKGGPY     180
BASF_AT2          ITDLPFSLYSTFVIESRHGFNKQTIWMFIRDMIKGTFLSVILGPPIVAAIIFIVQKGGPY     180
BASF-Corn         ITDLPFSLYSTFVIEARHGFNKQTIWLFIRDMIKGILLSMILGPPIVAAIIYIVQIGGPY      84
BASF-Soy          ITDLPFSLYSTFVIEARHGFNKQTPWLFFRDMLKGIFLSVIIGPPIVAAIIVIVQKGGPY     180
Consensus BASF    ITDLPFSLYSTFVIEXRHGFNKQTXWXFXRDMXKGXXLSXIXGPPIVAAIIXIVQXGGPY     180

                         190       200       210       220       230       240
                  ....|....|....|....|....|....|....|....|....|....|....|....|
BASF_AT1          LAIYLWAFMFILSLVMMTIYPVLIAPLFNKFTPLPDGDLREKIEKLASSLKFPLKKLFVV     240
BASF_AT2          LAIYLWAFMFILSLVMMTIYPVLIAPLFNKFTPLPDGDLREKIEKLASSLKFPLKKLFVV     240
BASF-Corn         LAIYLWGFMFVLALLMMTIYPIVIAPLFNKFTPLPEGVLREKIEKLAASLKFPLKKLFVV     144
BASF-Soy          LAIYLWVFTFGLSIVMMTLYPVLIAPLFNKFTPLPDGQLREKIEKLASSLNYPLKKLFVV     240
Consensus BASF    LAIYLWXFXFXLXXXMMTXYPXXIAPLFNKFTPLPXGXLREKIEKLAXSLXXPLKKLFVV     240

                         250       260       270       280       290       300
                  ....|....|....|....|....|....|....|....|....|....|....|....|
BASF_AT1          DGSTRSSGSNAYMYGFFKNKRIVLYDTLIQQCKNEDEIVAVIAHELGHWKLNHTTYSFIA     300
BASF_AT2          DGSTRSSGSNAYMYGFFKNKRIVLYDTLIQQCKNEDEIVAVIAHELGHWKLNHTTYSFIA     300
BASF-Corn         DGSTRSSGSNAYMYGFFKNKRIVLYDTLIQQSNEDEIVSVIAHELGHWKLNHTVYSFVA     204
BASF-Soy          DGSTRSSGSNAYMYGFFKNKRIVLYDTLIQQCKDDEEIVAVIAHELGHWKLNHTVYTFVA     300
Consensus BASF    DGSTRSSGSNAYMYGFFKNKRIVLYDTLIQQXXXXEIVXVIAHELGHWKLNHTXYXFXA     300

                         310       320       330       340       350       360
                  ....|....|....|....|....|....|....|....|....|....|....|....|
BASF_AT1          VQILAFLQFGGYTLVRNSTDLFRSFGFDTQPVLIGLIIFQHTVIPLQHPVSFGLNLVSRA     360
BASF_AT2          VQILAFLQFGGYTLVRNSTDLFRSFGFDTQPVLIGLIIFQHTVIPLQHLVSFGLNLVSRA     360
BASF-Corn         VQLLMFLQFGGYTLVRSSKDLFGSFGFKDQPVIIGLIIFPHTIIPIQHLLSFRLNLVSRA     264
BASF-Soy          MQILTLLQFGGYTLVRNSADLYRSFGFDTQPVLIGLIIFQHTVIPLQQLVSFGLNLVSRS     360
Consensus BASF    XQXLXXLQFGGYTLVRXSXDLXXSFGFXXQPVXIGLIIFXHTXIPXQXXXSFXLNLVSRX     360

                         370       380       390       400       410       420
                  ....|....|....|....|....|....|....|....|....|....|....|....|
BASF_AT1          FEFQADAFAVKLGYAKDLRPTLVKLQWWNLSAMNTDPLYSAYHYSHPPLVERLRAIDGED     420
BASF_AT2          FEFQADAFAVKLGYAKDLRPALVKLQWWNLSAMKTDLLYSAYHYSHPPLVERLRAIDGED     420
BASF-Corn         FEFQADAFAKNLGYAPQLRAALVKLQWWNLSAMNTDPWYSAYHYSHPPLVERLQALEDSD     324
BASF-Soy          FEFQADGFAKKLGYASGLRGGLVKLQWWNLSAMNTDPCSC--------------------     400
Consensus BASF    FEFQADXFAXXLGYAXXLRXXLVKLQWWNLSAMXTDXXXXXXXXXXXXXXXXXXXXXXXX     420

                         430       440       450       460       470       480
                  ....|....|....|....|....|....|....|....|....|....|....|....|
BASF_AT1          KKTD--------------------------------------------------------     424
BASF_AT2          KKTD--------------------------------------------------------     424
BASF-Corn         DKKEDSILVGLHMDFSLPHAHRFSAWMVRVLTECCQSFRVHLSVRCNSLSVIETYKRISY     384
BASF-Soy          ------------------------------------------------------------     400
Consensus BASF    XXXXXXXXXXXXXXXXXXXXXXXXXXXXXXXXXXXXXXXXXXXXXXXXXXXXXXXXXXXX     480

                         490       500       510       520       530       540
                  ....|....|....|....|....|....|....|....|....|....|....|....|
BASF_AT1          ------------------------------------------------------------     424
BASF_AT2          ------------------------------------------------------------     424
BASF-Corn         KKQNCCIKKKKKKETKKKKKKKKKKKKKKKVLCVVTTACPIVIVS---------------     429
BASF-Soy          ------------------------------------------------------------     400
Consensus BASF    XXXXXXXXXXXXXXXXXXXXXXXXXXXXXXXXXXXXXXXXXXXXX---------------     525

                         550       560       570       580       590       600
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525
```

TABLE 32-continued

ClustalW Analysis of BASF Amino Acids

```
                          610       620       630       640       650       660
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          670       680       690       700       710       720
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          730       740       750       760       770       780
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          790       800       810       820       830       840
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          850       860       870       880       890       900
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          910       920       930       940       950       960
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          970       980       990       1000      1010      1020
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          1030      1040      1050      1060      1070      1080
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          1090      1100      1110      1120      1130      1140
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525

                          1150      1160      1170      1180      1190      1200
                  ....|....|....|....|....|....|....|....|....|....|....|....|
BASF_AT1          ------------------------------------------------------------     424
BASF_AT2          ------------------------------------------------------------     424
BASF-Corn         ------------------------------------------------------------     429
BASF-Soy          ------------------------------------------------------------     400
Consensus BASF    ------------------------------------------------------------     525
```

TABLE 32-continued

ClustalW Analysis of BASF Amino Acids

```
                        1210      1220      1230      1240      1250      1260
                ....|....|....|....|....|....|....|....|....|....|....|....|
BASF_AT1        ------------------------------------------------------------     424
BASF_AT2        ------------------------------------------------------------     424
BASF-Corn       ------------------------------------------------------------     429
BASF-Soy        ------------------------------------------------------------     400
Consensus BASF  ------------------------------------------------------------     525

                        1270      1280      1290      1300      1310      1320
                ....|....|....|....|....|....|....|....|....|....|....|....|
BASF_AT1        ------------------------------------------------------------     424
BASF_AT2        ------------------------------------------------------------     424
BASF-Corn       ------------------------------------------------------------     429
BASF-Soy        ------------------------------------------------------------     400
Consensus BASF  ------------------------------------------------------------     525

                        1330      1340      1350      1360      1370      1380
                ....|....|....|....|....|....|....|....|....|....|....|....|
BASF_AT1        ------------------------------------------------------------     424
BASF_AT2        ------------------------------------------------------------     424
BASF-Corn       ------------------------------------------------------------     429
BASF-Soy        ------------------------------------------------------------     400
Consensus BASF  ------------------------------------------------------------     525
```

TABLE 33

ClustalW Analysis of Generic Nucleic Acids

```
1) afc1      (SEQ ID NO: 124)
2) AT4g01320 (SEQ ID NO: 126)
3) AF007269  (SEQ ID NO: 128)
4) Consensus (SEQ ID NO: 165)

                   10        20        30        40        50        60
           ....|....|....|....|....|....|....|....|....|....|....|....|
afc1       ------------------------------------------------------------     1
AT4g01320  ------------------------------------------------------------     1
AF007269   ATGGCGATTCCTTTCATGGAAACCGTCGTGGGTAAGCTTCAAAACCTTTTTCTGAGACAT    60
Consensus  XXXXXXXXXXXXXXXXXXXXXXXXXXXXXXXXXXXXXXXXXXXXXXXXXXXXXXXXXXXX    60

                   70        80        90       100       110       120
           ....|....|....|....|....|....|....|....|....|....|....|....|
afc1       ------------------------------------------------------------     1
AT4g01320  ------------------------------------------------------------     1
AF007269   TTTACTATCCTGTTTCACTCATCGTATTTCGTTTTTGTTTGGGTTTTGCTTTCTGTGTTG   120
Consensus  XXXXXXXXXXXXXXXXXXXXXXXXXXXXXXXXXXXXXXXXXXXXXXXXXXXXXXXXXXXX   120

                  130       140       150       160       170       180
           ....|....|....|....|....|....|....|....|....|....|....|....|
afc1       ------------------------------------------------------------     1
AT4g01320  ------------------------------------------------------------     1
AF007269   TGTGTGTTGAGATTCCATGACTCGTTTGTTTCATATACCATCGTCTCTGCTTCTCGTTTC   180
Consensus  XXXXXXXXXXXXXXXXXXXXXXXXXXXXXXXXXXXXXXXXXXXXXXXXXXXXXXXXXXXX   180

                  190       200       210       220       230       240
           ....|....|....|....|....|....|....|....|....|....|....|....|
afc1       ------------------------------------------------------------     1
AT4g01320  ------------------------------------------------------------     1
AF007269   TAAATTTTGTTCTTTTCTAATAGTGCGTACCTTGATCTGAGGTTTTATTACTCCTACTAG   240
Consensus  XXXXXXXXXXXXXXXXXXXXXXXXXXXXXXXXXXXXXXXXXXXXXXXXXXXXXXXXXXXX   240

                  250       260       270       280       290       300
           ....|....|....|....|....|....|....|....|....|....|....|....|
afc1       ------------------------------------------------------------     1
AT4g01320  ------------------------------------------------------------     1
AF007269   TTTCTTGTCTTACTCGTGCGTTTGATTTGATTTGAGCTTATGTGATTTCATCATCTCTTC   300
Consensus  XXXXXXXXXXXXXXXXXXXXXXXXXXXXXXXXXXXXXXXXXXXXXXXXXXXXXXXXXXXX   300

                  310       320       330       340       350       360
           ....|....|....|....|....|....|....|....|....|....|....|....|
afc1       ------------------------------------------------------------     1
AT4g01320  ------------------------------------------------------------     1
AF007269   CTCGGTTTTAGAATGTACGGAGCTTCTCTGTTAACCAAAATCTAGGATTTGGGAAGAAAA   360
Consensus  XXXXXXXXXXXXXXXXXXXXXXXXXXXXXXXXXXXXXXXXXXXXXXXXXXXXXXXXXXXX   360
```

TABLE 33-continued

ClustalW Analysis of Generic Nucleic Acids

```
                  370       380       390       400       410       420
          ....|....|....|....|....|....|....|....|....|....|....|....|
afc1      ------------------------------------------------------------    1
AT4g01320 ------------------------------------------------------------    1
AF007269  GTCGGAGTCTTTTTTTTCCTCATTCCCGATTGGAAATTGAGAATCTTGAAATTTTTCTTT  420
Consensus XXXXXXXXXXXXXXXXXXXXXXXXXXXXXXXXXXXXXXXXXXXXXXXXXXXXXXXXXXXX  420

                  430       440       450       460       470       480
          ....|....|....|....|....|....|....|....|....|....|....|....|
afc1      ------------------------------------------------------------    1
AT4g01320 ------------------------------------------------------------    1
AF007269  GTTCAAGTCATACAGCTTGAGGTTTTGGGTTTTCTTGTCAGGGTATTATTATGTTCGTGA  480
Consensus XXXXXXXXXXXXXXXXXXXXXXXXXXXXXXXXXXXXXXXXXXXXXXXXXXXXXXXXXXXX  480

                  490       500       510       520       530       540
          ....|....|....|....|....|....|....|....|....|....|....|....|
afc1      ------------------------------------------------------------    1
AT4g01320 ------------------------------------------------------------    1
AF007269  CTGCAACTAGAGTTTTCTGGAGTTTTTTGAAATGGGTTTTGTGTTGTGGAACCGTATGTG  540
Consensus XXXXXXXXXXXXXXXXXXXXXXXXXXXXXXXXXXXXXXXXXXXXXXXXXXXXXXXXXXXX  540

                  550       560       570       580       590       600
          ....|....|....|....|....|....|....|....|....|....|....|....|
afc1      ------------------------------------------------------------    1
AT4g01320 ------------------------------------------------------------    1
AF007269  AATGTTGCATCAAAACTCTTTCAGTGCTCCAATGTTTCCATCAGTAGTCAGCACAAGAGA  600
Consensus XXXXXXXXXXXXXXXXXXXXXXXXXXXXXXXXXXXXXXXXXXXXXXXXXXXXXXXXXXXX  600

                  610       620       630       640       650       660
          ....|....|....|....|....|....|....|....|....|....|....|....|
afc1      ------------------------------------------------------------    1
AT4g01320 ------------------------------------------------------------    1
AF007269  TCTTTTTATATCTGGTTGATCAAAAAAGTAGATGATGTTATTGAATTTTCAGTGATGGAG  660
Consensus XXXXXXXXXXXXXXXXXXXXXXXXXXXXXXXXXXXXXXXXXXXXXXXXXXXXXXXXXXXX  660

                  670       680       690       700       710       720
          ....|....|....|....|....|....|....|....|....|....|....|....|
afc1      ---------------------------------ATGGCGATTCCT--TTCATGGAAACCG   25
AT4g01320 ---------------------------------ATGGCGATTCCT--TTCATGGAAACCG   25
AF007269  TATCTGTTGTTGTGGCATTTAGAGTAGATTCGTATTTCATCTTCTGTTTTATTCTTTTTC  720
Consensus XXXXXXXXXXXXXXXXXXXXXXXXXXXXXXXXXATXXCXXXTXCTXXTTXATXXXXXXXX  720

                  730       740       750       760       770       780
          ....|....|....|....|....|....|....|....|....|....|....|....|
afc1      TCGTGGGTTTTATGATAGTGATGTACATTTTTGAGACGTATTTGGATCTGAGGCAACTCA   85
AT4g01320 TCGTGGGTTTTATGATAGTGATGTACATTTTTGAGACGTATTTGGATCTGAGGCAACTCA   85
AF007269  TTACAGGTTTTATGATAGTGATGTACATTTTTGAGACGTATTTGGATCTGAGGCAACTCA  780
Consensus TXXXXGGTTTTATGATAGTGATGTACATTTTTGAGACGTATTTGGATCTGAGGCAACTCA  780

                  790       800       810       820       830       840
          ....|....|....|....|....|....|....|....|....|....|....|....|
afc1      CTGCTCTCAAGCTTCCAACTCTCCCGAAAACCTTGGTTGGTGTAATTAGCCAAGAGAAGT  145
AT4g01320 CTGCTCTCAAGCTTCCAACTCTCCCGAAAACCTTGGTTGGTGTAATTAGCCAAGAGAAGT  145
AF007269  CTGCTCTCAAGCTTCCAACTCTCCCGAAAACCTTGGTTGGTGTAATTAGCCAAGAGAAGT  840
Consensus CTGCTCTCAAGCTTCCAACTCTCCCGAAAACCTTGGTTGGTGTAATTAGCCAAGAGAAGT  840

                  850       860       870       880       890       900
          ....|....|....|....|....|....|....|....|....|....|....|....|
afc1      TTGAGAAATCACGAGCATACAG--------------------------------------  167
AT4g01320 TTGAGAAATCACGAGCATACAGG-------------------------------------  168
AF007269  TTGAGAAATCACGAGCATACAGTCTTGACAAAAGGTTTCGTCTTGATCATATTTATATCA  900
Consensus TTGAGAAATCACGAGCATACAGXXXXXXXXXXXXXXXXXXXXXXXXXXXXXXXXXXXXXX  900

                  910       920       930       940       950       960
          ....|....|....|....|....|....|....|....|....|....|....|....|
afc1      ------------------------------------------TCTTGACAAA---AGCTA  182
AT4g01320 -------------------------GATATCATCACTGAGAACTTTAATATATGCAGCTA  203
AF007269  TTTTAGTTTTTTATAATTGCCAGGGGATATCATCACTGAGAACTTTAATATATGCAGCTA  960
Consensus XXXXXXXXXXXXXXXXXXXXXXXXXXXXXXXXXXXXXXXXXXXXTTXAXAXAXXXAGCTA  960

                  970       980       990      1000      1010      1020
          ....|....|....|....|....|....|....|....|....|....|....|....|
afc1      TTTTCACTTTGTTCATGAGTTTGTAACTATACTTATGGACTCTGCAATTTTGTTCTTTGG  242
AT4g01320 TTTTCACTTTGTTCATGAGTTTGTAACTATACTTATGGACTCTGCAATTTTGTTCTTTGG  263
AF007269  TTTTCACTTTGTTCATGAGTTTGTAACTATACTTATGGACTCTGCAATTTTGTTCTTTGG 1020
Consensus TTTTCACTTTGTTCATGAGTTTGTAACTATACTTATGGACTCTGCAATTTTGTTCTTTGG 1020
```

TABLE 33-continued

ClustalW Analysis of Generic Nucleic Acids

```
                    1030      1040      1050      1060      1070      1080
              ....|....|....|....|....|....|....|....|....|....|....|....|
afc1          GATCTTGCCTTGGTTTTGGAAG--------------------------------------   264
AT4g01320     GATCTTGCCTTGGTTTTGGAAG--------------------------------------   285
AF007269      GATCTTGCCTTGGTTTTGGAAGGTACATATCTGGTTTCGGTATACAGTATCTCATTTTGA  1080
Consensus     GATCTTGCCTTGGTTTTGGAAGXXXXXXXXXXXXXXXXXXXXXXXXXXXXXXXXXXXXXX  1080

                    1090      1100      1110      1120      1130      1140
              ....|....|....|....|....|....|....|....|....|....|....|....|
afc1          ------------------------------------------------ATGTCTGGAGCT   276
AT4g01320     ------------------------------------------------ATGTCTGGAGCT   297
AF007269      ATATAGAGTTGTTACATTACAATTGTAAAGTTTTCATTTTTACCTTAGATGTCTGGAGCT  1140
Consensus     XXXXXXXXXXXXXXXXXXXXXXXXXXXXXXXXXXXXXXXXXXXXXXXXATGTCTGGAGCT  1140

                    1150      1160      1170      1180      1190      1200
              ....|....|....|....|....|....|....|....|....|....|....|....|
afc1          GTTTTACCGAGGTTGGGCCTTGATCCAGAGAATGAAATACTGCATACTCTTTCATTCTTG   336
AT4g01320     GTTTTACCGAGGTTGGGCCTTGATCCAGAGAATGAAATACTGCATACTCTTTCATTCTTG   357
AF007269      GTTTTACCGAGGTTGGGCCTTGATCCAGAGAATGAAATACTGCATACTCTTTCATTCTTG  1200
Consensus     GTTTTACCGAGGTTGGGCCTTGATCCAGAGAATGAAATACTGCATACTCTTTCATTCTTG  1200

                    1210      1220      1230      1240      1250      1260
              ....|....|....|....|....|....|....|....|....|....|....|....|
afc1          GCTGGTGTTATGACATGGTCACAG------------------------------------   360
AT4g01320     GCTGGTGTTATGACATGGTCACAG------------------------------------   381
AF007269      GCTGGTGTTATGACATGGTCACAGGTGTTCCAAATAAACCCCTTCATATAGTCCTATACG  1260
Consensus     GCTGGTGTTATGACATGGTCACAGXXXXXXXXXXXXXXXXXXXXXXXXXXXXXXXXXXXX  1260

                    1270      1280      1290      1300      1310      1320
              ....|....|....|....|....|....|....|....|....|....|....|....|
afc1          ------------------------------------------------------------   360
AT4g01320     ------------------------------------------------------------   381
AF007269      TTTAGCATCAAAATATCTATTTTCTTAAGATAATAATATTTCTTTTATATTCTGATGCAG  1320
Consensus     XXXXXXXXXXXXXXXXXXXXXXXXXXXXXXXXXXXXXXXXXXXXXXXXXXXXXXXXXXXX  1320

                    1330      1340      1350      1360      1370      1380
              ....|....|....|....|....|....|....|....|....|....|....|....|
afc1          ATCACTGATTTGCCATTTTCTTTGTACTCAACTTTCGTGATCGAGTCTCGGCATGGGTTC   420
AT4g01320     ATCACTGATTTGCCATTTTCTTTGTACTCAACTTTCGTGATCGAGTCTCGGCATGGGTTC   441
AF007269      ATCACTGATTTGCCATTTTCTTTGTACTCAACTTTCGTGATCGAGTCTCGGCATGGGTTC  1380
Consensus     ATCACTGATTTGCCATTTTCTTTGTACTCAACTTTCGTGATCGAGTCTCGGCATGGGTTC  1380

                    1390      1400      1410      1420      1430      1440
              ....|....|....|....|....|....|....|....|....|....|....|....|
afc1          AACAAA------------------------------------------------------   426
AT4g01320     AACAAA------------------------------------------------------   447
AF007269      AACAAAGTATGTCGTATTTCCAACACTACCTTGTGACTTACGTTTTTTTATCAGAGATGT  1440
Consensus     AACAAAXXXXXXXXXXXXXXXXXXXXXXXXXXXXXXXXXXXXXXXXXXXXXXXXXXXXXX  1440

                    1450      1460      1470      1480      1490      1500
              ....|....|....|....|....|....|....|....|....|....|....|....|
afc1          --------------------------------CAAACAATATGGATGTTCATTAGGGACA   454
AT4g01320     --------------------------------CAAACAATATGGATGTTCATTAGGGACA   475
AF007269      GGATTAAATTTGCTTCTAAATTCTGTTGACAGCAAACAATATGGATGTTCATTAGGGACA  1500
Consensus     XXXXXXXXXXXXXXXXXXXXXXXXXXXXXXXXCAAACAATATGGATGTTCATTAGGGACA  1500

                    1510      1520      1530      1540      1550      1560
              ....|....|....|....|....|....|....|....|....|....|....|....|
afc1          TGATCAAAGGAACATTCCTCTCTGTCATACTAGGCCCACCCATTGTTGCTGCGATAATTT   514
AT4g01320     TGATCAAAGGAACATTCCTCTCTGTCATACTAGGCCCACCCATTGTTGCTGCGATAATTT   535
AF007269      TGATCAAAGGAACATTCCTCTCTGTCATACTAGGCCCACCCATTGTTGCTGCGATAATTT  1560
Consensus     TGATCAAAGGAACATTCCTCTCTGTCATACTAGGCCCACCCATTGTTGCTGCGATAATTT  1560

                    1570      1580      1590      1600      1610      1620
              ....|....|....|....|....|....|....|....|....|....|....|....|
afc1          TCATAGTCCAG-------------------------------------------------   525
AT4g01320     TCATAGTCCAG-------------------------------------------------   546
AF007269      TCATAGTCCAGGTTTGATGATTCTGGATTCATCTTATTTCTGAGTTTTTCACATGGATGA  1620
Consensus     TCATAGTCCAGXXXXXXXXXXXXXXXXXXXXXXXXXXXXXXXXXXXXXXXXXXXXXXXXX  1620

                    1630      1640      1650      1660      1670      1680
              ....|....|....|....|....|....|....|....|....|....|....|....|
afc1          ------------------------------------------------------------   525
AT4g01320     ------------------------------------------------------------   546
AF007269      CTATTCTCCATTGAGTGTGAGCTTCAAAGTTTTTAGTTTTCGTGTTAAAAATTTAAAATT  1680
Consensus     XXXXXXXXXXXXXXXXXXXXXXXXXXXXXXXXXXXXXXXXXXXXXXXXXXXXXXXXXXXX  1680
```

TABLE 33-continued

ClustalW Analysis of Generic Nucleic Acids

```
                  1690      1700      1710      1720      1730      1740
              ....|....|....|....|....|....|....|....|....|....|....|....|
afc1          ------------------------------------AAAGGAGGTCCTTATCTTGCCATC   549
AT4g01320     ------------------------------------AAAGGAGGTCCTTATCTTGCCATC   570
AF007269      TGCTTCTCTGAGCATGAAGTTTCTATCTTTTTCCAGAAAGGAGGTCCTTATCTTGCCATC  1740
Consensus     XXXXXXXXXXXXXXXXXXXXXXXXXXXXXXXXXXXXAAAGGAGGTCCTTATCTTGCCATC  1740

                  1750      1760      1770      1780      1790      1800
              ....|....|....|....|....|....|....|....|....|....|....|....|
afc1          TATCTGTGGGCATTCATGTTTATCCTGTCTCTAGTGATGATGACTATATACCCGGTCTTG   609
AT4g01320     TATCTGTGGGCATTCATGTTTATCCTGTCTCTAGTGATGATGACTATATACCCGGTCTTG   630
AF007269      TATCTGTGGGCATTCATGTTTATCCTGTCTCTAGTGATGATGACTATATACCCGGTCTTG  1800
Consensus     TATCTGTGGGCATTCATGTTTATCCTGTCTCTAGTGATGATGACTATATACCCGGTCTTG  1800

                  1810      1820      1830      1840      1850      1860
              ....|....|....|....|....|....|....|....|....|....|....|....|
afc1          ATAGCACCGCTCTTCAACAAGTTCACTCCT------------------------------   639
AT4g01320     ATAGCACCGCTCTTCAACAAGTTCACTCCT------------------------------   660
AF007269      ATAGCACCGCTCTTCAACAAGTTCACTCCTGTGTGTATTTCTGTCATGGCCATTTTACAA  1860
Consensus     ATAGCACCGCTCTTCAACAAGTTCACTCCTXXXXXXXXXXXXXXXXXXXXXXXXXXXXXX  1860

                  1870      1880      1890      1900      1910      1920
              ....|....|....|....|....|....|....|....|....|....|....|....|
afc1          ------------------------------------------------------------   639
AT4g01320     ------------------------------------------------------------   660
AF007269      TTCACTGCTTGTTTGCATATGTTGTTACCAGACAATATAATCTCCCGCTTTTTTATGGCT  1920
Consensus     XXXXXXXXXXXXXXXXXXXXXXXXXXXXXXXXXXXXXXXXXXXXXXXXXXXXXXXXXXXX  1920

                  1930      1940      1950      1960      1970      1980
              ....|....|....|....|....|....|....|....|....|....|....|....|
afc1          ----CTTCCAGATGGAGACCTCCGGGAGAAGATTGAGAAACTTGCTTCTTCTCTAAAGTT   695
AT4g01320     ----CTTCCAGATGGAGACCTCCGGGAGAAGATTGAGAAACTTGCTTCTTCTCTAAAGTT   716
AF007269      ATAGCTTCCAGATGGAGACCTCCGGGAGAAGATTGAGAAACTTGCTTCTTCTCTAAAGTT  1980
Consensus     XXXXCTTCCAGATGGAGACCTCCGGGAGAAGATTGAGAAACTTGCTTCTTCTCTAAAGTT  1980

                  1990      2000      2010      2020      2030      2040
              ....|....|....|....|....|....|....|....|....|....|....|....|
afc1          TCCTTTGAAGAAGCTGTTTGTTGTCGATGGATCTACAAGGTCAAGCCATAGCAATG----   751
AT4g01320     TCCTTTGAAGAAGCTGTTTGTTGTCGATGGATCTACAAGGTCAAGCCATAGCAATG----   772
AF007269      TCCTTTGAAGAAGCTGTTTGTTGTCGATGGATCTACAAGGTCAAGCCATAGCAATGTGAG  2040
Consensus     TCCTTTGAAGAAGCTGTTTGTTGTCGATGGATCTACAAGGTCAAGCCATAGCAATGXXXX  2040

                  2050      2060      2070      2080      2090      2100
              ....|....|....|....|....|....|....|....|....|....|....|....|
afc1          ------------------------------------------------------------   751
AT4g01320     ------------------------------------------------------------   772
AF007269      AAGCTTGAGATCTCTTCCTACCTACTTTACTCTAGTTTACCATTAGAAGCTTACGTATCT  2100
Consensus     XXXXXXXXXXXXXXXXXXXXXXXXXXXXXXXXXXXXXXXXXXXXXXXXXXXXXXXXXXXX  2100

                  2110      2120      2130      2140      2150      2160
              ....|....|....|....|....|....|....|....|....|....|....|....|
afc1          ----------------CTTACATGTATGGTTTCTTTAAGAACAAAAGGATTGTTCTTTAT   795
AT4g01320     ----------------CTTACATGTATGGTTTCTTTAAGAACAAAAGGATTGTTCTTTAT   816
AF007269      TGTTACATCATACAGGCTTACATGTATGGTTTCTTTAAGAACAAAAGGATTGTTCTTTAT  2160
Consensus     XXXXXXXXXXXXXXXXCTTACATGTATGGTTTCTTTAAGAACAAAAGGATTGTTCTTTAT  2160

                  2170      2180      2190      2200      2210      2220
              ....|....|....|....|....|....|....|....|....|....|....|....|
afc1          GATACGTTGATTCAGCAG------------------------------------------   813
AT4g01320     GATACGTTGATTCAGCAG------------------------------------------   834
AF007269      GATACGTTGATTCAGCAGGTACTGTGACTCTTGATGCTTCAAACGAGCTATACTCACATT  2220
Consensus     GATACGTTGATTCAGCAGXXXXXXXXXXXXXXXXXXXXXXXXXXXXXXXXXXXXXXXXXX  2220

                  2230      2240      2250      2260      2270      2280
              ....|....|....|....|....|....|....|....|....|....|....|....|
afc1          --------------------------------------------TGCAAGAATGAGGATG   829
AT4g01320     --------------------------------------------TGCAAGAATGAGGATG   850
AF007269      TCTGTTTCTGGTTCTGAAACATAACATAATCTTCTATTGTGCAGTGCAAGAATGAGGATG  2280
Consensus     XXXXXXXXXXXXXXXXXXXXXXXXXXXXXXXXXXXXXXXXXXXXTGCAAGAATGAGGATG  2280

                  2290      2300      2310      2320      2330      2340
              ....|....|....|....|....|....|....|....|....|....|....|....|
afc1          AAATTGTGGCGGTTATTGCACACGAGCTTGGACATTGGAAACTGAATCACACTACATACT   889
AT4g01320     AAATTGTGGCGGTTATTGCACACGAGCTTGGACATTGGAAACTGAATCACACTACATACT   910
AF007269      AAATTGTGGCGGTTATTGCACACGAGCTTGGACATTGGAAACTGAATCACACTACATACT  2340
Consensus     AAATTGTGGCGGTTATTGCACACGAGCTTGGACATTGGAAACTGAATCACACTACATACT  2340
```

TABLE 33-continued

ClustalW Analysis of Generic Nucleic Acids

```
                2350      2360      2370      2380      2390      2400
           ....|....|....|....|....|....|....|....|....|....|....|....|
afc1       CGTTCATTGCAGTTCAA-------------------------------------------   906
AT4g01320  CGTTCATTGCAGTTCAA-------------------------------------------   927
AF007269   CGTTCATTGCAGTTCAAGTGAGGCTCAACCGACAGTTCAAAAACTTACTCACATCTACAT  2400
Consensus  CGTTCATTGCAGTTCAAXXXXXXXXXXXXXXXXXXXXXXXXXXXXXXXXXXXXXXXXXXX  2400

                2410      2420      2430      2440      2450      2460
           ....|....|....|....|....|....|....|....|....|....|....|....|
afc1       ---------------------------------------------------ATCCTTGCC   915
AT4g01320  ---------------------------------------------------ATCCTTGCC   936
AF007269   TTCACTTAAGAAATCATGTCTTATGACCCTCTCTCAATGTTTTGCTTGCAGATCCTTGCC  2460
Consensus  XXXXXXXXXXXXXXXXXXXXXXXXXXXXXXXXXXXXXXXXXXXXXXXXXXXATCCTTGCC  2460

                2470      2480      2490      2500      2510      2520
           ....|....|....|....|....|....|....|....|....|....|....|....|
afc1       TTCTTACAATTTGGAGGATACACTCTTGTCAGAAACTCCACTGATCTCTTCAGGAGTTTC   975
AT4g01320  TTCTTACAATTTGGAGGATACACTCTTGTCAGAAACTCCACTGATCTCTTCAGGAGTTTC   996
AF007269   TTCTTACAATTTGGAGGATACACTCTTGTCAGAAACTCCACTGATCTCTTCAGGAGTTTC  2520
Consensus  TTCTTACAATTTGGAGGATACACTCTTGTCAGAAACTCCACTGATCTCTTCAGGAGTTTC  2520

                2530      2540      2550      2560      2570      2580
           ....|....|....|....|....|....|....|....|....|....|....|....|
afc1       GGATTTGATACACAGCCTGTTCTCATTGGTTTGATCATATTTCAG---------------  1020
AT4g01320  GGATTTGATACACAGCCTGTTCTCATTGGTTTGATCATATTTCAG---------------  1041
AF007269   GGATTTGATACACAGCCTGTTCTCATTGGTTTGATCATATTTCAGGTTTGTTATTTTTGC  2580
Consensus  GGATTTGATACACAGCCTGTTCTCATTGGTTTGATCATATTTCAGXXXXXXXXXXXXXXX  2580

                2590      2600      2610      2620      2630      2640
           ....|....|....|....|....|....|....|....|....|....|....|....|
afc1       ------------------------------------------------------------  1020
AT4g01320  ------------------------------------------------------------  1041
AF007269   CTTTTGACACTAATCTAATGAATCAAGGATGGATTAAGAAAAAAAAACTCTAAACCTTTG  2640
Consensus  XXXXXXXXXXXXXXXXXXXXXXXXXXXXXXXXXXXXXXXXXXXXXXXXXXXXXXXXXXXX  2640

                2650      2660      2670      2680      2690      2700
           ....|....|....|....|....|....|....|....|....|....|....|....|
afc1       ---------------------------CACACTGTAATACCACTGCAACATCTAGTAAGC  1053
AT4g01320  ---------------------------CACACTGTAATACCACTGCAACATCTAGTAAGC  1074
AF007269   GTTATATCTCCTGTCTGATTATCACAGCACACTGTAATACCACTGCAACATCTAGTAAGC  2700
Consensus  XXXXXXXXXXXXXXXXXXXXXXXXXXXCACACTGTAATACCACTGCAACATCTAGTAAGC  2700

                2710      2720      2730      2740      2750      2760
           ....|....|....|....|....|....|....|....|....|....|....|....|
afc1       TTTGGCCTGAACCTCGTTAGTCGAGCGTTTGAGTTTCAGG--------------------  1093
AT4g01320  TTTGGCCTGAACCTCGTTAGTCGAGCGTTTGAGTTTCAGG--------------------  1114
AF007269   TTTGGCCTGAACCTCGTTAGTCGAGCGTTTGAGTTTCAGGTACCATCTTACAATCCCTCA  2760
Consensus  TTTGGCCTGAACCTCGTTAGTCGAGCGTTTGAGTTTCAGGXXXXXXXXXXXXXXXXXXXX  2760

                2770      2780      2790      2800      2810      2820
           ....|....|....|....|....|....|....|....|....|....|....|....|
afc1       ------------------------------------------------------------  1093
AT4g01320  ------------------------------------------------------------  1114
AF007269   AGATCCAACCATAGTTTCTTTATTGCAATGGCAGCCTCATCTACTAATCTGAGTTAACGT  2820
Consensus  XXXXXXXXXXXXXXXXXXXXXXXXXXXXXXXXXXXXXXXXXXXXXXXXXXXXXXXXXXXX  2820

                2830      2840      2850      2860      2870      2880
           ....|....|....|....|....|....|....|....|....|....|....|....|
afc1       ------------CTGATGCTTTTGCCGTGAAGCTTGGCTATGCAAAAGATCTTCGTCCTG  1141
AT4g01320  ------------CTGATGCTTTTGCTGTGAAGCTTGGCTATGCAAAAGATCTTCGTCCTG  1162
AF007269   TCCTTTTGCAGGCTGATGCTTTTGCTGTGAAGCTTGGCTATGCAAAAGATCTTCGTCCTG  2880
Consensus  XXXXXXXXXXXXCTGATGCTTTTGCXGTGAAGCTTGGCTATGCAAAAGATCTTCGTCCTG  2880

                2890      2900      2910      2920      2930      2940
           ....|....|....|....|....|....|....|....|....|....|....|....|
afc1       CTCTAGTGAAACTACAGG------------------------------------------  1159
AT4g01320  CTCTAGTGAAACTACAGGTCAGAGAAGATAACAACAGAACACAAACTGTTACCTCAATTT  1222
AF007269   CTCTAGTGAAACTACAGGTCAGAGAAGATAACAACAGAACACAAACTGTTACCTCAATTT  2940
Consensus  CTCTAGTGAAACTACAGGXXXXXXXXXXXXXXXXXXXXXXXXXXXXXXXXXXXXXXXXXX  2940

                2950      2960      2970      2980      2990      3000
           ....|....|....|....|....|....|....|....|....|....|....|....|
afc1       ------------------------------------------AAGAGAACTTATCAGCAA  1177
AT4g01320  GTGTCACACACTTAAATGGATTTTTTGTTGGGATTTTGCAGGAAGAGAACTTATCAGCAA  1282
AF007269   GTGTCACACACTTAAATGGATTTTTTGTTGGGATTTTGCAGGAAGAGAACTTATCAGCAA  3000
Consensus  XXXXXXXXXXXXXXXXXXXXXXXXXXXXXXXXXXXXXXXXXXAAGAGAACTTATCAGCAA  3000
```

TABLE 33-continued

ClustalW Analysis of Generic Nucleic Acids

```
                3010      3020      3030      3040      3050      3060
           ....|....|....|....|....|....|....|....|....|....|....|....|
afc1       TGAACACTGATCCATTGCACTCAGCTTATCACTACTCACATCCTCCTCTTGTTGAAAGGC   1237
AT4g01320  TGAACACTGATCCATTGTACTCAGCTTATCACTACTCACATCCTCCTCTTGTTGAAAGGC   1342
AF007269   TGAACACTGATCCATTGTACTCAGCTTATCACTACTCACATCCTCCTCTTGTTGAAAGGC   3060
Consensus  TGAACACTGATCCATTGXACTCAGCTTATCACTACTCACATCCTCCTCTTGTTGAAAGGC   3060

                3070      3080      3090
           ....|....|....|....|....|....|....|...
afc1       TTCGAGCCATTGATGGAGAAGACAAGAAGACAGATTAA                         1275
AT4g01320  TTCGAGCCATTGATGGAGAAGACAAGAAGACAGATTAA                         1380
AF007269   TTCGAGCCATTGATGGAGAAGACAAGAAGACAGATTAA                         3098
Consensus  TTCGAGCCATTGATGGAGAAGACAAGAAGACAGATTAA                         3098
```

TABLE 34

ClustalW Analysis of Generic Amino Acids 1) afc1      (SEQ ID NO: 125)
2) AT4g01320 (SEQ ID NO: 127)
3) AF007269  (SEQ ID NO: 129)
4) Consensus (SEQ ID NO: 166)

```
                         10        20        30        40        50        60
                     ....|....|....|....|....|....|....|....|....|....|....|....|
afc1                 MAIPFMETVVGFMIVMYIFETYLDLRQLTALKLPTLPKTLVGVISQEKFEKSRAYS--LD    58
AT4g01320            MAIPFMETVVGFMIVMYIFETYLDLRQLTALKLPTLPKTLVGVISQEKFEKSRAYRDIIT    60
AF007269             MAIPFMETVVGFMIVMYIFETYLDLRQLTALKLPTLPKTLI-------------------    41
Consensus Publi      MAIPFMETVVGFMIVMYIFETYLDLRQLTALKLPTLPKTLXXXXXXXXXXXXXXXXXXXX    60

                         70        80        90       100       110       120
                     ....|....|....|....|....|....|....|....|....|....|....|....|
afc1                 K-----SYFHFVHEFVTILMDSAILFFGILPWFWKMSGAVLPRLGLDPENEILHTLSFLA   113
AT4g01320            ENFNICSYFHFVHEFVTILMDSAILFFGILPWFWKMSGAVLPRLGLDPENEILHTLSFLA   120
AF007269             -------------------------------------------------------T----    42
Consensus Publi      XXXXXXXXXXXXXXXXXXXXXXXXXXXXXXXXXXXXXGXXXXXXXXXXXXXXXXXXXXXX   120

                        130       140       150       160       170       180
                     ....|....|....|....|....|....|....|....|....|....|....|....|
afc1                 GVMTWSQITDLPFSLYSTFVIESRHGFNKQTIWMFIRDMIKGTFLSVILGPPIVAAIIFI   173
AT4g01320            GVMTWSQITDLPFSLYSTFVIESRHGFNKQTIWMFIRDMIKGTFLSVILGPPIVAAIIFI   180
AF007269             ---------DLPFSLYSTFVIESRHGFNKQTIWMFIRDMIKGTFLSVILGPPIVAAIIFI    93
Consensus Publi      XXXXXXXXXXXXXXXXXXXXXXXXXXXXXXXXXXXXXXXXXXXXXXXXXXXXXXXXXXXX   180

                        190       200       210       220       230       240
                     ....|....|....|....|....|....|....|....|....|....|....|....|
afc1                 VQKGGPYLAIYLWAFMFILSLVMMTIYPVLIAPLFNKFTPLPDGDLREKIEKLASSLKFP   233
AT4g01320            VQKGGPYLAIYLWAFMFILSLVMMTIYPVLIAPLFNKFTPLPDGDLREKIEKLASSLKFP   240
AF007269             VQKGGPYLAIYLWAFMFILSLVMMTIYPVLIAPLFNKFTPLPDGDLREKIEKLASSLKFP   153
Consensus Publi      XXXXXXXXXXXXXXXXXXXXXXXXXXXXXXXXXXXXXXXXXXXXXXXXXXXXXXXXXXXX   240

                        250       260       270       280       290       300
                     ....|....|....|....|....|....|....|....|....|....|....|....|
afc1                 LKKLFVVDGSTRSSHSNAYMYGFFKNKRIVLYDTLIQQCKNEDEIVAVIAHELGHWKLNH   293
AT4g01320            LKKLFVVDGSTRSSHSNAYMYGFFKNKRIVLYDTLIQQCKNEDEIVAVIAHELGHWKLNH   300
AF007269             LKKLFVVDGSTRSSHSNAYMYGFFKNKRIVLYDTLIQQCKNEDEIVAVIAHELGHWKLNH   213
Consensus Publi      XXXXXXXXXXXXXXXXXXXXXXXXXXXXXXXXXXXXXXXXXXXXXXXXXXXXXXXXXXXX   300

                        310       320       330       340       350       360
                     ....|....|....|....|....|....|....|....|....|....|....|....|
afc1                 TTYSFIAVQILAFLQFGGYTLVRNSTDLFRSFGFDTQPVLIGLIIFQHTVIPLQHLVSFG   353
AT4g01320            TTYSFIAVQILAFLQFGGYTLVRNSTDLFRSFGFDTQPVLIGLIIFQHTVIPLQHLVSFG   360
AF007269             TTYSFIAV--------------------------------------QHTVIPLQHLVSFG   235
Consensus Publi      XXXXXXXXXXXXXXXXXXXXLXRXXXXXXXXXXXXXXXXXXXXIXXQHXVXXXXXLVSXX   360

                        370       380       390       400       410       420
                     ....|....|....|....|....|....|....|....|....|....|....|....|
afc1                 LNLVSRAFEFQADAFAVKLGYAKDLRPALVKLQ---------------------------   386
AT4g01320            LNLVSRAFEFQADAFAVKLGYAKDLRPALVKLQVREDNNRTQTVTSICVTHLNGFFVGIL   420
AF007269             LNLVSRAFEFQADAFAVKLGYAKDLRPALVKLQVREDNNRTQT-----------------   278
Consensus Publi      XXXXXXAFXXXXXXXXXXXXXXXXLXXXXXXXXXXXXXXXXXXXXXXXXXXXXXXXXXXX   420
```

TABLE 34-continued

ClustalW Analysis of Generic Amino Acids

```
                          430       440       450       460       470       480
                    ....|....|....|....|....|....|....|....|....|....|....|....|
afc1                -EENLSAMNTDPLHSAYHYSHPPLVERLRAIDGEDKKTD---------------------   424
AT4g01320           QEENLSAMNTDPLYSAYHYSHPPLVERLRAIDGEDKKTD---------------------   459
AF007269            -EENLSAMNTDPLYSAYHYSHPPLVERLRAIDGEDKKTD---------------------   316
Consensus Publi     XXXXLSAMNTDPLYSAYHYSHPPLVERLRAIDGEDKKTD---------------------   480
```

TABLE 35

ClustalW Analysis of PPI Nucleic Acids

1) PPI-AtCPP (SEQ ID NO: 97)
2) PPI-BnCPP (SEQ ID NO: 109)
3) PPI-SoyCPP (SEQ ID NO: 112)
4) Consensus (SEQ ID NO: 167)

```
                      10        20        30        40        50        60
              ....|....|....|....|....|....|....|....|....|....|....|....|
PPI-AtCPP     ATGGCGATTCCTTTCATGGAAACCGTCGTGGGTTTTATGATAGTGATGTACATTTTTGAG     60
PPI-BnCPP     ATGGCGATTCCTTTCATGGAAACCGTCGTTGGTTTTATGATAGTGATGTACGTTTTTGAG     60
PPI-SoyCPP    ATGGCGTTTCCCTACATGGAAGCCGTTGTCGGATTTATGATATTAATGTACATTTTTGAA     60
Consensus     ATGGCGXTTCCXTXCATGGAAXCCGTXGTXGGXTTTATGATAXTXATGTACXTTTTTGAX     60

                      70        80        90       100       110       120
              ....|....|....|....|....|....|....|....|....|....|....|....|
PPI-AtCPP     ACGTATTTGGATCTGAGGCAACTCACTGCTCTCAAGCTTCCAACTCTCCCGAAAACCTTG     120
PPI-BnCPP     ACGTATTTGGATCTGAGGCAACATACTGCTCTCAAGCTTCCCACTCTCCCAAAGACTTTG     120
PPI-SoyCPP    ACTTACTTGGATGTGCGACAACATAGGCCCTCAAACTTCCTACTCTTCCAAAGACTTTA     120
Consensus     ACXTAXTTGGATXTGXGXCAACXXAXXGCXCTCAAXCTTCCXACTCTXCCXAAXACXTTX     120

                     130       140       150       160       170       180
              ....|....|....|....|....|....|....|....|....|....|....|....|
PPI-AtCPP     GTTGGTGTAATTAGCCAAGAGAAGTTTGAGAAATCACGAGCATACAGTCTTGACAAAAGC     180
PPI-BnCPP     GTTGGAGTCATTAGCCAAGAGAAGTTTGAGAAATCTCGAGCTTACAGTCTTGACAAAAGC     180
PPI-SoyCPP    GAGGGTGTTATCAGCCAAGAGAAATTTGAGAAATCTAGAGCCTATAGTCTTGATAAAAGC     180
Consensus     GXXGGXGTXATXAGCCAAGAGAAXTTTGAGAAATCXXGAGCXTAXAGTCTTGAXAAAAGC     180

                     190       200       210       220       230       240
              ....|....|....|....|....|....|....|....|....|....|....|....|
PPI-AtCPP     TATTTTCACTTTGTTCATGAGTTTGTAACTATACTTATGGACTCTGCAATTTTGTTCTTT     240
PPI-BnCPP     CATTTTCACTTTGTTCATGAGTTTGTTACTATACTTATGGACTCTGCGATTCTGTTCTTT     240
PPI-SoyCPP    CACTTCCATTTTGTTCACGAGTTTGTGACAATAGTGACAGACTCTACAATTTTGTACTTT     240
Consensus     XAXTTXCAXTTTGTTCAXGAGTTTGTXACXATAXTXAXXGACTCTXCXATTXTGTXCTTT     240

                     250       260       270       280       290       300
              ....|....|....|....|....|....|....|....|....|....|....|....|
PPI-AtCPP     GGGATCTTGCCTTGGTTTTGGAAGATGTCTGGAGCTGTTTTACCGAGGTTGGGCCTTGAT     300
PPI-BnCPP     GGGATCTTGCCTTGGTTTTGGAAGATATCTGGCGGCTTTCTACCAATGGTGGGACTCGAT     300
PPI-SoyCPP    GGGGTATTGCCCTGGTTTTGGAAGAAATCAGGAGATTTTATGACAATAGCTGGTTTCAAT     300
Consensus     GGGXTXTTGCCXTGGTTTTGGAAGAXXTCXGGXGXXXTTXTXXCXAXXXXXGGXXTXXAT     300

                     310       320       330       340       350       360
              ....|....|....|....|....|....|....|....|....|....|....|....|
PPI-AtCPP     CCGGAGAATGAAATACTGCATACTCTTTCATTCTTGGCTGGTGTTATGACATGGTCACAG     360
PPI-BnCPP     CCAGAGAATGAAATCCTGCACACTCTTTCATTCTTGGCTGGTCTTATGACATGGTCACAG     360
PPI-SoyCPP    GCTGAGAATGAAATACTGCATACCCTTGCCTTCTTAGCAGGGCTGATGATTTGGTCACAG     360
Consensus     XCXGAGAATGAAATXCTGCAXACXCTTXCXTTCTTXGCXGGXXTXATGAXXTGGTCACAG     360

                     370       380       390       400       410       420
              ....|....|....|....|....|....|....|....|....|....|....|....|
PPI-AtCPP     ATCACTGATTTGCCATTTTCTTTGTACTCAACTTTCGTGATCGAGTCTCGGCATGGGTTC     420
PPI-BnCPP     ATCACTGATTTGCCATTTTCTTTGTACTCAACTTTCGTGATCGAGTCTCGGCATGGGTTC     420
PPI-SoyCPP    ATAACAGATTTGCCCTTTTCTCTGTACTCAACTTTTGTGATTGAGGCCCGTCATGGTTTT     420
Consensus     ATXACXGATTTGCCXTTTTCTXTGTACTCAACTTTXGTGATXGAGXCXCGXCATGGXTTX     420

                     430       440       450       460       470       480
              ....|....|....|....|....|....|....|....|....|....|....|....|
PPI-AtCPP     AACAAACAAACAATATGGATGTTCATTAGGGACATGATCAAAGGAACATTCCTCTCTGTC     480
PPI-BnCPP     AACAAACAAACAATATGGATGTTCATTAGGGACATGATCAAAGGAATACTCCTCTCTGTC     480
PPI-SoyCPP    AATAAGCAAACACCATGGTTATTCTTTAGGGACATGCTTAAAGGAATTTTCCTTTCTGTA     480
Consensus     AAXAAXCAAACAXXATGGXTXTTCXTTAGGGACATGXTXAAAGGAAXXXTCCTXTCTGTX     480
```

TABLE 35-continued

ClustalW Analysis of PPI Nucleic Acids

```
                   490       500       510       520       530       540
           ....|....|....|....|....|....|....|....|....|....|....|....|
PPI-AtCPP  ATACTAGGCCCACCCATTGTTGCTGCGATAATTTTCATAGTCCAGAAAGGAGGTCCTTAT    540
PPI-BnCPP  ATACCTGCCCCTCCTATCGTTGCCGCAATTATTGTTATAGTTCAGAAAGGAGGTCCTTAC    540
PPI-SoyCPP ATAATTGGTCCACCTATTGTGGCTGCAATCATTGTAATAGTACAGAAAGGAGGTCCATAC    540
Consensus  ATAXXXGXXCCXCCXATXGTXGCXGCXATXATTXTXATAGTXCAGAAAGGAGGTCCXTAX    540

                   550       560       570       580       590       600
           ....|....|....|....|....|....|....|....|....|....|....|....|
PPI-AtCPP  CTTGCCATCTATCTGTGGGCATTCATGTTTATCCTGTCTCTAGTGATGATGACTATATAC    600
PPI-BnCPP  CTCGCCATCTATCTGTGGGCATTCATGTTTATCCTGTCTCTAGTGATGATGACTATATAC    600
PPI-SoyCPP TTGGCCATCTATCTTTGGGTTTTTACGTTTGGTCTTTCTATTGTGATGATGACCCTTTAT    600
Consensus  XTXGCCATCTATCTXTGGGXXTTXAXGTTTXXXCTXTCTXTXGTGATGATGACXXTXTAX    600

                   610       620       630       640       650       660
           ....|....|....|....|....|....|....|....|....|....|....|....|
PPI-AtCPP  CCGGTCTTGATAGCACCGCTCTTCAACAAATTCACTCCTCTTCCAGATGGAGACCTCCGG    660
PPI-BnCPP  CCTGTTTTGATTGCACCTCTTTTCAACAAGTTCACTCCTCTTCCTGATGGAGACCTCCGG    660
PPI-SoyCPP CCAGTACTAATAGCTCCACTCTTCAATAAGTTCACTCCACTTCCAGATGGTCAACTCAGG    660
Consensus  CCXGTXXTXATXGCXCCXCTXTTCAAXAAXTTCACTCCXCTTCCXGATGGXXAXCTCXGG    660

                   670       680       690       700       710       720
           ....|....|....|....|....|....|....|....|....|....|....|....|
PPI-AtCPP  GAGAAGATTGAGAAACTTGCTTCTTCCCTAAAGTTTCCTTTGAAGAAGCTGTTTGTTGTC    720
PPI-BnCPP  GAGAAGATTGAGAAACTTGCTTCTTCTCTAAAGTTTCCTCTGAAGAAGCTGTTTGTTGTC    720
PPI-SoyCPP GAGAAAATCGAGAAACTTGCTTCCTCCCTCAACTATCCGTTAAAGAAACTATTTGTTGTC    720
Consensus  GAGAAXATXGAGAAACTTGCTTCXTCXCTXAAXTXTCCXXTXAAGAAXCTXTTTGTTGTC    720

                   730       740       750       760       770       780
           ....|....|....|....|....|....|....|....|....|....|....|....|
PPI-AtCPP  GATGGATCTACAAGGTCAAGCCATAGCAATGCTTACATGTATGGTTTCTTTAAGAACAAA    780
PPI-BnCPP  GATGGATCTACAAGGTCAAGCCATAGTAATGCTTACATGTATGGTTTCTTCAAGAACAAA    780
PPI-SoyCPP GATGGATCCACAAGATCAAGTCACAGCAATGCCTATATGTATGGATTCTTCAAGAACAAG    780
Consensus  GATGGATCXACAAGXTCAAGXCAXAGXAATGCXTAXATGTATGGXTTCTTXAAGAACAAX    780

                   790       800       810       820       830       840
           ....|....|....|....|....|....|....|....|....|....|....|....|
PPI-AtCPP  AGGATTGTTCTTTATGATACGTTGATTCAGCAGTGCAAGAATGAGGATGAAATTGTGGCG    840
PPI-BnCPP  AGGATTGTTCTTTATGACACATTGATTCAGCAGTGCCAGAATGAGAATGAAATTGTGGCG    840
PPI-SoyCPP AGGATTGTCCCTTATGACACATTAATTCAACAGTGCAAAGACGATGAGGAAATTGTTGCT    840
Consensus  AGGATTGTXCXTTATGAXACXTTXATTCAXCAGTGCXAXXAXGAXXAXGAAATTGTXGCX    840

                   850       860       870       880       890       900
           ....|....|....|....|....|....|....|....|....|....|....|....|
PPI-AtCPP  GTTATTGCACACGAGCTTGGACATTGGAAACTGAATCACACTACATACTCGTTCATTGCA    900
PPI-BnCPP  GTTATTGCACACGAGCTGGGACACTGGAAGCTGAATCACACTACATACTCGTTCATTGCT    900
PPI-SoyCPP GTTATTGCCCATGAGTTGGGACACTGGAAGCTCAACCATACTGTGTACACATTTGTTGCT    900
Consensus  GTTATTGCXCAXGAGXTXGGACAXTGGAAXCTXAAXCAXACTXXXTACXCXTTXXTTGCX    900

                   910       920       930       940       950       960
           ....|....|....|....|....|....|....|....|....|....|....|....|
PPI-AtCPP  GTTCAAATCCTTGCCTTCTTACAATTTGGAGGATACACTCTTCTCAGAAACTCCACTGAT    960
PPI-BnCPP  GTTCAAATCCTTGCCTTCTTGCAATTTGGAGGATACACTCTTGTCAGAAACTCCACTGAT    960
PPI-SoyCPP ATGCAGATTCTTACACTTCTACAATTTGGAGGATATACACTAGTGCGAAATTCAGCTGAT    960
Consensus  XTXCAXATXCTTXCXXTXXTXCAATTTGGAGGATAXACXCTXXTXXGAAAXTCXXCTGAT    960

                   970       980       990      1000      1010      1020
           ....|....|....|....|....|....|....|....|....|....|....|....|
PPI-AtCPP  CTCTTCAGGAGTTTCGGATTTGATACACAGCCTGTTCTCATTGGTTTGATCATATTTCAG   1020
PPI-BnCPP  CTCTTCAGGAGTTTTGGTTTTGATACACAACCAGTTCTCATTGGTTTGATCATATTTCAG   1020
PPI-SoyCPP CTGTATCGAAGCTTTGGGTTTGATACGCAGCCAGTCCTCATTGGGCTCATCATATTTCAG   1020
Consensus  CTXTXXXGXAGXTTXGGXTTTGATACXCAXCCXGTXCTCATTGGXXTXATCATATTTCAG   1020

                  1030      1040      1050      1060      1070      1080
           ....|....|....|....|....|....|....|....|....|....|....|....|
PPI-AtCPP  CACACTGTAATACCACTGCAACATCTAGTAAGCTTTGGCCTGAACCTCGTTAGTCGAGCG   1080
PPI-BnCPP  CACACTGTAATACCACTTCAACACCTAGTAAGCTTTGACCTCAACCTTGTTAGTCGAGCG   1080
PPI-SoyCPP CATACTGTAATCCCACTTCAGCAATTGGTCAGCTTTGGTCTGAACCTAGTCAGCCGATCA   1080
Consensus  CAXACTGTAATXCCACTXCAXCAXXTXGTXAGCTTTGXXCTXAACCTXGTXAGXCGAXCX   1080

                  1090      1100      1110      1120      1130      1140
           ....|....|....|....|....|....|....|....|....|....|....|....|
PPI-AtCPP  TTTGAGTTTCAGGCTGATGCTTTTGCTGTGAAGCTTGACTATGCAAAAGATCTTCGTCCT   1140
PPI-BnCPP  TTTGAGTTTCAGGCTGATGCTTTTGCAGTGAATCTTGGTTATGCAAAGGATCTACGTCCT   1140
PPI-SoyCPP TTTGAATTTCAGGCTGATGGCTTTGCCAAGAAGCTTGGATATGCATCTGGATTACGCGGT   1140
Consensus  TTTGAXTTTCAGGCTGATGXXTTTGCXXXGAAXCTTGXXTATGCAXXXGXXXTXCGXXXT   1140
```

TABLE 35-continued

ClustalW Analysis of PPI Nucleic Acids

| | 1150 1160 1170 1180 1190 1200 | |
|---|---|---|
| PPI-AtCPP | GCTCTAGTGAAACTACAGGAAGAGAACTTATCAACAATGAACACTGATCCATTGTACTCA | 1200 |
| PPI-BnCPP | GCCCTAGTGAAGCTACAGGAAGAGAACTTATCAGCGATGAACACAGACCCATTGTACTCA | 1200 |
| PPI-SoyCPP | GGTCTTGTGAAACTACAGGAGGAGAATCTGTCAGCTATGAATACAGATCCTTGGTACTCT | 1200 |
| Consensus | GXXCTXGTGAAXCTACAGGAXGAGAAXXTXTCAXCXATGAAXACXGAXCCXTXGTACTCX | 1200 |

| | 1210 1220 1230 1240 1250 1260 | |
|---|---|---|
| PPI-AtCPP | GCTTATCACTACTCACATCCTCCTCTTGTTGAAAGGCTTCGAGCCACTGATGGAGAAGAC | 1260 |
| PPI-BnCPP | GCTTATCACTACTCACACCCTCCTCTTGTAGAGAGGCTTCGAGCCATTGATGGAGAAGAC | 1260 |
| PPI-SoyCPP | GCTTATCACTATTCTCATCCTCCCCTTGTTGAAAGATTGGCCGCGCTGGACGAACCGGAT | 1260 |
| Consensus | GCTTATCACTAXTCXCAXCCTCCXCTTGTXGAXAGXXTXXXXGCXXXXGAXGXAXXXGAX | 1260 |

| | 1270 | |
|---|---|---|
| PPI-AtCPP | AAGAAGACAGATTAA | 1275 |
| PPI-BnCPP | AAGAAGACAGATTAA | 1275 |
| PPI-SoyCPP | AAGAAGGAAGACTAA | 1275 |
| Consensus | AAGAAGXXAGAXTAA | 1275 |

TABLE 36

ClustalW Analysis of PPI Amino Acids

1) PPI-AtCPP (SEQ ID NO: 98)
2) PPI-BnCPP (SEQ ID NO: 110)
3) PPI-SoyCPP (SEQ ID NO: 113)
4) Consensus (SEQ ID NO: 168)

| | 10 20 30 40 50 60 | |
|---|---|---|
| PPI-AtCPP | MAFPYMEAVVGFMILMYIFETYLDVRQHRALKLPTLPKTLEGVISQEKFEKSRAYSLDKS | 60 |
| PPI-BnCPP | MAIPFMETVVGFMIVMYVFETYLDLRQHTALKLPTLPKTLVGVISQEKFEKSRAYSLDKS | 60 |
| PPI-SoyCPP | MAFPYMEAVVGFMILMYIFETYLDVRQHRALKLPTLPKTLEGVISQEKFEKSRAYSLDKS | 60 |
| Consensus PPI | MAXPXMEXVVGFMIXMYXFETYLDXRQHXALKLPTLPKTLXGVISQEKFEKSRAYSLDKS | 60 |

| | 70 80 90 100 110 120 | |
|---|---|---|
| PPI-AtCPP | HFHFVHEFVTIVTDSTILYFGVLPWFWKKSGDFMTIAGFNAENEILHTLAFLAGLMIWSQ | 120 |
| PPI-BnCPP | HFHFVHEFVTILMDSAILFFGILPWFWKISGGFLPMVGLDPENEILHTLSFLAGLMTWSQ | 120 |
| PPI-SoyCPP | HFHFVHEFVTIVTDSTILYFGVLPWFWKKSGDFMTIAGFNAENEILHTLAFLAGLMIWSQ | 120 |
| Consensus PPI | HFHFVHEFVTIXXDSXILXFGXLPWFWKXSGXFXXXXGXXXENEILHTLXFLAGLMXWSQ | 120 |

| | 130 140 150 160 170 180 | |
|---|---|---|
| PPI-AtCPP | ITDLPFSLYSTFVIEARHGFNKQTPWLFFRDMLKGIFLSVIIGPPIVAAIIVIVQKGGPY | 180 |
| PPI-BnCPP | ITDLPFSLYSTFVIESRHGFNKQTIWMFIRDMIKGILLSVIPAPPIVAAIIVIVQKGGPY | 180 |
| PPI-SoyCPP | ITDLPFSLYSTFVIEARHGFNKQTPWLFFRDMLKGIFLSVIIGPPIVAAIIVIVQKGGPY | 180 |
| Consensus PPI | ITDLPFSLYSTFVIEXRHGFNKQTXWXFXRDMXKGIXLSVIXXPPIVAAIIVIVQKGGPY | 180 |

| | 190 200 210 220 230 240 | |
|---|---|---|
| PPI-AtCPP | LAIYLWVFTFGLSIVMMTLYPVLIAPLFNKFTPLPDGQLREKIEKLASSLNYPLKKLFVV | 240 |
| PPI-BnCPP | LAIYLWAFMFILSLVMMTIYPVLIAPLFNKFTPLPDGDLREKIEKLASSLKFPLKKLFVV | 240 |
| PPI-SoyCPP | LAIYLWVFTFGLSIVMMTLYPVLIAPLFNKFTPLPDGQLREKIEKLASSLNYPLKKLFVV | 240 |
| Consensus PPI | LAIYLWXFXFXLSXVMMTXYPVLIAPLFNKFTPLPDGXLREKIEKLASSLXXPLKKLFVV | 240 |

| | 250 260 270 280 290 300 | |
|---|---|---|
| PPI-AtCPP | DGSTRSSHSNAYMYGFFKNKRIVPYDTLIQQCKDDEEIVAVIAHELGHWKLNHTVYTFVA | 300 |
| PPI-BnCPP | DGSTRSSHSNAYMYGFFKNKRIVLYDTLIQQCQNENEIVAVIAHELGHWKLNHTTYSFIA | 300 |
| PPI-SoyCPP | DGSTRSSHSNAYMYGFFKNKRIVPYDTLIQQCKDDEEIVAVIAHELGHWKLNHTVYTFVA | 300 |
| Consensus PPI | DGSTRSSHSNAYMYGFFKNKRIVXYDTLIQQCXXXXEIVAVIAHELGHWKLNHTXYXFXA | 300 |

| | 310 320 330 340 350 360 | |
|---|---|---|
| PPI-AtCPP | MQILTLLQFGGYTLVRNSADLYRSFGFDTQPVLIGLIIFQHTVIPLQQLVSFGLNLVSRS | 360 |
| PPI-BnCPP | VQILAFLQFGGYTLVRNSTDLFRSFGFDTQPVLIGLIIFQHTVIPLQHLVSFDLNLVSRA | 360 |
| PPI-SoyCPP | MQILTLLQFGGYTLVRNSADLYRSFGFDTQPVLIGLIIFQHTVIPLQQLVSFGLNLVSRS | 360 |
| Consensus PPI | XQILXXLQFGGYTLVRNSXDLXRSFGFDTQPVLIGLIIFQHTVIPLQXLVSFXLNLVSRX | 360 |

TABLE 36-continued

ClustalW Analysis of PPI Amino Acids

```
                        370       380       390       400       410       420
                ....|....|....|....|....|....|....|....|....|....|....|....|
PPI-AtCPP       FEFQADGFAKKLGYASGLRGGLVKLQEENLSAMNTDPWYSAYHYSHPPLVERLAALDEPD   420
PPI-BnCPP       FEFQADAFAVNLGYAKDLRPALVKLQEENLSAMNTDPLYSAYHYSHPPLVERLRAIDGED   420
PPI-SoyCPP      FEFQADGFAKKLGYASGLRGGLVKLQEENLSAMNTDPWYSAYHYSHPPLVERLAALDEPD   420
Consensus PPI   FEFQADXFAXXLGYAXXLRXXLVKLQEENLSAMNTDPXYSAYHYSHPPLVERLXAXDXXD   420

                        430       440       450       460       470       480
                ....|....|....|....|....|....|....|....|....|....|....|....|
PPI-AtCPP       KKED--------------------------------------------------------   424
PPI-BnCPP       KKTD--------------------------------------------------------   424
PPI-SoyCPP      KKED--------------------------------------------------------   424
Consensus PPI   KKXD                                                           480
```

TABLE 37

ClustalW Analysis of PPI/Generic Nucleic Acids

```
1) PPI-AtCPP  (SEQ ID NO: 97)
2) PPI-BnCPP  (SEQ ID NO: 109)
3) PPI-SoyCPP (SEQ ID NO: 112)
4) afc1       (SEQ ID NO: 124)
5) AT4g01320  (SEQ ID NO: 126)
6) AF007269   (SEQ ID NO: 128)
6) Consensus  (SEQ ID NO: 170)

                       10        20        30        40        50        60        70
               ....|....|....|....|....|....|....|....|....|....|....|....|....|....|
PPI-AtCPP NA   ----------------------------------------------------------------------
PPI-BnCPP      ----------------------------------------------------------------------
PPI-SoyCPP     ----------------------------------------------------------------------
afc1           ----------------------------------------------------------------------
AT4g01320      ----------------------------------------------------------------------
AF007269       ATGGCGATTCCTTTCATGGAAACCGTCGTGGGTAAGCTTCAAAACCTTTTTCTGAGACATTTTACTATCC
Consensus      ----------------------------------------------------------------------

                       80        90       100       110       120       130       140
               ....|....|....|....|....|....|....|....|....|....|....|....|....|....|
PPI-AtCPP NA   ----------ATGGCGTTTCCCTACATGGAAGCCGTTGTCGGATTTATGATATTAATGTACATTTTTGAA
PPI-BnCPP      ----------------------------------------------------------------------
PPI-SoyCPP     ----------ATGGCGTTTCCCTACATGGAAGCCGTTGTCGGATTTATGATATTAATGTACATTTTTGAA
afc1           ----------------------------------------------------------------------
AT4g01320      ----------------------------------------------------------------------
AF007269       TGTTTCACTCATCGTATTTCGTTTTTGTTTGGGTTTTGCTTTCTGTGTTGTGTGTGTTGAGATTCCATGA
Consensus      ----------ATGGCGATTCCTTTCATGGAAACCGTCGT-GGTTTTATGATAT--ATGTACATTTTTGAA

                      150       160       170       180       190       200       210
               ....|....|....|....|....|....|....|....|....|....|....|....|....|....|
PPI-AtCPP NA   ACTTACTTGGATG-TGCGACAACATAGGGCCCTCAAACTTCCTACTCTTCCAAAGACTTTAGAGGGTGTT
PPI-BnCPP      ----------------------------------------------------------------------
PPI-SoyCPP     ACTTACTTGGATG-TGCGACAACATAGGGCCCTCAAACTTCCTACTCTTCCAAAGACTTTAGAGGGTGTT
afc1           ----------------------------------------------------------------------
AT4g01320      ----------------------------------------------------------------------
AF007269       -CTCGTTTGTTTCATATACCATCGTCTCTGCTTCTCGTTTCTAAATTTTGTTCTTTTCTAATAGTGCGTA
Consensus      --CTATTTGGAT----TGGCAACATG----CCTCAA--CTTCCACTCTCC---AAACTTGGTGGTGTAT-

                      220       230       240       250       260       270       280
               ....|....|....|....|....|....|....|....|....|....|....|....|....|....|
PPI-AtCPP NA   ATCAGCCAAGAGAAATTTGAGAAATCTAGAGCCTATAGTCTTGATAAAAGCCACTTCCATTTTGTTCACG
PPI-BnCPP      ----------------------------------------------------------------------
PPI-SoyCPP     ATCAGCCAAGAGAAATTTGAGAAATCTAGAGCCTATAGTCTTGATAAAAGCCACTTCCATTTTGTTCACG
afc1           ----------------------------------------------------------------------
AT4g01320      ----------------------------------------------------------------------
AF007269       CCTTGATCTGAGGTTTTATTACTCCTACTAGTTTCTTGTCTTACTCGTG--CGTTT-GATTTGATTTGAG
Consensus      ---AGCCAAGAGAAGTTTGAGAAATCTGAG--CTACAGTCTTGAAAAAG--CATT--CATTT-GTTCA-G

                      290       300       310       320       330       340       350
               ....|....|....|....|....|....|....|....|....|....|....|....|....|....|
PPI-AtCPP NA   AGTTTGTGACAATAGTGACAGACTCTACAATTTTGTACTTTGGGGTATTGCCCTGGTTTTGGAA-----G
PPI-BnCPP      ----------------------------------------------------------------------
PPI-SoyCPP     AGTTTGTGACAATAGTGACAGACTCTACAATTTTGTACTTTGGGGTATTGCCCTGGTTTTGGAA-----G
afc1           ----------------------------------------------------------------------
AT4g01320      ----------------------------------------------------------------------
AF007269       CTTATGTGA-TTTCATCATCTCTTCCTCGGTTTTAGAATGTACGGAGCTTCTCTGTTAACCAAAATCTAG
Consensus      AGTTTGTA--CATAGT--TAGACTCT-CAATTTTGT-CTTTGGG---TTTGCCTGGTTTTGGAA-----G
```

TABLE 37-continued

ClustalW Analysis of PPI/Generic Nucleic Acids

```
                   360       370       380       390       400       410       420
              ....|....|....|....|....|....|....|....|....|....|....|....|....|....|
PPI-AtCPP NA  AAATCAGGAGATTTTATGACAATAGCTGGTTTCAATGCTGAGAATGAAATACTGCATACCCTTGCCTTCT
PPI-BnCPP     ----------------------------------------------------------------------
PPI-SoyCPP    AAATCAGGAGATTTTATGACAATAGCTGGTTTCAATGCTGAGAATGAAATACTGCATACCCTTGCCTTCT
afc1          ----------------------------------------------------------------------
AT4g01320     ----------------------------------------------------------------------
AF007269      GATTTGGGAAGAAAAGTCGGAGTCTTTTTTTTCCTCATTCCCGATTGGAAATTGAGAATCTTGAAATTTT
Consensus     AT-TCGGG---TTTTGCAA------TTGGT-----CATCGAGAATGAAAT-CTGCATACC-TT--CTTCT

                   430       440       450       460       470       480       490
              ....|....|....|....|....|....|....|....|....|....|....|....|....|....|
PPI-AtCPP NA  TAGCAGGGCTGATGATTTGGTCACAGATAACAGATTTGCCCTTTTCTCTGTACTCAACTTTT-----GTG
PPI-BnCPP     ----------------------------------------------------------------------
PPI-SoyCPP    TAGCAGGGCTGATGATTTGGTCACAGATAACAGATTTGCCCTTTTCTCTGTACTCAACTTTT-----GTG
afc1          ----------------------------------------------------------------------
AT4g01320     ----------------------------------------------------------------------
AF007269      TCTTTGTTCAAGTCATACAGCTTGAGGTTTTGGGTTTTCTTGTCAGGGTATTATTATGTTCGTGACTGCA
Consensus     T-GCGGT----ATGAT--GGTCACAGATA--CGATTTGCCTTTTCTT--GTACTCAACTTT------GTG

                   500       510       520       530       540       550       560
              ....|....|....|....|....|....|....|....|....|....|....|....|....|....|
PPI-AtCPP NA  ATTGAGGCCCGTCATGGTTTTAATAAGCAAACAC--CATGGTTATTCTTTAGGGACATGCTTAAAGGAAT
PPI-BnCPP     ----------------------------------------------------------------------
PPI-SoyCPP    ATTGAGGCCCGTCATGGTTTTAATAAGCAAACAC--CATGGTTATTCTTTAGGGACATGCTTAAAGGAAT
afc1          ----------------------------------------------------------------------
AT4g01320     ----------------------------------------------------------------------
AF007269      ACTAGAGTTTTCTGGAGTTTTTTGAAATGGGTTTTGTGTTGTGGAACCGTATGTGAATGTTGCATCAAAA
Consensus     AT--GAGTCCG-CATGGTTAAAACAAACA-------CATGGTT---TCTTAGGGACATG--TAAAGGAAT

                   570       580       590       600       610       620       630
              ....|....|....|....|....|....|....|....|....|....|....|....|....|....|
PPI-AtCPP NA  TTTCCTTTCTGTAATAATTGGTCCACCTATTGTGGCTGCAA------TCATTGTAA-TAGTACAGAAAGG
PPI-BnCPP     ----------------------------------------------------------------------
PPI-SoyCPP    TTTCCTTTCTGTAATAATTGGTCCACCTATTGTGGCTGCAA------TCATTGTAA-TAGTACAGAAAGG
afc1          ----------------------------------------------------------------------
AT4g01320     ----------------------------------------------------------------------
AF007269      CTCTTTCAGTGCTCCAATGTTTCCATCAGTAGTCAGCACAAGAGATCTTTTTATATCTGGTTGATCAAAA
Consensus     TTCCTTCTGTATA------G--CC-CCTATTGTG-CTGCAA------T-ATTGTA--TAGT-CAGAAAGG

                   640       650       660       670       680       690       700
              ....|....|....|....|....|....|....|....|....|....|....|....|....|....|
PPI-AtCPP NA  AGGTCCATA--CTTGGCCATCTATCTTTGGGTTTTTACGTTTGGTCTTTCTATTGTGATGATGACCCTTT
PPI-BnCPP     --------------------------------------------------------------------AT
PPI-SoyCPP    AGGTCCATA--CTTGGCCATCTATCTTTGGGTTTTTACGTTTGGTCTTTCTATTGTGATGATGACCCTTT
afc1          --------------------------------------------------------------------AT
AT4g01320     --------------------------------------------------------------------AT
AF007269      AAGTAGATGATGTTATTGAATTTTCAGTGATGGAGTATCTGTTGTTGTGGCATTTAGAGTAGATTCGTAT
Consensus     AGGTCC-----TATG-CCATCTATCTTGGG---------TTTAGTTTTCTTCTTGTGATGATGACC--TT

                   710       720       730       740       750       760       770
              ....|....|....|....|....|....|....|....|....|....|....|....|....|....|
PPI-AtCPP NA  ATCCAGTACTA-ATAGCTCCACTCTTCAATAAGTTCACTCCACT--TCCAGATGGTCAACTCAGGGAGAA
PPI-BnCPP     GGCGATTCCT--TTCATGGAAACCGTCGTTGGTTTTATGATAGTGATGTACGTTTTTGAGACGTATTTGG
PPI-SoyCPP    ATCCAGTACTA-ATAGCTCCACTCTTCAATAAGTTCACTCCACT--TCCAGATGGTCAACTCAGGGAGAA
afc1          GGCGATTCCT--TTCATGGAAACCGTCGTGGGTTTTATGATAGTGATGTACATTTTTGAGACGTATTTGG
AT4g01320     GGCGATTCCT--TTCATGGAAACCGTCGTGGGTTTTATGATAGTGATGTACATTTTTGAGACGTATTTGG
AF007269      TTCATCTTCTGTTTTATTCTTTTTCTTACAGGTTTTATGATAGTGATGTACATTTTTGAGACGTATTTGG
Consensus     A-CC--------GTTATGCCCCTCTTCAA-AAGTTCACTCC-CT--TCCAGATGG---ACTC-GGGAGAA

                   780       790       800       810       820       830       840
              ....|....|....|....|....|....|....|....|....|....|....|....|....|....|
PPI-AtCPP NA  AATCGAGA-AACTTGCTTCCTCCCT-CAACTATCCGTTAAAGAAACTATTTGTTGTCGATGGATCCACAA
PPI-BnCPP     ATCTGAGGCAACATACTGCTCTCAAGCTTCCCACTCTCCCAAAGACT-TTGGTTGGAG-TCATTAGCCAA
PPI-SoyCPP    AATCGAGA-AACTTGCTTCCTCCCT-CAACTATCCGTTAAAGAAACTATTTGTTGTCGATGGATCCACAA
afc1          ATCTGAGGCAACTCACTGCTCTCAAGCTTCCAACTCTCCCGAAAACC-TTGGTTGGTG-TAATTAGCCAA
AT4g01320     ATCTGAGGCAACTCACTGCTCTCAAGCTTCCAACTCTCCCGAAAACC-TTGGTTGGTG-TAATTAGCCAA
AF007269      ATCTGAGGCAACTCACTGCTCTCAAGCTTCCAACTCTCCCGAAAACC-TTGGTTGGTG-TAATTAGCCAA
Consensus     A--TGAGA-AACTTGCTTCTCCT----A---ATTCCTTAAG--AACTATTTGTTGTCGATGGATC-ACAA

                   850       860       870       880       890       900       910
              ....|....|....|....|....|....|....|....|....|....|....|....|....|....|
PPI-AtCPP NA  GATCAAGTCACAGCAATGCCTATATGTATGCATTCTTCAAGAACAAGAGGATTGTCC---CTTATGACAC
PPI-BnCPP     G-AGAAGTTTGAGAAATCTCGA-GCTTACAG---------------------------------------
PPI-SoyCPP    GATCAAGTCACAGCAATGCCTATATGTATGCATTCTTCAAGAACAAGAGGATTGTCC---CTTATGACAC
afc1          G-AGAAGTTTGAGAAATCACGA-GCATACAG---------------------------------------
AT4g01320     G-AGAAGTTTGAGAAATCACGA-GCATACAG---------------------------------------
AF007269      G-AGAAGTTTGAGAAATCACGA-GCATACAGTCTTGACAAAAGGTTTCGTCTTGATCATATTTATATCAT
Consensus     G-TCAAG-CATAG-AATGCTAA--TGTATGC--TTCTTAAGAACAA-AGGATTGTC-----TTATGACAC
```

TABLE 37-continued

ClustalW Analysis of PPI/Generic Nucleic Acids

```
                       920       930       940       950       960       970       980
                ....|....|....|....|....|....|....|....|....|....|....|....|....|....|
PPI-AtCPP NA    ATTAATTC-------------AACAGTGCAAAGAC-GATGAGGAAATTGTTG-CTGTTATTGCCCATGAG
PPI-BnCPP       -----------------------------------------TCTTGACAAA---AGCCATTTTCACTTTG
PPI-SoyCPP      ATTAATTC-------------AACAGTGCAAAGAC-GATGAGGAAATTGTTG-CTGTTATTGCCCATGAG
afc1            -----------------------------------------TCTTGACAAA---AGCTATTTTCACTTTG
AT4g01320       -----------------------GGATATCATCACTGAGAACTTTAATATATGCAGCTATTTTCACTTTG
AF007269        TTTAGTTTTTTATAATTGCCAGGGGATATCATCACTGAGAACTTTAATATATGCAGCTATTTTCACTTTG
Consensus       ATTATTC---------------ACAGTGCAA--------GAAGAAATTGTG---CGTTATTGCC---AGA

                       990      1000      1010      1020      1030      1040      1050
                ....|....|....|....|....|....|....|....|....|....|....|....|....|....|
PPI-AtCPP NA    TTGGGACACTGGAAGCTCAACCATACTGTGTACACATTTGTTGCTATGCAGATTCTTACACTTCTACAAT
PPI-BnCPP       TTCATGAGTTTGTTACTATA-CTTATGGACTCTGCGAT-TCTGTTCTTTGGGATCTTGC----CTTGGTT
PPI-SoyCPP      TTGGGACACTGGAAGCTCAACCATACTGTGTACACATTTGTTGCTATGCAGATTCTTACACTTCTACAAT
afc1            TTCATGAGTTTGTAACTATA-CTTATGGACTCTGCAAT-TTTGTTCTTTGGGATCTTGC----CTTGGTT
AT4g01320       TTCATGAGTTTGTAACTATA-CTTATGGACTCTGCAAT-TTTGTTCTTTGGGATCTTGC----CTTGGTT
AF007269        TTCATGAGTTTGTAACTATA-CTTATGGACTCTGCAAT-TTTGTTCTTTGGGATCTTGC----CTTGGTT
Consensus       GTGGGACACTGGAA-------CTAACAACTTACACATT-ATTGCTTC----AATCTT----CTTTACAAT

                      1060      1070      1080      1090      1100      1110      1120
                ....|....|....|....|....|....|....|....|....|....|....|....|....|....|
PPI-AtCPP NA    TTGGAGGATATACACTAGTGCGAAATTCAGCTGATCTGTATCGAAGCTTTGGGTTTGATACGCAGCCAGT
PPI-BnCPP       TTGGAAG---------------------------------------------------------------
PPI-SoyCPP      TTGGAGGATATACACTAGTGCGAAATTCAGCTGATCTGTATCGAAGCTTTGGGTTTGATACGCAGCCAGT
afc1            TTGGAAG---------------------------------------------------------------
AT4g01320       TTGGAAG---------------------------------------------------------------
AF007269        TTGGAAGGTACATATCTGGTTTCGGTATACAGTATCT-CATTTTGAATATAGAGTTGTTACATTACAA--
Consensus       TTGGAGGATACAC-CTAGTG--AAATCC---TGATCT----TGAG----TTGGTTTGATAC-CAGCCG--

                      1130      1140      1150      1160      1170      1180      1190
                ....|....|....|....|....|....|....|....|....|....|....|....|....|....|
PPI-AtCPP NA    CCTCATTGGGCTCATCATATTTCAGCATACTGTAATCCCACTTCAGCAATTGGTCAGCTTTGGTCT---G
PPI-BnCPP       --------------------------ATATCTGGCGGC-TTTCTACCAA-TGGTGGCACTCGATCCAGAG
PPI-SoyCPP      CCTCATTGGGCTCATCATATTTCAGCATACTGTAATCCCACTTCAGCAATTGGTCAGCTTTGGTCT---G
afc1            --------------------------ATGTCTGGAGCT-GTTTTACCGA-GGTTGGGCCTTGATCCAGAG
AT4g01320       --------------------------ATGTCTGGAGCT-GTTTTACCGA-GGTTGGGCCTTGATCCAGAG
AF007269        TTGTAAAGTTTTCATTTTTACCTTAGATGTCTGGAGCT-GTTTTACCGA-GGTTGGGCCTTGATCCAGAG
Consensus       TCTCATTGG---TATCATATTTCAGCATACTGTAATCC-ACTTCA-----CATGTAGCTTTGCT------

                      1200      1210      1220      1230      1240      1250      1260
                ....|....|....|....|....|....|....|....|....|....|....|....|....|....|
PPI-AtCPP NA    AACCTAGTCAGCCGATCATTTGAATTTCAGGCTGATGGCTTTGCCAAGAAGCTTGGATATGCATCTGGAT
PPI-BnCPP       AATGAAATCCTGCACACTCTTTCATTCTTGGCTGGTC-TTATGACATGGTCACAG---------------
PPI-SoyCPP      AACCTAGTCAGCCGATCATTTGAATTTCAGGCTGATGGCTTTGCCAAGAAGCTTGGATATGCATCTGGAT
afc1            AATGAAATACTGCATACTCTTTCATTCTTGGCTGGTG-TTATGACATGGTCACAG---------------
AT4g01320       AATGAAATACTGCATACTCTTTCATTCTTGGCTGGTG-TTATGACATGGTCACAG---------------
AF007269        AATGAAATACTGCATACTCTTTCATTCTTGGCTGGTG-TTATGACATGGTCACAGGTGTTCCAAATAAAC
Consensus       AACCTG------TAGCGACTTTGATTTCAGGCTGATG-CTTTGC---GAAGCTTGG-TATGCAGTCGG--

                      1270      1280      1290      1300      1310      1320      1330
                ....|....|....|....|....|....|....|....|....|....|....|....|....|....|
PPI-AtCPP NA    TACGCGGTG--GTCTTGTGAAACTACAGGAGGAGAATCTGTCAGCT----ATGAATACAGATCCTTGGTA
PPI-BnCPP       ----------------------------------------------------------------------
PPI-SoyCPP      TACGCGGTG--GTCTTGTGAAACTACAGGAGGAGAATCTGTCAGCT----ATGAATACAGATCCTTGGTA
afc1            ----------------------------------------------------------------------
AT4g01320       ----------------------------------------------------------------------
AF007269        CCCTTCATATAGTCCTATACGTTTAGCATCAAAATATCTATTTTCTTAAGATAATAATATTTCTTTTATA
Consensus       --T--------GTCTAGTGAA-CTACAGGAGAGAA---TGTCAGC-----ATGAA-ACAGATCCTTG-TA

                      1340      1350      1360      1370      1380      1390      1400
                ....|....|....|....|....|....|....|....|....|....|....|....|....|....|
PPI-AtCPP NA    CTCT---GCTTATCACTATTCTCATCCTCCCCT-----TGTTGAAAGATTGGCCGCGCTGGACGAA----
PPI-BnCPP       -----------ATCACTGATTTGCCATTTTCTTTG---TACTCAACTTTCG-------TGATCGAG----
PPI-SoyCPP      CTCT---GCTTATCACTATTCTCATCCTCCCCT-----TGTTGAAAGATTGGCCGCGCTGGACGAA----
afc1            -----------ATCACTGATTTGCCATTTTCTTTG---TACTCAACTTTCG-------TGATCGAG----
AT4g01320       -----------ATCACTGATTTGCCATTTTCTTTG---TACTCAACTTTCG-------TGATCGAG----
AF007269        TTCTGATGCAGATCACTGATTTGCCATTTTCTTTG---TACTCAACTTTCG-------TGATCGAG----
Consensus       CTC----GCTTATCACTATCCACCTCCCTTGTGAAAGATGCTGAGAGAAAGAAGAGATAATCTAAATTCT

                      1410      1420      1430      1440      1450      1460      1470
                ....|....|....|....|....|....|....|....|....|....|....|....|....|....|
PPI-AtCPP NA    --CCGGATAAGAAGGAAGACTAAE----------------------------------------------
PPI-BnCPP       --TCTCGGCATGGGTTCAACAAA-----------------------------------------------
PPI-SoyCPP      --CCGGATAAGAAGGAAGACTAA-----------------------------------------------
afc1            --TCTCGGCATGGGTTCAACAAA-----------------------------------------------
AT4g01320       --TCTCGGCATGGGTTCAACAAA-----------------------------------------------
AF007269        --TCTCGGCATGGGTTCAACAAAGTATGTCGTATTTCCAACACTACCTTGTGACTTACGTTTTTTTATCA
Consensus       TTCCTTTTCATGGAGGTAACAAAGTATGTCGTATTTCCAACACTACCTTGTGACTTACGTTTTTTTATCA
```

TABLE 37-continued

ClustalW Analysis of PPI/Generic Nucleic Acids

```
                    1480      1490      1500      1510      1520      1530      1540
            ....|....|....|....|....|....|....|....|....|....|....|....|....|....|
PPI-AtCPP NA ----------------------------------------------------------------------
PPI-BnCPP   ---------------------------------------CAAACAATATGGATGTTCATTAGGGACATGA
PPI-SoyCPP  ----------------------------------------------------------------------
afc1        ---------------------------------------CAAACAATATGGATGTTCATTAGGGACATGA
AT4g01320   ---------------------------------------CAAACAATATGGATGTTCATTAGGGACATGA
AF007269    GAGATGTGGATTAAATTTGCTTCTAAATTCTGTTGACAGCAAACAATATGGATGTTCATTAGGGACATGA
Consensus   GAGATGTGGATTAAATTTGCTTCTAAATTCTGTTGACAGCAAACAATATGGATGTTCATTAGGGACATGA

                    1550      1560      1570      1580      1590      1600      1610
            ....|....|....|....|....|....|....|....|....|....|....|....|....|
PPI-AtCPP NA ----------------------------------------------------------------------
PPI-BnCPP   TCAAAGGAATACTCCTCTCTGTCATACCTGCCCCTCCTATCGTTGCCGCAATTATTGTTATAGTTCAG--
PPI-SoyCPP  ----------------------------------------------------------------------
afc1        TCAAAGGAACATTCCTCTCTGTCATACTAGGCCCACCCATTGTTGCTGCGATAATTTTCATAGTCCAG--
AT4g01320   TCAAAGGAACATTCCTCTCTGTCATACTAGGCCCACCCATTGTTGCTGCGATAATTTTCATAGTCCAG--
AF007269    TCAAAGGAACATTCCTCTCTGTCATACTAGGCCCACCCATTGTTGCTGCGATAATTTTCATAGTCCAGGT
Consensus   TCAAAGGAACATTCCTCTCTGTCATACTAGGCCCACCCATTGTTGCTGCGATAATTTTCATAGTCCAGGT

                    1620      1630      1640      1650      1660      1670      1680
            ....|....|....|....|....|....|....|....|....|....|....|....|....|
PPI-AtCPP NA ----------------------------------------------------------------------
PPI-BnCPP   ----------------------------------------------------------------------
PPI-SoyCPP  ----------------------------------------------------------------------
afc1        ----------------------------------------------------------------------
AT4g01320   ----------------------------------------------------------------------
AF007269    TTGATGATTCTGGATTCATCTTATTTCTGAGTTTTTCACATGGATGACTATTCTCCATTGAGTGTGAGCT
Consensus   TTGATGATTCTGGATTCATCTTATTTCTGAGTTTTTCACATGGATGACTATTCTCCATTGAGTGTGAGCT

                    1690      1700      1710      1720      1730      1740      1750
            ....|....|....|....|....|....|....|....|....|....|....|....|....|
PPI-AtCPP NA ----------------------------------------------------------------------
PPI-BnCPP   ----------------------------------------------------------------------
PPI-SoyCPP  ----------------------------------------------------------------------
afc1        ----------------------------------------------------------------------
AT4g01320   ----------------------------------------------------------------------
AF007269    TCAAAGTTTTTAGTTTTCGTGTTAAAAATTTAAAATTTGCTTCTCTGAGCATGAAGTTTCTATCTTTTTC
Consensus   TCAAAGTTTTTAGTTTTCGTGTTAAAAATTTAAAATTTGCTTCTCTGAGCATGAAGTTTCTATCTTTTTC

                    1760      1770      1780      1790      1800      1810      1820
            ....|....|....|....|....|....|....|....|....|....|....|....|....|
PPI-AtCPP NA ----------------------------------------------------------------------
PPI-BnCPP   ---AAAGGAGGTCCTTACCTCGCCATCTATCTGTGGGCATTCATGTTTATCCTGTCTCTAGTGATGATGA
PPI-SoyCPP  ----------------------------------------------------------------------
afc1        ---AAAGGAGGTCCTTATCTTGCCATCTATCTGTGGGCATTCATGTTTATCCTGTCTCTAGTGATGATGA
AT4g01320   ---AAAGGAGGTCCTTATCTTGCCATCTATCTGTGGGCATTCATGTTTATCCTGTCTCTAGTGATGATGA
AF007269    CAGAAAGGAGGTCCTTATCTTGCCATCTATCTGTGGGCATTCATGTTTATCCTGTCTCTAGTGATGATGA
Consensus   CAGAAAGGAGGTCCTTATCTTGCCATCTATCTGTGGGCATTCATGTTTATCCTGTCTCTAGTGATGATGA

                    1830      1840      1850      1860      1870      1880      1890
            ....|....|....|....|....|....|....|....|....|....|....|....|....|
PPI-AtCPP NA ----------------------------------------------------------------------
PPI-BnCPP   CTATATACCCTGTTTTGATTGCACCTCTTTTCAACAAGTTCACTCCT-----------------------
PPI-SoyCPP  ----------------------------------------------------------------------
afc1        CTATATACCCGGTCTTGATAGCACCGCTCTTCAACAAGTTCACTCCT-----------------------
AT4g01320   CTATATACCCGGTCTTGATAGCACCGCTCTTCAACAAGTTCACTCCT-----------------------
AF007269    CTATATACCCGGTCTTGATAGCACCGCTCTTCAACAAGTTCACTCCTGTGTGTATTTCTGTCATGGCCAT
Consensus   CTATATACCCGGTCTTGATAGCACCGCTCTTCAACAAGTTCACTCCTGTGTGTATTTCTGTCATGGCCAT

                    1900      1910      1920      1930      1940      1950      1960
            ....|....|....|....|....|....|....|....|....|....|....|....|....|
PPI-AtCPP NA ----------------------------------------------------------------------
PPI-BnCPP   ----------------------------------------------------------------------
PPI-SoyCPP  ----------------------------------------------------------------------
afc1        ----------------------------------------------------------------------
AT4g01320   ----------------------------------------------------------------------
AF007269    TTTACAATTCACTGCTTGTTTGCATATGTTGTTACCAGACAATATAATCTCCCGCTTTTTTATGGCTATA
Consensus   TTTACAATTCACTGCTTGTTTGCATATGTTGTTACCAGACAATATAATCTCCCGCTTTTTTATGGCTATA

                    1970      1980      1990      2000      2010      2020      2030
            ....|....|....|....|....|....|....|....|....|....|....|....|....|
PPI-AtCPP NA ----------------------------------------------------------------------
PPI-BnCPP   -CTTCCTGATGGAGACCTCCGGGAGAAGATTGAGAAACTTGCTTCTTCTCTAAAGTTTCCTCTGAAGAAG
PPI-SoyCPP  ----------------------------------------------------------------------
afc1        -CTTCCAGATGGAGACCTCCGGGAGAAGATTGAGAAACTTGCTTCTTCTCTAAAGTTTCCTTTGAAGAAG
AT4g01320   -CTTCCAGATGGAGACCTCCGGGAGAAGATTGAGAAACTTGCTTCTTCTCTAAAGTTTCCTTTGAAGAAG
AF007269    GCTTCCAGATGGAGACCTCCGGGAGAAGATTGAGAAACTTGCTTCTTCTCTAAAGTTTCCTTTGAAGAAG
Consensus   GCTTCCAGATGGAGACCTCCGGGAGAAGATTGAGAAACTTGCTTCTTCTCTAAAGTTTCCTTTGAAGAAG
```

TABLE 37-continued

ClustalW Analysis of PPI/Generic Nucleic Acids

```
                  2040      2050      2060      2070      2080      2090      2100
              ....|....|....|....|....|....|....|....|....|....|....|....|....|....|
PPI-AtCPP NA  ----------------------------------------------------------------------
PPI-BnCPP     CTGTTTGTTGTCGATGGATCTACAAGGTCAAGCCATAGTAATG---------------------------
PPI-SoyCPP    ----------------------------------------------------------------------
afc1          CTGTTTGTTGTCGATGGATCTACAAGGTCAAGCCATAGCAATG---------------------------
AT4g01320     CTGTTTGTTGTCGATGGATCTACAAGGTCAAGCCATAGCAATG---------------------------
AF007269      CTGTTTGTTGTCGATGGATCTACAAGGTCAAGCCATAGCAATGTGAGAAGCTTGAGATCTCTTCCTACCT
Consensus     CTGTTTGTTGTCGATGGATCTACAAGGTCAAGCCATAGCAATGTGAGAAGCTTGAGATCTCTTCCTACCT

                  2110      2120      2130      2140      2150      2160      2170
              ....|....|....|....|....|....|....|....|....|....|....|....|....|....|
PPI-AtCPP NA  ----------------------------------------------------------------------
PPI-BnCPP     -----------------------------------------------------CTTACATGTATGGTTTC
PPI-SoyCPP    ----------------------------------------------------------------------
afc1          -----------------------------------------------------CTTACATGTATGGTTTC
AT4g01320     -----------------------------------------------------CTTACATGTATGGTTTC
AF007269      ACTTTACTCTAGTTTACCATTAGAAGCTTACGTATCTTGTTACATCATACAGGCTTACATGTATGGTTTC
Consensus     ACTTTACTCTAGTTTACCATTAGAAGCTTACGTATCTTGTTACATCATACAGGCTTACATGTATGGTTTC

                  2180      2190      2200      2210      2220      2230      2240
              ....|....|....|....|....|....|....|....|....|....|....|....|....|....|
PPI-AtCPP NA  ----------------------------------------------------------------------
PPI-BnCPP     TTCAAGAACAAAAGGATTGTTCTTTATGACACAATTGATTCAGCAG-------------------------
PPI-SoyCPP    ----------------------------------------------------------------------
afc1          TTTAAGAACAAAAGGATTGTTCTTTATGATACGTTGATTCAGCAG-------------------------
AT4g01320     TTTAAGAACAAAAGGATTGTTCTTTATGATACGTTGATTCAGCAG-------------------------
AF007269      TTTAAGAACAAAAGGATTGTTCTTTATGATACGTTGATTCAGCAGGTACTGTGACTCTTGATGCTTCAAA
Consensus     TTTAAGAACAAAAGGATTGTTCTTTATGATACGTTGATTCAGCAGGTACTGTGACTCTTGATGCTTCAAA

                  2250      2260      2270      2280      2290      2300      2310
              ....|....|....|....|....|....|....|....|....|....|....|....|....|....|
PPI-AtCPP NA  ----------------------------------------------------------------------
PPI-BnCPP     -------------------------------------------------------------TGCCAGAAT
PPI-SoyCPP    ----------------------------------------------------------------------
afc1          -------------------------------------------------------------TGCAAGAAT
AT4g01320     -------------------------------------------------------------TGCAAGAAT
AF007269      CGAGCTATACTCACATTTCTGTTTCTGGTTCTGAAACATAACATAATCTTCTATTGTGCAGTGCAAGAAT
Consensus     CGAGCTATACTCACATTTCTGTTTCTGGTTCTGAAACATAACATAATCTTCTATTGTGCAGTGCAAGAAT

                  2320      2330      2340      2350      2360      2370      2380
              ....|....|....|....|....|....|....|....|....|....|....|....|....|....|
PPI-AtCPP NA  ----------------------------------------------------------------------
PPI-BnCPP     GAGAATGAAATTGTGGCGGTTATTGCACACGAGCTCGGACACTGGAAGCTGAATCACACTACATACTCGT
PPI-SoyCPP    ----------------------------------------------------------------------
afc1          GAGGATGAAATTGTGGCGGTTATTGCACACGAGCTTGGACATTGGAAACTGAATCACACTACATACTCGT
AT4g01320     GAGGATGAAATTGTGGCGGTTATTGCACACGAGCTTGGACATTGGAAACTGAATCACACTACATACTCGT
AF007269      GAGGATGAAATTGTGGCGGTTATTGCACACGAGCTTGGACATTGGAAACTGAATCACACTACATACTCGT
Consensus     GAGGATGAAATTGTGGCGGTTATTGCACACGAGCTTGGACATTGGAAACTGAATCACACTACATACTCGT

                  2390      2400      2410      2420      2430      2440      2450
              ....|....|....|....|....|....|....|....|....|....|....|....|....|....|
PPI-AtCPP NA  ----------------------------------------------------------------------
PPI-BnCPP     TCATTGCTGTTCAA--------------------------------------------------------
PPI-SoyCPP    ----------------------------------------------------------------------
afc1          TCATTGCAGTTCAA--------------------------------------------------------
AT4g01320     TCATTGCAGTTCAA--------------------------------------------------------
AF007269      TCATTGCAGTTCAAGTGAGGCTCAACCGACAGTTCAAAAACTTACTCACATCTACATTTCACTTAAGAAA
Consensus     TCATTGCAGTTCAAGTGAGGCTCAACCGACAGTTCAAAAACTTACTCACATCTACATTTCACTTAAGAAA

                  2460      2470      2480      2490      2500      2510      2520
              ....|....|....|....|....|....|....|....|....|....|....|....|....|....|
PPI-AtCPP NA  ----------------------------------------------------------------------
PPI-BnCPP     --------------------------------------ATCCTTGCCTTCTTGCAATTTGGAGGATACAC
PPI-SoyCPP    ----------------------------------------------------------------------
afc1          --------------------------------------ATCCTTGCCTTCTTACAATTTGGAGGATACAC
AT4g01320     --------------------------------------ATCCTTGCCTTCTTACAATTTGGAGGATACAC
AF007269      TCATGTCTTATGACCCTCTCTCAATGTTTTGCTTGCAGATCCTTGCCTTCTTACAATTTGGAGGATACAC
Consensus     TCATGTCTTATGACCCTCTCTCAATGTTTTGCTTGCAGATCCTTGCCTTCTTACAATTTGGAGGATACAC

                  2530      2540      2550      2560      2570      2580      2590
              ....|....|....|....|....|....|....|....|....|....|....|....|....|....|
PPI-AtCPP NA  ----------------------------------------------------------------------
PPI-BnCPP     TCTTGTCAGAAACTCCACTGATCTCTTCAGGAGTTTTGGTTTTGATACACAACCAGTTCTCATTGGTTTG
PPI-SoyCPP    ----------------------------------------------------------------------
afc1          TCTTGTCAGAAACTCCACTGATCTCTTCAGGAGTTTCGGATTTGATACACAGCCTGTTCTCATTGGTTTG
AT4g01320     TCTTGTCAGAAACTCCACTGATCTCTTCAGGAGTTTCGGATTTGATACACAGCCTGTTCTCATTGGTTTG
AF007269      TCTTGTCAGAAACTCCACTGATCTCTTCAGGAGTTTCGGATTTGATACACAGCCTGTTCTCATTGGTTTG
Consensus     TCTTGTCAGAAACTCCACTGATCTCTTCAGGAGTTTCGGATTTGATACACAGCCTGTTCTCATTGGTTTG
```

TABLE 37-continued

ClustalW Analysis of PPI/Generic Nucleic Acids

```
                           2600      2610      2620      2630      2640      2650      2660
                   ....|....|....|....|....|....|....|....|....|....|....|....|....|....|
PPI-AtCPP NA       ----------------------------------------------------------------------
PPI-BnCPP          ATCATATTTCAG----------------------------------------------------------
PPI-SoyCPP         ----------------------------------------------------------------------
afc1               ATCATATTTCAG----------------------------------------------------------
AT4g01320          ATCATATTTCAG----------------------------------------------------------
AF007269           ATCATATTTCAGGTTTGTTATTTTTGCCTTTTGACACTAATCTAATGAATCAAGGATGGATTAAGAAAAA
Consensus          ATCATATTTCAGGTTTGTTATTTTTGCCTTTTGACACTAATCTAATGAATCAAGGATGGATTAAGAAAAA

                           2670      2680      2690      2700      2710      2720      2730
                   ....|....|....|....|....|....|....|....|....|....|....|....|....|....|
PPI-AtCPP NA       ----------------------------------------------------------------------
PPI-BnCPP          --------------------------------------------CACACTGTAATACCACTTCAACACCT
PPI-SoyCPP         ----------------------------------------------------------------------
afc1               --------------------------------------------CACACTGTAATACCACTGCAACATCT
AT4g01320          --------------------------------------------CACACTGTAATACCACTGCAACATCT
AF007269           AAAACTCTAAACCTTTGGTTATATCTCCTGTCTGATTATCACAGCACACTGTAATACCACTGCAACATCT
Consensus          AAAACTCTAAACCTTTGGTTATATCTCCTGTCTGATTATCACAGCACACTGTAATACCACTGCAACATCT

                           2740      2750      2760      2770      2780      2790      2800
                   ....|....|....|....|....|....|....|....|....|....|....|....|....|....|
PPI-AtCPP NA       ----------------------------------------------------------------------
PPI-BnCPP          AGTAAGCTTTGACCTCAACCTTGTTAGTCGAGCGTTTGAGTTTCAGG-----------------------
PPI-SoyCPP         ----------------------------------------------------------------------
afc1               AGTAAGCTTTGGCCTGAACCTCGTTAGTCGAGCGTTTGAGTTTCAGG-----------------------
AT4g01320          AGTAAGCTTTGGCCTGAACCTCGTTAGTCGAGCGTTTGAGTTTCAGG-----------------------
AF007269           AGTAAGCTTTGGCCTGAACCTCGTTAGTCGAGCGTTTGAGTTTCAGGTACCATCTTACAATCCCTCAAGA
Consensus          AGTAAGCTTTGGCCTGAACCTCGTTAGTCGAGCGTTTGAGTTTCAGGTACCATCTTACAATCCCTCAAGA

                           2810      2820      2830      2840      2850      2860      2870
                   ....|....|....|....|....|....|....|....|....|....|....|....|....|....|
PPI-AtCPP NA       ----------------------------------------------------------------------
PPI-BnCPP          ---------------------------------------------------------------------C
PPI-SoyCPP         ----------------------------------------------------------------------
afc1               ---------------------------------------------------------------------C
AT4g01320          ---------------------------------------------------------------------C
AF007269           TCCAACCATAGTTTCTTTATTGCAATGGCAGCCTCATCTACTAATCTGAGTTAACGTTCCTTTTGCAGGC
Consensus          TCCAACCATAGTTTCTTTATTGCAATGGCAGCCTCATCTACTAATCTGAGTTAACGTTCCTTTTGCAGGC

                           2880      2890      2900      2910      2920      2930      2940
                   ....|....|....|....|....|....|....|....|....|....|....|....|....|....|
PPI-AtCPP NA       ----------------------------------------------------------------------
PPI-BnCPP          TGATGCTTTTGCAGTGAATCTTGGTTATGCAAAGGATCTACGTCCTGCCCTAGTGAAGCTACAGG-----
PPI-SoyCPP         ----------------------------------------------------------------------
afc1               TGATGCTTTTGCCGTGAAGCTTGGCTATGCAAAAGATCTTCGTCCTGCTCTAGTGAAACTACAGG-----
AT4g01320          TGATGCTTTTGCTGTGAAGCTTGGCTATGCAAAAGATCTTCGTCCTGCTCTAGTGAAACTACAGGTCAGA
AF007269           TGATGCTTTTGCTGTGAAGCTTGGCTATGCAAAAGATCTTCGTCCTGCTCTAGTGAAACTACAGGTCAGA
Consensus          TGATGCTTTTGCTGTGAAGCTTGGCTATGCAAAAGATCTTCGTCCTGCTCTAGTGAAACTACAGGTCAGA

                           2950      2960      2970      2980      2990      3000      3010
                   ....|....|....|....|....|....|....|....|....|....|....|....|....|....|
PPI-AtCPP NA       ----------------------------------------------------------------------
PPI-BnCPP          ----------------------------------------------------------------------
PPI-SoyCPP         ----------------------------------------------------------------------
afc1               ----------------------------------------------------------------------
AT4g01320          GAAGATAACAACAGAACACAAACTGTTACCTCAATTTGTGTCACACACTTAAATGGATTTTTTGTTGGGA
AF007269           GAAGATAACAACAGAACACAAACTGTTACCTCAATTTGTGTCACACACTTAAATGGATTTTTTGTTGGGA
Consensus          GAAGATAACAACAGAACACAAACTGTTACCTCAATTTGTGTCACACACTTAAATGGATTTTTTGTTGGGA

                           3020      3030      3040      3050      3060      3070      3080
                   ....|....|....|....|....|....|....|....|....|....|....|....|....|....|
PPI-AtCPP NA       ----------------------------------------------------------------------
PPI-BnCPP          ------A---AGAGAACTTATCAGCGATGAACACAGACCCATTGTACTCAGCTTATCACTACTCACACCC
PPI-SoyCPP         ----------------------------------------------------------------------
afc1               ------A---AGAGAACTTATCAGCAATGAACACTGATCCATTGCACTCAGCTTATCACTACTCACATCC
AT4g01320          TTTTGCAGGAAGAGAACTTATCAGCAATGAACACTGATCCATTGTACTCAGCTTATCACTACTCACATCC
AF007269           TTTTGCAGGAAGAGAACTTATCAGCAATGAACACTGATCCATTGTACTCAGCTTATCACTACTCACATCC
Consensus          TTTTGCAGGAAGAGAACTTATCAGCAATGAACACTGATCCATTGTACTCAGCTTATCACTACTCACATCC

                           3090      3100      3110      3120      3130
                   ....|....|....|....|....|....|....|....|....|....|....|.
PPI-AtCPP NA       --------------------------------------------------------
PPI-BnCPP          TCCTCTTGTAGAGAGGCTTCGAGCCATTGATGGAGAAGACAAGAAGACAGATTAA-
PPI-SoyCPP         --------------------------------------------------------
afc1               TCCTCTTGTTGAAAGGCTTCGAGCCATTGATGGAGAAGACAAGAAGACAGATTAAA
AT4g01320          TCCTCTTGTTGAAAGGCTTCGAGCCATTGATGGAGAAGACAAGAAGACAGATTAAR
AF007269           TCCTCTTGTTGAAAGGCTTCGAGCCATTGATGGAGAAGACAAGAAGACAGATTAA-
Consensus          TCCTCTTGTTGAAAGGCTTCGAGCCATTGATGGAGAAGACAAGAAGACAGATTAA-
```

TABLE XX

ClustalW Analysis of PPI/Generic Nucleic Acids

1) PPI-AtCPP (SEQ ID NO: 97)
2) PPI-BnCPP (SEQ ID NO: 109)
3) PPI-SoyCPP (SEQ ID NO: 112)
4) afc1 (SEQ ID NO: 124)
5) AT4g01320 (SEQ ID NO: 126)
6) AF007269 (SEQ ID NO: 128)
6) Consensus (SEQ ID NO: 170)

```
                      10        20        30        40        50        60        70
              ....|....|....|....|....|....|....|....|....|....|....|....|....|....|
PPI-AtCPP NA  ----------------------------------------------------------------------
PPI-BnCPP     ----------------------------------------------------------------------
PPI-SoyCPP    ----------------------------------------------------------------------
afc1          ----------------------------------------------------------------------
AT4g01320     ----------------------------------------------------------------------
AF007269      ATGGCGATTCCTTTCATGGAAACCGTCGTGGGTAAGCTTCAAAACCTTTTTCTGAGACATTTTACTATCC
```

TABLE 38

ClustalW Analysis of PPI/Generic Amino Acids

1) PPI-AtCPP (SEQ ID NO: 98)
2) PPI-BnCPP (SEQ ID NO: 110)
3) PPI-SoyCPP (SEQ ID NO: 113)
4) afc1 (SEQ ID NO: 125)
5) AT4g01320 (SEQ ID NO: 127)
6) AF007269 (SEQ ID NO: 129)
7) Consensus Gener (SEQ ID NO: 169)

```
                          10        20        30        40        50        60
                  ....|....|....|....|....|....|....|....|....|....|....|....|
PPI-AtCPP         MAFPYMEAVVGFMILMYIFETYLDVRQHRALKLPTLPKTLEGVISQEKFEKSRAYS--LD   58
PPI-BnCPP         MAIPFMETVVGFMIVMYVFETYLDLRQHTALKLPTLPKTLVGVISQEKFEKSRAYS--LD   58
PPI-SoyCPP        MAFPYMEAVVGFMILMYIFETYLDVRQHRALKLPTLPKTLEGVISQEKFEKSRAYS--LD   58
afc1              MAIPFMETVVGFMIVMYIFETYLDLRQLTALKLPTLPKTLVGVISQEKFEKSRAYS--LD   58
AT4g01320         MAIPFMETVVGFMIVMYIFETYLDLRQLTALKLPTLPKTLVGVISQEKFEKSRAYRDIIT   60
AF007269          MAIPFMETVVGFMIVMYIFETYLDLRQLTALKLPTLPKTLI-------------------   41
Consensus Gener   MAXPXMEXVVGFMIXMYXFETYLDXRQXXALKLPTLPKTLXXXXXXXXXXXXXXXXXXXX   60

                          70        80        90       100       110       120
                  ....|....|....|....|....|....|....|....|....|....|....|....|
PPI-AtCPP         KS-----HFHFVHEFVTIVTDSTILYFGVLPWFWKKSGDFMTIAGFNAENEILHTLAFLA  113
PPI-BnCPP         KS-----HFHFVHEFVTILMDSAILFFGILPWFWKISGGFLPMVGLDPENEILHTLSFLA  113
PPI-SoyCPP        KS-----HFHFVHEFVTIVTDSTILYFGVLPWFWKKSGDFMTIAGFNAENEILHTLAFLA  113
afc1              KS-----YFHFVHEFVTILMDSAILFFGILPWFWKMSGAVLPRLGLDPENEILHTLSFLA  113
AT4g01320         ENFNICSYFHFVHEFVTILMDSAILFFGILPWFWKMSGAVLPRLGLDPENEILHTLSFLA  120
AF007269          ------------------------------------------------------------   41
Consensus Gener   XXXXXXXXXXXXXXXXXXXXXXXXXXXXXXXXXXXXXXXXXXXXXXXXXXXXXXXXXXXX  120

                         130       140       150       160       170       180
                  ....|....|....|....|....|....|....|....|....|....|....|....|
PPI-AtCPP         GLMIWSQITDLPFSLYSTFVIEARHGFNKQTPWLFFRDMLKGIFLSVIIGPPIVAAIIVI  173
PPI-BnCPP         GLMTWSQITDLPFSLYSTFVIESRHGFNKQTIWMFIRDMIKGILLSVIPAPPIVAAIIVI  173
PPI-SoyCPP        GLMIWSQITDLPFSLYSTFVIEARHGFNKQTPWLFFRDMLKGIFLSVIIGPPIVAAIIVI  173
afc1              GVMIWSQITDLPFSLYSTFVIESRHGFNKQTIWMFIRDMIKGIFLSVILGPPIVAAIIFI  173
AT4g01320         GVMTWSQITDLPFSLYSTFVIESRHGFNKQTIWMFIRDMIKGTFLSVILGPPIVAAIIFI  180
AF007269          --------TDLPFSLYSTFVIESRHGFNKQTIWMFIRDMIKGTFLSVILGPPIVAAIIFI   93
Consensus Gener   XXXXXXXXTDLPFSLYSTFVIEXRHGFNKQTXWXFXRDMXKGXXLSVIXXPPIVAAIIXI  180

                         190       200       210       220       230       240
                  ....|....|....|....|....|....|....|....|....|....|....|....|
PPI-AtCPP         VQKGGPYLAIYLWVFIFGLSIVMMTLYPVLIAPLFNKFTPLPDGQLREKIEKLASSLNYP  233
PPI-BnCPP         VQKGGPYLAIYLWAFMFILSLVMMTIYPVLIAPLFNKFTPLPDGDLREKIEKLASSLKFP  233
PPI-SoyCPP        VQKGGPYLAIYLWVFIFGLSIVMMTLYPVLIAPLFNKFTPLPDGQLREKIEKLASSLNYP  233
afc1              VQKGGPYLAIYLWAFMFILSLVMMTIYPVLIAPLFNKFTPLPDGDLREKIEKLASSLKFP  233
AT4g01320         VQKGGPYLAIYLWAFMFILSLVMMTIYPVLIAPLFNKFTPLPDGDLREKIEKLASSLKFP  240
AF007269          VQKGGPYLAIYLWAFMFILSLVMMTIYPVLIAPLFNKFTPLPDGDLREKIEKLASSLKFP  153
Consensus Gener   VQKGGPYLAIYLWXFXFXLSXVMMTXYPVLIAPLFNKFTPLPDGXLREKIEKLASSLXXP  240
```

TABLE 38-continued

ClustalW Analysis of PPI/Generic Amino Acids

| | 250 260 270 280 290 300 | |
|---|---|---|
| PPI-AtCPP | LKKLFVVDGSTRSSHSNAYMYGFFKNKRIVPYDTLIQQCKDDEEIVAVIAHELGHWKLNH | 293 |
| PPI-BnCPP | LKKLFVVDGSTRSSHSNAYMYGFFKNKRIVLYDTLIQQCQNENEIVAVIAHELGHWKLNH | 293 |
| PPI-SoyCPP | LKKLFVVDGSTRSSHSNAYMYGFFKNKRIVPYDTLIQQCKDDEEIVAVIAHELGHWKLNH | 293 |
| afc1 | LKKLFVVDGSTRSSHSNAYMYGFFKNKRIVLYDTLIQQCKNEDEIVAVIAHELGHWKLNH | 293 |
| AT4g01320 | LKKLFVVDGSTRSSHSNAYMYGFFKNKRIVLYDTLIQQCKNEDEIVAVIAHELGHWKLNH | 300 |
| AF007269 | LKKLFVVDGSTRSSHSNAYMYGFFKNKRIVLYDTLIQQCKNEDEIVAVIAHELGHWKLNH | 213 |
| Consensus Gener | LKKLFVVDGSTRSSHSNAYMYGFFKNKRIVXYDTLIQQCXXXXEIVAVIAHELGHWKLNH | 300 |

| | 310 320 330 340 350 360 | |
|---|---|---|
| PPI-AtCPP | TVYTFVAMQILTLLQFGGYTLVRNSADLYRSFGFDTQPVLIGLIIFQHTVIPLQQLVSFG | 353 |
| PPI-BnCPP | TTYSFIAVQILAFLQFGGYTLVRNSTDLFRSFGFDTQPVLIGLIIFQHTVIPLQHLVSFD | 353 |
| PPI-SoyCPP | TVYTFVAMQILTLLQFGGYTLVRNSADLYRSFGFDTQPVLIGLIIFQHTVIPLQQLVSFG | 353 |
| afc1 | TTYSFIAVQILAFLQFGGYTLVRNSTDLFRSFGFDTQPVLIGLIIFQHTVIPLQHLVSFG | 353 |
| AT4g01320 | TTYSFIAVQILAFLQFGGYTLVRNSTDLFRSFGFDTQPVLIGLIIFQHTVIPLQHLVSFG | 360 |
| AF007269 | TTYSFIAV-------------------------------------QHTVIPLQHLVSFG | 235 |
| Consensus Gener | TXYXFXAXXXXXXXXXXXXXXXXXXXXXXXXXXXXXXXXXXXXXQHTVIPLQXLVSFX | 360 |

| | 370 380 390 400 410 420 | |
|---|---|---|
| PPI-AtCPP | LNLVSRSFEFQADGFAKKLGYASGLRGGLVKLQ--------------------------- | 386 |
| PPI-BnCPP | LNLVSRAFEFQADAFAVNLGYAKDLRPALVKLQ--------------------------- | 386 |
| PPI-SoyCPP | LNLVSRSFEFQADGFAKKLGYASGLRGGLVKLQ--------------------------- | 386 |
| afc1 | LNLVSRAFEFQADAFAVKLGYAKDLRPALVKLQ--------------------------- | 386 |
| AT4g01320 | LNLVSRAFEFQADAFAVKLGYAKDLRPALVKLQVREDNNRTQTVTSICVTHLNGFFVGIL | 420 |
| AF007269 | LNLVSRAFEFQADAFAVKLGYAKDLRPALVKLQVREDNNRTQT----------------- | 278 |
| Consensus Gener | LNLVSRXFEFQADXFAXXLGYAXXLRXXLVKLQXXXXXXXXXXXXXXXXXXXXXXXXXXX | 420 |

| | 430 440 450 | |
|---|---|---|
| PPI-AtCPP | -EENLSAMNTDPWYSAYHYSHPPLVERLAALDEPDKKED | 424 |
| PPI-BnCPP | -EENLSAMNTDPLYSAYHYSHPPLVERLRAIDGEDKKTD | 424 |
| PPI-SoyCPP | -EENLSAMNTDPWYSAYHYSHPPLVERLAALDEPDKKED | 424 |
| afc1 | -EENLSAMNTDPLHSAYHYSHPPLVERLRAIDGEDKKTD | 424 |
| AT4g01320 | QEENLSAMNTDPLYSAYHYSHPPLVERLRAIDGEDKKTD | 459 |
| AF007269 | -EENLSAMNTDPLYSAYHYSHPPLVERLRAIDGEDKKTD | 316 |
| Consensus Gener | XEENLSAMNTDPXXSAYHYSHPPLVERLXAXDXXDKKXD | 459 |

Example 47

Cloning, Vector Construction and Over-Expression of AtFT-B Sequences in *Arabidopsis* Produces a Dominant-Negative Phenotype Farnesyltransferase is a heterodimer formed by its α- and β-subunits and its activity relies on the proper dimerization between these subunits. Increased ABA sensitivity can be achieved by the over-expression of a non-full-length form of AtFTB (SEQ ID NO:1) in *Arabidopsis*. In the corollary experiment, over-expression of the full-length AtFTB failed to alter the ABA sensitivity. These results suggest that the phenotype of enhanced ABA response is likely the result of dominant-negative effect of the truncated form AtFTB. The truncated AtFTB maybe nonfunctional or possess limited functionality in vivo as compared to a full length endogenous subunit. However. The reduction of Ft activity results in enhanced ABA sensitivity.

Cloning

The farnesyltransferase sequence described by SEQ ID NO:1 was cloned into an appropriate vector under the transcriptional control of the 35S CaMV promoter (pBI121 derived vector) in the sense orientation for expression in plant cells. This vector was designated ΔN90AtFTB and designated SEQ ID NO:79. The protein encoded by SEQ ID NO:1 has been determined to lack the 5' 270 nucleotides, and therefore does not code for the 5' terminal 90 amino acids. The full length farnesyltransferase sequence was obtained using the primer pair identified by SEQ ID NO:86 and SEQ ID NO:171 and methodology as described elsewhere in this document. The resulting sequence, identified as SEQ ID NO:172 was cloned into an appropriate vector under the transcriptional control of the 35S CaMV promoter (pBI121 derived vector) in the sense orientation for expression in plant cells. This vector was designated pBI121-AtFTB, SEQ ID NO:173. The protein encoded by SEQ ID NO:172 has been determined to represent the full length polypeptide.

*Agrobacterium*-Mediated Transformation, Transgenic Line Selection and ABA Test.

*Agrobacterium* strain GV3101 carrying the binary constructs described above were transformed into *Arabidopsis thaliana* via *agrobacterium*-mediated floral dipping transformation. Transformed *Arabidopsis* lines (T1) were selected on Murashige/Skoog (Sigma) plates containing kanamycin (50 μg/μl). Kanamycin-resistant seedlings were then transferred to soil. The subsequent T2 seeds were harvested from individual transgenic lines for ABA tests.

Northern Blot Analysis.

Total RNA was isolated from two-week-old T2 *Arabidopsis* plants of the pBI121-ΔN90AtFTB, as well as from wild-type Columbia and era1 mutant plants. After separated in the agarose gel, RNA was transferred onto the nitrocellulose membrane and was hybridized with the $^{32}P$-labelled ΔN90AtFTB DNA probe.

Over-Expression of pBI121-ΔN90AtFTB, not pBI121-AtFTB Resulted in Enhanced ABA Sensitivity:

Transgenic plants were selected and advanced to the second generation. T2 seeds of these two constructs were subjected to ABA test using 0.0, 0.25, 0.5 and 1.0 μM ABA in minimum MS-agarose plates. Of the fifteen pBI121-ΔN90AtFTB lines ten showed an enhanced ABA sensitivity phenotype. At 0.5 μM ABA, the seeds would germinate, however, the development of the seedlings for these 10 lines were retarded or arrested, showing a typical ABA hypersensitive response. In contrast, of the fifteen pBI121-AtFTB transgenic lines, all but one line showed normal wild-type like ABA response to seed germination and seedling development.

Northern blot analysis indicated that in the transgenic lines of pBI121-ΔN90AtFTB, the expression levels were higher than the endogenous AtFTB transcript level as depicted by the wild-type control. This indicates the ABA hypersensitive phenotype of these transgenic lines is unlikely due to transcriptional co-suppression. The enhanced ABA response correlates with the results of other methods of AtFTB down-regulation, such as anti-sense and RNAi, hairpin constructs. It is possible that the observed ABA hypersensitive response in ΔN90AtFTB transgenic lines are due to a dominant negative effect. The high transcript levels of ΔN90AtFTB should produce an abundance of the truncated form of AtFTB which may bind to the endogenous AtFTA and result in competitive inhibition of AtFTase activity.

Further support for the interaction of truncated FT-B with endogenous FT-A comes from a yeast two-hybrid interaction experiment. Use of the ΔN90AtFTB cDNA as bait, identified interacting clones the majority of which were found to encode FT-A.

```
SEQ ID NO: 79 pBI121-ΔN90AtFTB Truncated FT-B Vector
gtttacccgccaatatatcctgtcaaacactgatagtttaaactgaaggcgggaaacgacaatctgatcatgagcgg

agaattaagggagtcacgttatgacccccgccgatgacgcgggacaagccgttttacgtttggaactgacagaaccg

caacgttgaaggagccactcagccgcgggtttctggagtttaatgagctaagcacatacgtcagaaaccattattgc

gcgttcaaaagtcgcctaaggtcactatcagctagcaaatatttcttgtcaaaaatgctccactgacgttccataaa

ttcccctcggtatccaattagagtctcatattcactctcaatccaaataatctgcaccggatctggatcgtttcgca

tgattgaacaagatggattgcacgcaggttctccggccgcttgggtggagaggctattcggctatgactgggcacaa

cagacaatcggctgctctgatgccgccgtgttccggctgtcagcgcaggggcgcccggttctttttgtcaagaccga

cctgtccggtgccctgaatgaactgcaggacgaggcagcgcggctatcgtggctggccacgacgggcgttccttgcg

cagctgtgctcgacgttgtcactgaagcgggaagggactggctgctattgggcgaagtgccggggcaggatctcctg

tcatctcaccttgctcctgccgagaaagtatccatcatggctgatgcaatgcggcggctgcatacgcttgatccggc

tacctgcccattcgaccaccaagcgaaacatcgcatcgagcgagcacgtactcggatggaagccggtcttgtcgatc

aggatgatctggacgaagagcatcaggggctcgcgccagccgaactgttcgccaggctcaaggcgcgcatgcccgac

ggcgatgatctcgtcgtgacccatggcgatgcctgcttgccgaatatcatggtggaaaatggccgcttttctggatt

catcgactgtggccggctgggtgtggcggaccgctatcaggacatagcgttggctacccgtgatattgctgaagagc

ttggcggcgaatgggctgaccgcttcctcgtgctttacggtatcgccgctcccgattcgcagcgcatcgccttctat

cgccttcttgacgagttcttctgagcgggactctggggttcgaaatgaccgaccaagcgacgcccaacctgccatca

cgagatttcgattccaccgccgccttctatgaaaggttgggcttcggaatcgttttccgggacgccggctggatgat

cctccagcgcggggatctcatgctggagttcttcgcccacgggatctctgcggaacaggcggtcgaaggtgccgata

tcattacgacagcaacggccgacaagcacaacgccacgatcctgagcgacaatatgatcgggcccggcgtccacatc

aacggcgtcggcggcgactgcccaggcaagaccgagatgcaccgcgatatcttgctgcgttcggatattttcgtgga

gttcccgccacagacccggatgatccccgatcgttcaaacatttggcaataaagtttcttaagattgaatcctgttg

ccggtcttgcgatgattatcatataatttctgttgaattacgttaagcatgtaataattaacatgtaatgcatgacg

ttatttatgagatgggtttttatgattagagtcccgcaattatacatttaatacgcgatagaaaacaaaatatagcg

cgcaaactaggataaattatcgcgcgcggtgtcatctatgttactagatcgggcctcctgtcaatgctggcggcggc

tctggtggtggttctggtggcggctctgagggtggtggctctgagggtggcggttctgagggtggcggctctgaggg

aggcggttccggtggtggctctggttccggtgattttgattatgaaaagatggcaaacgctaataagggggctatga

ccgaaaatgccgatgaaaacgcgctacagtctgacgctaaaggcaaacttgattctgtcgctactgattacggtgct

gctatcgatggtttcattggtgacgtttccggccttgctaatggtaatggtgctactggtgattttgctggctctaa

ttcccaaatggctcaagtcggtgacggtgataattcacctttaatgaataatttccgtcaatatttaccttccctcc

ctcaatcggttgaatgtcgccctttttgtctttggcccaatacgcaaaccgcctctccccgcgcgttggccgattcat

taatgcagctggcacgacaggtttcccgactggaaagcgggcagtgagcgcaacgcaattaatgtgagttagctcac

tcattaggcaccccaggctttacactttatgcttccggctcgtatgttgtgtggaattgtgagcggataacaatttc
```

-continued acacaggaaacagctatgaccatgattacgccaagcttgcatgcctgcagcccacagatggttagagaggcttacgc agcaggtctcatcaagacgatctacccgagcaataatctccaggaaatcaaataccttcccaagaaggttaaagatg cagtcaaaagattcaggactaactgcatcaagaacacagagaaagatatatttctcaagatcagaagtactattcca gtatggacgattcaaggcttgcttcacaaaccaaggcaagtaatagagattggagtctctaaaaaggtagttcccac tgaatcaaaggccatggagtcaaagattcaaatagaggacctaacagaactcgccgtaaagactggcgaacagttca tacagagtctcttacgactcaatgacaagaagaaaatcttcgtcaacatggtggagcacgacacacttgtctactcc aaaaatatcaaagatacagtctcagaagaccaaagggcaattgagacttttcaacaaagggtaatatccggaaacct cctcggattccattgcccagctatctgtcactttattgtgaagatagtggaaaaggaaggtggctcctacaaatgcc atcattgcgataaaggaaaggccatcgttgaagatgcctctgccgacagtggtcccaaagatggacccccacccacg aggagcatcgtggaaaaagaagacgttccaaccacgtcttcaaagcaagtggattgatgtgatatctccactgacgt aagggatgacgcacaatcccactatccttcgcaagacccttcctctatataaggaagttcatttcatttggagagaaca cggggggactctagaGGATCCgtccggaattcccgggtcgacccacgcgtccgggagattcagcgagataagcaattggattatctg atgaaaggcttaaggcagcttggtccgcagttttcttccttagatgctaatcgaccttggctttgttactggattcttcattcaatagctttgc ttggggagactgtggatgatgaattagaaagcaatgccattgacttccttggacgctgccagggctctgaaggtggatacggtggtggtcctggc caacttccacatcttgcaactacttatgctgcagtgaatgcacttgttactttaggaggtgacaaagccctttcttcaattaatagagaaaaaat gtcttgtttttaagacggatgaaggatacaagtggaggtttcaggatgcatgatatgggagaaatggatgttcgtgcatgctacactgcaattt cggttgcaagcatcctaaatattatggatgatgaactcacccagggcctaggagattacatcttgagttgccaaacttatgaaggtggcattgga ggggaacctggctccgaagctcacggtgggtatacctactgtggtttggctgctatgattttaatcaatgaggtcgaccgtttgaatttggattc attaatgaattgggctgtacatcgacaaggagtagaaatgggatttcaaggtaggacgaacaaattggtcgatggttgctacacattttggca ggcagccccttgtgttctactacaaagattatattcaaccaatgatcatgacgttcatggatcatcacatatatcagaagggacaaatgaagaa catcatgctcatgatgaagatgaccttgaagacagtgatgatgatgatgattctgatgaggacaacgatgaagattcagtgaatggtcacaga atccatcatacatccacctacattaacaggagaatgcaactggtttttgatagcctcggcttgcagagatatgtactcttgtgctctaagatcc ctgacggtggattcagagacaagccgaggaaaccccgtgacttctaccacacatgttactgcctgagcggcttgtctgtggctcagcacgctt ggttaaaagacgaggacactcctcctttgactcgcgacattatgggtggctactcgaatctccttgaacctgttcaacttcttcacaacattgtc atggatcagtataatgaagctatcgagttcttctttaaagcagcatgaGGATCCctcgaatttccccgatcgttcaaacatttg gcaataaagtttcttaagattgaatcctgttgccggtcttgcgatgattatcatataatttctgttgaattacgtta agcatgtaataattaacatgtaatgcatgacgttatttatgagatgggtttttatgattagagtcccgcaattatac atttaatacgcgatagaaaacaaaatatagcgcgcaaactaggataaattatcgcgcgcggtgtcatctatgttact agatcgggaattcactggccgtcgttttacaacgtcgtgactgggaaaaccctggcgttacccaacttaatcgcctt gcagcacatccccctttcgccagctggcgtaatagcgaagaggcccgcaccgatcgcccttcccaacagttgcgcag cctgaatggcgcccgctcctttcgctttcttcccttcctttctcgccacgttcgccggctttccccgtcaagctcta aatcgggggctccctttagggttccgatttagtgctttacggcacctcgaccccaaaaaacttgatttgggtgatgg ttcacgtagtgggccatcgccctgatagacggtttttcgccctttgacgttggagtccacgttctttaatagtggac tcttgttccaaactggaacaacactcaaccctatctcgggctattcttttgatttataagggattttgccgatttcg gaaccaccatcaaacaggattttcgcctgctggggcaaaccagcgtggaccgcttgctgcaactctctcagggccag gcggtgaagggcaatcagctgttgcccgtctcactggtgaaaagaaaaaccaccccagtacattaaaaacgtccgca atgtgttattaagttgtctaagcgtcaattt*gtttacaccacaatatatcctgcca*

SEQ ID NO: 86 FORWARD Primer SacI site 5' aaaCCCGGGatgccagtagtaacccgc 3'
SEQ ID NO: 171 REV Primer BamHI site 5' aaaggatcctcatgctgctttaaagaagaactcgat 3'
SEQ ID NO: 172 Full length FT-B
cccgggatgccagtagtaacccgcttgattcgtttgaagtgtgtagggctcagacttgaccggagtggactcaatcg gcgaatctgtcacggaggacacggggaatcaacgcggcggagagtgatggaagagctttcaagcctaaccgtgagtc -continued agcgcgagcaatttctggtggagaacgatgtgttcgggatctataattacttcgacgccagcgacgtttctactcaa aaatacatgatggagattcagcgagataagcaattggattatctgatgaaaggcttaaggcagcttggtccgcagtt ttcttccttagatgctaatcgaccttggctttgttactggattcttcattcaatagctttgcttggggagactgtgg atgatgaattagaaagcaatgccattgacttccttggacgctgccagggctctgaaggtggatacggtggtggtcct ggccaacttccacatcttgcaactacttatgctgcagtgaatgcacttgttactttaggaggtgacaaagccctttc ttcaattaatagagaaaaaatgtcttgtttttaagacggatgaaggatacaagtggaggtttcaggatgcatgata tgggagaaatggatgttcgtgcatgctacactgcaatttcggttgcaagcatcctaaatattatggatgatgaactc acccagggcctaggagattacatcttgagttgccaaacttatgaaggtggcattggaggggaacctggctccgaagc tcacggtgggtatacctactgtggtttggctgctatgattttaatcaatgaggtcgaccgtttgaatttggattcat taatgaattgggctgtacatcgacaaggagtagaaatgggatttcaaggtaggacgaacaaattggtcgatggttgc tacacattttggcaggcagccccttgtgttctactacaaagattatattcaaccaatgatcatgacgttcatggatc atcacatatatcagaagggacaaatgaagaacatcatgctcatgatgaagatgaccttgaagacagtgatgatgatg atgattctgatgaggacaacgatgaagattcagtgaatggtcacagaatccatcatacatccacctacattaacagg agaatgcaactggtttttgatagcctcggcttgcagagatatgtactcttgtgctctaagatccctgacggtggatt cagagacaagccgaggaaaccccgtgacttctaccacacatgttactgcctgagcggcttgtctgtggctcagcacg cttggttaaaagacgaggacactcctcctttgactcgcgacattatgggtggctactcgaatctccttgaacctgtt caacttcttcacaacattgtcatggatcagtataatgaagctatcgagttcttctttaaagcagcatgaggatcc SEQ ID NO: 177 Full Length FT-B amino acid sequence encoded by SEQ ID NO: 172
MPVVTRLIRLKCVGLRLDRSGLNRRICHGGHGESTRRRVMEELSSLTVSQREQFLVENDVFGIYNYFDASDVSTQKY

MMEIQRDKQLDYLMKGLRQLGPQFSSLDANRPWLCYWILHSIALLGETVDDELESNAIDFLGRCQGSEGGYGGGPGQ

LPHLATTYAAVNALVTLGGDKALSSINREKMSCFLRRMKDTSGGFRMHDMGEMDVRACYTAISVASILNIMDDELTQ

GLGDYILSCQTYEGGIGGEPGSEAHGGYTYCGLAAMILINEVDRLNLDSLMNWAVHRQGVEMGFQGRTNKLVDGCYT

FWQAAPCVLLQRLYSTNDHDVHGSSHISEGTNEEHHAHDEDDLEDSDDDDSDEDNDEDSVNGHRIHHTSTYINRRM

QLVFDSLGLQRYVLLCSKIPDGGFRDKPRKPRDFYHTCYCLSGLSVAQHAWLKDEDTPPLTRDIMGGYSNLLEPVQL

LHNIVMDQYNEAIEFFFKAA

SEQ ID NO: 173 pBI121-AtFTB (Full length vector Over-expression)
*gtttacccgccaatatatcctgtc*aaacactgatagtttaaactgaaggcgggaaacgacaatctgatcatgagcgg agaattaagggagtcacgttatgacccccgccgatgacgcgggacaagccgttttacgtttggaactgacagaaccg caacgttgaaggagccactcagccgcgggtttctggagtttaatgagctaagcacatacgtcagaaaccattattgc gcgttcaaaagtcgcctaaggtcactatcagctagcaaatatttcttgtcaaaaatgctccactgacgttccataaa ttcccctcggtatccaattagagtctcatattcactctcaatccaaataatctgcaccggatctggatcgtttcgca tgattgaacaagatggattgcacgcaggttctccggccgcttgggtggagaggctattcggctatgactgggcacaa cagacaatcggctgctctgatgccgccgtgttccggctgtcagcgcaggggcgcccggttctttttgtcaagaccga cctgtccggtgccctgaatgaactgcaggacgaggcagcgcggctatcgtggctggccacgacgggcgttccttgcg cagctgtgctcgacgttgtcactgaagcgggaagggactggctgctattgggcgaagtgccggggcaggatctcctg tcatctcaccttgctcctgccgagaaagtatccatcatggctgatgcaatgcggcggctgcatacgcttgatccggc tacctgcccattcgaccaccaagcgaaacatcgcatcgagcgagcacgtactcggatggaagccggtcttgtcgatc aggatgatctggacgaagagcatcaggggctcgcgccagccgaactgttcgccaggctcaaggcgcgcatgcccgac ggcgatgatctcgtcgtgacccatggcgatgcctgcttgccgaatatcatggtggaaaatggccgcttttctggatt catcgactgtggccggctgggtgtggcggaccgctatcaggacatagcgttggctacccgtgatattgctgaagagc ttggcggcgaatgggctgaccgcttcctcgtgctttacggtatcgccgctcccgattcgcagcgcatcgccttctat cgccttcttgacgagttcttctgagcgggactctggggttcgaaatgaccgaccaagcgacgcccaacctgccatca -continued cgagatttcgattccaccgccgccttctatgaaaggttgggcttcggaatcgttttccgggacgccggctggatgat cctccagcgcggggatctcatgctggagttcttcgcccacgggatctctgcggaacaggcggtcgaaggtgccgata tcattacgacagcaacggccgacaagcacaacgccacgatcctgagcgacaatatgatcgggcccggcgtccacatc aacggcgtcggcggcgactgcccaggcaagaccgagatgcaccgcgatatcttgctgcgttcggatattttcgtgga gttcccgccacagacccggatgatccccgatcgttcaaacatttggcaataaagtttcttaagattgaatcctgttg ccggtcttgcgatgattatcatataatttctgttgaattacgttaagcatgtaataattaacatgtaatgcatgacg ttatttatgagatgggtttttatgattagagtcccgcaattatacatttaatacgcgatagaaaacaaaatatagcg cgcaaactaggataaattatcgcgcgcggtgtcatctatgttactagatcgggcctcctgtcaatgctggcggcggc tctggtggtggttctggtggcggctctgagggtggtggctctgagggtggcggttctgagggtggcggctctgaggg aggcggttccggtggtggctctggttccggtgattttgattatgaaaagatggcaaacgctaataagggggctatga ccgaaaatgccgatgaaaacgcgctacagtctgacgctaaaggcaaacttgattctgtcgctactgattacggtgct gctatcgatggtttcattggtgacgtttccggccttgctaatggtaatggtgctactggtgattttgctggctctaa ttcccaaatggctcaagtcggtgacggtgataattcacctttaatgaataatttccgtcaatatttaccttccctcc ctcaatcggttgaatgtcgcccttttgtctttggcccaatacgcaaaccgcctctccccgcgcgttggccgattcat taatgcagctggcacgacaggtttcccgactggaaagcgggcagtgagcgcaacgcaattaatgtgagttagctcac tcattaggcaccccaggctttacactttatgcttccggctcgtatgttgtgtggaattgtgagcggataacaatttc acacaggaaacagctatgaccatgattacgccaagcttgcatgcctgcagcccacagatggttagagaggcttacgc agcaggtctcatcaagacgatctacccgagcaataatctccaggaaatcaaataccttcccaagaaggttaaagatg cagtcaaaagattcaggactaactgcatcaagaacacagagaaagatatatttctcaagatcagaagtactattcca gtatggacgattcaaggcttgcttcacaaaccaaggcaagtaatagagattggagtctctaaaaaggtagttcccac tgaatcaaaggccatggagtcaaagattcaaatagaggacctaacagaactcgccgtaaagactggcgaacagttca tacagagtctcttacgactcaatgacaagaagaaaatcttcgtcaacatggtggagcacgacacacttgtctactcc aaaaatatcaaagatacagtctcagaagaccaaagggcaattgagacttttcaacaaagggtaatatccggaaacct cctcggattccattgcccagctatctgtcactttattgtgaagatagtggaaaaggaaggtggctcctacaaatgcc atcattgcgataaaggaaaggccatcgttgaagatgcctctgccgacagtggtcccaaagatggacccccacccacg aggagcatcgtggaaaaagaagacgttccaaccacgtcttcaaagcaagtggattgatgtgatatctccactgacgt aagggatgacgcacaatcccactatccttcgcaagacccttcctctatataaggaagttcatttcatttggagagaacacgg gggactctagaggatccCCCGGGatgccagtagtaacccgcttgattcgtttgaagtgtgtagggctca gacttgaccggagtggactcaatcggcgaatctgtcacggaggacacggggaatcaacgcggcggagagtgatggaagagcttt caagcctaaccgtgagtcagcgcgagcaatttctggtggagaacgatgtgttcgggatctataattacttcgacgccagcgacgttt ctactcaaaaatacatgatggagattcagcgagataagcaattggattatctgatgaaaggcttaaggcagcttggtccgcagttttc ttccttagatgctaatcgaccttggctttgttactggattcttcattcaatagctttgcttggggagactgtggatgatgaattagaaagcaa tgccattgacttccttggacgctgccagggctctgaaggtggatacggtggtggtcctggccaacttccacatcttgcaactacttatgc tgcagtgaatgcacttgttactttaggaggtgacaaagccctttcttcaattaatagagaaaaaatgtcttgtttttaagacggatgaagg atacaagtggaggtttcaggatgcatgatatgggagaaatggatgttcgtgcatgctacactgcaatttcggttgcaagcatcctaaata ttatggatgatgaactcacccagggcctaggagattacatcttgagttgccaaacttatgaaggtggcattggaggggaacctggctcc gaggctcacggtgggtatacctactgtggtttggctgctatgattttaatcaatgaggtcgaccgtttgaatttggattcattaatgaattggg ctgtacatcgacaaggagtagaaatgggatttcaaggtaggacgaacaaattggtcgatggttgctacacattttggcaggcagcccc ttgtgttctactacaaagattatattcaaccaatgatcatgacgttcatggatcatcacatatatcagaagggacaaatgaagaacatcat gctcatgatgaagatgaccttgaagacagtgatgatgatgatgattctgatgaggacaacgatgaagattcagtgaatggtcacagaa -continued

```
tccatcatacatccacctacattaacaggagaatgcaactggtttttgatagcctcggcttgcagagatatgtactcttgtgctctaagat

ccctgacggtggattcagagacaagccgaggaaaccccgtgacttctaccacacatgttactgcctgagcggcttgtctgtggctca

gcacgcttggttaaaagacgaggacactcctcctttgactcgcgacattatgggtggctactcgaatctccttgaacctgttcaacttct

tcacaacattgtcatggatcagtataatgaagctatcgagttcttctttaaagcagcatgaGGATCCctcgaatttccccgatcgttc

aaacatttggcaataaagtttcttaagattgaatcctgttgccggtcttgcgatgattatcatataatttctgttgaattacgttaagcatgtaa

taattaacatgtaatgcatgacgttatttatgagatgggtttttatgattagagtcccgcaattatacatttaatacgcgatagaaaacaaaat

atagcgcgcaaactaggataaattatcgcgcgcggtgtcatctatgttactagatcgggaattcactggccgtcgttttacaacg

tcgtgactgggaaaaccctggcgttacccaacttaatcgccttgcagcacatccccctttcgccagctggcgtaata

gcgaagaggcccgcaccgatcgcccttcccaacagttgcgcagcctgaatggcgcccgctcctttcgctttcttccc

ttcctttctcgccacgttcgccggctttccccgtcaagctctaaatcgggggctccctttagggttccgatttagtg

ctttacggcacctcgaccccaaaaaacttgatttgggtgatggttcacgtagtgggccatcgccctgatagacggtt

tttcgccctttgacgttggagtccacgttctttaatagtggactcttgttccaaactggaacaacactcaaccctat

ctcgggctattcttttgatttataagggattttgccgatttcggaaccaccatcaaacaggattttcgcctgctggg

gcaaaccagcgtggaccgcttgctgcaactctctcagggccaggcggtgaagggcaatcagctgttgcccgtctcac

tggtgaaaagaaaaaccaccccagtacattaaaaacgtccgcaatgtgttattaagttgtctaagcgtcaatttgtt

tacaccacaatatatcctgcca
```

Example 48

Cloning and Transformation of Isoprenylcysteine Carboxyl Methyltransferase

The *Arabidopsis* isoprenylcysteine carboxyl methyltransferase (ICMT) sequence was obtained by RT-PCR amplification using the protocol described above. The sequence was produced using the primer pair identified by SEQ ID NO:174 (5'-aaaggatccatgacagagatcttcagtgacacca-3') and SEQ ID NO:175 (5'-aaagagctctcagttcacaaatggaacaccaga-3'). The sequence is identical to that reported by Accession number AB007648, GI: 10177821 (December 2000).

The isolated sequence was used to generate plant transformation vectors designed either to express the encoded protein or down-regulate expression. The vectors were used to transform *Arabidopsis* by the flower dipping method described elsewhere. Transformed plants were selected and propagated. Molecular and physiological analysis of the transgenic lines can be performed as detailed in other examples. Such analysis can include; molecular studies such as PCR, Southern, Northern and Western analysis; physiological analysis such as; growth studies, tolerance to environmental stress (drought, salt, heat, cold) tolerance to biotic stress, nutritional stress, as well as biochemical analysis.

```
                                         SEQ ID NO: 176
atgacagagatcttcagtgacaccagcatcagacagttatctcaaatg

ctactatcactaatcttcttccacatatccgaatacattctagccatc

accattcacggagcatcaaacgtaactcttagttcgcttttaatcaccaa

gcattacgctttagcaatgcttctgtcgcttctcgaatacctaacggag

attatcctcttcccggggctgaaacaacactggtgggtcagcaacttt

ggactcataatgatcatcgttggggaaatcatcaggaaggcagcgata

ataacagcgggaagatcgttcactcacctcataaagatcaactacgaa
```

-continued

```
gagcatcacgggcttgtgactcatggtgtgtatagactaatgaggcat

ccaagttactgcggttttctcatctggtcggtcgggacacaagttatgct

ctgtaaccccgtttcagcagttgcgttcgcggttgtcgtgtggcggttt

tttgctcagagaataccgtacgaggagtattttctgaatcagtttttg

gggtacagtatctagagtatgcagagagtgttgcctctggtgttcc

atttgtgaactga
```

REFERENCES

Baskin, J M and Baskin, C C (1971) Can J Bot 50:277.

Chandler, P M and Robertson, M (1994) Gene expression regulated by abscisic acid and its relationship to stress tolerance. Ann Rev Plant Physiol and Plant Mol Biol 45:113-141.

Chen, W-J, Anders, D A, Goldstein, J L, Russell, D W, Brown, M S (1991) Cell 66:327

Cutler, S, Ghassemian, M, Bonetta, D, Cooney, S, McCourt, P (1996) A protein farnesyl transferase involved in abscisic acid signal transduction in *Arabidopsis*. Science 273:1239-1241.

Dellaporta, S. L., Wood, J. and Hicks, J. B. (1983). A plant DNA minipreparation: version II. Plant Mol. Biol. Rep. 1: 19-21.

Eisenmann, D. M. and Kim, S. K. (1994). Signal transduction and cell fate specification during *Caenorhabditis elegans* vulval development. Curr. Opin. Genet. Dev. 4:508-516.

Ellington, A. (1987). Preparation and Analysis of DNA. In Current Protocols in Molecular Biology F. Ausubel et al. eds. (Boston, Greene). pp 2.0.1-2.12.5.

Goodman, L E, Perou, C M, Fujiyama, A, Tamanoi, F (1988) Yeast 4:271

Haughn, G. and Somerville C. R. (1986). Sulfonylurea-resistant mutants of *Arabidopsis thaliana*. Mol. Gen. Genet. 204:430-434.

Koornneef, M, Reuling, G and Karssen, C M (1984) The isolation and characterization of abscisic acid-insensitive mutants of *Arabidopsis thaliana*. Physiol. Plant. 61:377-383.

Leung, J, Bouvier-Durand, M, Morris, P—C, Guerrier, D, Chefdor, F, and Giraudat, J (1994) *Arabidopsis* ABA-response gene ABI 1: features of a calcium-modulated protein phosphatase. Science 264:1448-1452.

Meyer, K, Leube, M P, and Grill, E (1994) A protein phosphatase 2C involved in ABA signal transduction in *Arabidopsis thaliana*. Science 264:1452-1455.

Randall, S K, Marshall, M S, Crowell, D N (1993) Protein isoprenylation in suspension-cultured tobacco cells. Plant Cell 5:433-442.

Reid, J B, and Howell, S H (1995) The function of hormones in plant growth and development. In Plant Hormones Physiology, Biochemistry and Molecular Biology. 2nd ed. P. Davies ed. (Dortrecht Kluwer) pp. 448-485.

Sambrook, J., E. F. Fritsch and Maniatis, T. (1989). Molecular Cloning: A Laboratory Manual, Second edition (Cold Spring Harbor, N.Y.: Cold Spring Harbor Laboratory Press)

Schafer, W R, and Rine, J (1992) Protein Prenylation: Genes, Enzymes, Targets and Functions. Ann Rev Genet. 30:209-237.

Shirley, B W, Hanley, S, Goodman, H M (1992) Plant Cell 4: 333

Verwoerd, T. C., Dekker, B. M. M. and Hoekema, A. (1989). A small-scale procedure for the rapid isolation of plant RNA's. Nucleic Acids Research 17:2362.

Yang, Z, Cramer, C L, and Watson, J C (1993) Protein farnesyl transferase in plants. Plant Physiology 101:667-674.

All citations in this application to materials and methods are hereby incorporated by reference.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A plant having a non-natural loss-of-function mutation in the gene encoding farnesyl transferase beta, wherein said mutation is due to a T-DNA insertion or fast neutron mutagenesis and results in reduced farnesyl transferase beta activity in said plant.

2. The plant of claim 1, wherein said reduced farnesyl transferase beta activity is sufficient to confer enhanced response to abscisic acid.

3. The plant of claim 1, wherein said plant is drought-resistant as compared to a wild-type plant.

4. The plant of claim 1, wherein said plant has delayed senescence as compared to a wild-type plant.

5. A seed produced by the plant of claim 1, wherein said seed produces a plant with reduced farnesyl transferase beta activity.

6. The seed of claim 5, wherein said seed fails to germinate at low concentrations of abscisic acid.

7. The seed of claim 6, wherein said seed fails to germinate on 50% of a concentration of abscisic acid that is sufficient to inhibit germination of a wild-type seed.

* * * * *

SEQUENCE LISTING

```
<160> NUMBER OF SEQ ID NOS: 178

<210> SEQ ID NO 1
<211> LENGTH: 3174
<212> TYPE: DNA
<213> ORGANISM: Arabidopsis sp.
<220> FEATURE:
<221> NAME/KEY: misc_feature
<222> LOCATION: (2703)
<223> OTHER INFORMATION: Wherein n is a or t or c or g.

<400> SEQUENCE: 1

atggagattc agcgagataa gcaattggat tatctgatga aaggcttaag gcagcttggt     60

ccgcagtttt cttccttaga tgctaagtaa gtgacatgat gcttggcttc ttgttttcat    120

gaatttctta gtacattttg tccagtgaga gagtaaagct ttggagcttt gccaatagac    180

ttagaagttt gattttggct ttttggattt tggaacagtc gaccttggct ttgttactgg    240

attcttcatt caatagcttt gcttggggag actgtggatg atgaattaga aagcaatgcc    300

attgacttcc ttggacgctg ccaggttagt ctcaattcct tttgcttgta cccaatcatg    360

aaaactcttc atatttgctc ttgcattctt cttgattttc tgctccttta gttcacgttt    420

tcttttcccg ttgctattag tgttatctgt tattgttctt tatgtactta gtttgctttc    480

tcatgtcgct tgtcagggct ctgaaggtgg atacggtggt ggtcctggcc aagtaagtat    540

atgtctgttt ctttaaagtg tgtggatcac tttcatttca tgcaattgga gaataaacat    600

tgagaccaga ttattttatt ctgccagatc tcttttaggt gtttttttta tgcatcatct    660

cattgtttgg ttgtgatgcc tttaattcaa gcagcacacg tagtttaagt ttaagttttt    720

ttctgtgaag acgtaaaatg gtgtctttag ttcaagcagc atttagttgt ttaagtttgt    780

ggttgtaaat tttccaaaca tggcagagaa agttaggata tataactttt ggtctgcctt    840

tttcagtttc cttttttttt ctactagtaa tggagatatt ttttcccagc ttccacatct    900

tgcaactact tatgctgcag tgaatgcact tgttacttta ggaggtgaca aagccctttc    960

ttcaattaat aggtggtgca ttctttttttc tttgtggtca gtttctttta ttaagagtct   1020

agtgatgttt cctctagaat acttacatgt gactcattct tctttcagag aaaaaatgtc   1080

ttgtttttta agacggatga aggatacaag tggaggtttc aggtttgatt ctctttctgc   1140
```

```
ttgaacttct taaaggcatc atttttactg acagcgcact ctttatgcat tcgtatcgct   1200

gttaatgcca taccttcagt catgttgttt ttttaattct tgcttaattc tacttactca   1260

ctgatcgtta ggatgcatga tatgggagaa attgatgttc gtgcatgcta cactgcaatt   1320

tcggtgagtt ttaccaactt ctattttcct tttctctgtt tttgtggaca ccaaaacttt   1380

ttaggattaa tgagatcaac aaagtctgga cccattatgc tatgtttctt ccgttttcat   1440

ggcttaaaca tcacattcag attacgatat gatcttatta tttgcacact tgcgcccacc   1500

aggatacttt gaatagagat tactcgtttt gagacttaca cgtcttgcaa atgcatccta   1560

tggctggttt tctccctgat atgtttgact tctctcttgt gacacaggtt gcaagcatcc   1620

taaatattat ggatgatgaa ctcacccagg gcctaggaga ttacatcttg aggtagcttt   1680

tcttattact tttatctcgc attatatata tatagctgaa ctactgttat acagttgtaa   1740

attcaggaat tcattaattt ccctgggaaa gctcttttaa ctcgatttat attgagcagt   1800

tgccaaactt atgaaggtgg cattggaggg gaacctggct ccgaagctca cggtgggtat   1860

ggtctccaac taacttccat tatgttgagg cttagataaa aattgtgctt tgcttccctc   1920

ttccttgatg acatggttat tgatggttaa gtataattaa ttttctgaaa taggatttgt   1980

cacctgcagc ttgcatgcct gccgctttgc ttattaccaa gttgtttttt gtttaggtat   2040

acctactgtg gtttggctgc tatgatttta atcaatgagg tcgaccgttt gaatttggat   2100

tcattaatgg taacatacaa tgctgtttgg agatgattaa taattttccc tgagagatat   2160

tttccttacc aaataatttc cttatgattc tagaattggg ctgtacatcg acaaggagta   2220

gaaatgggat ttcaaggtag gacgaacaaa ttggtcgatg gttgctacac atttggcag    2280

gttaactttc tatctttcag gattattatt ggccctactt ctaaattctt caccgttgtt   2340

gtcttttctt atttcctttg ggtatatgtt aaacaggcag ccccttgtgt tctactacaa   2400

agattatatt caaccaatga tcatgacgtt catggatcat cacatatatc agaagggaca   2460

aatgaagaac atcatgctca tgatgaagat gaccttgaag acagtgatga tgatgatgat   2520

tctgatgagg acaacgatga aggtattcaa tcaaatttct caaccatcaa gtccatctga   2580

taattcaaaa cacaacgaaa ttttagttag cttatatttg cagattcagt gaatggtcac   2640

agaatccatc atacatccac ctacattaac aggagaatgc aactggtttt tgatagcctc   2700

ggnttgcaga gatatgtact cttgtgctct aaggtcagtc cagaacaaaa catccagtca   2760

agttaacact taacatttgt ataacacaag cacacacact tgtatgcgca gatccctgac   2820

ggtggattca gagacaagcc gaggaaaccc cgtgacttct accacacatg ttactgcctg   2880

agcggcttgt ctgtggctca gcacgcttgg ttaaaagacg aggacactcc tcctttgact   2940

cgcgacatta tgggtggcta ctcgaatctc cttgaacctg ttcaacttct tcacaacatt   3000

gtcatggatc agtataatga agctatcgag ttcttcttta aagcagcatg acccgttgtt   3060

gctaatgtat gggaaacccc aaacataaga gtttccgtag tgttgtaact tgtaagattt   3120

caaaagaagt ttcactaatt taaccttaaa acctgttact ttttattacg tata         3174
```

<210> SEQ ID NO 2
<211> LENGTH: 400
<212> TYPE: PRT
<213> ORGANISM: Arabidopsis sp.

<400> SEQUENCE: 2

```
Met Glu Ile Gln Arg Asp Lys Gln Leu Asp Tyr Leu Met Lys Gly Leu
  1               5                   10                  15
```

```
Arg Gln Leu Gly Pro Gln Phe Ser Ser Leu Asp Ala Asn Arg Pro Trp
            20                  25                  30

Leu Cys Tyr Trp Ile Leu His Ser Ile Ala Leu Leu Gly Glu Thr Val
        35                  40                  45

Asp Asp Glu Leu Glu Ser Asn Ala Ile Asp Phe Leu Gly Arg Cys Gln
    50                  55                  60

Gly Ser Glu Gly Gly Tyr Gly Gly Gly Pro Gly Gln Leu Pro His Leu
65                  70                  75                  80

Ala Thr Thr Tyr Ala Ala Val Asn Ala Leu Val Thr Leu Gly Gly Asp
                85                  90                  95

Lys Ala Leu Ser Ser Ile Asn Arg Glu Lys Met Ser Cys Phe Leu Arg
            100                 105                 110

Arg Met Lys Asp Thr Ser Gly Gly Phe Arg Met His Asp Met Gly Glu
        115                 120                 125

Ile Asp Val Arg Ala Cys Tyr Thr Ala Ile Ser Val Ala Ser Ile Leu
    130                 135                 140

Asn Ile Met Asp Asp Glu Leu Thr Gln Gly Leu Gly Asp Tyr Ile Leu
145                 150                 155                 160

Ser Cys Gln Thr Tyr Glu Gly Gly Ile Gly Gly Glu Pro Gly Ser Glu
                165                 170                 175

Ala His Gly Gly Tyr Thr Tyr Cys Gly Leu Ala Ala Met Ile Leu Ile
            180                 185                 190

Asn Glu Val Asp Arg Leu Asn Leu Asp Ser Leu Met Asn Trp Ala Val
        195                 200                 205

His Arg Gln Gly Val Glu Met Gly Phe Gln Gly Arg Thr Asn Lys Leu
    210                 215                 220

Val Asp Gly Cys Tyr Thr Phe Trp Gln Ala Ala Pro Cys Val Leu Leu
225                 230                 235                 240

Gln Arg Leu Tyr Ser Thr Asn Asp His Asp Val His Gly Ser Ser His
                245                 250                 255

Ile Ser Glu Gly Thr Asn Glu Glu His His Ala His Asp Glu Asp Asp
            260                 265                 270

Leu Glu Asp Ser Asp Asp Asp Asp Asp Ser Asp Glu Asp Asn Asp Glu
        275                 280                 285

Asp Ser Val Asn Gly His Arg Ile His His Thr Ser Thr Tyr Ile Asn
    290                 295                 300

Arg Arg Met Gln Leu Val Phe Asp Ser Leu Gly Leu Gln Arg Tyr Val
305                 310                 315                 320

Leu Leu Cys Ser Lys Ile Pro Asp Gly Gly Phe Arg Asp Lys Pro Arg
                325                 330                 335

Lys Pro Arg Asp Phe Tyr His Thr Cys Tyr Cys Leu Ser Gly Leu Ser
            340                 345                 350

Val Ala Gln His Ala Trp Leu Lys Asp Glu Asp Thr Pro Pro Leu Thr
        355                 360                 365

Arg Asp Ile Met Gly Gly Tyr Ser Asn Leu Leu Glu Pro Val Gln Leu
    370                 375                 380

Leu His Asn Ile Val Met Asp Gln Tyr Asn Glu Ala Ile Glu Phe Phe
385                 390                 395                 400
```

<210> SEQ ID NO 3
<211> LENGTH: 2286
<212> TYPE: DNA
<213> ORGANISM: Artificial Sequence
<220> FEATURE:
<223> OTHER INFORMATION: Description of Artificial Sequence: ERA1 promoter
<220> FEATURE:
<221> NAME/KEY: misc_feature
<222> LOCATION: (79)
<223> OTHER INFORMATION: Wherein n is a or t or c or g.
<220> FEATURE:
<221> NAME/KEY: misc_feature
<222> LOCATION: (996)
<223> OTHER INFORMATION: Wherein n is a or t or c or g.
<220> FEATURE:
<221> NAME/KEY: misc_feature
<222> LOCATION: (1153)
<223> OTHER INFORMATION: Wherein n is a or t or c or g.
<220> FEATURE:
<221> NAME/KEY: misc_feature
<222> LOCATION: (1295..1296)
<223> OTHER INFORMATION: Wherein n is a or t or c or g.
<220> FEATURE:
<221> NAME/KEY: misc_feature
<222> LOCATION: (1779)
<223> OTHER INFORMATION: Wherein n is a or t or c or g.

<400> SEQUENCE: 3
ctcactcatt agcaccccag ctttacactt tatgcttccg ctcgtatgtt gtgtggaatt 60
gtgagcgata acaatttcna cacaggaaac agctatgaca tgattacgaa ttcaaaaaaa 120
tagagattgg caatatttta gtgtgtgaat aatattcatc cctaaaaaga agtcatcttt 180
cgactttgtg gcaacagttc tgttattaaa atgtgtgagc gtgacatatt ttgaagaggt 240
acctcgacaa aatcggaagg tgtctcattt tcttctatcg gaaggctttc tcgttgaagg 300
tagtcgttgt agctgaaaaa ttaagaaaac ctagtgagct cttcatgtat tcaaaaattc 360
aaccagtgta atcaaactca agaggtaaat agttaaaatc ccataccaaa ccgtgtaatc 420
tatgcaatac ctaattaaca aagttaaaag cgttagtcta gcagtaatat tgtatcaaaa 480
gctctaacag taattaataa ccagtgtcac cagaaacaaa tgtcaataac atggaaaatt 540
gaatttagtt gagtcctgga ggtcgtggac gtcgtggagg ctgtggacgt cgtgaatacg 600
cataaagaaa aatcttataa tcgtgcaaat attcaccgtt cttcttatac atcacctacg 660
gtaataaaag agttttattt cagcaatcgt acattcaaat tgaaacttag atacactata 720
tatttttcat cataactaac tataaactag tctaaacctt ttttgcttcg ttagcagaag 780
caaagtcaac aggccatagc acctatggat acgcttggcg gttacaaaaa gtcgaacacg 840
aacaacttct ccagcatctt tgaagaaatt gatgctgtaa caaacagtgt aaggtaaaaa 900
tatcagtcat gctcagagaa ggaaagtgga gattgaagat ggtgctactt acatatctga 960
tattttagtt tggggaggga tatggccatt aaagancgtc ttttttgtca cctggattta 1020
acagccaagt gtgttagcac aagattctta attgaacaga aatttgtaca aaatatctag 1080
caaatccgtt ggttgtttcc tcctgttaca tatgatacaa gatcaaagag tagccattag 1140
aagaagacag tgnaaagaag attgttttgt caaagaagaa gagtaatacg aggccatctt 1200
agggttacct tattctactt atgtctcttg agaatggaat tggtcaccaa atcatcttct 1260
tcagggttac gcttacctaa aagaagagca acaannaaaa aactcttgag acaagtttaa 1320
cacattagat aaaagagaga gagagagagg caaccaaaaa caaacccaat aaattgctac 1380
tagaagtggc catggagaag atgaaacgag gtttatgtat ttttccgtta agagcaagca 1440
ataatatagc cctaaagaaa tatagaccta gcctaggaag aagtttctaa gaccatcctt 1500
atcaatgaac tcttacataa agttctaaac aattttgata tacaaaataa tgtttaaaca 1560
ttagaatggc tcttacaaaa aaagagaata aagaaaaaaa aaacttagct aagagccatt 1620
tttcatttct taagcacact tttttatttt tttattctta ttttatttaa tataatattt 1680

```
tgatagttct tatgatattg ttaacaacct attgataagg atgctctaac taatcttata   1740

aataaaacaa tgaatctggt ttggtctggg cgtaacagna attatactct ttttttttt    1800

tgtcaagagg aaattatact aagaagcaac agattaaaca ttaaagcgta tagtaaaatt   1860

aattgtttga gaatcttaaa ccaaaccgaa ccggtattaa accggaacca aattggcaat   1920

gaaatttaga tgccagtagt aacccgcttg attcgtttga agtgtgtagg gctcagactt   1980

gaccggagtg gactcaatcg gcgaatctgt cacggaggac acggggaatc aacgcggcgg   2040

agagtgatgg aagagttttc aagcctaacc gtgagtcagc gcgagcaatt tctggtggag   2100

aacgatgtgt tcgggatcta taattacttc gacgccagcg acgtttctac tcaaaaatac   2160

atgtaagctg acggattgat tttctagttt tcttcatgat ctgatgaatt ttagtagcgt   2220

cgtgaaagaa ttattttcgt cgatagatga atcttactga tatggaagtt gttctatcct   2280

aggatg                                                              2286
```

<210> SEQ ID NO 4
<211> LENGTH: 192
<212> TYPE: PRT
<213> ORGANISM: Pisum sativum

<400> SEQUENCE: 4

```
Ala Ser Thr Ala Ala Glu Thr Pro Thr Pro Thr Val Ser Gln Asp Gln
  1               5                  10                  15

Trp Ile Val Glu Gln Val Phe His Ile Tyr Gln Leu Phe Ala Asn Ile
             20                  25                  30

Pro Pro Asn Ala Gln Ser Ile Ile Ile Ser Ile Asp Asp Thr Val Asn
         35                  40                  45

Asp Pro Asn Ala Met Thr Ile Glu Ser Ala Asn Leu Tyr Gly Met Gln
     50                  55                  60

Pro Asn Glu Val Leu Ile Lys Asn Val Phe Leu Ala Phe Gly Asn Asp
 65                  70                  75                  80

Pro Arg Leu Asp Val Phe Lys Cys Asp Gly Gly Ala Val Ala His Ile
                 85                  90                  95

Ile Glu Gln Met Ala Glu Ala Gln Phe Val Thr Val Ser Asp Ala Pro
            100                 105                 110

Glu Glu Lys Glu Cys Leu Gly Thr Ser Ser His Ala Thr Ser His Ile
        115                 120                 125

Arg His Gly Met Asn Ser Cys Ser Ser Asp Val Lys Asn Ile Gly Tyr
    130                 135                 140

Asn Phe Ile Ser Glu Trp Gln Ser Glu Pro Leu His Ile Ala Gln Ile
145                 150                 155                 160

Gln Glu Gln Leu Gly Arg His Ser Leu Cys Tyr Ser Ser Arg Pro Ser
                165                 170                 175

Pro Lys Val Val Pro Ile His Pro Phe Val Leu Arg Arg His Ser Gln
            180                 185                 190
```

<210> SEQ ID NO 5
<211> LENGTH: 311
<212> TYPE: PRT
<213> ORGANISM: Saccharomyces sp.

<400> SEQUENCE: 5

```
Arg Gln Arg Val Gly Arg Ser Ile Ala Arg Ala Lys Phe Ile Asn Thr
  1               5                  10                  15

Ala Leu Gly Arg Lys Arg Pro Val Met Glu Arg Val Val Asp Ile Ala
```

```
            20                  25                  30

His Val Asp Ser Ser Lys Ala Ile Gln Pro Leu Met Lys Glu Leu Glu
        35                  40                  45

Thr Asp Thr Thr Glu Ala Arg Tyr Lys Val Leu Gln Ser Val Leu Glu
    50                  55                  60

Ile Tyr Asp Asp Glu Lys Asn Ile Glu Pro Ala Leu Thr Lys Glu Phe
65                  70                  75                  80

His Lys Met Tyr Leu Asp Val Ala Phe Glu Ile Ser Leu Pro Pro Gln
                85                  90                  95

Met Thr Ala Leu Asp Ala Ser Gln Met Leu Ala Asn Leu Lys Val Met
            100                 105                 110

Asp Arg Asp Trp Leu Ser Asp Thr Lys Arg Lys Ile Val Lys Phe Thr
        115                 120                 125

Ile Ser Pro Gly Pro Phe Ser Ser Ile Ser Leu Cys Asp Asn Ile Asp
    130                 135                 140

Gly Cys Trp Asp Arg Asp Lys Gly Ile Tyr Gln Trp Ile Ser Leu Glu
145                 150                 155                 160

Pro Asn Lys Thr Cys Leu Glu Val Val Thr Gly Ile Cys Leu Ile Thr
                165                 170                 175

Leu Leu Thr Glu Glu Val Leu Asn Leu Lys Asn Asn Phe Ser Cys His
            180                 185                 190

Val Asp Phe Ala Thr Ser Leu Ala Arg Ser Met Gln Ile Val Glu Lys
        195                 200                 205

Leu Glu Ser Ser Ala Leu Gln Glu Arg Cys Ser Ser Val Gly Gly Ser
    210                 215                 220

Ala Ala Ile Glu Ala Phe Gly Gly Gln Cys Asn Lys His Ala Arg Asp
225                 230                 235                 240

Ile Tyr Cys Gln Glu Lys Glu Gln Pro Leu Gly Ala His Ser Asn Leu
                245                 250                 255

Ala Glu Ser Ser Tyr Ser Cys Thr Pro Asn Ser His Asn Ile Lys Cys
            260                 265                 270

Thr Pro Asp Arg Leu Ile Gly Ser Ser Lys Leu Thr Asp Val Asn Pro
        275                 280                 285

Val Tyr Gly Leu Pro Ile Glu Val Arg Lys Ile Ile His Tyr Phe Lys
    290                 295                 300

Ser Asn Leu Ser Ser Pro Ser
305                 310


<210> SEQ ID NO 6
<211> LENGTH: 270
<212> TYPE: PRT
<213> ORGANISM: Rattus norvegicus

<400> SEQUENCE: 6

Ala Ser Ser Ser Ser Phe Thr Tyr Tyr Cys Pro Pro Ser Ser Ser Pro
  1               5                  10                  15

Val Trp Ser Glu Pro Leu Tyr Arg Pro Glu His Ala Arg Glu Arg Leu
            20                  25                  30

Gln Asp Asp Ser Val Glu Thr Val Thr Ser Ile Glu Gln Ala Lys Val
        35                  40                  45

Glu Glu Lys Ile Gln Glu Val Phe Ser Ser Tyr Lys Phe Asn His Leu
    50                  55                  60

Val Pro Arg Leu Val Leu Gln Arg Glu Lys His Phe His Tyr Leu Lys
65                  70                  75                  80
```

```
Arg Gly Leu Arg Gln Leu Thr Asp Ala Tyr Glu Cys Leu Asp Ala Ser
                 85                  90                  95

Leu Glu Asp Pro Ile Pro Gln Ile Val Ala Thr Asp Val Cys Gln Glu
            100                 105                 110

Leu Ser Pro Asp Phe Tyr Pro Cys Ile Ile Thr Glu Glu Tyr Asn Val
        115                 120                 125

Leu Leu Gln Tyr Tyr Ser Leu Gln Pro Asp Ser Leu Val Gly Val Ser
    130                 135                 140

Ala Cys Ala Leu Thr Ile Thr Pro Asp Phe Glu Thr Ala Glu Trp Ala
145                 150                 155                 160

Arg Asn Trp Val Met Phe Leu Val Lys Lys Arg Ser Lys Leu Gln Val
                165                 170                 175

Thr Ser Met Arg Phe Gly Cys Ser Gly Leu Leu Pro His Ala His Ala
            180                 185                 190

Gln Gly Pro Ala Leu Ser Met His Trp Met His Gln Gln Ala Glu Ile
        195                 200                 205

Met Cys Gln Cys Ala Leu Leu Gly Ser Ile His Phe Gly Ser Gly Ala
    210                 215                 220

Met His Asp Val Val Val Pro Glu Val Gln Thr His Pro Val Tyr Gly
225                 230                 235                 240

Pro Lys Val Ile Gln Thr Thr His Leu Gln Lys Pro Val Pro Gly Phe
                245                 250                 255

Glu Glu Cys Glu Asp Ala Val Thr Ser Asp Pro Ala Thr Asp
            260                 265                 270
```

<210> SEQ ID NO 7
<211> LENGTH: 999
<212> TYPE: DNA
<213> ORGANISM: Arabidopsis thaliana

<400> SEQUENCE: 7

```
aaacccggga tgaatttcga cgagaccgtg ccactgagcc aacgattgga gtggtcagac      60

gtggtcccat tgactcagga cgatggtccg aatccagtgg tgccaattgc ctacaaggaa     120

gagttccgcg agactatgga ttacttccgt gcgatttact tttccgacga gcgatctcct     180

cgcgcactac gactcacgga agaaaccctc ctcttaaact ccggcaacta cacagtgtgg     240

catttcaggc gcctagtact cgaggccctt aatcacgact tgtttgaaga actcgagttc     300

atcgaacgca ttgctgagga taactctaag aactaccaac tgtggcatca tcggcgatgg     360

gttgcagaga aactgggtcc tgatgttgca gggagagaac ttgaatttac ccgtagagta     420

ctttcacttg atgccaaaca ttatcatgct tggtcacata ggcagtggac actacgggca     480

ttaggaggat gggaagatga gctcgattac tgtcacgagc tccttgaagc tgacgtcttt     540

aacaattccg cctggaatca gaggtattat gtcatcaccc aatctccttt gttgggaggc     600

ctagaagcca tgagagaatc tgaagtaagc tacacaatca aagccatttt aaccaatcct     660

gcaaacgaga gctcatggcg atacctaaaa gcgctttaca aagacgacaa agaatcctgg     720

attagtgatc caagtgtttc ctcagtctgt ttgaatgttc tatcccgcac agattgcttc     780

catggattcg ctctgagcac ccttttggat cttctatgtg atggactgag accaaccaac     840

gagcataaag actcagtgag agctctagct aatgaagaac cagagactaa cttggccaat     900

ttggtgtgta ctattcttgg tcgtgtagat cctataagag ctaactattg ggcatggagg     960

aagagcaaga ttacagtggc agcaatttga ggatcctt                             999
```

<210> SEQ ID NO 8
<211> LENGTH: 999
<212> TYPE: DNA
<213> ORGANISM: Artificial Sequence
<220> FEATURE:
<223> OTHER INFORMATION: Description of Artificial Sequence: Compliment
to Seq ID:07

<400> SEQUENCE: 8
aaaggatcct caaattgctg ccactgtaat cttgctcttc ctccatgccc aatagttagc 60
tcttatagga tctacacgac caagaatagt acacaccaaa ttggccaagt tagtctctgg 120
ttcttcatta gctagagctc tcactgagtc tttatgctcg ttggttggtc tcagtccatc 180
acatagaaga tccaaaaggg tgctcagagc gaatccatgg aagcaatctg tgcgggatag 240
aacattcaaa cagactgagg aaacacttgg atcactaatc caggattctt tgtcgtcttt 300
gtaaagcgct tttaggtatc gccatgagct ctcgtttgca ggattggtta aaatggcttt 360
gattgtgtag cttacttcag attctctcat ggcttctagg cctcccaaca aaggagattg 420
ggtgatgaca taatacctct gattccaggc ggaattgtta aagacgtcag cttcaaggag 480
ctcgtgacag taatcgagct catcttccca tcctcctaat gcccgtagtg tccactgcct 540
atgtgaccaa gcatgataat gtttggcatc aagtgaaagt actctacggg taaattcaag 600
ttctctccct gcaacatcag gacccagttt ctctgcaacc catcgccgat gatgccacag 660
ttggtagttc ttagagttat cctcagcaat gcgttcgatg aactcgagtt cttcaaacaa 720
gtcgtgatta agggcctcga gtactaggcg cctgaaatgc cacactgtgt agttgccgga 780
gtttaagagg agggtttctt ccgtgagtcg tagtgcgcga ggagatcgct cgtcggaaaa 840
gtaaatcgca cggaagtaat ccatagtctc gcggaactct tccttgtagg caattggcac 900
cactggattc ggaccatcgt cctgagtcaa tgggaccacg tctgaccact ccaatcgttg 960
gctcagtggc acggtctcgt cgaaattcat cccgggttt 999

<210> SEQ ID NO 9
<211> LENGTH: 989
<212> TYPE: DNA
<213> ORGANISM: Artificial Sequence
<220> FEATURE:
<223> OTHER INFORMATION: Description of Artificial Sequence: Compliment
to SEQ ID NO: 7 ligated

<400> SEQUENCE: 9
gatcctcaaa ttgctgccac tgtaatcttg ctcttcctcc atgcccaata gttagctctt 60
ataggatcta cacgaccaag aatagtacac accaaattgg ccaagttagt ctctggttct 120
tcattagcta gagctctcac tgagtcttta tgctcgttgg ttggtctcag tccatcacat 180
agaagatcca aaagggtgct cagagcgaat ccatggaagc aatctgtgcg ggatagaaca 240
ttcaaacaga ctgaggaaac acttggatca ctaatccagg attctttgtc gtctttgtaa 300
agcgctttta ggtatcgcca tgagctctcg tttgcaggat tggttaaaat ggctttgatt 360
gtgtagctta cttcagattc tctcatggct tctaggcctc ccaacaaagg agattgggtg 420
atgacataat acctctgatt ccaggcggaa ttgttaaaga cgtcagcttc aaggagctcg 480
tgacagtaat cgagctcatc ttcccatcct cctaatgccc gtagtgtcca ctgcctatgt 540
gaccaagcat gataatgttt ggcatcaagt gaaagtactc tacgggtaaa ttcaagttct 600
ctccctgcaa catcaggacc cagtttctct gcaacccatc gccgatgatg ccacagttgg 660
tagttcttag agttatcctc agcaatgcgt tcgatgaact cgagttcttc aaacaagtcg 720

```
tgattaaggg cctcgagtac taggcgcctg aaatgccaca ctgtgtagtt gccggagttt    780

aagaggaggg tttcttccgt gagtcgtagt gcgcgaggag atcgctcgtc ggaaaagtaa    840

atcgcacgga agtaatccat agtctcgcgg aactcttcct tgtaggcaat tggcaccact    900

ggattcggac catcgtcctg agtcaatggg accacgtctg accactccaa tcgttggctc    960

agtggcacgg tctcgtcgaa attcatccc                                      989


<210> SEQ ID NO 10
<211> LENGTH: 5250
<212> TYPE: DNA
<213> ORGANISM: Artificial Sequence
<220> FEATURE:
<223> OTHER INFORMATION: Description of Artificial Sequence:plasmid
      pBI121-35S-anti-AtFTA

<400> SEQUENCE: 10

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740
```

```
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcaaatt gctgccactg taatcttgct   3360
cttcctccat gcccaatagt tagctcttat aggatctaca cgaccaagaa tagtacacac   3420
caaattggcc aagttagtct ctggttcttc attagctaga gctctcactg agtctttatg   3480
ctcgttggtt ggtctcagtc catcacatag aagatccaaa agggtgctca gagcgaatcc   3540
atggaagcaa tctgtgcggg atagaacatt caaacagact gaggaaacac ttggatcact   3600
aatccaggat tctttgtcgt ctttgtaaag cgcttttagg tatcgccatg agctctcgtt   3660
tgcaggattg gttaaaatgg ctttgattgt gtagcttact tcagattctc tcatggcttc   3720
taggcctccc aacaaaggag attgggtgat gacataatac ctctgattcc aggcggaatt   3780
gttaaagacg tcagcttcaa ggagctcgtg acagtaatcg agctcatctt cccatcctcc   3840
taatgcccgt agtgtccact gcctatgtga ccaagcatga taatgtttgg catcaagtga   3900
aagtactcta cgggtaaatt caagttctct ccctgcaaca tcaggaccca gtttctctgc   3960
aacccatcgc cgatgatgcc acagttggta gttcttagag ttatcctcag caatgcgttc   4020
gatgaactcg agttcttcaa acaagtcgtg attaagggcc tcgagtacta ggcgcctgaa   4080
atgccacact gtgtagttgc cggagtttaa gaggagggtt tcttccgtga gtcgtagtgc   4140
```

```
gcgaggagat cgctcgtcgg aaaagtaaat cgcacggaag taatccatag tctcgcggaa   4200

ctcttccttg taggcaattg gcaccactgg attcggacca tcgtcctgag tcaatgggac   4260

cacgtctgac cactccaatc gttggctcag tggcacggtc tcgtcgaaat tcatcccctc   4320

gaatttcccc gatcgttcaa acatttggca ataaagtttc ttaagattga atcctgttgc   4380

cggtcttgcg atgattatca tataatttct gttgaattac gttaagcatg taataattaa   4440

catgtaatgc atgacgttat ttatgagatg ggtttttatg attagagtcc cgcaattata   4500

catttaatac gcgatagaaa acaaaatata gcgcgcaaac taggataaat tatcgcgcgc   4560

ggtgtcatct atgttactag atcgggaatt cactggccgt cgttttacaa cgtcgtgact   4620

gggaaaaccc tggcgttacc caacttaatc gccttgcagc acatccccct ttcgccagct   4680

ggcgtaatag cgaagaggcc cgcaccgatc gcccttccca acagttgcgc agcctgaatg   4740

gcgcccgctc ctttcgcttt cttcccttcc tttctcgcca cgttcgccgg ctttccccgt   4800

caagctctaa atcgggggct ccctttaggg ttccgattta gtgctttacg gcacctcgac   4860

cccaaaaaac ttgatttggg tgatggttca cgtagtgggc catcgccctg atagacggtt   4920

tttcgccctt tgacgttgga gtccacgttc tttaatagtg gactcttgtt ccaaactgga   4980

acaacactca accctatctc gggctattct tttgatttat aagggatttt gccgatttcg   5040

gaaccaccat caaacaggat tttcgcctgc tggggcaaac cagcgtggac cgcttgctgc   5100

aactctctca gggccaggcg gtgaagggca atcagctgtt gcccgtctca ctggtgaaaa   5160

gaaaaaccac cccagtacat taaaaacgtc cgcaatgtgt tattaagttg tctaagcgtc   5220

aatttgttta caccacaata tatcctgcca                                    5250
```

```
<210> SEQ ID NO 11
<211> LENGTH: 326
<212> TYPE: PRT
<213> ORGANISM: Arabidopsis thaliana

<400> SEQUENCE: 11

Met Asn Phe Asp Glu Thr Val Pro Leu Ser Gln Arg Leu Glu Trp Ser
1               5                   10                  15

Asp Val Val Pro Leu Thr Gln Asp Asp Gly Pro Asn Pro Val Val Pro
            20                  25                  30

Ile Ala Tyr Lys Glu Glu Phe Arg Glu Thr Met Asp Tyr Phe Arg Ala
        35                  40                  45

Ile Tyr Phe Ser Asp Glu Arg Ser Pro Arg Ala Leu Arg Leu Thr Glu
    50                  55                  60

Glu Thr Leu Leu Leu Asn Ser Gly Asn Tyr Thr Val Trp His Phe Arg
65                  70                  75                  80

Arg Leu Val Leu Glu Ala Leu Asn His Asp Leu Phe Glu Glu Leu Glu
                85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Arg Glu Leu Glu Phe Thr Arg Arg Val Leu Ser Leu Asp Ala Lys His
    130                 135                 140

Tyr His Ala Trp Ser His Arg Gln Trp Thr Leu Arg Ala Leu Gly Gly
145                 150                 155                 160

Trp Glu Asp Glu Leu Asp Tyr Cys His Glu Leu Leu Glu Ala Asp Val
                165                 170                 175
```

```
Phe Asn Asn Ser Ala Trp Asn Gln Arg Tyr Tyr Val Ile Thr Gln Ser
            180                 185                 190

Pro Leu Leu Gly Gly Leu Glu Ala Met Arg Glu Ser Glu Val Ser Tyr
        195                 200                 205

Thr Ile Lys Ala Ile Leu Thr Asn Pro Ala Asn Glu Ser Ser Trp Arg
    210                 215                 220

Tyr Leu Lys Ala Leu Tyr Lys Asp Asp Lys Glu Ser Trp Ile Ser Asp
225                 230                 235                 240

Pro Ser Val Ser Ser Val Cys Leu Asn Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Lys Asp Ser Val Arg Ala Leu Ala Asn
        275                 280                 285

Glu Glu Pro Glu Thr Asn Leu Ala Asn Leu Val Cys Thr Ile Leu Gly
    290                 295                 300

Arg Val Asp Pro Ile Arg Ala Asn Tyr Trp Ala Trp Arg Lys Ser Lys
305                 310                 315                 320

Ile Thr Val Ala Ala Ile
                325
```

<210> SEQ ID NO 12
<211> LENGTH: 822
<212> TYPE: DNA
<213> ORGANISM: Brassica napus

<400> SEQUENCE: 12

```
atggattact tccgtgcgat ttacttctcc gacgagcgtt ctgctcgcgc gctgcgactc      60

acggaagaag ctctccgctt aaactcgggc aactacaccg tgtggcactt cgggcgctta     120

gtactcgagg agcttaataa cgacttgtat gaagagctca agttcatcga aagcattgct     180

gaggataact ctaagaacta ccagttgtgg catcatcgac gatgggtcgc agagaaactg     240

ggtcctgatg ttgcaggaaa ggaacttgag tttactcgga gggtactatc acttgatgcc     300

aagcattatc atgcttggtc acataggcag tgggcgctac aagcattagg aggatgggaa     360

aatgagctta actactgcca cgagctcctt gaagctgacg tctttaacaa ctctgcatgg     420

aatcagaggt attacgttat aactagatca ccttcgttgg gaggcctaga agccatgaga     480

gaatctgaag taagctacac agtcaaagcc attttagcaa atcccgggaa cgagagctct     540

tggaggtacc tgaaagccct ttacaaagac gacacagagt cttggattag tgatccaagt     600

gtttcctcag tctgtttgaa agttctctca cgcgcggact gcttccatgg attcgctctg     660

agcacccttt tggatcttct gtgcgatggg ttgagaccaa ccaacgagca tagagactcg     720

gtgaaagctc tagctaatga agaaccagag actaacttgg ccaatttggt gtgtaccatt     780

ctgtgtcgtg ttgatccaat aagagctaac tattgggcat gg                        822
```

<210> SEQ ID NO 13
<211> LENGTH: 276
<212> TYPE: PRT
<213> ORGANISM: Brassica napus

<400> SEQUENCE: 13

```
Met Asp Tyr Phe Arg Ala Ile Tyr Phe Ser Asp Glu Arg Ser Ala Arg
  1               5                  10                  15

Ala Leu Arg Leu Thr Glu Glu Ala Leu Arg Leu Asn Ser Gly Asn Tyr
```

```
            20                  25                  30

Thr Val Trp His Phe Gly Arg Leu Val Leu Glu Glu Leu Asn Asn Asp
        35                  40                  45

Leu Tyr Glu Glu Leu Lys Phe Ile Glu Ser Ile Ala Glu Asp Asn Ser
    50                  55                  60

Lys Asn Tyr Gln Leu Trp His His Arg Arg Trp Val Ala Glu Lys Leu
65                  70                  75                  80

Gly Pro Asp Val Ala Gly Leu Glu Lys Glu Phe Thr Arg Arg Val Leu
                85                  90                  95

Ser Leu Asp Ala Lys His Tyr His Ala Trp Ser His Arg Gln Trp Ala
            100                 105                 110

Leu Gln Ala Leu Gly Gly Trp Glu Asn Glu Leu Asn Tyr Cys His Glu
        115                 120                 125

Leu Leu Glu Ala Asp Val Phe Asn Asn Ser Ala Trp Asn Gln Arg Tyr
    130                 135                 140

Tyr Val Ile Thr Arg Ser Pro Ser Leu Gly Gly Leu Glu Ala Met Arg
145                 150                 155                 160

Glu Ser Glu Val Ser Tyr Thr Val Lys Ala Ile Leu Ala Asn Pro Gly
                165                 170                 175

Asn Glu Ser Ser Trp Arg Tyr Leu Lys Ala Leu Tyr Lys Asp Asp Thr
            180                 185                 190

Glu Ser Trp Ile Ser Asp Pro Ser Val Ser Ser Val Cys Leu Lys Val
        195                 200                 205

Leu Ser Arg Ala Asp Cys Phe His Gly Phe Ala Leu Ser Thr Leu Leu
    210                 215                 220

Asp Leu Leu Cys Asp Gly Leu Arg Pro Thr Asn Glu His Arg Asp Ser
225                 230                 235                 240

Val Lys Ala Leu Ala Asn Glu Glu Pro Glu Thr Asn Leu Ala Asn Leu
                245                 250                 255

Val Cys Thr Ile Leu Cys Arg Val Asp Pro Ile Arg Ala Asn Tyr Trp
            260                 265                 270

Ala Trp Lys Leu
        275


<210> SEQ ID NO 14
<211> LENGTH: 1110
<212> TYPE: DNA
<213> ORGANISM: Brassica napus

<400> SEQUENCE: 14

tggctttgtt actggattct tcattcaatt gctttgcttg gggagtctgt ggatgatgac      60

ttagaaaaca atgcaatcga ttttcttgga cgttgccagg gttctgatgg tggatatggt     120

ggtggtcctg gccaacttcc acatcttgca acaagttatg ctgcagtgaa tacacttgtt     180

actttaggag gtgagaaagc cttctcttca attaacagag aacaaatggc ttgtttctta     240

agacgaatga aggatacaaa tggaggtttc aggatgcata atatgggaga aatagatgtg     300

cgagcgtgct acactgcgat tttgattgca agcatcctga acattgtgga tgatgaactc     360

acccgcggct taggagatta cattttgagt tgccaaactt atgaaggtgg cattggaggg     420

gaacctggct ccgaagctca tggtgggtac acgtactgtg ggttggctac tatgatttta     480

atcaatgaag tcgaccgctt gaatttggat tcgttaatga attgggttgt acatcgacaa     540

ggagtagaaa tgggattcca aggtaggacg aacaaattgg tcgacggttg ctacacgttt     600

tggcaggcag ccccctgtgt tctactacag cgattttttt catcccagga tatggcacct     660
```

```
catggatcat catcacatat gtcacaaggg acagatgaag atcacgagga acatggtcat    720

gatgaagatg atcctgaaga cagtgatgaa gatgattctg atgaggatag cgatgaagat    780

tcagggaatg gtcaccaagt tcatcatacg tctacctaca ttgacaggag aattcaacct    840

gtttttgata gcctcggctt gcaaagatat gtgctcttgt gctctcaggt tgctgatggt    900

ggattcagag acaagctgag gaaaccccgt gacttctacc acacatgtta ctgcctaagc    960

ggtctttccg tggctcaaca cgcttggtca aaagacgagg acactcctcc tttgactcgt   1020

gacattttgg gtggctacgc aaaccacctt gaacctgttc acctcctcca caacattgtc   1080

ttggatcggt attatgaagc ttctagattt                                    1110


<210> SEQ ID NO 15
<211> LENGTH: 370
<212> TYPE: PRT
<213> ORGANISM: Brassica napus

<400> SEQUENCE: 15

Trp Leu Cys Tyr Trp Ile Leu His Ser Ile Ala Leu Leu Gly Glu Ser
1               5                   10                  15

Val Asp Asp Asp Leu Glu Asn Asn Ala Ile Asp Phe Leu Gly Arg Cys
            20                  25                  30

Gln Gly Ser Asp Gly Gly Tyr Gly Gly Gly Pro Gly Gln Leu Pro His
        35                  40                  45

Leu Ala Thr Ser Tyr Ala Ala Val Asn Thr Leu Val Thr Leu Gly Gly
    50                  55                  60

Glu Lys Ala Phe Ser Ser Ile Asn Arg Glu Gln Met Ala Cys Phe Leu
65                  70                  75                  80

Arg Arg Met Lys Asp Thr Asn Gly Gly Phe Arg Met His Asn Met Gly
                85                  90                  95

Glu Ile Asp Val Arg Ala Cys Tyr Thr Ala Ile Leu Ile Ala Ser Ile
            100                 105                 110

Leu Asn Ile Val Asp Asp Glu Leu Thr Arg Gly Leu Gly Asp Tyr Ile
        115                 120                 125

Leu Ser Cys Gln Thr Tyr Glu Gly Gly Ile Gly Gly Glu Pro Gly Ser
    130                 135                 140

Glu Ala His Gly Gly Tyr Thr Tyr Cys Gly Leu Ala Thr Met Ile Leu
145                 150                 155                 160

Ile Asn Glu Val Asp Arg Leu Asn Leu Asp Ser Leu Met Asn Trp Val
                165                 170                 175

Val His Arg Gln Gly Val Glu Met Gly Phe Gln Gly Arg Thr Asn Lys
            180                 185                 190

Leu Val Asp Gly Cys Tyr Thr Phe Trp Gln Ala Ala Pro Cys Val Leu
        195                 200                 205

Leu Gln Arg Phe Phe Ser Ser Gln Asp Met Ala Pro His Gly Ser Ser
    210                 215                 220

Ser His Met Ser Gln Gly Thr Asp Glu Asp His Glu Glu His Gly His
225                 230                 235                 240

Asp Glu Asp Asp Pro Glu Asp Ser Asp Glu Asp Asp Ser Asp Glu Asp
                245                 250                 255

Ser Asp Glu Asp Ser Gly Asn Gly His Gln Val His His Thr Ser Thr
            260                 265                 270

Tyr Ile Asp Arg Arg Ile Gln Pro Val Phe Asp Ser Leu Gly Leu Gln
        275                 280                 285
```

-continued

```
Arg Tyr Val Leu Leu Cys Ser Gln Val Ala Asp Gly Gly Phe Arg Asp
    290                 295                 300

Lys Leu Arg Lys Pro Arg Asp Phe Tyr His Thr Cys Tyr Cys Leu Ser
305                 310                 315                 320

Gly Leu Ser Val Ala Gln His Ala Trp Ser Lys Asp Glu Asp Thr Pro
                325                 330                 335

Pro Leu Thr Arg Asp Ile Leu Gly Gly Tyr Ala Asn His Leu Glu Pro
            340                 345                 350

Val His Leu Leu His Asn Ile Leu Val Asp Arg Tyr Tyr Glu Ala Ser
        355                 360                 365

Arg Phe
    370


<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 16

gccgacagtg gtcccaaaga tgg                                              23


<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 17

aaaggatcct caaattgctg ccactgtaat                                       30


<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 18

aaacccggga tgaatttcga cgagaacgtg                                       30


<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 19

gcaagaccgg caacagga                                                    18


<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 20

tttaagcttg acagaaacag tcagcgagac                                       30
```

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 21
gctcttcctc catgccca 18

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 22
tttaagcttg gagccataga tgcaattcaa 30

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 23
cgggcattag gaggatggga a 21

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 24
gtccggaatt cccgggtc 18

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: PCR primer

<400> SEQUENCE: 25
ggatccatgg attacttccg tgcgatttac ttctcc 36

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 26
aaaaagcttc catgcccaat agttagctct tattggatc 39

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 27
aaaaagcttt ggctttgtta ctggattctt cattcaat 38

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 28
aaatctagaa gcttcataat accgatccaa gacaatgtt 39

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 29
aaaggatcca tggaatctgg gtctagcga 29

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 30
aaatctagaa ggaagtctgc tcttgcgc 28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 31
aaatctagag ccaccattcc tcgcaacg 28

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 32
aaagagctcg tggtggagaa tctgggtgc 29

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 33
ggcggatccc gacctaccga gg 22

<210> SEQ ID NO 34
<211> LENGTH: 29

<212> TYPE: DNA
<213> ORGANISM: Artificial Sequence
<220> FEATURE:
<223> OTHER INFORMATION: Description of Artificial Sequence: PCR primer

<400> SEQUENCE: 34
aaagagctcg tggatggatt ggctccagc 29

<210> SEQ ID NO 35
<211> LENGTH: 822
<212> TYPE: DNA
<213> ORGANISM: Artificial Sequence
<220> FEATURE:
<223> OTHER INFORMATION: Description of Artificial Sequence: Compiment to SEQ ID NO: 12

<400> SEQUENCE: 35
ccatgcccaa tagttagctc ttattggatc aacacgacac agaatggtac acaccaaatt 60
ggccaagtta gtctctggtt cttcattagc tagagctttc accgagtctc tatgctcgtt 120
ggttggtctc aacccatcgc acagaagatc caaaagggtg ctcagagcga atccatggaa 180
gcagtccgcg cgtgagagaa ctttcaaaca gactgaggaa acacttggat cactaatcca 240
agactctgtg tcgtctttgt aaagggcttt caggtacctc caagagctct cgttcccggg 300
atttgctaaa atggctttga ctgtgtagct tacttcagat tctctcatgg cttctaggcc 360
tcccaacgaa ggtgatctag ttataacgta atacctctga ttccatgcag agttgttaaa 420
gacgtcagct tcaaggagct cgtggcagta gttaagctca ttttcccatc ctcctaatgc 480
ttgtagcgcc cactgcctat gtgaccaagc atgataatgc ttggcatcaa gtgatagtac 540
cctccgagta aactcaagtt cctttcctgc aacatcagga cccagtttct ctgcgaccca 600
tcgtcgatga tgccacaact ggtagttctt agagttatcc tcagcaatgc tttcgatgaa 660
cttgagctct tcatacaagt cgttattaag ctcctcgagt actaagcgcc cgaagtgcca 720
cacggtgtag ttgcccgagt ttaagcggag agcttcttcc gtgagtcgca gcgcgcgagc 780
agaacgctcg tcggagaagt aaatcgcacg gaagtaatcc at 822

<210> SEQ ID NO 36
<211> LENGTH: 1110
<212> TYPE: DNA
<213> ORGANISM: Artificial Sequence
<220> FEATURE:
<223> OTHER INFORMATION: Description of Artificial Sequence: Compliment to SEQ ID NO: 14

<400> SEQUENCE: 36
aaatctagaa gcttcataat accgatccaa gacaatgttg tggaggaggt gaacaggttc 60
aaggtggttt gcgtagccac ccaaaatgtc acgagtcaaa ggaggagtgt cctcgtcttt 120
tgaccaagcg tgttgagcca cggaaagacc gcttaggcag taacatgtgt ggtagaagtc 180
acggggtttc ctcagcttgt ctctgaatcc accatcagca acctgagagc acaagagcac 240
atatctttgc aagccgaggc tatcaaaaac aggttgaatt ctcctgtcaa tgtaggtaga 300
cgtatgatga acttggtgac cattccctga atcttcatcg ctatcctcat cagaatcatc 360
ttcatcactg tcttcaggat catcttcatc atgaccatgt tcctcgtgat cttcatctgt 420
cccttgtgac atatgtgatg atgatccatg aggtgccata tcctgggatg aaaaaaatcg 480
ctgtagtaga acacaggggg ctgcctgcca aaacgtgtag caaccgtcga ccaatttgtt 540
cgtcctacct tggaatccca tttctactcc ttgtcgatgt acaacccaat tcattaacga 600

```
atccaaattc aagcggtcga cttcattgat taaaatcata gtagccaacc cacagtacgt    660

gtacccacca tgagcttcgg agccaggttc ccctccaatg ccaccttcat aagtttggca    720

actcaaaatg taatctccta agccgcgggt gagttcatca tccacaatgt tcaggatgct    780

tgcaatcaaa atcgcagtgt agcacgctcg cacatctatt tctcccatat tatgcatcct    840

gaaacctcca tttgtatcct tcattcgtct taagaaacaa gccatttgtt ctctgttaat    900

tgaagagaag gctttctcac ctcctaaagt aacaagtgta ttcactgcag cataacttgt    960

tgcaagatgt ggaagttggc caggaccacc accatatcca ccatcagaac cctggcaacg   1020

tccaagaaaa tcgattgcat tgttttctaa gtcatcatcc acagactccc caagcaaagc   1080

aattgaatga agaatccagt aacaaagcca                                    1110
```

<210> SEQ ID NO 37
<211> LENGTH: 1041
<212> TYPE: DNA
<213> ORGANISM: Glycine max
<220> FEATURE:
<221> NAME/KEY: misc_feature
<222> LOCATION: (360)
<223> OTHER INFORMATION: Wherein n is a or t or c or g.

<400> SEQUENCE: 37

```
atggaatctg ggtctagcga aggagaagag gtgcagcaac gcgtgccgtt gagggagaga     60

gtggagtggt cagatgttac tccggttcct caaaacgacg gccctaaccc tgtcgttccg    120

atccagtaca ctgaagagtt ttccgaagtt atggattact ttcgcgccgt ttacctcacc    180

gatgaacgct cccctcgcgc cctcgctctc acagccgaag ccgttcaatt caactccggc    240

aactacactg tgtggcattt ccgacggttg ttacttgagt cgctaaaagt cgacttgaac    300

gatgaactgg agtttgtgga gcgtatggcc gctggaaatt ctaaaaatta tcagatgtgn    360

atgttctgta ggcatcctag acgatgggtt gccgagaagt taggtcctga agctagaaac    420

aatgagctcg agttcaccaa aaagatactg tccgttgatg ccaaacatta tcatgcatgg    480

tctcatagac agtgggctct tcaaacacta ggaggatggg aagatgaact taattattgc    540

acagaactac ttaaagaaga catttttaac aattctgctt ggaatcagag atattttgtc    600

ataacaaggt ctcctttctt ggggggccta aaagctatga gagagtctga agtgctttac    660

accatcgaag ccattatagc ctaccctgaa aatgaaagct cgtggagata tctacgagga    720

ctttataaag gtgaaactac ttcatgggta aatgatcctc aagtttcttc agtatgctta    780

aagattttga gaactaagag caactacgtg tttgctctta gcactatttt agatcttata    840

tgctttggtt atcaaccaaa tgaagacatt agagatgcca ttgacgcctt aaagaccgca    900

gatatggata aacaagattt agatgatgat gagaaagggg aacaacaaaa tttaaatata    960

gcacgaaata tttgttctat cctaaaacaa gttgatccaa ttagaaccaa ctattggatt   1020

tggcgcaaga gcagacttcc t                                             1041
```

<210> SEQ ID NO 38
<211> LENGTH: 1041
<212> TYPE: DNA
<213> ORGANISM: Artificial Sequence
<220> FEATURE:
<223> OTHER INFORMATION: Description of Artificial Sequence: Compliment
to SEQ ID NO: 37
<220> FEATURE:
<221> NAME/KEY: misc_feature
<222> LOCATION: (682)
<223> OTHER INFORMATION: Wherein n is a or t or c or g.

<400> SEQUENCE: 38

```
aggaagtctg ctcttgcgcc aaatccaata gttggttcta attggatcaa cttgttttag     60
gatagaacaa atatttcgtg ctatatttaa attttgttgt tcccctttct catcatcatc    120
taaatcttgt ttatccatat ctgcggtctt taaggcgtca atggcatctc taatgtcttc    180
atttggttga taaccaaagc atataagatc taaaatagtg ctaagagcaa acacgtagtt    240
gctcttagtt ctcaaaatct ttaagcatac tgaagaaact tgaggatcat ttacccatga    300
agtagtttca cctttataaa gtcctcgtag atatctccac gagctttcat tttcagggta    360
ggctataatg gcttcgatgg tgtaaagcac ttcagactct ctcatagctt ttaggccccc    420
caagaaagga gaccttgtta tgacaaaata tctctgattc caagcagaat tgttaaaaat    480
gtcttcttta agtagttctg tgcaataatt aagttcatct tcccatcctc ctagtgtttg    540
aagagcccac tgtctatgag accatgcatg ataatgtttg gcatcaacgg acagtatctt    600
tttggtgaac tcgagctcat tgtttctagc ttcaggacct aacttctcgg caacccatcg    660
tctaggatgc ctacagaaca tncacatctg ataattttta gaatttccag cggccatacg    720
ctccacaaac tccagttcat cgttcaagtc gacttttagc gactcaagta acaaccgtcg    780
gaaatgccac acagtgtagt tgccggagtt gaattgaacg gcttcggctg tgagagcgag    840
ggcgcgaggg gagcgttcat cggtgaggta aacggcgcga aagtaatcca taacttcgga    900
aaactcttca gtgtactgga tcggaacgac agggttaggg ccgtcgtttt gaggaaccgg    960
agtaacatct gaccactcca ctctctccct caacggcacg cgttgctgca cctcttctcc   1020
ttcgctagac ccagattcca t                                             1041
```

<210> SEQ ID NO 39
<211> LENGTH: 347
<212> TYPE: PRT
<213> ORGANISM: Glycine max
<220> FEATURE:
<221> NAME/KEY: VARIANT
<222> LOCATION: (120)
<223> OTHER INFORMATION: Wherein Xaa is any amino acid.

<400> SEQUENCE: 39

```
Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
             20                  25                  30

Asp Gly Pro Asn Pro Val Val Pro Ile Gln Tyr Thr Glu Glu Phe Ser
         35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Glu Phe Val Glu Arg Met Ala Ala Gly
            100                 105                 110

Asn Ser Lys Asn Tyr Gln Met Xaa Met Phe Cys Arg His Pro Arg Arg
        115                 120                 125

Trp Val Ala Glu Lys Leu Gly Pro Glu Ala Arg Asn Asn Glu Leu Glu
    130                 135                 140

Phe Thr Lys Lys Ile Leu Ser Val Asp Ala Lys His Tyr His Ala Trp
145                 150                 155                 160
```

Ser His Arg Gln Trp Ala Leu Gln Thr Leu Gly Gly Trp Glu Asp Glu
165 170 175

Leu Asn Tyr Cys Thr Glu Leu Leu Lys Glu Asp Ile Phe Asn Asn Ser
180 185 190

Ala Trp Asn Gln Arg Tyr Phe Val Ile Thr Arg Ser Pro Phe Leu Gly
195 200 205

Gly Leu Lys Ala Met Arg Glu Ser Glu Val Leu Tyr Thr Ile Glu Ala
210 215 220

Ile Ile Ala Tyr Pro Glu Asn Glu Ser Ser Trp Arg Tyr Leu Arg Gly
225 230 235 240

Leu Tyr Lys Gly Glu Thr Thr Ser Trp Val Asn Asp Pro Gln Val Ser
245 250 255

Ser Val Cys Leu Lys Ile Leu Arg Thr Lys Ser Asn Tyr Val Phe Ala
260 265 270

Leu Ser Thr Ile Leu Asp Leu Ile Cys Phe Gly Tyr Gln Pro Asn Glu
275 280 285

Asp Ile Arg Asp Ala Ile Asp Ala Leu Lys Thr Ala Asp Met Asp Lys
290 295 300

Gln Asp Leu Asp Asp Asp Glu Lys Gly Glu Gln Gln Asn Leu Asn Ile
305 310 315 320

Ala Arg Asn Ile Cys Ser Ile Leu Lys Gln Val Asp Pro Ile Arg Thr
325 330 335

Asn Tyr Trp Ile Trp Arg Lys Ser Arg Leu Pro
340 345

<210> SEQ ID NO 40
<211> LENGTH: 1135
<212> TYPE: DNA
<213> ORGANISM: Glycine max

<400> SEQUENCE: 40
gccaccattc ctcgcaacgc ccaaaccctc atgttggagc ttcaacgcga taatcacatg 60
cagtatgtct ccaaaggcct tcgccatctc agttccgcat tttccgtttt ggacgctaat 120
cgaccctggc tctgctactg gatcttccac tccattgctt tgttgggaga atccgtcgat 180
gatgaactcg aagataacgc tatcgatttt cttaaccgtt gccaggatcc gaatggtgga 240
tatgccgggg gaccaggcca gatgcctcat attgccacaa cttatgctgc tgttaattca 300
cttattactt tgggtggtga gaaatccctg gcatcaatta atagagataa actgtatggg 360
tttctgcggc ggatgaagca accaaatggt ggattcagga tgcatgatga aggtgaaatt 420
gatgttcgag cttgctacac tgccatttct gttgcaagtg ttttgaacat tttggatgat 480
gagctgatcc agaatgttgg agactacatt ataagctgtc aaacatatga gggtggcatt 540
gctggtgagc ctggttctga ggctcatggt gggtacacct tttgtggatt agctacaatg 600
attctgattg gtgaggttaa tcacttggat ctgcctcgat tagttgactg ggtggtattc 660
cgacaaggta aggaatgtgg attccagggg agaacaaata aactggtgga tggatgctat 720
tccttttggc agggaggtgc tgttgctcta ttgcaaagat tatcttctat tatcaacaaa 780
cagatggaag agacatcaca gatttttgcg gtatcttatg tatctgaagc aaaagaaagt 840
ttggatggaa cctctagtca tgcaacatgc cgtggtgagc atgaaggcac cagtgaatcc 900
agttcatctg attttaaaaa tattgcctat aaatttatta atgagtggag agcacaagaa 960
ccactttttc acagtattgc tttacagcaa tatattctct tatgtgcaca ggagcaagag 1020
ggtggactga gagacaaacc gggtaaacgt agagatcatt atcacacatg ttactgttta 1080
agtggactct cattgtgcca gtatagttgg tcaaagcacc cagattctcc accac 1135

<210> SEQ ID NO 41
<211> LENGTH: 1135
<212> TYPE: DNA
<213> ORGANISM: Artificial Sequence
<220> FEATURE:
<223> OTHER INFORMATION: Description of Artificial Sequence: Compliment to SEQ ID NO: 40

<400> SEQUENCE: 41
gtggtggaga atctgggtgc tttgaccaac tatactggca caatgagagt ccacttaaac 60
agtaacatgt gtgataatga tctctacgtt tacccggttt gtctctcagt ccacccctctt 120 gctcctgtgc acataagaga atatattgct gtaaagcaat actgtgaaaa agtggttctt 180
gtgctctcca ctcattaata aatttatagg caatattttt aaaatcagat gaactggatt 240
cactggtgcc ttcatgctca ccacggcatg ttgcatgact agaggttcca tccaaacttt 300
cttttgcttc agatacataa gataccgcaa aaatctgtga tgtctcttcc atctgtttgt 360
tgataataga agataatctt tgcaatagag caacagcacc tccctgccaa aaggaatagc 420
atccatccac cagtttattt gttctcccct ggaatccaca ttccttacct tgtcggaata 480
ccacccagtc aactaatcga ggcagatcca agtgattaac ctcaccaatc agaatcattg 540
tagctaatcc acaaaaggtg tacccaccat gagcctcaga accaggctca ccagcaatgc 600
caccctcata tgtttgacag cttataatgt agtctccaac attctggatc agctcatcat 660
ccaaaatgtt caaaacactt gcaacagaaa tggcagtgta gcaagctcga acatcaattt 720
caccttcatc atgcatcctg aatccaccat ttggttgctt catccgccgc agaaacccat 780
acagtttatc tctattaatt gatgccaggg atttctcacc acccaaagta ataagtgaat 840
taacagcagc ataagttgtg gcaatatgag gcatctggcc tggtcccccg gcatatccac 900
cattcggatc ctggcaacgg ttaagaaaat cgatagcgtt atcttcgagt tcatcatcga 960
cggattctcc caacaaagca atggagtgga agatccagta gcagagccag ggtcgattag 1020
cgtccaaaac ggaaaatgcg gaactgagat ggcgaaggcc tttggagaca tactgcatgt 1080
gattatcgcg ttgaagctcc aacatgaggg tttgggcgtt gcgaggaatg gtggc 1135

<210> SEQ ID NO 42
<211> LENGTH: 378
<212> TYPE: PRT
<213> ORGANISM: Glycine max

<400> SEQUENCE: 42

Ala Thr Ile Pro Arg Asn Ala Gln Thr Leu Met Leu Glu Leu Gln Arg
1 5 10 15

Asp Asn His Met Gln Tyr Val Ser Lys Gly Leu Arg His Leu Ser Ser
20 25 30

Ala Phe Ser Val Leu Asp Ala Asn Arg Pro Trp Leu Cys Tyr Trp Ile
35 40 45

Phe His Ser Ile Ala Leu Leu Gly Glu Ser Val Asp Asp Glu Leu Glu
50 55 60

Asp Asn Ala Ile Asp Phe Leu Asn Arg Cys Gln Asp Pro Asn Gly Gly
65 70 75 80

Tyr Ala Gly Gly Pro Gly Gln Met Pro His Ile Ala Thr Thr Tyr Ala
85 90 95

```
Ala Val Asn Ser Leu Ile Thr Leu Gly Gly Glu Lys Ser Leu Ala Ser
            100                 105                 110

Ile Asn Arg Asp Lys Leu Tyr Gly Phe Leu Arg Arg Met Lys Gln Pro
        115                 120                 125

Asn Gly Gly Phe Arg Met His Asp Glu Gly Glu Ile Asp Val Arg Ala
    130                 135                 140

Cys Tyr Thr Ala Ile Ser Val Ala Ser Val Leu Asn Ile Leu Asp Asp
145                 150                 155                 160

Glu Leu Ile Gln Asn Val Gly Asp Tyr Ile Ile Ser Cys Gln Thr Tyr
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240

Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270

Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375
```

<210> SEQ ID NO 43
<211> LENGTH: 1245
<212> TYPE: DNA
<213> ORGANISM: Zea mays

<400> SEQUENCE: 43

```
ggcggatccc gacctaccga ggctcacggt gacgcaggtg gagcagatga aggtggaggc      60

cagggttggc gacatctacc gctccctctt cggggccgcg cccaacacga aatccatcat     120

gctagagctg tggcgtgatc agcatatcga gtatctgacg cctgggctga ggcatatggg     180

accagccttt catgttctag atgccaatcg ccccttggcta tgctactgga tggttcatcc     240

acttgctttg ctggatgaag cacttgatga tgatcttgag aatgatatca tagacttctt     300

agctcgatgt caggataaag atggtggata tagtggtgga cctggacagt tgcctcacct     360

agctacgact tatgctgctg taaatacact tgtgacaata gggagcgaaa gagcattgtc     420

atcaatcaat aggggcaacc tgtacaattt tatgctgcag atgaaagatg tatcaggtgc     480

tttcagaatg catgatggtg gcgaaattga tgtccgtgct tcctacaccg ctatatcggt     540
```

```
tgccagcctt gtgaatattc ttgattttaa actggcaaaa ggtgtaggcg actacatagc    600
aagatgtcaa acttatgaag gtggtattgc tggggagcct tatgctgaag cacatggtgg    660
gtatacattc tgtggattgg ctgctttgat cctgcttaat gaggcagaga aagttgactt    720
gcctagtttg attggctggg tggcttttcg tcaaggagtg gaatgcggat ttcaaggacg    780
aactaataaa ttggttgatg gttgctactc cttttggcag ggagctgcca ttgctttcac    840
acaaaagtta attacgattg ttgataagca attgaggtcc tcgtattcct gcaaaaggcc    900
atcaggagag gatgcctgca gcaccagttc atatgggtgc accgcgaata agtcttcctc    960
tgctgtggac tatgcgaagt ttggatttga ttttatacaa cagagcaacc aaattggccc   1020
actcttccat aacattgccc tgcaacaata catcctactt tgttctcagg tactagaggg   1080
aggcttgagg gataagcctg gaaagaacag agatcactat cattcatgct actgcctcag   1140
tggcctcgca gttagccagt acagtgccat gactgatact ggttcgtgcc cattacctca   1200
gcatgtgctt ggaccgtact ctaatttgct ggagccaatc catcc                   1245
```

<210> SEQ ID NO 44
<211> LENGTH: 1245
<212> TYPE: DNA
<213> ORGANISM: Artificial Sequence
<220> FEATURE:
<223> OTHER INFORMATION: Description of Artificial Sequence: Compliment
to SEQ ID NO: 43

<400> SEQUENCE: 44

```
ggatggattg gctccagcaa attagagtac ggtccaagca catgctgagg taatgggcac     60
gaaccagtat cagtcatggc actgtactgg ctaactgcga ggccactgag gcagtagcat    120
gaatgatagt gatctctgtt ctttccaggc ttatccctca agcctccctc tagtacctga    180
gaacaaagta ggatgtattg ttgcagggca atgttatgga agagtgggcc aatttggttg    240
ctctgttgta taaaatcaaa tccaaacttc gcatagtcca cagcagagga agacttattc    300
gcggtgcacc catatgaact ggtgctgcag gcatcctctc ctgatggcct tttgcaggaa    360
tacgaggacc tcaattgctt atcaacaatc gtaattaact tttgtgtgaa agcaatggca    420
gctccctgcc aaaaggagta gcaaccatca accaatttat tagttcgtcc ttgaaatccg    480
cattccactc cttgacgaaa agccacccag ccaatcaaac taggcaagtc aactttctct    540
gcctcattaa gcaggatcaa agcagccaat ccacagaatg tatacccacc atgtgcttca    600
gcataaggct ccccagcaat accaccttca taagtttgac atcttgctat gtagtcgcct    660
acaccttttg ccagtttaaa atcaagaata ttcacaaggc tggcaaccga tatagcggtg    720
taggaagcac ggacatcaat ttcgccacca tcatgcattc tgaaagcacc tgatacatct    780
ttcatctgca gcataaaatt gtacaggttg cccctattga ttgatgacaa tgctctttcg    840
ctccctattg tcacaagtgt atttacagca gcataagtcg tagctaggtg aggcaactgt    900
ccaggtccac cactatatcc accatcttta tcctgacatc gagctaagaa gtctatgata    960
tcattctcaa gatcatcatc aagtgcttca tccagcaaag caagtggatg aaccatccag   1020
tagcatagcc aagggcgatt ggcatctaga acatgaaagg ctggtcccat atgcctcagc   1080
ccaggcgtca gatactcgat atgctgatca cgccacagct ctagcatgat ggatttcgtg   1140
ttgggcgcgg ccccgaagag ggagcggtag atgtcgccaa ccctggcctc caccttcatc   1200
tgctccacct gcgtcaccgt gagcctcggt aggtcgggat ccgcc                   1245
```

<210> SEQ ID NO 45
<211> LENGTH: 414
<212> TYPE: PRT
<213> ORGANISM: Zea mays

<400> SEQUENCE: 45

```
Ala Asp Pro Asp Leu Pro Arg Leu Thr Val Thr Gln Val Glu Gln Met
  1               5                  10                  15

Lys Val Glu Ala Arg Val Gly Asp Ile Tyr Arg Ser Leu Phe Gly Ala
             20                  25                  30

Ala Pro Asn Thr Lys Ser Ile Met Leu Glu Leu Trp Arg Asp Gln His
         35                  40                  45

Ile Glu Tyr Leu Thr Pro Gly Leu Arg His Met Gly Pro Ala Phe His
     50                  55                  60

Val Leu Asp Ala Asn Arg Pro Trp Leu Cys Tyr Trp Met Val His Pro
 65                  70                  75                  80

Leu Ala Leu Leu Asp Glu Ala Leu Asp Asp Asp Leu Glu Asn Asp Ile
                 85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn
        115                 120                 125

Thr Leu Val Thr Ile Gly Ser Glu Arg Ala Leu Ser Ser Ile Asn Arg
    130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190

Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Arg Ser Ser Tyr Ser Cys Lys Arg Pro Ser Gly Glu Asp
    290                 295                 300

Ala Cys Ser Thr Ser Ser Tyr Gly Cys Thr Ala Asn Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380
```

```
Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410


<210> SEQ ID NO 46
<211> LENGTH: 5247
<212> TYPE: DNA
<213> ORGANISM: Artificial Sequence
<220> FEATURE:
<223> OTHER INFORMATION: Description of Artificial Sequence: Plasmid
      pBI121-35S-AtFTA

<400> SEQUENCE: 46

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740

tttaatacgc gatagaaaac aaaatatagc gcgcaaacta ggataaatta tcgcgcgcgg   1800

tgtcatctat gttactagat cgggcctcct gtcaatgctg gcggcggctc tggtggtggt   1860
```

-continued

```
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccatgaatt tcgacgagac cgtgccactg   3360
agccaacgat tggagtggtc agacgtggtc ccattgactc aggacgatgg tccgaatcca   3420
gtggtgccaa ttgcctacaa ggaagagttc cgcgagacta tggattactt ccgtgcgatt   3480
tacttttccg acgagcgatc tcctcgcgca ctacgactca cggaagaaac cctcctctta   3540
aactccggca actacacagt gtggcatttc aggcgcctag tactcgaggc ccttaatcac   3600
gacttgtttg aagaactcga gttcatcgaa cgcattgctg aggataactc taagaactac   3660
caactgtggc atcatcggcg atgggttgca gagaaactgg gtcctgatgt tgcaggggaga   3720
gaacttgaat ttacccgtag agtactttca cttgatgcca aacattatca tgcttggtca   3780
cataggcagt ggacactacg ggcattagga ggatgggaag atgagctcga ttactgtcac   3840
gagctccttg aagctgacgt ctttaacaat tccgcctgga atcagaggta ttatgtcatc   3900
acccaatctc ctttgttggg aggcctagaa gccatgagag aatctgaagt aagctacaca   3960
atcaaagcca ttttaaccaa tcctgcaaac gagagctcat ggcgatacct aaaagctctt   4020
tacaaagacg acaaagaatc ctggattagt gatccaagtg tttcctcagt ctgtttgaat   4080
gttctatccc gcacagattg cttccatgga ttcgctctga gcaccctttt ggatcttcta   4140
tgtgatggac tgagaccaac caacgagcat aaagactcag tgagagctct agctaatgaa   4200
gaaccagaga ctaacttggc caatttggtg tgtactattc ttggtcgtgt agatcctgta   4260
```

agagctaact attgggcatg gaggaagagc aagattacag tggcagcaat ttgactcgaa 4320
tttccccgat cgttcaaaca tttggcaata aagtttctta agattgaatc ctgttgccgg 4380
tcttgcgatg attatcatat aatttctgtt gaattacgtt aagcatgtaa taattaacat 4440
gtaatgcatg acgttattta tgagatgggt ttttatgatt agagtcccgc aattatacat 4500
ttaatacgcg atagaaaaca aaatatagcg cgcaaactag gataaattat cgcgcgcggt 4560
gtcatctatg ttactagatc gggaattcac tggccgtcgt tttacaacgt cgtgactggg 4620
aaaaccctgg cgttacccaa cttaatcgcc ttgcagcaca tccccctttc gccagctggc 4680
gtaatagcga agaggcccgc accgatcgcc cttcccaaca gttgcgcagc ctgaatggcg 4740
cccgctcctt tcgctttctt cccttccttt ctcgccacgt tcgccggctt tccccgtcaa 4800
gctctaaatc gggggctccc tttagggttc cgatttagtg ctttacggca cctcgacccc 4860
aaaaaacttg atttgggtga tggttcacgt agtgggccat cgccctgata gacggttttt 4920
cgccctttga cgttggagtc cacgttcttt aatagtggac tcttgttcca aactggaaca 4980
acactcaacc ctatctcggg ctattctttt gatttataag ggattttgcc gatttcggaa 5040
ccaccatcaa acaggatttt cgcctgctgg ggcaaaccag cgtggaccgc ttgctgcaac 5100
tctctcaggg ccaggcggtg aagggcaatc agctgttgcc cgtctcactg gtgaaaagaa 5160
aaaccacccc agtacattaa aaacgtccgc aatgtgttat taagttgtct aagcgtcaat 5220
ttgtttacac cacaatatat cctgcca 5247

<210> SEQ ID NO 47
<211> LENGTH: 5373
<212> TYPE: DNA
<213> ORGANISM: Artificial Sequence
<220> FEATURE:
<223> OTHER INFORMATION: Description of Artificial Sequence: Plasmid pBI121-rd29A-anti-AtFTA

<400> SEQUENCE: 47
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020

```
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
```

```
accctcctct gttttactca caaatatgca aactagaaaa caatcatcag gaataaaggg   3420
tttgattact tctattggaa agactctaga ggatcctcaa attgctgcca ctgtaatctt   3480
gctcttcctc catgcccaat agttagctct tataggatct acacgaccaa gaatagtaca   3540
caccaaattg gccaagttag tctctggttc ttcattagct agagctctca ctgagtcttt   3600
atgctcgttg gttggtctca gtccatcaca tagaagatcc aaaagggtgc tcagagcgaa   3660
tccatggaag caatctgtgc gggatagaac attcaaacag actgaggaaa cacttggatc   3720
actaatccag gattctttgt cgtctttgta aagcgctttt aggtatcgcc atgagctctc   3780
gtttgcagga ttggttaaaa tggctttgat tgtgtagctt acttcagatt ctctcatggc   3840
ttctaggcct cccaacaaag gagattgggt gatgacataa tacctctgat tccaggcgga   3900
attgttaaag acgtcagctt caaggagctc gtgacagtaa tcgagctcat cttcccatcc   3960
tcctaatgcc cgtagtgtcc actgcctatg tgaccaagca tgataatgtt tggcatcaag   4020
tgaaagtact ctacgggtaa attcaagttc tctccctgca acatcaggac ccagtttctc   4080
tgcaacccat cgccgatgat gccacagttg gtagttctta gagttatcct cagcaatgcg   4140
ttcgatgaac tcgagttctt caaacaagtc gtgattaagg gcctcgagta ctaggcgcct   4200
gaaatgccac actgtgtagt tgccggagtt taagaggagg gtttcttccg tgagtcgtag   4260
tgcgcgagga gatcgctcgt cggaaaagta aatcgcacgg aagtaatcca tagtctcgcg   4320
gaactcttcc ttgtaggcaa ttggcaccac tggattcgga ccatcgtcct gagtcaatgg   4380
gaccacgtct gaccactcca atcgttggct cagtggcacg gtctcgtcga aattcatccc   4440
ctcgaatttc cccgatcgtt caaacatttg gcaataaagt ttcttaagat tgaatcctgt   4500
tgccggtctt gcgatgatta tcatataatt tctgttgaat tacgttaagc atgtaataat   4560
taacatgtaa tgcatgacgt tatttatgag atgggttttt atgattagag tcccgcaatt   4620
atacatttaa tacgcgatag aaaacaaaat atagcgcgca aactaggata aattatcgcg   4680
cgcggtgtca tctatgttac tagatcggga attcactggc cgtcgtttta caacgtcgtg   4740
actgggaaaa ccctggcgtt acccaactta atcgccttgc agcacatccc cctttcgcca   4800
gctggcgtaa tagcgaagag gcccgcaccg atcgcccttc ccaacagttg cgcagcctga   4860
atggcgcccg ctcctttcgc tttcttccct tcctttctcg ccacgttcgc cggctttccc   4920
cgtcaagctc taaatcgggg gctcccttta gggttccgat ttagtgcttt acggcacctc   4980
gaccccaaaa aacttgattt gggtgatggt tcacgtagtg ggccatcgcc ctgatagacg   5040
gtttttcgcc ctttgacgtt ggagtccacg ttctttaata gtggactctt gttccaaact   5100
ggaacaacac tcaaccctat ctcgggctat tcttttgatt tataagggat tttgccgatt   5160
tcggaaccac catcaaacag gattttcgcc tgctggggca aaccagcgtg gaccgcttgc   5220
tgcaactctc tcagggccag gcggtgaagg gcaatcagct gttgcccgtc tcactggtga   5280
aaagaaaaac caccccagta cattaaaaac gtccgcaatg tgttattaag ttgtctaagc   5340
gtcaatttgt ttacaccaca atatatcctg cca                                5373
```

<210> SEQ ID NO 48
<211> LENGTH: 6285
<212> TYPE: DNA
<213> ORGANISM: Artificial Sequence
<220> FEATURE:
<223> OTHER INFORMATION: Description of Artificial Sequence: Plasmid
pBI121-35A-DA-AtFTA

<400> SEQUENCE: 48

-continued gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400

-continued

```
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcgctct tcctccatgc ccaatagtta   3360
gctcttacag gatctacacg accaagaata gtacacacca aattggccaa gttagtctct   3420
ggttcttcat tagctagagc tctcactgag tctttatgct cgttggttgg tctcagtcca   3480
tcacatagaa gatccaaaag ggtgctcaga gcgaatccat ggaagcaatc tgtgcgggat   3540
agaacattca aacagactga ggaaacactt ggatcactaa tccaggattc tttgtcgtct   3600
ttgtaaagag cttttaggta tcgccatgag ctctcgtttg caggattggt taaaatggct   3660
ttgattgtgt agcttacttc agattctctc atggcttcta ggcctcccaa caaaggagat   3720
tgggtgatga cataatacct ctgattccag gcggaattgt taaagacgtc agcttcaagg   3780
agctcgtgac agtaatcgag ctcatcttcc catcctccta atgcccggag gatccccatc   3840
tacccgcttc gcgtcggcat ccggtcagtg gcagtgaagg gcgaacagtt cctgattaac   3900
cacaaaccgt tctactttac tggctttggt cgtcatgaag atgcggactt gcgtggcaaa   3960
ggattcgata acgtgctgat ggtgcacgac cacgcattaa tggactggat tggggccaac   4020
tcctaccgta cctcgcatta cccttacgct gaagagatgc tcgactgggc agatgaacat   4080
ggcatcgtgg tgattgatga aactgctgct gtcggctttt cgctctcttt aggcattggt   4140
ttcgaagcgg gcaacaagcc gaaagaactg tacagcgaag aggcagtcaa cggggaaact   4200
cagcaagcgc acttacaggc gattaaagag ctgatagcgc gtgacaaaaa ccacccaagc   4260
gtggtgatgt ggagtattgc caacgaaccg gatacccgtc cgcaaggtgc acgggaatat   4320
ttcgcgccac tggcggaagc aacgcgtaaa ctcgacccga cgcgtccgat cacctgcgtc   4380
aatgtaatgt tctgcgacgc tcacaccgat accatcagcg atctctttga tgtgctgtgc   4440
ctgaaccgtt attacggatg gtatgtccaa agcggcgatt tggaaacggc agagaaggta   4500
ctggaaaaag aacttctggc ctggcaggag aaactgtaca ccgacatgtg gagtgaagag   4560
tatcagtgtg catggctgga tatgtatcac cgcgtctttg atcgcgtcag cgccgtcgtc   4620
ggtgaacagg tatggaattt cgccgatttt gcgacctcgc aaggcatatt gcgcgttggc   4680
ggtaacaaga aagggatctt cactcgcgac cgcaaaccga agtcggcggc ttttctgctg   4740
```

-continued

```
caaaaacgct ggactggcat gaacttcggt gaaaaaccgc agcagggagg caaacaatga   4800

atcaacaact ctcctggcgc accatcgtcg gctacagcct cgggaattgc taccgagctc   4860

gctcttcctc catgcccaat agttagctct tacaggatct acacgaccaa gaatagtaca   4920

caccaaattg gccaagttag tctctggttc ttcattagct agagctctca ctgagtcttt   4980

atgctcgttg gttggtctca gtccatcaca tagaagatcc aaaagggtgc tcagagcgaa   5040

tccatggaag caatctgtgc gggatagaac attcaaacag actgaggaaa cacttggatc   5100

actaatccag gattctttgt cgtctttgta aagagctttt aggtatcgcc atgagctctc   5160

gtttgcagga ttggttaaaa tggctttgat tgtgtagctt acttcagatt ctctcatggc   5220

ttctaggcct cccaacaaag gagattgggt gatgacataa tacctctgat tccaggcgga   5280

attgttaaag acgtcagctt caaggagctc gtgacagtaa tcgagctcat cttcccatcc   5340

tcctaatgcc cgctcgaatt tccccgatcg ttcaaacatt tggcaataaa gtttcttaag   5400

attgaatcct gttgccggtc ttgcgatgat tatcatataa tttctgttga attacgttaa   5460

gcatgtaata attaacatgt aatgcatgac gttatttatg agatgggttt ttatgattag   5520

agtcccgcaa ttatacattt aatacgcgat agaaaacaaa atatagcgcg caaactagga   5580

taaattatcg cgcgcggtgt catctatgtt actagatcgg gaattcactg gccgtcgttt   5640

tacaacgtcg tgactgggaa aaccctggcg ttacccaact taatcgcctt gcagcacatc   5700

ccccctttcgc cagctggcgt aatagcgaag aggcccgcac cgatcgccct tcccaacagt   5760

tgcgcagcct gaatggcgcc cgctcctttc gctttcttcc cttcctttct cgccacgttc   5820

gccggctttc cccgtcaagc tctaaatcgg gggctccctt tagggttccg atttagtgct   5880

ttacggcacc tcgaccccaa aaaacttgat ttgggtgatg gttcacgtag tgggccatcg   5940

ccctgataga cggtttttcg ccctttgacg ttggagtcca cgttctttaa tagtggactc   6000

ttgttccaaa ctggaacaac actcaaccct atctcgggct attcttttga tttataaggg   6060

attttgccga tttcggaacc accatcaaac aggattttcg cctgctgggg caaaccagcg   6120

tggaccgctt gctgcaactc tctcagggcc aggcggtgaa gggcaatcag ctgttgcccg   6180

tctcactggt gaaaagaaaa accaccccag tacattaaaa acgtccgcaa tgtgttatta   6240

agttgtctaa gcgtcaattt gtttacacca caatatatcc tgcca                   6285
```

```
<210> SEQ ID NO 49
<211> LENGTH: 6409
<212> TYPE: DNA
<213> ORGANISM: Artificial Sequence
<220> FEATURE:
<223> OTHER INFORMATION: Description of Artificial Sequence: Plasmid
      pBI121-RD29A-DA-AtFTA

<400> SEQUENCE: 49
```

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480
```

-continued

```
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
```

```
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctcg ctcttcctcc atgcccaata   3480
gttagctctt acaggatcta cacgaccaag aatagtacac accaaattgg ccaagttagt   3540
ctctggttct tcattagcta gagctctcac tgagtcttta tgctcgttgg ttggtctcag   3600
tccatcacat agaagatcca aaagggtgct cagagcgaat ccatggaagc aatctgtgcg   3660
ggatagaaca ttcaaacaga ctgaggaaac acttggatca ctaatccagg attctttgtc   3720
gtctttgtaa agagctttta ggtatcgcca tgagctctcg tttgcaggat tggttaaaat   3780
ggctttgatt gtgtagctta cttcagattc tctcatggct tctaggcctc ccaacaaagg   3840
agattgggtg atgacataat acctctgatt ccaggcggaa ttgttaaaga cgtcagcttc   3900
aaggagctcg tgacagtaat cgagctcatc ttcccatcct cctaatgccc ggaggatccc   3960
catctacccg cttcgcgtcg gcatccggtc agtggcagtg aagggcgaac agttcctgat   4020
taaccacaaa ccgttctact ttactggctt tggtcgtcat gaagatgcgg acttgcgtgg   4080
caaaggattc gataacgtgc tgatggtgca cgaccacgca ttaatggact ggattggggc   4140
caactcctac cgtacctcgc attaccctta cgctgaagag atgctcgact gggcagatga   4200
acatggcatc gtggtgattg atgaaactgc tgctgtcggc ttttcgctct ctttaggcat   4260
tggtttcgaa gcgggcaaca agccgaaaga actgtacagc gaagaggcag tcaacgggga   4320
aactcagcaa gcgcacttac aggcgattaa agagctgata gcgcgtgaca aaaaccaccc   4380
aagcgtggtg atgtggagta ttgccaacga accggatacc cgtccgcaag gtgcacggga   4440
atatttcgcg ccactggcgg aagcaacgcg taaactcgac ccgacgcgtc cgatcacctg   4500
cgtcaatgta atgttctgcg acgctcacac cgataccatc agcgatctct ttgatgtgct   4560
gtgcctgaac cgttattacg gatggtatgt ccaaagcggc gatttggaaa cggcagagaa   4620
ggtactggaa aaagaacttc tggcctggca ggagaaactg tacaccgaca tgtggagtga   4680
agagtatcag tgtgcatggc tggatatgta tcaccgcgtc tttgatcgcg tcagcgccgt   4740
cgtcggtgaa caggtatgga atttcgccga ttttgcgacc tcgcaaggca tattgcgcgt   4800
tggcggtaac aagaaaggga tcttcactcg cgaccgcaaa ccgaagtcgg cggcttttct   4860
gctgcaaaaa cgctggactg gcatgaactt cggtgaaaaa ccgcagcagg gaggcaaaca   4920
atgaatcaac aactctcctg gcgcaccatc gtcggctaca gcctcgggaa ttgctaccga   4980
gctcgctctt cctccatgcc caatagttag ctcttacagg atctacacga ccaagaatag   5040
tacacaccaa attggccaag ttagtctctg gttcttcatt agctagagct ctcactgagt   5100
ctttatgctc gttggttggt ctcagtccat cacatagaag atccaaaagg gtgctcagag   5160
cgaatccatg gaagcaatct gtgcgggata gaacattcaa acagactgag gaaacacttg   5220
```

gatcactaat ccaggattct ttgtcgtctt tgtaaagagc ttttaggtat cgccatgagc 5280
tctcgtttgc aggattggtt aaaatggctt tgattgtgta gcttacttca gattctctca 5340
tggcttctag gcctcccaac aaaggagatt gggtgatgac ataatacctc tgattccagg 5400
cggaattgtt aaagacgtca gcttcaagga gctcgtgaca gtaatcgagc tcatcttccc 5460
atcctcctaa tgcccgctcg aatttccccg atcgttcaaa catttggcaa taaagtttct 5520
taagattgaa tcctgttgcc ggtcttgcga tgattatcat ataatttctg ttgaattacg 5580
ttaagcatgt aataattaac atgtaatgca tgacgttatt tatgagatgg gtttttatga 5640
ttagagtccc gcaattatac atttaatacg cgatagaaaa caaaatatag cgcgcaaact 5700
aggataaatt atcgcgcgcg gtgtcatcta tgttactaga tcgggaattc actggccgtc 5760
gttttacaac gtcgtgactg ggaaaaccct ggcgttaccc aacttaatcg ccttgcagca 5820
catccccctt tcgccagctg gcgtaatagc gaagaggccc gcaccgatcg cccttcccaa 5880
cagttgcgca gcctgaatgg cgcccgctcc tttcgctttc ttcccttcct ttctcgccac 5940
gttcgccggc tttccccgtc aagctctaaa tcgggggctc cctttagggt tccgatttag 6000
tgctttacgg cacctcgacc ccaaaaaact tgatttgggt gatggttcac gtagtgggcc 6060
atcgccctga tagacggttt ttcgcccttt gacgttggag tccacgttct ttaatagtgg 6120
actcttgttc caaactggaa caacactcaa ccctatctcg ggctattctt ttgatttata 6180
agggattttg ccgatttcgg aaccaccatc aaacaggatt ttcgcctgct ggggcaaacc 6240
agcgtggacc gcttgctgca actctctcag ggccaggcgg tgaagggcaa tcagctgttg 6300
cccgtctcac tggtgaaaag aaaaaccacc ccagtacatt aaaaacgtcc gcaatgtgtt 6360
attaagttgt ctaagcgtca atttgtttac accacaatat atcctgcca 6409

<210> SEQ ID NO 50
<211> LENGTH: 1254
<212> TYPE: DNA
<213> ORGANISM: Artificial Sequence
<220> FEATURE:
<223> OTHER INFORMATION: Description of Artificial Sequence: Plasmid MuA-anti-GmFTA

<400> SEQUENCE: 50
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
aggaagtctg ctcttgcgcc aaatccaata gttggttcta attggatcaa cttgttttag 420
gatagaacaa atatttcgtg ctatatttaa attttgttgt tcccctttct catcatcatc 480
taaatcttgt ttatccatat ctgcggtctt taaggcgtca atggcatctc taatgtcttc 540
atttggttga taaccaaagc atataagatc taaaatagtg ctaagagcaa acacgtagtt 600
gctcttagtt ctcaaaatct ttaagcatac tgaagaaact tgaggatcat ttacccatga 660
agtagtttca cctttataaa gtcctcgtag atatctccac gagctttcat tttcagggta 720
ggctataatg gcttcgatgg tgtaaagcac ttcagactct ctcatagctt ttaggccccc 780
caagaaagga gaccttgtta tgacaaaata tctctgattc caagcagaat tgttaaaaat 840

```
gtcttcttta agtagttctg tgcaataatt aagttcatct tcccatcctc ctagtgtttg     900
aagagcccac tgtctatgag accatgcatg ataatgtttg gcatcaacgg acagtatctt     960
tttggtgaac tcgagctgag ctcgaatttc cccgatcgtt caaacatttg gcaataaagt    1020
ttcttaagat tgaatcctgt tgccggtctt gcgatgatta tcatataatt tctgttgaat    1080
tacgttaagc atgtaataat taacatgtaa tgcatgacgt tatttatgag atgggttttt    1140
atgattagag tcccgcaatt atacatttaa tacgcgatag aaaacaaaat atagcgcgca    1200
aactaggata aattatcgcg cgcggtgtca tctatgttac tagatcggga attc          1254
```

<210> SEQ ID NO 51
<211> LENGTH: 1822
<212> TYPE: DNA
<213> ORGANISM: Artificial Sequence
<220> FEATURE:
<223> OTHER INFORMATION: Description of Artificial Sequence: Plasmid RD29A-anti-GmFTA

<400> SEQUENCE: 51

```
ggagccatag atgcaattca atcaaactga aatttctgca agaatctcaa acacggagat      60
ctcaaagttt gaaagaaaat ttatttcttc gactcaaaac aaacttacga aatttaggta     120
gaacttatat acattatatt gtaatttttt gtaacaaaat gtttttatta ttattataga     180
attttactgg ttaaattaaa aatgaataga aaaggtgaat taagaggaga gaggaggtaa     240
acattttctt ctattttttc atattttcag gataaattat tgtaaaagtt tacaagattt     300
ccatttgact agtgtaaatg aggaatattc tctagtaaga tcattatttc atctacttct     360
tttatcttct accagtagag gaataaacaa tatttagctc ctttgtaaat acaaattaat     420
tttccttctt gacatcattc aattttaatt ttacgtataa aataaaagat catacctatt     480
agaacgatta aggagaaata caattcgaat gagaaggatg tgccgtttgt tataataaac     540
agccacacga cgtaaacgta aaatgaccac atgatgggcc aatagacatg gaccgactac     600
taataatagt aagttacatt ttaggatgga ataaatatca taccgacatc agttttgaaa     660
gaaaagggaa aaaaagaaaa aataaataaa agatatacta ccgacatgag ttccaaaaag     720
caaaaaaaaa gatcaagccg acacagacac gcgtagagag caaaatgact ttgacgtcac     780
accacgaaaa cagacgcttc atacgtgtcc ctttatctct ctcagtctct ctataaactt     840
agtgagaccc tcctctgttt tactcacaaa tatgcaaact agaaaacaat catcaggaat     900
aaagggtttg attacttcta ttggaaagag gaagtctgct cttgcgccaa atccaatagt     960
tggttctaat tggatcaact tgttttagga tagaacaaat atttcgtgct atatttaaat    1020
tttgttgttc ccctttctca tcatcatcta aatcttgttt atccatatct gcggtcttta    1080
aggcgtcaat ggcatctcta atgtcttcat ttggttgata accaaagcat ataagatcta    1140
aaatagtgct aagagcaaac acgtagttgc tcttagttct caaaatcttt aagcatactg    1200
aagaaacttg aggatcattt acccatgaag tagtttcacc tttataaagt cctcgtagat    1260
atctccacga gctttcattt tcagggtagg ctataatggc ttcgatggtg taaagcactt    1320
cagactctct catagctttt aggcccccca agaaaggaga ccttgttatg acaaaatatc    1380
tctgattcca agcagaattg ttaaaaatgt cttctttaag tagttctgtg caataattaa    1440
gttcatcttc ccatcctcct agtgtttgaa gagcccactg tctatgagac catgcatgat    1500
aatgtttggc atcaacggac agtatctttt tggtgaactc gagctgagct cgaatttccc    1560
cgatcgttca aacatttggc aataaagttt cttaagattg aatcctgttg ccggtcttgc    1620
```

gatgattatc atataatttc tgttgaatta cgttaagcat gtaataatta acatgtaatg 1680
catgacgtta tttatgagat gggtttttat gattagagtc ccgcaattat acatttaata 1740
cgcgatagaa aacaaaatat agcgcgcaaa ctaggataaa ttatcgcgcg cggtgtcatc 1800
tatgttacta gatcgggaat tc 1822

<210> SEQ ID NO 52
<211> LENGTH: 1570
<212> TYPE: DNA
<213> ORGANISM: Artificial Sequence
<220> FEATURE:
<223> OTHER INFORMATION: Description of Artificial Sequence: Plasmid
MuA-HP-GmFTA-Nos-Term

<400> SEQUENCE: 52
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
aggaagtctg ctcttgcgcc aaatccaata gttggttcta attggatcaa cttgttttag 420
gatagaacaa atatttcgtg ctatatttaa attttgttgt tcccctttct catcatcatc 480
taaatcttgt ttatccatat ctgcggtctt taaggcgtca atggcatctc taatgtcttc 540
atttggttga taaccaaagc atataagatc taaaatagtg ctaagagcaa acacgtagtt 600
gctcttagtt ctcaaaatct ttaagcatac tgaagaaact tgaggatcat ttacccatga 660
agtagtttca cctttataaa gtcctcgtag atatctccac gagctttcat tttcagggta 720
ggctataatg gcttcgatgg tgtaaagcac ttcagactct ctcatagctt ttaggccccc 780
caagaaagga gaccttgtta tgacaaaata tctctgattc caagcagaat tgttaaaaat 840
gtcttcttta agtagttctg tgcaataatt aagttcatct tcccatcctc ctagtgtttg 900
aagagcccac tgtctatgag accatgcatg ataatgtttg gcatcaacgg acagtatctt 960
tttggtgaac tcgagcttaa aggtgaaact acttcatggg taaatgatcc tcaagtttct 1020
tcagtatgct taaagatttt gagaactaag agcaactacg tgtttgctct tagcactatt 1080
ttagatctta tatgctttgg ttatcaacca aatgaagaca ttagagatgc cattgacgcc 1140
ttaaagaccg cagatatgga taaacaagat ttagatgatg atgagaaagg ggaacaacaa 1200
aatttaaata tagcacgaaa tatttgttct atcctaaaac aagttgatcc aattagaacc 1260
aactattgga tttggcgcaa gagcagactt cctgagctcg aatttccccg atcgttcaaa 1320
catttggcaa taaagtttct taagattgaa tcctgttgcc ggtcttgcga tgattatcat 1380
ataatttctg ttgaattacg ttaagcatgt aataattaac atgtaatgca tgacgttatt 1440
tatgagatgg gtttttatga ttagagtccc gcaattatac atttaatacg cgatagaaaa 1500
caaaatatag cgcgcaaact aggataaatt atcgcgcgcg gtgtcatcta tgttactaga 1560
tcgggaattc 1570

<210> SEQ ID NO 53
<211> LENGTH: 2138
<212> TYPE: DNA
<213> ORGANISM: Artificial Sequence
<220> FEATURE:

<223> OTHER INFORMATION: Description of Artificial Sequence: Plasmid RD29AP-HP-GmFTA-Nos-Term

<400> SEQUENCE: 53
ggagccatag atgcaattca atcaaactga aatttctgca agaatctcaa acacggagat 60
ctcaaagttt gaaagaaaat ttatttcttc gactcaaaac aaacttacga aatttaggta 120
gaacttatat acattatatt gtaatttttt gtaacaaaat gtttttatta ttattataga 180
attttactgg ttaaattaaa aatgaataga aaaggtgaat taagaggaga gaggaggtaa 240
acattttctt ctattttttc atattttcag gataaattat tgtaaaagtt tacaagattt 300
ccatttgact agtgtaaatg aggaatattc tctagtaaga tcattatttc atctacttct 360
tttatcttct accagtagag gaataaacaa tatttagctc ctttgtaaat acaaattaat 420
tttccttctt gacatcattc aattttaatt ttacgtataa aataaaagat catacctatt 480
agaacgatta aggagaaata caattcgaat gagaaggatg tgccgtttgt tataataaac 540
agccacacga cgtaaacgta aaatgaccac atgatgggcc aatagacatg gaccgactac 600
taataatagt aagttacatt ttaggatgga ataaatatca taccgacatc agttttgaaa 660
gaaaagggaa aaaaagaaaa aataaataaa agatatacta ccgacatgag ttccaaaaag 720
caaaaaaaaa gatcaagccg acacagacac gcgtagagag caaaatgact ttgacgtcac 780
accacgaaaa cagacgcttc atacgtgtcc ctttatctct ctcagtctct ctataaactt 840
agtgagaccc tcctctgttt tactcacaaa tatgcaaact agaaaacaat catcaggaat 900
aaagggtttg attacttcta ttggaaagag gaagtctgct cttgcgccaa atccaatagt 960
tggttctaat tggatcaact tgttttagga tagaacaaat atttcgtgct atatttaaat 1020
tttgttgttc ccctttctca tcatcatcta aatcttgttt atccatatct gcggtcttta 1080
aggcgtcaat ggcatctcta atgtcttcat ttggttgata accaaagcat ataagatcta 1140
aaatagtgct aagagcaaac acgtagttgc tcttagttct caaaatcttt aagcatactg 1200
aagaaacttg aggatcattt acccatgaag tagtttcacc tttataaagt cctcgtagat 1260
atctccacga gctttcattt tcagggtagg ctataatggc ttcgatggtg taaagcactt 1320
cagactctct catagctttt aggcccccca agaaaggaga ccttgttatg acaaaatatc 1380
tctgattcca agcagaattg ttaaaaatgt cttctttaag tagttctgtg caataattaa 1440
gttcatcttc ccatcctcct agtgtttgaa gagcccactg tctatgagac catgcatgat 1500
aatgtttggc atcaacggac agtatctttt tggtgaactc gagcttaaag gtgaaactac 1560
ttcatgggta aatgatcctc aagtttcttc agtatgctta aagattttga gaactaagag 1620
caactacgtg tttgctctta gcactatttt agatcttata tgctttggtt atcaaccaaa 1680
tgaagacatt agagatgcca ttgacgcctt aaagaccgca gatatggata aacaagattt 1740
agatgatgat gagaaagggg aacaacaaaa tttaaatata gcacgaaata tttgttctat 1800
cctaaaacaa gttgatccaa ttagaaccaa ctattggatt tggcgcaaga gcagacttcc 1860
tgagctcgaa tttccccgat cgttcaaaca tttggcaata aagtttctta agattgaatc 1920
ctgttgccgg tcttgcgatg attatcatat aatttctgtt gaattacgtt aagcatgtaa 1980
taattaacat gtaatgcatg acgttattta tgagatgggt ttttatgatt agagtcccgc 2040
aattatacat ttaatacgcg atagaaaaca aaatatagcg cgcaaactag gataaattat 2100
cgcgcgcggt gtcatctatg ttactagatc gggaattc 2138

<210> SEQ ID NO 54

<211> LENGTH: 5511
<212> TYPE: DNA
<213> ORGANISM: Artificial Sequence
<220> FEATURE:
<223> OTHER INFORMATION: Description of Artificial Sequence: Plasmid
pBI121-35S-Anti-AtFTB

<400> SEQUENCE: 54
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tccgtccgga attcccgggt cgacccacgc 3360
gtccgggaga ttcagcgaga taagcaattg gattatctga tgaaaggctt aaggcagctt 3420
ggtccgcagt tttcttcctt agatgctaat cgaccttggc tttgttactg gattcttcat 3480
tcaatagctt tgcttgggga gactgtggat gatgaattag aaagcaatgc cattgacttc 3540
cttggacgct gccagggctc tgaaggtgga tacggtggtg gtcctggcca acttccacat 3600
cttgcaacta cttatgctgc agtgaatgca cttgttactt taggaggtga caaagccctt 3660
tcttcaatta atagagaaaa aatgtcttgt tttttaagac ggatgaagga tacaagtgga 3720
ggtttcagga tgcatgatat gggagaaatg gatgttcgtg catgctacac tgcaatttcg 3780
gttgcaagca tcctaaatat tatggatgat gaactcaccc agggcctagg agattacatc 3840
ttgagttgcc aaacttatga aggtggcatt ggaggggaac ctggctccga agctcacggt 3900
gggtatacct actgtggttt ggctgctatg attttaatca atgaggtcga ccgtttgaat 3960
ttggattcat taatgaattg ggctgtacat cgacaaggag tagaaatggg atttcaaggt 4020
aggacgaaca aattggtcga tggttgctac acattttggc aggcagcccc ttgtgttcta 4080
ctacaaagat tatattcaac caatgatcat gacgttcatg gatcatcaca tatatcagaa 4140
gggacaaatg aagaacatca tgctcatgat gaagatgacc ttgaagacag tgatgatgat 4200
gatgattctg atgaggacaa cgatgaagat tcagtgaatg gtcacagaat ccatcataca 4260
tccacctaca ttaacaggag aatgcaactg gtttttgata gcctcggctt gcagagatat 4320
gtactcttgt gctctaagat ccctgacggt ggattcagag acaagccgag gaaaccccgt 4380
gacttctacc acacatgtta ctgcctgagc ggcttgtctg tggctcagca cgcttggtta 4440
aaagacgagg acactcctcc tttgactcgc gacattatgg gtggctactc gaatctcctt 4500
gaacctgttc aacttcttca caacattgtc atggatcagt ataatgaagc tatcgagttc 4560
ttctttaaag cagcatgact cgaatttccc cgatcgttca aacatttggc aataaagttt 4620
cttaagattg aatcctgttg ccggtcttgc gatgattatc atataatttc tgttgaatta 4680
cgttaagcat gtaataatta acatgtaatg catgacgtta tttatgagat gggtttttat 4740
gattagagtc ccgcaattat acatttaata cgcgatagaa aacaaaatat agcgcgcaaa 4800
ctaggataaa ttatcgcgcg cggtgtcatc tatgttacta gatcgggaat tcactggccg 4860
tcgttttaca acgtcgtgac tgggaaaacc ctggcgttac ccaacttaat cgccttgcag 4920
cacatccccc tttcgccagc tggcgtaata gcgaagaggc ccgcaccgat cgcccttccc 4980
aacagttgcg cagcctgaat ggcgcccgct cctttcgctt tcttcccttc ctttctcgcc 5040
acgttcgccg gctttccccg tcaagctcta aatcgggggc tccctttagg gttccgattt 5100
agtgctttac ggcacctcga ccccaaaaaa cttgatttgg gtgatggttc acgtagtggg 5160
ccatcgccct gatagacggt ttttcgccct ttgacgttgg agtccacgtt ctttaatagt 5220
ggactcttgt tccaaactgg aacaacactc aaccctatct cgggctattc ttttgattta 5280
taagggattt tgccgatttc ggaaccacca tcaaacagga ttttcgcctg ctggggcaaa 5340
ccagcgtgga ccgcttgctg caactctctc agggccaggc ggtgaagggc aatcagctgt 5400
tgcccgtctc actggtgaaa agaaaaacca ccccagtaca ttaaaaacgt ccgcaatgtg 5460
ttattaagtt gtctaagcgt caatttgttt acaccacaat atatcctgcc a 5511

<210> SEQ ID NO 55
<211> LENGTH: 5635
<212> TYPE: DNA
<213> ORGANISM: Artificial Sequence
<220> FEATURE:
<223> OTHER INFORMATION: Description of Artificial Sequence: Plasmid pBI12-RD29AP-Anti-AtFTB

<400> SEQUENCE: 55
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020

```
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
```

-continued

```
accctcctct gttttactca caaatatgca aactagaaaa caatcatcag gaataaaggg   3420
tttgattact tctattggaa aggactctag aggatccgtc cggaattccc gggtcgaccc   3480
acgcgtccgg gagattcagc gagataagca attggattat ctgatgaaag gcttaaggca   3540
gcttggtccg cagttttctt ccttagatgc taatcgacct tggctttgtt actggattct   3600
tcattcaata gctttgcttg gggagactgt ggatgatgaa ttagaaagca atgccattga   3660
cttccttgga cgctgccagg gctctgaagg tggatacggt ggtggtcctg gccaacttcc   3720
acatcttgca actacttatg ctgcagtgaa tgcacttgtt actttaggag gtgacaaagc   3780
cctttcttca attaatagag aaaaaatgtc ttgtttttta agacggatga aggatacaag   3840
tggaggtttc aggatgcatg atatgggaga aatggatgtt cgtgcatgct acactgcaat   3900
ttcggttgca agcatcctaa atattatgga tgatgaactc acccagggcc taggagatta   3960
catcttgagt tgccaaactt atgaaggtgg cattggaggg gaacctggct ccgaagctca   4020
cggtgggtat acctactgtg gtttggctgc tatgatttta atcaatgagg tcgaccgttt   4080
gaatttggat tcattaatga attgggctgt acatcgacaa ggagtagaaa tgggatttca   4140
aggtaggacg aacaaattgg tcgatggttg ctacacattt tggcaggcag ccccttgtgt   4200
tctactacaa agattatatt caaccaatga tcatgacgtt catggatcat cacatatatc   4260
agaagggaca aatgaagaac atcatgctca tgatgaagat gaccttgaag acagtgatga   4320
tgatgatgat tctgatgagg acaacgatga agattcagtg aatggtcaca gaatccatca   4380
tacatccacc tacattaaca ggagaatgca actggttttt gatagcctcg gcttgcagag   4440
atatgtactc ttgtgctcta agatccctga cggtggattc agagacaagc cgaggaaacc   4500
ccgtgacttc taccacacat gttactgcct gagcggcttg tctgtggctc agcacgcttg   4560
gttaaaagac gaggacactc ctcctttgac tcgcgacatt atgggtggct actcgaatct   4620
ccttgaacct gttcaacttc ttcacaacat tgtcatggat cagtataatg aagctatcga   4680
gttcttcttt aaagcagcat gactcgaatt tccccgatcg ttcaaacatt tggcaataaa   4740
gtttcttaag attgaatcct gttgccggtc ttgcgatgat tatcatataa tttctgttga   4800
attacgttaa gcatgtaata attaacatgt aatgcatgac gttatttatg agatgggttt   4860
ttatgattag agtcccgcaa ttatacattt aatacgcgat agaaaacaaa atatagcgcg   4920
caaactagga taaattatcg cgcgcggtgt catctatgtt actagatcgg gaattcactg   4980
gccgtcgttt tacaacgtcg tgactgggaa aaccctggcg ttacccaact taatcgcctt   5040
gcagcacatc ccccttttcgc cagctggcgt aatagcgaag aggcccgcac cgatcgccct   5100
tcccaacagt tgcgcagcct gaatggcgcc cgctcctttc gctttcttcc cttcctttct   5160
cgccacgttc gccggctttc cccgtcaagc tctaaatcgg gggctccctt tagggttccg   5220
atttagtgct ttacggcacc tcgaccccaa aaaacttgat ttgggtgatg gttcacgtag   5280
tgggccatcg ccctgataga cggtttttcg ccctttgacg ttggagtcca cgttctttaa   5340
tagtggactc ttgttccaaa ctggaacaac actcaaccct atctcgggct attcttttga   5400
tttataaggg attttgccga tttcggaacc accatcaaac aggattttcg cctgctgggg   5460
caaaccagcg tggaccgctt gctgcaactc tctcagggcc aggcggtgaa gggcaatcag   5520
ctgttgcccg tctcactggt gaaaagaaaa accaccccag tacattaaaa acgtccgcaa   5580
tgtgttatta agttgtctaa gcgtcaattt gtttacacca caatatatcc tgcca        5635
```

<210> SEQ ID NO 56
<211> LENGTH: 6299

<212> TYPE: DNA
<213> ORGANISM: Artificial Sequence
<220> FEATURE:
<223> OTHER INFORMATION: Description of Artificial Sequence: Plasmid
pBI121-35S-HP-AtFTB

<400> SEQUENCE: 56

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740

tttaatacgc gatagaaaac aaaatatagc gcgcaaacta ggataaatta tcgcgcgcgg   1800

tgtcatctat gttactagat cgggcctcct gtcaatgctg gcggcggctc tggtggtggt   1860

tctggtggcg gctctgaggg tggtggctct gagggtggcg gttctgaggg tggcggctct   1920

gagggaggcg gttccggtgg tggctctggt tccggtgatt ttgattatga aaagatggca   1980

aacgctaata agggggctat gaccgaaaat gccgatgaaa acgcgctaca gtctgacgct   2040

aaaggcaaac ttgattctgt cgctactgat tacggtgctg ctatcgatgg tttcattggt   2100

gacgtttccg gccttgctaa tggtaatggt gctactggtg attttgctgg ctctaattcc   2160
```

```
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcctcct aggccctggg tgagttcatc   3360
atccataata tttaggatgc ttgcaaccga aattgcagtg tagcatgcac gaacatccat   3420
ttctcccata tcatgcatcc tgaaacctcc acttgtatcc ttcatccgtc ttaaaaaaca   3480
agacattttt tctctattaa ttgaagaaag ggctttgtca cctcctaaag taacaagtgc   3540
attcactgca gcataagtag ttgcaagatg tggaagttgg ccaggaccac caccgtatcc   3600
accttcagag ccctggcagc gtccaaggaa gtcaatggca ttgctttcta attcatcatc   3660
cacagtctcc ccaagcaaag ctattgaatg aagaatccag taacaaagcc aaggtcgatt   3720
agcatctaag gaagaaaact gcggaccaag ctgccttaag cctttcatca gataatccaa   3780
ttgcttatct cgctgaatct cccggacgcg tgggtcgacc cgggaattcc ggacgaggat   3840
ccccatctac ccgcttcgcg tcggcatccg gtcagtggca gtgaagggcg aacagttcct   3900
gattaaccac aaaccgttct actttactgg ctttggtcgt catgaagatg cggacttgcg   3960
tggcaaagga ttcgataacg tgctgatggt gcacgaccac gcattaatgg actggattgg   4020
ggccaactcc taccgtacct cgcattaccc ttacgctgaa gagatgctcg actgggcaga   4080
tgaacatggc atcgtggtga ttgatgaaac tgctgctgtc ggcttttcgc tctctttagg   4140
cattggtttc gaagcgggca acaagccgaa agaactgtac agcgaagagg cagtcaacgg   4200
ggaaactcag caagcgcact tacaggcgat taaagagctg atagcgcgtg acaaaaacca   4260
cccaagcgtg gtgatgtgga gtattgccaa cgaaccggat acccgtccgc aaggtgcacg   4320
ggaatatttc gcgccactgg cggaagcaac gcgtaaactc gacccgacgc gtccgatcac   4380
ctgcgtcaat gtaatgttct gcgacgctca caccgatacc atcagcgatc tctttgatgt   4440
gctgtgcctg aaccgttatt acggatggta tgtccaaagc ggcgatttgg aaacggcaga   4500
```

```
gaaggtactg gaaaaagaac ttctggcctg gcaggagaaa ctgtacaccg acatgtggag   4560

tgaagagtat cagtgtgcat ggctggatat gtatcaccgc gtctttgatc gcgtcagcgc   4620

cgtcgtcggt gaacaggtat ggaatttcgc cgattttgcg acctcgcaag gcatattgcg   4680

cgttggcggt aacaagaaag ggatcttcac tcgcgaccgc aaaccgaagt cggcggcttt   4740

tctgctgcaa aaacgctgga ctggcatgaa cttcggtgaa aaaccgcagc agggaggcaa   4800

acaatgaatc aacaactctc ctggcgcacc atcgtcggct acagcctcgg gaattgctac   4860

cgagctcgtc cggaattccc gggtcgaccc acgcgtccgg gagattcagc gagataagca   4920

attggattat ctgatgaaag gcttaaggca gcttggtccg cagttttctt ccttagatgc   4980

taatcgacct tggctttgtt actggattct tcattcaata gctttgcttg gggagactgt   5040

ggatgatgaa ttagaaagca atgccattga cttccttgga cgctgccagg gctctgaagg   5100

tggatacggt ggtggtcctg gccaacttcc acatcttgca actacttatg ctgcagtgaa   5160

tgcacttgtt actttaggag gtgacaaagc cctttcttca attaatagag aaaaaatgtc   5220

ttgtttttta agacggatga aggatacaag tggaggtttc aggatgcatg atatgggaga   5280

aatggatgtt cgtgcatgct acactgcaat ttcggttgca agcatcctaa atattatgga   5340

tgatgaactc acccagggcc taggagctcg aatttccccg atcgttcaaa catttggcaa   5400

taaagtttct taagattgaa tcctgttgcc ggtcttgcga tgattatcat ataatttctg   5460

ttgaattacg ttaagcatgt aataattaac atgtaatgca tgacgttatt tatgagatgg   5520

gtttttatga ttagagtccc gcaattatac atttaatacg cgatagaaaa caaaatatag   5580

cgcgcaaact aggataaatt atcgcgcgcg gtgtcatcta tgttactaga tcgggaattc   5640

actggccgtc gttttacaac gtcgtgactg ggaaaaccct ggcgttaccc aacttaatcg   5700

ccttgcagca catccccctt tcgccagctg gcgtaatagc gaagaggccc gcaccgatcg   5760

cccttcccaa cagttgcgca gcctgaatgg cgcccgctcc tttcgctttc ttcccttcct   5820

ttctcgccac gttcgccggc tttccccgtc aagctctaaa tcgggggctc cctttagggt   5880

tccgatttag tgctttacgg cacctcgacc ccaaaaaact tgatttgggt gatggttcac   5940

gtagtgggcc atcgccctga tagacggttt ttcgcccttt gacgttggag tccacgttct   6000

ttaatagtgg actcttgttc caaactggaa caacactcaa ccctatctcg ggctattctt   6060

ttgatttata agggattttg ccgatttcgg aaccaccatc aaacaggatt ttcgcctgct   6120

ggggcaaacc agcgtggacc gcttgctgca actctctcag ggccaggcgg tgaagggcaa   6180

tcagctgttg cccgtctcac tggtgaaaag aaaaaccacc ccagtacatt aaaaacgtcc   6240

gcaatgtgtt attaagttgt ctaagcgtca atttgtttac accacaatat atcctgcca    6299
```

<210> SEQ ID NO 57
<211> LENGTH: 6423
<212> TYPE: DNA
<213> ORGANISM: Artificial Sequence
<220> FEATURE:
<223> OTHER INFORMATION: Description of Artificial Sequence: Plasmid pBI121-RD29AP-HP-AtFTB

<400> SEQUENCE: 57

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240
```

```
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
```

```
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctcc tcctaggccc tgggtgagtt   3480
catcatccat aatatttagg atgcttgcaa ccgaaattgc agtgtagcat gcacgaacat   3540
ccatttctcc catatcatgc atcctgaaac ctccacttgt atccttcatc cgtcttaaaa   3600
aacaagacat tttttctcta ttaattgaag aaagggcttt gtcacctcct aaagtaacaa   3660
gtgcattcac tgcagcataa gtagttgcaa gatgtggaag ttggccagga ccaccaccgt   3720
atccaccttc agagccctgg cagcgtccaa ggaagtcaat ggcattgctt tctaattcat   3780
catccacagt ctccccaagc aaagctattg aatgaagaat ccagtaacaa agccaaggtc   3840
gattagcatc taaggaagaa aactgcggac caagctgcct taagcctttc atcagataat   3900
ccaattgctt atctcgctga atctcccgga cgcgtgggtc gacccgggaa ttccggacga   3960
ggatccccat ctacccgctt cgcgtcggca tccggtcagt ggcagtgaag ggcgaacagt   4020
tcctgattaa ccacaaaccg ttctacttta ctggctttgg tcgtcatgaa gatgcggact   4080
tgcgtggcaa aggattcgat aacgtgctga tggtgcacga ccacgcatta atggactgga   4140
ttggggccaa ctcctaccgt acctcgcatt acccttacgc tgaagagatg ctcgactggg   4200
cagatgaaca tggcatcgtg gtgattgatg aaactgctgc tgtcggcttt tcgctctctt   4260
taggcattgg tttcgaagcg ggcaacaagc cgaaagaact gtacagcgaa gaggcagtca   4320
acggggaaac tcagcaagcg cacttacagg cgattaaaga gctgatagcg cgtgacaaaa   4380
accacccaag cgtggtgatg tggagtattg ccaacgaacc ggatacccgt ccgcaaggtg   4440
cacgggaata tttcgcgcca ctggcggaag caacgcgtaa actcgacccg acgcgtccga   4500
tcacctgcgt caatgtaatg ttctgcgacg ctcacaccga taccatcagc gatctctttg   4560
atgtgctgtg cctgaaccgt tattacggat ggtatgtcca aagcggcgat ttggaaacgg   4620
cagagaaggt actggaaaaa gaacttctgg cctggcagga gaaactgtac accgacatgt   4680
ggagtgaaga gtatcagtgt gcatggctgg atatgtatca ccgcgtcttt gatcgcgtca   4740
gcgccgtcgt cggtgaacag gtatggaatt tcgccgattt tgcgacctcg caaggcatat   4800
tgcgcgttgg cggtaacaag aaagggatct tcactcgcga ccgcaaaccg aagtcggcgg   4860
cttttctgct gcaaaaacgc tggactggca tgaacttcgg tgaaaaaccg cagcagggag   4920
gcaaacaatg aatcaacaac tctcctggcg caccatcgtc ggctacagcc tcgggaattg   4980
```

```
ctaccgagct cgtccggaat tcccgggtcg acccacgcgt ccgggagatt cagcgagata   5040

agcaattgga ttatctgatg aaaggcttaa ggcagcttgg tccgcagttt tcttccttag   5100

atgctaatcg accttggctt tgttactgga ttcttcattc aatagctttg cttggggaga   5160

ctgtggatga tgaattagaa agcaatgcca ttgacttcct tggacgctgc cagggctctg   5220

aaggtggata cggtggtggt cctggccaac ttccacatct tgcaactact tatgctgcag   5280

tgaatgcact tgttacttta ggaggtgaca aagccctttc ttcaattaat agagaaaaaa   5340

tgtcttgttt tttaagacgg atgaaggata caagtggagg tttcaggatg catgatatgg   5400

gagaaatgga tgttcgtgca tgctacactg caatttcggt tgcaagcatc ctaaatatta   5460

tggatgatga actcacccag ggcctaggag ctcgaatttc cccgatcgtt caaacatttg   5520

gcaataaagt ttcttaagat tgaatcctgt tgccggtctt gcgatgatta tcatataatt   5580

tctgttgaat tacgttaagc atgtaataat taacatgtaa tgcatgacgt tatttatgag   5640

atgggttttt atgattagag tcccgcaatt atacatttaa tacgcgatag aaaacaaaat   5700

atagcgcgca aactaggata aattatcgcg cgcggtgtca tctatgttac tagatcggga   5760

attcactggc cgtcgtttta caacgtcgtg actgggaaaa ccctggcgtt acccaactta   5820

atcgccttgc agcacatccc cctttcgcca gctggcgtaa tagcgaagag gcccgcaccg   5880

atcgcccttc ccaacagttg cgcagcctga atggcgcccg ctcctttcgc tttcttccct   5940

tcctttctcg ccacgttcgc cggctttccc cgtcaagctc taaatcgggg gctcccttta   6000

gggttccgat ttagtgcttt acggcacctc gaccccaaaa aacttgattt gggtgatggt   6060

tcacgtagtg ggccatcgcc ctgatagacg gtttttcgcc ctttgacgtt ggagtccacg   6120

ttctttaata gtggactctt gttccaaact ggaacaacac tcaaccctat ctcgggctat   6180

tcttttgatt tataagggat tttgccgatt tcggaaccac catcaaacag gattttcgcc   6240

tgctggggca aaccagcgtg gaccgcttgc tgcaactctc tcagggccag gcggtgaagg   6300

gcaatcagct gttgcccgtc tcactggtga aaagaaaaac caccccagta cattaaaaac   6360

gtccgcaatg tgttattaag ttgtctaagc gtcaatttgt ttacaccaca atatatcctg   6420

cca                                                                 6423
```

<210> SEQ ID NO 58
<211> LENGTH: 5715
<212> TYPE: DNA
<213> ORGANISM: Artificial Sequence
<220> FEATURE:
<223> OTHER INFORMATION: Description of Artificial Sequence: Plasmid
pBI121-35S-AtFTB

<400> SEQUENCE: 58

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttcttttgt caagaccgac    540
```

```
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
```

```
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccatgccag tagtaacccg cttgattcgt   3360
ttgaagtgtg tagggctcag acttgaccgg agtggactca atcggcgaat ctgtcacgga   3420
ggacacgggg aatcaacgcg gcggagagtg atggaagagc tttcaagcct aaccgtgagt   3480
cagcgcgagc aatttctggt ggagaacgat gtgttcggga tctataatta cttcgacgcc   3540
agcgacgttt ctactcaaaa atacatgatg gagattcagc gagataagca attggattat   3600
ctgatgaaag gcttaaggca gcttggtccg cagttttctt ccttagatgc taatcgacct   3660
tggctttgtt actggattct tcattcaata gctttgcttg gggagactgt ggatgatgaa   3720
ttagaaagca atgccattga cttccttgga cgctgccagg gctctgaagg tggatacggt   3780
ggtggtcctg gccaacttcc acatcttgca actacttatg ctgcagtgaa tgcacttgtt   3840
actttaggag gtgacaaagc cctttcttca attaatagag aaaaaatgtc ttgtttttta   3900
agacggatga aggatacaag tggaggtttc aggatgcatg atatgggaga aatggatgtt   3960
cgtgcatgct acactgcaat ttcggttgca agcatcctaa atattatgga tgatgaactc   4020
acccagggcc taggagatta catcttgagt tgccaaactt atgaaggtgg cattggaggg   4080
gaacctggct ccgaagctca cggtgggtat acctactgtg gtttggctgc tatgatttta   4140
atcaatgagg tcgaccgttt gaatttggat tcattaatga attgggctgt acatcgacaa   4200
ggagtagaaa tgggatttca aggtaggacg aacaaattgg tcgatggttg ctacacattt   4260
tggcaggcag ccccttgtgt tctactacaa agattatatt caaccaatga tcatgacgtt   4320
catggatcat cacatatatc agaagggaca aatgaagaac atcatgctca tgatgaagat   4380
gaccttgaag acagtgatga tgatgatgat tctgatgagg acaacgatga agattcagtg   4440
aatggtcaca gaatccatca tacatccacc tacattaaca ggagaatgca actggttttt   4500
gatagcctcg gcttgcagag atatgtactc ttgtgctcta agatccctga cggtggattc   4560
agagacaagc cgaggaaacc ccgtgacttc taccacacat gttactgcct gagcggcttg   4620
tctgtggctc agcacgcttg gttaaaagac gaggacactc ctcctttgac tcgcgacatt   4680
atgggtggct actcgaatct ccttgaacct gttcaacttc ttcacaacat tgtcatggat   4740
cagtataatg aagctatcga gttcttcttt aaagcagcat gactcgaatt tccccgatcg   4800
ttcaaacatt tggcaataaa gtttcttaag attgaatcct gttgccggtc ttgcgatgat   4860
tatcatataa tttctgttga attacgttaa gcatgtaata attaacatgt aatgcatgac   4920
gttatttatg agatgggttt ttatgattag agtcccgcaa ttatacattt aatacgcgat   4980
agaaaacaaa atatagcgcg caaactagga taaattatcg cgcgcggtgt catctatgtt   5040
actagatcgg gaattcactg gccgtcgttt tacaacgtcg tgactgggaa aaccctggcg   5100
ttacccaact taatcgcctt gcagcacatc ccccttttcgc cagctggcgt aatagcgaag   5160
aggcccgcac cgatcgccct tcccaacagt tgcgcagcct gaatggcgcc cgctcctttc   5220
gctttcttcc cttcctttct cgccacgttc gccggctttc cccgtcaagc tctaaatcgg   5280
```

gggctccctt tagggttccg atttagtgct ttacggcacc tcgaccccaa aaaacttgat 5340
ttgggtgatg gttcacgtag tgggccatcg ccctgataga cggtttttcg ccctttgacg 5400
ttggagtcca cgttctttaa tagtggactc ttgttccaaa ctggaacaac actcaaccct 5460
atctcgggct attcttttga tttataaggg attttgccga tttcggaacc accatcaaac 5520
aggattttcg cctgctgggg caaaccagcg tggaccgctt gctgcaactc tctcagggcc 5580
aggcggtgaa gggcaatcag ctgttgcccg tctcactggt gaaaagaaaa accaccccag 5640
tacattaaaa acgtccgcaa tgtgttatta agttgtctaa gcgtcaattt gtttacacca 5700
caatatatcc tgcca 5715

<210> SEQ ID NO 59
<211> LENGTH: 1772
<212> TYPE: DNA
<213> ORGANISM: Artificial Sequence
<220> FEATURE:
<223> OTHER INFORMATION: Description of Artificial Sequence: Plasmid MuA-anti-GmFTB-Nos-Term

<400> SEQUENCE: 59
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
gtggtggaga atctgggtgc tttgaccaac tatactggca caatgagagt ccacttaaac 420
agtaacatgt gtgataatga tctctacgtt tacccggttt gtctctcagt ccaccctctt 480
gctcctgtgc acataagaga atatattgct gtaaagcaat actgtgaaaa agtggttctt 540
gtgctctcca ctcattaata aatttatagg caatattttt aaaatcagat gaactggatt 600
cactggtgcc ttcatgctca ccacggcatg ttgcatgact agaggttcca tccaaacttt 660
cttttgcttc agatacataa gataccgcaa aaatctgtga tgtctcttcc atctgtttgt 720
tgataataga agataatctt tgcaatagag caacagcacc tccctgccaa aaggaatagc 780
atccatccac cagtttattt gttctcccct ggaatccaca ttccttacct tgtcggaata 840
ccacccagtc aactaatcga ggcagatcca agtgattaac ctcaccaatc agaatcattg 900
tagctaatcc acaaaaggtg tacccaccat gagcctcaga accaggctca ccagcaatgc 960
caccctcata tgtttgacag cttataatgt agtctccaac attctggatc agctcatcat 1020
ccaaaatgtt caaaacactt gcaacagaaa tggcagtgta gcaagctcga acatcaattt 1080
caccttcatc atgcatcctg aatccaccat ttggttgctt catccgccgc agaaacccat 1140
acagtttatc tctattaatt gatgccaggg atttctcacc acccaaagta ataagtgaat 1200
taacagcagc ataagttgtg gcaatatgag gcatctggcc tggtccccccg gcatatccac 1260 cattcggatc ctggcaacgg ttaagaaaat cgatagcgtt atcttcgagt tcatcatcga 1320
cggattctcc caacaaagca atggagtgga agatccagta gcagagccag ggtcgattag 1380
cgtccaaaac ggaaaatgcg gaactgagat ggcgaaggcc tttggagaca tactgcatgt 1440
gattatcgcg ttgaagctcc aacatgaggg tttgggcgtt gcgaggaatg gtggcgagct 1500
cgaatttccc cgatcgttca aacatttggc aataaagttt cttaagattg aatcctgttg 1560

```
ccggtcttgc gatgattatc atataatttc tgttgaatta cgttaagcat gtaataatta   1620

acatgtaatg catgacgtta tttatgagat gggtttttat gattagagtc ccgcaattat   1680

acatttaata cgcgatagaa aacaaaatat agcgcgcaaa ctaggataaa ttatcgcgcg   1740

cggtgtcatc tatgttacta gatcgggaat tc                                 1772


<210> SEQ ID NO 60
<211> LENGTH: 2340
<212> TYPE: DNA
<213> ORGANISM: Artificial Sequence
<220> FEATURE:
<223> OTHER INFORMATION: Description of Artificial Sequence: Plasmid
      RD29AP-anti-GmFTB-Nos-Term

<400> SEQUENCE: 60

ggagccatag atgcaattca atcaaactga aatttctgca agaatctcaa acacggagat     60

ctcaaagttt gaaagaaaat ttatttcttc gactcaaaac aaacttacga aatttaggta    120

gaacttatat acattatatt gtaatttttt gtaacaaaat gtttttatta ttattataga    180

attttactgg ttaaattaaa aatgaataga aaaggtgaat taagaggaga gaggaggtaa    240

acattttctt ctatttttc atattttcag gataaattat tgtaaaagtt tacaagattt    300

ccatttgact agtgtaaatg aggaatattc tctagtaaga tcattatttc atctacttct    360

tttatcttct accagtagag gaataaacaa tatttagctc ctttgtaaat acaaattaat    420

tttccttctt gacatcattc aattttaatt ttacgtataa aataaaagat catacctatt    480

agaacgatta aggagaaata caattcgaat gagaaggatg tgccgtttgt tataataaac    540

agccacacga cgtaaacgta aaatgaccac atgatgggcc aatagacatg gaccgactac    600

taataatagt aagttacatt ttaggatgga ataaatatca taccgacatc agttttgaaa    660

gaaaagggaa aaaaagaaaa aataaataaa agatatacta ccgacatgag ttccaaaaag    720

caaaaaaaaa gatcaagccg acacagacac gcgtagagag caaaatgact ttgacgtcac    780

accacgaaaa cagacgcttc atacgtgtcc ctttatctct ctcagtctct ctataaactt    840

agtgagaccc tcctctgttt tactcacaaa tatgcaaact agaaaacaat catcaggaat    900

aaagggtttg attacttcta ttggaaaggt ggtggagaat ctgggtgctt tgaccaacta    960

tactggcaca atgagagtcc acttaaacag taacatgtgt gataatgatc tctacgttta   1020

cccggtttgt ctctcagtcc accctcttgc tcctgtgcac ataagagaat atattgctgt   1080

aaagcaatac tgtgaaaaag tggttcttgt gctctccact cattaataaa tttataggca   1140

atatttttaa aatcagatga actggattca ctggtgcctt catgctcacc acggcatgtt   1200

gcatgactag aggttccatc caaactttct tttgcttcag atacataaga taccgcaaaa   1260

atctgtgatg tctcttccat ctgtttgttg ataatagaag ataatctttg caatagagca   1320

acagcacctc cctgccaaaa ggaatagcat ccatccacca gtttatttgt tctcccctgg   1380

aatccacatt ccttaccttg tcggaatacc acccagtcaa ctaatcgagg cagatccaag   1440

tgattaacct caccaatcag aatcattgta gctaatccac aaaaggtgta cccaccatga   1500

gcctcagaac caggctcacc agcaatgcca ccctcatatg tttgacagct tataatgtag   1560

tctccaacat tctggatcag ctcatcatcc aaaatgttca aaacacttgc aacagaaatg   1620

gcagtgtagc aagctcgaac atcaatttca ccttcatcat gcatcctgaa tccaccattt   1680

ggttgcttca tccgccgcag aaacccatac agtttatctc tattaattga tgccagggat   1740

ttctcaccac ccaaagtaat aagtgaatta acagcagcat aagttgtggc aatatgaggc   1800
```

atctggcctg gtcccccggc atatccacca ttcggatcct ggcaacggtt aagaaaatcg 1860
atagcgttat cttcgagttc atcatcgacg gattctccca acaaagcaat ggagtggaag 1920
atccagtagc agagccaggg tcgattagcg tccaaaacgg aaaatgcgga actgagatgg 1980
cgaaggcctt tggagacata ctgcatgtga ttatcgcgtt gaagctccaa catgagggtt 2040
tgggcgttgc gaggaatggt ggcgagctcg aatttccccg atcgttcaaa catttggcaa 2100
taaagtttct taagattgaa tcctgttgcc ggtcttgcga tgattatcat ataatttctg 2160
ttgaattacg ttaagcatgt aataattaac atgtaatgca tgacgttatt tatgagatgg 2220
gtttttatga ttagagtccc gcaattatac atttaatacg cgatagaaaa caaaatatag 2280
cgcgcaaact aggataaatt atcgcgcgcg gtgtcatcta tgttactaga tcgggaattc 2340

<210> SEQ ID NO 61
<211> LENGTH: 2298
<212> TYPE: DNA
<213> ORGANISM: Artificial Sequence
<220> FEATURE:
<223> OTHER INFORMATION: Description of Artificial Sequence: Plasmid
MuA-HP-GmFTB-Nos-Term

<400> SEQUENCE: 61
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360
gtggtggaga atctgggtgc tttgaccaac tatactggca caatgagagt ccacttaaac 420
agtaacatgt gtgataatga tctctacgtt tacccggttt gtctctcagt ccacccctctt 480 gctcctgtgc acataagaga atatattgct gtaaagcaat actgtgaaaa agtggttctt 540
gtgctctcca ctcattaata aatttatagg caatattttt aaaatcagat gaactggatt 600
cactggtgcc ttcatgctca ccacggcatg ttgcatgact agaggttcca tccaaacttt 660
cttttgcttc agatacataa gataccgcaa aaatctgtga tgtctcttcc atctgtttgt 720
tgataataga agataatctt tgcaatagag caacagcacc tccctgccaa aaggaatagc 780
atccatccac cagtttattt gttctcccct ggaatccaca ttccttacct tgtcggaata 840
ccacccagtc aactaatcga ggcagatcca agtgattaac ctcaccaatc agaatcattg 900
tagctaatcc acaaaaggtg tacccaccat gagcctcaga accaggctca ccagcaatgc 960
caccctcata tgtttgacag cttataatgt agtctccaac attctggatc agctcatcat 1020
ccaaaatgtt caaaacactt gcaacagaaa tggcagtgta gcaagctcga acatcaattt 1080
caccttcatc atgcatcctg aatccaccat ttggttgctt catccgccgc agaaacccat 1140
acagtttatc tctattaatt gatgccaggg atttctcacc acccaaagta ataagtgaat 1200
taacagcagc ataagttgtg gcaatatgag gcatctggcc tggtccccccg gcatatccac 1260 cattcggatc ctggcaacgg ttaagaaaat cgatagcgtt atcttcgagt tcatcatcga 1320
cggattctcc caacaaagca atggagtgga agatccagta gcagagccag ggtcgattag 1380
cgtccaaaac ggaaaatgcg gaactgagat ggcgaaggcc tttggagaca tactgcatgt 1440
gattatcgcg ttgaagctcc aacatgaggg tttgggcgtt gcgaggaatg gtggcggtga 1500
ggttaatcac ttggatctgc ctcgattagt tgactgggtg gtattccgac aaggtaagga 1560
atgtggattc caggggagaa caaataaact ggtggatgga tgctattcct tttggcaggg 1620
aggtgctgtt gctctattgc aaagattatc ttctattatc aacaaacaga tggaagagac 1680
atcacagatt tttgcggtat cttatgtatc tgaagcaaaa gaaagtttgg atggaacctc 1740
tagtcatgca acatgccgtg gtgagcatga aggcaccagt gaatccagtt catctgattt 1800
taaaaatatt gcctataaat ttattaatga gtggagagca caagaaccac tttttcacag 1860
tattgcttta cagcaatata ttctcttatg tgcacaggag caagagggtg gactgagaga 1920
caaaccgggt aaacgtagag atcattatca cacatgttac tgtttaagtg gactctcatt 1980
gtgccagtat agttggtcaa agcacccaga ttctccacca cgagctcgaa tttccccgat 2040
cgttcaaaca tttggcaata aagtttctta agattgaatc ctgttgccgg tcttgcgatg 2100
attatcatat aatttctgtt gaattacgtt aagcatgtaa taattaacat gtaatgcatg 2160
acgttattta tgagatgggt ttttatgatt agagtcccgc aattatacat ttaatacgcg 2220
atagaaaaca aaatatagcg cgcaaactag gataaattat cgcgcgcggt gtcatctatg 2280
ttactagatc gggaattc 2298

<210> SEQ ID NO 62
<211> LENGTH: 2866
<212> TYPE: DNA
<213> ORGANISM: Artificial Sequence
<220> FEATURE:
<223> OTHER INFORMATION: Description of Artificial Sequence: Plasmid RD29AP-HP-GmFTB-Nos-Term

<400> SEQUENCE: 62
ggagccatag atgcaattca atcaaactga aatttctgca agaatctcaa acacggagat 60
ctcaaagttt gaaagaaaat ttatttcttc gactcaaaac aaacttacga aatttaggta 120
gaacttatat acattatatt gtaatttttt gtaacaaaat gtttttatta ttattataga 180
attttactgg ttaaattaaa aatgaataga aaaggtgaat taagaggaga gaggaggtaa 240
acattttctt ctattttttc atattttcag gataaattat tgtaaaagtt tacaagattt 300
ccatttgact agtgtaaatg aggaatattc tctagtaaga tcattatttc atctacttct 360
tttatcttct accagtagag gaataaacaa tatttagctc ctttgtaaat acaaattaat 420
tttccttctt gacatcattc aattttaatt ttacgtataa aataaaagat catacctatt 480
agaacgatta aggagaaata caattcgaat gagaaggatg tgccgtttgt tataataaac 540
agccacacga cgtaaacgta aaatgaccac atgatgggcc aatagacatg gaccgactac 600
taataatagt aagttacatt ttaggatgga ataaatatca taccgacatc agttttgaaa 660
gaaaagggaa aaaaagaaaa aataaataaa agatatacta ccgacatgag ttccaaaaag 720
caaaaaaaaa gatcaagccg acacagacac gcgtagagag caaaatgact ttgacgtcac 780
accacgaaaa cagacgcttc atacgtgtcc ctttatctct ctcagtctct ctataaactt 840
agtgagaccc tcctctgttt tactcacaaa tatgcaaact agaaaacaat catcaggaat 900
aaagggtttg attacttcta ttggaaaggt ggtggagaat ctgggtgctt tgaccaacta 960
tactggcaca atgagagtcc acttaaacag taacatgtgt gataatgatc tctacgttta 1020
cccggtttgt ctctcagtcc accctcttgc tcctgtgcac ataagagaat atattgctgt 1080
aaagcaatac tgtgaaaaag tggttcttgt gctctccact cattaataaa tttataggca 1140
atatttttaa aatcagatga actggattca ctggtgcctt catgctcacc acggcatgtt 1200
gcatgactag aggttccatc caaactttct tttgcttcag atacataaga taccgcaaaa 1260
atctgtgatg tctcttccat ctgtttgttg ataatagaag ataatctttg caatagagca 1320
acagcacctc cctgccaaaa ggaatagcat ccatccacca gtttatttgt tctcccctgg 1380
aatccacatt ccttaccttg tcggaatacc acccagtcaa ctaatcgagg cagatccaag 1440
tgattaacct caccaatcag aatcattgta gctaatccac aaaaggtgta cccaccatga 1500
gcctcagaac caggctcacc agcaatgcca ccctcatatg tttgacagct tataatgtag 1560
tctccaacat tctggatcag ctcatcatcc aaaatgttca aaacacttgc aacagaaatg 1620
gcagtgtagc aagctcgaac atcaatttca ccttcatcat gcatcctgaa tccaccattt 1680
ggttgcttca tccgccgcag aaacccatac agtttatctc tattaattga tgccagggat 1740
ttctcaccac ccaaagtaat aagtgaatta acagcagcat aagttgtggc aatatgaggc 1800
atctggcctg gtcccccggc atatccacca ttcggatcct ggcaacggtt aagaaaatcg 1860
atagcgttat cttcgagttc atcatcgacg gattctccca acaaagcaat ggagtggaag 1920
atccagtagc agagccaggg tcgattagcg tccaaaacgg aaaatgcgga actgagatgg 1980
cgaaggcctt tggagacata ctgcatgtga ttatcgcgtt gaagctccaa catgagggtt 2040
tgggcgttgc gaggaatggt ggcggtgagg ttaatcactt ggatctgcct cgattagttg 2100
actgggtggt attccgacaa ggtaaggaat gtggattcca ggggagaaca aataaactgg 2160
tggatggatg ctattccttt tggcagggag gtgctgttgc tctattgcaa agattatctt 2220
ctattatcaa caaacagatg gaagagacat cacagatttt tgcggtatct tatgtatctg 2280
aagcaaaaga aagtttggat ggaacctcta gtcatgcaac atgccgtggt gagcatgaag 2340
gcaccagtga atccagttca tctgatttta aaaatattgc ctataaattt attaatgagt 2400
ggagagcaca agaaccactt tttcacagta ttgctttaca gcaatatatt ctcttatgtg 2460
cacaggagca agagggtgga ctgagagaca aaccgggtaa acgtagagat cattatcaca 2520
catgttactg tttaagtgga ctctcattgt gccagtatag ttggtcaaag cacccagatt 2580
ctccaccacg agctcgaatt tccccgatcg ttcaaacatt tggcaataaa gtttcttaag 2640
attgaatcct gttgccggtc ttgcgatgat tatcatataa tttctgttga attacgttaa 2700
gcatgtaata attaacatgt aatgcatgac gttatttatg agatgggttt ttatgattag 2760
agtcccgcaa ttatacattt aatacgcgat agaaaacaaa atatagcgcg caaactagga 2820
taaattatcg cgcgcggtgt catctatgtt actagatcgg gaattc 2866

<210> SEQ ID NO 63
<211> LENGTH: 1882
<212> TYPE: DNA
<213> ORGANISM: Artificial Sequence
<220> FEATURE:
<223> OTHER INFORMATION: Description of Artificial Sequence: Plasmid MuA-anti-Zea maizeFTB-Nos-Term

<400> SEQUENCE: 63
gaattcaaat ttttcgccag ttctaaatat ccggaaacct cttgggatgc cattgcccat 60
ctatctgtaa tttattgacg aaatagacga aaaggaaggt ggctcctata aagcacatca 120
ttgcgataac agaaaggcca ttgttgaaga tacctctgct gacattggtc cccaagtgga 180
agcaccaccc catgaggagc accgtggagt aagaagacgt tcgagccacg tcgaaaaagc 240
aagtgtgttg atgtagtatc tccattgacg taagggatga cgcacaatcc aactatccat 300
cgcaagacca ttgctctata taagaaagtt aatatcattt cgagtggcca cgctgagctc 360

```
ggatggattg gctccagcaa attagagtac ggtccaagca catgctgagg taatgggcac    420

gaaccagtat cagtcatggc actgtactgg ctaactgcga ggccactgag gcagtagcat    480

gaatgatagt gatctctgtt ctttccaggc ttatccctca agcctccctc tagtacctga    540

gaacaaagta ggatgtattg ttgcagggca atgttatgga agagtgggcc aatttggttg    600

ctctgttgta taaaatcaaa tccaaacttc gcatagtcca cagcagagga agacttattc    660

gcggtgcacc catatgaact ggtgctgcag gcatcctctc ctgatggcct tttgcaggaa    720

tacgaggacc tcaattgctt atcaacaatc gtaattaact tttgtgtgaa agcaatggca    780

gctccctgcc aaaaggagta gcaaccatca accaatttat tagttcgtcc ttgaaatccg    840

cattccactc cttgacgaaa agccacccag ccaatcaaac taggcaagtc aactttctct    900

gcctcattaa gcaggatcaa agcagccaat ccacagaatg tatacccacc atgtgcttca    960

gcataaggct ccccagcaat accaccttca taagtttgac atcttgctat gtagtcgcct   1020

acaccttttg ccagtttaaa atcaagaata ttcacaaggc tggcaaccga tatagcggtg   1080

taggaagcac ggacatcaat ttcgccacca tcatgcattc tgaaagcacc tgatacatct   1140

ttcatctgca gcataaaatt gtacaggttg cccctattga ttgatgacaa tgctctttcg   1200

ctccctattg tcacaagtgt atttacagca gcataagtcg tagctaggtg aggcaactgt   1260

ccaggtccac cactatatcc accatcttta tcctgacatc gagctaagaa gtctatgata   1320

tcattctcaa gatcatcatc aagtgcttca tccagcaaag caagtggatg aaccatccag   1380

tagcatagcc aagggcgatt ggcatctaga acatgaaagg ctggtcccat atgcctcagc   1440

ccaggcgtca gatactcgat atgctgatca cgccacagct ctagcatgat ggatttcgtg   1500

ttgggcgcgg ccccgaagag ggagcggtag atgtcgccaa ccctggcctc caccttcatc   1560

tgctccacct gcgtcaccgt gagcctcggt aggtcgggat ccgccgagct cgaatttccc   1620

cgatcgttca aacatttggc aataaagttt cttaagattg aatcctgttg ccggtcttgc   1680

gatgattatc atataatttc tgttgaatta cgttaagcat gtaataatta acatgtaatg   1740

catgacgtta tttatgagat gggtttttat gattagagtc ccgcaattat acatttaata   1800

cgcgatagaa aacaaaatat agcgcgcaaa ctaggataaa ttatcgcgcg cggtgtcatc   1860

tatgttacta gatcgggaat tc                                             1882
```

<210> SEQ ID NO 64
<211> LENGTH: 2505
<212> TYPE: DNA
<213> ORGANISM: Artificial Sequence
<220> FEATURE:
<223> OTHER INFORMATION: Description of Artificial Sequence: Plasmid MuA-HP-Zea MaizeFTB-Nos-Term

<400> SEQUENCE: 64

```
gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

ggatggattg gctccagcaa attagagtac ggtccaagca catgctgagg taatgggcac    420

gaaccagtat cagtcatggc actgtactgg ctaactgcga ggccactgag gcagtagcat    480
```

gaatgatagt gatctctgtt ctttccaggc ttatccctca agcctccctc tagtacctga 540
gaacaaagta ggatgtattg ttgcagggca atgttatgga agagtgggcc aatttggttg 600
ctctgttgta taaaatcaaa tccaaacttc gcatagtcca cagcagagga agacttattc 660
gcggtgcacc catatgaact ggtgctgcag gcatcctctc ctgatggcct tttgcaggaa 720
tacgaggacc tcaattgctt atcaacaatc gtaattaact tttgtgtgaa agcaatggca 780
gctccctgcc aaaaggagta gcaaccatca accaatttat tagttcgtcc ttgaaatccg 840
cattccactc cttgacgaaa agccacccag ccaatcaaac taggcaagtc aactttctct 900
gcctcattaa gcaggatcaa agcagccaat ccacagaatg tatacccacc atgtgcttca 960
gcataaggct ccccagcaat accaccttca taagtttgac atcttgctat gtagtcgcct 1020
acaccttttg ccagtttaaa atcaagaata ttcacaaggc tggcaaccga tatagcggtg 1080
taggaagcac ggacatcaat ttcgccacca tcatgcattc tgaaagcacc tgatacatct 1140
ttcatctgca gcataaaatt gtacaggttg cccctattga ttgatgacaa tgctctttcg 1200
ctccctattg tcacaagtgt atttacagca gcataagtcg tagctaggtg aggcaactgt 1260
ccaggtccac cactatatcc accatcttta tcctgacatc gagctaagaa gtctatgata 1320
tcattctcaa gatcatcatc aagtgcttca tccagcaaag caagtggatg aaccatccag 1380
tagcatagcc aagggcgatt ggcatctaga acatgaaagg ctggtcccat atgcctcagc 1440
ccaggcgtca gatactcgat atgctgatca cgccacagct ctagcatgat ggatttcgtg 1500
ttgggcgcgg ccccgaagag ggagcggtag atgtcgccaa ccctggcctc caccttcatc 1560
tgctccacct gcgtcaccgt gagcctcggt aggtcgggat ccgccggatc cgctggggag 1620
ccttatgctg aagcacatgg tgggtataca ttctgtggat tggctgcttt gatcctgctt 1680
aatgaggcag agaaagttga cttgcctagt ttgattggct gggtggcttt tcgtcaagga 1740
gtggaatgcg gatttcaagg acgaactaat aaattggttg atggttgcta ctccttttgg 1800
cagggagctg ccattgcttt cacacaaaag ttaattacga ttgttgataa gcaattgagg 1860
tcctcgtatt cctgcaaaag gccatcagga gaggatgcct gcagcaccag ttcatatggg 1920
tgcaccgcga ataagtcttc ctctgctgtg gactatgcga agtttggatt tgattttata 1980
caacagagca accaaattgg cccactcttc cataacattg ccctgcaaca atacatccta 2040
ctttgttctc aggtactaga gggaggcttg agggataagc ctggaaagaa cagagatcac 2100
tatcattcat gctactgcct cagtggcctc gcagttagcc agtacagtgc catgactgat 2160
actggttcgt gcccattacc tcagcatgtg cttggaccgt actctaattt gctggagcca 2220
atccatccaa gcttgaattt ccccgatcgt tcaaacattt ggcaataaag tttcttaaga 2280
ttgaatcctg ttgccggtct tgcgatgatt atcatataat ttctgttgaa ttacgttaag 2340
catgtaataa ttaacatgta atgcatgacg ttatttatga gatgggtttt tatgattaga 2400
gtcccgcaat tatacattta atacgcgata gaaaacaaaa tatagcgcgc aaactaggat 2460
aaattatcgc gcgcggtgtc atctatgtta ctagatcgga agctt 2505

<210> SEQ ID NO 65
<211> LENGTH: 1323
<212> TYPE: DNA
<213> ORGANISM: Pisum sativum

<400> SEQUENCE: 65
caacacctac ctagtgcttc tagttctggt tctaggactg agagtaaaca gaagtgaaga 60
agaatccaga acatggccgg gaatatcgaa gttgaagaag acgatcgtgt gccgctaaga 120

```
ttacgacctg agtggtcaga tgttactccg atcccacaag acgatggccc tagtcccgtc    180
gtgccgatca actactccga agagttttca gaagttatgg attactttcg tgctgtttac    240
ttcgccaaag aactttcctc tcgcgctctt gctctcaccg ccgaagctat cggtttaaac    300
gccggaaact acactgtgtg gcatttccgg cggttattac ttgagtcact gaaagttgac    360
ctacatgttg aacgggaatt cgtggagcgt gttgccagtg gcaattcaaa aaattatcag    420
atttggcatc atagacgatg ggttgctgag aaattaggac ctgaagctag aaacagtgaa    480
cttgagttca ccaaaaagat tctgtctgtt gacgccaaac actatcatgc atggtctcat    540
aggcagtggg ttcttcaaaa tctaggagga tgggaagatg aactcagtta ttgtagtgaa    600
ctgcttgcag aagacatatt taacaattct gcttggaatc agagatactt cgtcataaca    660
aggtctcccg tcttgggagg gctaaaagcc atgagagagt ctgaagtgct tttcaccgtt    720
gaagccatta tttcttaccc agaaaatgaa agctcatgga gatatcttcg aggacttttc    780
aaagatgaat ccacgttata tgtaaatgat gcccaagtat cttcattatg tttaaagatt    840
ttgaaaacta agagcaacta tttgtttgct ctaagtactc tgctggatct atctgcctcg    900
gttattcaac caaatgaaga tttcagagat gccattgagg ctttaagact tcagattttg    960
ataaaacaag attcagatat agcaataact atttgttcta ttttagaaca agttgatcca   1020
attagagtca actattgggt ctggcggaag agtagacttc ctcaggcagc gtaaaggaca   1080
aacttatgtc atatgtgtaa tttttagtct attggaattt gacgtcatgg ataacagggt   1140
ggttgttttt gttatgatat gttttccaga tgtatttcta tatttaacag caaagttgat   1200
ttaacattgg tgttaacaaa ccaatgatct ccaaaaaatc aatgttttat ttctcttcat   1260
ttgtctgatt ttgtggcata acattcttga tgattttgtg gtaaaaaaaa aaaaaaaaaa   1320
aaa                                                                 1323
```

<210> SEQ ID NO 66
<211> LENGTH: 1505
<212> TYPE: DNA
<213> ORGANISM: Lycopersicon esculentum

<400> SEQUENCE: 66

```
taccccgaag gcaattccag tattgaacta ccgccggcag ttttccgatc ggatcccgga     60
gccgagtatc aaatggacag ttgtgaggtg acgaaaacgc gaattccttt caaggaaagg    120
cccgactggg ccgatgtgaa gcccgttccg caagacgacg ggccctgccc ggttgttccc    180
atagcctaca cagaagactt ctctgaaacc atggactact tccgggcaat ttacgtagcc    240
gatgagcgat ctacacgcgc cctccagctt actggtgaag ctattcagct aaaccctgga    300
aattacactg tatggcaatt taggcgtgtt gtgctggagg cattgggtgt tgatttacgt    360
gaagaattga agtttgttga tcgcattgct ggggagaata ccaaaaatta tcaaatatgg    420
catcatagac ggtggcttgc tgagaagctg ggagctgatg ctgtgacaaa tgagctagaa    480
ttcaccaaga aaatattttc tcaggatgca aaaaattatc atgcttggtc ccatcggcag    540
tgggtccttc aagcacttgg aggatgggaa gatgagcttg cttattgtca acaactcctt    600
gaagatgata tttacaacaa ttctgcttgg aatcagagat actttgtcgt aacacgatca    660
cctctactag ggggcctagt ggcaatgagg gaattggaag tgaattacac agttcaagcc    720
atcagagcta gtccagagaa tgaaagtcct tggaggtatc ttcgtggtct ttacaagaat    780
gatacacaat ctctagttca ggattctcaa gtagcatcag tactttggga cgtcttaacc    840
```

```
tcccaaaata gtcatgtgca cgctctgagg ttcttgttgg atcttctttg tcatgatttg     900

gaaccgagcc aagaattgaa aagtgctgta gatgttctta ctccccagtc atgctcacca     960

gatttagcac tgacaaagaa aatttgttcc atcttggaac atgctgatcc aatgagagta    1020

aaatattgga attggcgcaa gagcatggtt cgggttcaat tacttcagag tcagaatgca    1080

gagaggttgg ctaatttgag tgttcaagaa tgacttgtga gaatattgta ctgtgtttac    1140

gaaatacata cttgcatcta aggtgatcct tcgggcacat gtgctgggaa gtgactgaat    1200

atcacgaaga actaaaaaaa ctgtgattgg caacattgta ctactccaaa taggtcactt    1260

tcgatgactt tttgtactgc cttgagtttt ggctctgcta tgttttgtaa gttttggata    1320

tggatgcata gcttattgat acttttggtg acttaaaata ctctggaagg caggtagcat    1380

gtgtataatt cactgttact tcccatgtcg agttagatgc ttgaaaattt tagtaggtgt    1440

tcttttatga agcacacatt aatgtggaaa aaaaaaaaaa aaaaaaaaaa aaaaaaaaaa    1500

aaaaa                                                                1505
```

<210> SEQ ID NO 67
<211> LENGTH: 1218
<212> TYPE: DNA
<213> ORGANISM: Oryza sp.

<400> SEQUENCE: 67

```
gcacgaggtt ctaacgccgc cgccgccgcc gccgtctccg cagaatctga tcgatggcgc      60

cgtcgtcgac gtcgtcggag ggtgcctccg acgagtggtt gccacccagc cggcggccgg     120

agctggcgga cgtggtcccc gtgacgcagg acgacgggcc ccaccccgtg gtggccatcg     180

cctaccggga cgagttccgc gaggtcatgg actacttccg cgccctctac ttcgccggcg     240

agcgcagcgt ccgcgccctc cacctcaccg ccgaggtcat cgaccttaat cccggcaact     300

acacggtgtg gcattttagg cgtcttgttc tagaggcact ggatgctgat ctgcgtgagg     360

aaatggattt tgtggaccga attgtcgaat gtaacccaaa aaattatcaa atctggcatc     420

acaagagatg gcttgcggag aaattaggac cagatattgc aaataaagag cacgaattta     480

caaggaagat actttctatg gatgctaaaa attaccatgc ttggtctcat aggcagtggg     540

ttcttcaagc actgggtgga tgggagactg aactacagta ttgcaaccag ctgcttgagg     600

aagacgtctt caataattca gcttggaatc agagatacct tgtaataaca agttcaccac     660

ttcttggagg ccttgcagca atgcgtgact cggaagtgga ttacacagtt ggggctattc     720

tggctaaccc tcagaatgaa agcccctgga gatacctcaa aggcctgtac aagggtgaaa     780

ataacttgct gatggctgat gagcgcatct ctgatgtttg tctcaaggtc ctgaaacatg     840

attcgacctg cgtatttgct ttgagcttgc tgctcgatct tcttcaaatt ggtttacaac     900

cttcagatga actcaaagga actatcgaag caataaagaa ctctgatcct gaagcagatg     960

aagcagtaga tgctgatctt gcgactgcaa tctgctcaat attgcagaga tgtgatcccc    1020

tgcggataaa ttactggtcc tggtacagga ccactatttc ttctcaaacc tgaagcatgc    1080

agtggcctcc atgaggtcat aatggagata tcttctatct tcgtgtgatt ctgggcgttg    1140

aggtgcctag ctacatttgt tatgaacttt ccttgggcat aactgatcac tgatattact    1200

ccaatattgt gttctaaa                                                  1218
```

<210> SEQ ID NO 68
<211> LENGTH: 1426
<212> TYPE: DNA
<213> ORGANISM: Zea mays

<400> SEQUENCE: 68
gcacgagaca gcgcaattac ttaagctatt tgtattcgga tctgatccaa ccctggtggt 60
cagctggact catcgcccat ggagcacact aagtcaggcc ccagcagttg gccagaactg 120
gccgacgtgg tgccggtgcc gcaggacgat gggcctagcc ctgtggtgtc catcgcctat 180
cgagatgact ttcgtgaggt catggattac ttccgcgccc tctacctcac cggtgagcga 240
agccctcgcg ctctccgcct caccgccgag gccatcgagc tcaaccccgg caactacact 300
gtctggcatt tccggcgcct tattctggag tcactagatt ttgatttact agaggagatg 360
aaatttgtcg aaaaaattgc tgaatgcaat ccaaaaaatt accaaatctg gcaccataag 420
agatggcttg ctgagaaatt aggacctggt attgcaaaca aagagcatga attcacaatg 480
aagatacttg ctattgatgc aaaaaattat catgcttggt ctcataggca gtgggttctt 540
caagcgttgg ggggatggga gactgaatta gaatactgtg accacttact taaggaagac 600
gtcttcaata attcagcttg gaatcagaga tactttgtta taacaagatc accatttctt 660
ggtggccttg cggcaatgcg tgattcagaa gtagactaca caattgaagc tattctagca 720
aacgctcaga atgaaagccc ctggaggtac ctcaagggtc tatacaaggg tgagaataac 780
ctgctagtag aggacgagcg catctctgct gtttgtttca aggtcctgaa gaatgattgg 840
acttgtgtat ttgctttgag tttgctgctc gatcttctct gcactggttt gcagccttca 900
gatgaactta ggtccactct tgaaacaata aggagctccc atcctgaaac cgcggatgat 960
gatcctgcag ccgctgtttg ctgtatcctg cagaaatgtg atcccctgcg ggtaaattat 1020
tggtcttggt tcaaggacac tctttctcag atctcatgac ttcacatggg ttcacccctt 1080
gtccgcgctg gtccgggctc tgtgagatag acatgtttta gatagtttca ttggacaccc 1140
aaacagagcg gacagagtgt atggctgcta ccttctccgt gactgaaagc agtgcttgta 1200
acgattttgt ttagtaaaat ttgtgagtgt tactgctcca aacaacacct tatgcaacca 1260
tatttgaata tttcacatgt aagcttgaat ccaggtgtgt ttgttaatgt attacacttg 1320
ccatgggagc ctaaatgaga cccataatca cttccactag agtcggaaga ccgtgtcgag 1380
cagttcactc atatggtcac ttaaagcaaa aaaaaaaaaa aaaaaa 1426

<210> SEQ ID NO 69
<211> LENGTH: 1261
<212> TYPE: DNA
<213> ORGANISM: Glycine max

<400> SEQUENCE: 69
gcacgaggat taacgaagga tggaatctgg gtctagcgaa ggagaagagg tgcagcaacg 60
cgtgccgttg agggagagag tggagtggtc agatgttact ccggttcctc aaaacgacgg 120
ccctaaccct gtcgttccga tccagtacac tgaagagttt tccgaagtta tggattactt 180
tcgcgccgtt tacctcaccg atgaacgctc ccctcgcgcc ctcgctctca cagccgaagc 240
cgttcaattc aactccggca actacactgt gtggcatttc cgacggttgt tacttgagtc 300
gctaaaagtc gacttgaacg atgaactgga ttttgtggag cgtatggccg ctggaaattc 360
taaaaattat cagatgtggc atcatagacg atgggttgcc gagaagttag gtcctgaagc 420
tagaaacaat gagctcgagt tcaccaaaaa gatactgtcc gttgatgcca aacattatca 480
tgcatggtct catagacagt gggctcttca aacactagga ggatgggaag atgaacttaa 540
ttattgcaca gaactactta aagaagacat ttttaacaat tctgcttgga atcagagata 600
ttttgtcata acaaggtctc ctttcttggg gggcctaaaa gctatgagag agtctgaagt 660
gctttacacc attgaagcca ttatagccta ccctgaaaat gaaagctcgt ggagatatct 720
acgaggactt tataaaggtg aaactacttc atgggtaaat gatcctcaag tttcttcagt 780
atgcttaaag attttgagaa ctaagagcaa ctacgtgttt gctcttagca ctattttaga 840
tcttatatgc tttggttatc aaccaaatga agacattaga gatgccattg acgccttaaa 900
gaccgcagat atggataaac aagatttaga tgatgatgag aaaggggaac aacaaaattt 960
aaatatagca cgaaatattt gttctatcct aaaacaagtt gatccaatta gaaccaacta 1020
ttggatttgg cgcaagagca gacttcctct atcagcttag taaccaaagt aattaaaggg 1080
caactctgtg ttatgtgtaa cctagtttat tgaaactgga tttttattta ttattatttt 1140
ttatgttgtc atgtatctgt ttgtgcaaat ttatcttttt gtcatgccat tactggcatt 1200
tgagtgtaag gattgaaagc catgcagaat aagaaattta agttttttttt tccgttgaaa 1260 a 1261

<210> SEQ ID NO 70
<211> LENGTH: 1333
<212> TYPE: DNA
<213> ORGANISM: Glycine max

<400> SEQUENCE: 70
gcacgagctt gcgtgtggag tgaagaagat taacgaagga tggaatctgg gtctagcgaa 60
ggagaagagg tgcagcaacg cgtgccgttg agggagagag tggagtggtc agatgttact 120
ccggttcctc aaaacgacgg ccctaaccct gtcgttccga tccagtacac tgaagagttt 180
tccgaagtta tggattactt tcgcgccgtt tacctcaccg atgaacgctc ccctcgcgcc 240
ctcgctctca cagccgaagc cgttcaattc aactccggca actacactgt gtggcatttc 300
cgacggttgt tacttgagtc gctaaaagtc gacttgaacg atgaactgga gtttgtggag 360
cgtatggccg ctggaaattc taaaaattat cagatgtggt gtgatgctct gctctgctct 420
ttcttccata ctttgcatca tagacgatgg gttgccgaga agttaggtcc tgaagctaga 480
aacaatgagc tcgagttcac caaaaagata ctgtccgttg atgccaaaca ttatcatgca 540
tggtctcata gacagtgggc tcttcaaaca ctaggaggat gggaagatga acttaattat 600
tgcacagaac tacttaaaga agacattttt aacaattctg cttggaatca gagatatttt 660
gtcataacaa ggtctccttt cttggggggc ctaaaagcta tgagagagtc tgaagtgctt 720
tacaccattg aagccattat agcctaccct gaaaatgaaa gctcgtggag atatctacga 780
ggactttata aaggtgaaac tacttcatgg gtaaatgatc ctcaagtttc ttcagtatgc 840
ttaaagattt tgagaactaa gagcaactac gtgtttgctc ttagcactat tttagatctt 900
atatgctttg gttatcaacc aaatgaagac attagagatg ccattgacgc cttaaagacc 960
gcagatatgg ataaacaaga tttagatgat gatgagaaag gggaacaaca aaatttaaat 1020
atagcacgaa atatttgttc tatcctaaaa caagttgatc caattagaac caactattgg 1080
atttggcgca agagcagact tcctctatca gcttagtaac caaagtaatt aaagggcaac 1140
tctgtgttat gtgtaaccta gtttattgaa actggatgtt tatttattat tatttttat 1200 gttgtcatgt atctgtttgt gcaaatttat ctttttgtca tgccattact ggcatttgag 1260
tgtaaggatt gaaagccatg cagaataaga aatttaagtt tttttttccg ttgaaaaaaa 1320
aaaaaaaaaa aaa 1333

-continued

<210> SEQ ID NO 71
<211> LENGTH: 1339
<212> TYPE: DNA
<213> ORGANISM: Triticum sp.

<400> SEQUENCE: 71
cggacgtggc gccgctgccg caggccgacg ggccctgccc cgtcgtctcc atcgcttacc 60
gcggcgactt ccgcgaggtc atggactact tccgcgccct ctacgccgcc ggcgagcgca 120
gcccccgcgc cctccgcctc accgccgacg ccatccacct caaccccggc aactacactg 180
tatggcattt caggcgcgtt gttctagagg cactggatgc tgatttattg ctagaaatgc 240
attttgtgga ccaaattgct gaatctaatc caaaaaatta ccaagtctgg catcacaaga 300
gatggcttgc tgagaaaata ggaccagatg ctgcaaatag tgaacatgac ttcacaagga 360
agatacttgc tatggatgct aaaaactacc atgcttggtc ccataggcag tgggttcttc 420
aagcattggg tggatgggag agtgaactgc agtactgcaa ccagcttctt gaggaagatg 480
tcttcaataa ctcagcttgg aatcagagat accttgtggt aacacgatca ccaattcttg 540
ggggccttgc ggcaatgcgc gactcagaag tagattacac agttgaggcc attatggtga 600
accctcagaa tgaaagcccc tggagatacc tcagaggttt atataaggat gataacaatt 660
tgctggtggc tgataatcgc atttctgatg cttgcctcaa ggtcctgaat aaggattgga 720
catgcgtatt tgctttgagc ttcctgcttg atcttcttcg catgggtttg cagccttcga 780
atgaacttaa aggaaccatc gaagcaatgg agaactctga tcctgaaacg ggacatgctg 840
atattgcagt agctgtctgc tcaatcctgc agaaatgtga tcccctgcgg ataaactact 900
ggtcatggta ccagaccact ctttcttctt agacatctga aaattcagct gaagacagtt 960
ttagcagcat gatgtaaact caatcgaagg ggttgacgca gtgtatgaaa aacctttcct 1020
gtgatcttgg tgcggagcaa tttgtactga ttttactggg aaaaatcaat caatgacagc 1080
atgcccaaca atgtcttgtg tgaatatgtt actgcctgat attcacatgt tagcagaatg 1140
agaataacca atcaaactcc aacgagcaga ttgttacagt aacggccact ggtggtgtga 1200
aaatcctgaa atctgcttca gtcactttgc cttgtttaca gttgagtctg ttgttgtgat 1260
ctgtacctaa tgcatgtaca caatcatcaa attattagtt tttgtaccaa tgagtattcg 1320
atgaaaaaaa aaaaaaaaa 1339

<210> SEQ ID NO 72
<211> LENGTH: 333
<212> TYPE: PRT
<213> ORGANISM: Pisum sativum

<400> SEQUENCE: 72

Met Ala Gly Asn Ile Glu Val Glu Glu Asp Asp Arg Val Pro Leu Arg
1 5 10 15

Leu Arg Pro Glu Trp Ser Asp Val Thr Pro Ile Pro Gln Asp Asp Gly
20 25 30

Pro Ser Pro Val Val Pro Ile Asn Tyr Ser Glu Glu Phe Ser Glu Val
35 40 45

Met Asp Tyr Phe Arg Ala Val Tyr Phe Ala Lys Glu Leu Ser Ser Arg
50 55 60

Ala Leu Ala Leu Thr Ala Glu Ala Ile Gly Leu Asn Ala Gly Asn Tyr
65 70 75 80

Thr Val Trp His Phe Arg Arg Leu Leu Leu Glu Ser Leu Lys Val Asp
85 90 95

```
Leu His Val Glu Arg Glu Phe Val Glu Arg Val Ala Ser Gly Asn Ser
            100                 105                 110

Lys Asn Tyr Gln Ile Trp His His Arg Arg Trp Val Ala Glu Lys Leu
        115                 120                 125

Gly Pro Glu Ala Arg Asn Ser Glu Leu Glu Phe Thr Lys Lys Ile Leu
    130                 135                 140

Ser Val Asp Ala Lys His Tyr His Ala Trp Ser His Arg Gln Trp Val
145                 150                 155                 160

Leu Gln Asn Leu Gly Gly Trp Glu Asp Glu Leu Ser Tyr Cys Ser Glu
                165                 170                 175

Leu Leu Ala Glu Asp Ile Phe Asn Asn Ser Ala Trp Asn Gln Arg Tyr
            180                 185                 190

Phe Val Ile Thr Arg Ser Pro Val Leu Gly Gly Leu Lys Ala Met Arg
        195                 200                 205

Glu Ser Glu Val Leu Phe Thr Val Glu Ala Ile Ile Ser Tyr Pro Glu
    210                 215                 220

Asn Glu Ser Ser Trp Arg Tyr Leu Arg Gly Leu Phe Lys Asp Glu Ser
225                 230                 235                 240

Thr Leu Tyr Val Asn Asp Ala Gln Val Ser Ser Leu Cys Leu Lys Ile
                245                 250                 255

Leu Lys Thr Lys Ser Asn Tyr Leu Phe Ala Leu Ser Thr Leu Leu Asp
            260                 265                 270

Leu Ser Ala Ser Val Ile Gln Pro Asn Glu Asp Phe Arg Asp Ala Ile
        275                 280                 285

Glu Ala Leu Arg Leu Gln Ile Leu Ile Lys Gln Asp Ser Asp Ile Ala
    290                 295                 300

Ile Thr Ile Cys Ser Ile Leu Glu Gln Val Asp Pro Ile Arg Val Asn
305                 310                 315                 320

Tyr Trp Val Trp Arg Lys Ser Arg Leu Pro Gln Ala Ala
                325                 330


<210> SEQ ID NO 73
<211> LENGTH: 346
<212> TYPE: PRT
<213> ORGANISM: Lycopersicon esculentum

<400> SEQUENCE: 73

Met Asp Ser Cys Glu Val Thr Lys Thr Arg Ile Pro Phe Lys Glu Arg
  1               5                  10                  15

Pro Asp Trp Ala Asp Val Lys Pro Val Pro Gln Asp Asp Gly Pro Cys
             20                  25                  30

Pro Val Val Pro Ile Ala Tyr Thr Glu Asp Phe Ser Glu Thr Met Asp
         35                  40                  45

Tyr Phe Arg Ala Ile Tyr Val Ala Asp Glu Arg Ser Thr Arg Ala Leu
     50                  55                  60

Gln Leu Thr Gly Glu Ala Ile Gln Leu Asn Pro Gly Asn Tyr Thr Val
 65                  70                  75                  80

Trp Gln Phe Arg Arg Val Val Leu Glu Ala Leu Gly Val Asp Leu Arg
                 85                  90                  95

Glu Glu Leu Lys Phe Val Asp Arg Ile Ala Gly Glu Asn Thr Lys Asn
            100                 105                 110

Tyr Gln Ile Trp His His Arg Arg Trp Leu Ala Glu Lys Leu Gly Ala
        115                 120                 125

Asp Ala Val Thr Asn Glu Leu Glu Phe Thr Lys Lys Ile Phe Ser Gln
    130                 135                 140
```

```
Asp Ala Lys Asn Tyr His Ala Trp Ser His Arg Gln Trp Val Leu Gln
145                 150                 155                 160

Ala Leu Gly Gly Trp Glu Asp Glu Leu Ala Tyr Cys Gln Gln Leu Leu
                165                 170                 175

Glu Asp Asp Ile Tyr Asn Asn Ser Ala Trp Asn Gln Arg Tyr Phe Val
            180                 185                 190

Val Thr Arg Ser Pro Leu Leu Gly Gly Leu Val Ala Met Arg Glu Leu
        195                 200                 205

Glu Val Asn Tyr Thr Val Gln Ala Ile Arg Ala Ser Pro Glu Asn Glu
    210                 215                 220

Ser Pro Trp Arg Tyr Leu Arg Gly Leu Tyr Lys Asn Asp Thr Gln Ser
225                 230                 235                 240

Leu Val Gln Asp Ser Gln Val Ala Ser Val Leu Trp Asp Val Leu Thr
                245                 250                 255

Ser Gln Asn Ser His Val His Ala Leu Arg Phe Leu Leu Asp Leu Leu
            260                 265                 270

Cys His Asp Leu Glu Pro Ser Gln Glu Leu Lys Ser Ala Val Asp Val
        275                 280                 285

Leu Thr Pro Gln Ser Cys Ser Pro Asp Leu Ala Leu Thr Lys Lys Ile
    290                 295                 300

Cys Ser Ile Leu Glu His Ala Asp Pro Met Arg Val Lys Tyr Trp Asn
305                 310                 315                 320

Trp Arg Lys Ser Met Val Arg Val Gln Leu Leu Gln Ser Gln Asn Ala
                325                 330                 335

Glu Arg Leu Ala Asn Leu Ser Val Gln Glu
            340                 345


<210> SEQ ID NO 74
<211> LENGTH: 339
<212> TYPE: PRT
<213> ORGANISM: Oryza sp.

<400> SEQUENCE: 74

Met Ala Pro Ser Ser Thr Ser Ser Glu Gly Ala Ser Asp Glu Trp Leu
  1               5                  10                  15

Pro Pro Ser Arg Arg Pro Glu Leu Ala Asp Val Val Pro Val Thr Gln
             20                  25                  30

Asp Asp Gly Pro His Pro Val Val Ala Ile Ala Tyr Arg Asp Glu Phe
         35                  40                  45

Arg Glu Val Met Asp Tyr Phe Arg Ala Leu Tyr Phe Ala Gly Glu Arg
     50                  55                  60

Ser Val Arg Ala Leu His Leu Thr Ala Glu Val Ile Asp Leu Asn Pro
 65                  70                  75                  80

Gly Asn Tyr Thr Val Trp His Phe Arg Arg Leu Val Leu Glu Ala Leu
                 85                  90                  95

Asp Ala Asp Leu Arg Glu Glu Met Asp Phe Val Asp Arg Ile Val Glu
            100                 105                 110

Cys Asn Pro Lys Asn Tyr Gln Ile Trp His His Lys Arg Trp Leu Ala
        115                 120                 125

Glu Lys Leu Gly Pro Asp Ile Ala Asn Lys Glu His Glu Phe Thr Arg
    130                 135                 140

Lys Ile Leu Ser Met Asp Ala Lys Asn Tyr His Ala Trp Ser His Arg
145                 150                 155                 160

Gln Trp Val Leu Gln Ala Leu Gly Gly Trp Glu Thr Glu Leu Gln Tyr
```

```
                165                 170                 175

Cys Asn Gln Leu Leu Glu Glu Asp Val Phe Asn Asn Ser Ala Trp Asn
            180                 185                 190

Gln Arg Tyr Leu Val Ile Thr Ser Ser Pro Leu Leu Gly Gly Leu Ala
        195                 200                 205

Ala Met Arg Asp Ser Glu Val Asp Tyr Thr Val Gly Ala Ile Leu Ala
    210                 215                 220

Asn Pro Gln Asn Glu Ser Pro Trp Arg Tyr Leu Lys Gly Leu Tyr Lys
225                 230                 235                 240

Gly Glu Asn Asn Leu Leu Met Ala Asp Glu Arg Ile Ser Asp Val Cys
                245                 250                 255

Leu Lys Val Leu Lys His Asp Ser Thr Cys Val Phe Ala Leu Ser Leu
            260                 265                 270

Leu Leu Asp Leu Leu Gln Ile Gly Leu Gln Pro Ser Asp Glu Leu Lys
        275                 280                 285

Gly Thr Ile Glu Ala Ile Lys Asn Ser Asp Pro Glu Ala Asp Glu Ala
    290                 295                 300

Val Asp Ala Asp Leu Ala Thr Ala Ile Cys Ser Ile Leu Gln Arg Cys
305                 310                 315                 320

Asp Pro Leu Arg Ile Asn Tyr Trp Ser Trp Tyr Arg Thr Thr Ile Ser
                325                 330                 335

Ser Gln Thr


<210> SEQ ID NO 75
<211> LENGTH: 326
<212> TYPE: PRT
<213> ORGANISM: Zea mays

<400> SEQUENCE: 75

Met Glu His Thr Leu Ser Gly Pro Ser Ser Trp Pro Glu Leu Ala Asp
  1               5                  10                  15

Val Val Pro Val Pro Gln Asp Asp Gly Pro Ser Pro Val Val Ser Ile
             20                  25                  30

Ala Tyr Arg Asp Asp Phe Arg Gly Val Met Asp Tyr Phe Arg Ala Leu
         35                  40                  45

Tyr Leu Thr Gly Glu Arg Ser Pro Arg Ala Leu Arg Leu Thr Ala Glu
     50                  55                  60

Ala Ile Glu Leu Asn Pro Gly Asn Tyr Thr Val Trp His Phe Arg Arg
 65                  70                  75                  80

Leu Ile Leu Glu Ser Leu Asp Phe Asp Leu Leu Glu Glu Met Lys Phe
                 85                  90                  95

Val Glu Leu Ile Ala Glu Cys Asn Pro Lys Asn Tyr Gln Ile Trp His
            100                 105                 110

His Leu Arg Trp Leu Ala Glu Lys Leu Gly Pro Gly Ile Ala Asn Lys
        115                 120                 125

Glu His Glu Phe Thr Met Lys Ile Leu Ala Ile Asp Ala Leu Asn Tyr
    130                 135                 140

His Ala Trp Ser His Arg Gln Trp Val Leu Gln Ala Leu Gly Gly Trp
145                 150                 155                 160

Glu Thr Glu Leu Glu Tyr Cys Asp His Leu Leu Lys Glu Asp Val Phe
                165                 170                 175

Asn Asn Ser Ala Trp Asn Gln Arg Tyr Phe Val Ile Thr Arg Ser Pro
            180                 185                 190

Phe Leu Gly Gly Leu Ala Ala Met Arg Asp Ser Gly Val Asp Tyr Thr
```

```
        195                 200                 205

Ile Glu Ala Ile Leu Ala Asn Ala Gln Asn Gly Ser Pro Trp Arg Tyr
    210                 215                 220

Leu Lys Gly Leu Tyr Lys Gly Glu Asn Asn Leu Leu Val Glu Asp Gly
225                 230                 235                 240

Arg Ile Ser Ala Val Cys Phe Lys Val Leu Lys Asn Asp Trp Thr Cys
                245                 250                 255

Val Phe Ala Leu Ser Leu Leu Leu Asp Leu Leu Cys Thr Gly Leu Gln
            260                 265                 270

Pro Ser Asp Gly Leu Arg Ser Thr Leu Gly Thr Ile Arg Ser Ser His
        275                 280                 285

Pro Glu Thr Ala Asp Asp Asp Pro Ala Ala Ala Val Cys Cys Ile Leu
    290                 295                 300

Gln Lys Cys Asp Pro Leu Ala Val Asn Tyr Trp Ser Trp Phe Lys Asp
305                 310                 315                 320

Thr Leu Ser Gln Ile Ser
                325


<210> SEQ ID NO 76
<211> LENGTH: 346
<212> TYPE: PRT
<213> ORGANISM: Glycine max

<400> SEQUENCE: 76

Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
            20                  25                  30

Asp Gly Pro Asn Pro Val Val Pro Ile Gln Tyr Thr Glu Glu Phe Ser
        35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Asp Phe Val Glu Arg Met Ala Ala Gly
            100                 105                 110

Asn Ser Lys Asn Tyr Gln Met Trp His His Arg Arg Trp Val Ala Glu
        115                 120                 125

Lys Leu Gly Pro Glu Ala Arg Asn Asn Glu Leu Glu Phe Thr Lys Lys
    130                 135                 140

Ile Leu Ser Val Asp Ala Lys His Tyr His Ala Trp Ser His Arg Gln
145                 150                 155                 160

Trp Ala Leu Gln Thr Leu Gly Gly Trp Glu Asp Glu Leu Asn Tyr Cys
                165                 170                 175

Thr Glu Leu Leu Lys Glu Asp Ile Phe Asn Asn Ser Ala Trp Asn Gln
            180                 185                 190

Arg Tyr Phe Val Ile Thr Arg Ser Pro Phe Leu Gly Gly Leu Lys Ala
        195                 200                 205

Met Arg Glu Ser Glu Val Leu Tyr Thr Ile Glu Ala Ile Ile Ala Tyr
    210                 215                 220

Pro Glu Asn Glu Ser Ser Trp Arg Tyr Leu Arg Gly Leu Tyr Lys Gly
225                 230                 235                 240
```

```
Glu Thr Thr Ser Trp Val Asn Asp Pro Gln Val Ser Ser Val Cys Leu
                245                 250                 255

Lys Ile Leu Arg Thr Lys Ser Asn Tyr Val Phe Ala Leu Ser Thr Ile
            260                 265                 270

Leu Asp Leu Ile Cys Phe Gly Tyr Gln Pro Asn Glu Asp Ile Arg Asp
        275                 280                 285

Ala Ile Asp Ala Leu Lys Thr Ala Asp Met Asp Lys Gln Asp Leu Asp
    290                 295                 300

Asp Asp Glu Lys Gly Glu Gln Gln Asn Leu Asn Ile Ala Arg Asn Ile
305                 310                 315                 320

Cys Ser Ile Leu Lys Gln Val Asp Pro Ile Arg Thr Asn Tyr Trp Ile
                325                 330                 335

Trp Arg Lys Ser Arg Leu Pro Leu Ser Ala
            340                 345


<210> SEQ ID NO 77
<211> LENGTH: 358
<212> TYPE: PRT
<213> ORGANISM: Glycine max

<400> SEQUENCE: 77

Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
            20                  25                  30

Asp Gly Pro Asn Pro Val Val Pro Ile Gln Tyr Thr Glu Glu Phe Ser
        35                  40                  45

Glu Val Met Asp Tyr Phe Arg Ala Val Tyr Leu Thr Asp Glu Arg Ser
    50                  55                  60

Pro Arg Ala Leu Ala Leu Thr Ala Glu Ala Val Gln Phe Asn Ser Gly
65                  70                  75                  80

Asn Tyr Thr Val Trp His Phe Arg Arg Leu Leu Leu Glu Ser Leu Lys
                85                  90                  95

Val Asp Leu Asn Asp Glu Leu Glu Phe Val Glu Arg Met Ala Ala Gly
            100                 105                 110

Asn Ser Lys Asn Tyr Gln Met Trp Cys Asp Ala Leu Leu Cys Ser Phe
        115                 120                 125

Phe His Thr Leu His His Arg Arg Trp Val Ala Glu Lys Leu Gly Pro
    130                 135                 140

Glu Ala Arg Asn Asn Glu Leu Glu Phe Thr Lys Lys Ile Leu Ser Val
145                 150                 155                 160

Asp Ala Lys His Tyr His Ala Trp Ser His Arg Gln Trp Ala Leu Gln
                165                 170                 175

Thr Leu Gly Gly Trp Glu Asp Glu Leu Asn Tyr Cys Thr Glu Leu Leu
            180                 185                 190

Lys Glu Asp Ile Phe Asn Asn Ser Ala Trp Asn Gln Arg Tyr Phe Val
        195                 200                 205

Ile Thr Arg Ser Pro Phe Leu Gly Gly Leu Lys Ala Met Arg Glu Ser
    210                 215                 220

Glu Val Leu Tyr Thr Ile Glu Ala Ile Ile Ala Tyr Pro Glu Asn Glu
225                 230                 235                 240

Ser Ser Trp Arg Tyr Leu Arg Gly Leu Tyr Lys Gly Glu Thr Thr Ser
                245                 250                 255

Trp Val Asn Asp Pro Gln Val Ser Ser Val Cys Leu Lys Ile Leu Arg
            260                 265                 270
```

```
Thr Lys Ser Asn Tyr Val Phe Ala Leu Ser Thr Ile Leu Asp Leu Ile
        275                 280                 285

Cys Phe Gly Tyr Gln Pro Asn Glu Asp Ile Arg Asp Ala Ile Asp Ala
    290                 295                 300

Leu Lys Thr Ala Asp Met Asp Lys Gln Asp Leu Asp Asp Asp Glu Lys
305                 310                 315                 320

Gly Glu Gln Gln Asn Leu Asn Ile Ala Arg Asn Ile Cys Ser Ile Leu
                325                 330                 335

Lys Gln Val Asp Pro Ile Arg Thr Asn Tyr Trp Ile Trp Arg Lys Ser
            340                 345                 350

Arg Leu Pro Leu Ser Ala
        355


<210> SEQ ID NO 78
<211> LENGTH: 309
<212> TYPE: PRT
<213> ORGANISM: Triticum sp.

<400> SEQUENCE: 78

Asp Val Ala Pro Leu Pro Gln Ala Asp Gly Pro Cys Pro Val Val Ser
  1               5                  10                  15

Ile Ala Tyr Arg Gly Asp Phe Arg Glu Val Met Asp Tyr Phe Arg Ala
            20                  25                  30

Leu Tyr Ala Ala Gly Glu Arg Ser Pro Arg Ala Leu Arg Leu Thr Ala
        35                  40                  45

Asp Ala Ile His Leu Asn Pro Gly Asn Tyr Thr Val Trp His Phe Arg
     50                  55                  60

Arg Val Val Leu Gly Ala Leu Asp Ala Asp Leu Leu Leu Glu Met His
 65                  70                  75                  80

Phe Val Asp Gln Ile Ala Glu Ser Asn Pro Leu Asn Tyr Gln Val Trp
                85                  90                  95

His His Lys Arg Trp Leu Ala Glu Lys Ile Gly Pro Asp Ala Ala Asn
            100                 105                 110

Ser Glu His Asp Phe Thr Arg Lys Ile Leu Ala Met Asp Ala Lys Asn
        115                 120                 125

Tyr His Ala Trp Ser His Arg Gln Trp Val Leu Gln Ala Leu Gly Gly
    130                 135                 140

Trp Glu Ser Glu Leu Gln Tyr Cys Asn Gln Leu Leu Glu Glu Asp Val
145                 150                 155                 160

Phe Asn Asn Ser Ala Trp Asn Gln Arg Tyr Leu Val Val Thr Arg Ser
                165                 170                 175

Pro Ile Leu Gly Gly Leu Ala Ala Met Arg Asp Ser Glu Val Asp Tyr
            180                 185                 190

Thr Val Glu Ala Ile Met Val Asn Pro Gln Asn Glu Ser Pro Trp Arg
        195                 200                 205

Tyr Leu Arg Gly Leu Tyr Lys Asp Asp Asn Asn Leu Leu Val Ala Asp
    210                 215                 220

Asn Arg Ile Ser Asp Ala Cys Leu Lys Val Leu Asn Lys Asp Trp Thr
225                 230                 235                 240

Cys Val Phe Ala Leu Ser Phe Leu Leu Asp Leu Leu Arg Met Gly Leu
                245                 250                 255

Gln Pro Ser Asn Glu Leu Lys Gly Thr Ile Glu Ala Met Glu Asn Ser
            260                 265                 270

Asp Pro Glu Thr Gly His Ala Asp Ile Ala Val Ala Val Cys Ser Ile
```

```
        275                 280                 285

Leu Gln Lys Cys Asp Pro Leu Arg Ile Asn Tyr Trp Ser Trp Tyr Gln
    290                 295                 300

Thr Thr Leu Ser Ser
305


<210> SEQ ID NO 79
<211> LENGTH: 5517
<212> TYPE: DNA
<213> ORGANISM: Artificial Sequence
<220> FEATURE:
<223> OTHER INFORMATION: Description of Artificial Sequence: DN90AtFTB
      vector

<400> SEQUENCE: 79

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740

tttaatacgc gatagaaaac aaaatatagc gcgcaaacta ggataaatta tcgcgcgcgg   1800
```

-continued

```
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccgtccgga attcccgggt cgacccacgc   3360
gtccgggaga ttcagcgaga taagcaattg gattatctga tgaaaggctt aaggcagctt   3420
ggtccgcagt ttcttcctt agatgctaat cgaccttggc tttgttactg gattcttcat   3480
tcaatagctt tgcttgggga gactgtggat gatgaattag aaagcaatgc cattgacttc   3540
cttggacgct gccagggctc tgaaggtgga tacggtggtg gtcctggcca acttccacat   3600
cttgcaacta cttatgctgc agtgaatgca cttgttactt taggaggtga caaagccctt   3660
tcttcaatta atagagaaaa aatgtcttgt tttttaagac ggatgaagga tacaagtgga   3720
ggtttcagga tgcatgatat gggagaaatg gatgttcgtg catgctacac tgcaatttcg   3780
gttgcaagca tcctaaatat tatggatgat gaactcaccc agggcctagg agattacatc   3840
ttgagttgcc aaacttatga aggtggcatt ggaggggaac ctggctccga agctcacggt   3900
gggtatacct actgtggttt ggctgctatg attttaatca atgaggtcga ccgtttgaat   3960
ttggattcat taatgaattg ggctgtacat cgacaaggag tagaaatggg atttcaaggt   4020
aggacgaaca aattggtcga tggttgctac acattttggc aggcagcccc ttgtgttcta   4080
ctacaaagat tatattcaac caatgatcat gacgttcatg gatcatcaca tatatcagaa   4140
gggacaaatg aagaacatca tgctcatgat gaagatgacc ttgaagacag tgatgatgat   4200
```

gatgattctg atgaggacaa cgatgaagat tcagtgaatg gtcacagaat ccatcataca 4260
tccacctaca ttaacaggag aatgcaactg gtttttgata gcctcggctt gcagagatat 4320
gtactcttgt gctctaagat ccctgacggt ggattcagag acaagccgag gaaaccccgt 4380
gacttctacc acacatgtta ctgcctgagc ggcttgtctg tggctcagca cgcttggtta 4440
aaagacgagg acactcctcc tttgactcgc gacattatgg gtggctactc gaatctcctt 4500
gaacctgttc aacttcttca caacattgtc atggatcagt ataatgaagc tatcgagttc 4560
ttctttaaag cagcatgagg atccctcgaa tttccccgat cgttcaaaca tttggcaata 4620
aagtttctta agattgaatc ctgttgccgg tcttgcgatg attatcatat aatttctgtt 4680
gaattacgtt aagcatgtaa taattaacat gtaatgcatg acgttattta tgagatgggt 4740
ttttatgatt agagtcccgc aattatacat ttaatacgcg atagaaaaca aaatatagcg 4800
cgcaaactag gataaattat cgcgcgcggt gtcatctatg ttactagatc gggaattcac 4860
tggccgtcgt tttacaacgt cgtgactggg aaaaccctgg cgttacccaa cttaatcgcc 4920
ttgcagcaca tccccctttc gccagctggc gtaatagcga agaggcccgc accgatcgcc 4980
cttcccaaca gttgcgcagc ctgaatggcg cccgctcctt tcgctttctt cccttccttt 5040
ctcgccacgt tcgccggctt tccccgtcaa gctctaaatc gggggctccc tttagggttc 5100
cgatttagtg ctttacggca cctcgacccc aaaaaacttg atttgggtga tggttcacgt 5160
agtgggccat cgccctgata gacggttttt cgccctttga cgttggagtc cacgttcttt 5220
aatagtggac tcttgttcca aactggaaca acactcaacc ctatctcggg ctattctttt 5280
gatttataag ggattttgcc gatttcggaa ccaccatcaa acaggatttt cgcctgctgg 5340
ggcaaaccag cgtggaccgc ttgctgcaac tctctcaggg ccaggcggtg aagggcaatc 5400
agctgttgcc cgtctcactg gtgaaaagaa aaaccacccc agtacattaa aaacgtccgc 5460
aatgtgttat taagttgtct aagcgtcaat ttgtttacac cacaatatat cctgcca 5517

<210> SEQ ID NO 80
<211> LENGTH: 1627
<212> TYPE: DNA
<213> ORGANISM: Unknown Organism
<220> FEATURE:
<223> OTHER INFORMATION: Description of Unknown Organism: Wiggum Gene

<400> SEQUENCE: 80
atgccagtag taacccgctt gattcgtttg aagtgtgtag ggctcagact tgaccggagt 60
ggactcaatc ggcgaatctg tcacggagga cacggggaat caacgcggcg gagagtgatg 120
gaagagcttt caagcctaac cgtgagtcag cgcgagcaat ttctggtgga gaacgatgtg 180
ttcgggatct ataattactt cgacgccagc gacgtttcta ctcaaaaata catgatggag 240
attcagcgag ataagcaatt ggattatctg atgaaaggct taaggcagct tggtccgcag 300
ttttcttcct tagatgctaa tcgaccttgg ctttgttact ggattcttca ttcaatagct 360
ttgcttgggg agactgtgga tgatgaatta gaaagcaatg ccattgactt ccttggacgc 420
tgccagggct ctgaaggtgg atacggtggt ggtcctggcc aacttccaca tcttgcaact 480
acttatgctg cagtgaatgc acttgttact ttaggaggtg acaaagccct ttcttcaatt 540
aatagagaaa aaatgtcttg ttttttaaga cggatgaagg atacaagtgg aggtttcagg 600
atgcatgata tgggagaaat ggatgttcgt gcatgctaca ctgcaatttc ggttgcaagc 660
atcctaaata ttatggatga tgaactcacc cagggcctag gagattacat cttgagttgc 720

-continued caaacttatg aaggtggcat tggaggggaa cctggctccg aagctcacgg tgggtatacc 780
tactgtggtt tggctgctat gattttaatc aatgaggtcg accgtttgaa tttggattca 840
ttaatgaatt gggctgtaca tcgacaagga gtagaaatgg gatttcaagg taggacgaac 900
aaattggtcg atggttgcta cacattttgg caggcagccc cttgtgttct actacaaaga 960
ttatattcaa ccaatgatca tgacgttcat ggatcatcac atatatcaga agggacaaat 1020
gaagaacatc atgctcatga tgaagatgac cttgaagaca gtgatgatga tgatgattct 1080
gatgaggaca acgatgaaga ttcagtgaat ggtcacagaa tccatcatac atccacctac 1140
attaacagga gaatgcaact ggtttttgat agcctcggct tgcagagata tgtactcttg 1200
tgctctaaga tccctgacgg tggattcaga gacaagccga ggaaaccccg tgacttctac 1260
cacacatgtt actgcctgag cggcttgtct gtggctcagc acgcttggtt aaaagacgag 1320
gacactcctc ctttgactcg cgacattatg ggtggctact cgaatctcct tgaacctgtt 1380
caacttcttc acaacattgt catggatcag tataatgaag ctatcgagtt cttctttaaa 1440
gcagcatgac ccgttgttgc taatgtatgg gaaactccaa acataagagt tttcgtagtg 1500
ttgtaacttg taagatttca aaagaagttt cactaattta accttaaaac ctgttacttt 1560
tttattacgt atataccatt tatcatatct ttggtttacg acttaaagaa tttgatgatt 1620
gttgaaa 1627

<210> SEQ ID NO 81
<211> LENGTH: 1135
<212> TYPE: DNA
<213> ORGANISM: Glycine max

<400> SEQUENCE: 81
gccaccattc ctcgcaacgc ccaaaccctc atgttggagc ttcaacgcga taatcacatg 60
cagtatgtct ccaaaggcct tcgccatctc agttccgcat tttccgtttt ggacgctaat 120
cgaccctggc tctgctactg gatcttccac tccattgctt tgtcgggaga atccgtcgat 180
gatgaactcg aagataacgc tatcgatttt cttaaccgtt gccaggatcc gaatggtgga 240
tatgccgggg gaccaggcca gatgcctcat attgccacaa cttatgctgc tgttaattca 300
cttattactt tgggtggtga gaaatccctg gcatcaatta atagagataa actgtatggg 360
tttctgcggc ggatgaagca accaaatggt ggattcagga tgcatgatga aggtgaaatt 420
gatgttcgag cttgctacac tgccatttct gttgcaagtg ttttgaacat tttggatgat 480
gagctgatcc agaatgttgg agactacatt ataagctgtc aaacatatga gggtggcatt 540
gctggtgagc ctggttctga ggctcatggt gggtacacct tttgtggatt agctacaatg 600
attctgattg gtgaggttaa tcacttggat ctgcctcgat tagttgactg ggtggtattc 660
cgacaaggta aggaatgtgg attccagggg agaacaaata aactggtgga tggatgctat 720
tccttttggc agggaggtgc tgttgctcta ttgcaaagat tatcttctat tatcaacaaa 780
cagatggaag agacatcaca gatttttgcg gtatcttatg tatctgaagc aaaagaaagt 840
ttggatggaa cctctagtca tgcaacatgc cgtggtgagc atgaaggcac cagtgaatcc 900
agttcatctg attttaaaaa tattgcctat aaatttatta atgagtggag agcacaagaa 960
ccactttttc acagtattgc tttacagcaa tatattctct tatgtgcaca ggagcaagag 1020
ggtggactga gagacaaacc gggtaaacgt agagatcatt atcacacatg ttactgttta 1080
agtggactct cattgtgcca gtatagttgg tcaaagcacc cagattctcc accac 1135

<210> SEQ ID NO 82
<211> LENGTH: 1245
<212> TYPE: DNA
<213> ORGANISM: Glycine max

<400> SEQUENCE: 82
ggcggatccc gacctaccga ggctcacggt gacgcaggtg gagcagatga aggtggaggc 60
cagggttggc gacatctacc gctccctctt cggggccgcg cccaacacga aatccatcat 120
gctagagctg tggcgtgatc agcatatcga gtatctgacg cctgggctga ggcatatggg 180
accagccttt catgttctag atgccaatcg cccttggcta tgctactgga tggttcatcc 240
acttgctttg ctggatgaag cacttgatga tgatcttgag aatgatatca tagacttctt 300
agctcgatgt caggataaag atggtggata tagtggtgga cctggacagt tgcctcacct 360
agctacgact tatgctgctg taaatacact tgtgacaata gggagccaaa gagcattgtc 420
atcaatcaat aggggcaacc tgtacaattt tatgctgcag atgaaagatg tatcaggtgc 480
tttcagaatg catgatggtg gcgaaattga tgtccgtgct tcctacaccg ctatatcggt 540
tgccagcctt gtgaatattc ttgattttaa actggcaaaa ggtgtaggcg actacatagc 600
aagatgtcaa acttatgaag gtggtattgc tggggagcct tatgctgaag cacatggtgg 660
gtatacattc tgtggattgg ctgctttgat cctgcttaat gaggcagaga aagttgactt 720
gcctagtttg attggctggg tggcttttcg tcaaggagtg gaatgcggat ttcaaggacg 780
aactaataaa ttggttgatg gttgctactc cttttggcag ggagctgcca ttgctttcac 840
acaaaagtta attacgattg ttgataagca attgaagtcc tcgtattcct gcaaaaggcc 900
atcaggagag gatgcctgca gcaccagttc atatgggtgc accgcgaaaa agtcttcctc 960
tgctgtggac tatgcgaagt ttggatttga ttttatacaa cagagcaacc aaattggccc 1020
actcttccat aacattgccc tgcaacaata catcctactt tgttctcagg tactagaggg 1080
aggcttgagg gataagcctg gaaagaacag agatcactac cattcatgct actgcctcag 1140
tggcctcgca gttagccagt acagtgccat gactgatact ggttcgtgcc cattacctca 1200
gcatgtgctt ggaccgtact ctaatttgct ggagccaatc catcc 1245

<210> SEQ ID NO 83
<211> LENGTH: 1648
<212> TYPE: DNA
<213> ORGANISM: Pisum sativum

<400> SEQUENCE: 83
cggacccccc cgtccacaat cgtgatgatg acgtctccgc gagcatttca acaaccagtt 60
actcaaacca ccgcggagta acacatggaa gcttcaaccg cggcggagac accaactccg 120
acggtgagtc agagagatca atggatagta gaatcacagg tctttcatat ttatcaactc 180
ttcgccaata ttcctcctaa cgcccaatct atcattcgac cttggctgtg ttactggatt 240
attcattcaa ttgctttgtt gggagaatct attgatgatg atctcgaaga taacactgtc 300
gattttctta accgttgcca ggatccaaat ggtggatatg ctgggggacc tggtcagatg 360
cctcatcttg ccacaactta tgctgcagtc aatactctta ttactctggg tggtgagaaa 420
tctttggcat ctattaatag aaataagttg tacgggttta tgcggcggat gaaacagcca 480
aacggcggat tcaggatgca tgacgaggga gaaattgacg ttcgagcttg ctacactgcc 540
atctctgtgg caagtgttct gaacattttg gatgatgagc tgatcaagaa tgttggagac 600
ttcattttaa gctgtcaaac atatgaggga ggccttgctg gtgagcctgg gtctgaggct 660

```
catggcgggt ataccttttg tgggttagct gcaatgattc tgattggtga ggttaatcgc     720
ttggatctgc ctcgtttact tgattgggtt gtgtttcggc aaggtaaaga gtgtggattt     780
caggggagaa cgaataaatt ggtagatgga tgctactcgt tttggcaggg aggtgctgtt     840
gccctattgc aaagattaca ttctattatc gacgaacaaa tggcagaggc atcacagttt     900
gttacagtat ctgatgcacc tgaagaaaag gaatgtttgg acggaacctc aagtcatgca     960
acttcccata ttaggcatga aggcatgaat gaatcctgct catctgacgt taaaaatatt    1020
ggttataact ttattagtga gtggagacaa agtgaaccac tttttcacag cattgcctta    1080
cagcaatata ttcttttatg ttcacaggag caagatggtg ggctcaggga caaaccgggt    1140
aaacgcaggg atcattatca ttcatgttac tgtttaagtg ggttgtcact gtgccagtat    1200
agttggtcga agcgcccaga ttctccaccg ctgcctaagg tagtaatggg cccatactcc    1260
aatctcttag aacccatcca tcctctcttt aatgttgttt tggatcgata tcgtgaagct    1320
catgaattct tttctcagtt gtgacggatg acaaggtttt agctaccaat agctcgatca    1380
ttagaatgta aaatgtaaac taaaatatga aatatgaaat accaaaaaga tattattgga    1440
tgaaattcac gtggatctaa tacaactgcg tggttttcat tcctgatttg attttgattt    1500
acatgagtta aaacgttaaa cccttcttat tcatacattt gttaagagct taaggcttaa    1560
tggttaagcc aatgatataa atatttatgc agaaagctgt tgcttatcac caacggtaat    1620
attaataagc aaacaagtat tctgtgat                                       1648
```

<210> SEQ ID NO 84
<211> LENGTH: 1832
<212> TYPE: DNA
<213> ORGANISM: Lycopersicon esculentum

<400> SEQUENCE: 84

```
gtaaacgagc gttgatttgt cgctgacgaa atttacagtc aagagtagta accggttgta      60
gtgaaaaaat ggagtcgagg aaagtgacga agacgctgga agatcaatgg gtggtggagc     120
gtcgagtccg agagatatac gattatttct acagcatttc cccaactctc ccgtccgacc     180
tcatagagat cgaacgtgac aaacacttcg gttatctaag ccaaggtctc agaaaacttg     240
gtccgtcgtt ttccgttttg gatgccagtc gaccatggct ttgctactgg acacttcatt     300
caatcgcttt gttgggagaa tctattggtg gcaaactgga aaatgatgca attgactttc     360
tgacccgttg ccaggataaa gatggtggct atggaggtgg acctggtcag atgcctcatc     420
ttgcaactac ttatgctgca gtcaattcac taataacttt gggcaaacct gaagctctgt     480
catcaattaa tagagaaaag ttgtacacat ttttgctgcg aatgaaagac gcaagtggtg     540
gattcaggat gcacgatggt ggagaagtag atgttcgtgc ctgttatact gccatttctg     600
ttgcaaatat attaaacatt gtggatgacg agctgattca tggtgttgga aattacatcc     660
taagttgtca gacttatgaa ggtggaattg ctggcgaacc aggttctgaa gctcatggtg     720
ggtatacttt ctgtgggttg gctgcaatga ttctgatcaa cgaagtagat cgattggact     780
tgccaggttt aattgattgg gtggtattta gacaaggggt cgaaggtgga tttcaaggca     840
ggacaaataa attagtcgat ggctgctatt cctttttggca gggcgcggta gtgtttctta     900
tacaaagact aaatttgata gtccatgaac aactagggct gtcaaatgac ctcagtacag     960
aaagtgctga tgattcttca gagtcagagt tatctgatga agaagagcat ttggaaggga    1020
tatcctctca tgttcaggat actttccctc ttggacaagc aggtgcttgt caagaaaatg    1080
cttctcatag cccaaaaata gcagatactg gatatgagtt tatcaaccga cccatagcta    1140
```

-continued

```
tgaggcctct ctttgacagc atgtatctgc agcaatatgt tcttctttgc tctcagattg    1200

aagttggtgg tttcagagac aaacctggga agggtagaga ctactaccat acctgttact    1260

gtttaagtgg tctttcaatt gctcagtata gctggaccga cgaagctgat tctacaccat    1320

tacccaggga tgtatttggt ccttattcca aatgtctgtt ggaacaggtt cacccactct    1380

tcaacgtagt gttggatcgg tattatgaag ctcgcgaata ctctcaggct tgtgagactg    1440

tttcaccact ttcattagca ccaacttttt cagaaactta gttgcaatcc agaagttaaa    1500

agtgtcattg ggttcaaaag agttgtgatc gtttatgtac atatccttgc atttgtatac    1560

gtgatacaag ttgagagaat aacgggtact ttctgaactt gctgaactag cacgtaaatt    1620

cgtctctggt ttagtgaggt ctgtaaacat caatgtgaaa ttgcgagata tgcatgtaat    1680

agtggctaag atttacaaat ctggataccg gttattagtg atcagaaatt tcattcaatt    1740

tcccaaacgg tcacctaagt ttaggatatt gctttaaaat attatttatt tttcatttaa    1800

gaatcaaaaa aaaaaaaaaa aaaaaaaaaa aa                                  1832
```

<210> SEQ ID NO 85
<211> LENGTH: 1449
<212> TYPE: DNA
<213> ORGANISM: Nicotiana sp.
<220> FEATURE:
<221> NAME/KEY: misc_feature
<222> LOCATION: (87)
<223> OTHER INFORMATION: Wherein n is a or t or c or g.
<220> FEATURE:
<221> NAME/KEY: misc_feature
<222> LOCATION: (1038)
<223> OTHER INFORMATION: Wherein n is a or t or c or g.

<400> SEQUENCE: 85

```
ggcacgagcg gcacgaggac actggaagat caatggatgg tggagcgtca agttcgggag      60

atatacaatt ttttctacag cattccnccc aattcccact tagagacttc aacagaaaag     120

cacttcgatt atctcactcg aggtctcaga aaacttggtc cgtcgttctc cgtcttggat     180

gctaatcgac catggctttg ctactggata cttcattcaa tcgctttgtt gggagaatct     240

attgatgccc aactggaaaa tgatgcaatt gactttctga gccgttgcca ggatgaagat     300

ggtggctatg gtggtggacc tggtcagatg cctcatcttg caactactta tgctgcagtc     360

aattcactca taactttggg cagccctaaa gctctgtcat caatcaatag agaaaaattg     420

tatacatttt ggctgcaaat gaaagacaca agtggtggct tcaggatgca tgatggtgga     480

gaagtagatg ttcgtgcctg ttatactgcc atttctgttg caagtatatt gcaaattgtg     540

gatgatgaac tgattaatga tgttgggaat tacatcctaa gttgtcagac ttatgaaggt     600

ggaattgctg gcgaaccagg ttctgaagct catggtgggt ataccttctg tgggttggct     660

gcaatgattc tgattaacga agcgaatcga ttggacttgc caagattaat tgattgggtg     720

gtatttagac aaggagtcga aggtggattt caaggcagga caaataaatt agtcgatggc     780

tgctattcct tttggcaggc cgcggtagct tttcttatac aaagattaaa atcgacagtc     840

catgaacaac tagggctgtc aaatgaactc agtacagaaa gtgctgatga ttcttcggag     900

tcagagttat ctgatgaaga gcatttgcaa gggacatcat ctcatgttca gaagacttgc     960

cctcttggac aagaaggaca ggaaaatgct tcagatccca caaagatagc agatactggt    1020

tatgattttg tcaatcgnac gatagctatg cgacctgtgt ttgacagctt ttatctgcag    1080

caatacgttc ttctctgctc ccagatagat ggaggtttca gagacaaacc tgggaagggt    1140
```

-continued

```
agagaccact accatacttg ctactgttta agtggtcttt caattgctca atatagctgg   1200

accaacgaag ctgatgcgcc accattaccc agggatgtat ttggtcctta ttctcaaaat   1260

cttttggaac agattcaccc actttacaac gtagtgttgg atcggtatta tgaagctcgt   1320

agcttcttct catgcttgtg ataatatttt acgcgatagc tgtagctgga atgttacctc   1380

tagttgttca gaatcagaga ctaatctatt attttgaggg attggattca aaaaaaaaaa   1440

aaaaaaaaa                                                           1449
```

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: FORWARD Primer SacI site

<400> SEQUENCE: 86

```
aaacccggga tgccagtagt aacccgc                                         27
```

<210> SEQ ID NO 87
<211> LENGTH: 482
<212> TYPE: PRT
<213> ORGANISM: Unknown Organism
<220> FEATURE:
<223> OTHER INFORMATION: Description of Unknown Organism: Wiggum gene

<400> SEQUENCE: 87

```
Met Pro Val Val Thr Arg Leu Ile Arg Leu Lys Cys Val Gly Leu Arg
  1               5                  10                  15

Leu Asp Arg Ser Gly Leu Asn Arg Arg Ile Cys His Gly Gly His Gly
             20                  25                  30

Glu Ser Thr Arg Arg Arg Val Met Glu Glu Leu Ser Ser Leu Thr Val
         35                  40                  45

Ser Gln Arg Glu Gln Phe Leu Val Glu Asn Asp Val Phe Gly Ile Tyr
     50                  55                  60

Asn Tyr Phe Asp Ala Ser Asp Val Ser Thr Gln Lys Tyr Met Met Glu
 65                  70                  75                  80

Ile Gln Arg Asp Lys Gln Leu Asp Tyr Leu Met Lys Gly Leu Arg Gln
                 85                  90                  95

Leu Gly Pro Gln Phe Ser Ser Leu Asp Ala Asn Arg Pro Trp Leu Cys
            100                 105                 110

Tyr Trp Ile Leu His Ser Ile Ala Leu Leu Gly Glu Thr Val Asp Asp
        115                 120                 125

Glu Leu Glu Ser Asn Ala Ile Asp Phe Leu Gly Arg Cys Gln Gly Ser
    130                 135                 140

Glu Gly Gly Tyr Gly Gly Gly Pro Gly Gln Leu Pro His Leu Ala Thr
145                 150                 155                 160

Thr Tyr Ala Ala Val Asn Ala Leu Val Thr Leu Gly Gly Asp Lys Ala
                165                 170                 175

Leu Ser Ser Ile Asn Arg Glu Lys Met Ser Cys Phe Leu Arg Arg Met
            180                 185                 190

Lys Asp Thr Ser Gly Gly Phe Arg Met His Asp Met Gly Glu Met Asp
        195                 200                 205

Val Arg Ala Cys Tyr Thr Ala Ile Ser Val Ala Ser Ile Leu Asn Ile
    210                 215                 220

Met Asp Asp Glu Leu Thr Gln Gly Leu Gly Asp Tyr Ile Leu Ser Cys
225                 230                 235                 240
```

```
Gln Thr Tyr Glu Gly Gly Ile Gly Gly Glu Pro Gly Ser Glu Ala His
                245                 250                 255

Gly Gly Tyr Thr Tyr Cys Gly Leu Ala Ala Met Ile Leu Ile Asn Glu
            260                 265                 270

Val Asp Arg Leu Asn Leu Asp Ser Leu Met Asn Trp Ala Val His Arg
        275                 280                 285

Gln Gly Val Glu Met Gly Phe Gln Gly Arg Thr Asn Lys Leu Val Asp
    290                 295                 300

Gly Cys Tyr Thr Phe Trp Gln Ala Ala Pro Cys Val Leu Leu Gln Arg
305                 310                 315                 320

Leu Tyr Ser Thr Asn Asp His Asp Val His Gly Ser Ser His Ile Ser
                325                 330                 335

Glu Gly Thr Asn Glu Glu His His Ala His Asp Glu Asp Asp Leu Glu
            340                 345                 350

Asp Ser Asp Asp Asp Asp Asp Ser Asp Glu Asp Asn Asp Glu Asp Ser
        355                 360                 365

Val Asn Gly His Arg Ile His His Thr Ser Thr Tyr Ile Asn Arg Arg
    370                 375                 380

Met Gln Leu Val Phe Asp Ser Leu Gly Leu Gln Arg Tyr Val Leu Leu
385                 390                 395                 400

Cys Ser Lys Ile Pro Asp Gly Gly Phe Arg Asp Lys Pro Arg Lys Pro
                405                 410                 415

Arg Asp Phe Tyr His Thr Cys Tyr Cys Leu Ser Gly Leu Ser Val Ala
            420                 425                 430

Gln His Ala Trp Leu Lys Asp Glu Asp Thr Pro Pro Leu Thr Arg Asp
        435                 440                 445

Ile Met Gly Gly Tyr Ser Asn Leu Leu Glu Pro Val Gln Leu Leu His
    450                 455                 460

Asn Ile Val Met Asp Gln Tyr Asn Glu Ala Ile Glu Phe Phe Phe Lys
465                 470                 475                 480

Ala Ala


<210> SEQ ID NO 88
<211> LENGTH: 378
<212> TYPE: PRT
<213> ORGANISM: Glycine max

<400> SEQUENCE: 88

Ala Thr Ile Pro Arg Asn Ala Gln Thr Leu Met Leu Glu Leu Gln Arg
  1               5                  10                  15

Asp Asn His Met Gln Tyr Val Ser Lys Gly Leu Arg His Leu Ser Ser
            20                  25                  30

Ala Phe Ser Val Leu Asp Ala Asn Arg Pro Trp Leu Cys Tyr Trp Ile
        35                  40                  45

Phe His Ser Ile Ala Leu Ser Gly Glu Ser Val Asp Asp Glu Leu Glu
     50                  55                  60

Asp Asn Ala Ile Asp Phe Leu Asn Arg Cys Gln Asp Pro Asn Gly Gly
 65                  70                  75                  80

Tyr Ala Gly Gly Pro Gly Gln Met Pro His Ile Ala Thr Thr Tyr Ala
                 85                  90                  95

Ala Val Asn Ser Leu Ile Thr Leu Gly Gly Glu Lys Ser Leu Ala Ser
            100                 105                 110

Ile Asn Arg Asp Lys Leu Tyr Gly Phe Leu Arg Arg Met Lys Gln Pro
        115                 120                 125
```

Asn Gly Gly Phe Arg Met His Asp Glu Gly Glu Ile Asp Val Arg Ala
    130                 135                 140

Cys Tyr Thr Ala Ile Ser Val Ala Ser Val Leu Asn Ile Leu Asp Asp
145                 150                 155                 160

Glu Leu Ile Gln Asn Val Gly Asp Tyr Ile Ile Ser Cys Gln Thr Tyr
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240

Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270

Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375

<210> SEQ ID NO 89
<211> LENGTH: 414
<212> TYPE: PRT
<213> ORGANISM: Zea mays

<400> SEQUENCE: 89

Ala Asp Pro Asp Leu Pro Arg Leu Thr Val Thr Gln Val Glu Gln Met
  1               5                  10                  15

Lys Val Glu Ala Arg Val Gly Asp Ile Tyr Arg Ser Leu Phe Gly Ala
            20                  25                  30

Ala Pro Asn Thr Lys Ser Ile Met Leu Glu Leu Trp Arg Asp Gln His
        35                  40                  45

Ile Glu Tyr Leu Thr Pro Gly Leu Arg His Met Gly Pro Ala Phe His
     50                  55                  60

Val Leu Asp Ala Asn Arg Pro Trp Leu Cys Tyr Trp Met Val His Pro
 65                  70                  75                  80

Leu Ala Leu Leu Asp Glu Ala Leu Asp Asp Asp Leu Glu Asn Asp Ile
                 85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn

```
        115                 120                 125

Thr Leu Val Thr Ile Gly Ser Gln Arg Ala Leu Ser Ser Ile Asn Arg
    130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190

Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Lys Ser Ser Tyr Ser Cys Lys Arg Pro Ser Gly Glu Asp
    290                 295                 300

Ala Cys Ser Thr Ser Ser Tyr Gly Cys Thr Ala Lys Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380

Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410


<210> SEQ ID NO 90
<211> LENGTH: 420
<212> TYPE: PRT
<213> ORGANISM: Pisum sativum

<400> SEQUENCE: 90

Met Glu Ala Ser Thr Ala Ala Glu Thr Pro Thr Pro Thr Val Ser Gln
  1               5                  10                  15

Arg Asp Gln Trp Ile Val Glu Ser Gln Val Phe His Ile Tyr Gln Leu
             20                  25                  30

Phe Ala Asn Ile Pro Pro Asn Ala Gln Ser Ile Ile Arg Pro Trp Leu
         35                  40                  45

Cys Tyr Trp Ile Ile His Ser Ile Ala Leu Leu Gly Glu Ser Ile Asp
     50                  55                  60

Asp Asp Leu Glu Asp Asn Thr Val Asp Phe Leu Asn Arg Cys Gln Asp
 65                  70                  75                  80
```

Pro Asn Gly Gly Tyr Ala Gly Gly Pro Gly Gln Met Pro His Leu Ala
85 90 95

Thr Thr Tyr Ala Ala Val Asn Thr Leu Ile Thr Leu Gly Gly Glu Lys
100 105 110

Ser Leu Ala Ser Ile Asn Arg Asn Lys Leu Tyr Gly Phe Met Arg Arg
115 120 125

Met Lys Gln Pro Asn Gly Gly Phe Arg Met His Asp Glu Gly Glu Ile
130 135 140

Asp Val Arg Ala Cys Tyr Thr Ala Ile Ser Val Ala Ser Val Leu Asn
145 150 155 160

Ile Leu Asp Asp Glu Leu Ile Lys Asn Val Gly Asp Phe Ile Leu Ser
165 170 175

Cys Gln Thr Tyr Glu Gly Gly Leu Ala Gly Glu Pro Gly Ser Glu Ala
180 185 190

His Gly Gly Tyr Thr Phe Cys Gly Leu Ala Ala Met Ile Leu Ile Gly
195 200 205

Glu Val Asn Arg Leu Asp Leu Pro Arg Leu Leu Asp Trp Val Val Phe
210 215 220

Arg Gln Gly Lys Glu Cys Gly Phe Gln Gly Arg Thr Asn Lys Leu Val
225 230 235 240

Asp Gly Cys Tyr Ser Phe Trp Gln Gly Gly Ala Val Ala Leu Leu Gln
245 250 255

Arg Leu His Ser Ile Ile Asp Glu Gln Met Ala Glu Ala Ser Gln Phe
260 265 270

Val Thr Val Ser Asp Ala Pro Glu Glu Lys Glu Cys Leu Asp Gly Thr
275 280 285

Ser Ser His Ala Thr Ser His Ile Arg His Glu Gly Met Asn Glu Ser
290 295 300

Cys Ser Ser Asp Val Lys Asn Ile Gly Tyr Asn Phe Ile Ser Glu Trp
305 310 315 320

Arg Gln Ser Glu Pro Leu Phe His Ser Ile Ala Leu Gln Gln Tyr Ile
325 330 335

Leu Leu Cys Ser Gln Glu Gln Asp Gly Gly Leu Arg Asp Lys Pro Gly
340 345 350

Lys Arg Arg Asp His Tyr His Ser Cys Tyr Cys Leu Ser Gly Leu Ser
355 360 365

Leu Cys Gln Tyr Ser Trp Ser Lys Arg Pro Asp Ser Pro Pro Leu Pro
370 375 380

Lys Val Val Met Gly Pro Tyr Ser Ser Asn Leu Leu Glu Pro Ile His
385 390 395 400

Pro Leu Phe Asn Val Val Leu Asp Arg Tyr Arg Glu Ala His Glu Phe
405 410 415

Phe Ser Gln Leu
420

<210> SEQ ID NO 91
<211> LENGTH: 470
<212> TYPE: PRT
<213> ORGANISM: Lycopersicon esculentum

<400> SEQUENCE: 91

Met Glu Ser Arg Lys Val Thr Lys Thr Leu Glu Asp Gln Trp Val Val
1 5 10 15

Glu Arg Arg Val Arg Glu Ile Tyr Asp Tyr Phe Tyr Ser Ile Ser Pro
20 25 30

```
Asn Ser Pro Ser Asp Leu Ile Glu Ile Glu Arg Asp Lys His Phe Gly
        35                  40                  45

Tyr Leu Ser Gln Gly Leu Arg Lys Leu Gly Pro Ser Phe Ser Val Leu
    50                  55                  60

Asp Ala Ser Arg Pro Trp Leu Cys Tyr Trp Thr Leu His Ser Ile Ala
65                  70                  75                  80

Leu Leu Gly Glu Ser Ile Gly Gly Lys Leu Glu Asn Asp Ala Ile Asp
                85                  90                  95

Phe Leu Thr Arg Cys Gln Asp Lys Asp Gly Gly Tyr Gly Gly Gly Pro
            100                 105                 110

Gly Gln Met Pro His Leu Ala Thr Thr Tyr Ala Ala Val Asn Ser Leu
        115                 120                 125

Ile Thr Leu Gly Lys Pro Glu Ala Leu Ser Ser Ile Asn Arg Glu Lys
    130                 135                 140

Leu Tyr Thr Phe Leu Leu Arg Met Lys Asp Ala Ser Gly Gly Phe Arg
145                 150                 155                 160

Met His Asp Gly Gly Glu Val Asp Val Arg Ala Cys Tyr Thr Ala Ile
                165                 170                 175

Ser Val Ala Asn Ile Leu Asn Ile Val Asp Asp Glu Leu Ile His Gly
            180                 185                 190

Val Gly Asn Tyr Ile Leu Ser Cys Gln Thr Tyr Glu Gly Gly Ile Ala
        195                 200                 205

Gly Glu Pro Gly Ser Glu Ala His Gly Gly Tyr Thr Phe Cys Gly Leu
    210                 215                 220

Ala Ala Met Ile Leu Ile Asn Glu Val Asp Arg Leu Asp Leu Pro Gly
225                 230                 235                 240

Leu Ile Asp Trp Val Val Phe Arg Gln Gly Val Glu Gly Gly Phe Gln
                245                 250                 255

Gly Arg Thr Asn Lys Leu Val Asp Gly Cys Tyr Ser Phe Trp Gln Gly
            260                 265                 270

Ala Val Val Phe Leu Ile Gln Arg Leu Asn Leu Ile Val His Glu Gln
        275                 280                 285

Leu Gly Leu Ser Asn Asp Leu Ser Thr Glu Ser Ala Asp Asp Ser Ser
    290                 295                 300

Glu Ser Glu Leu Ser Asp Glu Glu Glu His Leu Glu Gly Ile Ser Ser
305                 310                 315                 320

His Val Gln Asp Thr Phe Pro Leu Gly Gln Ala Gly Ala Cys Gln Glu
                325                 330                 335

Asn Ala Ser His Ser Pro Lys Ile Ala Asp Thr Gly Tyr Glu Phe Ile
            340                 345                 350

Asn Arg Pro Ile Ala Met Arg Pro Leu Phe Asp Ser Met Tyr Leu Gln
        355                 360                 365

Gln Tyr Val Leu Leu Cys Ser Gln Ile Glu Val Gly Gly Phe Arg Asp
    370                 375                 380

Lys Pro Gly Lys Gly Arg Asp Tyr Tyr His Thr Cys Tyr Cys Leu Ser
385                 390                 395                 400

Gly Leu Ser Ile Ala Gln Tyr Ser Trp Thr Asp Glu Ala Asp Ser Thr
                405                 410                 415

Pro Leu Pro Arg Asp Val Phe Gly Pro Tyr Ser Lys Cys Leu Leu Glu
            420                 425                 430

Gln Val His Pro Leu Phe Asn Val Val Leu Asp Arg Tyr Tyr Glu Ala
        435                 440                 445
```

```
Arg Glu Tyr Ser Gln Ala Cys Glu Thr Val Ser Pro Leu Ser Leu Ala
    450                 455                 460

Pro Thr Phe Ser Glu Thr
465                 470
```

<210> SEQ ID NO 92
<211> LENGTH: 446
<212> TYPE: PRT
<213> ORGANISM: Nicotiana sp.

<400> SEQUENCE: 92

```
Gly Thr Ser Gly Thr Arg Thr Leu Glu Asp Gln Trp Met Val Glu Arg
  1               5                  10                  15

Gln Val Arg Glu Ile Tyr Asn Phe Phe Tyr Ser Ile Pro Pro Asn Ser
             20                  25                  30

His Leu Glu Thr Ser Thr Glu Lys His Phe Asp Tyr Leu Thr Arg Gly
         35                  40                  45

Leu Arg Lys Leu Gly Pro Ser Phe Ser Val Leu Asp Ala Asn Arg Pro
     50                  55                  60

Trp Leu Cys Tyr Trp Ile Leu His Ser Ile Ala Leu Leu Gly Glu Ser
 65                  70                  75                  80

Ile Asp Ala Gln Leu Glu Asn Asp Ala Ile Asp Phe Leu Ser Arg Cys
                 85                  90                  95

Gln Asp Glu Asp Gly Gly Tyr Gly Gly Gly Pro Gly Gln Met Pro His
            100                 105                 110

Leu Ala Thr Thr Tyr Ala Ala Val Asn Ser Leu Ile Thr Leu Gly Ser
        115                 120                 125

Pro Lys Ala Leu Ser Ser Ile Asn Arg Glu Lys Leu Tyr Thr Phe Trp
    130                 135                 140

Leu Gln Met Lys Asp Thr Ser Gly Gly Phe Arg Met His Asp Gly Gly
145                 150                 155                 160

Glu Val Asp Val Arg Ala Cys Tyr Thr Ala Ile Ser Val Ala Ser Ile
                165                 170                 175

Leu Gln Ile Val Asp Asp Glu Leu Ile Asn Asp Val Gly Asn Tyr Ile
            180                 185                 190

Leu Ser Cys Gln Thr Tyr Glu Gly Gly Ile Ala Gly Glu Pro Gly Ser
        195                 200                 205

Glu Ala His Gly Gly Tyr Thr Phe Cys Gly Leu Ala Ala Met Ile Leu
    210                 215                 220

Ile Asn Glu Ala Asn Arg Leu Asp Leu Pro Arg Leu Ile Asp Trp Val
225                 230                 235                 240

Val Phe Arg Gln Gly Val Glu Gly Gly Phe Gln Gly Arg Thr Asn Lys
                245                 250                 255

Leu Val Asp Gly Cys Tyr Ser Phe Trp Gln Ala Ala Val Ala Phe Leu
            260                 265                 270

Ile Gln Arg Leu Lys Ser Thr Val His Glu Gln Leu Gly Leu Ser Asn
        275                 280                 285

Glu Leu Ser Thr Glu Ser Ala Asp Asp Ser Ser Glu Ser Glu Leu Ser
    290                 295                 300

Asp Glu Glu His Leu Gln Gly Thr Ser Ser His Val Gln Lys Thr Cys
305                 310                 315                 320

Pro Leu Gly Gln Glu Gly Gln Glu Asn Ala Ser Asp Pro Thr Lys Ile
                325                 330                 335

Ala Asp Thr Gly Tyr Asp Phe Val Asn Arg Thr Ile Ala Met Arg Pro
            340                 345                 350
```

```
Val Phe Asp Ser Phe Tyr Leu Gln Gln Tyr Val Leu Leu Cys Ser Gln
        355                 360                 365

Ile Asp Gly Gly Phe Arg Asp Lys Pro Gly Lys Gly Arg Asp His Tyr
    370                 375                 380

His Thr Cys Tyr Cys Leu Ser Gly Leu Ser Ile Ala Gln Tyr Ser Trp
385                 390                 395                 400

Thr Asn Glu Ala Asp Ala Pro Pro Leu Pro Arg Asp Val Phe Gly Pro
                405                 410                 415

Tyr Ser Gln Asn Leu Leu Glu Gln Ile His Pro Leu Tyr Asn Val Val
            420                 425                 430

Leu Asp Arg Tyr Tyr Glu Ala Arg Ser Phe Phe Ser Cys Leu
        435                 440                 445
```

```
<210> SEQ ID NO 93
<211> LENGTH: 323
<212> TYPE: PRT
<213> ORGANISM: Artificial Sequence
<220> FEATURE:
<223> OTHER INFORMATION: Description of Artificial Sequence: Consensus
      FTA
<220> FEATURE:
<221> NAME/KEY: VARIANT
<222> LOCATION: (1)..(6)
<223> OTHER INFORMATION: Wherein Xaa is any amino acid.
<220> FEATURE:
<221> NAME/KEY: VARIANT
<222> LOCATION: (10)..(11)
<223> OTHER INFORMATION: Wherein Xaa is any amino acid.
<220> FEATURE:
<221> NAME/KEY: VARIANT
<222> LOCATION: (13)
<223> OTHER INFORMATION: Wherein Xaa is any amino acid.
<220> FEATURE:
<221> NAME/KEY: VARIANT
<222> LOCATION: (19)
<223> OTHER INFORMATION: Wherein Xaa is any amino acid.
<220> FEATURE:
<221> NAME/KEY: VARIANT
<222> LOCATION: (21)..(22)
<223> OTHER INFORMATION: Wherein Xaa is any amino acid.
<220> FEATURE:
<221> NAME/KEY: VARIANT
<222> LOCATION: (24)
<223> OTHER INFORMATION: Wherein Xaa is any amino acid.
<220> FEATURE:
<221> NAME/KEY: VARIANT
<222> LOCATION: (34)
<223> OTHER INFORMATION: Wherein Xaa is any amino acid.
<220> FEATURE:
<221> NAME/KEY: VARIANT
<222> LOCATION: (36)
<223> OTHER INFORMATION: Wherein Xaa is any amino acid.
<220> FEATURE:
<221> NAME/KEY: VARIANT
<222> LOCATION: (40)
<223> OTHER INFORMATION: Wherein Xaa is any amino acid.
<220> FEATURE:
<221> NAME/KEY: VARIANT
<222> LOCATION: (42)
<223> OTHER INFORMATION: Wherein Xaa is any amino acid.
<220> FEATURE:
<221> NAME/KEY: VARIANT
<222> LOCATION: (68)
<223> OTHER INFORMATION: Wherein Xaa is any amino acid.
<220> FEATURE:
<221> NAME/KEY: VARIANT
<222> LOCATION: (86)
<223> OTHER INFORMATION: Wherein Xaa is any amino acid.
<220> FEATURE:
<221> NAME/KEY: VARIANT
<222> LOCATION: (89)
<223> OTHER INFORMATION: Wherein Xaa is any amino acid.
```

<220> FEATURE:
<221> NAME/KEY: VARIANT
<222> LOCATION: (92)
<223> OTHER INFORMATION: Wherein Xaa is any amino acid.
<220> FEATURE:
<221> NAME/KEY: VARIANT
<222> LOCATION: (92)
<223> OTHER INFORMATION: Wherein Xaa is any amino acid.
<220> FEATURE:
<221> NAME/KEY: VARIANT
<222> LOCATION: (129)
<223> OTHER INFORMATION: Wherein Xaa is any amino acid.
<220> FEATURE:
<221> NAME/KEY: VARIANT
<222> LOCATION: (194)
<223> OTHER INFORMATION: Wherein Xaa is any amino acid.
<220> FEATURE:
<221> NAME/KEY: VARIANT
<222> LOCATION: (218)
<223> OTHER INFORMATION: Wherein Xaa is any amino acid.
<220> FEATURE:
<221> NAME/KEY: VARIANT
<222> LOCATION: (284)
<223> OTHER INFORMATION: Wherein Xaa is any amino acid.
<220> FEATURE:
<221> NAME/KEY: VARIANT
<222> LOCATION: (304)
<223> OTHER INFORMATION: Wherein Xaa is any amino acid.
<220> FEATURE:
<221> NAME/KEY: VARIANT
<222> LOCATION: (320)..(323)
<223> OTHER INFORMATION: Wherein Xaa is any amino acid.

<400> SEQUENCE: 93

```
Xaa Xaa Xaa Xaa Xaa Xaa Val Pro Leu Xaa Xaa Arg Xaa Glu Trp Ser
  1               5                  10                  15

Asp Val Xaa Pro Xaa Xaa Gln Xaa Asp Gly Pro Asn Pro Val Val Pro
             20                  25                  30

Ile Xaa Tyr Xaa Glu Glu Phe Xaa Glu Xaa Met Asp Tyr Phe Arg Ala
         35                  40                  45

Ile Tyr Phe Ser Asp Glu Arg Ser Pro Arg Ala Leu Arg Leu Thr Glu
     50                  55                  60

Glu Ala Leu Xaa Leu Asn Ser Gly Asn Tyr Thr Val Trp His Phe Arg
 65                  70                  75                  80

Arg Leu Val Leu Glu Xaa Leu Asn Xaa Asp Leu Xaa Glu Glu Leu Glu
                 85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Xaa Glu Leu Glu Phe Thr Arg Arg Val Leu Ser Leu Asp Ala Lys His
    130                 135                 140

Tyr His Ala Trp Ser His Arg Gln Trp Ala Leu Gln Ala Leu Gly Gly
145                 150                 155                 160

Trp Glu Asp Glu Leu Asn Tyr Cys His Glu Leu Leu Glu Ala Asp Val
                165                 170                 175

Phe Asn Asn Ser Ala Trp Asn Gln Arg Tyr Tyr Val Ile Thr Arg Ser
            180                 185                 190

Pro Xaa Leu Gly Gly Leu Glu Ala Met Arg Glu Ser Glu Val Ser Tyr
        195                 200                 205

Thr Ile Lys Ala Ile Leu Ala Asn Pro Xaa Asn Glu Ser Ser Trp Arg
    210                 215                 220

Tyr Leu Lys Ala Leu Tyr Lys Asp Asp Thr Glu Ser Trp Ile Ser Asp
225                 230                 235                 240
```

```
Pro Ser Val Ser Ser Val Cys Leu Lys Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Arg Asp Ser Val Xaa Ala Leu Ala Asn
        275                 280                 285

Glu Glu Pro Glu Thr Asn Leu Ala Asn Leu Val Cys Thr Ile Leu Xaa
    290                 295                 300

Arg Val Asp Pro Ile Arg Ala Asn Tyr Trp Ala Trp Arg Lys Ser Xaa
305                 310                 315                 320

Xaa Xaa Xaa


<210> SEQ ID NO 94
<211> LENGTH: 394
<212> TYPE: PRT
<213> ORGANISM: Artificial Sequence
<220> FEATURE:
<223> OTHER INFORMATION: Description of Artificial Sequence: Consensus
      FTB
<220> FEATURE:
<221> NAME/KEY: VARIANT
<222> LOCATION: (1)
<223> OTHER INFORMATION: Wherein Xaa is any amino acid.
<220> FEATURE:
<221> NAME/KEY: VARIANT
<222> LOCATION: (3)..(5)
<223> OTHER INFORMATION: Wherein Xaa is any amino acid.
<220> FEATURE:
<221> NAME/KEY: VARIANT
<222> LOCATION: (7)..(10)
<220> FEATURE:
<221> NAME/KEY: VARIANT
<222> LOCATION: (15)
<223> OTHER INFORMATION: Wherein Xaa is any amino acid.
<220> FEATURE:
<221> NAME/KEY: VARIANT
<222> LOCATION: (18)
<223> OTHER INFORMATION: Wherein Xaa is any amino acid.
<220> FEATURE:
<221> NAME/KEY: VARIANT
<222> LOCATION: (20)..(21)
<223> OTHER INFORMATION: Wherein Xaa is any amino acid.
<220> FEATURE:
<221> NAME/KEY: VARIANT
<222> LOCATION: (23)..(25)
<223> OTHER INFORMATION: Wherein Xaa is any amino acid.
<220> FEATURE:
<221> NAME/KEY: VARIANT
<222> LOCATION: (30)..(32)
<223> OTHER INFORMATION: Wherein Xaa is any amino acid.
<220> FEATURE:
<221> NAME/KEY: VARIANT
<222> LOCATION: (35)
<223> OTHER INFORMATION: Wherein Xaa is any amino acid.
<220> FEATURE:
<221> NAME/KEY: VARIANT
<222> LOCATION: (49)
<223> OTHER INFORMATION: Wherein Xaa is any amino acid.
<220> FEATURE:
<221> NAME/KEY: VARIANT
<222> LOCATION: (72)
<223> OTHER INFORMATION: Wherein Xaa is any amino acid.
<220> FEATURE:
<221> NAME/KEY: VARIANT
<222> LOCATION: (77)
<223> OTHER INFORMATION: Wherein Xaa is any amino acid.
<220> FEATURE:
<221> NAME/KEY: VARIANT
<222> LOCATION: (82)
<223> OTHER INFORMATION: Wherein Xaa is any amino acid.
<220> FEATURE:
<221> NAME/KEY: VARIANT
```

<222> LOCATION: (116)
<223> OTHER INFORMATION: Wherein Xaa is any amino acid.
<220> FEATURE:
<221> NAME/KEY: VARIANT
<222> LOCATION: (117)
<223> OTHER INFORMATION: Wherein Xaa is any amino acid.
<220> FEATURE:
<221> NAME/KEY: VARIANT
<222> LOCATION: (120)
<223> OTHER INFORMATION: Wherein Xaa is any amino acid.
<220> FEATURE:
<221> NAME/KEY: VARIANT
<222> LOCATION: (128)
<223> OTHER INFORMATION: Wherein Xaa is any amino acid.
<220> FEATURE:
<221> NAME/KEY: VARIANT
<222> LOCATION: (137)
<223> OTHER INFORMATION: Wherein Xaa is any amino acid.
<220> FEATURE:
<221> NAME/KEY: VARIANT
<222> LOCATION: (154)
<223> OTHER INFORMATION: Wherein Xaa is any amino acid.
<220> FEATURE:
<221> NAME/KEY: VARIANT
<222> LOCATION: (163)..(164)
<223> OTHER INFORMATION: Wherein Xaa is any amino acid.
<220> FEATURE:
<221> NAME/KEY: VARIANT
<222> LOCATION: (171)
<223> OTHER INFORMATION: Wherein Xaa is any amino acid.
<220> FEATURE:
<221> NAME/KEY: VARIANT
<222> LOCATION: (207)..(208)
<223> OTHER INFORMATION: Wherein Xaa is any amino acid.
<220> FEATURE:
<221> NAME/KEY: VARIANT
<222> LOCATION: (215)..(216)
<223> OTHER INFORMATION: Wherein Xaa is any amino acid.
<220> FEATURE:
<221> NAME/KEY: VARIANT
<222> LOCATION: (248)
<223> OTHER INFORMATION: Wherein Xaa is any amino acid.
<220> FEATURE:
<221> NAME/KEY: VARIANT
<222> LOCATION: (255)
<223> OTHER INFORMATION: Wherein Xaa is any amino acid.
<220> FEATURE:
<221> NAME/KEY: VARIANT
<222> LOCATION: (258)
<223> OTHER INFORMATION: Wherein Xaa is any amino acid.
<220> FEATURE:
<221> NAME/KEY: VARIANT
<222> LOCATION: (262)..(264)
<223> OTHER INFORMATION: Wherein Xaa is any amino acid.
<220> FEATURE:
<221> NAME/KEY: VARIANT
<222> LOCATION: (267)..(269)
<223> OTHER INFORMATION: Wherein Xaa is any amino acid.
<220> FEATURE:
<221> NAME/KEY: VARIANT
<222> LOCATION: (271)..(276)
<223> OTHER INFORMATION: Wherein Xaa is any amino acid.
<220> FEATURE:
<221> NAME/KEY: VARIANT
<222> LOCATION: (278)..(280)
<223> OTHER INFORMATION: Wherein Xaa is any amino acid.
<220> FEATURE:
<221> NAME/KEY: VARIANT
<222> LOCATION: (285)..(287)
<223> OTHER INFORMATION: Wherein Xaa is any amino acid.
<220> FEATURE:
<221> NAME/KEY: VARIANT
<222> LOCATION: (289)..(296)
<223> OTHER INFORMATION: Wherein Xaa is any amino acid.
<220> FEATURE:
<221> NAME/KEY: VARIANT
<222> LOCATION: (300)..(301)
<223> OTHER INFORMATION: Wherein Xaa is any amino acid.
<220> FEATURE:

<221> NAME/KEY: VARIANT
<222> LOCATION: (303)..(304)
<223> OTHER INFORMATION: Wherein Xaa is any amino acid.
<220> FEATURE:
<221> NAME/KEY: VARIANT
<222> LOCATION: (306)..(309)
<223> OTHER INFORMATION: Wherein Xaa is any amino acid.
<220> FEATURE:
<221> NAME/KEY: VARIANT
<222> LOCATION: (312)..(314)
<223> OTHER INFORMATION: Wherein Xaa is any amino acid.
<220> FEATURE:
<221> NAME/KEY: VARIANT
<222> LOCATION: (316)
<223> OTHER INFORMATION: Wherein Xaa is any amino acid.
<220> FEATURE:
<221> NAME/KEY: VARIANT
<222> LOCATION: (318)
<223> OTHER INFORMATION: Wherein Xaa is any amino acid.
<220> FEATURE:
<221> NAME/KEY: VARIANT
<222> LOCATION: (337)
<223> OTHER INFORMATION: Wherein Xaa is any amino acid.
<220> FEATURE:
<221> NAME/KEY: VARIANT
<222> LOCATION: (348)
<223> OTHER INFORMATION: Wherein Xaa is any amino acid.
<220> FEATURE:
<221> NAME/KEY: VARIANT
<222> LOCATION: (364)
<223> OTHER INFORMATION: Wherein Xaa is any amino acid.
<220> FEATURE:
<221> NAME/KEY: VARIANT
<222> LOCATION: (372)
<223> OTHER INFORMATION: Wherein Xaa is any amino acid.
<220> FEATURE:
<221> NAME/KEY: VARIANT
<222> LOCATION: (378)..(381)
<223> OTHER INFORMATION: Wherein Xaa is any amino acid.
<220> FEATURE:
<221> NAME/KEY: VARIANT
<222> LOCATION: (384)
<223> OTHER INFORMATION: Wherein Xaa is any amino acid.
<220> FEATURE:
<221> NAME/KEY: VARIANT
<222> LOCATION: (386)
<223> OTHER INFORMATION: Wherein Xaa is any amino acid.
<220> FEATURE:
<221> NAME/KEY: VARIANT
<222> LOCATION: (388)
<223> OTHER INFORMATION: Wherein Xaa is any amino acid.
<220> FEATURE:
<221> NAME/KEY: VARIANT
<222> LOCATION: (392)
<223> OTHER INFORMATION: Wherein Xaa is any amino acid.
<220> FEATURE:
<221> NAME/KEY: VARIANT
<222> LOCATION: (394)
<223> OTHER INFORMATION: Wherein Xaa is any amino acid.

<400> SEQUENCE: 94

```
Xaa Thr Xaa Xaa Xaa Asn Xaa Xaa Xaa Xaa Met Leu Glu Leu Xaa Arg
  1               5                  10                  15

Asp Xaa His Xaa Xaa Tyr Xaa Xaa Xaa Gly Leu Arg His Xaa Xaa Xaa
             20                  25                  30

Ala Phe Xaa Val Leu Asp Ala Asn Arg Pro Trp Leu Cys Tyr Trp Ile
         35                  40                  45

Xaa His Ser Ile Ala Leu Leu Gly Glu Ser Val Asp Asp Asp Leu Glu
     50                  55                  60

Asn Asn Ala Ile Asp Phe Leu Xaa Arg Cys Gln Asp Xaa Asp Gly Gly
 65                  70                  75                  80

Tyr Xaa Gly Gly Pro Gly Gln Leu Pro His Leu Ala Thr Thr Tyr Ala
                 85                  90                  95
```

Ala Val Asn Thr Leu Val Thr Leu Gly Gly Glu Lys Ala Leu Ser Ser
100 105 110

Ile Asn Arg Xaa Xaa Leu Tyr Xaa Phe Leu Arg Arg Met Lys Asp Xaa
115 120 125

Asn Gly Gly Phe Arg Met His Asp Xaa Gly Glu Ile Asp Val Arg Ala
130 135 140

Cys Tyr Thr Ala Ile Ser Val Ala Ser Xaa Leu Asn Ile Leu Asp Asp
145 150 155 160

Glu Leu Xaa Xaa Gly Val Gly Asp Tyr Ile Xaa Ser Cys Gln Thr Tyr
165 170 175

Glu Gly Gly Ile Ala Gly Glu Pro Gly Ser Glu Ala His Gly Gly Tyr
180 185 190

Thr Phe Cys Gly Leu Ala Thr Met Ile Leu Ile Asn Glu Val Xaa Xaa
195 200 205

Leu Asp Leu Pro Ser Leu Xaa Xaa Trp Val Val Phe Arg Gln Gly Val
210 215 220

Glu Cys Gly Phe Gln Gly Arg Thr Asn Lys Leu Val Asp Gly Cys Tyr
225 230 235 240

Ser Phe Trp Gln Gly Ala Ala Xaa Ala Leu Leu Gln Arg Leu Xaa Ser
245 250 255

Ile Xaa Asp Lys Gln Xaa Xaa Xaa Ser Ser Xaa Xaa Xaa Ser Xaa Xaa
260 265 270

Xaa Xaa Xaa Xaa Glu Xaa Xaa Xaa Gly Thr Ser Ser Xaa Xaa Xaa Cys
275 280 285

Xaa Xaa Xaa Xaa Xaa Xaa Xaa Xaa Glu Ser Ser Xaa Xaa Asp Xaa Xaa
290 295 300

Asn Xaa Xaa Xaa Xaa Phe Ile Xaa Xaa Xaa Arg Xaa Ile Xaa Pro Leu
305 310 315 320

Phe His Ser Ile Ala Leu Gln Gln Tyr Ile Leu Leu Cys Ser Gln Val
325 330 335

Xaa Glu Gly Gly Leu Arg Asp Lys Pro Gly Lys Xaa Arg Asp His Tyr
340 345 350

His Thr Cys Tyr Cys Leu Ser Gly Leu Ser Val Xaa Gln Tyr Ser Trp
355 360 365

Ser Lys Asp Xaa Asp Ser Pro Pro Leu Xaa Xaa Xaa Xaa Leu Gly Xaa
370 375 380

Tyr Xaa Asn Xaa Leu Glu Pro Xaa His Xaa
385 390

<210> SEQ ID NO 95
<211> LENGTH: 1018
<212> TYPE: DNA
<213> ORGANISM: Artificial Sequence
<220> FEATURE:
<223> OTHER INFORMATION: Description of Artificial Sequence: Consensus FTA
<220> FEATURE:
<221> NAME/KEY: misc_feature
<222> LOCATION: (1)..(4)
<223> OTHER INFORMATION: Wherein n is a or t or c or g.
<220> FEATURE:
<221> NAME/KEY: misc_feature
<222> LOCATION: (7)..(8)
<223> OTHER INFORMATION: Wherein n is a or t or c or g.
<220> FEATURE:
<221> NAME/KEY: misc_feature
<222> LOCATION: (10)
<223> OTHER INFORMATION: Wherein n is a or t or c or g.
<220> FEATURE:

<221> NAME/KEY: misc_feature
<222> LOCATION: (12)
<223> OTHER INFORMATION: Wherein n is a or t or c or g.
<220> FEATURE:
<221> NAME/KEY: misc_feature
<222> LOCATION: (14)
<223> OTHER INFORMATION: Wherein n is a or t or c or g.
<220> FEATURE:
<221> NAME/KEY: misc_feature
<222> LOCATION: (17)..(18)
<223> OTHER INFORMATION: Wherein n is a or t or c or g.
<220> FEATURE:
<221> NAME/KEY: misc_feature
<222> LOCATION: (20)
<223> OTHER INFORMATION: Wherein n is a or t or c or g.
<220> FEATURE:
<221> NAME/KEY: misc_feature
<222> LOCATION: (22)..(23)
<223> OTHER INFORMATION: Wherein n is a or t or c or g.
<220> FEATURE:
<221> NAME/KEY: misc_feature
<222> LOCATION: (25)
<223> OTHER INFORMATION: Wherein n is a or t or c or g.
<220> FEATURE:
<221> NAME/KEY: misc_feature
<222> LOCATION: (27)..(28)
<223> OTHER INFORMATION: Wherein n is a or t or c or g.
<220> FEATURE:
<221> NAME/KEY: misc_feature
<222> LOCATION: (35)..(36)
<223> OTHER INFORMATION: Wherein n is a or t or c or g.
<220> FEATURE:
<221> NAME/KEY: misc_feature
<222> LOCATION: (41)..(42)
<223> OTHER INFORMATION: Wherein n is a or t or c or g.
<220> FEATURE:
<221> NAME/KEY: misc_feature
<222> LOCATION: (44)..(45)
<223> OTHER INFORMATION: Wherein n is a or t or c or g.
<220> FEATURE:
<221> NAME/KEY: misc_feature
<222> LOCATION: (48)
<223> OTHER INFORMATION: Wherein n is a or t or c or g.
<220> FEATURE:
<221> NAME/KEY: misc_feature
<222> LOCATION: (62)
<223> OTHER INFORMATION: Wherein n is a or t or c or g.
<220> FEATURE:
<221> NAME/KEY: misc_feature
<222> LOCATION: (65)..(68)
<223> OTHER INFORMATION: Wherein n is a or t or c or g.
<220> FEATURE:
<221> NAME/KEY: misc_feature
<222> LOCATION: (71)..(72)
<223> OTHER INFORMATION: Wherein n is a or t or c or g.
<220> FEATURE:
<221> NAME/KEY: misc_feature
<222> LOCATION: (74)..(75)
<223> OTHER INFORMATION: Wherein n is a or t or c or g.
<220> FEATURE:
<221> NAME/KEY: misc_feature
<222> LOCATION: (80)..(81)
<223> OTHER INFORMATION: Wherein n is a or t or c or g.
<220> FEATURE:
<221> NAME/KEY: misc_feature
<222> LOCATION: (86)
<223> OTHER INFORMATION: Wherein n is a or t or c or g.
<220> FEATURE:
<221> NAME/KEY: misc_feature
<222> LOCATION: (89)
<223> OTHER INFORMATION: Wherein n is a or t or c or g.
<220> FEATURE:
<221> NAME/KEY: misc_feature
<222> LOCATION: (92)
<223> OTHER INFORMATION: Wherein n is a or t or c or g.
<220> FEATURE:
<221> NAME/KEY: misc_feature
<222> LOCATION: (95)
<223> OTHER INFORMATION: Wherein n is a or t or c or g.

<220> FEATURE:
<221> NAME/KEY: misc_feature
<222> LOCATION: (98)
<223> OTHER INFORMATION: Wherein n is a or t or c or g.
<220> FEATURE:
<221> NAME/KEY: misc_feature
<222> LOCATION: (101)
<223> OTHER INFORMATION: Wherein n is a or t or c or g.
<220> FEATURE:
<221> NAME/KEY: misc_feature
<222> LOCATION: (104)
<223> OTHER INFORMATION: Wherein n is a or t or c or g.
<220> FEATURE:
<221> NAME/KEY: misc_feature
<222> LOCATION: (107)
<223> OTHER INFORMATION: Wherein n is a or t or c or g.
<220> FEATURE:
<221> NAME/KEY: misc_feature
<222> LOCATION: (110)..(113)
<223> OTHER INFORMATION: Wherein n is a or t or c or g.
<220> FEATURE:
<221> NAME/KEY: misc_feature
<222> LOCATION: (118)..(119)
<223> OTHER INFORMATION: Wherein n is a or t or c or g.
<220> FEATURE:
<221> NAME/KEY: misc_feature
<222> LOCATION: (128)..(130)
<223> OTHER INFORMATION: Wherein n is a or t or c or g.
<220> FEATURE:
<221> NAME/KEY: misc_feature
<222> LOCATION: (134)..(136)
<223> OTHER INFORMATION: Wherein n is a or t or c or g.
<220> FEATURE:
<221> NAME/KEY: misc_feature
<222> LOCATION: (176)
<223> OTHER INFORMATION: Wherein n is a or t or c or g.
<220> FEATURE:
<221> NAME/KEY: misc_feature
<222> LOCATION: (188)
<223> OTHER INFORMATION: Wherein n is a or t or c or g.
<220> FEATURE:
<221> NAME/KEY: misc_feature
<222> LOCATION: (191)
<223> OTHER INFORMATION: Wherein n is a or t or c or g.
<220> FEATURE:
<221> NAME/KEY: misc_feature
<222> LOCATION: (214)
<223> OTHER INFORMATION: Wherein n is a or t or c or g.
<220> FEATURE:
<221> NAME/KEY: misc_feature
<222> LOCATION: (236)
<220> FEATURE:
<221> NAME/KEY: misc_feature
<222> LOCATION: (249)
<223> OTHER INFORMATION: Wherein n is a or t or c or g.
<220> FEATURE:
<221> NAME/KEY: misc_feature
<222> LOCATION: (276)
<223> OTHER INFORMATION: Wherein n is a or t or c or g.
<220> FEATURE:
<221> NAME/KEY: misc_feature
<222> LOCATION: (342)
<223> OTHER INFORMATION: Wherein n is a or t or c or g.
<220> FEATURE:
<221> NAME/KEY: misc_feature
<222> LOCATION: (395)
<223> OTHER INFORMATION: Wherein n is a or t or c or g.
<220> FEATURE:
<221> NAME/KEY: misc_feature
<222> LOCATION: (398)
<223> OTHER INFORMATION: Wherein n is a or t or c or g.
<220> FEATURE:
<221> NAME/KEY: misc_feature
<222> LOCATION: (416)
<223> OTHER INFORMATION: Wherein n is a or t or c or g.
<220> FEATURE:
<221> NAME/KEY: misc_feature
<222> LOCATION: (425)
<223> OTHER INFORMATION: Wherein n is a or t or c or g.

<220> FEATURE:
<221> NAME/KEY: misc_feature
<222> LOCATION: (473)
<223> OTHER INFORMATION: Wherein n is a or t or c or g.
<220> FEATURE:
<221> NAME/KEY: misc_feature
<222> LOCATION: (554)
<223> OTHER INFORMATION: Wherein n is a or t or c or g.
<220> FEATURE:
<221> NAME/KEY: misc_feature
<222> LOCATION: (581)
<223> OTHER INFORMATION: Wherein n is a or t or c or g.
<220> FEATURE:
<221> NAME/KEY: misc_feature
<222> LOCATION: (664)
<223> OTHER INFORMATION: Wherein n is a or t or c or g.
<220> FEATURE:
<221> NAME/KEY: misc_feature
<222> LOCATION: (677)
<223> OTHER INFORMATION: Wherein n is a or t or c or g.
<220> FEATURE:
<221> NAME/KEY: misc_feature
<222> LOCATION: (695)
<223> OTHER INFORMATION: Wherein n is a or t or c or g.
<220> FEATURE:
<221> NAME/KEY: misc_feature
<222> LOCATION: (716)
<223> OTHER INFORMATION: Wherein n is a or t or c or g.
<220> FEATURE:
<221> NAME/KEY: misc_feature
<222> LOCATION: (719)
<223> OTHER INFORMATION: Wherein n is a or t or c or g.
<220> FEATURE:
<221> NAME/KEY: misc_feature
<222> LOCATION: (758)
<223> OTHER INFORMATION: Wherein n is a or t or c or g.
<220> FEATURE:
<221> NAME/KEY: misc_feature
<222> LOCATION: (764)
<223> OTHER INFORMATION: Wherein n is a or t or c or g.
<220> FEATURE:
<221> NAME/KEY: misc_feature
<222> LOCATION: (767)
<223> OTHER INFORMATION: Wherein n is a or t or c or g.
<220> FEATURE:
<221> NAME/KEY: misc_feature
<222> LOCATION: (773)
<223> OTHER INFORMATION: Wherein n is a or t or c or g.
<220> FEATURE:
<221> NAME/KEY: misc_feature
<222> LOCATION: (776)
<223> OTHER INFORMATION: Wherein n is a or t or c or g.
<220> FEATURE:
<221> NAME/KEY: misc_feature
<222> LOCATION: (827)
<223> OTHER INFORMATION: Wherein n is a or t or c or g.
<220> FEATURE:
<221> NAME/KEY: misc_feature
<222> LOCATION: (857)
<223> OTHER INFORMATION: Wherein n is a or t or c or g.
<220> FEATURE:
<221> NAME/KEY: misc_feature
<222> LOCATION: (914)
<223> OTHER INFORMATION: Wherein n is a or t or c or g.
<220> FEATURE:
<221> NAME/KEY: misc_feature
<222> LOCATION: (921)
<223> OTHER INFORMATION: Wherein n is a or t or c or g.
<220> FEATURE:
<221> NAME/KEY: misc_feature
<222> LOCATION: (960)..(962)
<223> OTHER INFORMATION: Wherein n is a or t or c or g.
<220> FEATURE:
<221> NAME/KEY: misc_feature
<222> LOCATION: (965)
<223> OTHER INFORMATION: Wherein n is a or t or c or g.
<220> FEATURE:
<221> NAME/KEY: misc_feature
<222> LOCATION: (967)..(970)

<223> OTHER INFORMATION: Wherein n is a or t or c or g.
<220> FEATURE:
<221> NAME/KEY: misc_feature
<222> LOCATION: (974)..(976)
<223> OTHER INFORMATION: Wherein n is a or t or c or g.
<220> FEATURE:
<221> NAME/KEY: misc_feature
<222> LOCATION: (978)
<223> OTHER INFORMATION: Wherein n is a or t or c or g.
<220> FEATURE:
<221> NAME/KEY: misc_feature
<222> LOCATION: (980)
<223> OTHER INFORMATION: Wherein n is a or t or c or g.
<220> FEATURE:
<221> NAME/KEY: misc_feature
<222> LOCATION: (982)
<223> OTHER INFORMATION: Wherein n is a or t or c or g.
<220> FEATURE:
<221> NAME/KEY: misc_feature
<222> LOCATION: (984)
<223> OTHER INFORMATION: Wherein n is a or t or c or g.
<220> FEATURE:
<221> NAME/KEY: misc_feature
<222> LOCATION: (988)
<223> OTHER INFORMATION: Wherein n is a or t or c or g.
<220> FEATURE:
<221> NAME/KEY: misc_feature
<222> LOCATION: (990)..(994)
<223> OTHER INFORMATION: Wherein n is a or t or c or g.
<220> FEATURE:
<221> NAME/KEY: misc_feature
<222> LOCATION: (997)
<223> OTHER INFORMATION: Wherein n is a or t or c or g.
<220> FEATURE:
<221> NAME/KEY: misc_feature
<222> LOCATION: (1000)
<223> OTHER INFORMATION: Wherein n is a or t or c or g.
<220> FEATURE:
<221> NAME/KEY: misc_feature
<222> LOCATION: (1004)..(1006)
<223> OTHER INFORMATION: Wherein n is a or t or c or g.
<220> FEATURE:
<221> NAME/KEY: misc_feature
<222> LOCATION: (1008)..(1009)
<223> OTHER INFORMATION: Wherein n is a or t or c or g.
<220> FEATURE:
<221> NAME/KEY: misc_feature
<222> LOCATION: (1011)..(1015)
<223> OTHER INFORMATION: Wherein n is a or t or c or g.
<220> FEATURE:
<221> NAME/KEY: misc_feature
<222> LOCATION: (1017)
<223> OTHER INFORMATION: Wherein n is a or t or c or g.

<400> SEQUENCE: 95
nnnncgnngn ananganntn cnncnanncg tgccnntgag nnanngantg gagtggtcag 60
angtnnnncc nntnnctcan nacganggnc cnaanccngt ngtnccnatn nnntacanng 120
aagagttnnn cgannntatg gattacttcc gtgcgattta cttctccgac gagcgntctc 180
ctcgcgcnct ncgactcacg gaagaagccc tccncttaaa ctccggcaac tacacngtgt 240
ggcatttcng gcgcttagta ctcgaggcgc ttaatnacga cttgtatgaa gaactcgagt 300
tcatcgaacg cattgctgag gataactcta agaactacca gntgtggcat catcgacgat 360
gggttgcaga gaaactgggt cctgatgttg caggnaanga acttgagttt acccgnaggg 420
tactntcact tgatgccaaa cattatcatg cttggtcaca taggcagtgg gcnctacaag 480
cattaggagg atgggaagat gagcttaatt actgccacga gctccttgaa gctgacgtct 540
ttaacaattc tgcntggaat cagaggtatt atgtcataac nagatctcct ttgttgggag 600
gcctagaagc catgagagaa tctgaagtaa gctacacaat caaagccatt ttagccaatc 660
ctgnaaacga gagctcntgg agatacctaa aagcncttta caaagacgac acagantcnt 720

```
ggattagtga tccaagtgtt tcctcagtct gtttgaangt tctntcncgc acngantgct    780

tccatggatt cgctctgagc acccttttgg atcttctatg cgatggnttg agaccaacca    840

acgagcatag agactcngtg aaagctctag ctaatgaaga accagagact aacttggcca    900

atttggtgtg tacnattctg ngtcgtgtag atccaataag agctaactat tgggcatggn    960

nnaanannnn gatnnnantn gnancaantn nnnnatntgn cgcnnnanna nnnnncnt     1018
```

<210> SEQ ID NO 96
<211> LENGTH: 1237
<212> TYPE: DNA
<213> ORGANISM: Artificial Sequence
<220> FEATURE:
<223> OTHER INFORMATION: Description of Artificial Sequence: Consensus
      FTB
<220> FEATURE:
<221> NAME/KEY: misc_feature
<222> LOCATION: (1)..(34)
<223> OTHER INFORMATION: Wherein n is a or t or c or g.
<220> FEATURE:
<221> NAME/KEY: misc_feature
<222> LOCATION: (36)
<223> OTHER INFORMATION: Wherein n is a or t or c or g.
<220> FEATURE:
<221> NAME/KEY: misc_feature
<222> LOCATION: (40)
<223> OTHER INFORMATION: Wherein n is a or t or c or g.
<220> FEATURE:
<221> NAME/KEY: misc_feature
<222> LOCATION: (42)..(45)
<223> OTHER INFORMATION: Wherein n is a or t or c or g.
<220> FEATURE:
<221> NAME/KEY: misc_feature
<222> LOCATION: (48)
<223> OTHER INFORMATION: Wherein n is a or t or c or g.
<220> FEATURE:
<221> NAME/KEY: misc_feature
<222> LOCATION: (52)
<223> OTHER INFORMATION: Wherein n is a or t or c or g.
<220> FEATURE:
<221> NAME/KEY: misc_feature
<222> LOCATION: (54)
<223> OTHER INFORMATION: Wherein n is a or t or c or g.
<220> FEATURE:
<221> NAME/KEY: misc_feature
<222> LOCATION: (57)..(58)
<223> OTHER INFORMATION: Wherein n is a or t or c or g.
<220> FEATURE:
<221> NAME/KEY: misc_feature
<222> LOCATION: (60)..(61)
<223> OTHER INFORMATION: Wherein n is a or t or c or g.
<220> FEATURE:
<221> NAME/KEY: misc_feature
<222> LOCATION: (63)
<223> OTHER INFORMATION: Wherein n is a or t or c or g.
<220> FEATURE:
<221> NAME/KEY: misc_feature
<222> LOCATION: (67)
<223> OTHER INFORMATION: Wherein n is a or t or c or g.
<220> FEATURE:
<221> NAME/KEY: misc_feature
<222> LOCATION: (69)..(75)
<223> OTHER INFORMATION: Wherein n is a or t or c or g.
<220> FEATURE:
<221> NAME/KEY: misc_feature
<222> LOCATION: (78)..(79)
<223> OTHER INFORMATION: Wherein n is a or t or c or g.
<220> FEATURE:
<221> NAME/KEY: misc_feature
<222> LOCATION: (81)..(82)
<223> OTHER INFORMATION: Wherein n is a or t or c or g.
<220> FEATURE:
<221> NAME/KEY: misc_feature
<222> LOCATION: (84)
<223> OTHER INFORMATION: Wherein n is a or t or c or g.

<220> FEATURE:
<221> NAME/KEY: misc_feature
<222> LOCATION: (87)..(88)
<223> OTHER INFORMATION: Wherein n is a or t or c or g.
<220> FEATURE:
<221> NAME/KEY: misc_feature
<222> LOCATION: (90)..(91)
<223> OTHER INFORMATION: Wherein n is a or t or c or g.
<220> FEATURE:
<221> NAME/KEY: misc_feature
<222> LOCATION: (93)..(94)
<223> OTHER INFORMATION: Wherein n is a or t or c or g.
<220> FEATURE:
<221> NAME/KEY: misc_feature
<222> LOCATION: (96)..(99)
<223> OTHER INFORMATION: Wherein n is a or t or c or g.
<220> FEATURE:
<221> NAME/KEY: misc_feature
<222> LOCATION: (103)..(109)
<223> OTHER INFORMATION: Wherein n is a or t or c or g.
<220> FEATURE:
<221> NAME/KEY: misc_feature
<222> LOCATION: (111)
<223> OTHER INFORMATION: Wherein n is a or t or c or g.
<220> FEATURE:
<221> NAME/KEY: misc_feature
<222> LOCATION: (114)
<223> OTHER INFORMATION: Wherein n is a or t or c or g.
<220> FEATURE:
<221> NAME/KEY: misc_feature
<222> LOCATION: (117)
<223> OTHER INFORMATION: Wherein n is a or t or c or g.
<220> FEATURE:
<221> NAME/KEY: misc_feature
<222> LOCATION: (123)
<223> OTHER INFORMATION: Wherein n is a or t or c or g.
<220> FEATURE:
<221> NAME/KEY: misc_feature
<222> LOCATION: (126)
<223> OTHER INFORMATION: Wherein n is a or t or c or g.
<220> FEATURE:
<221> NAME/KEY: misc_feature
<222> LOCATION: (132)
<223> OTHER INFORMATION: Wherein n is a or t or c or g.
<220> FEATURE:
<221> NAME/KEY: misc_feature
<222> LOCATION: (135)
<223> OTHER INFORMATION: Wherein n is a or t or c or g.
<220> FEATURE:
<221> NAME/KEY: misc_feature
<222> LOCATION: (144)..(145)
<223> OTHER INFORMATION: Wherein n is a or t or c or g.
<220> FEATURE:
<221> NAME/KEY: misc_feature
<222> LOCATION: (165)
<223> OTHER INFORMATION: Wherein n is a or t or c or g.
<220> FEATURE:
<221> NAME/KEY: misc_feature
<222> LOCATION: (168)
<223> OTHER INFORMATION: Wherein n is a or t or c or g.
<220> FEATURE:
<221> NAME/KEY: misc_feature
<222> LOCATION: (171)..(172)
<223> OTHER INFORMATION: Wherein n is a or t or c or g.
<220> FEATURE:
<221> NAME/KEY: misc_feature
<222> LOCATION: (174)
<223> OTHER INFORMATION: Wherein n is a or t or c or g.
<220> FEATURE:
<221> NAME/KEY: misc_feature
<222> LOCATION: (177)
<223> OTHER INFORMATION: Wherein n is a or t or c or g.
<220> FEATURE:
<221> NAME/KEY: misc_feature
<222> LOCATION: (186)..(187)
<223> OTHER INFORMATION: Wherein n is a or t or c or g.
<220> FEATURE:
<221> NAME/KEY: misc_feature
<222> LOCATION: (189)

<223> OTHER INFORMATION: Wherein n is a or t or c or g.
<220> FEATURE:
<221> NAME/KEY: misc_feature
<222> LOCATION: (195)
<223> OTHER INFORMATION: Wherein n is a or t or c or g.
<220> FEATURE:
<221> NAME/KEY: misc_feature
<222> LOCATION: (201)
<223> OTHER INFORMATION: Wherein n is a or t or c or g.
<220> FEATURE:
<221> NAME/KEY: misc_feature
<222> LOCATION: (204)
<223> OTHER INFORMATION: Wherein n is a or t or c or g.
<220> FEATURE:
<221> NAME/KEY: misc_feature
<222> LOCATION: (207)
<223> OTHER INFORMATION: Wherein n is a or t or c or g.
<220> FEATURE:
<221> NAME/KEY: misc_feature
<222> LOCATION: (210)
<223> OTHER INFORMATION: Wherein n is a or t or c or g.
<220> FEATURE:
<221> NAME/KEY: misc_feature
<222> LOCATION: (215)..(216)
<223> OTHER INFORMATION: Wherein n is a or t or c or g.
<220> FEATURE:
<221> NAME/KEY: misc_feature
<222> LOCATION: (219)
<223> OTHER INFORMATION: Wherein n is a or t or c or g.
<220> FEATURE:
<221> NAME/KEY: misc_feature
<222> LOCATION: (227)
<223> OTHER INFORMATION: Wherein n is a or t or c or g.
<220> FEATURE:
<221> NAME/KEY: misc_feature
<222> LOCATION: (229)
<223> OTHER INFORMATION: Wherein n is a or t or c or g.
<220> FEATURE:
<221> NAME/KEY: misc_feature
<222> LOCATION: (231)
<223> OTHER INFORMATION: Wherein n is a or t or c or g.
<220> FEATURE:
<221> NAME/KEY: misc_feature
<222> LOCATION: (252)
<223> OTHER INFORMATION: Wherein n is a or t or c or g.
<220> FEATURE:
<221> NAME/KEY: misc_feature
<222> LOCATION: (261)..(262)
<223> OTHER INFORMATION: Wherein n is a or t or c or g.
<220> FEATURE:
<221> NAME/KEY: misc_feature
<222> LOCATION: (264)
<223> OTHER INFORMATION: Wherein n is a or t or c or g.
<220> FEATURE:
<221> NAME/KEY: misc_feature
<222> LOCATION: (267)
<223> OTHER INFORMATION: Wherein n is a or t or c or g.
<220> FEATURE:
<221> NAME/KEY: misc_feature
<222> LOCATION: (276)
<223> OTHER INFORMATION: Wherein n is a or t or c or g.
<220> FEATURE:
<221> NAME/KEY: misc_feature
<222> LOCATION: (279)
<223> OTHER INFORMATION: Wherein n is a or t or c or g.
<220> FEATURE:
<221> NAME/KEY: misc_feature
<222> LOCATION: (291)
<223> OTHER INFORMATION: Wherein n is a or t or c or g.
<220> FEATURE:
<221> NAME/KEY: misc_feature
<222> LOCATION: (294)
<223> OTHER INFORMATION: Wherein n is a or t or c or g.
<220> FEATURE:
<221> NAME/KEY: misc_feature
<222> LOCATION: (298)
<223> OTHER INFORMATION: Wherein n is a or t or c or g.
<220> FEATURE:
<221> NAME/KEY: misc_feature
<222> LOCATION: (315)
<223> OTHER INFORMATION: Wherein n is a or t or c or g.
<220> FEATURE:
<221> NAME/KEY: misc_feature
<222> LOCATION: (321)
<223> OTHER INFORMATION: Wherein n is a or t or c or g.
<220> FEATURE:
<221> NAME/KEY: misc_feature
<222> LOCATION: (328)
<223> OTHER INFORMATION: Wherein n is a or t or c or g.
<220> FEATURE:
<221> NAME/KEY: misc_feature
<222> LOCATION: (330)
<223> OTHER INFORMATION: Wherein n is a or t or c or g.
<220> FEATURE:
<221> NAME/KEY: misc_feature
<222> LOCATION: (333)
<223> OTHER INFORMATION: Wherein n is a or t or c or g.
<220> FEATURE:
<221> NAME/KEY: misc_feature
<222> LOCATION: (348)
<223> OTHER INFORMATION: Wherein n is a or t or c or g.
<220> FEATURE:
<221> NAME/KEY: misc_feature
<222> LOCATION: (352)
<223> OTHER INFORMATION: Wherein n is a or t or c or g.
<220> FEATURE:
<221> NAME/KEY: misc_feature
<222> LOCATION: (356)
<223> OTHER INFORMATION: Wherein n is a or t or c or g.
<220> FEATURE:
<221> NAME/KEY: misc_feature
<222> LOCATION: (358)
<223> OTHER INFORMATION: Wherein n is a or t or c or g.
<220> FEATURE:
<221> NAME/KEY: misc_feature
<222> LOCATION: (364)
<223> OTHER INFORMATION: Wherein n is a or t or c or g.
<220> FEATURE:
<221> NAME/KEY: misc_feature
<222> LOCATION: (366)..(367)
<223> OTHER INFORMATION: Wherein n is a or t or c or g.
<220> FEATURE:
<221> NAME/KEY: misc_feature
<222> LOCATION: (369)
<223> OTHER INFORMATION: Wherein n is a or t or c or g.
<220> FEATURE:
<221> NAME/KEY: misc_feature
<222> LOCATION: (382)
<223> OTHER INFORMATION: Wherein n is a or t or c or g.
<220> FEATURE:
<221> NAME/KEY: misc_feature
<222> LOCATION: (386)
<223> OTHER INFORMATION: Wherein n is a or t or c or g.
<220> FEATURE:
<221> NAME/KEY: misc_feature
<222> LOCATION: (390)
<223> OTHER INFORMATION: Wherein n is a or t or c or g.
<220> FEATURE:
<221> NAME/KEY: misc_feature
<222> LOCATION: (409)..(411)
<223> OTHER INFORMATION: Wherein n is a or t or c or g.
<220> FEATURE:
<221> NAME/KEY: misc_feature
<222> LOCATION: (414)
<223> OTHER INFORMATION: Wherein n is a or t or c or g.
<220> FEATURE:
<221> NAME/KEY: misc_feature
<222> LOCATION: (426)
<223> OTHER INFORMATION: Wherein n is a or t or c or g.
<220> FEATURE:
<221> NAME/KEY: misc_feature
<222> LOCATION: (429)
<223> OTHER INFORMATION: Wherein n is a or t or c or g.
<220> FEATURE:
<221> NAME/KEY: misc_feature
<222> LOCATION: (432)
<223> OTHER INFORMATION: Wherein n is a or t or c or g.
<220> FEATURE:

-continued

<221> NAME/KEY: misc_feature
<222> LOCATION: (444)
<223> OTHER INFORMATION: Wherein n is a or t or c or g.
<220> FEATURE:
<221> NAME/KEY: misc_feature
<222> LOCATION: (460)
<223> OTHER INFORMATION: Wherein n is a or t or c or g.
<220> FEATURE:
<221> NAME/KEY: misc_feature
<222> LOCATION: (462)..(463)
<223> OTHER INFORMATION: Wherein n is a or t or c or g.
<220> FEATURE:
<221> NAME/KEY: misc_feature
<222> LOCATION: (468)
<223> OTHER INFORMATION: Wherein n is a or t or c or g.
<220> FEATURE:
<221> NAME/KEY: misc_feature
<222> LOCATION: (472)
<223> OTHER INFORMATION: Wherein n is a or t or c or g.
<220> FEATURE:
<221> NAME/KEY: misc_feature
<222> LOCATION: (486)
<223> OTHER INFORMATION: Wherein n is a or t or c or g.
<220> FEATURE:
<221> NAME/KEY: misc_feature
<222> LOCATION: (492)
<223> OTHER INFORMATION: Wherein n is a or t or c or g.
<220> FEATURE:
<221> NAME/KEY: misc_feature
<222> LOCATION: (495)..(496)
<223> OTHER INFORMATION: Wherein n is a or t or c or g.
<220> FEATURE:
<221> NAME/KEY: misc_feature
<222> LOCATION: (504)
<223> OTHER INFORMATION: Wherein n is a or t or c or g.
<220> FEATURE:
<221> NAME/KEY: misc_feature
<222> LOCATION: (510)..(511)
<223> OTHER INFORMATION: Wherein n is a or t or c or g.
<220> FEATURE:
<221> NAME/KEY: misc_feature
<222> LOCATION: (513)
<223> OTHER INFORMATION: Wherein n is a or t or c or g.
<220> FEATURE:
<221> NAME/KEY: misc_feature
<222> LOCATION: (516)
<223> OTHER INFORMATION: Wherein n is a or t or c or g.
<220> FEATURE:
<221> NAME/KEY: misc_feature
<222> LOCATION: (519)
<223> OTHER INFORMATION: Wherein n is a or t or c or g.
<220> FEATURE:
<221> NAME/KEY: misc_feature
<222> LOCATION: (542)..(543)
<223> OTHER INFORMATION: Wherein n is a or t or c or g.
<220> FEATURE:
<221> NAME/KEY: misc_feature
<222> LOCATION: (549)
<223> OTHER INFORMATION: Wherein n is a or t or c or g.
<220> FEATURE:
<221> NAME/KEY: misc_feature
<222> LOCATION: (555)
<223> OTHER INFORMATION: Wherein n is a or t or c or g.
<220> FEATURE:
<221> NAME/KEY: misc_feature
<222> LOCATION: (558)
<223> OTHER INFORMATION: Wherein n is a or t or c or g.
<220> FEATURE:
<221> NAME/KEY: misc_feature
<222> LOCATION: (576)
<223> OTHER INFORMATION: Wherein n is a or t or c or g.
<220> FEATURE:
<221> NAME/KEY: misc_feature
<222> LOCATION: (579)
<223> OTHER INFORMATION: Wherein n is a or t or c or g.
<220> FEATURE:
<221> NAME/KEY: misc_feature
<222> LOCATION: (581)
<223> OTHER INFORMATION: Wherein n is a or t or c or g.

<220> FEATURE:
<221> NAME/KEY: misc_feature
<222> LOCATION: (588)
<223> OTHER INFORMATION: Wherein n is a or t or c or g.
<220> FEATURE:
<221> NAME/KEY: misc_feature
<222> LOCATION: (595)
<223> OTHER INFORMATION: Wherein n is a or t or c or g.
<220> FEATURE:
<221> NAME/KEY: misc_feature
<222> LOCATION: (604)
<223> OTHER INFORMATION: Wherein n is a or t or c or g.
<220> FEATURE:
<221> NAME/KEY: misc_feature
<222> LOCATION: (606)
<223> OTHER INFORMATION: Wherein n is a or t or c or g.
<220> FEATURE:
<221> NAME/KEY: misc_feature
<222> LOCATION: (609)
<223> OTHER INFORMATION: Wherein n is a or t or c or g.
<220> FEATURE:
<221> NAME/KEY: misc_feature
<222> LOCATION: (618)
<223> OTHER INFORMATION: Wherein n is a or t or c or g.
<220> FEATURE:
<221> NAME/KEY: misc_feature
<222> LOCATION: (621)
<223> OTHER INFORMATION: Wherein n is a or t or c or g.
<220> FEATURE:
<221> NAME/KEY: misc_feature
<222> LOCATION: (623)..(624)
<223> OTHER INFORMATION: Wherein n is a or t or c or g.
<220> FEATURE:
<221> NAME/KEY: misc_feature
<222> LOCATION: (628)
<223> OTHER INFORMATION: Wherein n is a or t or c or g.
<220> FEATURE:
<221> NAME/KEY: misc_feature
<222> LOCATION: (634)..(635)
<223> OTHER INFORMATION: Wherein n is a or t or c or g.
<220> FEATURE:
<221> NAME/KEY: misc_feature
<222> LOCATION: (637)..(639)
<223> OTHER INFORMATION: Wherein n is a or t or c or g.
<220> FEATURE:
<221> NAME/KEY: misc_feature
<222> LOCATION: (645)..(646)
<223> OTHER INFORMATION: Wherein n is a or t or c or g.
<220> FEATURE:
<221> NAME/KEY: misc_feature
<222> LOCATION: (648)
<223> OTHER INFORMATION: Wherein n is a or t or c or g.
<220> FEATURE:
<221> NAME/KEY: misc_feature
<222> LOCATION: (654)
<223> OTHER INFORMATION: Wherein n is a or t or c or g.
<220> FEATURE:
<221> NAME/KEY: misc_feature
<222> LOCATION: (658)..(659)
<223> OTHER INFORMATION: Wherein n is a or t or c or g.
<220> FEATURE:
<221> NAME/KEY: misc_feature
<222> LOCATION: (672)
<223> OTHER INFORMATION: Wherein n is a or t or c or g.
<220> FEATURE:
<221> NAME/KEY: misc_feature
<222> LOCATION: (676)..(678)
<223> OTHER INFORMATION: Wherein n is a or t or c or g.
<220> FEATURE:
<221> NAME/KEY: misc_feature
<222> LOCATION: (684)
<223> OTHER INFORMATION: Wherein n is a or t or c or g.
<220> FEATURE:
<221> NAME/KEY: misc_feature
<222> LOCATION: (690)
<223> OTHER INFORMATION: Wherein n is a or t or c or g.
<220> FEATURE:
<221> NAME/KEY: misc_feature
<222> LOCATION: (693)

<223> OTHER INFORMATION: Wherein n is a or t or c or g.
<220> FEATURE:
<221> NAME/KEY: misc_feature
<222> LOCATION: (696)
<223> OTHER INFORMATION: Wherein n is a or t or c or g.
<220> FEATURE:
<221> NAME/KEY: misc_feature
<222> LOCATION: (699)
<223> OTHER INFORMATION: Wherein n is a or t or c or g.
<220> FEATURE:
<221> NAME/KEY: misc_feature
<222> LOCATION: (708)
<223> OTHER INFORMATION: Wherein n is a or t or c or g.
<220> FEATURE:
<221> NAME/KEY: misc_feature
<222> LOCATION: (721)
<223> OTHER INFORMATION: Wherein n is a or t or c or g.
<220> FEATURE:
<221> NAME/KEY: misc_feature
<222> LOCATION: (723)
<223> OTHER INFORMATION: Wherein n is a or t or c or g.
<220> FEATURE:
<221> NAME/KEY: misc_feature
<222> LOCATION: (734)
<223> OTHER INFORMATION: Wherein n is a or t or c or g.
<220> FEATURE:
<221> NAME/KEY: misc_feature
<222> LOCATION: (738)..(739)
<223> OTHER INFORMATION: Wherein n is a or t or c or g.
<220> FEATURE:
<221> NAME/KEY: misc_feature
<222> LOCATION: (741)..(743)
<223> OTHER INFORMATION: Wherein n is a or t or c or g.
<220> FEATURE:
<221> NAME/KEY: misc_feature
<222> LOCATION: (746)
<223> OTHER INFORMATION: Wherein n is a or t or c or g.
<220> FEATURE:
<221> NAME/KEY: misc_feature
<222> LOCATION: (751)
<223> OTHER INFORMATION: Wherein n is a or t or c or g.
<220> FEATURE:
<221> NAME/KEY: misc_feature
<222> LOCATION: (764)
<223> OTHER INFORMATION: Wherein n is a or t or c or g.
<220> FEATURE:
<221> NAME/KEY: misc_feature
<222> LOCATION: (768)
<223> OTHER INFORMATION: Wherein n is a or t or c or g.
<220> FEATURE:
<221> NAME/KEY: misc_feature
<222> LOCATION: (770)..(774)
<223> OTHER INFORMATION: Wherein n is a or t or c or g.
<220> FEATURE:
<221> NAME/KEY: misc_feature
<222> LOCATION: (779)
<223> OTHER INFORMATION: Wherein n is a or t or c or g.
<220> FEATURE:
<221> NAME/KEY: misc_feature
<222> LOCATION: (781)..(787)
<223> OTHER INFORMATION: Wherein n is a or t or c or g.
<220> FEATURE:
<221> NAME/KEY: misc_feature
<222> LOCATION: (789)
<223> OTHER INFORMATION: Wherein n is a or t or c or g.
<220> FEATURE:
<221> NAME/KEY: misc_feature
<222> LOCATION: (791)..(793)
<223> OTHER INFORMATION: Wherein n is a or t or c or g.
<220> FEATURE:
<221> NAME/KEY: misc_feature
<222> LOCATION: (799)..(811)
<223> OTHER INFORMATION: Wherein n is a or t or c or g.
<220> FEATURE:
<221> NAME/KEY: misc_feature
<222> LOCATION: (813)
<223> OTHER INFORMATION: Wherein n is a or t or c or g.
<220> FEATURE:
<221> NAME/KEY: misc_feature
<222> LOCATION: (815)..(816)
<223> OTHER INFORMATION: Wherein n is a or t or c or g.
<220> FEATURE:
<221> NAME/KEY: misc_feature
<222> LOCATION: (818)..(819)
<223> OTHER INFORMATION: Wherein n is a or t or c or g.
<220> FEATURE:
<221> NAME/KEY: misc_feature
<222> LOCATION: (821)
<223> OTHER INFORMATION: Wherein n is a or t or c or g.
<220> FEATURE:
<221> NAME/KEY: misc_feature
<222> LOCATION: (823)
<223> OTHER INFORMATION: Wherein n is a or t or c or g.
<220> FEATURE:
<221> NAME/KEY: misc_feature
<222> LOCATION: (825)..(826)
<223> OTHER INFORMATION: Wherein n is a or t or c or g.
<220> FEATURE:
<221> NAME/KEY: misc_feature
<222> LOCATION: (828)
<223> OTHER INFORMATION: Wherein n is a or t or c or g.
<220> FEATURE:
<221> NAME/KEY: misc_feature
<222> LOCATION: (831)..(834)
<223> OTHER INFORMATION: Wherein n is a or t or c or g.
<220> FEATURE:
<221> NAME/KEY: misc_feature
<222> LOCATION: (836)
<223> OTHER INFORMATION: Wherein n is a or t or c or g.
<220> FEATURE:
<221> NAME/KEY: misc_feature
<222> LOCATION: (838)
<223> OTHER INFORMATION: Wherein n is a or t or c or g.
<220> FEATURE:
<221> NAME/KEY: misc_feature
<222> LOCATION: (840)..(841)
<223> OTHER INFORMATION: Wherein n is a or t or c or g.
<220> FEATURE:
<221> NAME/KEY: misc_feature
<222> LOCATION: (845)
<223> OTHER INFORMATION: Wherein n is a or t or c or g.
<220> FEATURE:
<221> NAME/KEY: misc_feature
<222> LOCATION: (847)
<223> OTHER INFORMATION: Wherein n is a or t or c or g.
<220> FEATURE:
<221> NAME/KEY: misc_feature
<222> LOCATION: (850)
<223> OTHER INFORMATION: Wherein n is a or t or c or g.
<220> FEATURE:
<221> NAME/KEY: misc_feature
<222> LOCATION: (852)..(856)
<223> OTHER INFORMATION: Wherein n is a or t or c or g.
<220> FEATURE:
<221> NAME/KEY: misc_feature
<222> LOCATION: (861)..(863)
<223> OTHER INFORMATION: Wherein n is a or t or c or g.
<220> FEATURE:
<221> NAME/KEY: misc_feature
<222> LOCATION: (865)..(871)
<223> OTHER INFORMATION: Wherein n is a or t or c or g.
<220> FEATURE:
<221> NAME/KEY: misc_feature
<222> LOCATION: (873)..(875)
<223> OTHER INFORMATION: Wherein n is a or t or c or g.
<220> FEATURE:
<221> NAME/KEY: misc_feature
<222> LOCATION: (879)
<223> OTHER INFORMATION: Wherein n is a or t or c or g.
<220> FEATURE:
<221> NAME/KEY: misc_feature
<222> LOCATION: (882)..(883)
<223> OTHER INFORMATION: Wherein n is a or t or c or g.
<220> FEATURE:
<221> NAME/KEY: misc_feature
<222> LOCATION: (885)
<223> OTHER INFORMATION: Wherein n is a or t or c or g.
<220> FEATURE:

<221> NAME/KEY: misc_feature
<222> LOCATION: (889)
<223> OTHER INFORMATION: Wherein n is a or t or c or g.
<220> FEATURE:
<221> NAME/KEY: misc_feature
<222> LOCATION: (891)
<223> OTHER INFORMATION: Wherein n is a or t or c or g.
<220> FEATURE:
<221> NAME/KEY: misc_feature
<222> LOCATION: (893)
<223> OTHER INFORMATION: Wherein n is a or t or c or g.
<220> FEATURE:
<221> NAME/KEY: misc_feature
<222> LOCATION: (895)
<223> OTHER INFORMATION: Wherein n is a or t or c or g.
<220> FEATURE:
<221> NAME/KEY: misc_feature
<222> LOCATION: (897)..(898)
<223> OTHER INFORMATION: Wherein n is a or t or c or g.
<220> FEATURE:
<221> NAME/KEY: misc_feature
<222> LOCATION: (902)..(906)
<223> OTHER INFORMATION: Wherein n is a or t or c or g.
<220> FEATURE:
<221> NAME/KEY: misc_feature
<222> LOCATION: (912)
<223> OTHER INFORMATION: Wherein n is a or t or c or g.
<220> FEATURE:
<221> NAME/KEY: misc_feature
<222> LOCATION: (914)
<223> OTHER INFORMATION: Wherein n is a or t or c or g.
<220> FEATURE:
<221> NAME/KEY: misc_feature
<222> LOCATION: (917)..(918)
<223> OTHER INFORMATION: Wherein n is a or t or c or g.
<220> FEATURE:
<221> NAME/KEY: misc_feature
<222> LOCATION: (920)
<223> OTHER INFORMATION: Wherein n is a or t or c or g.
<220> FEATURE:
<221> NAME/KEY: misc_feature
<222> LOCATION: (922)
<223> OTHER INFORMATION: Wherein n is a or t or c or g.
<220> FEATURE:
<221> NAME/KEY: misc_feature
<222> LOCATION: (925)..(926)
<223> OTHER INFORMATION: Wherein n is a or t or c or g.
<220> FEATURE:
<221> NAME/KEY: misc_feature
<222> LOCATION: (929)..(932)
<223> OTHER INFORMATION: Wherein n is a or t or c or g.
<220> FEATURE:
<221> NAME/KEY: misc_feature
<222> LOCATION: (936)..(937)
<223> OTHER INFORMATION: Wherein n is a or t or c or g.
<220> FEATURE:
<221> NAME/KEY: misc_feature
<222> LOCATION: (939)
<223> OTHER INFORMATION: Wherein n is a or t or c or g.
<220> FEATURE:
<221> NAME/KEY: misc_feature
<222> LOCATION: (942)..(944)
<223> OTHER INFORMATION: Wherein n is a or t or c or g.
<220> FEATURE:
<221> NAME/KEY: misc_feature
<222> LOCATION: (946)..(951)
<223> OTHER INFORMATION: Wherein n is a or t or c or g.
<220> FEATURE:
<221> NAME/KEY: misc_feature
<222> LOCATION: (955)..(957)
<223> OTHER INFORMATION: Wherein n is a or t or c or g.
<220> FEATURE:
<221> NAME/KEY: misc_feature
<222> LOCATION: (961)..(962)
<223> OTHER INFORMATION: Wherein n is a or t or c or g.
<220> FEATURE:
<221> NAME/KEY: misc_feature
<222> LOCATION: (967)..(968)
<223> OTHER INFORMATION: Wherein n is a or t or c or g.

<220> FEATURE:
<221> NAME/KEY: misc_feature
<222> LOCATION: (974)
<223> OTHER INFORMATION: Wherein n is a or t or c or g.
<220> FEATURE:
<221> NAME/KEY: misc_feature
<222> LOCATION: (980)
<223> OTHER INFORMATION: Wherein n is a or t or c or g.
<220> FEATURE:
<221> NAME/KEY: misc_feature
<222> LOCATION: (982)
<223> OTHER INFORMATION: Wherein n is a or t or c or g.
<220> FEATURE:
<221> NAME/KEY: misc_feature
<222> LOCATION: (984)
<223> OTHER INFORMATION: Wherein n is a or t or c or g.
<220> FEATURE:
<221> NAME/KEY: misc_feature
<222> LOCATION: (991)..(993)
<223> OTHER INFORMATION: Wherein n is a or t or c or g.
<220> FEATURE:
<221> NAME/KEY: misc_feature
<222> LOCATION: (998)
<223> OTHER INFORMATION: Wherein n is a or t or c or g.
<220> FEATURE:
<221> NAME/KEY: misc_feature
<222> LOCATION: (1000)
<223> OTHER INFORMATION: Wherein n is a or t or c or g.
<220> FEATURE:
<221> NAME/KEY: misc_feature
<222> LOCATION: (1006)
<223> OTHER INFORMATION: Wherein n is a or t or c or g.
<220> FEATURE:
<221> NAME/KEY: misc_feature
<222> LOCATION: (1009)
<223> OTHER INFORMATION: Wherein n is a or t or c or g.
<220> FEATURE:
<221> NAME/KEY: misc_feature
<222> LOCATION: (1018)
<223> OTHER INFORMATION: Wherein n is a or t or c or g.
<220> FEATURE:
<221> NAME/KEY: misc_feature
<222> LOCATION: (1020)..(1021)
<223> OTHER INFORMATION: Wherein n is a or t or c or g.
<220> FEATURE:
<221> NAME/KEY: misc_feature
<222> LOCATION: (1024)
<223> OTHER INFORMATION: Wherein n is a or t or c or g.
<220> FEATURE:
<221> NAME/KEY: misc_feature
<222> LOCATION: (1033)
<223> OTHER INFORMATION: Wherein n is a or t or c or g.
<220> FEATURE:
<221> NAME/KEY: misc_feature
<222> LOCATION: (1046)
<223> OTHER INFORMATION: Wherein n is a or t or c or g.
<220> FEATURE:
<221> NAME/KEY: misc_feature
<222> LOCATION: (1048)
<223> OTHER INFORMATION: Wherein n is a or t or c or g.
<220> FEATURE:
<221> NAME/KEY: misc_feature
<222> LOCATION: (1053)
<223> OTHER INFORMATION: Wherein n is a or t or c or g.
<220> FEATURE:
<221> NAME/KEY: misc_feature
<222> LOCATION: (1055)
<223> OTHER INFORMATION: Wherein n is a or t or c or g.
<220> FEATURE:
<221> NAME/KEY: misc_feature
<222> LOCATION: (1057)
<223> OTHER INFORMATION: Wherein n is a or t or c or g.
<220> FEATURE:
<221> NAME/KEY: misc_feature
<222> LOCATION: (1060)..(1062)
<223> OTHER INFORMATION: Wherein n is a or t or c or g.
<220> FEATURE:
<221> NAME/KEY: misc_feature
<222> LOCATION: (1066)

<223> OTHER INFORMATION: Wherein n is a or t or c or g.
<220> FEATURE:
<221> NAME/KEY: misc_feature
<222> LOCATION: (1084)
<223> OTHER INFORMATION: Wherein n is a or t or c or g.
<220> FEATURE:
<221> NAME/KEY: misc_feature
<222> LOCATION: (1087)
<223> OTHER INFORMATION: Wherein n is a or t or c or g.
<220> FEATURE:
<221> NAME/KEY: misc_feature
<222> LOCATION: (1090)
<223> OTHER INFORMATION: Wherein n is a or t or c or g.
<220> FEATURE:
<221> NAME/KEY: misc_feature
<222> LOCATION: (1093)
<223> OTHER INFORMATION: Wherein n is a or t or c or g.
<220> FEATURE:
<221> NAME/KEY: misc_feature
<222> LOCATION: (1096)
<223> OTHER INFORMATION: Wherein n is a or t or c or g.
<220> FEATURE:
<221> NAME/KEY: misc_feature
<222> LOCATION: (1100)..(1102)
<223> OTHER INFORMATION: Wherein n is a or t or c or g.
<220> FEATURE:
<221> NAME/KEY: misc_feature
<222> LOCATION: (1106)
<223> OTHER INFORMATION: Wherein n is a or t or c or g.
<220> FEATURE:
<221> NAME/KEY: misc_feature
<222> LOCATION: (1109)..(1110)
<223> OTHER INFORMATION: Wherein n is a or t or c or g.
<220> FEATURE:
<221> NAME/KEY: misc_feature
<222> LOCATION: (1116)
<223> OTHER INFORMATION: Wherein n is a or t or c or g.
<220> FEATURE:
<221> NAME/KEY: misc_feature
<222> LOCATION: (1120)
<223> OTHER INFORMATION: Wherein n is a or t or c or g.
<220> FEATURE:
<221> NAME/KEY: misc_feature
<222> LOCATION: (1124)..(1126)
<223> OTHER INFORMATION: Wherein n is a or t or c or g.
<220> FEATURE:
<221> NAME/KEY: misc_feature
<222> LOCATION: (1129)..(1130)
<223> OTHER INFORMATION: Wherein n is a or t or c or g.
<220> FEATURE:
<221> NAME/KEY: misc_feature
<222> LOCATION: (1135)
<223> OTHER INFORMATION: Wherein n is a or t or c or g.
<220> FEATURE:
<221> NAME/KEY: misc_feature
<222> LOCATION: (1138)
<223> OTHER INFORMATION: Wherein n is a or t or c or g.
<220> FEATURE:
<221> NAME/KEY: misc_feature
<222> LOCATION: (1141)..(1142)
<223> OTHER INFORMATION: Wherein n is a or t or c or g.
<220> FEATURE:
<221> NAME/KEY: misc_feature
<222> LOCATION: (1146)..(1148)
<223> OTHER INFORMATION: Wherein n is a or t or c or g.
<220> FEATURE:
<221> NAME/KEY: misc_feature
<222> LOCATION: (1150)..(1151)
<223> OTHER INFORMATION: Wherein n is a or t or c or g.
<220> FEATURE:
<221> NAME/KEY: misc_feature
<222> LOCATION: (1153)..(1154)
<223> OTHER INFORMATION: Wherein n is a or t or c or g.
<220> FEATURE:
<221> NAME/KEY: misc_feature
<222> LOCATION: (1156)
<223> OTHER INFORMATION: Wherein n is a or t or c or g.
<220> FEATURE:
<221> NAME/KEY: misc_feature
<222> LOCATION: (1159)..(1162)
<223> OTHER INFORMATION: Wherein n is a or t or c or g.
<220> FEATURE:
<221> NAME/KEY: misc_feature
<222> LOCATION: (1166)
<223> OTHER INFORMATION: Wherein n is a or t or c or g.
<220> FEATURE:
<221> NAME/KEY: misc_feature
<222> LOCATION: (1168)
<223> OTHER INFORMATION: Wherein n is a or t or c or g.
<220> FEATURE:
<221> NAME/KEY: misc_feature
<222> LOCATION: (1171)..(1174)
<223> OTHER INFORMATION: Wherein n is a or t or c or g.
<220> FEATURE:
<221> NAME/KEY: misc_feature
<222> LOCATION: (1177)
<223> OTHER INFORMATION: Wherein n is a or t or c or g.
<220> FEATURE:
<221> NAME/KEY: misc_feature
<222> LOCATION: (1180)
<223> OTHER INFORMATION: Wherein n is a or t or c or g.
<220> FEATURE:
<221> NAME/KEY: misc_feature
<222> LOCATION: (1183)..(1184)
<223> OTHER INFORMATION: Wherein n is a or t or c or g.
<220> FEATURE:
<221> NAME/KEY: misc_feature
<222> LOCATION: (1186)
<223> OTHER INFORMATION: Wherein n is a or t or c or g.
<220> FEATURE:
<221> NAME/KEY: misc_feature
<222> LOCATION: (1186)
<223> OTHER INFORMATION: Wherein n is a or t or c or g.
<220> FEATURE:
<221> NAME/KEY: misc_feature
<222> LOCATION: (1189)
<223> OTHER INFORMATION: Wherein n is a or t or c or g.
<220> FEATURE:
<221> NAME/KEY: misc_feature
<222> LOCATION: (1191)..(1237)
<223> OTHER INFORMATION: Wherein n is a or t or c or g.

<400> SEQUENCE: 96
nnnnnnnnnn nnnnnnnnnn nnnnnnnnnn nnnntngagn tnnnncgnga tnancanntn 60
nantatntnn nnnnnggnnt nngncanntn ngnncnnnnt ttnnnnnnnt ngangcnaat 120
cgnccntggc tntgntactg gatnnttcat tcaattgctt tgctnggnga nncngtngat 180
gatganntng aaaanaatgc natnganttn cttgnncgnt gccaggntnc ngatggtgga 240
tatggtggtg gncctggcca nntnccncat cttgcnacna cttatgctgc ngtnaatnca 300
cttgttactt taggnggtga naaagccntn tcntcaatta atagaganaa antgtntngt 360
tttntnngnc ggatgaagga tncaantggn ggtttcagga tgcatgatnn nggngaaatt 420
gatgtncgng cntgctacac tgcnatttcg gttgcaagcn tnntgaanat tntggatgat 480
gaactnaccc anggnntagg agantacatn ntnagntgnc aaacttatga aggtggcatt 540 gnnggggganc ctggntcnga agctcatggt gggtanacnt nctgtggntt ggctnctatg 600
attntnatna atgaggtnga ncnnttgnat ttgnntnnnt taatnnantg ggtngtannt 660
cgacaaggag tngaannngg attncaaggn agnacnaana aattggtnga tggttgctac 720
ncnttttggc aggnagcnnc nnntgntcta ntacaaagat tatnttcnan nnnngatang 780
nnnnnnnang nnncatcann nnnnnnnnnn ngngnnannt nangnncntg nnnnanangn 840
ncatnangan gnnnnncctg nnnannnnnn ngnnnatgnt gnntntgang ngnanannga 900
tnnnnnttca gngnatnntn anaannttnn nnatanntnt annnannnnn ncagnnnaat 960
nnaaccnntt tttnatagcn tngncttgca nnnatatntn ctcttntgnt ctcaggtncn 1020

```
nganggtgga ttnagagaca agccgngnaa acncngngan nnctancaca catgttactg   1080

cctnagnggn ctntcngtgn nncagnacnn ttggtnaaan gacnnngann ctccnccntt   1140

nnctcnnnan ntnntnggnn nntacncnaa nnnnctngan ccnntncanc nnnnnnnnnn   1200

nnnnnnnnnn nnnnnnnnnn nnnnnnnnnn nnnnnnn                            1237


<210> SEQ ID NO 97
<211> LENGTH: 1275
<212> TYPE: DNA
<213> ORGANISM: Arabidopsis thaliana

<400> SEQUENCE: 97

atggcgattc ctttcatgga aaccgtcgtg ggttttatga tagtgatgta catttttgag     60

acgtatttgg atctgaggca actcactgct ctcaagcttc caactctccc gaaaaccttg    120

gttggtgtaa ttagccaaga gaagtttgag aaatcacgag catacagtct tgacaaaagc    180

tattttcact ttgttcatga gtttgtaact atacttatgg actctgcaat tttgttcttt    240

gggatcttgc cttggttttg gaagatgtct ggagctgttt taccgaggtt gggccttgat    300

ccggagaatg aaatactgca tactctttca ttcttggctg gtgttatgac atggtcacag    360

atcactgatt tgccattttc tttgtactca actttcgtga tcgagtctcg gcatgggttc    420

aacaaacaaa caatatggat gttcattagg gacatgatca aaggaacatt cctctctgtc    480

atactaggcc cacccattgt tgctgcgata attttcatag tccagaaagg aggtccttat    540

cttgccatct atctgtgggc attcatgttt atcctgtctc tagtgatgat gactatatac    600

ccggtcttga tagcaccgct cttcaacaaa ttcactcctc ttccagatgg agacctccgg    660

gagaagattg agaaacttgc ttcttcccta aagtttcctt tgaagaagct gtttgttgtc    720

gatggatcta caaggtcaag ccatagcaat gcttacatgt atggtttctt taagaacaaa    780

aggattgttc tttatgatac gttgattcag cagtgcaaga atgaggatga aattgtggcg    840

gttattgcac acgagcttgg acattggaaa ctgaatcaca ctacatactc gttcattgca    900

gttcaaatcc ttgccttctt acaatttgga ggatacactc ttctcagaaa ctccactgat    960

ctcttcagga gtttcggatt tgatacacag cctgttctca ttggtttgat catatttcag   1020

cacactgtaa taccactgca acatctagta agctttggcc tgaacctcgt tagtcgagcg   1080

tttgagtttc aggctgatgc ttttgctgtg aagcttgact atgcaaaaga tcttcgtcct   1140

gctctagtga aactacagga agagaactta tcaacaatga acactgatcc attgtactca   1200

gcttatcact actcacatcc tcctcttgtt gaaaggcttc gagccactga tggagaagac   1260

aagaagacag attaa                                                     1275


<210> SEQ ID NO 98
<211> LENGTH: 424
<212> TYPE: PRT
<213> ORGANISM: Arabidopsis thaliana

<400> SEQUENCE: 98

Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Val Gly Val Ile Ser Gln Glu Lys
         35                  40                  45

Phe Glu Lys Ser Arg Ala Tyr Ser Leu Asp Lys Ser Tyr Phe His Phe
     50                  55                  60
```

```
Val His Glu Phe Val Thr Ile Leu Met Asp Ser Ala Ile Leu Phe Phe
 65                  70                  75                  80

Gly Ile Leu Pro Trp Phe Trp Lys Met Ser Gly Ala Val Leu Pro Arg
                 85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Leu Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
        355                 360                 365

Ala Val Lys Leu Asp Tyr Ala Lys Asp Leu Arg Pro Ala Leu Val Lys
    370                 375                 380

Leu Gln Glu Glu Asn Leu Ser Thr Met Asn Thr Asp Pro Leu Tyr Ser
385                 390                 395                 400

Ala Tyr His Tyr Ser His Pro Pro Leu Val Glu Arg Leu Arg Ala Thr
                405                 410                 415

Asp Gly Glu Asp Lys Lys Thr Asp
            420
```

<210> SEQ ID NO 99
<211> LENGTH: 5544
<212> TYPE: DNA
<213> ORGANISM: Artificial Sequence
<220> FEATURE:
<223> OTHER INFORMATION: Description of Artificial Sequence: Plasmid
pBI121-AtCPP

<400> SEQUENCE: 99
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tccatggcga ttcctttcat ggaaaccgtc 3360
gtgggtttta tgatagtgat gtacattttt gagacgtatt tggatctgag gcaactcact 3420
gctctcaagc ttccaactct cccgaaaacc ttggttggtg taattagcca agagaagttt 3480
gagaaatcac gagcatacag tcttgacaaa agctattttc actttgttca tgagtttgta 3540
actatactta tggactctgc aattttgttc tttgggatct tgccttggtt ttggaagatg 3600
tctggagctg ttttaccgag gttgggcctt gatccggaga atgaaatact gcatactctt 3660
tcattcttgg ctggtgttat gacatggtca cagatcactg atttgccatt ttctttgtac 3720
tcaactttcg tgatcgagtc tcggcatggg ttcaacaaac aaacaatatg gatgttcatt 3780
agggacatga tcaaaggaac attcctctct gtcatactag gcccacccat tgttgctgcg 3840
ataattttca tagtccagaa aggaggtcct tatcttgcca tctatctgtg ggcattcatg 3900
tttatcctgt ctctagtgat gatgactata tacccggtct tgatagcacc gctcttcaac 3960
aaattcactc ctcttccaga tggagacctc cgggagaaga ttgagaaact tgcttcttcc 4020
ctaaagtttc ctttgaagaa gctgtttgtt gtcgatggat ctacaaggtc aagccatagc 4080
aatgcttaca tgtatggttt ctttaagaac aaaaggattg ttctttatga tacgttgatt 4140
cagcagtgca agaatgagga tgaaattgtg gcggttattg cacacgagct tggacattgg 4200
aaactgaatc acactacata ctcgttcatt gcagttcaaa tccttgcctt cttacaattt 4260
ggaggataca ctcttctcag aaactccact gatctcttca ggagtttcgg atttgataca 4320
cagcctgttc tcattggttt gatcatattt cagcacactg taataccact gcaacatcta 4380
gtaagctttg gcctgaacct cgttagtcga gcgtttgagt ttcaggctga tgcttttgct 4440
gtgaagcttg actatgcaaa agatcttcgt cctgctctag tgaaactaca ggaagagaac 4500
ttatcaacaa tgaacactga tccattgtac tcagcttatc actactcaca tcctcctctt 4560
gttgaaaggc ttcgagccac tgatggagaa gacaagaaga cagattaacc cctcgaattt 4620
ccccgatcgt tcaaacattt ggcaataaag tttcttaaga ttgaatcctg ttgccggtct 4680

```
tgcgatgatt atcatataat ttctgttgaa ttacgttaag catgtaataa ttaacatgta   4740

atgcatgacg ttatttatga gatgggtttt tatgattaga gtcccgcaat tatacattta   4800

atacgcgata gaaaacaaaa tatagcgcgc aaactaggat aaattatcgc gcgcggtgtc   4860

atctatgtta ctagatcggg aattcactgg ccgtcgtttt acaacgtcgt gactgggaaa   4920

accctggcgt tacccaactt aatcgccttg cagcacatcc ccctttcgcc agctggcgta   4980

atagcgaaga ggcccgcacc gatcgccctt cccaacagtt gcgcagcctg aatggcgccc   5040

gctcctttcg ctttcttccc ttcctttctc gccacgttcg ccggctttcc ccgtcaagct   5100

ctaaatcggg ggctcccttt agggttccga tttagtgctt tacggcacct cgaccccaaa   5160

aaacttgatt tgggtgatgg ttcacgtagt gggccatcgc cctgatagac ggtttttcgc   5220

cctttgacgt tggagtccac gttctttaat agtggactct tgttccaaac tggaacaaca   5280

ctcaacccta tctcgggcta ttcttttgat ttataaggga ttttgccgat ttcggaacca   5340

ccatcaaaca ggattttcgc ctgctggggc aaaccagcgt ggaccgcttg ctgcaactct   5400

ctcagggcca ggcggtgaag ggcaatcagc tgttgcccgt ctcactggtg aaaagaaaaa   5460

ccaccccagt acattaaaaa cgtccgcaat gtgttattaa gttgtctaag cgtcaatttg   5520

tttacaccac aatatatcct gcca                                          5544
```

<210> SEQ ID NO 100
<211> LENGTH: 6484
<212> TYPE: DNA
<213> ORGANISM: Artificial Sequence
<220> FEATURE:
<223> OTHER INFORMATION: Description of Artificial Sequence: Plasmid pBI121-HP-AtCpp

<400> SEQUENCE: 100

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140
```

-continued

```
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcccaat gtccaagctc gtgtgcaata   3360
accgccacaa tttcatcctc attcttgcac tgctgaatca acgtatcata aagaacaatc   3420
cttttgttct taaagaaacc atacatgtaa gcattgctat ggcttgacct tgtagatcca   3480
tcgacaacaa acagcttctt caaaggaaac tttagggaag aagcaagttt ctcaatcttc   3540
```

-continued tcccggaggt ctccatctgg aagaggagtg aatttgttga agagcggtgc tatcaagacc 3600
gggtatatag tcatcatcac tagagacagg ataaacatga atgcccacag atagatggca 3660
agataaggac ctcctttctg gactatgaaa attatcgcag caacaatggg tgggcctagt 3720
atgacagaga ggaatgttcc tttgatcatg tccctaatga acatccatat tgtttgtttg 3780
ttgaacccat gccgagactc gatcacgaaa gttgagtaca aagaaaatgg caaatcagtg 3840
atctgtgacc atgtcataac accagccaag aatgaaagag tatgcagtat ttcattctcc 3900
ggatcaaggc ccaacctcgg taaaagagga tccccatcta cccgcttcgc gtcggcatcc 3960
ggtcagtggc agtgaagggc gaacagttcc tgattaacca caaaccgttc tactttactg 4020
gctttggtcg tcatgaagat gcggacttgc gtggcaaagg attcgataac gtgctgatgg 4080
tgcacgacca cgcattaatg gactggattg ggccaactc ctaccgtacc tcgcattacc 4140
cttacgctga agagatgctc gactgggcag atgaacatgg catcgtggtg attgatgaaa 4200
ctgctgctgt cggctttttcg ctctctttag gcattggttt cgaagcgggc aacaagccga 4260
aagaactgta cagcgaagag gcagtcaacg gggaaactca gcaagcgcac ttacaggcga 4320
ttaaagagct gatagcgcgt gacaaaaacc acccaagcgt ggtgatgtgg agtattgcca 4380
acgaaccgga tacccgtccg caaggtgcac gggaatattt cgcgccactg gcggaagcaa 4440
cgcgtaaact cgacccgacg cgtccgatca cctgcgtcaa tgtaatgttc tgcgacgctc 4500
acaccgatac catcagcgat ctctttgatg tgctgtgcct gaaccgttat tacggatggt 4560
atgtccaaag cggcgatttg gaaacggcag agaaggtact ggaaaaagaa cttctggcct 4620
ggcaggagaa actgtacacc gacatgtgga gtgaagagta tcagtgtgca tggctggata 4680
tgtatcaccg cgtctttgat cgcgtcagcg ccgtcgtcgg tgaacaggta tggaatttcg 4740
ccgattttgc gacctcgcaa ggcatattgc gcgttggcgg taacaagaaa gggatcttca 4800
ctcgcgaccg caaaccgaag tcggcggctt ttctgctgca aaaacgctgg actggcatga 4860
acttcggtga aaaaccgcag cagggaggca aacaatgaat caacaactct cctggcgcac 4920
catcgtcggc tacagcctcg ggaattgcta ccgagctctt ttaccgaggt tgggccttga 4980
tccggagaat gaaatactgc atactctttc attcttggct ggtgttatga catggtcaca 5040
gatcactgat ttgccatttt ctttgtactc aactttcgtg atcgagtctc ggcatgggtt 5100
caacaaacaa acaatatgga tgttcattag ggacatgatc aaaggaacat tcctctctgt 5160
catactaggc ccacccattg ttgctgcgat aattttcata gtccagaaag gaggtcctta 5220
tcttgccatc tatctgtggg cattcatgtt tatcctgtct ctagtgatga tgactatata 5280
cccggtcttg atagcaccgc tcttcaacaa attcactcct cttccagatg gagacctccg 5340
ggagaagatt gagaaacttg cttcttccct aaagtttcct ttgaagaagc tgtttgttgt 5400
cgatggatct acaaggtcaa gccatagcaa tgcttacatg tatggtttct ttaagaacaa 5460
aaggattgtt ctttatgata cgttgattca gcagtgcaag aatgaggatg aaattgtggc 5520
ggttattgca cacgagcttg gacattggga gctcgaattt ccccgatcgt tcaaacattt 5580
ggcaataaag tttcttaaga ttgaatcctg ttgccggtct tgcgatgatt atcatataat 5640
ttctgttgaa ttacgttaag catgtaataa ttaacatgta atgcatgacg ttatttatga 5700
gatgggtttt tatgattaga gtcccgcaat tatacattta atacgcgata gaaaacaaaa 5760
tatagcgcgc aaactaggat aaattatcgc gcgcggtgtc atctatgtta ctagatcggg 5820
aattcactgg ccgtcgtttt acaacgtcgt gactgggaaa accctggcgt tacccaactt 5880
aatcgccttg cagcacatcc ccctttcgcc agctggcgta atagcgaaga ggcccgcacc 5940
gatcgccctt cccaacagtt gcgcagcctg aatggcgccc gctcctttcg ctttcttccc 6000
ttcctttctc gccacgttcg ccggctttcc ccgtcaagct ctaaatcggg ggctcccttt 6060
agggttccga tttagtgctt tacggcacct cgaccccaaa aaacttgatt tgggtgatgg 6120
ttcacgtagt gggccatcgc cctgatagac ggtttttcgc cctttgacgt tggagtccac 6180
gttctttaat agtggactct tgttccaaac tggaacaaca ctcaacccta tctcgggcta 6240
ttcttttgat ttataaggga ttttgccgat ttcggaacca ccatcaaaca ggattttcgc 6300
ctgctggggc aaaccagcgt ggaccgcttg ctgcaactct ctcagggcca ggcggtgaag 6360
ggcaatcagc tgttgcccgt ctcactggtg aaaagaaaaa ccaccccagt acattaaaaa 6420
cgtccgcaat gtgttattaa gttgtctaag cgtcaatttg tttacaccac aatatatcct 6480
gcca 6484

<210> SEQ ID NO 101
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 101
aaaggatcca tggcgattcc tttcatgg 28

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 102
aaacccgggt taatctgtct tcttgtcttc tcca 34

<210> SEQ ID NO 103
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 103
ctggagctct tttaccgagg ttgggccttg atcc 34

<210> SEQ ID NO 104
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 104
attgagctcc caatgtccaa gctcgtgtgc aata 34

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 105
gccgacagtg gtcccaaaga tgg 23

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 106
aaacccggga tggcgattcc tttcatgg 28

<210> SEQ ID NO 107
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 107
aaaggatcct taatctgtct tcttgtcttc tcca 34

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 108
gcaagaccgg caacagga 18

<210> SEQ ID NO 109
<211> LENGTH: 1275
<212> TYPE: DNA
<213> ORGANISM: Brassica napus

<400> SEQUENCE: 109
atggcgattc ctttcatgga aaccgtcgtt ggttttatga tagtgatgta cgtttttgag 60
acgtatttgg atctgaggca acatactgct ctcaagcttc ccactctccc aaagactttg 120
gttggagtca ttagccaaga gaagtttgag aaatctcgag cttacagtct tgacaaaagc 180
cattttcact ttgttcatga gtttgttact atacttatgg actctgcgat tctgttcttt 240
gggatcttgc cttggttttg gaagatatct ggcggctttc taccaatggt gggactcgat 300
ccagagaatg aaatcctgca cactctttca ttcttggctg gtcttatgac atggtcacag 360
atcactgatt tgccattttc tttgtactca actttcgtga tcgagtctcg gcatgggttc 420
aacaaacaaa caatatggat gttcattagg gacatgatca aaggaatact cctctctgtc 480
atacctgccc ctcctatcgt tgccgcaatt attgttatag ttcagaaagg aggtccttac 540
ctcgccatct atctgtgggc attcatgttt atcctgtctc tagtgatgat gactatatac 600
cctgttttga ttgcacctct tttcaacaag ttcactcctc ttcctgatgg agacctccgg 660
gagaagattg agaaacttgc ttcttctcta aagtttcctc tgaagaagct gtttgttgtc 720
gatggatcta caaggtcaag ccatagtaat gcttacatgt atggtttctt caagaacaaa 780
aggattgttc tttatgacac attgattcag cagtgccaga atgagaatga aattgtggcg 840
gttattgcac acgagctggg acactggaag ctgaatcaca ctacatactc gttcattgct 900
gttcaaatcc ttgccttctt gcaatttgga ggatacactc ttgtcagaaa ctccactgat 960
ctcttcagga gttttggttt tgatacacaa ccagttctca ttggtttgat catatttcag 1020
cacactgtaa taccacttca acacctagta agctttgacc tcaaccttgt tagtcgagcg 1080
tttgagtttc aggctgatgc ttttgcagtg aatcttggtt atgcaaagga tctacgtcct 1140
gccctagtga agctacagga agagaactta tcagcgatga acacagaccc attgtactca 1200
gcttatcact actcacaccc tcctcttgta gagaggcttc gagccattga tggagaagac 1260
aagaagacag attaa 1275

<210> SEQ ID NO 110
<211> LENGTH: 424
<212> TYPE: PRT
<213> ORGANISM: Brassica napus

<400> SEQUENCE: 110

Met Ala Ile Pro Phe Met Glu Thr Val Val Gly Phe Met Ile Val Met
1 5 10 15

Tyr Val Phe Glu Thr Tyr Leu Asp Leu Arg Gln His Thr Ala Leu Lys
20 25 30

Leu Pro Thr Leu Pro Lys Thr Leu Val Gly Val Ile Ser Gln Glu Lys
35 40 45

Phe Glu Lys Ser Arg Ala Tyr Ser Leu Asp Lys Ser His Phe His Phe
50 55 60

Val His Glu Phe Val Thr Ile Leu Met Asp Ser Ala Ile Leu Phe Phe
65 70 75 80

Gly Ile Leu Pro Trp Phe Trp Lys Ile Ser Gly Gly Phe Leu Pro Met
85 90 95

Val Gly Leu Asp Pro Glu Asn Glu Ile Leu His Thr Leu Ser Phe Leu
100 105 110

Ala Gly Leu Met Thr Trp Ser Gln Ile Thr Asp Leu Pro Phe Ser Leu
115 120 125

Tyr Ser Thr Phe Val Ile Glu Ser Arg His Gly Phe Asn Lys Gln Thr
130 135 140

Ile Trp Met Phe Ile Arg Asp Met Ile Lys Gly Ile Leu Leu Ser Val
145 150 155 160

Ile Pro Ala Pro Pro Ile Val Ala Ala Ile Ile Val Ile Val Gln Lys
165 170 175

Gly Gly Pro Tyr Leu Ala Ile Tyr Leu Trp Ala Phe Met Phe Ile Leu
180 185 190

Ser Leu Val Met Met Thr Ile Tyr Pro Val Leu Ile Ala Pro Leu Phe
195 200 205

Asn Lys Phe Thr Pro Leu Pro Asp Gly Asp Leu Arg Glu Lys Ile Glu
210 215 220

Lys Leu Ala Ser Ser Leu Lys Phe Pro Leu Lys Lys Leu Phe Val Val
225 230 235 240

Asp Gly Ser Thr Arg Ser Ser His Ser Asn Ala Tyr Met Tyr Gly Phe
245 250 255

Phe Lys Asn Lys Arg Ile Val Leu Tyr Asp Thr Leu Ile Gln Gln Cys
260 265 270

Gln Asn Glu Asn Glu Ile Val Ala Val Ile Ala His Glu Leu Gly His
275 280 285

Trp Lys Leu Asn His Thr Thr Tyr Ser Phe Ile Ala Val Gln Ile Leu
290 295 300

Ala Phe Leu Gln Phe Gly Gly Tyr Thr Leu Val Arg Asn Ser Thr Asp
305 310 315 320

```
Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Asp Leu Asn Leu Val Ser Arg Ala Phe Glu Phe Gln Ala Asp Ala Phe
        355                 360                 365

Ala Val Asn Leu Gly Tyr Ala Lys Asp Leu Arg Pro Ala Leu Val Lys
    370                 375                 380

Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

```
<210> SEQ ID NO 111
<211> LENGTH: 1275
<212> TYPE: DNA
<213> ORGANISM: Artificial Sequence
<220> FEATURE:
<223> OTHER INFORMATION: Description of Artificial Sequence: Compliment
      to SEQ ID NO: 109

<400> SEQUENCE: 111

ttaatctgtc ttcttgtctt ctccatcaat ggctcgaagc ctctctacaa gaggagggtg     60

tgagtagtga taagctgagt acaatgggtc tgtgttcatc gctgataagt tctcttcctg    120

tagcttcact agggcaggac gtagatcctt tgcataacca agattcactg caaaagcatc    180

agcctgaaac tcaaacgctc gactaacaag gttgaggtca aagcttacta ggtgttgaag    240

tggtattaca gtgtgctgaa atatgatcaa accaatgaga actggttgtg tatcaaaacc    300

aaaactcctg aagagatcag tggagtttct gacaagagtg tatcctccaa attgcaagaa    360

ggcaaggatt tgaacagcaa tgaacgagta tgtagtgtga ttcagcttcc agtgtcccag    420

ctcgtgtgca ataaccgcca caatttcatt ctcattctgg cactgctgaa tcaatgtgtc    480

ataaagaaca atccttttgt tcttgaagaa accatacatg taagcattac tatggcttga    540

ccttgtagat ccatcgacaa caaacagctt cttcagagga aactttagag aagaagcaag    600

tttctcaatc ttctcccgga ggtctccatc aggaagagga gtgaacttgt tgaaaagagg    660

tgcaatcaaa acagggtata tagtcatcat cactagagac aggataaaca tgaatgccca    720

cagatagatg gcgaggtaag gacctccttt ctgaactata acaataattg cggcaacgat    780

aggaggggca ggtatgacag agaggagtat tcctttgatc atgtccctaa tgaacatcca    840

tattgtttgt ttgttgaacc catgccgaga ctcgatcacg aaagttgagt acaaagaaaa    900

tggcaaatca gtgatctgtg accatgtcat aagaccagcc aagaatgaaa gagtgtgcag    960

gatttcattc tctggatcga gtcccaccat tggtagaaag ccgccagata tcttccaaaa   1020

ccaaggcaag atcccaaaga acagaatcgc agagtccata agtatagtaa caaactcatg   1080

aacaaagtga aaatggcttt tgtcaagact gtaagctcga gatttctcaa acttctcttg   1140

gctaatgact ccaaccaaag tctttgggag agtgggaagc ttgagagcag tatgttgcct   1200

cagatccaaa tacgtctcaa aaacgtacat cactatcata aaaccaacga cggtttccat   1260

gaaaggaatc gccat                                                    1275

<210> SEQ ID NO 112
```

<211> LENGTH: 1275
<212> TYPE: DNA
<213> ORGANISM: Glycine max

<400> SEQUENCE: 112
atggcgtttc cctacatgga agccgttgtc ggatttatga tattaatgta catttttgaa 60
acttacttgg atgtgcgaca acatagggcc ctcaaacttc ctactcttcc aaagacttta 120
gagggtgtta tcagccaaga gaaatttgag aaatctagag cctatagtct tgataaaagc 180
cacttccatt ttgttcacga gtttgtgaca atagtgacag actctacaat tttgtacttt 240
ggggtattgc cctggttttg gaagaaatca ggagatttta tgacaatagc tggtttcaat 300
gctgagaatg aaatactgca taccettgcc ttcttagcag ggctgatgat ttggtcacag 360
ataacagatt tgccctttte tctgtactca acttttgtga ttgaggcccg tcatggtttt 420
aataagcaaa caccatggtt attctttagg gacatgctta aaggaatttt cctttctgta 480
ataattggtc cacctattgt ggctgcaatc attgtaatag tacagaaagg aggtccatac 540
ttggccatct atctttgggt ttttacgttt ggtctttcta ttgtgatgat gaccctttat 600
ccagtactaa tagctccact cttcaataag ttcactccac ttccagatgg tcaactcagg 660
gagaaaatcg agaaacttgc ttcctccctc aactatccgt taaagaaact atttgttgtc 720
gatggatcca caagatcaag tcacagcaat gcctatatgt atggattctt caagaacaag 780
aggattgtcc cttatgacac attaattcaa cagtgcaaag acgatgagga aattgttgct 840
gttattgccc atgagttggg acactggaag ctcaaccata ctgtgtacac atttgttgct 900
atgcagattc ttacacttct acaatttgga ggatatacac tagtgcgaaa ttcagctgat 960
ctgtatcgaa gctttgggtt tgatacgcag ccagtcctca ttgggctcat catatttcag 1020
catactgtaa tcccacttca gcaattggtc agctttggtc tgaacctagt cagccgatca 1080
tttgaatttc aggctgatgg ctttgccaag aagcttggat atgcatctgg attacgcggt 1140
ggtcttgtga aactacagga ggagaatctg tcagctatga atacagatcc ttggtactct 1200
gcttatcact attctcatcc tccccttgtt gaaagattgg ccgcgctgga cgaaccggat 1260
aagaaggaag actaa 1275

<210> SEQ ID NO 113
<211> LENGTH: 424
<212> TYPE: PRT
<213> ORGANISM: Glycine max

<400> SEQUENCE: 113

Met Ala Phe Pro Tyr Met Glu Ala Val Val Gly Phe Met Ile Leu Met
1 5 10 15

Tyr Ile Phe Glu Thr Tyr Leu Asp Val Arg Gln His Arg Ala Leu Lys
20 25 30

Leu Pro Thr Leu Pro Lys Thr Leu Glu Gly Val Ile Ser Gln Glu Lys
35 40 45

Phe Glu Lys Ser Arg Ala Tyr Ser Leu Asp Lys Ser His Phe His Phe
50 55 60

Val His Glu Phe Val Thr Ile Val Thr Asp Ser Thr Ile Leu Tyr Phe
65 70 75 80

Gly Val Leu Pro Trp Phe Trp Lys Lys Ser Gly Asp Phe Met Thr Ile
85 90 95

Ala Gly Phe Asn Ala Glu Asn Glu Ile Leu His Thr Leu Ala Phe Leu
100 105 110

-continued

```
Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Ile Val Ile Val Gln Lys
                165                 170                 175

Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
        195                 200                 205

Asn Lys Phe Thr Pro Leu Pro Asp Gly Gln Leu Arg Glu Lys Ile Glu
    210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Pro Tyr Asp Thr Leu Ile Gln Gln Cys
            260                 265                 270

Lys Asp Asp Glu Glu Ile Val Ala Val Ile Ala His Glu Leu Gly His
        275                 280                 285

Trp Lys Leu Asn His Thr Val Tyr Thr Phe Val Ala Met Gln Ile Leu
    290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
                325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
        355                 360                 365

Ala Lys Lys Leu Gly Tyr Ala Ser Gly Leu Arg Gly Gly Leu Val Lys
    370                 375                 380

Leu Gln Glu Glu Asn Leu Ser Ala Met Asn Thr Asp Pro Trp Tyr Ser
385                 390                 395                 400

Ala Tyr His Tyr Ser His Pro Pro Leu Val Glu Arg Leu Ala Ala Leu
                405                 410                 415

Asp Glu Pro Asp Lys Lys Glu Asp
            420
```

<210> SEQ ID NO 114
<211> LENGTH: 1275
<212> TYPE: DNA
<213> ORGANISM: Artificial Sequence
<220> FEATURE:
<223> OTHER INFORMATION: Description of Artificial Sequence: Compliment to SEQ ID NO: 112

<400> SEQUENCE: 114

```
ttagtcttcc ttcttatccg gttcgtccag cgcggccaat ctttcaacaa ggggaggatg      60

agaatagtga taagcagagt accaaggatc tgtattcata gctgacagat tctcctcctg     120

tagtttcaca agaccaccgc gtaatccaga tgcatatcca agcttcttgg caaagccatc     180

agcctgaaat tcaaatgatc ggctgactag gttcagacca aagctgacca attgctgaag     240
```

```
tgggattaca gtatgctgaa atatgatgag cccaatgagg actggctgcg tatcaaaccc    300

aaagcttcga tacagatcag ctgaatttcg cactagtgta tatcctccaa attgtagaag    360

tgtaagaatc tgcatagcaa caaatgtgta cacagtatgg ttgagcttcc agtgtcccaa    420

ctcatgggca ataacagcaa caatttcctc atcgtctttg cactgttgaa ttaatgtgtc    480

ataagggaca atcctcttgt tcttgaagaa tccatacata taggcattgc tgtgacttga    540

tcttgtggat ccatcgacaa caaatagttt ctttaacgga tagttgaggg aggaagcaag    600

tttctcgatt ttctccctga gttgaccatc tggaagtgga gtgaacttat tgaagagtgg    660

agctattagt actggataaa gggtcatcat cacaatagaa agaccaaacg taaaaaccca    720

aagatagatg gccaagtatg gacctccttt ctgtactatt acaatgattg cagccacaat    780

aggtggacca attattacag aaaggaaaat tcctttaagc atgtccctaa agaataacca    840

tggtgtttgc ttattaaaac catgacgggc ctcaatcaca aaagttgagt acagagaaaa    900

gggcaaatct gttatctgtg accaaatcat cagccctgct aagaaggcaa gggtatgcag    960

tatttcattc tcagcattga aaccagctat tgtcataaaa tctcctgatt tcttccaaaa   1020

ccagggcaat accccaaagt acaaaattgt agagtctgtc actattgtca caaactcgtg   1080

aacaaaatgg aagtggcttt tatcaagact ataggctcta gatttctcaa atttctcttg   1140

gctgataaca ccctctaaag tctttggaag agtaggaagt ttgagggccc tatgttgtcg   1200

cacatccaag taagtttcaa aaatgtacat taatatcata aatccgacaa cggcttccat   1260

gtagggaaac gccat                                                     1275


<210> SEQ ID NO 115
<211> LENGTH: 1275
<212> TYPE: DNA
<213> ORGANISM: Artificial Sequence
<220> FEATURE:
<223> OTHER INFORMATION: Description of Artificial Sequence: Compliment
      to SEQ ID NO: 97

<400> SEQUENCE: 115

ttaatctgtc ttcttgtctt ctccatcagt ggctcgaagc ctttcaacaa gaggaggatg     60

tgagtagtga taagctgagt acaatggatc agtgttcatt gttgataagt tctcttcctg    120

tagtttcact agagcaggac gaagatcttt tgcatagtca agcttcacag caaaagcatc    180

agcctgaaac tcaaacgctc gactaacgag gttcaggcca aagcttacta gatgttgcag    240

tggtattaca gtgtgctgaa atatgatcaa accaatgaga acaggctgtg tatcaaatcc    300

gaaactcctg aagagatcag tggagtttct gagaagagtg tatcctccaa attgtaagaa    360

ggcaaggatt tgaactgcaa tgaacgagta tgtagtgtga ttcagtttcc aatgtccaag    420

ctcgtgtgca ataaccgcca caatttcatc ctcattcttg cactgctgaa tcaacgtatc    480

ataaagaaca atccttttgt tcttaaagaa accatacatg taagcattgc tatggcttga    540

ccttgtagat ccatcgacaa caaacagctt cttcaaagga aactttaggg aagaagcaag    600

tttctcaatc ttctcccgga ggtctccatc tggaagagga gtgaatttgt tgaagagcgg    660

tgctatcaag accgggtata tagtcatcat cactagagac aggataaaca tgaatgccca    720

cagatagatg gcaagataag gacctccttt ctggactatg aaaattatcg cagcaacaat    780

gggtgggcct agtatgacag agaggaatgt tcctttgatc atgtccctaa tgaacatcca    840

tattgtttgt ttgttgaacc catgccgaga ctcgatcacg aaagttgagt acaaagaaaa    900

tggcaaatca gtgatctgtg accatgtcat aacaccagcc aagaatgaaa gagtatgcag    960
```

```
tatttcattc tccggatcaa ggcccaacct cggtaaaaca gctccagaca tcttccaaaa   1020

ccaaggcaag atcccaaaga acaaaattgc agagtccata agtatagtta caaactcatg   1080

aacaaagtga aaatagcttt tgtcaagact gtatgctcgt gatttctcaa acttctcttg   1140

gctaattaca ccaaccaagg ttttcgggag agttggaagc ttgagagcag tgagttgcct   1200

cagatccaaa tacgtctcaa aaatgtacat cactatcata aaacccacga cggtttccat   1260

gaaaggaatc gccat                                                    1275
```

<210> SEQ ID NO 116
<211> LENGTH: 1275
<212> TYPE: DNA
<213> ORGANISM: Arabidopsis thaliana

<400> SEQUENCE: 116

```
atggcgattc ctttcatgga aaccgtcgtg ggttttatga tagtgatgta catttttgag     60

acgtatttgg atctgaggca actcactgct ctcaagcttc caactctccc gaaaaccttg    120

gttggtgtaa ttagccaaga gaagtttgag aaatcacgag catacagtct tgacaaaagc    180

tattttcact ttgttcatga gtttgtaact atacttatgg actctgcaat tttgttcttt    240

gggatcttgc cttggttttg gaagatgtct ggagctgttt taccgaggtt gggccttgat    300

ccagagaatg aaatactgca tactctttca ttcttggctg gtgttatgac atggtcacac    360

atcactgatt tgccattttc tttgtactca actttcgtga tcgagtctcg gcatgggttc    420

aacaaacaaa caatatggat gttcattagg gacatgatca aaggaacatt cctctctgtc    480

atactaggcc cacccattgt tgccgcgata attttcatag tccagaaagg aggtccttat    540

cttgccatct atctgtgggc attcatgttt atcctgtctc tagtgatgat gactatatac    600

ccggtcttga tagcaccgct cttcaacaag ttcactcctc ttccagatgg agacctccgg    660

gagaagattg agaaacttgc ttcttctcta aagtttcctt tgaagaagct gtttgttgtc    720

gatggatcta caaggtcaag ccatagcaat gcttacatgt atggtttctt taagaacaaa    780

aggattgttc tttatgatac gttgattcag cagtgcaaga atgaggatga aattgtggcg    840

gttattgcac acgagcttgg acattggaaa ctgaatcaca ctacatactc gttcattgca    900

gttcaaatcc ttgccttctt acaatttgga ggatacactc ttgtcagaaa ctccactgat    960

ctcttcagga gtttcggatt tgatacacag cctgttctca ttggtttgat catatttcag   1020

cacactgtaa taccactgca acatccagta agctttggcc tcaaccttgt tagtcgagcg   1080

tttgagtttc aggctgatgc ttttgctgtg aagcttggct atgcaaaaga tcttcgtcct   1140

actctagtga aactacagga agagaactta tcagcaatga atactgatcc attgtactca   1200

gcttatcact actcacatcc tcctcttgtt gaaaggcttc gagccattga tggagaagac   1260

aagaagacag attaa                                                    1275
```

<210> SEQ ID NO 117
<211> LENGTH: 424
<212> TYPE: PRT
<213> ORGANISM: Arabidopsis thaliana

<400> SEQUENCE: 117

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Val Gly Val Ile Ser Gln Glu Lys
```

```
        35                  40                  45

Phe Glu Lys Ser Arg Ala Tyr Ser Leu Asp Lys Ser Tyr Phe His Phe
     50                  55                  60

Val His Glu Phe Val Thr Ile Leu Met Asp Ser Ala Ile Leu Phe Phe
 65                  70                  75                  80

Gly Ile Leu Pro Trp Phe Trp Lys Met Ser Gly Ala Val Leu Pro Arg
                 85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Pro Val Ser Phe
            340                 345                 350

Gly Leu Asn Leu Val Ser Arg Ala Phe Glu Phe Gln Ala Asp Ala Phe
        355                 360                 365

Ala Val Lys Leu Gly Tyr Ala Lys Asp Leu Arg Pro Thr Leu Val Lys
    370                 375                 380

Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

<210> SEQ ID NO 118
<211> LENGTH: 1275
<212> TYPE: DNA
<213> ORGANISM: Arabidopsis thaliana

<400> SEQUENCE: 118

```
atggcgattc ctttcatgga aaccgtcgtg ggttttatga tagtgatgta cattttttgag     60
acgtatttgg atctgaggca actcactgct ctcaagcttc caactctccc gaaaaccttg    120
gttggtgtaa ttagccaaga gaagtttgag aaatcacgag catacagtct tgacaaaagc    180
tattttcact ttgttcatga gtttgtaact atacttatgg actctgcaat tttgttcttt    240
gggatcttgc cttggttttg gaagatgtct ggagcagttt taccgaggtt gggccttgat    300
ccagagaatg aaatactgca tactctttca ttcttggctg gtgttatgac atggtcacag    360
atcactgatt tgccattttc tttgtactca actttcgtga tcgagtctcg gcatgggttc    420
aacaaacaaa caatatggat gttcattagg gacatgatca aaggaacatt cctctctgtc    480
atactaggcc cacccattgt tgctgcgata attttcatag tccagaaagg aggtccttat    540
cttgccatct atctgtgggc attcatgttt atcctgtctc tagtgatgat gactatatac    600
ccggtcttga tagcaccgct cttcaacaag ttcactcctc ttccagatgg agacctccgg    660
gagaagattg agaaacttgc ttcttctcta aagtttcctt tgaagaagct gtttgttgtc    720
gatggatcta caaggtcaag ccatagcaat gcttacatgt atggtttctt taagaacaaa    780
aggattgttc tttatgatac gttgattcag cagtgcaaga atgaggatga aattgtggcg    840
gttattgcac acgagcttgg acattggaaa ctgaatcaca ctacatactc gttcattgca    900
gttcaaatcc ttgccttctt acaatttgga ggatacactc ttgtcagaaa ctccactgat    960
ctcttcagga gtttcggatt tgatacacag cctgttctca ttggtttgat catatttcag   1020
cacactgtaa taccactgca acatctagta agctttggcc tgaacctcgt tagtcgagcg   1080
tttgagtttc aggctgatgc ttttgctgtg aagcttggct atgcaaaaga tcttcgtcct   1140
gctctagtga aactacagga agagaactta tcagcaatga aaactgatct attgtactca   1200
gcttatcact actcacatcc tcctcttgtt gaaaggcttc gagccattga tggagaagac   1260
aagaagacag attaa                                                     1275
```

<210> SEQ ID NO 119
<211> LENGTH: 424
<212> TYPE: PRT
<213> ORGANISM: Arabidopsis thaliana

<400> SEQUENCE: 119

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Val Gly Val Ile Ser Gln Glu Lys
        35                  40                  45

Phe Glu Lys Ser Arg Ala Tyr Ser Leu Asp Lys Ser Tyr Phe His Phe
    50                  55                  60

Val His Glu Phe Val Thr Ile Leu Met Asp Ser Ala Ile Leu Phe Phe
65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125
```

```
Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
        355                 360                 365

Ala Val Lys Leu Gly Tyr Ala Lys Asp Leu Arg Pro Ala Leu Val Lys
    370                 375                 380

Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

<210> SEQ ID NO 120
<211> LENGTH: 1249
<212> TYPE: DNA
<213> ORGANISM: Zea mays

<400> SEQUENCE: 120

```
acgaggctga gtgctgagaa tgagataata cacacccttg ctttcttagc tggttccatg      60

gtttggtcgc agattacaga cttgccgttc tctctctatt caacttttgt tatagaggct     120

cgacatggtt ttaacaagca aactatatgg ctcttcatta gggatatgat caaaggaatt     180

ttactatcca tgatattggg gccaccaatc gtggctgcta tcatctacat agtacagatt     240

ggaggacctt acctggctat atatctctgg ggttttatgt ttgtattagc tctactgatg     300

atgacaatat accccattgt gatagctcct ctgttcaaca agttcactcc tcttcctgaa     360

ggagtcctca gggaaaaaat agagaagctg gcagcttccc tcaagtttcc tttgaaaaag     420
```

```
cttttcgtgg tagatgggtc taccagatca agccacagta atgcctacat gtatggtttt    480

ttcaagaaca agcgcatagt actctatgac acattgattc agcagtgtag caatgaggat    540

gagatagttt ctgttatagc acatgaactt ggacactgga aactcaatca tactgtctat    600

tcctttgtag ctgtccagct gcttatgttt cttcaatttg gaggatatac tctagtaagg    660

agctccaaag atctatttgg aagttttggc ttcaaggacc agccagtaat aattggattg    720

atcattttcc cgcacaccat aatacccatc caacaccttc tgagctttcg cctgaacctt    780

gtcagcagag catttgaatt tcaggctgat gcctttgcca agaaccttgg atatgcccct    840

cagctccgag cagcccttgt taaactacag gaggagaact tgtctgcgat gaacaccgat    900

ccttggtatt cggcatatca ctactcccac ccaccactcg tcgagaggct gcaagctttg    960

gaagattcag acgacaaaaa agaagattag tcgatccttg tatgaggttt acatatggat   1020

ttttccctgc cacatgcaca ccgattcagt gcttggatgg tgagggtttt gacataggag   1080

tgttgtcaaa gctttagagt gcatctttcg gtcaggtgca acagcctttc ggtcattgag   1140

acatataagc gaattagcta ttaaaaaaaa cagaactgtt gcatcaaaaa aaaaaaaaaa   1200

aaagaaacaa aaaaaaaaaa aaaaaaaaaa aagaaaaaaa aaaaaaaaa               1249


<210> SEQ ID NO 121
<211> LENGTH: 329
<212> TYPE: PRT
<213> ORGANISM: Zea mays

<400> SEQUENCE: 121

Thr Arg Leu Ser Ala Glu Asn Glu Ile Ile His Thr Leu Ala Phe Leu
  1               5                  10                  15

Ala Gly Ser Met Val Trp Ser Gln Ile Thr Asp Leu Pro Phe Ser Leu
             20                  25                  30

Tyr Ser Thr Phe Val Ile Glu Ala Arg His Gly Phe Asn Lys Gln Thr
         35                  40                  45

Ile Trp Leu Phe Ile Arg Asp Met Ile Lys Gly Ile Leu Leu Ser Met
     50                  55                  60

Ile Leu Gly Pro Pro Ile Val Ala Ala Ile Ile Tyr Ile Val Gln Ile
 65                  70                  75                  80

Gly Gly Pro Tyr Leu Ala Ile Tyr Leu Trp Gly Phe Met Phe Val Leu
                 85                  90                  95

Ala Leu Leu Met Met Thr Ile Tyr Pro Ile Val Ile Ala Pro Leu Phe
            100                 105                 110

Asn Lys Phe Thr Pro Leu Pro Glu Gly Val Leu Arg Glu Lys Ile Glu
        115                 120                 125

Lys Leu Ala Ala Ser Leu Lys Phe Pro Leu Lys Lys Leu Phe Val Val
    130                 135                 140

Asp Gly Ser Thr Arg Ser Ser His Ser Asn Ala Tyr Met Tyr Gly Phe
145                 150                 155                 160

Phe Lys Asn Lys Arg Ile Val Leu Tyr Asp Thr Leu Ile Gln Gln Cys
                165                 170                 175

Ser Asn Glu Asp Glu Ile Val Ser Val Ile Ala His Glu Leu Gly His
            180                 185                 190

Trp Lys Leu Asn His Thr Val Tyr Ser Phe Val Ala Val Gln Leu Leu
        195                 200                 205

Met Phe Leu Gln Phe Gly Gly Tyr Thr Leu Val Arg Ser Ser Lys Asp
    210                 215                 220

Leu Phe Gly Ser Phe Gly Phe Lys Asp Gln Pro Val Ile Ile Gly Leu
```

-continued

```
225                 230                 235                 240

Ile Ile Phe Pro His Thr Ile Ile Pro Ile Gln His Leu Leu Ser Phe
                245                 250                 255

Arg Leu Asn Leu Val Ser Arg Ala Phe Glu Phe Gln Ala Asp Ala Phe
            260                 265                 270

Ala Lys Asn Leu Gly Tyr Ala Pro Gln Leu Arg Ala Ala Leu Val Lys
        275                 280                 285

Leu Gln Glu Glu Asn Leu Ser Ala Met Asn Thr Asp Pro Trp Tyr Ser
    290                 295                 300

Ala Tyr His Tyr Ser His Pro Pro Leu Val Glu Arg Leu Gln Ala Leu
305                 310                 315                 320

Glu Asp Ser Asp Asp Lys Lys Glu Asp
                325


<210> SEQ ID NO 122
<211> LENGTH: 1434
<212> TYPE: DNA
<213> ORGANISM: Glycine max

<400> SEQUENCE: 122

ctaatacgac tcactatagg gcaagcagtg gtaacaacgc agagtacgcg gggggagacg      60

catggttctg aactaattgt tataaataat acctaaaatt ttgagttgtc ctaaacattg     120

gggtttaaac aaatccaatc tctcaatata aaacccaatg atctcaccct cactccgttt     180

ctgatttctc actcttcgtt tctcgttcgg ttcatcagcg tgtgtctcag ccatggcgtt     240

tccctacatg gaagccgttg tcggatttat gatattaatg tacatttttg aaacttactt     300

ggatgtgcga caacataggg ccctcaaact tcctactctt ccaaagactt tagaaggtgt     360

tatcagccaa gagaaatttg agaaatctag agcctatagt cttgataaaa gccacttcca     420

ttttgttcac gagtttgtga caatagtgac agactctaca attttgtact ttggggtatt     480

gccctggttt tggaagaaat caggagattt tatgacaata gctggtttca atgctgagaa     540

tgaaatactg catacccttg ccttcttagc agggctgatg atttggtcac agataacaga     600

tttgcccttt tctctgtact caacttttgt gattgaggcc cgtcatggtt ttaataagca     660

aacaccatgg ttattcttta gggacatgct taaaggaatt ttcctttccg taataattgg     720

tccacctatt gtggctgcaa tcattgtaat agtacagaaa ggaggtccat acttggccat     780

ctatctttgg gtttttacgt ttggtctttc tattgtgatg atgacccttt atccagtact     840

aatagctcca ctcttcaata agttcactcc acttccagat ggtcaactca gggagaaaat     900

cgagaaactt gcttcctccc tcaactatcc gttaaagaaa ctatttgttg tcgatggatc     960

cacaagatca agtcacagca atgcctatat gtatggattc ttcaagaaca agaggattgt    1020

cctttatgac acattaattc aacagtgcaa agacgatgag gaaattgttg ctgttattgc    1080

ccatgagttg ggacactgga agctcaacca tactgtgtac acatttgttg ctatgcagat    1140

tcttacactt ctacaatttg gaggatatac actagtgcga aattcagctg atctgtatcg    1200

aagctttggg tttgatacgc agccagtcct cattgggctc atcatatttc agcatactgt    1260

aatcccactt cagcaattgg tcagctttgg tctgaaccta gtcagccgat catttgaatt    1320

tcaggctgat ggctttgcca agaagcttgg atatgcatct ggattacgcg gtggtcttgt    1380

gaaactacag gaggagaatc tgtcagctat gaatacagat ccttgctcgt gccg          1434


<210> SEQ ID NO 123
<211> LENGTH: 400
```

<212> TYPE: PRT
<213> ORGANISM: Glycine max

<400> SEQUENCE: 123

```
Met Ala Phe Pro Tyr Met Glu Ala Val Val Gly Phe Met Ile Leu Met
  1               5                  10                  15

Tyr Ile Phe Glu Thr Tyr Leu Asp Val Arg Gln His Arg Ala Leu Lys
             20                  25                  30

Leu Pro Thr Leu Pro Lys Thr Leu Glu Gly Val Ile Ser Gln Glu Lys
         35                  40                  45

Phe Glu Lys Ser Arg Ala Tyr Ser Leu Asp Lys Ser His Phe His Phe
     50                  55                  60

Val His Glu Phe Val Thr Ile Val Thr Asp Ser Thr Ile Leu Tyr Phe
 65                  70                  75                  80

Gly Val Leu Pro Trp Phe Trp Lys Lys Ser Gly Asp Phe Met Thr Ile
                 85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Ile Val Ile Val Gln Lys
                165                 170                 175

Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
        195                 200                 205

Asn Lys Phe Thr Pro Leu Pro Asp Gly Gln Leu Arg Glu Lys Ile Glu
    210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asp Asp Glu Glu Ile Val Ala Val Ile Ala His Glu Leu Gly His
        275                 280                 285

Trp Lys Leu Asn His Thr Val Tyr Thr Phe Val Ala Met Gln Ile Leu
    290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
                325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
        355                 360                 365

Ala Lys Lys Leu Gly Tyr Ala Ser Gly Leu Arg Gly Gly Leu Val Lys
    370                 375                 380

Leu Gln Glu Glu Asn Leu Ser Ala Met Asn Thr Asp Pro Cys Ser Cys
385                 390                 395                 400
```

<210> SEQ ID NO 124
<211> LENGTH: 1275
<212> TYPE: DNA
<213> ORGANISM: Arabidopsis thaliana

<400> SEQUENCE: 124

```
atggcgattc ctttcatgga aaccgtcgtg ggttttatga tagtgatgta catttttgag     60

acgtatttgg atctgaggca actcactgct ctcaagcttc caactctccc gaaaaccttg    120

gttggtgtaa ttagccaaga gaagtttgag aaatcacgag catacagtct tgacaaaagc    180

tattttcact ttgttcatga gtttgtaact atacttatgg actctgcaat tttgttcttt    240

gggatcttgc cttggttttg gaagatgtct ggagctgttt taccgaggtt gggccttgat    300

ccagagaatg aaatactgca tactctttca ttcttggctg gtgttatgac atggtcacag    360

atcactgatt tgccattttc tttgtactca actttcgtga tcgagtctcg gcatgggttc    420

aacaaacaaa caatatggat gttcattagg gacatgatca aaggaacatt cctctctgtc    480

atactaggcc cacccattgt tgctgcgata attttcatag tccagaaagg aggtccttat    540

cttgccatct atctgtgggc attcatgttt atcctgtctc tagtgatgat gactatatac    600

ccggtcttga tagcaccgct cttcaacaag ttcactcctc ttccagatgg agacctccgg    660

gagaagattg agaaacttgc ttcttctcta aagtttcctt tgaagaagct gtttgttgtc    720

gatggatcta caaggtcaag ccatagcaat gcttacatgt atggtttctt taagaacaaa    780

aggattgttc tttatgatac gttgattcag cagtgcaaga atgaggatga aattgtggcg    840

gttattgcac acgagcttgg acattggaaa ctgaatcaca ctacatactc gttcattgca    900

gttcaaatcc ttgccttctt acaatttgga ggatacactc ttgtcagaaa ctccactgat    960

ctcttcagga gtttcggatt tgatacacag cctgttctca ttggtttgat catatttcag   1020

cacactgtaa taccactgca acatctagta agctttggcc tgaacctcgt tagtcgagcg   1080

tttgagtttc aggctgatgc ttttgccgtg aagcttggct atgcaaaaga tcttcgtcct   1140

gctctagtga aactacagga agagaactta tcagcaatga acactgatcc attgcactca   1200

gcttatcact actcacatcc tcctcttgtt gaaaggcttc gagccattga tggagaagac   1260

aagaagacag attaa                                                    1275
```

<210> SEQ ID NO 125
<211> LENGTH: 424
<212> TYPE: PRT
<213> ORGANISM: Arabidopsis thaliana

<400> SEQUENCE: 125

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Val Gly Val Ile Ser Gln Glu Lys
        35                  40                  45

Phe Glu Lys Ser Arg Ala Tyr Ser Leu Asp Lys Ser Tyr Phe His Phe
    50                  55                  60

Val His Glu Phe Val Thr Ile Leu Met Asp Ser Ala Ile Leu Phe Phe
65                  70                  75                  80

Gly Ile Leu Pro Trp Phe Trp Lys Met Ser Gly Ala Val Leu Pro Arg
                85                  90                  95
```

```
Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
        355                 360                 365

Ala Val Lys Leu Gly Tyr Ala Lys Asp Leu Arg Pro Ala Leu Val Lys
    370                 375                 380

Leu Gln Glu Glu Asn Leu Ser Ala Met Asn Thr Asp Pro Leu His Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420
```

<210> SEQ ID NO 126
<211> LENGTH: 1380
<212> TYPE: DNA
<213> ORGANISM: Arabidopsis thaliana

<400> SEQUENCE: 126

```
atggcgattc ctttcatgga aaccgtcgtg ggttttatga tagtgatgta catttttgag      60

acgtatttgg atctgaggca actcactgct ctcaagcttc caactctccc gaaaaccttg     120

gttggtgtaa ttagccaaga gaagtttgag aaatcacgag catacaggga tatcatcact     180

gagaacttta atatatgcag ctattttcac tttgttcatg agtttgtaac tatacttatg     240
```

```
gactctgcaa ttttgttctt tgggatcttg ccttggtttt ggaagatgtc tggagctgtt    300

ttaccgaggt tgggccttga tccagagaat gaaatactgc atactctttc attcttggct    360

ggtgttatga catggtcaca gatcactgat ttgccatttt ctttgtactc aactttcgtg    420

atcgagtctc ggcatgggtt caacaaacaa acaatatgga tgttcattag ggacatgatc    480

aaaggaacat tcctctctgt catactaggc ccacccattg ttgctgcgat aattttcata    540

gtccagaaag gaggtcctta tcttgccatc tatctgtggg cattcatgtt tatcctgtct    600

ctagtgatga tgactatata cccggtcttg atagcaccgc tcttcaacaa gttcactcct    660

cttccagatg gagacctccg ggagaagatt gagaaacttg cttcttctct aaagtttcct    720

ttgaagaagc tgtttgttgt cgatggatct acaaggtcaa gccatagcaa tgcttacatg    780

tatggtttct ttaagaacaa aaggattgtt ctttatgata cgttgattca gcagtgcaag    840

aatgaggatg aaattgtggc ggttattgca cacgagcttg gacattggaa actgaatcac    900

actacatact cgttcattgc agttcaaatc cttgccttct tacaatttgg aggatacact    960

cttgtcagaa actccactga tctcttcagg agtttcggat ttgatacaca gcctgttctc   1020

attggtttga tcatatttca gcacactgta ataccactgc aacatctagt aagctttggc   1080

ctgaacctcg ttagtcgagc gtttgagttt caggctgatg cttttgctgt gaagcttggc   1140

tatgcaaaag atcttcgtcc tgctctagtg aaactacagg tcagagaaga taacaacaga   1200

acacaaactg ttacctcaat ttgtgtcaca cacttaaatg gattttttgt tgggattttg   1260

caggaagaga acttatcagc aatgaacact gatccattgt actcagctta tcactactca   1320

catcctcctc ttgttgaaag gcttcgagcc attgatggag aagacaagaa gacagattaa   1380
```

```
<210> SEQ ID NO 127
<211> LENGTH: 459
<212> TYPE: PRT
<213> ORGANISM: Arabidopsis thaliana

<400> SEQUENCE: 127

Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Val Gly Val Ile Ser Gln Glu Lys
         35                  40                  45

Phe Glu Lys Ser Arg Ala Tyr Arg Asp Ile Ile Thr Glu Asn Phe Asn
     50                  55                  60

Ile Cys Ser Tyr Phe His Phe Val His Glu Phe Val Thr Ile Leu Met
 65                  70                  75                  80

Asp Ser Ala Ile Leu Phe Phe Gly Ile Leu Pro Trp Phe Trp Lys Met
                 85                  90                  95

Ser Gly Ala Val Leu Pro Arg Leu Gly Leu Asp Pro Glu Asn Glu Ile
            100                 105                 110

Leu His Thr Leu Ser Phe Leu Ala Gly Val Met Thr Trp Ser Gln Ile
        115                 120                 125

Thr Asp Leu Pro Phe Ser Leu Tyr Ser Thr Phe Val Ile Glu Ser Arg
    130                 135                 140

His Gly Phe Asn Lys Gln Thr Ile Trp Met Phe Ile Arg Asp Met Ile
145                 150                 155                 160

Lys Gly Thr Phe Leu Ser Val Ile Leu Gly Pro Pro Ile Val Ala Ala
                165                 170                 175
```

```
Ile Ile Phe Ile Val Gln Lys Gly Gly Pro Tyr Leu Ala Ile Tyr Leu
            180                 185                 190

Trp Ala Phe Met Phe Ile Leu Ser Leu Val Met Met Thr Ile Tyr Pro
        195                 200                 205

Val Leu Ile Ala Pro Leu Phe Asn Lys Phe Thr Pro Leu Pro Asp Gly
    210                 215                 220

Asp Leu Arg Glu Lys Ile Glu Lys Leu Ala Ser Ser Leu Lys Phe Pro
225                 230                 235                 240

Leu Lys Lys Leu Phe Val Val Asp Gly Ser Thr Arg Ser Ser His Ser
                245                 250                 255

Asn Ala Tyr Met Tyr Gly Phe Phe Lys Asn Lys Arg Ile Val Leu Tyr
            260                 265                 270

Asp Thr Leu Ile Gln Gln Cys Lys Asn Glu Asp Glu Ile Val Ala Val
        275                 280                 285

Ile Ala His Glu Leu Gly His Trp Lys Leu Asn His Thr Thr Tyr Ser
    290                 295                 300

Phe Ile Ala Val Gln Ile Leu Ala Phe Leu Gln Phe Gly Gly Tyr Thr
305                 310                 315                 320

Leu Val Arg Asn Ser Thr Asp Leu Phe Arg Ser Phe Gly Phe Asp Thr
                325                 330                 335

Gln Pro Val Leu Ile Gly Leu Ile Ile Phe Gln His Thr Val Ile Pro
            340                 345                 350

Leu Gln His Leu Val Ser Phe Gly Leu Asn Leu Val Ser Arg Ala Phe
        355                 360                 365

Glu Phe Gln Ala Asp Ala Phe Ala Val Lys Leu Gly Tyr Ala Lys Asp
    370                 375                 380

Leu Arg Pro Ala Leu Val Lys Leu Gln Val Arg Glu Asp Asn Asn Arg
385                 390                 395                 400

Thr Gln Thr Val Thr Ser Ile Cys Val Thr His Leu Asn Gly Phe Phe
                405                 410                 415

Val Gly Ile Leu Gln Glu Glu Asn Leu Ser Ala Met Asn Thr Asp Pro
            420                 425                 430

Leu Tyr Ser Ala Tyr His Tyr Ser His Pro Pro Leu Val Glu Arg Leu
        435                 440                 445

Arg Ala Ile Asp Gly Glu Asp Lys Lys Thr Asp
    450                 455
```

<210> SEQ ID NO 128
<211> LENGTH: 3098
<212> TYPE: DNA
<213> ORGANISM: Arabidopsis thaliana

<400> SEQUENCE: 128

```
atggcgattc ctttcatgga aaccgtcgtg ggtaagcttc aaaacctttt tctgagacat     60

tttactatcc tgtttcactc atcgtatttc gtttttgttt gggttttgct ttctgtgttg    120

tgtgtgttga gattccatga ctcgtttgtt tcatatacca tcgtctctgc ttctcgtttc    180

taaattttgt tcttttctaa tagtgcgtac cttgatctga ggttttatta ctcctactag    240

tttcttgtct tactcgtgcg tttgatttga tttgagctta tgtgatttca tcatctcttc    300

ctcggtttta gaatgtacgg agcttctctg ttaaccaaaa tctaggattt gggaagaaaa    360

gtcggagtct tttttttcct cattcccgat tggaaattga gaatcttgaa atttttcttt    420

gttcaagtca tacagcttga ggttttgggt tttcttgtca gggtattatt atgttcgtga    480

ctgcaactag agtttttctgg agttttttga aatgggtttt gtgttgtgga accgtatgtg    540
```

-continued

```
aatgttgcat caaaactctt tcagtgctcc aatgtttcca tcagtagtca gcacaagaga    600
tctttttata tctggttgat caaaaaagta gatgatgtta ttgaattttc agtgatggag    660
tatctgttgt tgtggcattt agagtagatt cgtatttcat cttctgtttt attctttttc    720
ttacaggttt tatgatagtg atgtacattt ttgagacgta tttggatctg aggcaactca    780
ctgctctcaa gcttccaact ctcccgaaaa ccttggttgg tgtaattagc caagagaagt    840
ttgagaaatc acgagcatac agtcttgaca aaaggtttcg tcttgatcat atttatatca    900
ttttagtttt ttataattgc caggggatat catcactgag aactttaata tatgcagcta    960
ttttcacttt gttcatgagt ttgtaactat acttatggac tctgcaattt tgttctttgg   1020
gatcttgcct tggttttgga aggtacatat ctggtttcgg tatacagtat ctcattttga   1080
atatagagtt gttacattac aattgtaaag ttttcatttt taccttagat gtctggagct   1140
gttttaccga ggttgggcct tgatccagag aatgaaatac tgcatactct ttcattcttg   1200
gctggtgtta tgacatggtc acaggtgttc caaataaacc ccttcatata gtcctatacg   1260
tttagcatca aaatatctat tttcttaaga taataatatt tcttttatat tctgatgcag   1320
atcactgatt tgccattttc tttgtactca actttcgtga tcgagtctcg gcatgggttc   1380
aacaaagtat gtcgtatttc caacactacc ttgtgactta cgttttttta tcagagatgt   1440
ggattaaatt tgcttctaaa ttctgttgac agcaaacaat atggatgttc attagggaca   1500
tgatcaaagg aacattcctc tctgtcatac taggcccacc cattgttgct gcgataattt   1560
tcatagtcca ggtttgatga ttctggattc atcttatttc tgagtttttc acatggatga   1620
ctattctcca ttgagtgtga gcttcaaagt tttagtttt cgtgttaaaa atttaaaatt   1680
tgcttctctg agcatgaagt ttctatcttt ttccagaaag gaggtcctta tcttgccatc   1740
tatctgtggg cattcatgtt tatcctgtct ctagtgatga tgactatata cccggtcttg   1800
atagcaccgc tcttcaacaa gttcactcct gtgtgtattt ctgtcatggc cattttacaa   1860
ttcactgctt gtttgcatat gttgttacca gacaatataa tctcccgctt ttttatggct   1920
atagcttcca gatggagacc tccgggagaa gattgagaaa cttgcttctt ctctaaagtt   1980
tcctttgaag aagctgtttg ttgtcgatgg atctacaagg tcaagccata gcaatgtgag   2040
aagcttgaga tctcttccta cctactttac tctagtttac cattagaagc ttacgtatct   2100
tgttacatca tacaggctta catgtatggt ttctttaaga acaaaaggat tgttctttat   2160
gatacgttga ttcagcaggt actgtgactc ttgatgcttc aaacgagcta tactcacatt   2220
tctgtttctg gttctgaaac ataacataat cttctattgt gcagtgcaag aatgaggatg   2280
aaattgtggc ggttattgca cacgagcttg gacattggaa actgaatcac actacatact   2340
cgttcattgc agttcaagtg aggctcaacc gacagttcaa aaacttactc acatctacat   2400
ttcacttaag aaatcatgtc ttatgaccct ctctcaatgt tttgcttgca gatccttgcc   2460
ttcttacaat ttggaggata cactcttgtc agaaactcca ctgatctctt caggagtttc   2520
ggatttgata cacagcctgt tctcattggt ttgatcatat ttcaggtttg ttatttttgc   2580
cttttgacac taatctaatg aatcaaggat ggattaagaa aaaaaaactc taaacctttg   2640
gttatatctc ctgtctgatt atcacagcac actgtaatac cactgcaaca tctagtaagc   2700
tttggcctga acctcgttag tcgagcgttt gagtttcagg taccatctta caatccctca   2760
agatccaacc atagtttctt tattgcaatg gcagcctcat ctactaatct gagttaacgt   2820
tccttttgca ggctgatgct tttgctgtga agcttggcta tgcaaaagat cttcgtcctg   2880
```

ctctagtgaa actacaggtc agagaagata acaacagaac acaaactgtt acctcaattt 2940
gtgtcacaca cttaaatgga ttttttgttg ggattttgca ggaagagaac ttatcagcaa 3000
tgaacactga tccattgtac tcagcttatc actactcaca tcctcctctt gttgaaaggc 3060
ttcgagccat tgatggagaa gacaagaaga cagattaa 3098

<210> SEQ ID NO 129
<211> LENGTH: 316
<212> TYPE: PRT
<213> ORGANISM: Arabidopsis thaliana

<400> SEQUENCE: 129

Met Ala Ile Pro Phe Met Glu Thr Val Val Gly Phe Met Ile Val Met
1 5 10 15

Tyr Ile Phe Glu Thr Tyr Leu Asp Leu Arg Gln Leu Thr Ala Leu Lys
20 25 30

Leu Pro Thr Leu Pro Lys Thr Leu Ile Thr Asp Leu Pro Phe Ser Leu
35 40 45

Tyr Ser Thr Phe Val Ile Glu Ser Arg His Gly Phe Asn Lys Gln Thr
50 55 60

Ile Trp Met Phe Ile Arg Asp Met Ile Lys Gly Thr Phe Leu Ser Val
65 70 75 80

Ile Leu Gly Pro Pro Ile Val Ala Ala Ile Ile Phe Ile Val Gln Lys
85 90 95

Gly Gly Pro Tyr Leu Ala Ile Tyr Leu Trp Ala Phe Met Phe Ile Leu
100 105 110

Ser Leu Val Met Met Thr Ile Tyr Pro Val Leu Ile Ala Pro Leu Phe
115 120 125

Asn Lys Phe Thr Pro Leu Pro Asp Gly Asp Leu Arg Glu Lys Ile Glu
130 135 140

Lys Leu Ala Ser Ser Leu Lys Phe Pro Leu Lys Lys Leu Phe Val Val
145 150 155 160

Asp Gly Ser Thr Arg Ser Ser His Ser Asn Ala Tyr Met Tyr Gly Phe
165 170 175

Phe Lys Asn Lys Arg Ile Val Leu Tyr Asp Thr Leu Ile Gln Gln Cys
180 185 190

Lys Asn Glu Asp Glu Ile Val Ala Val Ile Ala His Glu Leu Gly His
195 200 205

Trp Lys Leu Asn His Thr Thr Tyr Ser Phe Ile Ala Val Gln His Thr
210 215 220

Val Ile Pro Leu Gln His Leu Val Ser Phe Gly Leu Asn Leu Val Ser
225 230 235 240

Arg Ala Phe Glu Phe Gln Ala Asp Ala Phe Ala Val Lys Leu Gly Tyr
245 250 255

Ala Lys Asp Leu Arg Pro Ala Leu Val Lys Leu Gln Val Arg Glu Asp
260 265 270

Asn Asn Arg Thr Gln Thr Glu Glu Asn Leu Ser Ala Met Asn Thr Asp
275 280 285

Pro Leu Tyr Ser Ala Tyr His Tyr Ser His Pro Pro Leu Val Glu Arg
290 295 300

Leu Arg Ala Ile Asp Gly Glu Asp Lys Lys Thr Asp
305 310 315

<210> SEQ ID NO 130
<211> LENGTH: 5544

<212> TYPE: DNA
<213> ORGANISM: Artificial Sequence
<220> FEATURE:
<223> OTHER INFORMATION: Description of Artificial Sequence: Plasmid
pBI121-antisense-AtCPP

<400> SEQUENCE: 130
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160

-continued caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tccttaatct gtcttcttgt cttctccatc 3360
agtggctcga agcctttcaa caagaggagg atgtgagtag tgataagctg agtacaatgg 3420
atcagtgttc attgttgata agttctcttc ctgtagtttc actagagcag gacgaagatc 3480
ttttgcatag tcaagcttca cagcaaaagc atcagcctga aactcaaacg ctcgactaac 3540
gaggttcagg ccaaagctta ctagatgttg cagtggtatt acagtgtgct gaaatatgat 3600
caaaccaatg agaacaggct gtgtatcaaa tccgaaactc ctgaagagat cagtggagtt 3660
tctgagaaga gtgtatcctc caaattgtaa gaaggcaagg atttgaactg caatgaacga 3720
gtatgtagtg tgattcagtt tccaatgtcc aagctcgtgt gcaataaccg ccacaatttc 3780
atcctcattc ttgcactgct gaatcaacgt atcataaaga acaatccttt tgttcttaaa 3840
gaaaccatac atgtaagcat tgctatggct tgaccttgta gatccatcga caacaaacag 3900
cttcttcaaa ggaaacttta gggaagaagc aagtttctca atcttctccc ggaggtctcc 3960
atctggaaga ggagtgaatt tgttgaagag cggtgctatc aagaccgggt atatagtcat 4020
catcactaga gacaggataa acatgaatgc ccacagatag atggcaagat aaggacctcc 4080
tttctggact atgaaaatta tcgcagcaac aatgggtggg cctagtatga cagagaggaa 4140
tgttcctttg atcatgtccc taatgaacat ccatattgtt tgtttgttga acccatgccg 4200
agactcgatc acgaaagttg agtacaaaga aaatggcaaa tcagtgatct gtgaccatgt 4260
cataacacca gccaagaatg aaagagtatg cagtatttca ttctccggat caaggcccaa 4320
cctcggtaaa acagctccag acatcttcca aaaccaaggc aagatcccaa agaacaaaat 4380
tgcagagtcc ataagtatag ttacaaactc atgaacaaag tgaaaatagc ttttgtcaag 4440
actgtatgct cgtgatttct caaacttctc ttggctaatt acaccaacca aggttttcgg 4500

```
gagagttgga agcttgagag cagtgagttg cctcagatcc aaatacgtct caaaaatgta   4560

catcactatc ataaaaccca cgacggtttc catgaaagga atcgccatcc cctcgaattt   4620

ccccgatcgt tcaaacattt ggcaataaag tttcttaaga ttgaatcctg ttgccggtct   4680

tgcgatgatt atcatataat ttctgttgaa ttacgttaag catgtaataa ttaacatgta   4740

atgcatgacg ttatttatga gatgggtttt tatgattaga gtcccgcaat tatacattta   4800

atacgcgata gaaaacaaaa tatagcgcgc aaactaggat aaattatcgc gcgcggtgtc   4860

atctatgtta ctagatcggg aattcactgg ccgtcgtttt acaacgtcgt gactgggaaa   4920

accctggcgt tacccaactt aatcgccttg cagcacatcc ccctttcgcc agctggcgta   4980

atagcgaaga ggcccgcacc gatcgccctt cccaacagtt gcgcagcctg aatggcgccc   5040

gctcctttcg ctttcttccc ttcctttctc gccacgttcg ccggctttcc ccgtcaagct   5100

ctaaatcggg ggctcccttt agggttccga tttagtgctt tacggcacct cgaccccaaa   5160

aaacttgatt tgggtgatgg ttcacgtagt gggccatcgc cctgatagac ggtttttcgc   5220

cctttgacgt tggagtccac gttctttaat agtggactct tgttccaaac tggaacaaca   5280

ctcaacccta tctcgggcta ttcttttgat ttataaggga ttttgccgat ttcggaacca   5340

ccatcaaaca ggattttcgc ctgctggggc aaaccagcgt ggaccgcttg ctgcaactct   5400

ctcagggcca ggcggtgaag ggcaatcagc tgttgcccgt ctcactggtg aaaagaaaaa   5460

ccaccccagt acattaaaaa cgtccgcaat gtgttattaa gttgtctaag cgtcaatttg   5520

tttacaccac aatatatcct gcca                                          5544
```

<210> SEQ ID NO 131
<211> LENGTH: 5668
<212> TYPE: DNA
<213> ORGANISM: Artificial Sequence
<220> FEATURE:
<223> OTHER INFORMATION: Description of Artificial Sequence: Plasmid pRD29A-AtCPP

<400> SEQUENCE: 131

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960
```

-continued

```
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
```

-continued

```
accctcctct gttttactca caaatatgca aactagaaaa caatcatcag gaataaaggg   3420
tttgattact tctattggaa aggactctag aggatccatg gcgattcctt tcatggaaac   3480
cgtcgtgggt tttatgatag tgatgtacat ttttgagacg tatttggatc tgaggcaact   3540
cactgctctc aagcttccaa ctctcccgaa aaccttggtt ggtgtaatta gccaagagaa   3600
gtttgagaaa tcacgagcat acagtcttga caaaagctat tttcactttg ttcatgagtt   3660
tgtaactata cttatggact ctgcaatttt gttctttggg atcttgcctt ggttttggaa   3720
gatgtctgga gctgttttac cgaggttggg ccttgatccg gagaatgaaa tactgcatac   3780
tctttcattc ttggctggtg ttatgacatg gtcacagatc actgatttgc cattttcttt   3840
gtactcaact ttcgtgatcg agtctcggca tgggttcaac aaacaaacaa tatggatgtt   3900
cattagggac atgatcaaag gaacattcct ctctgtcata ctaggcccac ccattgttgc   3960
tgcgataatt ttcatagtcc agaaaggagg tccttatctt gccatctatc tgtgggcatt   4020
catgtttatc ctgtctctag tgatgatgac tatatacccg gtcttgatag caccgctctt   4080
caacaaattc actcctcttc cagatggaga cctccgggag aagattgaga aacttgcttc   4140
ttccctaaag tttcctttga agaagctgtt tgttgtcgat ggatctacaa ggtcaagcca   4200
tagcaatgct tacatgtatg gtttctttaa gaacaaaagg attgttcttt atgatacgtt   4260
gattcagcag tgcaagaatg aggatgaaat tgtggcggtt attgcacacg agcttggaca   4320
ttggaaactg aatcacacta catactcgtt cattgcagtt caaatccttg ccttcttaca   4380
atttggagga tacactcttc tcagaaactc cactgatctc ttcaggagtt tcggatttga   4440
tacacagcct gttctcattg gtttgatcat atttcagcac actgtaatac cactgcaaca   4500
tctagtaagc tttggcctga acctcgttag tcgagcgttt gagtttcagg ctgatgcttt   4560
tgctgtgaag cttgactatg caaaagatct tcgtcctgct ctagtgaaac tacaggaaga   4620
gaacttatca acaatgaaca ctgatccatt gtactcagct tatcactact cacatcctcc   4680
tcttgttgaa aggcttcgag ccactgatgg agaagacaag aagacagatt aacccctcga   4740
atttccccga tcgttcaaac atttggcaat aaagtttctt aagattgaat cctgttgccg   4800
gtcttgcgat gattatcata taatttctgt tgaattacgt taagcatgta ataattaaca   4860
tgtaatgcat gacgttattt atgagatggg tttttatgat tagagtcccg caattataca   4920
tttaatacgc gatagaaaac aaaatatagc gcgcaaacta ggataaatta tcgcgcgcgg   4980
tgtcatctat gttactagat cgggaattca ctggccgtcg ttttacaacg tcgtgactgg   5040
gaaaaccctg gcgttaccca acttaatcgc cttgcagcac atcccccttt cgccagctgg   5100
cgtaatagcg aagaggcccg caccgatcgc ccttcccaac agttgcgcag cctgaatggc   5160
gcccgctcct ttcgctttct tcccttcctt tctcgccacg ttcgccggct ttccccgtca   5220
agctctaaat cgggggctcc ctttagggtt ccgatttagt gctttacggc acctcgaccc   5280
caaaaaactt gatttgggtg atggttcacg tagtgggcca tcgccctgat agacggtttt   5340
tcgccctttg acgttggagt ccacgttctt taatagtgga ctcttgttcc aaactggaac   5400
aacactcaac cctatctcgg gctattcttt tgatttataa gggattttgc cgatttcgga   5460
accaccatca aacaggattt tcgcctgctg gggcaaacca gcgtggaccg cttgctgcaa   5520
ctctctcagg gccaggcggt gaagggcaat cagctgttgc ccgtctcact ggtgaaaaga   5580
aaaaccaccc cagtacatta aaaacgtccg caatgtgtta ttaagttgtc taagcgtcaa   5640
tttgtttaca ccacaatata tcctgcca                                      5668
```

<210> SEQ ID NO 132
<211> LENGTH: 6608
<212> TYPE: DNA
<213> ORGANISM: Artificial Sequence
<220> FEATURE:
<223> OTHER INFORMATION: Description of Artificial Sequence: Plasmid pRD29A-HP-AtCPP

<400> SEQUENCE: 132
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040

```
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctcc caatgtccaa gctcgtgtgc   3480
aataaccgcc acaatttcat cctcattctt gcactgctga atcaacgtat cataaagaac   3540
aatccttttg ttcttaaaga aaccatacat gtaagcattg ctatggcttg accttgtaga   3600
tccatcgaca acaaacagct tcttcaaagg aaactttagg gaagaagcaa gtttctcaat   3660
cttctcccgg aggtctccat ctggaagagg agtgaatttg ttgaagagcg gtgctatcaa   3720
gaccgggtat atagtcatca tcactagaga caggataaac atgaatgccc acagatagat   3780
ggcaagataa ggacctcctt tctggactat gaaaattatc gcagcaacaa tgggtgggcc   3840
tagtatgaca gagaggaatg ttcctttgat catgtcccta atgaacatcc atattgtttg   3900
tttgttgaac ccatgccgag actcgatcac gaaagttgag tacaaagaaa atggcaaatc   3960
agtgatctgt gaccatgtca taacaccagc caagaatgaa agagtatgca gtatttcatt   4020
ctccggatca aggcccaacc tcggtaaaag aggatcccca tctacccgct tcgcgtcggc   4080
atccggtcag tggcagtgaa gggcgaacag ttcctgatta accacaaacc gttctacttt   4140
actggctttg gtcgtcatga agatgcggac ttgcgtggca aaggattcga taacgtgctg   4200
atggtgcacg accacgcatt aatggactgg attggggcca actcctaccg tacctcgcat   4260
taccccttacg ctgaagagat gctcgactgg gcagatgaac atggcatcgt ggtgattgat   4320
gaaactgctg ctgtcggctt ttcgctctct ttaggcattg gtttcgaagc gggcaacaag   4380
ccgaaagaac tgtacagcga agaggcagtc aacggggaaa ctcagcaagc gcacttacag   4440
```

gcgattaaag agctgatagc gcgtgacaaa aaccacccaa gcgtggtgat gtggagtatt 4500
gccaacgaac cggatacccg tccgcaaggt gcacgggaat atttcgcgcc actggcggaa 4560
gcaacgcgta aactcgaccc gacgcgtccg atcacctgcg tcaatgtaat gttctgcgac 4620
gctcacaccg ataccatcag cgatctcttt gatgtgctgt gcctgaaccg ttattacgga 4680
tggtatgtcc aaagcggcga tttggaaacg gcagagaagg tactggaaaa agaacttctg 4740
gcctggcagg agaaactgta caccgacatg tggagtgaag agtatcagtg tgcatggctg 4800
gatatgtatc accgcgtctt tgatcgcgtc agcgccgtcg tcggtgaaca ggtatggaat 4860
ttcgccgatt ttgcgacctc gcaaggcata ttgcgcgttg gcggtaacaa gaaagggatc 4920
ttcactcgcg accgcaaacc gaagtcggcg gcttttctgc tgcaaaaacg ctggactggc 4980
atgaacttcg gtgaaaaacc gcagcaggga ggcaaacaat gaatcaacaa ctctcctggc 5040
gcaccatcgt cggctacagc ctcgggaatt gctaccgagc tcttttaccg aggttgggcc 5100
ttgatccgga gaatgaaata ctgcatactc tttcattctt ggctggtgtt atgacatggt 5160
cacagatcac tgatttgcca ttttctttgt actcaacttt cgtgatcgag tctcggcatg 5220
ggttcaacaa acaaacaata tggatgttca ttagggacat gatcaaagga acattcctct 5280
ctgtcatact aggcccaccc attgttgctg cgataatttt catagtccag aaaggaggtc 5340
cttatcttgc catctatctg tgggcattca tgtttatcct gtctctagtg atgatgacta 5400
tatacccggt cttgatagca ccgctcttca acaaattcac tcctcttcca gatggagacc 5460
tccgggagaa gattgagaaa cttgcttctt ccctaaagtt tcctttgaag aagctgtttg 5520
ttgtcgatgg atctacaagg tcaagccata gcaatgctta catgtatggt ttctttaaga 5580
acaaaaggat tgttctttat gatacgttga ttcagcagtg caagaatgag gatgaaattg 5640
tggcggttat tgcacacgag cttggacatt gggagctcga atttccccga tcgttcaaac 5700
atttggcaat aaagtttctt aagattgaat cctgttgccg gtcttgcgat gattatcata 5760
taatttctgt tgaattacgt taagcatgta ataattaaca tgtaatgcat gacgttattt 5820
atgagatggg tttttatgat tagagtcccg caattataca tttaatacgc gatagaaaac 5880
aaaatatagc gcgcaaacta ggataaatta tcgcgcgcgg tgtcatctat gttactagat 5940
cgggaattca ctggccgtcg ttttacaacg tcgtgactgg gaaaaccctg gcgttaccca 6000
acttaatcgc cttgcagcac atcccccttt cgccagctgg cgtaatagcg aagaggcccg 6060
caccgatcgc ccttcccaac agttgcgcag cctgaatggc gcccgctcct ttcgctttct 6120
tcccttcctt tctcgccacg ttcgccggct ttccccgtca agctctaaat cgggggctcc 6180
ctttagggtt ccgatttagt gctttacggc acctcgaccc caaaaaactt gatttgggtg 6240
atggttcacg tagtgggcca tcgccctgat agacggtttt tcgccctttg acgttggagt 6300
ccacgttctt taatagtgga ctcttgttcc aaactggaac aacactcaac cctatctcgg 6360
gctattcttt tgatttataa gggattttgc cgatttcgga accaccatca aacaggattt 6420
tcgcctgctg gggcaaacca gcgtggaccg cttgctgcaa ctctctcagg gccaggcggt 6480
gaagggcaat cagctgttgc ccgtctcact ggtgaaaaga aaaaccaccc cagtacatta 6540
aaaacgtccg caatgtgtta ttaagttgtc taagcgtcaa tttgtttaca ccacaatata 6600
tcctgcca 6608

<210> SEQ ID NO 133
<211> LENGTH: 5668
<212> TYPE: DNA

<213> ORGANISM: Artificial Sequence
<220> FEATURE:
<223> OTHER INFORMATION: Description of Artificial Sequence: Plasmid pRD29A-antisense-AtCPP

<400> SEQUENCE: 133

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
```

-continued

```
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctta atctgtcttc ttgtcttctc   3480
catcagtggc tcgaagcctt tcaacaagag gaggatgtga gtagtgataa gctgagtaca   3540
atggatcagt gttcattgtt gataagttct cttcctgtag tttcactaga gcaggacgaa   3600
gatcttttgc atagtcaagc ttcacagcaa aagcatcagc ctgaaactca aacgctcgac   3660
taacgaggtt caggccaaag cttactagat gttgcagtgg tattacagtg tgctgaaata   3720
tgatcaaacc aatgagaaca ggctgtgtat caaatccgaa actcctgaag agatcagtgg   3780
agtttctgag aagagtgtat cctccaaatt gtaagaaggc aaggatttga actgcaatga   3840
acgagtatgt agtgtgattc agtttccaat gtccaagctc gtgtgcaata accgccacaa   3900
tttcatcctc attcttgcac tgctgaatca acgtatcata aagaacaatc cttttgttct   3960
taaagaaacc atacatgtaa gcattgctat ggcttgacct tgtagatcca tcgacaacaa   4020
acagcttctt caaaggaaac tttagggaag aagcaagttt ctcaatcttc tcccggaggt   4080
ctccatctgg aagaggagtg aatttgttga agagcggtgc tatcaagacc gggtatatag   4140
tcatcatcac tagagacagg ataaacatga atgcccacag atagatggca agataaggac   4200
ctcctttctg gactatgaaa attatcgcag caacaatggg tgggcctagt atgacagaga   4260
ggaatgttcc tttgatcatg tccctaatga acatccatat tgtttgtttg ttgaacccat   4320
gccgagactc gatcacgaaa gttgagtaca aagaaaatgg caaatcagtg atctgtgacc   4380
atgtcataac accagccaag aatgaaagag tatgcagtat ttcattctcc ggatcaaggc   4440
ccaacctcgg taaaacagct ccagacatct tccaaaacca aggcaagatc ccaaagaaca   4500
aaattgcaga gtccataagt atagttacaa actcatgaac aaagtgaaaa tagcttttgt   4560
```

caagactgta tgctcgtgat ttctcaaact tctcttggct aattacacca accaaggttt 4620
tcgggagagt tggaagcttg agagcagtga gttgcctcag atccaaatac gtctcaaaaa 4680
tgtacatcac tatcataaaa cccacgacgg tttccatgaa aggaatcgcc atcccctcga 4740
atttccccga tcgttcaaac atttggcaat aaagtttctt aagattgaat cctgttgccg 4800
gtcttgcgat gattatcata taatttctgt tgaattacgt taagcatgta ataattaaca 4860
tgtaatgcat gacgttattt atgagatggg tttttatgat tagagtcccg caattataca 4920
tttaatacgc gatagaaaac aaaatatagc gcgcaaacta ggataaatta tcgcgcgcgg 4980
tgtcatctat gttactagat cgggaattca ctggccgtcg ttttacaacg tcgtgactgg 5040
gaaaaccctg gcgttaccca acttaatcgc cttgcagcac atcccccttt cgccagctgg 5100
cgtaatagcg aagaggcccg caccgatcgc ccttcccaac agttgcgcag cctgaatggc 5160
gcccgctcct ttcgctttct tcccttcctt tctcgccacg ttcgccggct ttccccgtca 5220
agctctaaat cgggggctcc ctttagggtt ccgatttagt gctttacggc acctcgaccc 5280
caaaaaactt gatttgggtg atggttcacg tagtgggcca tcgccctgat agacggtttt 5340
tcgccctttg acgttggagt ccacgttctt taatagtgga ctcttgttcc aaactggaac 5400
aacactcaac cctatctcgg gctattcttt tgatttataa gggattttgc cgatttcgga 5460
accaccatca aacaggattt tcgcctgctg gggcaaacca gcgtggaccg cttgctgcaa 5520
ctctctcagg gccaggcggt gaagggcaat cagctgttgc ccgtctcact ggtgaaaaga 5580
aaaaccaccc cagtacatta aaaacgtccg caatgtgtta ttaagttgtc taagcgtcaa 5640
tttgtttaca ccacaatata tcctgcca 5668

<210> SEQ ID NO 134
<211> LENGTH: 5074
<212> TYPE: DNA
<213> ORGANISM: Artificial Sequence
<220> FEATURE:
<223> OTHER INFORMATION: Description of Artificial Sequence: Plasmid
MuA-AtCPP

<400> SEQUENCE: 134
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900

-continued

```
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
atagacgaaa aggaaggtgg ctcctataaa gcacatcatt gcgataacag aaaggccatt   2640
gttgaagata cctctgctga cattggtccc caagtggaag caccacccca tgaggagcac   2700
cgtggagtaa gaagacgttc gagccacgtc gaaaaagcaa gtgtgttgat gtagtatctc   2760
cattgacgta agggatgacg cacaatccaa ctatccatcg caagaccatt gctctatata   2820
agaaagttaa tatcatttcg agtggccacg ctgaggggga tccatggcga ttcctttcat   2880
ggaaaccgtc gtgggtttta tgatagtgat gtacattttt gagacgtatt tggatctgag   2940
gcaactcact gctctcaagc ttccaactct cccgaaaacc ttggttggtg taattagcca   3000
agagaagttt gagaaatcac gagcatacag tcttgacaaa agctattttc actttgttca   3060
tgagtttgta actatactta tggactctgc aattttgttc tttgggatct tgccttggtt   3120
ttggaagatg tctggagctg ttttaccgag gttgggcctt gatccggaga atgaaatact   3180
gcatactctt tcattcttgg ctggtgttat gacatggtca cagatcactg atttgccatt   3240
```

-continued

```
ttctttgtac tcaactttcg tgatcgagtc tcggcatggg ttcaacaaac aaacaatatg   3300

gatgttcatt agggacatga tcaaaggaac attcctctct gtcatactag gcccacccat   3360

tgttgctgcg ataattttca tagtccagaa aggaggtcct tatcttgcca tctatctgtg   3420

ggcattcatg tttatcctgt ctctagtgat gatgactata tacccggtct tgatagcacc   3480

gctcttcaac aaattcactc ctcttccaga tggagacctc cgggagaaga ttgagaaact   3540

tgcttcttcc ctaaagtttc ctttgaagaa gctgtttgtt gtcgatggat ctacaaggtc   3600

aagccatagc aatgcttaca tgtatggttt ctttaagaac aaaaggattg ttctttatga   3660

tacgttgatt cagcagtgca agaatgagga tgaaattgtg gcggttattg cacacgagct   3720

tggacattgg aaactgaatc acactacata ctcgttcatt gcagttcaaa tccttgcctt   3780

cttacaattt ggaggataca ctcttctcag aaactccact gatctcttca ggagtttcgg   3840

atttgataca cagcctgttc tcattggttt gatcatattt cagcacactg taataccact   3900

gcaacatcta gtaagctttg gcctgaacct cgttagtcga gcgtttgagt ttcaggctga   3960

tgcttttgct gtgaagcttg actatgcaaa agatcttcgt cctgctctag tgaaactaca   4020

ggaagagaac ttatcaacaa tgaacactga tccattgtac tcagcttatc actactcaca   4080

tcctcctctt gttgaaaggc ttcgagccac tgatggagaa gacaagaaga cagattaacc   4140

cctcgaattt ccccgatcgt tcaaacattt ggcaataaag tttcttaaga ttgaatcctg   4200

ttgccggtct tgcgatgatt atcatataat ttctgttgaa ttacgttaag catgtaataa   4260

ttaacatgta atgcatgacg ttatttatga gatgggtttt tatgattaga gtcccgcaat   4320

tatacattta atacgcgata gaaaacaaaa tatagcgcgc aaactaggat aaattatcgc   4380

gcgcggtgtc atctatgtta ctagatcggg aattcactgg ccgtcgtttt acaacgtcgt   4440

gactgggaaa accctggcgt tacccaactt aatcgccttg cagcacatcc ccctttcgcc   4500

agctggcgta atagcgaaga ggcccgcacc gatcgccctt cccaacagtt gcgcagcctg   4560

aatggcgccc gctcctttcg ctttcttccc ttcctttctc gccacgttcg ccggctttcc   4620

ccgtcaagct ctaaatcggg ggctcccttt agggttccga tttagtgctt tacggcacct   4680

cgaccccaaa aaacttgatt tgggtgatgg ttcacgtagt gggccatcgc cctgatagac   4740

ggtttttcgc cctttgacgt tggagtccac gttctttaat agtggactct tgttccaaac   4800

tggaacaaca ctcaacccta tctcgggcta ttcttttgat ttataaggga ttttgccgat   4860

ttcggaacca ccatcaaaca ggattttcgc ctgctggggc aaaccagcgt ggaccgcttg   4920

ctgcaactct ctcagggcca ggcggtgaag ggcaatcagc tgttgcccgt ctcactggtg   4980

aaaagaaaaa ccaccccagt acattaaaaa cgtccgcaat gtgttattaa gttgtctaag   5040

cgtcaatttg tttacaccac aatatatcct gcca                              5074
```

```
<210> SEQ ID NO 135
<211> LENGTH: 5076
<212> TYPE: DNA
<213> ORGANISM: Artificial Sequence
<220> FEATURE:
<223> OTHER INFORMATION: Description of Artificial Sequence: Plasmid
      MuA-GmCPP

<400> SEQUENCE: 135

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180
```

-continued

```
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
```

-continued atagacgaaa aggaaggtgg ctcctataaa gcacatcatt gcgataacag aaaggccatt 2640
gttgaagata cctctgctga cattggtccc caagtggaag caccacccca tgaggagcac 2700
cgtggagtaa gaagacgttc gagccacgtc gaaaaagcaa gtgtgttgat gtagtatctc 2760
cattgacgta agggatgacg cacaatccaa ctatccatcg caagaccatt gctctatata 2820
agaaagttaa tatcatttcg agtggccacg ctgaggggga tcgggatggc gtttccctac 2880
atggaagccg ttgtcggatt tatgatatta atgtacattt ttgaaactta cttggatgtg 2940
cgacaacata gggccctcaa acttcctact cttccaaaga ctttagaggg tgttatcagc 3000
caagagaaat ttgagaaatc tagagcctat agtcttgata aaagccactt ccattttgtt 3060
cacgagtttg tgacaatagt gacagactct acaattttgt actttggggt attgccctgg 3120
ttttggaaga aatcaggaga ttttatgaca atagctggtt tcaatgctga gaatgaaata 3180
ctgcataccc ttgccttctt agcagggctg atgatttggt cacagataac agatttgccc 3240
ttttctctgt actcaacttt tgtgattgag gcccgtcatg gttttaataa gcaaacacca 3300
tggttattct ttagggacat gcttaaagga attttccttt ctgtaataat tggtccacct 3360
attgtggctg caatcattgt aatagtacag aaaggaggtc catacttggc catctatctt 3420
tgggttttta cgtttggtct ttctattgtg atgatgaccc tttatccagt actaatagct 3480
ccactcttca ataagttcac tccacttcca gatggtcaac tcagggagaa aatcgagaaa 3540
cttgcttcct ccctcaacta tccgttaaag aaactatttg ttgtcgatgg atccacaaga 3600
tcaagtcaca gcaatgccta tatgtatgga ttcttcaaga acaagaggat tgtcccttat 3660
gacacattaa ttcaacagtg caaagacgat gaggaaattg ttgctgttat tgcccatgag 3720
ttgggacact ggaagctcaa ccatactgtg tacacatttg ttgctatgca gattcttaca 3780
cttctacaat ttggaggata tacactagtg cgaaattcag ctgatctgta tcgaagcttt 3840
gggtttgata cgcagccagt cctcattggg ctcatcatat ttcagcatac tgtaatccca 3900
cttcagcaat tggtcagctt tggtctgaac ctagtcagcc gatcatttga atttcaggct 3960
gatggctttg ccaagaagct tggatatgca tctggattac gcggtggtct tgtgaaacta 4020
caggaggaga atctgtcagc tatgaataca gatccttggt actctgctta tcactattct 4080
catcctcccc ttgttgaaag attggccgcg ctggacgaac cggataagaa ggaagactaa 4140
gagctcgaat ttccccgatc gttcaaacat ttggcaataa agtttcttaa gattgaatcc 4200
tgttgccggt cttgcgatga ttatcatata atttctgttg aattacgtta agcatgtaat 4260
aattaacatg taatgcatga cgttatttat gagatgggtt tttatgatta gagtcccgca 4320
attatacatt taatacgcga tagaaaacaa aatatagcgc gcaaactagg ataaattatc 4380
gcgcgcggtg tcatctatgt tactagatcg ggaattcact ggccgtcgtt ttacaacgtc 4440
gtgactggga aaaccctggc gttacccaac ttaatcgcct tgcagcacat ccccctttcg 4500
ccagctggcg taatagcgaa gaggcccgca ccgatcgccc ttcccaacag ttgcgcagcc 4560
tgaatggcgc ccgctccttt cgctttcttc ccttcctttc tcgccacgtt cgccggcttt 4620
ccccgtcaag ctctaaatcg ggggctccct ttagggttcc gatttagtgc tttacggcac 4680
ctcgacccca aaaaacttga tttgggtgat ggttcacgta gtgggccatc gccctgatag 4740
acggtttttc gccctttgac gttggagtcc acgttcttta atagtggact cttgttccaa 4800
actggaacaa cactcaaccc tatctcgggc tattcttttg atttataagg gattttgccg 4860
atttcggaac caccatcaaa caggattttc gcctgctggg gcaaaccagc gtggaccgct 4920
tgctgcaact ctctcagggc caggcggtga agggcaatca gctgttgccc gtctcactgg 4980
tgaaaagaaa aaccacccca gtacattaaa aacgtccgca atgtgttatt aagttgtcta 5040
agcgtcaatt tgtttacacc acaatatatc ctgcca 5076

<210> SEQ ID NO 136
<211> LENGTH: 5549
<212> TYPE: DNA
<213> ORGANISM: Artificial Sequence
<220> FEATURE:
<223> OTHER INFORMATION: Description of Artificial Sequence: Plasmid pBI121-GmCPP

<400> SEQUENCE: 136
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860

-continued

```
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccccgggat ggcgtttccc tacatggaag   3360
ccgttgtcgg atttatgata ttaatgtaca tttttgaaac ttacttggat gtgcgacaac   3420
atagggccct caaacttcct actcttccaa agactttaga gggtgttatc agccaagaga   3480
aatttgagaa atctagagcc tatagtcttg ataaaagcca cttccatttt gttcacgagt   3540
ttgtgacaat agtgacagac tctacaattt tgtactttgg ggtattgccc tggttttgga   3600
agaaatcagg agattttatg acaatagctg gtttcaatgc tgagaatgaa atactgcata   3660
cccttgcctt cttagcaggg ctgatgattt ggtcacagat aacagatttg ccctttttctc   3720
tgtactcaac ttttgtgatt gaggcccgtc atggttttaa taagcaaaca ccatggttat   3780
tctttaggga catgcttaaa ggaattttcc tttctgtaat aattggtcca cctattgtgg   3840
ctgcaatcat tgtaatagta cagaaaggag gtccatactt ggccatctat ctttgggttt   3900
ttacgtttgg tctttctatt gtgatgatga ccctttatcc agtactaata gctccactct   3960
tcaataagtt cactccactt ccagatggtc aactcaggga gaaaatcgag aaacttgctt   4020
cctccctcaa ctatccgtta aagaaactat ttgttgtcga tggatccaca agatcaagtc   4080
acagcaatgc ctatatgtat ggattcttca agaacaagag gattgtccct tatgacacat   4140
taattcaaca gtgcaaagac gatgaggaaa ttgttgctgt tattgcccat gagttgggac   4200
actggaagct caaccatact gtgtacacat ttgttgctat gcagattctt acacttctac   4260
```

aatttggagg atatacacta gtgcgaaatt cagctgatct gtatcgaagc tttgggtttg 4320
atacgcagcc agtcctcatt gggctcatca tatttcagca tactgtaatc ccacttcagc 4380
aattggtcag ctttggtctg aacctagtca gccgatcatt tgaatttcag gctgatggct 4440
ttgccaagaa gcttggatat gcatctggat tacgcggtgg tcttgtgaaa ctacaggagg 4500
agaatctgtc agctatgaat acagatcctt ggtactctgc ttatcactat tctcatcctc 4560
cccttgttga aagattggcc gcgctggacg aaccggataa gaaggaagac taagagctcg 4620
aatttccccg atcgttcaaa catttggcaa taaagtttct taagattgaa tcctgttgcc 4680
ggtcttgcga tgattatcat ataatttctg ttgaattacg ttaagcatgt aataattaac 4740
atgtaatgca tgacgttatt tatgagatgg gtttttatga ttagagtccc gcaattatac 4800
atttaatacg cgatagaaaa caaaatatag cgcgcaaact aggataaatt atcgcgcgcg 4860
gtgtcatcta tgttactaga tcgggaattc actggccgtc gttttacaac gtcgtgactg 4920
ggaaaaccct ggcgttaccc aacttaatcg ccttgcagca catccccctt tcgccagctg 4980
gcgtaatagc gaagaggccc gcaccgatcg cccttcccaa cagttgcgca gcctgaatgg 5040
cgcccgctcc tttcgctttc ttcccttcct ttctcgccac gttcgccggc tttccccgtc 5100
aagctctaaa tcgggggctc cctttagggt tccgatttag tgctttacgg cacctcgacc 5160
ccaaaaaact tgatttgggt gatggttcac gtagtgggcc atcgccctga tagacggttt 5220
ttcgcccttt gacgttggag tccacgttct ttaatagtgg actcttgttc caaactggaa 5280
caacactcaa ccctatctcg ggctattctt ttgatttata agggattttg ccgatttcgg 5340
aaccaccatc aaacaggatt ttcgcctgct ggggcaaacc agcgtggacc gcttgctgca 5400
actctctcag ggccaggcgg tgaagggcaa tcagctgttg cccgtctcac tggtgaaaag 5460
aaaaaccacc ccagtacatt aaaaacgtcc gcaatgtgtt attaagttgt ctaagcgtca 5520
atttgtttac accacaatat atcctgcca 5549

<210> SEQ ID NO 137
<211> LENGTH: 6352
<212> TYPE: DNA
<213> ORGANISM: Artificial Sequence
<220> FEATURE:
<223> OTHER INFORMATION: Description of Artificial Sequence: Plasmid pBI121-HP-GmCPP

<400> SEQUENCE: 137
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720

-continued

```
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
```

-continued

```
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagaccg gttcgtccag cgcggccaat ctttcaacaa   3360
ggggaggatg agaatagtga taagcagagt accaaggatc tgtattcata gctgacagat   3420
tctcctcctg tagtttcaca agaccaccgc gtaatccaga tgcatatcca agcttcttgg   3480
caaagccatc agcctgaaat tcaaatgatc ggctgactag gttcagacca aagctgacca   3540
attgctgaag tgggattaca gtatgctgaa atatgatgag cccaatgagg actggctgcg   3600
tatcaaaccc aaagcttcga tacagatcag ctgaatttcg cactagtgta tatcctccaa   3660
attgtagaag tgtaagaatc tgcatagcaa caaatgtgta cacagtatgg ttgagcttcc   3720
agtgtcccaa ctcatgggca ataacagcaa caatttcctc atcgtctttg cactgttgaa   3780
ttaatgtgtc ataagggaca atcctcttgt tcttgaagaa tccatacata taggcattgc   3840
tgtgacttga tcttgtggat ccccatctac ccgcttcgcg tcggcatccg gtcagtggca   3900
gtgaagggcg aacagttcct gattaaccac aaaccgttct actttactgg ctttggtcgt   3960
catgaagatg cggacttgcg tggcaaagga ttcgataacg tgctgatggt gcacgaccac   4020
gcattaatgg actggattgg ggccaactcc taccgtacct cgcattaccc ttacgctgaa   4080
gagatgctcg actgggcaga tgaacatggc atcgtggtga ttgatgaaac tgctgctgtc   4140
ggctttttcgc tctctttagg cattggtttc gaagcgggca acaagccgaa agaactgtac   4200
agcgaagagg cagtcaacgg ggaaactcag caagcgcact tacaggcgat taaagagctg   4260
atagcgcgtg acaaaaacca cccaagcgtg gtgatgtgga gtattgccaa cgaaccggat   4320
acccgtccgc aaggtgcacg ggaatatttc gcgccactgg cggaagcaac gcgtaaactc   4380
gacccgacgc gtccgatcac ctgcgtcaat gtaatgttct gcgacgctca caccgatacc   4440
atcagcgatc tctttgatgt gctgtgcctg aaccgttatt acggatggta tgtccaaagc   4500
ggcgatttgg aaacggcaga gaaggtactg gaaaaagaac ttctggcctg gcaggagaaa   4560
ctgtacaccg acatgtggag tgaagagtat cagtgtgcat ggctggatat gtatcaccgc   4620
gtctttgatc gcgtcagcgc cgtcgtcggt gaacaggtat ggaatttcgc cgattttgcg   4680
acctcgcaag gcatattgcg cgttggcggt aacaagaaag ggatcttcac tcgcgaccgc   4740
aaaccgaagt cggcggcttt tctgctgcaa aaacgctgga ctggcatgaa cttcggtgaa   4800
aaaccgcagc agggaggcaa acaatgaatc aacaactctc ctggcgcacc atcgtcggct   4860
acagcctcgg gaattgctac cgagctcaca agatcaagtc acagcaatgc ctatatgtat   4920
ggattcttca agaacaagag gattgtccct tatgacacat taattcaaca gtgcaaagac   4980
gatgaggaaa ttgttgctgt tattgcccat gagttgggac actggaagct caaccatact   5040
gtgtacacat ttgttgctat gcagattctt acacttctac aatttggagg atatacacta   5100
gtgcgaaatt cagctgatct gtatcgaagc tttgggtttg atacgcagcc agtcctcatt   5160
gggctcatca tatttcagca tactgtaatc ccacttcagc aattggtcag ctttggtctg   5220
aacctagtca gccgatcatt tgaatttcag gctgatggct ttgccaagaa gcttggatat   5280
gcatctggat tacgcggtgg tcttgtgaaa ctacaggagg agaatctgtc agctatgaat   5340
acagatcctt ggtactctgc ttatcactat tctcatcctc cccttgttga aagattggcc   5400
gcgctggacg aaccgggagc tcgaatttcc ccgatcgttc aaacatttgg caataaagtt   5460
```

tcttaagatt gaatcctgtt gccggtcttg cgatgattat catataattt ctgttgaatt 5520
acgttaagca tgtaataatt aacatgtaat gcatgacgtt atttatgaga tgggttttta 5580
tgattagagt cccgcaatta tacatttaat acgcgataga aaacaaaata tagcgcgcaa 5640
actaggataa attatcgcgc gcggtgtcat ctatgttact agatcgggaa ttcactggcc 5700
gtcgttttac aacgtcgtga ctgggaaaac cctggcgtta cccaacttaa tcgccttgca 5760
gcacatcccc ctttcgccag ctggcgtaat agcgaagagg cccgcaccga tcgcccttcc 5820
caacagttgc gcagcctgaa tggcgcccgc tcctttcgct ttcttccctt cctttctcgc 5880
cacgttcgcc ggctttcccc gtcaagctct aaatcggggg ctccctttag ggttccgatt 5940
tagtgcttta cggcacctcg accccaaaaa acttgatttg ggtgatggtt cacgtagtgg 6000
gccatcgccc tgatagacgg tttttcgccc tttgacgttg gagtccacgt tctttaatag 6060
tggactcttg ttccaaactg gaacaacact caaccctatc tcgggctatt cttttgattt 6120
ataagggatt ttgccgattt cggaaccacc atcaaacagg attttcgcct gctggggcaa 6180
accagcgtgg accgcttgct gcaactctct cagggccagg cggtgaaggg caatcagctg 6240
ttgcccgtct cactggtgaa aagaaaaacc accccagtac attaaaaacg tccgcaatgt 6300
gttattaagt tgtctaagcg tcaatttgtt tacaccacaa tatatcctgc ca 6352

<210> SEQ ID NO 138
<211> LENGTH: 5549
<212> TYPE: DNA
<213> ORGANISM: Artificial Sequence
<220> FEATURE:
<223> OTHER INFORMATION: Description of Artificial Sequence: Plasmid pBI121-antisense-GmCPP

<400> SEQUENCE: 138
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140

```
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccccgggtt agtcttcctt cttatccggt   3360
tcgtccagcg cggccaatct ttcaacaagg ggaggatgag aatagtgata agcagagtac   3420
caaggatctg tattcatagc tgacagattc tcctcctgta gtttcacaag accaccgcgt   3480
```

aatccagatg catatccaag cttcttggca aagccatcag cctgaaattc aaatgatcgg 3540
ctgactaggt tcagaccaaa gctgaccaat tgctgaagtg ggattacagt atgctgaaat 3600
atgatgagcc caatgaggac tggctgcgta tcaaacccaa agcttcgata cagatcagct 3660
gaatttcgca ctagtgtata tcctccaaat tgtagaagtg taagaatctg catagcaaca 3720
aatgtgtaca cagtatggtt gagcttccag tgtcccaact catgggcaat aacagcaaca 3780
atttcctcat cgtctttgca ctgttgaatt aatgtgtcat aagggacaat cctcttgttc 3840
ttgaagaatc catacatata ggcattgctg tgacttgatc ttgtggatcc atcgacaaca 3900
aatagtttct ttaacggata gttgagggag gaagcaagtt tctcgatttt ctccctgagt 3960
tgaccatctg gaagtggagt gaacttattg aagagtggag ctattagtac tggataaagg 4020
gtcatcatca caatagaaag accaaacgta aaaacccaaa gatagatggc caagtatgga 4080
cctcctttct gtactattac aatgattgca gccacaatag gtggaccaat tattacagaa 4140
aggaaaattc ctttaagcat gtccctaaag aataaccatg gtgtttgctt attaaaacca 4200
tgacgggcct caatcacaaa agttgagtac agagaaaagg gcaaatctgt tatctgtgac 4260
caaatcatca gccctgctaa gaaggcaagg gtatgcagta tttcattctc agcattgaaa 4320
ccagctattg tcataaaatc tcctgatttc ttccaaaacc agggcaatac cccaaagtac 4380
aaaattgtag agtctgtcac tattgtcaca aactcgtgaa caaaatggaa gtggctttta 4440
tcaagactat aggctctaga tttctcaaat ttctcttggc tgataacacc ctctaaagtc 4500
tttggaagag taggaagttt gagggcccta tgttgtcgca catccaagta agtttcaaaa 4560
atgtacatta atatcataaa tccgacaacg gcttccatgt agggaaacgc catgagctcg 4620
aatttccccg atcgttcaaa catttggcaa taaagtttct taagattgaa tcctgttgcc 4680
ggtcttgcga tgattatcat ataatttctg ttgaattacg ttaagcatgt aataattaac 4740
atgtaatgca tgacgttatt tatgagatgg gtttttatga ttagagtccc gcaattatac 4800
atttaatacg cgatagaaaa caaaatatag cgcgcaaact aggataaatt atcgcgcgcg 4860
gtgtcatcta tgttactaga tcgggaattc actggccgtc gttttacaac gtcgtgactg 4920
ggaaaaccct ggcgttaccc aacttaatcg ccttgcagca catccccctt tcgccagctg 4980
gcgtaatagc gaagaggccc gcaccgatcg cccttcccaa cagttgcgca gcctgaatgg 5040
cgcccgctcc tttcgctttc ttcccttcct ttctcgccac gttcgccggc tttccccgtc 5100
aagctctaaa tcgggggctc cctttagggt tccgatttag tgctttacgg cacctcgacc 5160
ccaaaaaact tgatttgggt gatggttcac gtagtgggcc atcgccctga tagacggttt 5220
ttcgcccttt gacgttggag tccacgttct ttaatagtgg actcttgttc caaactggaa 5280
caacactcaa ccctatctcg ggctattctt ttgatttata agggattttg ccgatttcgg 5340
aaccaccatc aaacaggatt ttcgcctgct ggggcaaacc agcgtggacc gcttgctgca 5400
actctctcag ggccaggcgg tgaagggcaa tcagctgttg cccgtctcac tggtgaaaag 5460
aaaaaccacc ccagtacatt aaaaacgtcc gcaatgtgtt attaagttgt ctaagcgtca 5520
atttgtttac accacaatat atcctgcca 5549

<210> SEQ ID NO 139
<211> LENGTH: 5673
<212> TYPE: DNA
<213> ORGANISM: Artificial Sequence
<220> FEATURE:
<223> OTHER INFORMATION: Description of Artificial Sequence: Plasmid
pRD29A-GmCPP

<400> SEQUENCE: 139

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
```

tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagggagcc 2520
atagatgcaa ttcaatcaaa ctgaaatttc tgcaagaatc tcaaacacgg agatctcaaa 2580
gtttgaaaga aaatttattt cttcgactca aaacaaactt acgaaattta ggtagaactt 2640
atatacatta tattgtaatt ttttgtaaca aaatgttttt attattatta tagaatttta 2700
ctggttaaat taaaaatgaa tagaaaaggt gaattaagag gagagaggag gtaaacattt 2760
tcttctattt tttcatattt tcaggataaa ttattgtaaa agtttacaag atttccattt 2820
gactagtgta aatgaggaat attctctagt aagatcatta tttcatctac ttcttttatc 2880
ttctaccagt agaggaataa acaatattta gctcctttgt aaatacaaat taattttcct 2940
tcttgacatc attcaatttt aattttacgt ataaaataaa agatcatacc tattagaacg 3000
attaaggaga aatacaattc gaatgagaag gatgtgccgt ttgttataat aaacagccac 3060
acgacgtaaa cgtaaaatga ccacatgatg ggccaataga catggaccga ctactaataa 3120
tagtaagtta cattttagga tggaataaat atcataccga catcagtttt gaaagaaaag 3180
ggaaaaaaag aaaaaataaa taaaagatat actaccgaca tgagttccaa aaagcaaaaa 3240
aaaagatcaa gccgacacag acacgcgtag agagcaaaat gactttgacg tcacaccacg 3300
aaaacagacg cttcatacgt gtccctttat ctctctcagt ctctctataa acttagtgag 3360
accctcctct gttttactca caaatatgca aactagaaaa caatcatcag gaataaaggg 3420
tttgattact tctattggaa aggactctag aggatccccg ggatggcgtt tccctacatg 3480
gaagccgttg tcggatttat gatattaatg tacatttttg aaacttactt ggatgtgcga 3540
caacataggg ccctcaaact tcctactctt ccaaagactt tagagggtgt tatcagccaa 3600
gagaaatttg agaaatctag agcctatagt cttgataaaa gccacttcca ttttgttcac 3660
gagtttgtga caatagtgac agactctaca attttgtact ttggggtatt gccctggttt 3720
tggaagaaat caggagattt tatgacaata gctggtttca atgctgagaa tgaaatactg 3780
catacccttg ccttcttagc agggctgatg atttggtcac agataacaga tttgcccttt 3840
tctctgtact caacttttgt gattgaggcc cgtcatggtt ttaataagca aacaccatgg 3900
ttattcttta gggacatgct taaaggaatt ttcctttctg taataattgg tccacctatt 3960
gtggctgcaa tcattgtaat agtacagaaa ggaggtccat acttggccat ctatctttgg 4020
gtttttacgt ttggtctttc tattgtgatg atgaccottt atccagtact aatagctcca 4080
ctcttcaata agttcactcc acttccagat ggtcaactca gggagaaaat cgagaaactt 4140
gcttcctccc tcaactatcc gttaaagaaa ctatttgttg tcgatggatc cacaagatca 4200
agtcacagca atgcctatat gtatggattc ttcaagaaca agaggattgt cccttatgac 4260
acattaattc aacagtgcaa agacgatgag gaaattgttg ctgttattgc ccatgagttg 4320
ggacactgga agctcaacca tactgtgtac acatttgttg ctatgcagat tcttacactt 4380
ctacaatttg gaggatatac actagtgcga aattcagctg atctgtatcg aagctttggg 4440
tttgatacgc agccagtcct cattgggctc atcatatttc agcatactgt aatcccactt 4500
cagcaattgg tcagctttgg tctgaaccta gtcagccgat catttgaatt tcaggctgat 4560
ggctttgcca agaagcttgg atatgcatct ggattacgcg gtggtcttgt gaaactacag 4620
gaggagaatc tgtcagctat gaatacagat ccttggtact ctgcttatca ctattctcat 4680

-continued

```
cctccccttg ttgaaagatt ggccgcgctg gacgaaccgg ataagaagga agactaagag   4740
ctcgaatttc cccgatcgtt caaacatttg gcaataaagt ttcttaagat tgaatcctgt   4800
tgccggtctt gcgatgatta tcatataatt tctgttgaat tacgttaagc atgtaataat   4860
taacatgtaa tgcatgacgt tatttatgag atgggttttt atgattagag tcccgcaatt   4920
atacatttaa tacgcgatag aaaacaaaat atagcgcgca aactaggata aattatcgcg   4980
cgcggtgtca tctatgttac tagatcggga attcactggc cgtcgtttta caacgtcgtg   5040
actgggaaaa ccctggcgtt acccaactta atcgccttgc agcacatccc cctttcgcca   5100
gctggcgtaa tagcgaagag gcccgcaccg atcgcccttc ccaacagttg cgcagcctga   5160
atggcgcccg ctcctttcgc tttcttccct tcctttctcg ccacgttcgc cggctttccc   5220
cgtcaagctc taaatcgggg gctcccttta gggttccgat ttagtgcttt acggcacctc   5280
gaccccaaaa aacttgattt gggtgatggt tcacgtagtg ggccatcgcc ctgatagacg   5340
gtttttcgcc ctttgacgtt ggagtccacg ttctttaata gtggactctt gttccaaact   5400
ggaacaacac tcaaccctat ctcgggctat tcttttgatt tataagggat tttgccgatt   5460
tcggaaccac catcaaacag gattttcgcc tgctggggca aaccagcgtg gaccgcttgc   5520
tgcaactctc tcagggccag gcggtgaagg gcaatcagct gttgcccgtc tcactggtga   5580
aaagaaaaac caccccagta cattaaaaac gtccgcaatg tgttattaag ttgtctaagc   5640
gtcaatttgt ttacaccaca atatatcctg cca                                5673
```

```
<210> SEQ ID NO 140
<211> LENGTH: 6476
<212> TYPE: DNA
<213> ORGANISM: Artificial Sequence
<220> FEATURE:
<223> OTHER INFORMATION: Description of Artificial Sequence: Plasmid
      pRD29A-HP-GmCPP

<400> SEQUENCE: 140
```

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
```

-continued ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagggagcc 2520
atagatgcaa ttcaatcaaa ctgaaatttc tgcaagaatc tcaaacacgg agatctcaaa 2580
gtttgaaaga aaatttattt cttcgactca aaacaaactt acgaaattta ggtagaactt 2640
atatacatta tattgtaatt ttttgtaaca aaatgttttt attattatta tagaatttta 2700
ctggttaaat taaaaatgaa tagaaaaggt gaattaagag gagagaggag gtaaacattt 2760
tcttctattt tttcatattt tcaggataaa ttattgtaaa agtttacaag atttccattt 2820
gactagtgta aatgaggaat attctctagt aagatcatta tttcatctac ttcttttatc 2880
ttctaccagt agaggaataa acaatattta gctcctttgt aaatacaaat taattttcct 2940
tcttgacatc attcaatttt aattttacgt ataaaataaa agatcatacc tattagaacg 3000
attaaggaga aatacaattc gaatgagaag gatgtgccgt ttgttataat aaacagccac 3060
acgacgtaaa cgtaaaatga ccacatgatg ggccaataga catggaccga ctactaataa 3120
tagtaagtta cattttagga tggaataaat atcataccga catcagtttt gaaagaaaag 3180
ggaaaaaaag aaaaaataaa taaaagatat actaccgaca tgagttccaa aaagcaaaaa 3240
aaaagatcaa gccgacacag acacgcgtag agagcaaaat gactttgacg tcacaccacg 3300
aaaacagacg cttcatacgt gtccctttat ctctctcagt ctctctataa acttagtgag 3360
accctcctct gttttactca caaatatgca aactagaaaa caatcatcag gaataaaggg 3420

-continued tttgattact tctattggaa aggactctag accggttcgt ccagcgcggc caatctttca 3480
acaaggggag gatgagaata gtgataagca gagtaccaag gatctgtatt catagctgac 3540
agattctcct cctgtagttt cacaagacca ccgcgtaatc cagatgcata tccaagcttc 3600
ttggcaaagc catcagcctg aaattcaaat gatcggctga ctaggttcag accaaagctg 3660
accaattgct gaagtgggat tacagtatgc tgaaatatga tgagcccaat gaggactggc 3720
tgcgtatcaa acccaaagct tcgatacaga tcagctgaat ttcgcactag tgtatatcct 3780
ccaaattgta gaagtgtaag aatctgcata gcaacaaatg tgtacacagt atggttgagc 3840
ttccagtgtc ccaactcatg ggcaataaca gcaacaattt cctcatcgtc tttgcactgt 3900
tgaattaatg tgtcataagg gacaatcctc ttgttcttga agaatccata catataggca 3960
ttgctgtgac ttgatcttgt ggatccccat ctacccgctt cgcgtcggca tccggtcagt 4020
ggcagtgaag ggcgaacagt tcctgattaa ccacaaaccg ttctacttta ctggctttgg 4080
tcgtcatgaa gatgcggact tgcgtggcaa aggattcgat aacgtgctga tggtgcacga 4140
ccacgcatta atggactgga ttggggccaa ctcctaccgt acctcgcatt acccttacgc 4200
tgaagagatg ctcgactggg cagatgaaca tggcatcgtg gtgattgatg aaactgctgc 4260
tgtcggcttt tcgctctctt taggcattgg tttcgaagcg ggcaacaagc cgaaagaact 4320
gtacagcgaa gaggcagtca acggggaaac tcagcaagcg cacttacagg cgattaaaga 4380
gctgatagcg cgtgacaaaa accacccaag cgtggtgatg tggagtattg ccaacgaacc 4440
ggatacccgt ccgcaaggtg cacgggaata tttcgcgcca ctggcggaag caacgcgtaa 4500
actcgacccg acgcgtccga tcacctgcgt caatgtaatg ttctgcgacg ctcacaccga 4560
taccatcagc gatctctttg atgtgctgtg cctgaaccgt tattacggat ggtatgtcca 4620
aagcggcgat ttggaaacgg cagagaaggt actggaaaaa gaacttctgg cctggcagga 4680
gaaactgtac accgacatgt ggagtgaaga gtatcagtgt gcatggctgg atatgtatca 4740
ccgcgtcttt gatcgcgtca gcgccgtcgt cggtgaacag gtatggaatt tcgccgattt 4800
tgcgacctcg caaggcatat tgcgcgttgg cggtaacaag aaagggatct tcactcgcga 4860
ccgcaaaccg aagtcggcgg cttttctgct gcaaaaacgc tggactggca tgaacttcgg 4920
tgaaaaaccg cagcagggag gcaaacaatg aatcaacaac tctcctggcg caccatcgtc 4980
ggctacagcc tcgggaattg ctaccgagct cacaagatca agtcacagca atgcctatat 5040
gtatggattc ttcaagaaca agaggattgt cccttatgac acattaattc aacagtgcaa 5100
agacgatgag gaaattgttg ctgttattgc ccatgagttg ggacactgga agctcaacca 5160
tactgtgtac acatttgttg ctatgcagat tcttacactt ctacaatttg gaggatatac 5220
actagtgcga aattcagctg atctgtatcg aagctttggg tttgatacgc agccagtcct 5280
cattgggctc atcatatttc agcatactgt aatcccactt cagcaattgg tcagctttgg 5340
tctgaaccta gtcagccgat catttgaatt tcaggctgat ggctttgcca agaagcttgg 5400
atatgcatct ggattacgcg gtggtcttgt gaaactacag gaggagaatc tgtcagctat 5460
gaatacagat ccttggtact ctgcttatca ctattctcat cctccccttg ttgaaagatt 5520
ggccgcgctg gacgaaccgg gagctcgaat ttccccgatc gttcaaacat ttggcaataa 5580
agtttcttaa gattgaatcc tgttgccggt cttgcgatga ttatcatata atttctgttg 5640
aattacgtta agcatgtaat aattaacatg taatgcatga cgttatttat gagatgggtt 5700
tttatgatta gagtcccgca attatacatt taatacgcga tagaaaacaa aatatagcgc 5760

```
gcaaactagg ataaattatc gcgcgcggtg tcatctatgt tactagatcg ggaattcact   5820

ggccgtcgtt ttacaacgtc gtgactggga aaaccctggc gttacccaac ttaatcgcct   5880

tgcagcacat ccccctttcg ccagctggcg taatagcgaa gaggcccgca ccgatcgccc   5940

ttcccaacag ttgcgcagcc tgaatggcgc ccgctccttt cgctttcttc ccttcctttc   6000

tcgccacgtt cgccggcttt ccccgtcaag ctctaaatcg ggggctccct ttagggttcc   6060

gatttagtgc tttacggcac ctcgacccca aaaaacttga tttgggtgat ggttcacgta   6120

gtgggccatc gccctgatag acggtttttc gccctttgac gttggagtcc acgttcttta   6180

atagtggact cttgttccaa actggaacaa cactcaaccc tatctcgggc tattcttttg   6240

atttataagg gattttgccg atttcggaac caccatcaaa caggattttc gcctgctggg   6300

gcaaaccagc gtggaccgct tgctgcaact ctctcagggc caggcggtga agggcaatca   6360

gctgttgccc gtctcactgg tgaaaagaaa aaccaccccca gtacattaaa aacgtccgca   6420

atgtgttatt aagttgtcta agcgtcaatt tgtttacacc acaatatatc ctgcca       6476
```

<210> SEQ ID NO 141
<211> LENGTH: 5673
<212> TYPE: DNA
<213> ORGANISM: Artificial Sequence
<220> FEATURE:
<223> OTHER INFORMATION: Description of Artificial Sequence: Plasmid pRD29A-antisense-GmCPP

<400> SEQUENCE: 141

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320
```

-continued

```
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccccg ggttagtctt ccttcttatc   3480
cggttcgtcc agcgcggcca atctttcaac aaggggagga tgagaatagt gataagcaga   3540
gtaccaagga tctgtattca tagctgacag attctcctcc tgtagtttca caagaccacc   3600
gcgtaatcca gatgcatatc caagcttctt ggcaaagcca tcagcctgaa attcaaatga   3660
tcggctgact aggttcagac caaagctgac caattgctga agtgggatta cagtatgctg   3720
```

aaatatgatg agcccaatga ggactggctg cgtatcaaac ccaaagcttc gatacagatc 3780
agctgaattt cgcactagtg tatatcctcc aaattgtaga agtgtaagaa tctgcatagc 3840
aacaaatgtg tacacagtat ggttgagctt ccagtgtccc aactcatggg caataacagc 3900
aacaatttcc tcatcgtctt tgcactgttg aattaatgtg tcataaggga caatcctctt 3960
gttcttgaag aatccataca tataggcatt gctgtgactt gatcttgtgg atccatcgac 4020
aacaaatagt ttctttaacg gatagttgag ggaggaagca agtttctcga ttttctccct 4080
gagttgacca tctggaagtg gagtgaactt attgaagagt ggagctatta gtactggata 4140
aagggtcatc atcacaatag aaagaccaaa cgtaaaaacc caaagataga tggccaagta 4200
tggacctcct ttctgtacta ttacaatgat tgcagccaca ataggtggac caattattac 4260
agaaaggaaa attcctttaa gcatgtccct aaagaataac catggtgttt gcttattaaa 4320
accatgacgg gcctcaatca caaaagttga gtacagagaa aagggcaaat ctgttatctg 4380
tgaccaaatc atcagccctg ctaagaaggc aagggtatgc agtatttcat tctcagcatt 4440
gaaaccagct attgtcataa aatctcctga tttcttccaa aaccagggca ataccccaaa 4500
gtacaaaatt gtagagtctg tcactattgt cacaaactcg tgaacaaaat ggaagtggct 4560
tttatcaaga ctataggctc tagatttctc aaatttctct tggctgataa caccctctaa 4620
agtctttgga agagtaggaa gtttgagggc cctatgttgt cgcacatcca agtaagtttc 4680
aaaaatgtac attaatatca taaatccgac aacggcttcc atgtagggaa acgccatgag 4740
ctcgaatttc cccgatcgtt caaacatttg gcaataaagt ttcttaagat tgaatcctgt 4800
tgccggtctt gcgatgatta tcatataatt tctgttgaat tacgttaagc atgtaataat 4860
taacatgtaa tgcatgacgt tatttatgag atgggttttt atgattagag tcccgcaatt 4920
atacatttaa tacgcgatag aaaacaaaat atagcgcgca aactaggata aattatcgcg 4980
cgcggtgtca tctatgttac tagatcggga attcactggc cgtcgtttta caacgtcgtg 5040
actgggaaaa ccctggcgtt acccaactta atcgccttgc agcacatccc cctttcgcca 5100
gctggcgtaa tagcgaagag gcccgcaccg atcgcccttc ccaacagttg cgcagcctga 5160
atggcgcccg ctcctttcgc tttcttccct tcctttctcg ccacgttcgc cggctttccc 5220
cgtcaagctc taaatcgggg gctcccttta gggttccgat ttagtgcttt acggcacctc 5280
gaccccaaaa aacttgattt gggtgatggt tcacgtagtg ggccatcgcc ctgatagacg 5340
gtttttcgcc ctttgacgtt ggagtccacg ttctttaata gtggactctt gttccaaact 5400
ggaacaacac tcaaccctat ctcgggctat tcttttgatt tataagggat tttgccgatt 5460
tcggaaccac catcaaacag gattttcgcc tgctggggca aaccagcgtg gaccgcttgc 5520
tgcaactctc tcagggccag gcggtgaagg gcaatcagct gttgcccgtc tcactggtga 5580
aaagaaaaac caccccagta cattaaaaac gtccgcaatg tgttattaag ttgtctaagc 5640
gtcaatttgt ttacaccaca atatatcctg cca 5673

<210> SEQ ID NO 142
<211> LENGTH: 5544
<212> TYPE: DNA
<213> ORGANISM: Artificial Sequence
<220> FEATURE:
<223> OTHER INFORMATION: Description of Artificial Sequence: Plasmid
pBI121-BnCPP

<400> SEQUENCE: 142
gtttacccgc caatatatcc tgtcaaacac tgatagttta aactgaaggc gggaaacgac 60

-continued

```
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
```

```
caggctttac actttatgct tccggctcgt atgttgtgtg gaattgtgag cggataacaa   2460

tttcacacag gaaacagcta tgaccatgat tacgccaagc ttgcatgcct gcagcccaca   2520

gatggttaga gaggcttacg cagcaggtct catcaagacg atctacccga gcaataatct   2580

ccaggaaatc aaataccttc ccaagaaggt taaagatgca gtcaaaagat tcaggactaa   2640

ctgcatcaag aacacagaga aagatatatt tctcaagatc agaagtacta ttccagtatg   2700

gacgattcaa ggcttgcttc acaaaccaag gcaagtaata gagattggag tctctaaaaa   2760

ggtagttccc actgaatcaa aggccatgga gtcaaagatt caaatagagg acctaacaga   2820

actcgccgta aagactggcg aacagttcat acagagtctc ttacgactca atgacaagaa   2880

gaaaatcttc gtcaacatgg tggagcacga cacacttgtc tactccaaaa atatcaaaga   2940

tacagtctca gaagaccaaa gggcaattga gacttttcaa caaagggtaa tatccggaaa   3000

cctcctcgga ttccattgcc cagctatctg tcactttatt gtgaagatag tggaaaagga   3060

aggtggctcc tacaaatgcc atcattgcga taaaggaaag gccatcgttg aagatgcctc   3120

tgccgacagt ggtcccaaag atggaccccc acccacgagg agcatcgtgg aaaaagaaga   3180

cgttccaacc acgtcttcaa agcaagtgga ttgatgtgat atctccactg acgtaaggga   3240

tgacgcacaa tcccactatc cttcgcaaga cccttcctct atataaggaa gttcatttca   3300

tttggagaga acacggggga ctctagagga tccatggcga ttcctttcat ggaaaccgtc   3360

gttggtttta tgatagtgat gtacgttttt gagacgtatt tggatctgag gcaacatact   3420

gctctcaagc ttcccactct cccaaagact ttggttggag tcattagcca agagaagttt   3480

gagaaatctc gagcttacag tcttgacaaa agccattttc actttgttca tgagtttgtt   3540

actatactta tggactctgc gattctgttc tttgggatct tgccttggtt ttggaagata   3600

tctggcggct ttctaccaat ggtgggactc gatccagaga atgaaatcct gcacactctt   3660

tcattcttgg ctggtcttat gacatggtca cagatcactg atttgccatt ttctttgtac   3720

tcaactttcg tgatcgagtc tcggcatggg ttcaacaaac aaacaatatg gatgttcatt   3780

agggacatga tcaaaggaat actcctctct gtcatacctg cccctcctat cgttgccgca   3840

attattgtta tagttcagaa aggaggtcct tacctcgcca tctatctgtg ggcattcatg   3900

tttatcctgt ctctagtgat gatgactata taccctgttt tgattgcacc tcttttcaac   3960

aagttcactc ctcttcctga tggagacctc cgggagaaga ttgagaaact tgcttcttct   4020

ctaaagtttc ctctgaagaa gctgtttgtt gtcgatggat ctacaaggtc aagccatagt   4080

aatgcttaca tgtatggttt cttcaagaac aaaaggattg ttctttatga cacattgatt   4140

cagcagtgcc agaatgagaa tgaaattgtg gcggttattg cacacgagct gggacactgg   4200

aagctgaatc acactacata ctcgttcatt gctgttcaaa tccttgcctt cttgcaattt   4260

ggaggataca ctcttgtcag aaactccact gatctcttca ggagttttgg ttttgataca   4320

caaccagttc tcattggttt gatcatattt cagcacactg taataccact tcaacaccta   4380

gtaagctttg acctcaacct tgttagtcga gcgtttgagt ttcaggctga tgcttttgca   4440

gtgaatcttg gttatgcaaa ggatctacgt cctgccctag tgaagctaca ggaagagaac   4500

ttatcagcga tgaacacaga cccattgtac tcagcttatc actactcaca ccctcctctt   4560

gtagagaggc ttcgagccat tgatggagaa gacaagaaga cagattaacc cctcgaattt   4620

ccccgatcgt tcaaacattt ggcaataaag tttcttaaga ttgaatcctg ttgccggtct   4680

tgcgatgatt atcatataat ttctgttgaa ttacgttaag catgtaataa ttaacatgta   4740

atgcatgacg ttatttatga gatgggtttt tatgattaga gtcccgcaat tatacattta   4800
```

atacgcgata gaaaacaaaa tatagcgcgc aaactaggat aaattatcgc gcgcggtgtc 4860
atctatgtta ctagatcggg aattcactgg ccgtcgtttt acaacgtcgt gactgggaaa 4920
accctggcgt tacccaactt aatcgccttg cagcacatcc ccctttcgcc agctggcgta 4980
atagcgaaga ggcccgcacc gatcgccctt cccaacagtt gcgcagcctg aatggcgccc 5040
gctcctttcg ctttcttccc ttcctttctc gccacgttcg ccggctttcc ccgtcaagct 5100
ctaaatcggg ggctcccttt agggttccga tttagtgctt tacggcacct cgaccccaaa 5160
aaacttgatt tgggtgatgg ttcacgtagt gggccatcgc cctgatagac ggtttttcgc 5220
cctttgacgt tggagtccac gttctttaat agtggactct tgttccaaac tggaacaaca 5280
ctcaacccta tctcgggcta ttcttttgat ttataaggga ttttgccgat ttcggaacca 5340
ccatcaaaca ggattttcgc ctgctggggc aaaccagcgt ggaccgcttg ctgcaactct 5400
ctcagggcca ggcggtgaag ggcaatcagc tgttgcccgt ctcactggtg aaaagaaaaa 5460
ccaccccagt acattaaaaa cgtccgcaat gtgttattaa gttgtctaag cgtcaatttg 5520
tttacaccac aatatatcct gcca 5544

<210> SEQ ID NO 143
<211> LENGTH: 6474
<212> TYPE: DNA
<213> ORGANISM: Artificial Sequence
<220> FEATURE:
<223> OTHER INFORMATION: Description of Artificial Sequence: Plasmid
pBI121-HP-BnCPP

<400> SEQUENCE: 143
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260

-continued atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagacca gtgtcccagc tcgtgtgcaa taaccgccac 3360
aatttcattc tcattctggc actgctgaat caatgtgtca taaagaacaa tccttttgtt 3420
cttgaagaaa ccatacatgt aagcattact atggcttgac cttgtagatc catcgacaac 3480
aaacagcttc ttcagaggaa actttagaga agaagcaagt ttctcaatct tctcccggag 3540
gtctccatca ggaagaggag tgaacttgtt gaaaagaggt gcaatcaaaa cagggtatat 3600

-continued agtcatcatc actagagaca ggataaacat gaatgcccac agatagatgg cgaggtaagg 3660
acctcctttc tgaactataa caataattgc ggcaacgata ggaggggcag gtatgacaga 3720
gaggagtatt cctttgatca tgtccctaat gaacatccat attgtttgtt tgttgaaccc 3780
atgccgagac tcgatcacga aagttgagta caaagaaaat ggcaaatcag tgatctgtga 3840
ccatgtcata agaccagcca agaatgaaag agtgtgcagg atttcattct ctggatcgag 3900
tcccaccatt ggtagaagga tccccatcta cccgcttcgc gtcggcatcc ggtcagtggc 3960
agtgaagggc gaacagttcc tgattaacca caaaccgttc tactttactg gctttggtcg 4020
tcatgaagat gcggacttgc gtggcaaagg attcgataac gtgctgatgg tgcacgacca 4080
cgcattaatg gactggattg gggccaactc ctaccgtacc tcgcattacc cttacgctga 4140
agagatgctc gactgggcag atgaacatgg catcgtggtg attgatgaaa ctgctgctgt 4200
cggcttttcg ctctctttag gcattggttt cgaagcgggc aacaagccga aagaactgta 4260
cagcgaagag gcagtcaacg gggaaactca gcaagcgcac ttacaggcga ttaaagagct 4320
gatagcgcgt gacaaaaacc acccaagcgt ggtgatgtgg agtattgcca acgaaccgga 4380
tacccgtccg caaggtgcac gggaatattt cgcgccactg gcggaagcaa cgcgtaaact 4440
cgacccgacg cgtccgatca cctgcgtcaa tgtaatgttc tgcgacgctc acaccgatac 4500
catcagcgat ctctttgatg tgctgtgcct gaaccgttat tacggatggt atgtccaaag 4560
cggcgatttg gaaacggcag agaaggtact ggaaaaagaa cttctggcct ggcaggagaa 4620
actgtacacc gacatgtgga gtgaagagta tcagtgtgca tggctggata tgtatcaccg 4680
cgtctttgat cgcgtcagcg ccgtcgtcgg tgaacaggta tggaatttcg ccgattttgc 4740
gacctcgcaa ggcatattgc gcgttggcgg taacaagaaa gggatcttca ctcgcgaccg 4800
caaaccgaag tcggcggctt ttctgctgca aaaacgctgg actggcatga acttcggtga 4860
aaaaccgcag cagggaggca aacaatgaat caacaactct cctggcgcac catcgtcggc 4920
tacagcctcg ggaattgcta ccgagctctt ctaccaatgg tgggactcga tccagagaat 4980
gaaatcctgc acactctttc attcttggct ggtcttatga catggtcaca gatcactgat 5040
ttgccatttt ctttgtactc aactttcgtg atcgagtctc ggcatgggtt caacaaacaa 5100
acaatatgga tgttcattag ggacatgatc aaaggaatac tcctctctgt catacctgcc 5160
cctcctatcg ttgccgcaat tattgttata gttcagaaag gaggtcctta cctcgccatc 5220
tatctgtggg cattcatgtt tatcctgtct ctagtgatga tgactatata ccctgttttg 5280
attgcacctc ttttcaacaa gttcactcct cttcctgatg gagacctccg ggagaagatt 5340
gagaaacttg cttcttctct aaagtttcct ctgaagaagc tgtttgttgt cgatggatct 5400
acaaggtcaa gccatagtaa tgcttacatg tatggtttct tcaagaacaa aaggattgtt 5460
ctttatgaca cattgattca gcagtgccag aatgagaatg aaattgtggc ggttattgca 5520
cacgagctgg gacactggga gctcgaattt ccccgatcgt tcaaacattt ggcaataaag 5580
tttcttaaga ttgaatcctg ttgccggtct tgcgatgatt atcatataat ttctgttgaa 5640
ttacgttaag catgtaataa ttaacatgta atgcatgacg ttatttatga gatgggtttt 5700
tatgattaga gtcccgcaat tatacattta atacgcgata gaaaacaaaa tatagcgcgc 5760
aaactaggat aaattatcgc gcgcggtgtc atctatgtta ctagatcggg aattcactgg 5820
ccgtcgtttt acaacgtcgt gactgggaaa accctggcgt tacccaactt aatcgccttg 5880
cagcacatcc ccctttcgcc agctggcgta atagcgaaga ggcccgcacc gatcgccctt 5940
cccaacagtt gcgcagcctg aatggcgccc gctcctttcg ctttcttccc ttcctttctc 6000
gccacgttcg ccggctttcc ccgtcaagct ctaaatcggg ggctcccttt agggttccga 6060
tttagtgctt tacggcacct cgaccccaaa aaacttgatt tgggtgatgg ttcacgtagt 6120
gggccatcgc cctgatagac ggtttttcgc cctttgacgt tggagtccac gttctttaat 6180
agtggactct tgttccaaac tggaacaaca ctcaacccta tctcgggcta ttcttttgat 6240
ttataaggga ttttgccgat ttcggaacca ccatcaaaca ggattttcgc ctgctggggc 6300
aaaccagcgt ggaccgcttg ctgcaactct ctcagggcca ggcggtgaag ggcaatcagc 6360
tgttgcccgt ctcactggtg aaaagaaaaa ccaccccagt acattaaaaa cgtccgcaat 6420
gtgttattaa gttgtctaag cgtcaatttg tttacaccac aatatatcct gcca 6474

<210> SEQ ID NO 144
<211> LENGTH: 5544
<212> TYPE: DNA
<213> ORGANISM: Artificial Sequence
<220> FEATURE:
<223> OTHER INFORMATION: Description of Artificial Sequence: Plasmid
Plasmid pBI121-antisense-BnCPP

<400> SEQUENCE: 144
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980
aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tccttaatct gtcttcttgt cttctccatc 3360
aatggctcga agcctctcta caagaggagg gtgtgagtag tgataagctg agtacaatgg 3420
gtctgtgttc atcgctgata agttctcttc ctgtagcttc actagggcag gacgtagatc 3480
ctttgcataa ccaagattca ctgcaaaagc atcagcctga aactcaaacg ctcgactaac 3540
aaggttgagg tcaaagctta ctaggtgttg aagtggtatt acagtgtgct gaaatatgat 3600
caaaccaatg agaactggtt gtgtatcaaa accaaaactc ctgaagagat cagtggagtt 3660
tctgacaaga gtgtatcctc caaattgcaa gaaggcaagg atttgaacag caatgaacga 3720
gtatgtagtg tgattcagct tccagtgtcc cagctcgtgt gcaataaccg ccacaatttc 3780
attctcattc tggcactgct gaatcaatgt gtcataaaga acaatccttt tgttcttgaa 3840
gaaaccatac atgtaagcat tactatggct tgaccttgta gatccatcga caacaaacag 3900
cttcttcaga ggaaacttta gagaagaagc aagtttctca atcttctccc ggaggtctcc 3960
atcaggaaga ggagtgaact tgttgaaaag aggtgcaatc aaaacagggt atatagtcat 4020
catcactaga gacaggataa acatgaatgc ccacagatag atggcgaggt aaggacctcc 4080
tttctgaact ataacaataa ttgcggcaac gataggaggg gcaggtatga cagagaggag 4140
tattcctttg atcatgtccc taatgaacat ccatattgtt tgtttgttga acccatgccg 4200
agactcgatc acgaaagttg agtacaaaga aaatggcaaa tcagtgatct gtgaccatgt 4260
cataagacca gccaagaatg aaagagtgtg caggatttca ttctctggat cgagtcccac 4320
cattggtaga aagccgccag atatcttcca aaaccaaggc aagatcccaa agaacagaat 4380
cgcagagtcc ataagtatag taacaaactc atgaacaaag tgaaaatggc ttttgtcaag 4440
actgtaagct cgagatttct caaacttctc ttggctaatg actccaacca aagtctttgg 4500
gagagtggga agcttgagag cagtatgttg cctcagatcc aaatacgtct caaaaacgta 4560
catcactatc ataaaaccaa cgacggtttc catgaaagga atcgccatcc cctcgaattt 4620
ccccgatcgt tcaaacattt ggcaataaag tttcttaaga ttgaatcctg ttgccggtct 4680
tgcgatgatt atcatataat ttctgttgaa ttacgttaag catgtaataa ttaacatgta 4740
atgcatgacg ttatttatga gatgggtttt tatgattaga gtcccgcaat tatacattta 4800
atacgcgata gaaaacaaaa tatagcgcgc aaactaggat aaattatcgc gcgcggtgtc 4860
atctatgtta ctagatcggg aattcactgg ccgtcgtttt acaacgtcgt gactgggaaa 4920
accctggcgt tacccaactt aatcgccttg cagcacatcc ccctttcgcc agctggcgta 4980
atagcgaaga ggcccgcacc gatcgccctt cccaacagtt gcgcagcctg aatggcgccc 5040
gctcctttcg ctttcttccc ttcctttctc gccacgttcg ccggctttcc ccgtcaagct 5100
ctaaatcggg ggctcccttt agggttccga tttagtgctt tacggcacct cgaccccaaa 5160
aaacttgatt tgggtgatgg ttcacgtagt gggccatcgc cctgatagac ggtttttcgc 5220
cctttgacgt tggagtccac gttctttaat agtggactct tgttccaaac tggaacaaca 5280
ctcaacccta tctcgggcta ttcttttgat ttataaggga ttttgccgat ttcggaacca 5340
ccatcaaaca ggattttcgc ctgctggggc aaaccagcgt ggaccgcttg ctgcaactct 5400
ctcagggcca ggcggtgaag ggcaatcagc tgttgcccgt ctcactggtg aaaagaaaaa 5460
ccaccccagt acattaaaaa cgtccgcaat gtgttattaa gttgtctaag cgtcaatttg 5520
tttacaccac aatatatcct gcca 5544

<210> SEQ ID NO 145
<211> LENGTH: 5668
<212> TYPE: DNA
<213> ORGANISM: Artificial Sequence
<220> FEATURE:
<223> OTHER INFORMATION: Description of Artificial Sequence: Plasmid pRD29A-BnCPP

<400> SEQUENCE: 145
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360

-continued

```
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
```

-continued

```
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccatg gcgattcctt tcatggaaac   3480
cgtcgttggt tttatgatag tgatgtacgt ttttgagacg tatttggatc tgaggcaaca   3540
tactgctctc aagcttccca ctctcccaaa gactttggtt ggagtcatta gccaagagaa   3600
gtttgagaaa tctcgagctt acagtcttga caaaagccat tttcactttg ttcatgagtt   3660
tgttactata cttatggact ctgcgattct gttctttggg atcttgcctt ggttttggaa   3720
gatatctggc ggctttctac caatggtggg actcgatcca gagaatgaaa tcctgcacac   3780
tctttcattc ttggctggtc ttatgacatg gtcacagatc actgatttgc cattttcttt   3840
gtactcaact ttcgtgatcg agtctcggca tgggttcaac aaacaaacaa tatggatgtt   3900
cattagggac atgatcaaag gaatactcct ctctgtcata cctgcccctc ctatcgttgc   3960
cgcaattatt gttatagttc agaaaggagg tccttacctc gccatctatc tgtgggcatt   4020
catgtttatc ctgtctctag tgatgatgac tatataccct gttttgattg cacctctttt   4080
caacaagttc actcctcttc ctgatggaga cctccgggag aagattgaga aacttgcttc   4140
ttctctaaag tttcctctga agaagctgtt tgttgtcgat ggatctacaa ggtcaagcca   4200
tagtaatgct tacatgtatg gtttcttcaa gaacaaaagg attgttcttt atgacacatt   4260
gattcagcag tgccagaatg agaatgaaat tgtggcggtt attgcacacg agctgggaca   4320
ctggaagctg aatcacacta catactcgtt cattgctgtt caaatccttg ccttcttgca   4380
atttggagga tacactcttg tcagaaactc cactgatctc ttcaggagtt ttggttttga   4440
tacacaacca gttctcattg gtttgatcat atttcagcac actgtaatac cacttcaaca   4500
cctagtaagc tttgacctca accttgttag tcgagcgttt gagtttcagg ctgatgcttt   4560
tgcagtgaat cttggttatg caaaggatct acgtcctgcc ctagtgaagc tacaggaaga   4620
gaacttatca gcgatgaaca cagacccatt gtactcagct tatcactact cacaccctcc   4680
tcttgtagag aggcttcgag ccattgatgg agaagacaag aagacagatt aacccctcga   4740
atttccccga tcgttcaaac atttggcaat aaagtttctt aagattgaat cctgttgccg   4800
gtcttgcgat gattatcata taatttctgt tgaattacgt taagcatgta ataattaaca   4860
tgtaatgcat gacgttattt atgagatggg tttttatgat tagagtcccg caattataca   4920
tttaatacgc gatagaaaac aaaatatagc gcgcaaacta ggataaatta tcgcgcgcgg   4980
tgtcatctat gttactagat cgggaattca ctggccgtcg ttttacaacg tcgtgactgg   5040
gaaaaccctg gcgttaccca acttaatcgc cttgcagcac atcccccttt cgccagctgg   5100
```

cgtaatagcg aagaggcccg caccgatcgc ccttcccaac agttgcgcag cctgaatggc 5160
gcccgctcct ttcgctttct tcccttcctt tctcgccacg ttcgccggct ttccccgtca 5220
agctctaaat cgggggctcc ctttagggtt ccgatttagt gctttacggc acctcgaccc 5280
caaaaaactt gatttgggtg atggttcacg tagtgggcca tcgccctgat agacggtttt 5340
tcgccctttg acgttggagt ccacgttctt taatagtgga ctcttgttcc aaactggaac 5400
aacactcaac cctatctcgg gctattcttt tgatttataa gggattttgc cgatttcgga 5460
accaccatca aacaggattt tcgcctgctg gggcaaacca gcgtggaccg cttgctgcaa 5520
ctctctcagg gccaggcggt gaagggcaat cagctgttgc ccgtctcact ggtgaaaaga 5580
aaaaccaccc cagtacatta aaaacgtccg caatgtgtta ttaagttgtc taagcgtcaa 5640
tttgtttaca ccacaatata tcctgcca 5668

<210> SEQ ID NO 146
<211> LENGTH: 6598
<212> TYPE: DNA
<213> ORGANISM: Artificial Sequence
<220> FEATURE:
<223> OTHER INFORMATION: Description of Artificial Sequence:Plasmid
pRD29A-HP-BnCPP

<400> SEQUENCE: 146
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440

-continued

```
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag accagtgtcc cagctcgtgt gcaataaccg   3480
ccacaatttc attctcattc tggcactgct gaatcaatgt gtcataaaga acaatccttt   3540
tgttcttgaa gaaaccatac atgtaagcat tactatggct tgaccttgta gatccatcga   3600
caacaaacag cttcttcaga ggaaacttta gagaagaagc aagtttctca atcttctccc   3660
ggaggtctcc atcaggaaga ggagtgaact tgttgaaaag aggtgcaatc aaaacagggt   3720
atatagtcat catcactaga gacaggataa acatgaatgc ccacagatag atggcgaggt   3780
aaggacctcc tttctgaact ataacaataa ttgcggcaac gataggaggg gcaggtatga   3840
```

cagagaggag tattcctttg atcatgtccc taatgaacat ccatattgtt tgtttgttga 3900
acccatgccg agactcgatc acgaaagttg agtacaaaga aaatggcaaa tcagtgatct 3960
gtgaccatgt cataagacca gccaagaatg aaagagtgtg caggatttca ttctctggat 4020
cgagtcccac cattggtaga aggatcccca tctacccgct tcgcgtcggc atccggtcag 4080
tggcagtgaa gggcgaacag ttcctgatta accacaaacc gttctacttt actggctttg 4140
gtcgtcatga agatgcggac ttgcgtggca aaggattcga taacgtgctg atggtgcacg 4200
accacgcatt aatggactgg attggggcca actcctaccg tacctcgcat tacccttacg 4260
ctgaagagat gctcgactgg gcagatgaac atggcatcgt ggtgattgat gaaactgctg 4320
ctgtcggctt ttcgctctct ttaggcattg gtttcgaagc gggcaacaag ccgaaagaac 4380
tgtacagcga agaggcagtc aacggggaaa ctcagcaagc gcacttacag gcgattaaag 4440
agctgatagc gcgtgacaaa aaccacccaa gcgtggtgat gtggagtatt gccaacgaac 4500
cggatacccg tccgcaaggt gcacgggaat atttcgcgcc actggcggaa gcaacgcgta 4560
aactcgaccc gacgcgtccg atcacctgcg tcaatgtaat gttctgcgac gctcacaccg 4620
ataccatcag cgatctcttt gatgtgctgt gcctgaaccg ttattacgga tggtatgtcc 4680
aaagcggcga tttggaaacg gcagagaagg tactggaaaa agaacttctg gcctggcagg 4740
agaaactgta caccgacatg tggagtgaag agtatcagtg tgcatggctg gatatgtatc 4800
accgcgtctt tgatcgcgtc agcgccgtcg tcggtgaaca ggtatggaat ttcgccgatt 4860
ttgcgacctc gcaaggcata ttgcgcgttg gcggtaacaa gaaagggatc ttcactcgcg 4920
accgcaaacc gaagtcggcg gcttttctgc tgcaaaaacg ctggactggc atgaacttcg 4980
gtgaaaaacc gcagcaggga ggcaaacaat gaatcaacaa ctctcctggc gcaccatcgt 5040
cggctacagc ctcgggaatt gctaccgagc tcttctacca atggtgggac tcgatccaga 5100
gaatgaaatc ctgcacactc tttcattctt ggctggtctt atgacatggt cacagatcac 5160
tgatttgcca ttttctttgt actcaacttt cgtgatcgag tctcggcatg ggttcaacaa 5220
acaaacaata tggatgttca ttagggacat gatcaaagga atactcctct ctgtcatacc 5280
tgcccctcct atcgttgccg caattattgt tatagttcag aaaggaggtc cttacctcgc 5340
catctatctg tgggcattca tgtttatcct gtctctagtg atgatgacta tataccctgt 5400
tttgattgca cctcttttca acaagttcac tcctcttcct gatggagacc tccgggagaa 5460
gattgagaaa cttgcttctt ctctaaagtt tcctctgaag aagctgtttg ttgtcgatgg 5520
atctacaagg tcaagccata gtaatgctta catgtatggt ttcttcaaga acaaaaggat 5580
tgttctttat gacacattga ttcagcagtg ccagaatgag aatgaaattg tggcggttat 5640
tgcacacgag ctgggacact gggagctcga atttccccga tcgttcaaac atttggcaat 5700
aaagtttctt aagattgaat cctgttgccg gtcttgcgat gattatcata taatttctgt 5760
tgaattacgt taagcatgta ataattaaca tgtaatgcat gacgttattt atgagatggg 5820
tttttatgat tagagtcccg caattataca tttaatacgc gatagaaaac aaaatatagc 5880
gcgcaaacta ggataaatta tcgcgcgcgg tgtcatctat gttactagat cgggaattca 5940
ctggccgtcg ttttacaacg tcgtgactgg gaaaaccctg gcgttaccca acttaatcgc 6000
cttgcagcac atcccccttt cgccagctgg cgtaatagcg aagaggcccg caccgatcgc 6060
ccttcccaac agttgcgcag cctgaatggc gcccgctcct ttcgctttct tcccttcctt 6120
tctcgccacg ttcgccggct ttccccgtca agctctaaat cgggggctcc ctttagggtt 6180
ccgatttagt gctttacggc acctcgaccc caaaaaactt gatttgggtg atggttcacg 6240
tagtgggcca tcgccctgat agacggtttt tcgccctttg acgttggagt ccacgttctt 6300
taatagtgga ctcttgttcc aaactggaac aacactcaac cctatctcgg gctattcttt 6360
tgatttataa gggattttgc cgatttcgga accaccatca aacaggattt tcgcctgctg 6420
gggcaaacca gcgtggaccg cttgctgcaa ctctctcagg gccaggcggt gaagggcaat 6480
cagctgttgc ccgtctcact ggtgaaaaga aaaaccaccc cagtacatta aaaacgtccg 6540
caatgtgtta ttaagttgtc taagcgtcaa tttgtttaca ccacaatata tcctgcca 6598

<210> SEQ ID NO 147
<211> LENGTH: 5668
<212> TYPE: DNA
<213> ORGANISM: Artificial Sequence
<220> FEATURE:
<223> OTHER INFORMATION: Description of Artificial Sequence: Plasmid
pRD29A-antisense-BnCPP

<400> SEQUENCE: 147
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620

```
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctta atctgtcttc ttgtcttctc   3480
catcaatggc tcgaagcctc tctacaagag gagggtgtga gtagtgataa gctgagtaca   3540
atgggtctgt gttcatcgct gataagttct cttcctgtag cttcactagg gcaggacgta   3600
gatcctttgc ataaccaaga ttcactgcaa aagcatcagc ctgaaactca aacgctcgac   3660
taacaaggtt gaggtcaaag cttactaggt gttgaagtgg tattacagtg tgctgaaata   3720
tgatcaaacc aatgagaact ggttgtgtat caaaaccaaa actcctgaag agatcagtgg   3780
agtttctgac aagagtgtat cctccaaatt gcaagaaggc aaggatttga acagcaatga   3840
acgagtatgt agtgtgattc agcttccagt gtcccagctc gtgtgcaata accgccacaa   3900
tttcattctc attctggcac tgctgaatca atgtgtcata aagaacaatc cttttgttct   3960
tgaagaaacc atacatgtaa gcattactat ggcttgacct tgtagatcca tcgacaacaa   4020
```

```
acagcttctt cagaggaaac tttagagaag aagcaagttt ctcaatcttc tcccggaggt   4080

ctccatcagg aagaggagtg aacttgttga aaagaggtgc aatcaaaaca gggtatatag   4140

tcatcatcac tagagacagg ataaacatga atgcccacag atagatggcg aggtaaggac   4200

ctcctttctg aactataaca ataattgcgg caacgatagg aggggcaggt atgacagaga   4260

ggagtattcc tttgatcatg tccctaatga acatccatat tgtttgtttg ttgaacccat   4320

gccgagactc gatcacgaaa gttgagtaca aagaaaatgg caaatcagtg atctgtgacc   4380

atgtcataag accagccaag aatgaaagag tgtgcaggat ttcattctct ggatcgagtc   4440

ccaccattgg tagaaagccg ccagatatct tccaaaacca aggcaagatc ccaaagaaca   4500

gaatcgcaga gtccataagt atagtaacaa actcatgaac aaagtgaaaa tggcttttgt   4560

caagactgta agctcgagat ttctcaaact tctcttggct aatgactcca accaaagtct   4620

ttgggagagt gggaagcttg agagcagtat gttgcctcag atccaaatac gtctcaaaaa   4680

cgtacatcac tatcataaaa ccaacgacgg tttccatgaa aggaatcgcc atcccctcga   4740

atttccccga tcgttcaaac atttggcaat aaagtttctt aagattgaat cctgttgccg   4800

gtcttgcgat gattatcata taatttctgt tgaattacgt taagcatgta ataattaaca   4860

tgtaatgcat gacgttattt atgagatggg tttttatgat tagagtcccg caattataca   4920

tttaatacgc gatagaaaac aaaatatagc gcgcaaacta ggataaatta tcgcgcgcgg   4980

tgtcatctat gttactagat cgggaattca ctggccgtcg ttttacaacg tcgtgactgg   5040

gaaaaccctg gcgttaccca acttaatcgc cttgcagcac atcccccttt cgccagctgg   5100

cgtaatagcg aagaggcccg caccgatcgc ccttcccaac agttgcgcag cctgaatggc   5160

gcccgctcct ttcgctttct tcccttcctt tctcgccacg ttcgccggct ttccccgtca   5220

agctctaaat cgggggctcc ctttagggtt ccgatttagt gctttacggc acctcgaccc   5280

caaaaaactt gatttgggtg atggttcacg tagtgggcca tcgccctgat agacggtttt   5340

tcgccctttg acgttggagt ccacgttctt taatagtgga ctcttgttcc aaactggaac   5400

aacactcaac cctatctcgg gctattcttt tgatttataa gggattttgc cgatttcgga   5460

accaccatca aacaggattt tcgcctgctg gggcaaacca gcgtggaccg cttgctgcaa   5520

ctctctcagg gccaggcggt gaagggcaat cagctgttgc ccgtctcact ggtgaaaaga   5580

aaaaccaccc cagtacatta aaaacgtccg caatgtgtta ttaagttgtc taagcgtcaa   5640

tttgtttaca ccacaatata tcctgcca                                      5668
```

<210> SEQ ID NO 148
<211> LENGTH: 5074
<212> TYPE: DNA
<213> ORGANISM: Artificial Sequence
<220> FEATURE:
<223> OTHER INFORMATION: Description of Artificial Sequence: Plasmid MuA-BnCPP

<400> SEQUENCE: 148

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360
```

-continued

```
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
atagacgaaa aggaaggtgg ctcctataaa gcacatcatt gcgataacag aaaggccatt   2640
gttgaagata cctctgctga cattggtccc caagtggaag caccacccca tgaggagcac   2700
```

-continued

```
cgtggagtaa gaagacgttc gagccacgtc gaaaaagcaa gtgtgttgat gtagtatctc   2760
cattgacgta agggatgacg cacaatccaa ctatccatcg caagaccatt gctctatata   2820
agaaagttaa tatcatttcg agtggccacg ctgaggggga tccatggcga ttcctttcat   2880
ggaaaccgtc gttggtttta tgatagtgat gtacgttttt gagacgtatt tggatctgag   2940
gcaacatact gctctcaagc ttcccactct cccaaagact ttggttggag tcattagcca   3000
agagaagttt gagaaatctc gagcttacag tcttgacaaa agccattttc actttgttca   3060
tgagtttgtt actatactta tggactctgc gattctgttc tttgggatct tgccttggtt   3120
ttggaagata tctggcggct ttctaccaat ggtgggactc gatccagaga atgaaatcct   3180
gcacactctt tcattcttgg ctggtcttat gacatggtca cagatcactg atttgccatt   3240
ttctttgtac tcaactttcg tgatcgagtc tcggcatggg ttcaacaaac aaacaatatg   3300
gatgttcatt agggacatga tcaaaggaat actcctctct gtcatacctg cccctcctat   3360
cgttgccgca attattgtta tagttcagaa aggaggtcct tacctcgcca tctatctgtg   3420
ggcattcatg tttatcctgt ctctagtgat gatgactata taccctgttt tgattgcacc   3480
tcttttcaac aagttcactc ctcttcctga tggagacctc cgggagaaga ttgagaaact   3540
tgcttcttct ctaaagtttc ctctgaagaa gctgtttgtt gtcgatggat ctacaaggtc   3600
aagccatagt aatgcttaca tgtatggttt cttcaagaac aaaaggattg ttctttatga   3660
cacattgatt cagcagtgcc agaatgagaa tgaaattgtg gcggttattg cacacgagct   3720
gggacactgg aagctgaatc acactacata ctcgttcatt gctgttcaaa tccttgcctt   3780
cttgcaattt ggaggataca ctcttgtcag aaactccact gatctcttca ggagttttgg   3840
ttttgataca caaccagttc tcattggttt gatcatattt cagcacactg taataccact   3900
tcaacaccta gtaagctttg acctcaacct tgttagtcga gcgtttgagt ttcaggctga   3960
tgcttttgca gtgaatcttg gttatgcaaa ggatctacgt cctgccctag tgaagctaca   4020
ggaagagaac ttatcagcga tgaacacaga cccattgtac tcagcttatc actactcaca   4080
ccctcctctt gtagagaggc ttcgagccat tgatggagaa gacaagaaga cagattaacc   4140
cctcgaattt ccccgatcgt tcaaacattt ggcaataaag tttcttaaga ttgaatcctg   4200
ttgccggtct tgcgatgatt atcatataat ttctgttgaa ttacgttaag catgtaataa   4260
ttaacatgta atgcatgacg ttatttatga gatgggtttt tatgattaga gtcccgcaat   4320
tatacattta atacgcgata gaaaacaaaa tatagcgcgc aaactaggat aaattatcgc   4380
gcgcggtgtc atctatgtta ctagatcggg aattcactgg ccgtcgtttt acaacgtcgt   4440
gactgggaaa accctggcgt tacccaactt aatcgccttg cagcacatcc ccctttcgcc   4500
agctggcgta atagcgaaga ggcccgcacc gatcgccctt cccaacagtt gcgcagcctg   4560
aatggcgccc gctcctttcg ctttcttccc ttcctttctc gccacgttcg ccggctttcc   4620
ccgtcaagct ctaaatcggg ggctcccttt agggttccga tttagtgctt tacggcacct   4680
cgaccccaaa aaacttgatt tgggtgatgg ttcacgtagt gggccatcgc cctgatagac   4740
ggtttttcgc cctttgacgt tggagtccac gttctttaat agtggactct tgttccaaac   4800
tggaacaaca ctcaacccta tctcgggcta ttcttttgat ttataaggga ttttgccgat   4860
ttcggaacca ccatcaaaca ggattttcgc ctgctggggc aaaccagcgt ggaccgcttg   4920
ctgcaactct ctcagggcca ggcggtgaag ggcaatcagc tgttgcccgt ctcactggtg   4980
aaaagaaaaa ccaccccagt acattaaaaa cgtccgcaat gtgttattaa gttgtctaag   5040
cgtcaatttg tttacaccac aatatatcct gcca                               5074
```

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 149
aaacccggga tggcgtttcc ctacatggaa gcc 33

<210> SEQ ID NO 150
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 150
aaagagctct tagtcttcct tcttatccgg ttcg 34

<210> SEQ ID NO 151
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 151
aaacccggga tggcgattcc tttcatgg 28

<210> SEQ ID NO 152
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 152
aaaggatcct taatctgtct tcttgtcttc tcc 33

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 153
aaagagctct tctaccaatg gtgggactcg 30

<210> SEQ ID NO 154
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 154
aaagagctcc cagtgtccca gctcgtgtg 29

<210> SEQ ID NO 155
<211> LENGTH: 30
<212> TYPE: DNA
<213> ORGANISM: Artificial Sequence
<220> FEATURE:

<223> OTHER INFORMATION: Description of Artificial Sequence: PCR Primer

<400> SEQUENCE: 155
aaaggatcct tctaccaatg gtgggactcg 30

<210> SEQ ID NO 156
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 156
aaatctagac cagtgtccca gctcgtgtg 29

<210> SEQ ID NO 157
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 157
gatgagctca caagatcaag tcacagcaat gcct 34

<210> SEQ ID NO 158
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 158
aaagagctcc cggttcgtcc agcgcggcc 29

<210> SEQ ID NO 159
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 159
gatggatcca caagatcaag tcacagcaat gcct 34

<210> SEQ ID NO 160
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 160
ccttctagac cggttcgtcc agcgcggcc 29

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 161
tttaagcttg gagccataga tgcaattcaa 30

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 162
gcaagaccgg caacagga 18

<210> SEQ ID NO 163
<211> LENGTH: 603
<212> TYPE: DNA
<213> ORGANISM: Artificial Sequence
<220> FEATURE:
<223> OTHER INFORMATION: Description of Artificial Sequence: Consensus sequence BASF

<400> SEQUENCE: 163
gttcgagaat gaatatcaac cttcttcttg cggatgtggt ccaatacgat tgcctttctt 60
tatcaacttt gtatgagccg catggttaaa acaaacatgg tttcttaggg aatgtaaagg 120
aattcttcta tatggccacc atgtgcgcat atatagtcag aggaggccta tgcattatct 180
tgggttagtt ttctttgatg atgacttacc ttatagcccc tttcaaaagt tcactccctt 240
ccgaggctcg ggaaaatgag aactgcctcc taattcctta aaactttgtg tgatggtcac 300
agtcaagcaa gaatgctaat gtatggtttt aagaacaaga tgtcttatga acttattcac 360
agtgaagaga gaatgtcgtt atgccagatg gacatggaac taacaactta ctttgctcat 420
cttttcaatt tggaggataa cctgtgatcg atcttgagtt ggttacagcc gttattggta 480
tcatttcgca actaatcctc acatagcttt gctaacctgt aggactttga tttcaggctg 540
atgtttgcga acttggtatg ctcgctgtaa actacaggag agaattcgca tgaaacgatc 600
tgc 603

<210> SEQ ID NO 164
<211> LENGTH: 525
<212> TYPE: PRT
<213> ORGANISM: Artificial Sequence
<220> FEATURE:
<223> OTHER INFORMATION: Description of Artificial Sequence: Consensus sequence BASF
<220> FEATURE:
<221> NAME/KEY: VARIANT
<222> LOCATION: (1)..(101)
<223> OTHER INFORMATION: Wherein Xaa is any amino acid.
<220> FEATURE:
<221> NAME/KEY: VARIANT
<222> LOCATION: (106)
<223> OTHER INFORMATION: Wherein Xaa is any amino acid.
<220> FEATURE:
<221> NAME/KEY: VARIANT
<222> LOCATION: (110)
<223> OTHER INFORMATION: Wherein Xaa is any amino acid.
<220> FEATURE:
<221> NAME/KEY: VARIANT
<222> LOCATION: (115)
<223> OTHER INFORMATION: Wherein Xaa is any amino acid.
<220> FEATURE:
<221> NAME/KEY: VARIANT
<222> LOCATION: (117)
<223> OTHER INFORMATION: Wherein Xaa is any amino acid.
<220> FEATURE:
<221> NAME/KEY: VARIANT
<222> LOCATION: (120)
<223> OTHER INFORMATION: Wherein Xaa is any amino acid.
<220> FEATURE:
<221> NAME/KEY: VARIANT
<222> LOCATION: (136)

<223> OTHER INFORMATION: Wherein Xaa is any amino acid.
<220> FEATURE:
<221> NAME/KEY: VARIANT
<222> LOCATION: (145)
<223> OTHER INFORMATION: Wherein Xaa is any amino acid.
<220> FEATURE:
<221> NAME/KEY: VARIANT
<222> LOCATION: (147)
<223> OTHER INFORMATION: Wherein Xaa is any amino acid.
<220> FEATURE:
<221> NAME/KEY: VARIANT
<222> LOCATION: (149)
<223> OTHER INFORMATION: Wherein Xaa is any amino acid.
<220> FEATURE:
<221> NAME/KEY: VARIANT
<222> LOCATION: (153)
<223> OTHER INFORMATION: Wherein Xaa is any amino acid.
<220> FEATURE:
<221> NAME/KEY: VARIANT
<222> LOCATION: (156)..(157)
<223> OTHER INFORMATION: Wherein Xaa is any amino acid.
<220> FEATURE:
<221> NAME/KEY: VARIANT
<222> LOCATION: (160)
<223> OTHER INFORMATION: Wherein Xaa is any amino acid.
<220> FEATURE:
<221> NAME/KEY: VARIANT
<222> LOCATION: (162)
<223> OTHER INFORMATION: Wherein Xaa is any amino acid.
<220> FEATURE:
<221> NAME/KEY: VARIANT
<222> LOCATION: (172)
<223> OTHER INFORMATION: Wherein Xaa is any amino acid.
<220> FEATURE:
<221> NAME/KEY: VARIANT
<222> LOCATION: (176)
<223> OTHER INFORMATION: Wherein Xaa is any amino acid.
<220> FEATURE:
<221> NAME/KEY: VARIANT
<222> LOCATION: (187)
<223> OTHER INFORMATION: Wherein Xaa is any amino acid.
<220> FEATURE:
<221> NAME/KEY: VARIANT
<222> LOCATION: (189)
<223> OTHER INFORMATION: Wherein Xaa is any amino acid.
<220> FEATURE:
<221> NAME/KEY: VARIANT
<222> LOCATION: (191)
<223> OTHER INFORMATION: Wherein Xaa is any amino acid.
<220> FEATURE:
<221> NAME/KEY: VARIANT
<222> LOCATION: (193)..(195)
<223> OTHER INFORMATION: Wherein Xaa is any amino acid.
<220> FEATURE:
<221> NAME/KEY: VARIANT
<222> LOCATION: (195)
<223> OTHER INFORMATION: Wherein Xaa is any amino acid.
<220> FEATURE:
<221> NAME/KEY: VARIANT
<222> LOCATION: (199)
<223> OTHER INFORMATION: Wherein Xaa is any amino acid.
<220> FEATURE:
<221> NAME/KEY: VARIANT
<222> LOCATION: (202)
<223> OTHER INFORMATION: Wherein Xaa is any amino acid.
<220> FEATURE:
<221> NAME/KEY: VARIANT
<222> LOCATION: (203)
<223> OTHER INFORMATION: Wherein Xaa is any amino acid.
<220> FEATURE:
<221> NAME/KEY: VARIANT
<222> LOCATION: (216)
<223> OTHER INFORMATION: Wherein Xaa is any amino acid.
<220> FEATURE:
<221> NAME/KEY: VARIANT
<222> LOCATION: (218)
<223> OTHER INFORMATION: Wherein Xaa is any amino acid.
<220> FEATURE:
<221> NAME/KEY: VARIANT
<222> LOCATION: (228)
<223> OTHER INFORMATION: Wherein Xaa is any amino acid.
<220> FEATURE:
<221> NAME/KEY: VARIANT
<222> LOCATION: (231)..(232)
<223> OTHER INFORMATION: Wherein Xaa is any amino acid.
<220> FEATURE:
<221> NAME/KEY: VARIANT
<222> LOCATION: (273)..(276)
<223> OTHER INFORMATION: Wherein Xaa is any amino acid.
<220> FEATURE:
<221> NAME/KEY: VARIANT
<222> LOCATION: (280)
<223> OTHER INFORMATION: Wherein Xaa is any amino acid.
<220> FEATURE:
<221> NAME/KEY: VARIANT
<222> LOCATION: (295)
<223> OTHER INFORMATION: Wherein Xaa is any amino acid.
<220> FEATURE:
<221> NAME/KEY: VARIANT
<222> LOCATION: (297)
<223> OTHER INFORMATION: Wherein Xaa is any amino acid.
<220> FEATURE:
<221> NAME/KEY: VARIANT
<222> LOCATION: (299)
<223> OTHER INFORMATION: Wherein Xaa is any amino acid.
<220> FEATURE:
<221> NAME/KEY: VARIANT
<222> LOCATION: (301)
<223> OTHER INFORMATION: Wherein Xaa is any amino acid.
<220> FEATURE:
<221> NAME/KEY: VARIANT
<222> LOCATION: (303)
<223> OTHER INFORMATION: Wherein Xaa is any amino acid.
<220> FEATURE:
<221> NAME/KEY: VARIANT
<222> LOCATION: (305)..(306)
<223> OTHER INFORMATION: Wherein Xaa is any amino acid.
<220> FEATURE:
<221> NAME/KEY: VARIANT
<222> LOCATION: (317)
<223> OTHER INFORMATION: Wherein Xaa is any amino acid.
<220> FEATURE:
<221> NAME/KEY: VARIANT
<222> LOCATION: (319)
<223> OTHER INFORMATION: Wherein Xaa is any amino acid.
<220> FEATURE:
<221> NAME/KEY: VARIANT
<222> LOCATION: (322)..(323)
<223> OTHER INFORMATION: Wherein Xaa is any amino acid.
<220> FEATURE:
<221> NAME/KEY: VARIANT
<222> LOCATION: (328)..(329)
<223> OTHER INFORMATION: Wherein Xaa is any amino acid.
<220> FEATURE:
<221> NAME/KEY: VARIANT
<222> LOCATION: (333)
<223> OTHER INFORMATION: Wherein Xaa is any amino acid.
<220> FEATURE:
<221> NAME/KEY: VARIANT
<222> LOCATION: (340)
<223> OTHER INFORMATION: Wherein Xaa is any amino acid.
<220> FEATURE:
<221> NAME/KEY: VARIANT
<222> LOCATION: (343)
<223> OTHER INFORMATION: Wherein Xaa is any amino acid.
<220> FEATURE:
<221> NAME/KEY: VARIANT
<222> LOCATION: (346)
<223> OTHER INFORMATION: Wherein Xaa is any amino acid.
<220> FEATURE:
<221> NAME/KEY: VARIANT
<222> LOCATION: (348)..(350)
<223> OTHER INFORMATION: Wherein Xaa is any amino acid.
<220> FEATURE:
<221> NAME/KEY: VARIANT
<222> LOCATION: (353)
<223> OTHER INFORMATION: Wherein Xaa is any amino acid.
<220> FEATURE:

<221> NAME/KEY: VARIANT
<222> LOCATION: (360)
<223> OTHER INFORMATION: Wherein Xaa is any amino acid.
<220> FEATURE:
<221> NAME/KEY: VARIANT
<222> LOCATION: (367)
<223> OTHER INFORMATION: Wherein Xaa is any amino acid.
<220> FEATURE:
<221> NAME/KEY: VARIANT
<222> LOCATION: (370)..(371)
<223> OTHER INFORMATION: Wherein Xaa is any amino acid.
<220> FEATURE:
<221> NAME/KEY: VARIANT
<222> LOCATION: (376)..(377)
<223> OTHER INFORMATION: Wherein Xaa is any amino acid.
<220> FEATURE:
<221> NAME/KEY: VARIANT
<222> LOCATION: (380)..(381)
<223> OTHER INFORMATION: Wherein Xaa is any amino acid.
<220> FEATURE:
<221> NAME/KEY: VARIANT
<222> LOCATION: (394)
<223> OTHER INFORMATION: Wherein Xaa is any amino acid.
<220> FEATURE:
<221> NAME/KEY: VARIANT
<222> LOCATION: (397)..(525)
<223> OTHER INFORMATION: Wherein Xaa is any amino acid.

<400> SEQUENCE: 164

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Glu Asn Glu Ile Xaa His Thr Leu Xaa Phe Leu
            100                 105                 110

Ala Gly Xaa Met Xaa Trp Ser Xaa Ile Thr Asp Leu Pro Phe Ser Leu
        115                 120                 125

Tyr Ser Thr Phe Val Ile Glu Xaa Arg His Gly Phe Asn Lys Gln Thr
    130                 135                 140

Xaa Trp Xaa Phe Xaa Arg Asp Met Xaa Lys Gly Xaa Xaa Leu Ser Xaa
145                 150                 155                 160

Ile Xaa Gly Pro Pro Ile Val Ala Ala Ile Ile Xaa Ile Val Gln Xaa
                165                 170                 175

Gly Gly Pro Tyr Leu Ala Ile Tyr Leu Trp Xaa Phe Xaa Phe Xaa Leu
            180                 185                 190

Xaa Xaa Xaa Met Met Thr Xaa Tyr Pro Xaa Xaa Ile Ala Pro Leu Phe
        195                 200                 205

Asn Lys Phe Thr Pro Leu Pro Xaa Gly Xaa Leu Arg Glu Lys Ile Glu
    210                 215                 220

Lys Leu Ala Xaa Ser Leu Xaa Xaa Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
```

```
            260                 265                 270

Xaa Xaa Xaa Xaa Glu Ile Val Xaa Val Ile Ala His Glu Leu Gly His
        275                 280                 285

Trp Lys Leu Asn His Thr Xaa Tyr Xaa Phe Xaa Ala Xaa Gln Xaa Leu
    290                 295                 300

Xaa Xaa Leu Gln Phe Gly Gly Tyr Thr Leu Val Arg Xaa Ser Xaa Asp
305                 310                 315                 320

Leu Xaa Xaa Ser Phe Gly Phe Xaa Xaa Gln Pro Val Xaa Ile Gly Leu
                325                 330                 335

Ile Ile Phe Xaa His Thr Xaa Ile Pro Xaa Gln Xaa Xaa Xaa Ser Phe
            340                 345                 350

Xaa Leu Asn Leu Val Ser Arg Xaa Phe Glu Phe Gln Ala Asp Xaa Phe
        355                 360                 365

Ala Xaa Xaa Leu Gly Tyr Ala Xaa Xaa Leu Arg Xaa Xaa Leu Val Lys
    370                 375                 380

Leu Gln Glu Glu Asn Leu Ser Ala Met Xaa Thr Asp Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa
        515                 520                 525
```

<210> SEQ ID NO 165
<211> LENGTH: 1249
<212> TYPE: DNA
<213> ORGANISM: Artificial Sequence
<220> FEATURE:
<223> OTHER INFORMATION: Description of Artificial Sequence: Consensus
sequence Generic

<400> SEQUENCE: 165

```
atctctttat tggttttatg atagtgatgt acatttttga gacgtatttg gatctgaggc     60

aactcactgc tctcaagctt ccaactctcc cgaaaacctt ggttggtgta attagccaag    120

agaagtttga gaaatcacga gcatacagtt aaaagctatt ttcactttgt tcatgagttt    180

gtaactatac ttatggactc tgcaattttg ttctttggga tcttgccttg gttttggaag    240

atgtctggag ctgttttacc gaggttgggc cttgatccag agaatgaaat actgcatact    300

ctttcattct tggctggtgt tatgacatgg tcacagatca ctgatttgcc attttctttg    360

tactcaactt tcgtgatcga gtctcggcat gggttcaaca aacaaacaat atggatgttc    420

attagggaca tgatcaaagg aacattcctc tctgtcatac taggcccacc cattgttgct    480

gcgataattt tcatagtcca gaaaggaggt ccttatcttg ccatctatct gtgggcattc    540
```

-continued

```
atgtttatcc tgtctctagt gatgatgact atatacccgg tcttgatagc accgctcttc    600

aacaagttca ctcctcttcc agatggagac ctccgggaga agattgagaa acttgcttct    660

tctctaaagt ttcctttgaa gaagctgttt gttgtcgatg gatctacaag gtcaagccat    720

agcaatgctt acatgtatgg tttctttaag aacaaaagga ttgttcttta tgatacgttg    780

attcagcagt gcaagaatga ggatgaaatt gtggcggtta ttgcacacga gcttggacat    840

tggaaactga atcacactac atactcgttc attgcagttc aaatccttgc cttcttacaa    900

tttggaggat acactcttgt cagaaactcc actgatctct tcaggagttt cggatttgat    960

acacagcctg ttctcattgg tttgatcata tttcagcaca ctgtaatacc actgcaacat   1020

ctagtaagct ttggcctgaa cctcgttagt cgagcgtttg agtttcaggc tgatgctttt   1080

gcgtgaagct tggctatgca aaagatcttc gtcctgctct agtgaaacta caggaagaga   1140

acttatcagc aatgaacact gatccattga ctcagcttat cactactcac atcctcctct   1200

tgttgaaagg cttcgagcca ttgatggaga agacaagaag acagattaa               1249
```

<210> SEQ ID NO 166
<211> LENGTH: 459
<212> TYPE: PRT
<213> ORGANISM: Artificial Sequence
<220> FEATURE:
<223> OTHER INFORMATION: Description of Artificial Sequence: Consensus
      sequence generic
<220> FEATURE:
<221> NAME/KEY: VARIANT
<222> LOCATION: (41)..(97)
<223> OTHER INFORMATION: Wherein Xaa is any amino acid.
<220> FEATURE:
<221> NAME/KEY: VARIANT
<222> LOCATION: (98)..(320)
<223> OTHER INFORMATION: Wherein Xaa is any amino acid.
<220> FEATURE:
<221> NAME/KEY: VARIANT
<222> LOCATION: (322)
<223> OTHER INFORMATION: Wherein Xaa is any amino acid.
<220> FEATURE:
<221> NAME/KEY: VARIANT
<222> LOCATION: (324)..(343)
<223> OTHER INFORMATION: Wherein Xaa is any amino acid.
<220> FEATURE:
<221> NAME/KEY: VARIANT
<222> LOCATION: (345)..(346)
<223> OTHER INFORMATION: Wherein Xaa is any amino acid.
<220> FEATURE:
<221> NAME/KEY: VARIANT
<222> LOCATION: (349)
<223> OTHER INFORMATION: Wherein Xaa is any amino acid.
<220> FEATURE:
<221> NAME/KEY: VARIANT
<222> LOCATION: (351)..(355)
<223> OTHER INFORMATION: Wherein Xaa is any amino acid.
<220> FEATURE:
<221> NAME/KEY: VARIANT
<222> LOCATION: (359)..(366)
<223> OTHER INFORMATION: Wherein Xaa is any amino acid.
<220> FEATURE:
<221> NAME/KEY: VARIANT
<222> LOCATION: (369)..(384)
<223> OTHER INFORMATION: Wherein Xaa is any amino acid.
<220> FEATURE:
<221> NAME/KEY: VARIANT
<222> LOCATION: (386)..(417)
<223> OTHER INFORMATION: Wherein Xaa is any amino acid.
<220> FEATURE:
<221> NAME/KEY: VARIANT
<222> LOCATION: (419)..(424)
<223> OTHER INFORMATION: Wherein Xaa is any amino acid.

<400> SEQUENCE: 166

-continued

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Gly Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Leu Xaa Arg Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Ile Xaa Xaa Gln His Xaa Val Xaa Xaa
            340                 345                 350

Xaa Xaa Xaa Leu Val Ser Xaa Xaa Xaa Xaa Xaa Xaa Xaa Xaa Ala Phe
        355                 360                 365

Xaa Xaa Xaa Xaa Xaa Xaa Xaa Xaa Xaa Xaa Xaa Xaa Xaa Xaa Xaa Xaa
    370                 375                 380

Leu Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Gly Xaa Xaa Xaa Xaa Xaa Xaa Leu Ser Ala Met Asn Thr Asp Pro
```

420 425 430

Leu Tyr Ser Ala Tyr His Tyr Ser His Pro Pro Leu Val Glu Arg Leu
435 440 445

Arg Ala Ile Asp Gly Glu Asp Lys Lys Thr Asp
450 455

<210> SEQ ID NO 167
<211> LENGTH: 945
<212> TYPE: DNA
<213> ORGANISM: Artificial Sequence
<220> FEATURE:
<223> OTHER INFORMATION: Description of Artificial Sequence: Consensus sequence PPI

<400> SEQUENCE: 167
atggcgttcc tcatggaacc gtgtggttta tgatatatgt actttttgaa ctattggatt 60
ggcaacagcc tcaacttcca ctctccaaac ttggggtata gccaagagaa tttgagaaat 120
cgagctaagt cttgaaaaag cattcatttg ttcagagttt gtacatatag actctcattt 180
gtctttgggt ttgcctggtt ttggaagatc gggtttcagg tatcgagaat gaaatctgca 240
accttcttct tgcggtatga tggtcacaga tacgatttgc cttttcttgt actcaacttt 300
gtgatgagcc gcatggttaa aacaaacaat ggtttcttag ggacatgtaa aggaatcctt 360
ctgtatagcc ccatgtgcgc atatttatag tcagaaagga ggtcctatgc catctatctt 420
gggttagttt cttcttgtga tgatgactta ccgttatgcc cctttcaaaa ttcactccct 480
tccgatggac tcgggagaaa tgagaaactt gcttctccta attcctaaga acttttgttg 540
tcgatggatc acaagtcaag caagaatgct aatgtatggt tcttaagaac aaaggattgt 600
cttatgaact tattcacagt gcaagaagaa attgtgcgtt attgccagag tggacatgga 660
actaacaact tacctttgc tcaatcttct tcaatttgga ggataacctt gaaatcctga 720
tcttgagttg gtttgatacc accgtctcat tggtatcata tttcagcaac tgtaatccac 780
tcacatgtag ctttgctaac ctgtagcgac tttgatttca ggctgatgtt tgcgaacttg 840
tatgcagtcg tgctgtgaac tacaggagag aattcacatg aaacgacctg tactcgctta 900
tcactatcca cctcccttgt gaagtgcgag agaaagaaga gataa 945

<210> SEQ ID NO 168
<211> LENGTH: 206
<212> TYPE: PRT
<213> ORGANISM: Artificial Sequence
<220> FEATURE:
<223> OTHER INFORMATION: Description of Artificial Sequence: Consensus sequence PPI

<400> SEQUENCE: 168

Met Ala Met Val Val Gly Met Met Tyr Thr Tyr Asp Arg His Ala Lys
1 5 10 15

Thr Lys Thr Gly Val Ser Lys Lys Ser Arg Ala Tyr Ser Asp Lys Ser
20 25 30

His His Val His Val Thr Asp Ser Gly Trp Trp Lys Ser Gly Gly Asn
35 40 45

His Thr Ala Gly Met Trp Ser Thr Asp Ser Tyr Ser Thr Val Arg His
50 55 60

Gly Asn Lys Thr Trp Arg Asp Met Lys Gly Ser Val Val Ala Ala Val
65 70 75 80

Val Lys Gly Gly Tyr Ala Tyr Trp Ser Val Met Met Thr Tyr Val Ala
85 90 95

```
Asn Lys Thr Asp Gly Arg Lys Lys Ala Ser Ser Lys Lys Val Val Asp
            100                 105                 110

Gly Ser Thr Arg Ser Ser His Ser Asn Ala Tyr Met Tyr Gly Lys Asn
        115                 120                 125

Lys Arg Val Tyr Asp Thr Cys Val Ala Val Ala His Gly His Trp Lys
    130                 135                 140

Asn His Thr Tyr Ala Gly Gly Tyr Thr Val Arg Asn Ser Asp Arg Ser
145                 150                 155                 160

Gly Asp Thr Val Gly His Thr Val Val Ser Asn Val Ser Arg Ala Asp
                165                 170                 175

Ala Gly Tyr Ala Arg Val Lys Asn Ser Ala Met Asn Thr Asp Tyr Ser
            180                 185                 190

Ala Tyr His Tyr Ser His Val Arg Ala Asp Asp Lys Lys Asp
        195                 200                 205


<210> SEQ ID NO 169
<211> LENGTH: 151
<212> TYPE: PRT
<213> ORGANISM: Artificial Sequence
<220> FEATURE:
<223> OTHER INFORMATION: Description of Artificial Sequence: Consensus
      Sequence PPI/generic

<400> SEQUENCE: 169

Met Ala Met Val Val Gly Met Met Tyr Thr Tyr Asp Arg Ala Lys Thr
  1               5                  10                  15

Lys Thr Thr Asp Ser Tyr Ser Thr Val Arg His Gly Asn Lys Thr Trp
             20                  25                  30

Arg Asp Met Lys Gly Ser Val Val Ala Ala Val Lys Gly Gly Tyr Ala
         35                  40                  45

Tyr Trp Ser Val Met Met Thr Tyr Val Ala Asn Lys Thr Asp Gly Arg
     50                  55                  60

Lys Lys Ala Ser Ser Lys Lys Val Val Asp Gly Ser Thr Arg Ser Ser
 65                  70                  75                  80

His Ser Asn Ala Tyr Met Tyr Gly Lys Asn Lys Arg Val Tyr Asp Thr
                 85                  90                  95

Cys Val Ala Val Ala His Gly His Trp Lys Asn His Thr Tyr Ala His
            100                 105                 110

Thr Val Val Ser Asn Val Ser Arg Ala Asp Ala Gly Tyr Ala Arg Val
        115                 120                 125

Lys Asn Ser Ala Met Asn Thr Asp Ser Ala Tyr His Tyr Ser His Val
    130                 135                 140

Arg Ala Asp Asp Lys Lys Asp
145                 150


<210> SEQ ID NO 170
<211> LENGTH: 2765
<212> TYPE: DNA
<213> ORGANISM: Artificial Sequence
<220> FEATURE:
<223> OTHER INFORMATION: Description of Artificial Sequence: Consensus
      Sequence PPI/generic

<400> SEQUENCE: 170

atggcgattc ctttcatgga aaccgtcgtg gttttatgat atatgtacat ttttgaacta      60

tttggattgg caacatgcct caacttccac tctccaaact tggtggtgta tagccaagag     120

aagtttgaga aatctgagct acagtcttga aaaagcattc atttgttcag agtttgtaca     180
```

```
tagttagact ctcaattttg tctttgggtt tgcctggttt tggaagattc gggttttgca    240
attggtcatc gagaatgaaa tctgcatacc ttcttcttgc ggtatgatgg tcacagatac    300
gatttgcctt ttcttgtact caactttgtg atgagtccgc atggttaaaa caaacacatg    360
gtttcttagg gacatgtaaa ggaatttcct tctgtatagc ccctattgtg ctgcaatatt    420
gtatagtcag aaaggaggtc ctatgccatc tatcttgggt ttagttttct tcttgtgatg    480
atgaccttac cgttatgccc ctcttcaaaa gttcactccc ttccagatgg actcgggaga    540
aatgagaaac ttgcttctcc taattcctta agaactattt gttgtcgatg gatcacaagt    600
caagcataga atgctaatgt atggttctta agaacaaagg attgtcttat gacacattat    660
tcacagtgca agaagaaatt gtgcgttatt gccagagtgg gacactggaa ctaacaactt    720
acacattatt gcttcaatct tctttacaat ttggaggata cacctagtga aatcctgatc    780
ttgagttggt ttgataccag ccgtctcatt ggtatcatat ttcagcatac tgtaatccac    840
ttcacatgta gctttgctaa cctgtagcga ctttgatttc aggctgatgc tttgcgaagc    900
ttggtatgca gtcggtgtct agtgaactac aggagagaat gtcagcatga aacagatcct    960
tgtactcgct tatcactatc cacctccctt gtgaaagatg ctgagagaaa gaagagataa   1020
tctaaattct ttcctttca tggaggtaac aaagtatgtc gtatttccaa cactaccttg   1080
tgacttacgt tttttatca gagatgtgga ttaaatttgc ttctaaattc tgttgacagc   1140
aaacaatatg gatgttcatt agggacatga tcaaaggaac attcctctct gtcatactag   1200
gcccacccat tgttgctgcg ataattttca tagtccaggt ttgatgattc tggattcatc   1260
ttatttctga gtttttcaca tggatgacta ttctccattg agtgtgagct tcaaagtttt   1320
tagttttcgt gttaaaaatt taaaatttgc ttctctgagc atgaagtttc tatcttttc    1380
cagaaaggag gtccttatct tgccatctat ctgtgggcat tcatgtttat cctgtctcta   1440
gtgatgatga ctatataccc ggtcttgata gcaccgctct tcaacaagtt cactcctgtg   1500
tgtatttctg tcatggccat tttacaattc actgcttgtt tgcatatgtt gttaccagac   1560
aatataatct cccgcttttt tatggctata gcttccagat ggagacctcc gggagaagat   1620
tgagaaactt gcttcttctc taaagtttcc tttgaagaag ctgtttgttg tcgatggatc   1680
tacaaggtca agccatagca atgtgagaag cttgagatct cttcctacct actttactct   1740
agtttaccat tagaagctta cgtatcttgt tacatcatac aggcttacat gtatggtttc   1800
tttaagaaca aaaggattgt tctttatgat acgttgattc agcaggtact gtgactcttg   1860
atgcttcaaa cgagctatac tcacatttct gtttctggtt ctgaaacata acataatctt   1920
ctattgtgca gtgcaagaat gaggatgaaa ttgtggcggt tattgcacac gagcttggac   1980
attggaaact gaatcacact acatactcgt tcattgcagt tcaagtgagg ctcaaccgac   2040
agttcaaaaa cttactcaca tctacatttc acttaagaaa tcatgtctta tgaccctctc   2100
tcaatgtttt gcttgcagat ccttgccttc ttacaatttg gaggatacac tcttgtcaga   2160
aactccactg atctcttcag gagtttcgga tttgatacac agcctgttct cattggtttg   2220
atcatatttc aggtttgtta tttttgcctt ttgacactaa tctaatgaat caaggatgga   2280
ttaagaaaaa aaaactctaa acctttggtt atatctcctg tctgattatc acagcacact   2340
gtaataccac tgcaacatct agtaagcttt ggcctgaacc tcgttagtcg agcgtttgag   2400
tttcaggtac catcttacaa tccctcaaga tccaaccata gtttctttat tgcaatggca   2460
gcctcatcta ctaatctgag ttaacgttcc ttttgcaggc tgatgctttt gctgtgaagc   2520
```

ttggctatgc aaaagatctt cgtcctgctc tagtgaaact acaggtcaga gaagataaca 2580
acagaacaca aactgttacc tcaatttgtg tcacacactt aaatggattt tttgttggga 2640
ttttgcagga agagaactta tcagcaatga acactgatcc attgtactca gcttatcact 2700
actcacatcc tcctcttgtt gaaaggcttc gagccattga tggagaagac aagaagacag 2760
attaa 2765

<210> SEQ ID NO 171
<211> LENGTH: 36
<212> TYPE: DNA
<213> ORGANISM: Artificial Sequence
<220> FEATURE:
<223> OTHER INFORMATION: Description of Artificial Sequence: REV Primer BamHI site

<400> SEQUENCE: 171
aaaggatcct catgctgctt taaagaagaa ctcgat 36

<210> SEQ ID NO 172
<211> LENGTH: 1461
<212> TYPE: DNA
<213> ORGANISM: Arabidopsis sp.

<400> SEQUENCE: 172
cccgggatgc cagtagtaac ccgcttgatt cgtttgaagt gtgtagggct cagacttgac 60
cggagtggac tcaatcggcg aatctgtcac ggaggacacg gggaatcaac gcggcggaga 120
gtgatggaag agctttcaag cctaaccgtg agtcagcgcg agcaatttct ggtggagaac 180
gatgtgttcg ggatctataa ttacttcgac gccagcgacg tttctactca aaaatacatg 240
atggagattc agcgagataa gcaattggat tatctgatga aaggcttaag gcagcttggt 300
ccgcagtttt cttccttaga tgctaatcga ccttggcttt gttactggat tcttcattca 360
atagctttgc ttggggagac tgtggatgat gaattagaaa gcaatgccat tgacttcctt 420
ggacgctgcc agggctctga aggtggatac ggtggtggtc ctggccaact tccacatctt 480
gcaactactt atgctgcagt gaatgcactt gttactttag gaggtgacaa agccctttct 540
tcaattaata gagaaaaaat gtcttgtttt ttaagacgga tgaaggatac aagtggaggt 600
ttcaggatgc atgatatggg agaaatggat gttcgtgcat gctacactgc aatttcggtt 660
gcaagcatcc taaatattat ggatgatgaa ctcacccagg gcctaggaga ttacatcttg 720
agttgccaaa cttatgaagg tggcattgga ggggaacctg gctccgaagc tcacggtggg 780
tatacctact gtggtttggc tgctatgatt ttaatcaatg aggtcgaccg tttgaatttg 840
gattcattaa tgaattgggc tgtacatcga caaggagtag aaatgggatt tcaaggtagg 900
acgaacaaat tggtcgatgg ttgctacaca ttttggcagg cagccccttg tgttctacta 960
caaagattat attcaaccaa tgatcatgac gttcatggat catcacatat atcagaaggg 1020
acaaatgaag aacatcatgc tcatgatgaa gatgaccttg aagacagtga tgatgatgat 1080
gattctgatg aggacaacga tgaagattca gtgaatggtc acagaatcca tcatacatcc 1140
acctacatta acaggagaat gcaactggtt tttgatagcc tcggcttgca gagatatgta 1200
ctcttgtgct ctaagatccc tgacggtgga ttcagagaca agccgaggaa accccgtgac 1260
ttctaccaca catgttactg cctgagcggc ttgtctgtgg ctcagcacgc ttggttaaaa 1320
gacgaggaca ctcctccttt gactcgcgac attatgggtg gctactcgaa tctccttgaa 1380
cctgttcaac ttcttcacaa cattgtcatg gatcagtata atgaagctat cgagttcttc 1440

```
tttaaagcag catgaggatc c                                             1461


<210> SEQ ID NO 173
<211> LENGTH: 5727
<212> TYPE: DNA
<213> ORGANISM: Artificial Sequence
<220> FEATURE:
<223> OTHER INFORMATION: Description of Artificial Sequence: pBI121-
      AtFTB vector

<400> SEQUENCE: 173

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500

tgcaccgcga tatcttgctg cgttcggata ttttcgtgga gttcccgcca cagacccgga   1560

tgatccccga tcgttcaaac atttggcaat aaagtttctt aagattgaat cctgttgccg   1620

gtcttgcgat gattatcata taatttctgt tgaattacgt taagcatgta ataattaaca   1680

tgtaatgcat gacgttattt atgagatggg tttttatgat tagagtcccg caattataca   1740

tttaatacgc gatagaaaac aaaatatagc gcgcaaacta ggataaatta tcgcgcgcgg   1800

tgtcatctat gttactagat cgggcctcct gtcaatgctg gcggcggctc tggtggtggt   1860

tctggtggcg gctctgaggg tggtggctct gagggtggcg gttctgaggg tggcggctct   1920

gagggaggcg gttccggtgg tggctctggt tccggtgatt ttgattatga aaagatggca   1980
```

aacgctaata agggggctat gaccgaaaat gccgatgaaa acgcgctaca gtctgacgct 2040
aaaggcaaac ttgattctgt cgctactgat tacggtgctg ctatcgatgg tttcattggt 2100
gacgtttccg gccttgctaa tggtaatggt gctactggtg attttgctgg ctctaattcc 2160
caaatggctc aagtcggtga cggtgataat tcacctttaa tgaataattt ccgtcaatat 2220
ttaccttccc tccctcaatc ggttgaatgt cgcccttttg tctttggccc aatacgcaaa 2280
ccgcctctcc ccgcgcgttg gccgattcat taatgcagct ggcacgacag gtttcccgac 2340
tggaaagcgg gcagtgagcg caacgcaatt aatgtgagtt agctcactca ttaggcaccc 2400
caggctttac actttatgct tccggctcgt atgttgtgtg gaattgtgag cggataacaa 2460
tttcacacag gaaacagcta tgaccatgat tacgccaagc ttgcatgcct gcagcccaca 2520
gatggttaga gaggcttacg cagcaggtct catcaagacg atctacccga gcaataatct 2580
ccaggaaatc aaataccttc ccaagaaggt taaagatgca gtcaaaagat tcaggactaa 2640
ctgcatcaag aacacagaga aagatatatt tctcaagatc agaagtacta ttccagtatg 2700
gacgattcaa ggcttgcttc acaaaccaag gcaagtaata gagattggag tctctaaaaa 2760
ggtagttccc actgaatcaa aggccatgga gtcaaagatt caaatagagg acctaacaga 2820
actcgccgta aagactggcg aacagttcat acagagtctc ttacgactca atgacaagaa 2880
gaaaatcttc gtcaacatgg tggagcacga cacacttgtc tactccaaaa atatcaaaga 2940
tacagtctca gaagaccaaa gggcaattga gacttttcaa caaagggtaa tatccggaaa 3000
cctcctcgga ttccattgcc cagctatctg tcactttatt gtgaagatag tggaaaagga 3060
aggtggctcc tacaaatgcc atcattgcga taaaggaaag gccatcgttg aagatgcctc 3120
tgccgacagt ggtcccaaag atggaccccc acccacgagg agcatcgtgg aaaaagaaga 3180
cgttccaacc acgtcttcaa agcaagtgga ttgatgtgat atctccactg acgtaaggga 3240
tgacgcacaa tcccactatc cttcgcaaga cccttcctct atataaggaa gttcatttca 3300
tttggagaga acacggggga ctctagagga tcccccggga tgccagtagt aacccgcttg 3360
attcgtttga agtgtgtagg gctcagactt gaccggagtg gactcaatcg gcgaatctgt 3420
cacggaggac acggggaatc aacgcggcgg agagtgatgg aagagctttc aagcctaacc 3480
gtgagtcagc gcgagcaatt tctggtggag aacgatgtgt tcgggatcta taattacttc 3540
gacgccagcg acgtttctac tcaaaaatac atgatggaga ttcagcgaga taagcaattg 3600
gattatctga tgaaaggctt aaggcagctt ggtccgcagt tttcttcctt agatgctaat 3660
cgaccttggc tttgttactg gattcttcat tcaatagctt tgcttgggga gactgtggat 3720
gatgaattag aaagcaatgc cattgacttc cttggacgct gccagggctc tgaaggtgga 3780
tacggtggtg gtcctggcca acttccacat cttgcaacta cttatgctgc agtgaatgca 3840
cttgttactt taggaggtga caaagccctt tcttcaatta atagagaaaa aatgtcttgt 3900
tttttaagac ggatgaagga tacaagtgga ggtttcagga tgcatgatat gggagaaatg 3960
gatgttcgtg catgctacac tgcaatttcg gttgcaagca tcctaaatat tatggatgat 4020
gaactcaccc agggcctagg agattacatc ttgagttgcc aaacttatga aggtggcatt 4080
ggaggggaac ctggctccga agctcacggt gggtatacct actgtggttt ggctgctatg 4140
attttaatca atgaggtcga ccgtttgaat ttggattcat taatgaattg ggctgtacat 4200
cgacaaggag tagaaatggg atttcaaggt aggacgaaca aattggtcga tggttgctac 4260
acattttggc aggcagcccc ttgtgttcta ctacaaagat tatattcaac caatgatcat 4320
gacgttcatg gatcatcaca tatatcagaa gggacaaatg aagaacatca tgctcatgat 4380

```
gaagatgacc ttgaagacag tgatgatgat gatgattctg atgaggacaa cgatgaagat   4440

tcagtgaatg gtcacagaat ccatcataca tccacctaca ttaacaggag aatgcaactg   4500

gtttttgata gcctcggctt gcagagatat gtactcttgt gctctaagat ccctgacggt   4560

ggattcagag acaagccgag gaaaccccgt gacttctacc acacatgtta ctgcctgagc   4620

ggcttgtctg tggctcagca cgcttggtta aaagacgagg acactcctcc tttgactcgc   4680

gacattatgg gtggctactc gaatctcctt gaacctgttc aacttcttca caacattgtc   4740

atggatcagt ataatgaagc tatcgagttc ttctttaaag cagcatgagg atccctcgaa   4800

tttccccgat cgttcaaaca tttggcaata aagtttctta agattgaatc ctgttgccgg   4860

tcttgcgatg attatcatat aatttctgtt gaattacgtt aagcatgtaa taattaacat   4920

gtaatgcatg acgttattta tgagatgggt ttttatgatt agagtcccgc aattatacat   4980

ttaatacgcg atagaaaaca aaatatagcg cgcaaactag gataaattat cgcgcgcggt   5040

gtcatctatg ttactagatc gggaattcac tggccgtcgt tttacaacgt cgtgactggg   5100

aaaaccctgg cgttacccaa cttaatcgcc ttgcagcaca tccccctttc gccagctggc   5160

gtaatagcga agaggcccgc accgatcgcc cttcccaaca gttgcgcagc ctgaatggcg   5220

cccgctcctt tcgctttctt cccttccttt ctcgccacgt tcgccggctt tccccgtcaa   5280

gctctaaatc gggggctccc tttagggttc cgatttagtg ctttacggca cctcgacccc   5340

aaaaaacttg atttgggtga tggttcacgt agtgggccat cgccctgata gacggttttt   5400

cgccctttga cgttggagtc cacgttcttt aatagtggac tcttgttcca aactggaaca   5460

acactcaacc ctatctcggg ctattctttt gatttataag ggattttgcc gatttcggaa   5520

ccaccatcaa acaggatttt cgcctgctgg ggcaaaccag cgtggaccgc ttgctgcaac   5580

tctctcaggg ccaggcggtg aagggcaatc agctgttgcc cgtctcactg gtgaaaagaa   5640

aaaccacccc agtacattaa aaacgtccgc aatgtgttat taagttgtct aagcgtcaat   5700

ttgtttacac cacaatatat cctgcca                                       5727
```

<210> SEQ ID NO 174
<211> LENGTH: 34
<212> TYPE: DNA
<213> ORGANISM: Artificial Sequence
<220> FEATURE:
<223> OTHER INFORMATION: Description of Artificial Sequence: isoprenylcysteine carboxyl methyltransferase forward primer

<400> SEQUENCE: 174

```
aaaggatcca tgacagagat cttcagtgac acca                                 34
```

<210> SEQ ID NO 175
<211> LENGTH: 33
<212> TYPE: DNA
<213> ORGANISM: Artificial Sequence
<220> FEATURE:
<223> OTHER INFORMATION: Description of Artificial Sequence: isoprenylcysteine carboxyl methyltransferase reverse primer

<400> SEQUENCE: 175

```
aaagagctct cagttcacaa atggaacacc aga                                  33
```

<210> SEQ ID NO 176
<211> LENGTH: 594
<212> TYPE: DNA

<213> ORGANISM: Arabidopsis sp.

<400> SEQUENCE: 176

```
atgacagaga tcttcagtga caccagcatc agacagttat ctcaaatgct actatcacta     60
atcttcttcc acatatccga atacattcta gccatcacca ttcacggagc atcaaacgta    120
actcttagtt cgcttttaat caccaagcat tacgctttag caatgcttct gtcgcttctc    180
gaatacctaa cggagattat cctcttcccg gggctgaaac aacactggtg ggtcagcaac    240
tttggactca taatgatcat cgttggggaa atcatcagga aggcagcgat aataacagcg    300
ggaagatcgt tcactcacct cataaagatc aactacgaag agcatcacgg gcttgtgact    360
catggtgtgt atagactaat gaggcatcca agttactgcg gttttctcat ctggtcggtc    420
gggacacaag ttatgctctg taaccccgtt tcagcagttg cgttcgcggt tgtcgtgtgg    480
cggtttttttg ctcagagaat accgtacgag gagtattttc tgaatcagtt ttttggggta    540
cagtatctag agtatgcaga gagtgttgcc tctggtgttc catttgtgaa ctga          594
```

<210> SEQ ID NO 177
<211> LENGTH: 482
<212> TYPE: PRT
<213> ORGANISM: Arabidopsis sp.

<400> SEQUENCE: 177

```
Met Pro Val Val Thr Arg Leu Ile Arg Leu Lys Cys Val Gly Leu Arg
1               5                   10                  15

Leu Asp Arg Ser Gly Leu Asn Arg Arg Ile Cys His Gly Gly His Gly
            20                  25                  30

Glu Ser Thr Arg Arg Arg Val Met Glu Glu Leu Ser Ser Leu Thr Val
        35                  40                  45

Ser Gln Arg Glu Gln Phe Leu Val Glu Asn Asp Val Phe Gly Ile Tyr
    50                  55                  60

Asn Tyr Phe Asp Ala Ser Asp Val Ser Thr Gln Lys Tyr Met Met Glu
65                  70                  75                  80

Ile Gln Arg Asp Lys Gln Leu Asp Tyr Leu Met Lys Gly Leu Arg Gln
                85                  90                  95

Leu Gly Pro Gln Phe Ser Ser Leu Asp Ala Asn Arg Pro Trp Leu Cys
            100                 105                 110

Tyr Trp Ile Leu His Ser Ile Ala Leu Leu Gly Glu Thr Val Asp Asp
        115                 120                 125

Glu Leu Glu Ser Asn Ala Ile Asp Phe Leu Gly Arg Cys Gln Gly Ser
    130                 135                 140

Glu Gly Gly Tyr Gly Gly Gly Pro Gly Gln Leu Pro His Leu Ala Thr
145                 150                 155                 160

Thr Tyr Ala Ala Val Asn Ala Leu Val Thr Leu Gly Gly Asp Lys Ala
                165                 170                 175

Leu Ser Ser Ile Asn Arg Glu Lys Met Ser Cys Phe Leu Arg Arg Met
            180                 185                 190

Lys Asp Thr Ser Gly Gly Phe Arg Met His Asp Met Gly Glu Met Asp
        195                 200                 205

Val Arg Ala Cys Tyr Thr Ala Ile Ser Val Ala Ser Ile Leu Asn Ile
    210                 215                 220

Met Asp Asp Glu Leu Thr Gln Gly Leu Gly Asp Tyr Ile Leu Ser Cys
225                 230                 235                 240

Gln Thr Tyr Glu Gly Gly Ile Gly Gly Glu Pro Gly Ser Glu Ala His
                245                 250                 255
```

```
Gly Gly Tyr Thr Tyr Cys Gly Leu Ala Ala Met Ile Leu Ile Asn Glu
            260                 265                 270

Val Asp Arg Leu Asn Leu Asp Ser Leu Met Asn Trp Ala Val His Arg
        275                 280                 285

Gln Gly Val Glu Met Gly Phe Gln Gly Arg Thr Asn Lys Leu Val Asp
    290                 295                 300

Gly Cys Tyr Thr Phe Trp Gln Ala Ala Pro Cys Val Leu Leu Gln Arg
305                 310                 315                 320

Leu Tyr Ser Thr Asn Asp His Asp Val His Gly Ser Ser His Ile Ser
                325                 330                 335

Glu Gly Thr Asn Glu Glu His His Ala His Asp Glu Asp Asp Leu Glu
            340                 345                 350

Asp Ser Asp Asp Asp Asp Asp Ser Asp Glu Asp Asn Asp Glu Asp Ser
        355                 360                 365

Val Asn Gly His Arg Ile His His Thr Ser Thr Tyr Ile Asn Arg Arg
    370                 375                 380

Met Gln Leu Val Phe Asp Ser Leu Gly Leu Gln Arg Tyr Val Leu Leu
385                 390                 395                 400

Cys Ser Lys Ile Pro Asp Gly Gly Phe Arg Asp Lys Pro Arg Lys Pro
                405                 410                 415

Arg Asp Phe Tyr His Thr Cys Tyr Cys Leu Ser Gly Leu Ser Val Ala
            420                 425                 430

Gln His Ala Trp Leu Lys Asp Glu Asp Thr Pro Pro Leu Thr Arg Asp
        435                 440                 445

Ile Met Gly Gly Tyr Ser Asn Leu Leu Glu Pro Val Gln Leu Leu His
    450                 455                 460

Asn Ile Val Met Asp Gln Tyr Asn Glu Ala Ile Glu Phe Phe Phe Lys
465                 470                 475                 480

Ala Ala


<210> SEQ ID NO 178
<211> LENGTH: 1290
<212> TYPE: DNA
<213> ORGANISM: Arabidopsis sp.

<400> SEQUENCE: 178

atggagattc agcgagataa gcaattggat tatctgatga aaggcttaag gcagcttggt     60

ccgcagtttt cttccttaga tgctaatcga ccttggcttt gttactggat tcttcattca    120

atagctttgc ttggggagac tgtggatgat gaattagaaa gcaatgccat tgacttcctt    180

ggacgctgcc agggctctga aggtggatac ggtggtggtc ctggccaact tccacatctt    240

gcaactactt atgctgcagt gaatgcactt gttactttag gaggtgacaa agccctttct    300

tcaattaata gagaaaaaat gtcttgtttt ttaagacgga tgaaggatac aagtggaggt    360

ttcaggatgc atgatatggg agaaattgat gttcgtgcat gctacactgc aatttcggtt    420

gcaagcatcc taaatattat ggatgatgaa ctcacccagg gcctaggaga ttacatcttg    480

agttgccaaa cttatgaagg tggcattgga ggggaacctg gctccgaagc tcacggtggg    540

tatacctact gtggtttggc tgctatgatt ttaatcaatg aggtcgaccg tttgaatttg    600

gattcattaa tgaattgggc tgtacatcga caaggagtag aaatgggatt tcaaggtagg    660

acgaacaaat tggtcgatgg ttgctacaca ttttggcagg cagccccttg tgttctacta    720

caaagattat attcaaccaa tgatcatgac gttcatggat catcacatat atcagaaggg    780
```

-continued

```
acaaatgaag aacatcatgc tcatgatgaa gatgaccttg aagacagtga tgatgatgat    840

gattctgatg aggacaacga tgaagattca gtgaatggtc acagaatcca tcatacatcc    900

acctacatta acaggagaat gcaactggtt tttgatagcc tcggcttgca gagatatgta    960

ctcttgtgct ctaagatccc tgacggtgga ttcagagaca agccgaggaa accccgtgac   1020

ttctaccaca catgttactg cctgagcggc ttgtctgtgg ctcagcacgc ttggttaaaa   1080

gacgaggaca ctcctccttt gactcgcgac attatgggtg gctactcgaa tctccttgaa   1140

cctgttcaac ttcttcacaa cattgtcatg gatcagtata atgaagctat cgagttcttc   1200

tttaaagcag catgacccgt tgttgctaat gtatgggaaa ccccaaacat aagagtttcc   1260

gtagtgttgt aacttgtaag atttcaaaag                                     1290
```